US009481889B2

(12) United States Patent
Singh et al.

(10) Patent No.: US 9,481,889 B2
(45) Date of Patent: Nov. 1, 2016

(54) GENE CONTROLLING SHELL PHENOTYPE IN PALM

(71) Applicant: Malaysian Palm Oil Board, Kajang (MY)

(72) Inventors: Rajinder Singh, Kuala Lumpur (MY); Leslie Low Eng Ti, Kuala Lumpur (MY); Leslie Ooi Cheng Li, Kuala Lumpur (MY); Meilina Ong Abdullah, Seremban (MY); Rajanaidu Nookiah, Kuala Lumpur (MY); Ravigadevi Sambanthamurthi, Selangor (MY); Steven W. Smith, Fitchburg, WI (US); Nathan D. Lakey, Chesterfield, MO (US); Rob Martienssen, Cold Spring Harbor, NY (US); Jared Ordway, St. Louis, MO (US); Michael Hogan, Ballwin, MO (US)

(73) Assignee: THE MALASIAN PALM OIL BOARD, Kajang (MY)

( * ) Notice: Subject to any disclaimer, the term of this patent is extended or adjusted under 35 U.S.C. 154(b) by 675 days.

(21) Appl. No.: 13/800,652

(22) Filed: Mar. 13, 2013

(65) Prior Publication Data
US 2013/0247249 A1 Sep. 19, 2013

Related U.S. Application Data

(60) Provisional application No. 61/612,885, filed on Mar. 19, 2012.

(51) Int. Cl.
*A01H 5/08* (2006.01)
*A01H 1/04* (2006.01)
*C12N 15/82* (2006.01)
*C07K 14/415* (2006.01)
*C12Q 1/68* (2006.01)

(52) U.S. Cl.
CPC ............ *C12N 15/8261* (2013.01); *A01H 1/04* (2013.01); *C07K 14/415* (2013.01); *C12N 15/8247* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,310,893 A | 5/1994 | Erlich et al. |
| 5,451,512 A | 9/1995 | Apple et al. |
| 5,468,613 A | 11/1995 | Erlich et al. |
| 5,604,099 A | 2/1997 | Erlich et al. |
| 6,307,123 B1 | 10/2001 | Kriz et al. |
| 6,646,264 B1 | 11/2003 | Modiano et al. |
| 6,880,771 B2 | 4/2005 | Deppermann |
| 7,367,155 B2 | 5/2008 | Kotyk et al. |
| 7,402,731 B2 | 7/2008 | Penner et al. |
| 7,454,989 B2 | 11/2008 | Deppermann |
| 7,600,642 B2 | 10/2009 | Deppermann |
| 7,673,572 B2 | 3/2010 | Deppermann et al. |
| 7,685,768 B2 | 3/2010 | Deppermann |
| 7,909,276 B2 | 3/2011 | Deppermann et al. |
| 7,998,669 B2 | 8/2011 | Deppermann et al. |
| 8,076,076 B2 | 12/2011 | Osborn et al. |
| 8,221,968 B2 | 7/2012 | Becker et al. |
| 8,237,016 B2 | 8/2012 | Ye et al. |
| 8,241,914 B2 | 8/2012 | Durack et al. |
| 8,281,935 B2 | 10/2012 | Deppermann |
| 8,312,672 B2 | 11/2012 | Deppermann et al. |
| 8,362,317 B2 | 1/2013 | Calabotta et al. |
| 8,401,271 B2 | 3/2013 | Deppermann et al. |
| 8,443,545 B2 | 5/2013 | Deppermann et al. |
| 2004/0110142 A1 | 6/2004 | Bennett et al. |
| 2008/0000815 A1 | 1/2008 | Deppermann |
| 2008/0289061 A1 | 11/2008 | Penner et al. |
| 2009/0070891 A1 | 3/2009 | Foley et al. |
| 2010/0143906 A1 | 6/2010 | Becker et al. |
| 2011/0079544 A1 | 4/2011 | Hunger et al. |
| 2011/0132721 A1 | 6/2011 | Kevin et al. |
| 2011/0195866 A1 | 8/2011 | Deppermann et al. |
| 2012/0117865 A1 | 5/2012 | Deppermann et al. |
| 2012/0180386 A1 | 7/2012 | Deppermann et al. |
| 2013/0079917 A1 | 3/2013 | Deppermann et al. |
| 2013/0104454 A1 | 5/2013 | Deppermann et al. |

FOREIGN PATENT DOCUMENTS

| | | |
|---|---|---|
| EP | 0 235 726 A2 | 9/1987 |
| WO | 89/11548 A1 | 11/1989 |
| WO | 95/00119 A1 | 1/1995 |
| WO | 03/040369 A2 | 5/2003 |
| WO | 2010/056107 A2 | 5/2010 |
| WO | 2010/146357 A1 | 12/2010 |
| WO | 2011/119390 A1 | 9/2011 |
| WO | 2011/119394 A1 | 9/2011 |

OTHER PUBLICATIONS

Barcelos et al. (Pesq. agropec. bras., Brasilia, v. 37, n. 8, p. 1105-1114, 2002).*
Billotte et al. (Theor Appl Genet (2005) 110: 754-765).*
Arias, "Genetic Similarity Among Commercial Oil Palm Materials Based on Microsatellite Markers", Agronomia Colombiana, vol. 30, No. 2, pp. 188-195 (2012). Retrieved from http://www.bdigital.unai.edu.co/30352/1/29152-156322-2-PB.pdf.
Conner et al., "Detection of sickle cell beta S-globin allele by hybridization with oligonucleotides", Proc. Natl. Acad. Sci. USA, 80:278-282 (1983).

(Continued)

Primary Examiner — Elizabeth McElwain
Assistant Examiner — Charles Logsdon
(74) Attorney, Agent, or Firm — Kilpatrick Townsend & Stockton LLP

(57) ABSTRACT

Nucleic acid sequences for predicting and controlling shell phenotype in palm.

20 Claims, 7 Drawing Sheets

(56) References Cited

OTHER PUBLICATIONS

Gill et al., "Nucleic Acid Isothermal Amplification Technologies—A Review", *Nucleosides, Nucleotides, and Nucleic Acids*, 27: 224-43 (2008).

Mayes et al., "The use of Molecular Markers to Investigate the Genetic Structure of an Oil Palm Breeding Programme", Heredity (edinb) vol. 85, Part 3, pp. 288-293, PMID: 11012733 (2000).

Notomi et al., "Loop-mediated isothermal amplification of DNA", *Nucleic Acids Research*, 28(12), e63 i-vii, (2000).

Saiki et al., "Analysis of enzymaticaly amplified beta-globin and HLA-DQ alpha DNA with allele-specific oligonucleotide probes", *Nature*, 324: 163-166, (1986).

Seng et al., "Genetic Linkage Map of a High Yielding FELDS Deli x Yangambi Oil Palm Cross", Plos One, vol. 6, No. 11, e26593 (2011).

Singh et al., "Mapping Quantitative Trait Loci (QTLs) for Fatty Acid Composition in an Interspecific Cross of Oil Palm", BMC Plant Biol., vol. 9, pp. 114 (2009).

Stoneking et al., "Population variation of human mtDNA control region sequences detected by enzymatic amplification and sequence-specific oligonucleotide probes", *Am. J. Hum. Genet.* 48:370-382, 1991.

Walbot, Genomic Sequences Found Using Engineered RescueMu Transpson, National Center for Biotechnology Infomration, Genbank accession BH891314 (2001). Retrieved from http://www.ncbi.him.nih.gov/nucgss/222227?report=genbank.

International Search Report and Written Opinion dated Dec. 12, 2014 for International Patent Application No. PCT/US2014/047171, 11 pages.

The Intenrational Search Report and Written Opinion from PCT/US2013/030803, dated Jun. 14, 2013.

Adam et al.; "MADS Box Genes in Oil Palm (*Elaeis guineensis*): Patterns in the Evolution of the *Squamosa, Deficiens, Globosa, Agamous* and *Sepallata* Subfamilies"; *J. Mol. Evol.*; 62:15-31 (2006).

Billotte et al.; "Microsatellite-based high density linkage map in oil palm (*Elaeis guineensis* Jacq.)"; *Theor. Appl. Genet.*; 110:754-765 (2005).

Billotte et al.; "QTL detection by multi-parent linkage mapping in oil palm (*Elaeis guineensis* Jacq.)"; *Theor. Appl. Genet.*; 120:1673-7687(2010).

Moertzsohn et al.; "RAPD linkage mapping the shell thickness locus in palm oil (*Elaeis guineensis* Jacq.)"; *Theor. Appl. Genet.*; 100:63-70 (2000).

Singh et al.; "Identification of cDNA-RFLP Markers and Their Use for Molecular Mapping Oil Palm (*Elaeis guineensis*)"; *Asia Pacific Journal of Molecular Biology and Biotechnology*; 16(3):53-63 (2008).

\* cited by examiner

GENE CONTROLLING SHELL PHENOTYPE IN PALM

CROSS-REFERENCE TO RELATED PATENT APPLICATIONS

The present patent application claims benefit of priority to U.S. Provisional Patent Application No. 61/612,885, filed Mar. 19, 2012, which is incorporated by reference for all purposes.

BACKGROUND OF THE INVENTION

The oil palm (*E. guineensis* and *E. oleifera*) can be classified into separate groups based on its fruit characteristics, and has three naturally occurring fruit types which vary in shell thickness and oil yield. *Dura* type palms are homozygous for a wild type allele of the shell gene ($sh^+/sh^+$), have a thick seed coat or shell (2-8 mm) and produce approximately 5.3 tons of oil per hectare per year. *Tenera* type palms are heterozygous for a wild type and mutant allele of the shell gene ($sh^+/sh^-$), have a relatively thin shell surrounded by a distinct fiber ring, and produce approximately 7.4 tons of oil per hectare per year. Finally, *pisifera* type palms are homozygous for a mutant allele of the shell gene ($sh^-/sh^-$), have no seed coat or shell, and are usually female sterile (Hartley, 1988) (Table 1). Therefore, the inheritance of the single gene controlling shell phenotype is a major contributor to palm oil yield.

*Tenera* palms are hybrids between the *dura* and *pisifera* palms. Whitmore (1973) described the various fruit forms as different varieties of oil palm. However, Latiff (2000) was in agreement with Purseglove (1972) that varieties or cultivars as proposed by Whitmore (1973), do not occur in the strict sense in this species. As such, Latiff (2000) proposed the term "race" to differentiate *dura*, *pisifera* and *tenera*. Race was considered an appropriate term as it reflects a permanent microspecies, where the different races are capable of exchanging genes with one another, which has been adequately demonstrated in the different fruit forms observed in oil palm (Latiff, 2000). In fact, the characteristics of the three different races turn out to be controlled simply by the inheritance of a single gene. Genetic studies revealed that the shell gene shows co-dominant monogenic inheritance, which is exploitable in breeding programmes (Beirnaert and Vanderweyen, 1941).

The shell gene responsible for this phenotype was first reported in the Belgian Congo in the 1940's (Beirnaert and Venderweyan, 1941). However, *tenera* fruit forms were recognized and exploited in Africa well before then (Devuyst, 1953; Godding, 1930; Sousa et al., 2011). Given the central role played by the shell gene, oil palm breeding utilizes reciprocal recurrent selection of maternal (*dura*) and paternal (*pisifera*) pools using the North Carolina Model 1 maize breeding design (Rajanaidu et al., 2000). The Deli *dura* population, direct descendants of the four original African palms planted in Bogor Botanical Garden, Indonesia (1848), has excellent combining ability with the AVROS (Algemene Vereniging van Rubberplanters ter Oostkust van Sumatra) and other *pisifera* parental palms. AVROS *pisifera* palms were derived from the famous "Djongo" palm from Congo, but more recently several different accessions of *dura* and *pisifera* have also been sourced from Africa (Rajanaidu et al. 2000).

*Tenera* fruit types have a higher mesocarp to fruit ratio, which directly translates to significantly higher oil yield than either the *dura* or *pisifera* palm (as illustrated in Table 1).

TABLE 1

Comparison of dura, tenera and pisifera fruit forms

| | Fruit Form | | |
|---|---|---|---|
| Characteristic | Dura | Tenera | Pisifera* |
| Shell thickness (mm) | 2-8 | 0.5-3 | Absence of shell |
| Fibre Ring ** | Absent | Present | Absent |
| Mesocarp Content (% fruit weight) | 35-55 | 60-96 | 95 |
| Kernel Content (% fruit weight) | 7-20 | 3-15 | 3-5 |
| Oil to Bunch (%) | 16 | 26 | — |
| Oil Yield (t/ha/yr) | 5.3 | 7.4 | — |

*usually female sterile, bunches rot prematurely
** fibre ring is present in the mesocarp and often used as diagnostic tool to differentiate dura and tenera palms.
(Source: Hardon et al., 1985; Hartley, 1988)

Since the crux of the breeding programmes in oil palm is to produce planting materials with higher oil yield, the *tenera* palm is the preferred choice for commercial planting. It is for this reason that substantial resources are invested by commercial seed producers to cross selected *dura* and *pisifera* palms in hybrid seed production. And despite the many advances which have been made in the production of hybrid oil palm seeds, two significant problems remain in the seed production process. First, batches of *tenera* seeds, which will produce the high oil yield *tenera* type palm, are often contaminated with *dura* seeds (Donough and Law, 1995). Today, it is estimated that *dura* contamination of *tenera* seeds can reach rates of approximately 5% (reduced from as high as 20-30% in the early 1990's as the result of improved quality control practices). Seed contamination is due in part to the difficulties of producing pure *tenera* seeds in open plantation conditions, where workers use ladders to manually pollinate tall trees, and where palm flowers for a given bunch mature over a period time, making it difficult to pollinate all flowers in a bunch with a single manual pollination event. Some flowers of the bunch may have matured prior to manual pollination and therefore may have had the opportunity to be wind pollinated from an unknown tree, thereby producing contaminant seeds in the bunch. Alternatively premature flowers may exist in the bunch at the time of manual pollination, and may mature after the pollination occurred allowing them to be wind pollinated from an unknown tree thereby producing contaminant seeds in the bunch. Prior to the invention described herein, it was not possible to identify the fruit type of a given seed of a given plant arising from a seed until it matured enough to produce a first batch of fruit, which typically takes approximately six years after germination. Notably, in the four to five years interval from germination to fruit production, significant land, labor, financial and energy resources are invested into what are believed to be *tenera* trees, some of which will ultimately be of the unwanted low yielding contaminant fruit types. By the time these suboptimal trees are identified, it is impractical to remove them from the field and replace them with *tenera* trees, and thus growers achieve lower palm oil yields for the 25 to 30 year production life of the contaminant trees. Therefore, the issue of contamination of batches of *tenera* seeds with *dura* or *pisifera* seeds is a problem for oil palm breeding, underscoring the need for a method to predict the fruit type of seeds and nursery plantlets with high accuracy.

A second problem in the seed production process is the investment seed producers make in maintaining *dura* and *pisifera* lines, and in the other expenses incurred in the hybrid seed production process. Prior to the present invention, there was no know way to produce a tree with an optimal shell phenotype which when crossed to itself or to another tree with optimal shell phenotype would produce seeds which would only generate optimal shell phenotypes. Therefore, there is a need to engineer trees to breed true from one generation to the next for optimal shell phenotype.

The genetic mapping of the shell gene was initially attempted by Mayes et al. (1997). A second group in Brazil, using a combination of bulked segregation analysis (BSA) and genetic mapping, reported two random amplified polymorphic DNA (RAPD) markers flanking the shell locus (Moretzsohn et al., 2000). More recently, Billotte et al., (2005) reported a simple sequence repeat (SSR)-based high density linkage map for oil palm, involving a cross between a thin shelled *E. guineensis* (*tenera*) palm and a thick shelled *E. guineensis* (*dura*) palm. A patent filed by the Malaysian Palm Oil Board (MPOB) describes the identification of a marker using restriction fragment technology, in particular a Restriction Fragment Length Polymorphism (RFLP) marker linked to the shell gene for plant identification and breeding purposes (RAJINDER SINGH, LESLIE OOI CHENG-LI, RAHIMAH A, RAHMAN AND LESLIE LOW ENG TI. 2008. Method for identification of a molecular marker linked to the shell gene of oil palm. Patent Application No. PI 20084563. Patent Filed on 13 Nov. 2008). The RFLP marker (SFB 83) was identified by way of generation or construction of a genetic map for a *tenera* fruit type palm.

BRIEF SUMMARY OF THE INVENTION

In this patent, we describe the genetic mapping and identification of the shell gene responsible for the different fruit forms and methods for determining the shell phenotype of a palm plant (including but not limited to a whole palm plant or palm seed). We used homozygosity mapping by sequencing to overcome challenges posed by phenotyping experimental populations, and we found two independent mutations in the DNA binding domain of an oil palm MADS-box gene substantially similar to *Arabidopsis* SEEDSTICK (STK), also referred to as AGAMOUS-like 11 (AGL11), as well as to *Arabidopsis* SHATTERPROOF (SHP1), also referred to as AGAMOUS-like 1 (AGL1). For brevity, herein we refer to the shell gene as SHELL. We demonstrate that SHELL is responsible for the shell phenotype in both cultivated and wild palms from sub-Saharan Africa. Furthermore, our findings provide a genetic explanation for the single gene heterosis attributed to SHELL. This is the first demonstration of a gene mutation explaining an economic trait in oil palm, and has important implications for the competing interests of global edible oil production, biofuels and rainforest conservation (Danielsen et al., 2009).

In some embodiments, methods for determining the shell phenotype of a palm (e.g., oil palm) plant (including but not limited to a whole palm plant or palm seed) are provided. In some embodiments, the method comprises, providing a sample from the plant or seed; and determining from the sample the genotype of at least one polymorphic marker in the genomic region corresponding to SEQ ID NO:8218, wherein heterozygosity within the region indicates the presence of the *tenera* shell phenotype. In some embodiments, the plant or seed is generated from i) a cross between a plant having the *dura* shell phenotype and a plant having the *pisifera* shell phenotype, ii) the selfing of a *tenera* palm, iii) a cross between two plants having the *tenera* shell phenotype, iv) a cross between a plant having the *dura* shell phenotype and a plant having the *tenera* shell phenotype, or v) a cross between a plant having the *tenera* shell phenotype and a plant having the *pisifera* shell phenotype. In some embodiments, the plant is less than 5 years old. In some embodiments, the plant is less than one year old.

In some embodiments, the polymorphic marker is within a position in the genomic region corresponding to SEQ ID NO:8219. In some embodiments, the polymorphic marker is within 1, 10, 20, 50, 100, 200, 500, 1000, 200, 3000 kb from a position in the genomic region corresponding to SEQ ID NO:8219. In some embodiments, the polymorphic marker is at least 86, 88, 90, 92, 94, 96, 97, 98, or 99% predictive of the *tenera* phenotype.

In some embodiments, the method further comprises selecting the seed or plant for cultivation if the plant is heterozygous for the polymorphic marker. In some embodiments, the plants or seeds are discarded if the plants or seeds do not have a genotype predictive of the *tenera* shell phenotype.

Also provided is a method for segregating a plurality of palm (e.g., oil palm) plants into different categories based on predicted shell phenotype. In some embodiments, the method comprises, providing a sample from each plant in the plurality of plants; determining from the samples the genotype of at least one polymorphic marker in the genetic region corresponding to SEQ ID NO:8218; and segregating the plants into groups based on the genotype of the polymorphic marker, wherein the groups correspond to plants predicted to have the *tenera* shell phenotype, plants predicted to have the *dura* shell phenotype, and plants predicted to have the *pisifera* shell phenotype.

Also provided are kits for determining the shell phenotype of a palm seed or plant. In some embodiments, the kit comprises, one or more oligonucleotide primer or probe that comprises:

a sequence of at least, e.g., 6, 7, 8, 9, 10, 11, 12, 13, 14, 15, 16, 17, or 18 (or 20, 22, 24, or more) nucleotides of SEQ ID NO:8218; or;

a sequence 100% complementary to at least e.g., 6, 7, 8, 9, 10, 11, 12, 13, 14, 15, 16, 17, or 18 (or 20, 22, 24, or more) nucleotides of SEQ ID NO:8218.

In some embodiments, the primer or probe specifically hybridizes to palm plant DNA or RNA.

In some embodiments, the primer or probe comprises:

a sequence of at least, e.g., 6, 7, 8, 9, 10, 11, 12, 13, 14, 15, 16, 17, or 18 (or 20, 22, 24, or more) nucleotides of SEQ ID NO:8219; or;

a sequence 100% complementary to at least, e.g., 6, 7, 8, 9, 10, 11, 12, 13, 14, 15, 16, 17, or 18 (or 20, 22, 24, or more) nucleotides of SEQ ID NO:8219.

In some embodiments, a detectable label is linked to the oligonucleotide. In some embodiments, the detectable label is fluorescent.

In some embodiments, the kit further comprises a polynucleotide encoding a polypeptide comprising a sequence substantially (e.g., a least 80, 85, 90, 95, 97, 98, 99%) identical or identical to SEQ ID NO:8220, 8221, or 8222.

Also provided is an isolated nucleic acid comprising a polynucleotide encoding a polypeptide comprising a sequence substantially (e.g., a least 80, 85, 90, 95, 97, 98, 99%) identical or identical to SEQ ID NO:8220, 8221, or 8222.

Also provided is a cell or seed or plant comprising a heterologous expression cassette, the expression cassette comprising a heterologous promoter operably linked to a polynucleotide encoding a polypeptide comprising a sequence substantially (e.g., a least 80, 85, 90, 95, 97, 98, 99%) identical or identical to SEQ ID NO:8220, 8221, or 8222. In some embodiments, the seed or plant is a palm (e.g., oil palm) seed or palm (e.g., oil palm) plant. In some embodiments, the polypeptide comprises SEQ ID NO:8220, 8221, or 8222. In some embodiments, the heterologous promoter results in expression level of an RNA encoding the polypeptide in the seed or plant that is less than, equal to, or more than expression of an endogenous SHELL RNA in the seed or plant. In some embodiments, the seed or plant comprises two *pisifera* alleles of an endogenous SHELL gene. In some embodiments, the seed or plant makes mature shells that are on average less than 2 mm thick.

Also provided is a cell or seed or plant comprising a heterologous expression cassette, the expression cassette comprising a promoter operably linked to a polynucleotide, which polynucleotide, when expressed in the seed or plant, reduces expression of a SHELL polypeptide in the seed or plant (compared to a control plant lacking the expression cassette), wherein reduced expression of the SHELL polypeptide results in reduced shell thickness of the future seeds produced by the plant.

In some embodiments, the polynucleotide comprises at least 20 contiguous nucleotides, or the complement thereof, of an endogenous nucleic acid encoding a SHELL polypeptide substantially (e.g., a least 80, 85, 90, 95, 97, 98, 99%) identical or identical to SEQ ID NO:8220, 8221, or 8222, such that expression of the polynucleotide inhibits expression of the endogenous SHELL gene. In some embodiments, the polynucleotide comprises a sequence at least 80% identical to at least 100 contiguous nucleotides, or the complement thereof, of an endogenous nucleic acid encoding a SHELL polypeptide substantially (e.g., a least 80, 85, 90, 95, 97, 98, 99%) identical or identical to SEQ ID NO:8220, 8221, or 8222, such that expression of the polynucleotide inhibits expression of the endogenous SHELL gene. In some embodiments, the polynucleotide encodes an siRNA, antisense polynucleotide, a microRNA, or a sense suppression nucleic acid, thereby suppressing expression of an endogenous SHELL gene. In some embodiments, the seed or plant makes mature shells that are on average less than 2 mm thick.

Also provided is a plant comprising a heterologous expression cassette, the expression cassette comprising a promoter operably linked to a polynucleotide encoding a polypeptide comprising a SHELL M, I, and K domain but lacks a functional C domain. In some embodiments, the polypeptide comprises an amino acid sequence substantially (e.g., a least 80, 85, 90, 95, 97, 98, 99%) identical or identical to the palm SHELL polypeptide. In some embodiments, the polypeptide comprises a non-functional C domain. In some embodiments, the plant is a palm plant. In some embodiments, the palm plant is in the *dura* background.

Also provided is a method of making a plant as described above or elsewhere herein, comprising introducing the expression cassette into a plant.

Also provided is a method of cultivating the plants described herein.

Other embodiments will be evident from reading the rest of the disclosure.

DEFINITIONS

A "shell phenotype" refers to the three fruit forms of *E. guineensis*—*dura, tenera* and *pisifera* caused by the presence or absence of the shell or the thickness of the shell.

A "polymorphic marker" refers to a genetic marker that distinguishes between two alleles.

A genomic region "corresponding to" a test sequence refers to a genomic DNA that aligns with the test sequence. It is generally expected that a plant genome will have only one genomic region (i.e., a locus represented by two alleles in a diploid plant) corresponding to the test sequence. To the extent more than one genomic region from a plant can be aligned to the test sequence, the "corresponding" genomic region is the genomic region with the highest percent of identical nucleotides. Sequence comparisons can be performed using any BLAST™ including BLAST 2.2 algorithm with default parameters, described in Altschul et al., *Nuc. Acids Res.* 25:3389 3402 (1977) and Altschul et al., *J. Mol. Biol.* 215:403 410 (1990), respectively.

As used herein, the terms "nucleic acid," "polynucleotide" and "oligonucleotide" refer to nucleic acid regions, nucleic acid segments, primers, probes, amplicons and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA.

A nucleic acid, polynucleotide or oligonucleotide can comprise, for example, phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases.

Optimal alignment of sequences for comparison may be conducted by the local homology algorithm of Smith and Waterman *Add. APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST™, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polypeptide sequences means that a polypeptide comprises a sequence that has at least 75% sequence identity. Alternatively, percent identity can be any integer from 75% to 100%. Exemplary embodiments include at least: 75%, 80%, 85%, 90%, 95%, or 99% compared to a reference sequence using the programs described herein; preferably BLAST™ using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

The term "promoter" or "regulatory element" refers to a region or sequence determinants located upstream or downstream from the start of transcription and which are involved in recognition and binding of RNA polymerase and other proteins to initiate transcription. Promoters need not be of plant origin, for example, promoters derived from plant viruses, such as the CaMV35S promoter, can be used.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A polynucleotide sequence is "heterologous to" an organism or a second polynucleotide sequence if it originates from a foreign species, or, if from the same species, is modified from its original form. For example, a heterologous promoter operably linked to a coding sequence refers to a promoter from a species different from that from which the coding sequence was derived, or, if from the same species, a promoter which is different from any naturally occurring allelic variants.

Tenera Allele Angola, Madagascar, Nigeria (371), Tanzania=SEQ ID NO:8226, Nigeria (Palm T128)=SEQ ID NO:8227. Nigeria (88)=SEQ ID NO:8228.

Figure 6:
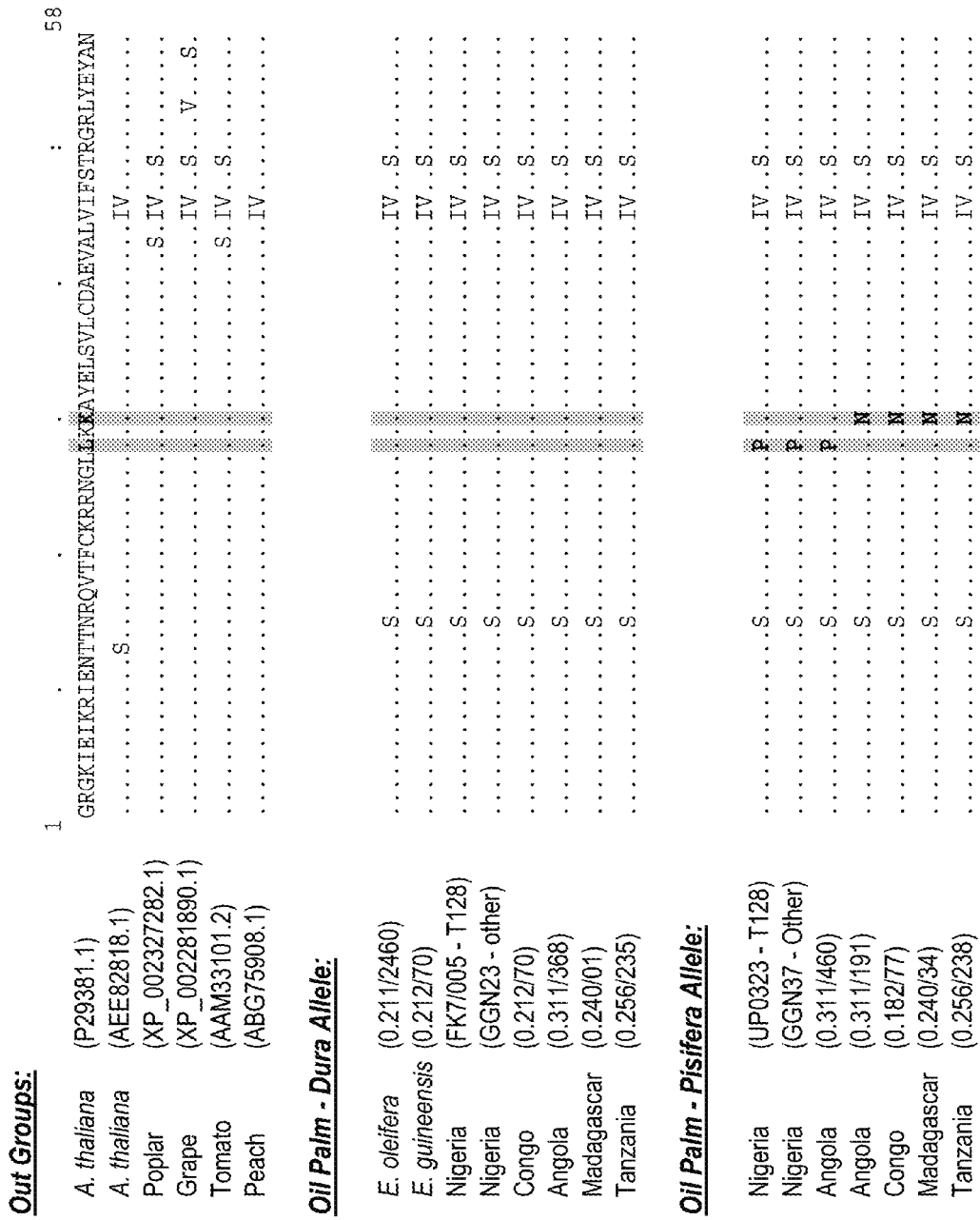

FIG. 6. Protein sequence of the MADS domain, amino acid substitutions in *pisifera* palms and expression of shell. a, Multiple sequence alignment of *Arabidopsis* SHP (P29381.1; SEQ ID NO:8229) and STK (AEE828 18.1; SEQ ID NO:8230) proteins, poplar predicted protein (XP_002327282.1; SEQ ID NO:8231), grape MADS-box protein 5 (XP_002281890.1; SEQ ID NO:8232), tomato TAGL1 (AAM33101.2; SEQ ID NO:8231) and peach SHATTERPROOF-like (ABG75908.1; SEQ ID NO:8233) (Out Groups), *E. oleifera, E. guineensis* and exemplars of Deli *dura* (Oil Palm—*Dura* Allele) (SEQ ID NO:8234), and exemplars of *pisifera* from T128—Nigerian and AVROS— Congo (Oil Palm—*Pisifera* Allele). The *pisifera* fruit form is caused by two disruptive SNPs (SEQ ID NOS:8235 and 8236) that affect a highly conserved amino acid motif in the MADS box DNA binding and dimerization domain. Sequence accession numbers (out group examples) or sample identifiers (oil palm examples) are in parentheses.

Figure 7:
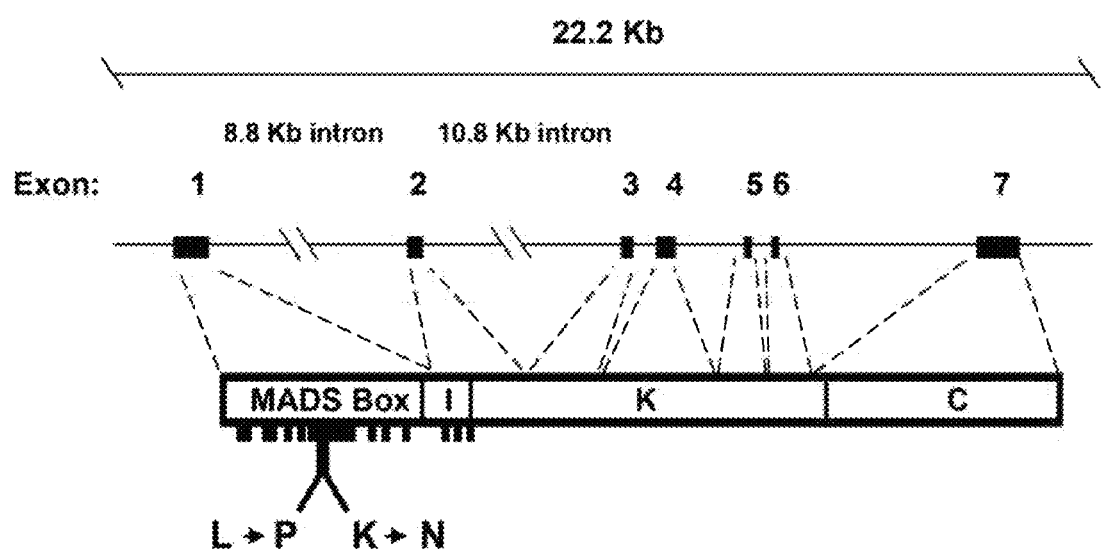

FIG. 7. SHELL gene model. Exons (boxes) and introns (horizontal lines) were validated by RNA-seq. A diagram of protein domains encoded by the indicated exons is provided below the gene diagram. MADS box, I, K and C domains of the SHELL protein are indicated. The locations of mutated amino acids (L to P and K to N) in the MADS box domain are highlighted. The location of conserved residues involved in DNA binding and/or MADS box protein homo- or heterodimerization are indicated by vertical marks below the MADS box and I domains.

DETAILED DESCRIPTION OF THE INVENTION

I. Introduction

The present disclosure describes the construction of a dense genetic map for a selfed *tenera* palm, designated T128 from MPOB's Nigerian germplasm collection. The position of the shell locus was determined on the genetic map. The markers located on the linkage group containing the shell gene were used to pull out the genome scaffolds generated from whole genome DNA sequencing of *pisifera* corresponding to the linkage group. The gene linked to the shell locus was subsequently identified in the genome scaffold. Disclosed herein, the gene responsible for fruit shell type is substantially similar to *Arabidopsis* SEEDSTICK (STK), also referred to as AGAMOUS-like 11 (AGL11), as well as to *Arabidopsis* SHATTERPROOF (SHP1), also referred to as AGAMOUS-like 1 (AGL1). For brevity, herein we refer to the shell gene as SHELL. Two independent mutations in the DNA binding domain of this type II MADS-box transcription factor gene were identified and validated in 336 individual oil palms, one occurring in the *pisifera* collected from Nigeria and the other occurring in the *pisifera* collected from Zaire. The genotype at either of these two positions explains 96.7% of the fruit shell phenotypes of the 336 sample population (148 *tenera*, 100 *pisifera*, 86 *dura* and 2 with unknown phenotypes). In total, the SHELL genotype was discordant with the fruit type phenotype in only 11 palms (3 *tenera*, 2 *pisifera* and 6 *dura*) of the 334 that had phenotypes. The 3.3% discordance rate is within the range of the rate of incorrect phenotyping or genotyping based on either questionable fruit type classification or collection of samples from unintended trees in the field, respectively (approximately 5%). This represents the first demonstration of a gene mutation explaining an important economic trait in oil palm. Furthermore, the findings provide a genetic explanation for the single gene heterosis characteristic of the fruit shell phenotype, and they have implications in oil palm breeding and commercial seed production.

A polymorphic marker closely linked to the shell gene character, or the identification of the shell gene itself and the use of a polymorphic marker located within the gene itself, is of significant commercial importance, as it can be used by seed producers as a quality control tool to i) reduce or eliminate *dura* or *pisifera* contamination of *tenera* seed or plantlets, and ii) positively identify *tenera* seeds or plantlets which are then selected as suitable planting material for commercial palm oil production. The identification of the shell gene or a marker genetically linked to shell trait is also of importance in breeding programmes. The marker or the alleles of the gene responsible for the trait can be used to separate the *dura, tenera* and *pisifera* plants in the nursery; the advantage here being that they could be planted separately based on shell phenotype. This is of interest as the *pisifera* palms usually show very vigorous vegetative growth, so in a trial consisting of all three types, distortion of results could occur due to intra-cross competition. Furthermore, separating out the *pisifera* palms and planting them in high density encourages male inflorescence and this facilitates pollen production which is used in breeding programmes (Jack et al. 1998). Accordingly, following detection of the presence or absence of *dura, pisifera*, or *tenera* SHELL genotype, or a linked marker as described below, a further step of: (1) reduction elimination of *dura* or *pisifera* contamination of *tenera* seed or plantlets, (2) positive identification of *tenera* seeds or plantlets which are then selected as suitable planting material for commercial palm oil production, or (3) separating *dura, tenera* and *pisifera* plants into two or more groups (e.g., plants predicted to be *tenera* in one group and plants predicted to be *dura* or *pisifera* in a second group; plants predicted to be *dura* in one group and plants predicted to be *tenera* or *pisifera* in a second group; plants predicted to be *pisifera* in one group and plants predicted to be *dura* or *tenera* in a second group, or separating into three groups: *dura, pisifera,* and *tenera*) with can be achieved.

Any marker that exists that is polymorphic between the parent *dura* and *pisifera* trees in a cross and is linked to the shell locus has the potential to serve as a molecular signal to identify *tenera* trees in a cross. For example, if a *dura* tree, which is homozygous for "T" (i.e., T/T) at a given SNP position near the shell locus is crossed with a *pisifera* tree that is homozygous for "A" (i.e., A/A) at the same SNP position, then one could genotype seeds of the cross, or one could genotype plantlets arising from seeds of the cross, at the SNP position to track and identify contaminant seeds or plantlets. Seeds that are determined to be heterozygous at the SNP position, (i.e., A/T) are very likely to be *tenera*, unless a recombination between the marker and the shell gene had occurred in the individual being genotyped. Similarly, seeds which are homozygous at the SNP position for "A" or "T", (i.e., A/A or T/T), are *pisifera* or *dura* contaminant trees respectively, and when these trees become sexually mature in several years, they will produce suboptimal fruit types. Additionally, seeds or plantlets which have a "C" or "G" in the SNP position, neither of which is present in paternal palm of the cross, are likely trees arising from a different pollen donor than the one intended in the cross, and therefore can be discarded as contaminant seeds or plantlets. Markers that are in closer proximity to the shell locus would have higher predictive accuracy than markers that are farther away from the shell locus, because the closer the marker is to the shell gene, the less likely a recombination could occur which would break the linkage between the marker and the shell gene. Consequently, polymorphic markers within the shell gene itself are expected to have the strongest predictive power, and analysis of multiple markers closely linked to or within the shell gene may be advantageous.

II. Determination of Shell Phenotype Based on Nucleic Acid Detection

In view of the discovery that the SHELL genotype segregates with the *tenera/pisifera/dura* shell phenotype, genotyping a plant or seed at the SHELL locus or at adjacent genomic regions can be used to predict the shell phenotype of a palm plant.

SEQ ID NO:8220 represents the predicted amino acid sequence of the N-terminal 181 amino acids of the protein expressed in oil palm of the *dura* fruit type. The endogenous protein includes additional C-terminal amino acids not included in SEQ ID NO:8220. In oil palm of the *dura* fruit type, the proteins derived from both alleles of the gene include a leucine (L) amino acid at the $28^{th}$ amino acid position and a lysine (K) amino acid at the $30^{th}$ amino acid position.

SEQ ID NO:8221 represents the predicted amino acid sequence of the N-terminal 18 amino acids of the protein expressed in oil palm of the *pisifera* fruit type that is derived from the Zaire line. The endogenous protein includes additional C-terminal amino acids not included in SEQ ID NO:8221. This polypeptide includes a leucine (L) amino acid at the $28^{th}$ amino acid position and an asparagine (N) amino acid at the $30^{th}$ amino acid position.

SEQ ID NO:8222 represents the predicted amino acid sequence of the N-terminal 181 amino acids of the protein expressed in oil palm of the *pisifera* fruit type that is derived from the Nigerian line. The endogenous protein includes additional C-terminal amino acids not included here. This polypeptide includes a proline (P) amino acid at the $28^{th}$ amino acid position and a lysine (K) at the $30^{th}$ amino acid position.

Oil palm trees of the *pisifera* fruit type are the result of one of at least three possibilities: i) both alleles coding for the SEQ ID NO:8221 protein sequence, ii) both alleles coding for the SEQ ID NO:8222 protein sequence, or iii) one allele coding for the SEQ ID NO:8221 protein sequence and the other allele coding for the SEQ ID NO:8222 protein sequence.

Oil palm trees of the *tenera* fruit type are the result of one of at least two possibilities: i) one allele coding for the SEQ ID NO:8220 protein sequence and the other allele coding for the SEQ ID NO:8221 protein sequence, or ii) one allele coding for the SEQ ID NO:8220 protein sequence and the other allele coding for the SEQ ID NO:8222 protein sequence.

It will be appreciated that SEQ ID NOS:8220, 8221, and 8222 are representative sequences and that different individual palms may have an amino acid sequence having one or more amino acid changes relative to SEQ ID NOS:8220, 8221, and 8222 due, for example, to natural variation.

One or more polymorphism(s) between *pisifera* and *dura* SHELL alleles can be used to determine the shell phenotype of a palm or other plant. For example, when the polymorphism is co-dominant (detectable independent of the other allele) then:

the presence of only a *dura* SHELL allele indicates that the plant has or will have a *dura* shell phenotype;

the presence of only a *pisifera* SHELL allele indicates that the plant has or will have a *pisifera* shell phenotype; and the presence of a *pisifera* SHELL allele and a *dura* SHELL allele indicates that the plant has or will have a *tenera* shell phenotype.

SEQ ID NO:922 and 923 represent SNPs (single nucleotide polymorphisms) corresponding to those within the SHELL gene sequence itself.

However, genomic regions adjacent to the SHELL gene are also useful to determining whether a palm plant will likely manifest a particular shell phenotype. Because of genetic linkage to the SHELL gene, polymorphisms adjacent to the SHELL locus are predictive of shell phenotype, albeit with reduced accuracy as a function of increased distance from the SHELL locus. SEQ ID NO:8218 provides an approximately 3.4 MB genomic region of the palm genome that comprises the SHELL gene. Table A provides a listing of more than 8200 SNPs identified within SEQ ID NO:8218. A small selection of the SNPs in Table A have been genetically mapped relative to the SHELL locus. Table A provides an estimated predictive value for each SNP provided based on the selection of markers mapped. Thus, as an example, SEQ ID NO:1 represents a SNP that is accurate in predicting shell phenotype 83% of the time. Said another way, using the SNP of SEQ ID NO:1 as a genetic marker, one can correctly predict shell phenotype of palm plants 83 out of 100 times. Thus, even at a significant physical distance from the SHELL locus on the palm chromosome, polymorphic markers allow for relatively accurate prediction of shell phenotype of plants. In some embodiments, the polymorphic marker is within 1, 10, 20, 50, 100, 200, 500, 1000 kb from the SHELL gene (e.g., the gene corresponding to SEQ ID NO:8219).

Accordingly, methods of detecting one or more polymorphic marker within a region of the palm genome corresponding to SEQ ID NO:8218 are provided. Such methods are useful for predicting shell phenotype of palm plants for example. While over 8200 specific polymorphisms are provided in Table A, it should be appreciated that the polymorphisms represented in Table A are merely an example of polymorphisms within the genomic region corresponding to SEQ ID NO:8218. Additional polymorphisms can be identified as desired and also be used to predict shell phenotype of a palm plant. Such additional polymorphisms are intended to be encompassed in the methods described herein. Moreover, it will be appreciated that SEQ ID NO:8218 is a representative sequence and that different individual palms may have a corresponding genomic region having one or more nucleotide changes relative to SEQ ID NO:8218 due, for example, to natural variation. As noted elsewhere herein, nevertheless, identifying the region of a genome corresponding to SEQ ID NO:8218 can be readily determined using alignment programs, etc.

The nucleic acid sequences provided herein were generated by nucleotide sequencing and on occasion, include one or more stretches of "N's." These stretches of N's represent gaps in assembly of sequences of an estimated size. The precise number of N's in a sequence is an estimate (for example, 100 N's may only represent 30 bases). N's can be any base, and are likely repetitive sequence in the genome.

Detecting specific polymorphic markers can be accomplished by methods known in the art for detecting sequences at polymorphic sites. For example, standard techniques for genotyping for the presence of SNPs and/or microsatellite markers can be used, such as fluorescence-based techniques (Chen, X. et al., Genome Res. 9(5): 492-98 (1999)), utilizing PCR, LCR, Nested PCR and other techniques for nucleic acid amplification. Specific commercial methodologies available for SNP genotyping include, but are not limited to, TaqMan™ genotyping assays and SNPlex platforms (Applied Biosystems), gel electrophoresis (Applied Biosystems), mass spectrometry (e.g., MassARRAY system from Sequenom), minisequencing methods, real-time PCR, BioPlex system (BioRad), CEQ and SNPstream systems (Beckman), array hybridization technology (e.g., Affymetrix GeneChip; Perlegen), BeadArray Technologies (e.g., Illumina GoldenGate and Infinium assays), array tag technology (e.g., Parallele), and endonuclease-based fluorescence hybridization technology (Invader, Third Wave). Some of the available array platforms, including Affymetrix SNP Array 6.0 and Illumina CNV370-Duo and IM BeadChips, include SNPs that tag certain copy number variants.

In certain embodiments, polymorphic markers are detected by sequencing technologies. Obtaining sequence information about an individual plant identifies particular nucleotides in the context of a sequence. For SNPs, sequence information about a single unique sequence site is sufficient to identify alleles at that particular SNP. For markers comprising more than one nucleotide, sequence information about the nucleotides of the individual that contain the polymorphic site identifies the alleles of the individual for the particular site.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have been developed, and such methods are also contemplated to be useful for obtaining sequence information of a plant, if desired. These include pyrosequencing technology (Ronaghi, M. et al. *Anal Biochem* 267:65-71 (1999); Ronaghi, et al., *Biotechniques* 25:876-878 (1998)), e.g. 454 pyrosequencing (Nyren, P., et al. *Anal Biochem* 208:171-175 (1993)), Illumina/Solexa sequencing technology (http://www.illumina.com; see also Strausberg, R L, et al *Drug Disc Today* 13:569-577 (2008)), and Supported Oligonucleotide Ligation and Detection Platform (SOLiD) technology (Applied Biosystems, http://www.appliedbiosystems.com); Strausberg, R L, et al *Drug Disc Today* 13:569-577 (2008).

Methods of polymorphism detection can be performed on any type of biological sample from the plant that contains nucleic acids (e.g., DNA, RNA). As one particular advantage of the methods is to predict the shell phenotype of young plants before cultivation in the field, in some embodiments, the samples are obtained from a plant that has been germinated less than 1, 2, 4, 6, months or less than 1, 2, 3, 4, or 5 years. In some embodiments, the plants are generated from i) a cross between *dura* and *pisifera* palms ii) the selfing of a *tenera* palm, iii) a cross between two plants having the *tenera* shell phenotype, iv) a cross between *dura* and *tenera* palms, and v) a cross between *tenera* and *pisifera* palms. Because such crosses are not 100% efficient, such crosses result in some percentage of seeds or plants that will not in the future produce seeds or plants with the *tenera* shell phenotype, (in case of i) and the observed number of *tenera* palms observed do not follow the expected Mendellian segregation (ii, iii & iv). By testing seeds or plants resulting from the attempted crosses, one can reduce or eliminate non-*tenera* contaminant seeds or plants from material planted for cultivation (optionally discarding those plants that are predicted to be *dura* and/or *pisifera*). Alternatively, one can identify and segregate plants based on their predicted shell genotype, allowing for selection and cultivation of fields of pure *pisifera* and *dura* trees, if desired, e.g., for later breeding purposes.

III. Transgenic Plants

As discussed above, the SHELL gene of palm has been discovered to control shell phenotype. Thus in some embodiments, plants having modulated expression of a SHELL polypeptide are provided. The more desirable shell phenotype (*tenera*, having a shell less than 2 mm thick) occurs naturally as a heterozygote of the between the *dura* and *pisifera* allele.

It has been discovered that *pisifera* SHELL alleles contain missense mutations in portions of the gene encoding the MADS box domain of the protein, which plays a role in transcription regulation. Thus, it is possible that the *tenera* phenotype results from a reduced level of SHELL protein compared to *dura* plants, which have two copies of the active protein. Accordingly, in some embodiments, plants having reduced level of active SHELL protein compared to a *dura* plant are provided. Such plants can be generated, for example, using gene inhibition technology, including but not limited to siRNA technology, to reduce, but not eliminate, endogenous SHELL gene expression of an active SHELL protein (e.g., in a *dura* or *tenera* background).

Alternatively, a heterologous expression cassette (i.e., a transgene) can be introduced into a *pisifera* background where the expression cassette controls expression of SHELL at a reduced level compared to the native SHELL promoter. This can be achieved, for example, by operably linking a mutated SHELL promoter to a polynucleotide encoding a SHELL polypeptide, thereby weakening the "strength" of the promoter, or by operably linking a heterologous promoter that is weaker than the native SHELL promoter to a polynucleotide encoding a SHELL polypeptide.

Alternatively, it is possible that the *tenera* phenotype results from a mechanism involving the protein:protein interaction of non-DNA binding *pisifera* types of SHELL proteins with fully functional types of SHELL (homodimers) or other MADS-box family members (heterodimers). Thus, in some embodiments, plants that heterologously express a SHELL polypeptide with a functional M, I, and K domain and a non-function C-(MADsbox) domain are provided. M, 1, K, and C domains are described in, e.g., Gramzow and Theissen, 2010 *Genome Biology* 11: 214-224 and the corresponding domains can be identified in the palm sequences described herein. By expressing such a protein having active protein:protein interaction domains but a non-functional DNA binding domain, proteins that interact with the modified SHELL protein will be removed from biological action, thereby resulting in a reduced shell thickness. Thus, for example, one can express either of the *pisifera* alleles described herein under control of a heterologous promoter in the plant (e.g., a palm plant, e.g., a *dura* background), thereby resulting in the reduced shell thickness.

A. Inhibition or Suppression of Gene Expression

The invention provides methods for controlling shell trait in a palm (e.g., oil palm, coconut, or date palm) or other plant by reducing expression of an endogenous nucleic acid molecule encoding a SHELL polypeptide. For example, in a transgenic plant, a nucleic acid molecule, or antisense, siRNA, microRNA, or dsRNA constructs thereof, targeting a SHELL gene product, or fragment thereof, or a SHELL mRNA, or fragment thereof can be operatively linked to an exogenous regulatory element, wherein expression of the construct suppresses endogenous SHELL expression.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the protein of interest, see, e.g., Sheehy et al., *Proc. Nat. Acad. Sci. USA*, 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of a SHELL-encoding sequence can be useful for producing a plant in which SHELL expression is suppressed. The vectors of the present invention can be designed such that the inhibitory effect applies to other proteins within a family of genes exhibiting homology or substantial homology to the target gene, or alternatively such that other family members are not substantially inhibited.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. In some embodiments, a sequence of at least, e.g., 15, 20, 25 30, 50, 100, 200, or more continuous nucleotides (up to mRNA full length) substantially identical to an endogenous SHELL mRNA, or a complement thereof, can be used.

Catalytic RNA molecules or ribozymes can also be used to inhibit expression of SHELL genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiforum* mottle virus and subterranean clover mottle virus. The design and use of target RNA-specific ribozymes is described in Haseloff et al. *Nature*, 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. In some embodiments, the level of identity is more than about 80% or about 95%. As with antisense regulation, the effect can apply to any other proteins within a similar family of genes exhibiting homology or substantial homology and thus which area of the endogenous gene is targeted will depend whether one wished to inhibit, or avoid inhibition, of other gene family members.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed by way of RNA interference (RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. The resulting plants may then be screened for a phenotype associated with the target protein and/or by monitoring steady-state RNA levels for transcripts encoding the protein. Although the genes used for RNAi need not be completely identical to the target gene, they may be at least 70%, 80%. 90%, 95% or more identical to the target gene sequence. See, e.g., U.S.

Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

One of skill in the art will recognize that using technology based on specific nucleotide sequences (e.g., antisense or sense suppression, siRNA, microRNA technology, etc.), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Yet another way to suppress expression of an endogenous plant gene is by recombinant expression of a microRNA that suppresses a target (e.g., a SHELL gene). Artificial microRNAs are single-stranded RNAs (e.g., between 18-25 mers, generally 21 mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

B. Use of Nucleic Acids of the Invention to Enhance Gene Expression

Nucleic acid sequences encoding all or an active part of a SHELL polypeptide (including but not limited to polypeptides substantially identical to SEQ ID NO:8220, 8221, or 8222, or SHELL polypeptides having a functional M, 1, and K domain and a non-function C, which when expressed control shell thickness) can be used to prepare expression cassettes that enhance, or increase SHELL gene expression. Where overexpression of a gene is desired, the desired SHELL gene from a different species may be used to decrease potential sense suppression effects.

Any of a number of means well known in the art can be used to increase SHELL activity in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, a SHELL gene can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

III. Preparation of Recombinant Vectors

In some embodiments, to use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention can optionally comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

SHELL nucleic acid operably linked to a promoter is provided that, in some embodiments, is capable of driving the transcription of the SHELL coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. In some embodiments, as discussed above, desired promoters are identified by analyzing the 5' sequences of a genomic clone corresponding to a SHELL gene as described here.

V. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Various palm transformation methods have been described. See, e.g., Masani and Parveez, *Electronic Journal of Biotechnology* Vol. 11 No. 3, Jul. 15, 2008; Chowdury et al., *Plant Cell Reports*, Volume 16, Number 5, 277-281 (1997).

Microinjection techniques are known in the art and well described in the scientific and patent literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells that are derived from any transformation technique can be cultured to regenerate a whole plant that possesses the transformed genotype and thus the desired phenotype. Such regeneration techniques rely on manipulation of certain phytohormones in a tissue culture growth medium, optionally relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glcine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solaum, Sorghum, Trigonella, Triticum, Vitis, Vigna, and, Zea*. Plants having a shell, and thus those that have use in the present invention, include but are not limited to dicotyledons and monocotyledons including but not limited to palm.

EXAMPLES

The following examples are offered to illustrate, but not to limit the claimed invention.

i. Example 1

Plant Materials, DNA Extraction and Restriction Enzyme Digestion

The mapping family used for generating the genetic linkage map was derived from the selfing of the high iodine value (IV) *tenera* palm, T128, from MPOB's Nigerian germplasm collection (Rajanaidu, 1990). Controlled self-pollination was used to generate the mapping family. A total of 241 palms were originally planted at several locations in Malaysia, including the MPOB-UKM Research Station at Bangi, Selangor, Ulu Paka Research Station at Terengganu, Keratong Research Station at Pahang, Lahad Datu Research Station at Sabah, United Plantations, Teluk Intan, Perak and FELDA Research Station at Jerantut, Pahang. Of the 241 palms, 240 were still available for both marker and phenotype analysis.

Unopened leaf samples (spear leaf) were collected from individual palms and immediately frozen under liquid nitrogen and then stored at −80° C. until DNA preparation. DNA from the leaf samples was extracted and purified using the method described by Doyle and Doyle (1990).

Standard RFLP analysis was performed as described by Singh et al., 2009. The RFLP probes used in this study were complementary DNA (cDNA) clones obtained from various cDNA libraries (young etiolated seedling, mesocarp, kernel and root) constructed previously as described by Cheah et al. (1996). cDNA clones from a subtracted flower library (Cheah and Rajinder, 1998) were also used to screen the mapping population.

The cDNA clones were picked at random from the various libraries. Plasmid DNA was prepared from individual clones by using column purification, with Qiagen-tip 20 (Qiagen) as described by the manufacturer. The concentration of the prepared plasmids was determined by using ethidium bromide plates (Sambrook et al. 1989).

The presence of DNA insert was examined by restriction digestion of 1 ug plasmid DNA with 10 U of the appropriate restriction enzyme for 3 hours, to release the insert DNA. One fifth (⅕) volume of loading buffer, FOG, was added to the digestion mix and the fragments were separated by electrophoresis through a 1.5% agarose gel. cDNA clones with insert size larger than 500 base-pairs (bp) were selected to screen for their ability to detect RFLP in the mapping population.

Probes for mapping were derived from the selected plasmids as polymerase chain reaction (PCR) amplified DNA fragments. Bacterial clones containing selected probes were maintained as frozen glycerol stocks at −80° C.

The DNA probes were labeled for RFLP analysis as described by Singh et al., 2009.

ii. Example 2

Simple Sequence Repeat (SSR) Analysis and SNP Analysis

SSR analysis was carried out essentially as described by Singh et al., 2009. The SSR primers were sourced as follows: i) A SSR enriched library described by Singh et al., 2007, ii) the published microsatellite primer pairs (Billotte et al., 2005) were also tested on the mapping populations, and iii) SSR primers derived from MPOB's in-house expressed sequence tag (EST) collection and genomic sequences were also used in map construction.

The OPSNP3 SNP set comprising 4,451 SNPs was interrogated using the Illumina iSelect Infinium 11 assay. The automatic allele calling for each SNP locus was accomplished with the GenCall software (Illumina San Diego, Calif.). The Genome Studio software (version 2010.3) was used to analyze the SNP genotyping data.

The individual RFLP, SSR and SNP loci were scored as co-dominant markers and, for this selfed cross, loci segregating in the 1:2:1 ratios were scored. Some RFLP probes and SSR primers revealed complex patterns, for which the alleles were difficult to determine. For such cases, segregating bands were individually scored as being absent or present.

Table 2 below illustrates the 2 different types of segregation patterns observed in the mapping family from RFLP, SSR, SNP and AFLP markers.

iii.

TABLE 2 iii. Illustration of the two different types of segregation patterns observed in the mapping family from RFLP, SSR, SNP and AFLP markers.

| | Parent phenotype | Progeny phenotype | Phenotype ratio in the progeny |
|---|---|---|---|
| Loci defined by a single band | | | 3:1 |
| Loci defined by allelic bands | 2 alleles | | 1:2:1 |

Example 3

Determining and Evaluating Fruit Form in the Mapping Family

In the present study, the identification of the shell gene was of interest. The monogenic trait scored was the fruit form. The trait was evaluated on ripened bunches in the field. All 240 F1 progeny, derived by controlled self-pollination of the Nigerian *tenera* accession T128 and grown over two decades in plantations throughout Malaysia, were scored for fruit form phenotype (Rajanaidu et al., 1989). Oil palm trees were grown to maturity in open plantations, making accurate phenotyping of fruit form for some samples difficult due to variation in fertility, yield and environment. Several fruits were harvested from each palm, and shell thickness and fruit form was determined using established criteria.

In order to determine the fruit form, the individual fruits were cut into two equal halves using a sharp knife. A visual observation was made of the shell and classified according to Corley & Tinker, 2003 and Hartley 1988, as follows:

*dura*: thick shelled (2-8 mm), with no fibre ring

*tenera*: thin shelled (0.5-3 mm), with a fibre ring surrounding the shell

*pisifera*: shell-less

In most cases, the presence of the fibre ring was sufficient to distinguish between *dura* and *tenera* fruit forms. An experienced oil palm breeder assisted with the evaluation of the traits.

To assess the accuracy of the fruit form phenotypic data used in the study, we reviewed 460 phenotype calls which were made between 2003 and 2012. In this period, up to three independent attempts were made to visually determine the fruit form phenotypes of 339 palms, 240 of which were from the T-128 selfed population used to map SHELL, and 99 from a different population for which re-phenotyping data were available. In the data, ambiguous calls were made 26 times (or 5.7% of total phenotype determinations) where breeders were unsure of the fruit form phenotype.

The segregation data for the phenotypic characters observed in the mapping family is listed in Table 3.

iv.

TABLE 3 iv. Analysis of palms for fruit form

| | | Fruit Type | | | | | | |
|---|---|---|---|---|---|---|---|---|
| Number of palms | Expected Ratio | | | Observed Number | | | | |
| genotyped[#] | Dura | Tenera | Pisifera | Dura | Tenera | Pisifera | Total[#] | $\chi^2$ |
| 240 | 1 | 2 | 1 | 68 | 124 | 46 | 238 | 1.63 |

[#]There was a discrepancy between the total number of palms genotyped and that observed for fruit type because two palms could not be phenotyped accurately..

The shell gene trait in the mapping family used in this study met the expected Mendelian ratio (1:2:1 for the *dura, tenera* and *pisifera* fruit forms, respectively). The other three reports to date on mapping of the shell gene locus (Mayes et al., 1997; Moretszohn et al., 2000 and Bilotte et al., 2005) did not indicate if the trait met the expected Mendelian ratio in the mapping families employed in their study.

v. Example 4

Map Construction and Evaluation of Monogenic Traits

In constructing the genetic map, apart from the 200 RFLP and SSR markers, the progeny consisting of 240 palms were genotyped for 4,451 SNP markers derived from the oil palm genome sequence by the Infinium iSelect® Assay (Illumina). Map construction for the 240 available progeny palms obtained from self-pollination of the Nigerian *tenera* palm T128 was carried out by using the Joinmap ver. 4.0 computer programme (Ooijen, 2006). The oil palm is an out-breeding species, and as such, a high degree of heterozygosity can be expected in its genome. The progeny palms from the selfed cross can thus be expected to behave like an $F_2$ population.

However, in map construction, it is useful to first determine the "phases" of the markers, either in coupling or repulsion. For this reason, two sets of the genotype data were then created, whereby one set is the converse of the other to account for phase differences in the T128 selfed F2 population. Markers that exhibited severe distortion (p<0.0001) and markers having more than 10% missing data were excluded. Both sets of genotype data were then grouped at a recombination frequency of ≤0.2. Eighteen nodes were selected to create 18 initial groups for calculating the linkage groups.

The linkages were calculated and loci ordered based on the maximum likelihood algorithm. None of the markers showed severe distortion (p<0.0001). The few distorted markers observed were significant at p<0.05-0.1. These markers were removed from further analysis when necessary. Markers exhibiting nearest neighbour stress (N.N, Stress) value >2 (cM) were identified and excluded from the analysis. Markers contributing to insufficient linkages were also determined and removed. The T128 co-dominant map constructed consisted of 16 groups. The number of linkage groups observed matched the haploid chromosome number of oil palm (Maria et al. 1995).

Figure 1:
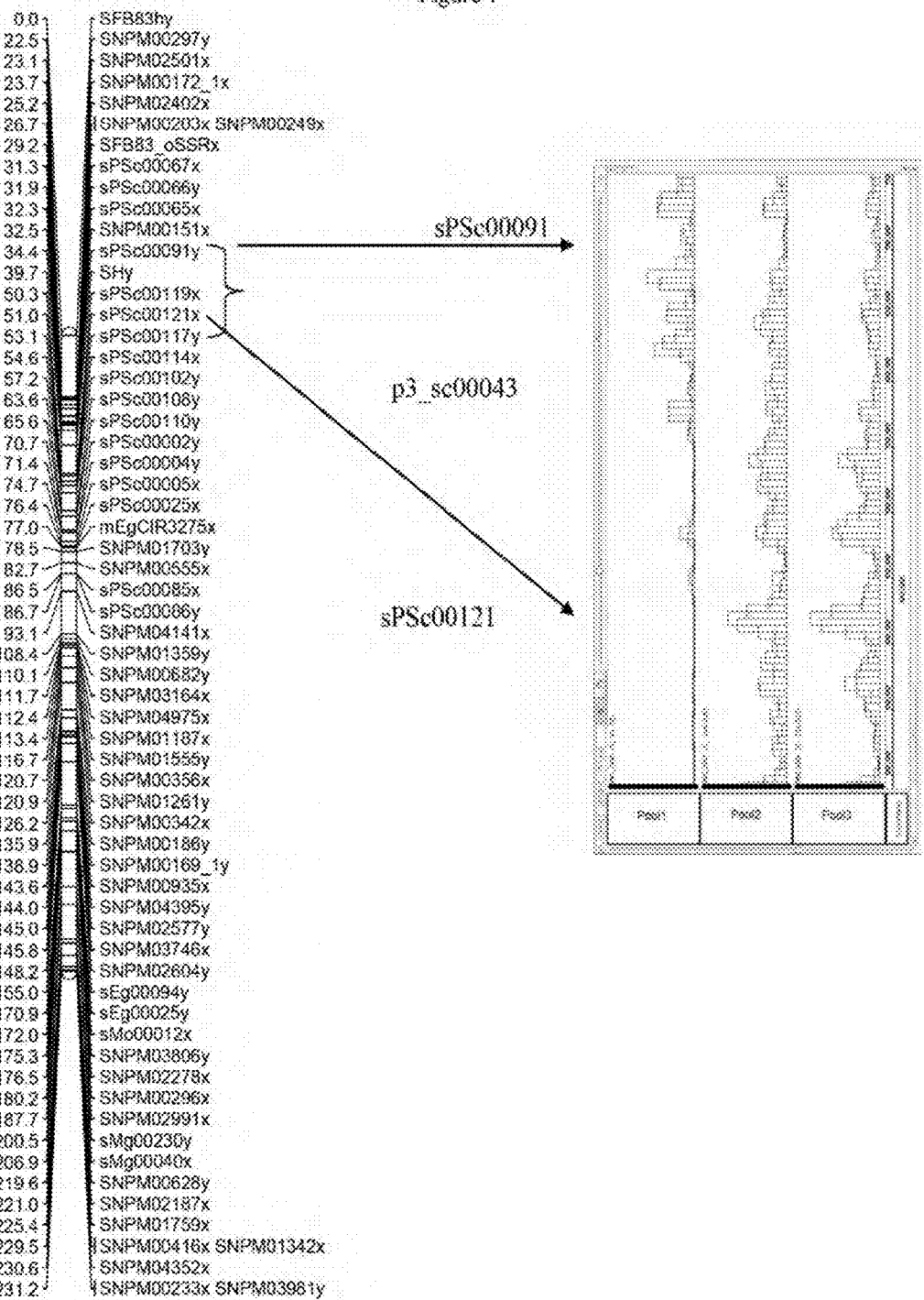
FIG. 1. Genomic scaffolds corresponding to linkage group 7 and resulting homozygosity profile. Based on genetic mapping, the Shell gene (Sh) was placed at 39.7 cM on linkage group 7. Once markers from this region were compared to the reference genomic sequence for *Pisifera*, the gene was localized to scaffold 43 (SEQ ID NO:8218). SNP frequency was greatly reduced in this region for AVROS palms with *Pisifera* fruit type (pool1) as compared to Nigerian palms with *Pisifera* fruit (pool2), and to *Dura* and *Tenera* palms (pool3). Because it is known that in the AVROS line the *Pisifera* trait came from a single progenitor, this homozygous region is indicative of carrying the Shell gene.

After construction of the consensus map, shell was placed on linkage group 7 (FIG. 1) and comparison of the linkage group to that published by Billotte et al., (2005) indicated shell was located within the expected region. More importantly the shell gene was flanked by two SSR markers, sPSc00119 (about 10 cM) on one side, and sPSc00091 (about 5 cM) on the other side.

The SHELL gene had been previously mapped 4.7 cM and 9.8 cM away from the closest molecular marker (Billotte et al., 2005; Mayes et al., 1997; Moretzsohn et al. 2000) but has proven extremely challenging to identify given the large genome, long generation times and difficulty of phenotyping in experimental populations of oil palm, which are widely distributed among different plantations. To help with identification of the shell gene, great care was taken to phenotype the monogenic trait carefully as described above. Subsequently we took advantage of the oil palm genome sequence to identify the shell gene.

Example 5

Whole Genome Sequencing and Assembly, Comparison of Linkage Group with Genome Scaffolds, Homozygosity Mapping and the Evaluation of Candidate Genes An AVROS *Pisifera* palm was sequenced to high coverage on the 454 XL next generation sequencing platform (454/Roche). Sequence reads were generated from DNA fragment libraries and from a complex series of linker libraries (or jumping libraries) where read ends span fragment sizes ranging from 0.75 kb to >30 kb. Sequence reads were assembled with the Newbler assembler (Roche 454, Bradford, Conn.) producing a reference sequence of the oil palm genome. Scaffolds from the reference assembly containing markers genetically mapped in the shell interval were identified. A BAC physical map was constructed from a 10 fold BAC library constructed from the same AVROS *Pisifera* used to generate the reference sequence. BAC end sequences were also generated from each BAC in the library using standard Sanger sequencing on the 3730 sequencing platform (Life Technologies). BAC end sequences were assembled into the reference genome with the Newbler assembler. A minimum tiling path of BAC clones spanning the SHELL interval was selected, and BAC clones in the tiling path were sequenced in pools to high coverage with 454 XL technology. The reference genome was reassembled including the original 454 whole genome shotgun sequence data, the BAC pool sequence data and all BAC end sequences. Improved scaffold coverage and scaffold length spanning the shell interval was produced. Two pedigrees were used in homozygosity mapping studies. A total of 43 individual AVROS *pisifera* palms (originating from Zaire, Africa) were the first pedigree used. Additionally, a total of 14 of the AVROS *Pisifera* palms were independently sequenced while the DNA from the remaining 29 palms were pooled together for deep sequencing (Pool 1). The second pedigree was the progeny palms from the selfing of the Nigerian *tenera* palm T128. The DNA of thirty (30) *pisifera* palms from the Nigerian selfed palm were also pooled and sequenced (Pool 2). In Pool 3, DNA from 17 Nigerian *dura* palms and 20 Nigerian *tenera* palms were pooled and sequenced. Whole genome shotgun sequence data was generated on the HISEQ 2000 (Illumina). Individual trees and pools of trees were sequenced to 20 and 40 fold raw sequence coverage respectively. Individual reads from each tree and from each pool were read mapped to sequence scaffolds form the reference genome assembly described above.

The SNP markers on linkage group 7 were subsequently mapped by sequence similarity to a 3.4 Mb assembly Scaffold 43 (p3-sc00043). The scaffolds corresponding to linkage group 7 containing the SHELL gene is presented in FIG. 1. The order of the markers on the linkage group corresponded to the physical order of the markers on the scaffolds, providing confidence on the genetic map constructed. We predicted that the shell gene is most likely contained in Scaffold 43 (p3_sc00043), the scaffold containing the highest probability interval. A tiling path of BAC contigs corresponding to Scaffold 43 was selected from a high-information content physical map of *pisifera* and sequenced. Additional 50 SNP assays were designed from an improved assembly corresponding to Scaffold 43.

Thirty additional SNP markers were also designed from the scaffolds p3-sc00191, p3-sc00203 and p3-sc02216, which were also associated with linkage Group 7. These 80

SNP markers (designated as SNPE) were also genotyped on the 240 palms from the Nigerian T128 selfed population using the Sequenom MassArray® iPlex platform. Of the 80 SNPE SNP markers tested, 63 (78%) were polymorphic. The additional 63 SNP genotypes were incorporated into the map as above giving a final co-dominant genetic linkage map consisting of 828 markers [722 SNP (inclusive of SNPE), 103 SSR, 2 RFLP markers and shell in 16 linkage groups (FIG. 2).

Shell remained in linkage group 7 (FIG. 2), together with the 63 SNPE markers developed from the selected scaffolds. The final size of linkage group 7 is 172.2 cM with an average of 1.2 cM between two adjacent markers.

Figure 2:
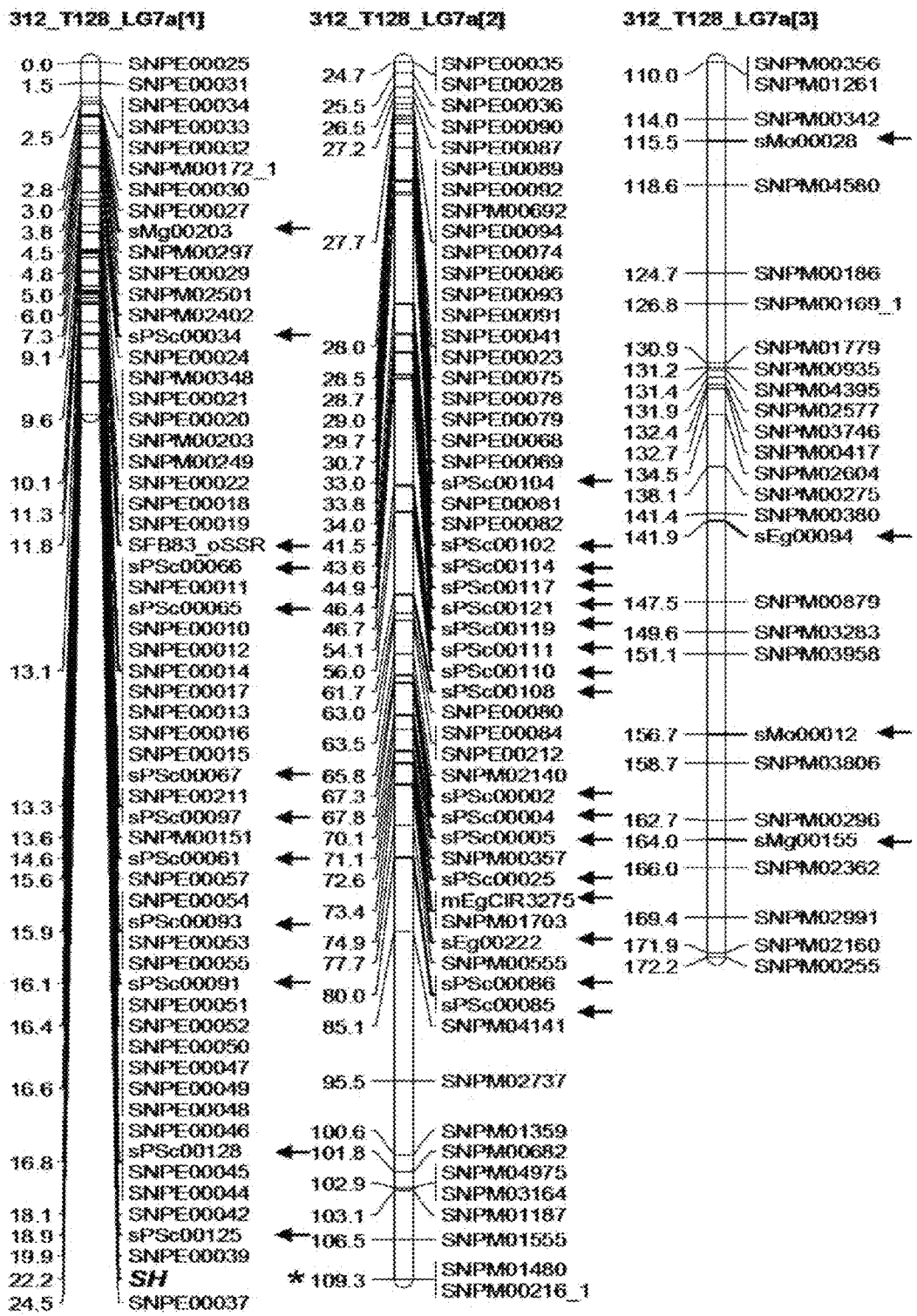
FIG. 2. Linkage Group 7 containing SHELL. A map of the SHELL chromosome (Linkage Group 7) derived from the T128 population. Arrows denote the SSR markers. The SHELL gene is marked by (SH and an asterisk). All other markers are SNP markers.

The shell gene locus was successfully mapped in Group 7, this time flanked by two SNP markers, namely SNPE00039, SNPE00037 (about 3 cM) on either side (FIG. 2). Table 4 shows that the predictability of the markers for the trait in the mapping family was about 95% for both markers. In a review of single marker data, recombinant breakpoints were identified indicating the gene lay in a 450 kb interval in Scaffold 43.

TABLE 4

Linkage of SNP markers to the shell gene locus in the mapping family

| Marker | No. of palms with genotype & phenotype | No. palms matching expected profile | No. of recombinants | Position in Linkage Group 7 | % predict-ability |
|---|---|---|---|---|---|
| SNPE00047 | 234 | 217 | 17 | 16.60 | 92.74 |
| SNPE00048 | 234 | 217 | 17 | 16.60 | 92.74 |
| SNPE00049 | 234 | 217 | 17 | 16.60 | 92.74 |
| SNPE00044 | 235 | 219 | 16 | 16.85 | 93.19 |
| SNPE00046 | 235 | 219 | 16 | 16.85 | 93.19 |
| SNPE00045 | 234 | 218 | 16 | 16.85 | 93.16 |
| sPSc00128 | 234 | 217 | 17 | 16.85 | 92.74 |
| SNPE00042 | 234 | 222 | 12 | 18.11 | 94.87 |
| sPSc00125 | 233 | 216 | 17 | 18.86 | 92.70 |
| SNPE00039 | 235 | 224 | 11 | 19.87 | 95.32 |
| Shell Locus | | | | | |
| SNPE00037 | 235 | 224 | 11 | 24.46 | 95.32 |
| SNPE00035 | 235 | 224 | 11 | 24.71 | 95.32 |
| SNPE00028 | 235 | 223 | 12 | 24.71 | 94.89 |
| SNPE00036 | 233 | 220 | 13 | 25.46 | 94.42 |
| SNPE00090 | 233 | 216 | 17 | 26.47 | 92.70 |
| SNPE00087 | 233 | 216 | 17 | 27.22 | 92.70 |

Figure 3:
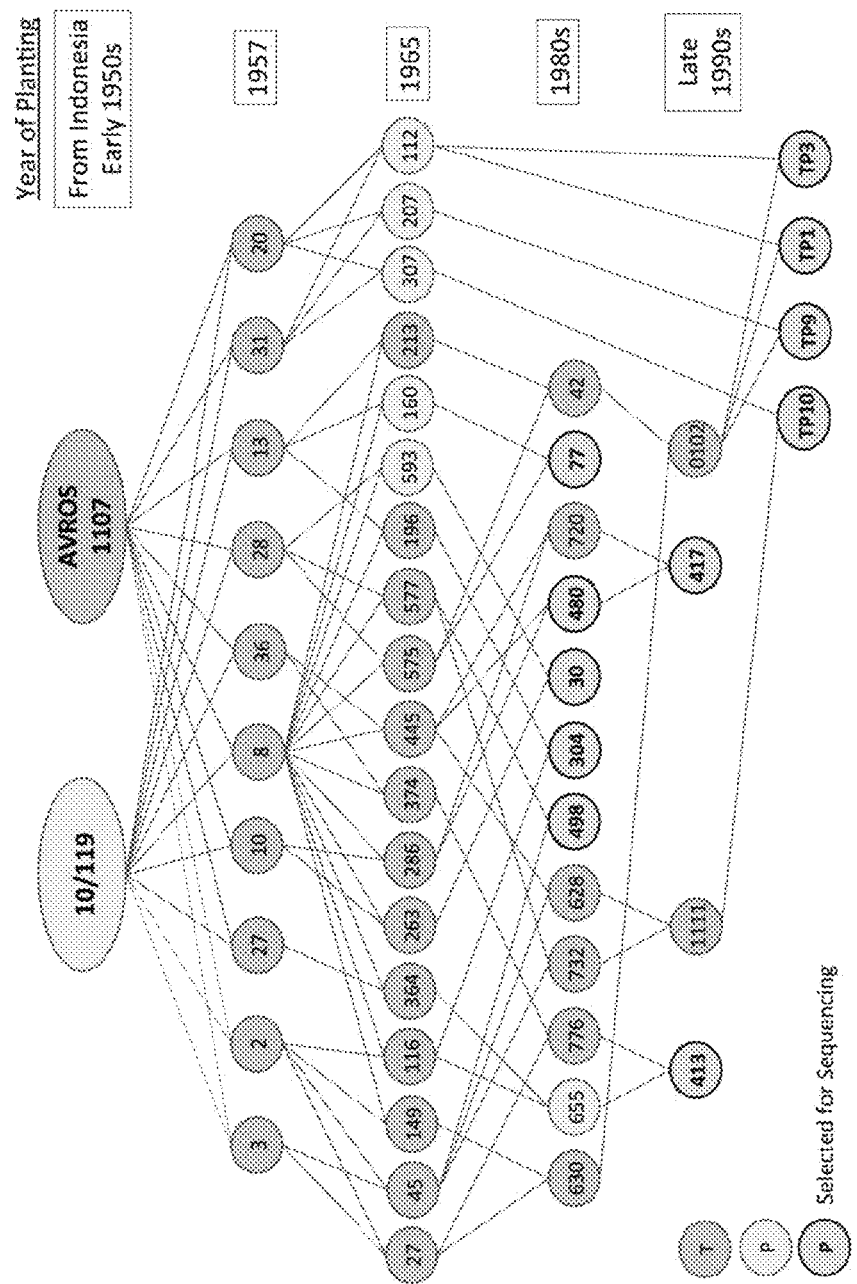
FIG. 3. The AVROS pedigree for homozygosity mapping. Palms heterozygous (*tenera:* 1107, 3, 2, 27, 10, 8, 36, 28, 13, 31, 20, 27, 45, 149, 116, 364, 263, 286, 374, 445, 575, 577, 196, 213, 630, 776, 732, 628, 720, 42, 1111, 0102) and homozygous (*pisifera:* 10/119, 593, 160, 307, 207, 112, 655, 498, 304, 30, 480, 77, 413, 417, TP10, TP9, TP1, TP3) for the SHELL gene are indicated, linked to parents and progeny planted over 5 decades. Eleven of the individually sequenced palms are: 498, 304, 30, 480, 77, 413, 417, TP10, TP9, TP1, TP3. Three additional *pisifera* palms from this extended pedigree were also individually sequenced (not shown) while the remaining *pisifera* palms were sequenced as a pool.
Figure 4:
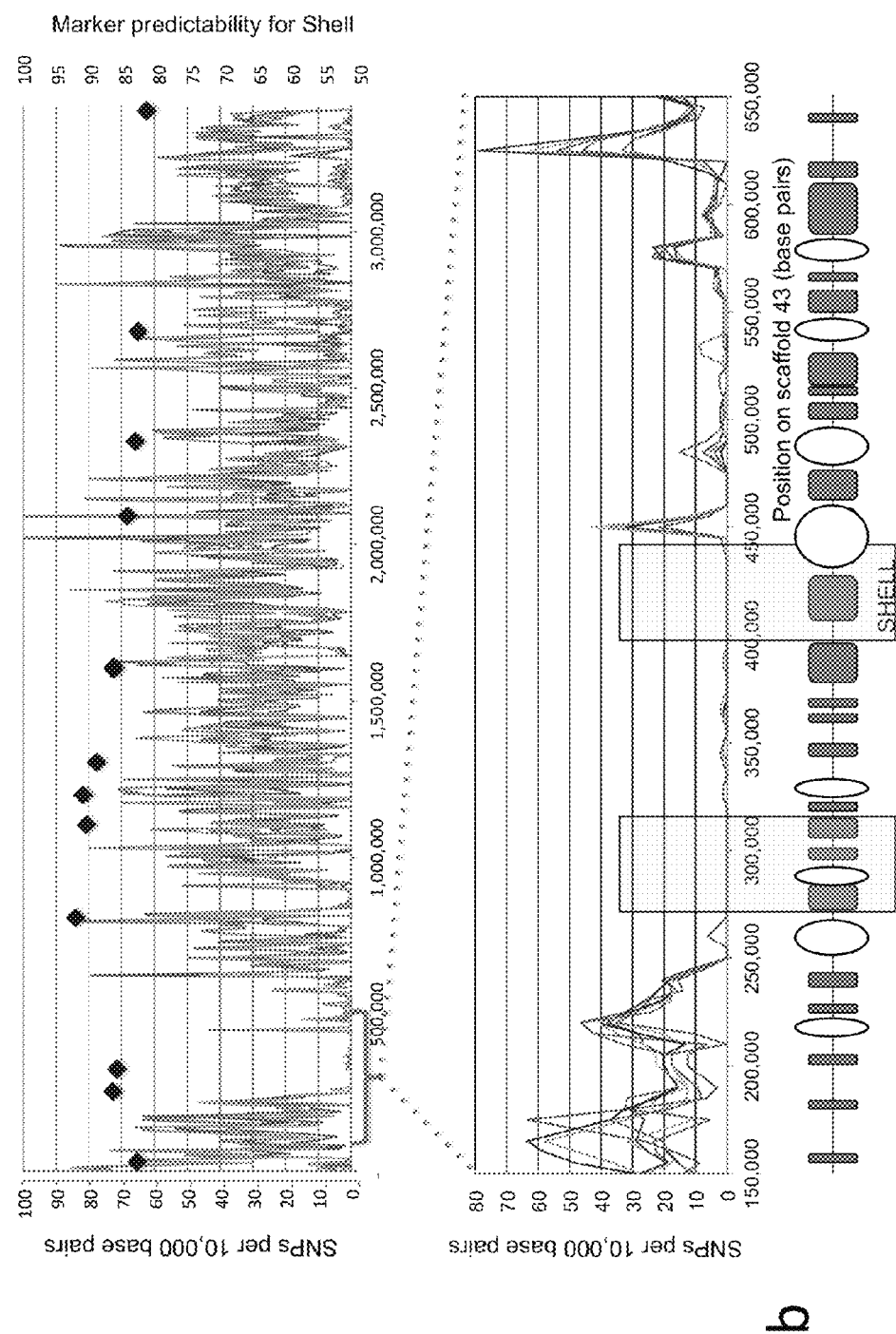
FIG. 4. Homozygosity mapping of the shell trait in oil palm. a, The SHELL locus was mapped onto scaffold p3-sc00043 (3.4 Mb) and SNP density was determined in 14 individual and 29 pooled *pisifera* palms from the AVROS pedigree and plotted along the scaffold (upper panel). Markers surrounding the SHELL gene are plotted against the % of *pisifera* palms with the SNP haplotype in the Nigerian T128 F1 mapping population. The SHELL gene was mapped to between flanking markers, (denoted by diamonds) at 400 Kb and 1 Mb. A local diversity minima of 200 Kb was found within this interval (inset). b, The local diversity minima contained 5 homozygous genes (boxes), only one of which was located between the flanking markers (SHELL). Unshaded ovals denote repetitive elements.

Next, we employed homozygosity mapping using the AVROS pedigree (FIG. 3) and whole genome re-sequencing. In this technique, candidate genes appear as regions with low diversity in homozygous inbred individuals (Gschwend et al., 1996; Lander and Botstein, 1987). Fourteen individual *pisifera* palm genomes were sequenced at 20× genomic coverage (Illumina HISEQ 2000) and 29 additional *pisifera* palms were sequenced as a pool at 40× coverage (pool 1). Individual reads were mapped to sequence scaffolds from the *pisifera* reference genome assembly, and highest probability SNPs were located on scaffold 43 of the *pisifera* Build 3 (p3-sc00043). In each of the 14 genome sequences, SNPs were summed over 10 Kb windows along the scaffold and plotted against map location. This scaffold was computationally annotated for genes by comparing to public databases for the *A. thaliana* and rice genomes using the NCBI BLAST™ similarity searching tool. The genes with the highest homozygosity within the predicted interval from the genetic map were screened for putative function and for nucleic and amino acid changes between the *pisifera* and *dura* lines, as well as for amino acid differences in other species. SNPs were called throughout the genome, and those in Scaffold 43 were scored. The resulting homozygosity plot had a local minima of 200 kb (centered around 400,000 bp in p3-sc00043, FIG. 4A). This 200 kb region contained about 30 annotated genes, only five of which were fully homozygous, and only one of which lay in the genetic interval containing SHELL (FIG. 4B). This gene encodes an ortholog of *Arabidopsis* SHPT, SHP2 and STK known to impact fruit development (Ferrandiz et al., 2000; Liljegren et al., 2000).

*Arabidopsis* SlHP1, SHP2 and FRUITFULL (FUL), for example, are Type II MADS-box proteins of the MIKC$^c$ class, and form a network of transcription factors that controls differentiation of the endocarp. In Brassicaceae, the endocarp comprises lignified cells that separate the valve from the replum and control shattering of the seedpod (Dinneny and Yanofsky, 2005). Failure to differentiate the endocarp in shp1 shp2 double mutants in *Arabidopsis* results in indehiscent fruit pods that do not shatter (Liljegren et al. 2000; Pinyopich et al., 2003), while mesophyll cells in ful carpels become lignified due to ectopic SP expression, and burst randomly when full of seed (Dinneny and Yanofsky, 2005; Gu et al., 1998). Interestingly, the ortholog of SHP in tomato controls fleshy fruit expansion in the endocarp (Vrebalov et al., 2009) while homologs of FUL and SHP have been implicated in split-pit formation in peaches, which are also drupes (Tani et al., 2007). SHP proteins bind to DNA as homodimers or as heterodimers (Huang et al., 1996), and the highly conserved MADS domain is involved in both DNA binding and in dimerization (Immink et al., 2010).

Figure 5:
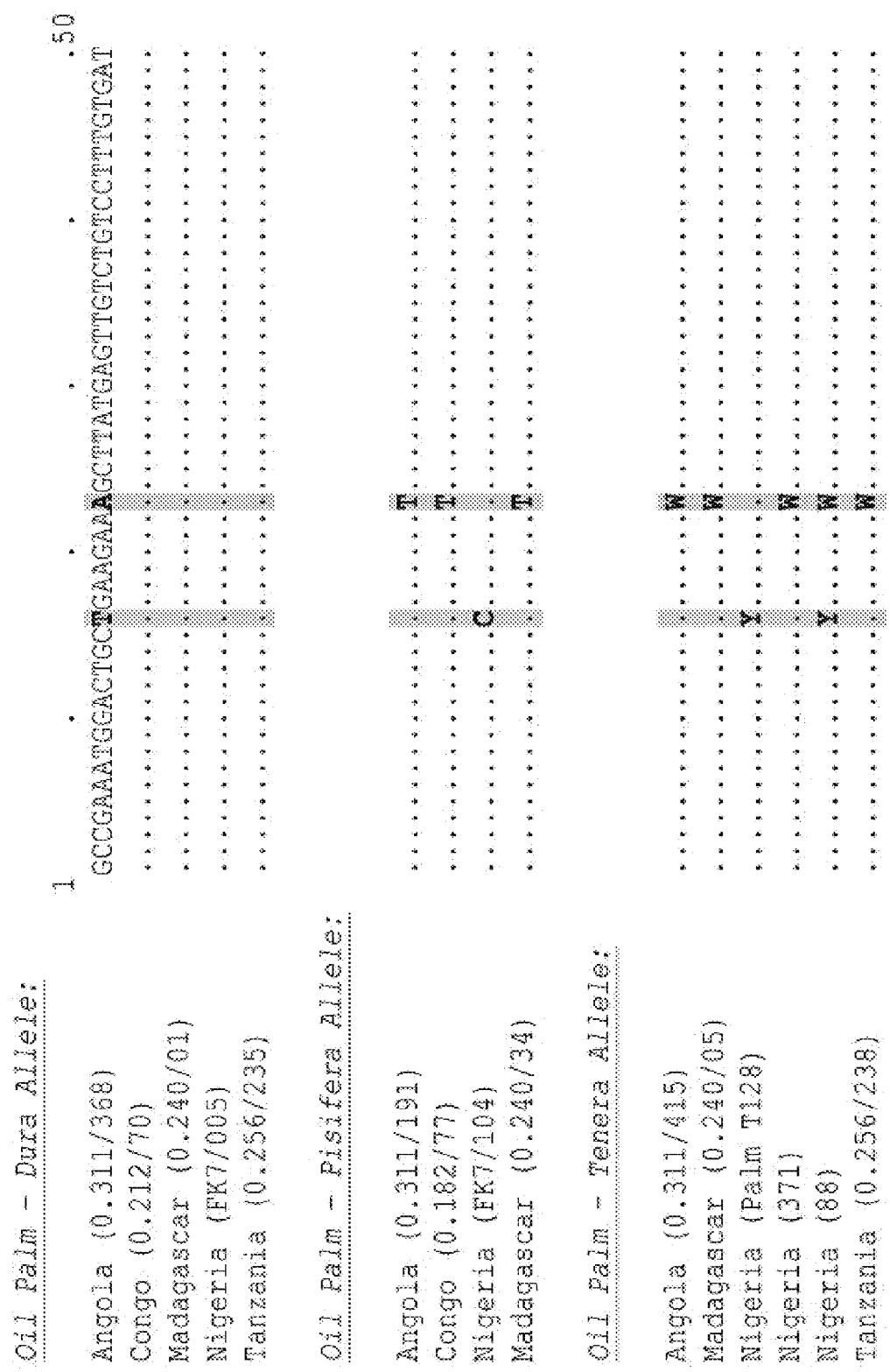
FIG. 5. Sequence conservation at the SHELL locus. Sequence conservation at the SHELL gene extends for 200 bp (not shown) either side of the shell phenotype causative SNPs (highlighted in grey) found in Nigerian (C/T=Y) and other African palms (A/T=W). Oil Palm—*Dura* Allele=SEQ ID NO:8223; *Pisifera* Allele Angola, Congo, Madagascar=SEQ ID NO:8224, Nigeria=SEQ ID NO:8225.

Analysis of 10,916,126 RNA-seq reads from 22 different oil palm libraries revealed only 159 reads matching oil palm SHELL, all of which were found in just four libraries: whole florets one day after anthesis, kernels 10 and 15 weeks after anthesis, and mesocarp 15 weeks after anthesis. These libraries correspond to the stages of shell development (Hartley, 1988; Bhasker and Mohankumar, 2001). PCR Amplicon sequencing (see Example 6) identified allelic differences between the SHELL orthologs in Deli *dura* (Sh$^{DeliDura}$), and those in the AVROS (sh$^{AVROS}$) and T128 (sh$^{MPOB}$) *pisifera* haplotypes derived from Congo and Nigeria, respectively (FIG. 5). The DNA sequence change associated with the *pisifera* fruit form in sh$^{MPOB}$ results in a leucine to proline amino acid change in the conserved DNA binding and dimerization domain, while the DNA sequence change associated with the *pisifera* fruit form in sh$^{AVROS}$ results in a lysine to asparagine amino acid change only two amino acids removed (FIG. 6). This highly conserved lysine residue is involved in nuclear localization, and in direct DNA binding by MADS-box proteins (Huang et al, 1996; Immink et al., 2010) while the substitution by a proline only two amino acid residues N-terminal to this position would disrupt the alpha helix structure that is involved in MADS dimerization and DNA binding (Immink et al., 2010) (FIG. 7). Analysis of an additional 336 palms was used to validate these alleles within established phenotyping norms. These included four *pisifera* palms from introgression trials of sh$^{MPOB}$ into *tenera* carrying the sh$^{AVROS}$ allele. Sequencing confirmed that these four palms were heteroallelic, indicating that the two alleles failed to complement, and confirmed the identity of the gene. Transgenic complementation experiments are not possible in oil palm, but similar experiments in tomato have confirmed the importance of the SHP gene, for example, in regulating mesocarp thickness in fleshy fruits (Verbalov et al., 2009). Therefore, the DNA sequence changes in the oil palm SHELL gene disclosed in this invention would have apparent effects on the function of the SHELL protein, thereby leading to the fruit type phenotype.

To further explore segregation in *E. guineensis* populations, SHELL Exon 1 sequence was generated from a diversity panel of 379 palms representing nine distinct wild oil palm populations collected from Angola (Rajanaidu et al., 2000), Madagascar (Rajanaidu et al., 2000), Nigeria (Hartley, 1988) and Tanzania (Rajanaidu et al., 2000), and a subset of a 110,000-accession seed bank collected over the past five decades (Rajanaidu et al., 2000) (see also Example 5). We found that all palms carried either the Sh$^{DeliDura}$, sh$^{AVROS}$ or sh$^{MPOB}$ alleles in exon 1 (FIG. 5). *Tenera* palms are thought to have been selected by pre-colonial cultures in West Africa due to their higher oil yields, and are the basis for modern oil palm breeding (Rajanaidu et al., 2000). The mutations we have detected in SHELL could account for these higher yields and for the remarkable single gene heterosis exhibited in *tenera* palms (Beirnaert and Vanderweyen, 1941). This is because the alleles would disrupt not only DNA binding, but also dimerization (Huang et al., 1996). Dimerization of the non-functional SHELL protein from shell-less AVROS (sh$^{AVROS}$) and T128 (sh$^{MPOB}$) *pisifera* fruit forms with the functional SHELL or other MADS box proteins from thick-shelled Deli *dura* (Sh$^{DeliDura}$) would be expected to reduce functional activity of the hetero- as well as the homo-dimer (Huang et al., 1996), resulting in the observed thin shell *tenera* phenotype in heterozygotes. Overdominance at a single locus accounts for similarly remarkable increases in hybrid yield in tomato (Krieger et al., 2010), and heterodimerization between transcription factors has been proposed to account for hybrid vigor in maize (Birchler et al., 2003).

Example 6

SHELL Gene Sequencing

DNA sequencing of the eight exons of the SHELL gene was carried out initially for 12 palms from the T128 selfed mapping population. Exon 1 of the gene was sequenced from all palms of the mapping family as well as the AVROS *pisifera* palms used in homozygosity mapping. In addition, Exon 1 from the palms listed in Table 5 was also sequenced.

TABLE 5

Additional palm samples used in SHELL Exon 1 DNA sequencing.

| No | Cross Type | Trial No. | Location | No. of Palms tested | Genetic Background |
|---|---|---|---|---|---|
| 1 | Tenera (T) × Tenera (T) | 0.305 | MPOB-UKM Station, Bangi, Selangor | 21 | 0.151/128 × AAR 0.127/13 |
| 2 | Tenera (T) × Tenera (T) | TT108 | United Plantations, Teluk Intan, Perak | 15 | Jenderata TT-Yocoubue × Nigerian Tenera |
| 3 | Tenera (T) × Tenera (T) | GGN | FFELDA, Jerantut, Pahang | 10 | T1791 (Nigerian selfed) |
| 4 | Tenera × Tenera | AA | FFELDA, Jerantut, Pahang | 9 | ML180T × 0.149/11525T (Yangambi × Nigerian origin |

[1]Palms on the left of the symbol 'x' denote the female parent, while the palm on the right is the male parent.
[2]In the populations listed above, the female parent of population 1 is palm T128, which was self-pollinated to generate the population used for map construction, in this study.
[3]Populations 1-5 above were segregating for the shell gene PCR primers were designed based on the reference *pisifera* genome sequence to amplify the entirety of SHELL exon 1 (SEQ ID NO:8237):

TTTTGATCTATGGAAATTAATAAGTCAATATGTCAGTATGTGAAGGTCTA

GGCCATGTTAGTCCCATCATTTCATTTATAGTTTAGATGATGATTTTTtC

TTTGTTCTTGGCAATATTCTAGACCAACTTCAGCAGACAGAGGTGAAAGA

GAGATCATGGGTAGAGGAAAGATTGAGATCAAGAGGATCGAGAACACCAC

AAGCCGGCAGGTCACTTTCTGCAAACGCCGAAATGGACTGCTGAAGAATG

CTTATGAGTTGTCTGTCCTTTGTGATGCTGAGGTTGCCCTTATTGTCTTC

TCCAGCCGGGGCCGCCTCTATGAGTACGCCAATAACAGGTATGCTTTGAT

GACGCCTTCTCTTCCTTCGCTCATATCAAGTTAATTTTATGGCTTCATTT

GTTCTATGGCCAAGCCAAATTCTTTTTAAAGTTCTAGAATGTTATGATGG

TAGTTTTGCTCCTCTTCAATTTATTT

Primer sequences were confirmed to be unique in the reference *pisifera* genome, and to avoid any identified polymorphic nucleotides. A 5' M13 forward sequence tag was added to the Exon 1 forward PCR primer (TTGCTTT-TAATTTTGCTTGAATACC; SEQ ID NO: 8238). A 5' M13 reverse sequence tag was added to the Exon 1 reverse primer (TTTGGATCAGGGATAAAAGGGAAGC; SEQ ID No: 8239). SHELL exon 1 was amplified from genomic DNA initially from DNA from 12 oil palm trees, and subsequently from a total of 336 oil palm samples (148 *tenera*, 100 *pisifera* and 86 *dura* and two palms where phenotype calls could not be made), PCR amplification was performed on 20 ng of genomic DNA under standard PCR amplification conditions. Amplicons were treated with exonuclease I and shrimp alkaline phosphatase to remove unincorporated primers and deoxynucleotides. An aliquot of each amplicon was sequenced using M13 forward as primer on an ABI 3730 instrument using standard conditions. Each amplicon was sequenced twice in the forward direction. An aliquot of each amplicon was additionally sequenced using M13 reverse as primer. Each amplicon was sequenced twice in the reverse direction.

All sequencing data was aligned to the reference *pisifera* genome sequence. Data were analyzed to determine the genotype at each of the two SNP positions identified to be associated with the *pisifera* fruit type.

At the SNP position of SEQ ID NO:922, *dura* trees were found to be homozygous for T (T/T), encoding a leucine amino acid at the corresponding position of the SHELL protein. At the same nucleotide position, *pisifera* trees were either homozygous T/T (if derived from the Zaire line) or homozygous C/C (if derived from the Nigerian line), encoding either a leucine or proline amino acid at the corresponding position of the SHELL protein, respectively. Therefore, *tenera* trees derived from a cross including Congo-derived *pisifera* should be homozygous T/T at the same position, while *tenera* trees derived from a cross including Nigerian-derived *pisifera* will be heterozygous C/T at the same position.

At the SNP position of SEQ ID NO:923, *dura* trees are homozygous A/A, encoding a lysine amino acid at the corresponding position of the SHELL protein. At the same position, *pisifera* trees are either homozygous A/A (if derived from the Nigerian line) or homozygous T/T (if derived from the Zaire line), encoding either a lysine or asparagine amino acid at the corresponding position of the SHELL protein, respectively. In addition, *pisifera* trees may be heterozygous C/T at the SNP position of SEQ ID NO:922, and heterozygous A/T at the SNP position of SEQ ID NO:923 as a result of having contribution from both Zaire and Nigerian derived lines. Therefore, *tenera* trees derived from a cross including Nigerian-derived *pisifera* should be homozygous A/A at the SNP position of SEQ ID NO: 923, while *tenera* trees derived from a cross including Zaire-derived *pisifera* will be heterozygous A/T at the same position.

Therefore, if derived from a cross involving Nigerian derived *pisifera*, *tenera* palms are heterozygous at the SNP position of SEQ ID NO:922 (T/C, where the *dura* derived T allele codes for leucine at the corresponding amino acid position and the *pisifera* derived C allele codes for proline at the same amino acid position), and they are homozygous (A/A) at the SNP position of SEQ ID NO:923 (where both alleles code for lysine). Conversely, if derived from a cross involving Zaire derived *pisifera*, *tenera* palms are homozygous T/T at the SNP position of SEQ ID NO:922 (where both alleles "T" code for leucine), and they are heterozygous at the SNP position of SEQ ID NO:923 (A/T, where the *dura* derived "A" allele codes for lysine and the *pisifera* derived "T" allele codes for asparagine at the same amino acid position).

DNA sequencing of the eight exons of SHELL was carried out for all palms of the mapping family as well as the AVROS *pisifera* palms used in homozygosity mapping. One of the 14 sequenced *pisifera* palms (TP10) proved to be heterozygous for the Zaire ($sh^{AVROS}$) and Nigerian ($sh^{MPOB}$) haplotypes, due to contamination in a breeding trial, and was not used for the homozygosity analysis. PCR primers were designed based on the reference *pisifera* genome sequence to amplify the entirety of SHELL exon 1. SHELL-specific primer sequences were TTGCTTTTAATTTTGCTT-GAATACC (forward primer upstream of exon 1; SEQ ID NO:8238) and TTTGGATCAGGGATAAAAGGGAAGC (reverse primer downstream of exon 1; SEQ ID NO:8239). Primer sequences were confirmed to be unique in the reference *pisifera* genome, and to avoid any identified polymorphic nucleotides. A 5' M13 forward sequence tag (GTTTTCCCAGTCACGACGTTGTA; SEQ ID NO:8240) was added to the Exon 1 forward PCR primer. A 5' M13 reverse sequence tag (AGGAAACAGCTATGACCAT; SEQ ID NO:8241) was added to the Exon 1 reverse primer. SHELL exon 1 was amplified from genomic DNA and PCR amplification was performed using 20 ng of purified genomic DNA under standard PCR amplification conditions. Amplicons were treated with exonuclease I and shrimp alkaline phosphatase to remove unincorporated primers and deoxynucleotides. An aliquot of each amplicon was sequenced using M13 forward as primer on an ABI 3730 instrument using standard conditions. Each amplicon was sequenced twice in the forward direction. An aliquot of each amplicon was additionally sequenced using M13 reverse as primer. Each amplicon was sequenced twice in the reverse direction. All sequencing data was aligned to the reference *pisifera* genome sequence. Data were analyzed to determine the genotype at each of the two SNP positions identified to be associated with the *pisifera* fruit form.

We sequenced SHELL Exon 1 from 336 individual palms from the T-128 mapping population, the samples used to construct homozygosity maps, and a collection of palms in crosses with advanced lines (100 *pisifera*, 148 *tenera*, 86 *dura* and 2 with ambiguous phenotype). 323 (96.7%) had SHELL genotypes concordant with their phenotype, and 11 (3.3%) had discordant phenotypes, reflecting the accuracy of phenotyping in the plantation (see above). SHELL exon 1 was also sequenced from all 4 *pisifera* palms derived from T×T crosses between Nigerian ($sh^{MPOB}$) and Zaire ($sh^{AVROS}$) (Felda AA and MPOB 0.305), and proved to be heteroallelic as predicted. An additional 3 *pisifera* palms were also found to be heteroallelic, including TP10 which was sequenced completely and proved to be a contaminant in the AVROS pedigree (see above). The other 2 heteroallelic palms were likely similarly contaminated.

A second attempt was made to phenotype and re-sequence the 11 apparently discordant trees, enabling the re-evaluation of 9 trees for fruit type. The second phenotype call of 1 palm was concordant with the genotype prediction, while the second phenotype calls of 7 palms were ambiguous, and I palm retained the original phenotype. This palm was re-genotyped and proved to have a consistent genotype. It is plausible that the 9 palms remaining (or 2.7% of the genotyped population) had been misphenotyped originally, given that fruit form phenotyping error is believed to be in excess of 5% (see above), highlighting the need for a molecular assay which more accurately predicts fruit form. This assumption was confirmed in 6 of the 9 palms for which haplotypes were available, as haplotypes were consistent with genotype not phenotype, ruling out recombination as an explanation for discrepancy. The map expansion immediately around SHELL is similarly explained by mis-phenotyped palms. That is, the 4 SNP markers closest to the mapped shell locus (see FIG. 2) surround the gene we have identified as SHELL, but all have 9/238 "recombinants" including 6 of the 9 mis-phenotyped palms.

Overall, a 2 to 3% discordance rate is within the range of the rate of incorrect phenotyping or genotyping based on either questionable fruit type classification or collection of samples from unintended trees in the field, respectively (approximately 5%). Furthermore, the two palms where the phenotype call could not be made were predicted as *pisifera*, by the SHELL genotype. This is in line with reports describing some *pisifera* palms as not being able to produce mature bunches—a trait observed for these two palms and the reason why fruit form could not be assigned.

In situ hybridization was performed on fruits between 1 and 5 WAA, at the earliest stages of shell formation (Singh et al., submitted). Uniform but weak hybridization signals were detected in the mesocarp of both the thick-shelled (*Dura*) and shell-less (*pisifera*) fruit forms, but very strong signals were detected in the outer layers of the developing kernel in only the *Dura* type, consistent with the function of Shell.

Therefore, the DNA sequence changes in the oil palm SHELL gene disclosed in this invention would clearly have effects on the function of the SHELL protein, thereby leading to the fruit type phenotype.

TABLE A

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1. | GCAAGGTTTGAAGTACTAAAGTAT[G,A]GGGAGTCCTGTTCAGGTTTCGGCAC | 94,205 | 83 |
| 2. | CGGACAGCACATGGTACTTGCTGC[G,A]GGACATACCTTAGTATGCCTCATGA | 94,307 | 83 |
| 3. | AGCACTCGAGTTGGCCCTTAGTCT[G,C]TCACTTATAGTGGTAAACTTTGGGC | 94,566 | 83 |
| 4. | CAAGTGATTGTGATGAATAGTTGA[C,T]CCCATGCATTTTTAGGATCTTGTGG | 94,744 | 83 |
| 5. | GGCAAACCTTGAAAATTAGGAGTT[G,T]GGgAAGGTCTGGTTGGTGCAGTCAC | 95,576 | 83 |
| 6. | GTAGGCTATCAAAGTAACATTGTC[T,C]GTAGACTCCGTACTTTATATGAAAG | 96,098 | 83 |
| 7. | CTTTGAAATTTACCATTCATTATT[A,T]TAGGGTTAACATTTTCTTCCAAAAa | 96,236 | 83 |
| 8. | TTGTCTCCGCTGTAGCCACTATCA[G,A]ACACACTATGATCAAAGTTCACCTT | 97,720 | 83 |
| 9. | ATGGTTTGAGGTACCCCGGAACGG[A,G]CGCATACCAGTCACATACTGACATG | 98,326 | 83 |
| 10. | CTACTTGGACCTGGGTAATTTGGC[A,G]AaTGTGAAGCTGGCCCATCTATTGC | 99,241 | 83 |
| 11. | GGGGAACAGGGGAGGGCGAGGAAT[T,A]tGTGTAGTTTGCTATTCTTGGGGAA | 99,333 | 83 |
| 12. | GTAAAATAGGGAGAGGTGGAGGGA[C,A]GGAGAGGAGAAGAGGGTGGGAGGAT | 100,485 | 83 |
| 13. | ATAAAATAATGTGTTTTACATTGA[C,T]CcAATGTCATATCATCCAAACTTCA | 102,416 | 83 |
| 14. | TGTTCACCTTGATGGTTTTTTCAG[C,T]GTTCAAAGAAGATAATTCCCTTTGT | 103,291 | 83 |
| 15. | TAGCAGGCTTAGTGAAACCAATGA[G,T]TATCCAATTACTGTGGGCAATCAA | 103,497 | 83 |
| 16. | TTGTCTTAAATCTTACCATCCTCA[A,G]TGTGTGGGAAGGATCCTTCCTTCT | 104,201 | 83 |
| 17. | TATGGTTTGCCGAACTGCCCCAAA[T,C]GGTACTGGTGGCCAACTGGCGATGG | 105,803 | 83 |
| 18. | TATGTATGCACACACACACACACA[T,C]ATATATACATACTTATATATATAGG | 110,017 | 83 |
| 19. | GAGAAAATAGAAGGGGCTTATGGG[A,C]TTTGGCTGGGATTCCTAAATTGAAG | 111,511 | 83 |
| 20. | TGTTTAAGAGTACTATTTTTGAGT[C,A]TAACGAACTAATTTACGGAAAAGTG | 111,781 | 83 |
| 21. | GGTGGCCACCGCCGATGCCTCTAC[C,T]GGTCTCCCTTTTCTTTCCTCCCTCT | 116,728 | 83 |
| 22. | TCTTAACAGTTTGGATTTTTtCTT[T,C]CTATATTTTAATAAGCTCACCCTAA | 117,200 | 83 |
| 23. | TATAGGGTTGGTTCAGCATATGGA[T,C]GCTCGATATGTTGCACGTACTGAGT | 117,367 | 83 |
| 24. | CAGTTATGTTACTCGTGAGGAATT[G,C]CCATTAGGATAAACAAAAGGTTCAT | 118,689 | 83 |
| 25. | ATTCAGTCTAAGTGTCCTTTATCC[A,G]TTTCTTCCTGTTATTCCAATGCTAT | 120,124 | 83 |
| 26. | GCACTGCATGTATGTTAGCATGGC[A,G]CAAAATGTTCCTTGCcGGCCTTTGG | 120,464 | 83 |
| 27. | AGCATGGCaCAAAATGTTCCTTGC[C,T]GGCCTTTGGCCAGAACGCTTCATGC | 120,480 | 83 |
| 28. | GGCCAGTCCAAGAATGTAGTTCCC[A,T]aTTGGTATAGTGGGAAGAATACAAA | 121,782 | 83 |
| 29. | TCTCGTTTCAAGAATAAGTCACTA[T,C]GATGATTAGATATGAAATATGGTGA | 122,461 | 83 |
| 30. | ACGCCCACGACTAAGTTCTTCGCC[T,A]GTGCCTCAGACTTCGAGAAGACCAG | 122,933 | 83 |
| 31. | GTCTAGTAGTCCCTCTTTGAGACA[C,T]CGCATCTCGGCAGAGACTTGTTGAT | 123,051 | 83 |
| 32. | GTTACTGTTGCTGAGATAGCTCCT[C,T]AGTCTGTTGTCGAAGTGGCTCCTCA | 123,865 | 83 |
| 33. | TCAGTCTGTTGTCGAAGTGGCTCC[T,C]CAACCGCTGATCGAAGTGGCCCCTC | 123,888 | 83 |
| 34. | TTTTtATCCGATCTCACCTAACCC[G,A]ATCTTGGTTTAATTGTCATATATAG | 124,168 | 83 |
| 35. | TCCTCATTTGGTCGGACTATATGA[C,T]cTTATTTGGACAATTATTTTATATC | 124,799 | 83 |
| 36. | AATTCTCAATTCTATATGCTCCCA[A,G]GCGGATTACTTCGGTAACTTGGTAG | 125,025 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 37. | ATTATCAGTGATAATGATTTGAGG[C,T]AAATCAAAGTGGCAGACAATTGATT | 125,609 | 83 |
| 38. | GAAGAGTTTCGATGCTGGATTTTT[T,C]GAGGTAGTAGATAAGAATTTTTAGT | 126,221 | 83 |
| 39. | TCAAAAAaTAGGCTGAACTGGACC[A,G]AaCCAGTGGGTTCGGTATGGTATCA | 126,634 | 83 |
| 40. | TATGATATCGGTTGGCAATCGATA[T,C]GGGTTTTGGTATCAAgTCCGCAAAT | 126,840 | 83 |
| 41. | AATCGATAtGGGTTTTGGTATCAA[G,T]TCCGCAAATCTTGGTTTGAAGTATT | 126,856 | 83 |
| 42. | GGACATTCAGGGACAATACCTTCA[A,G]GATTAGCTAAAATTAAACCAGCTCC | 126,920 | 83 |
| 43. | ACTTTAGAGGTTGATCATTTAAGA[C,T]GACGATTGAGTGGGCTTGGAAATAA | 127,203 | 83 |
| 44. | ACTTCAACTGGTTTGGACAATAAT[T,G]GGGGTGAATCGAGATATTTCTTAAG | 127,436 | 83 |
| 45. | CGGTGTAATCAATACAAATCCTCC[A,G]GTTGTCATTTGCATTTTTGACCATA | 128,135 | 83 |
| 46. | GCTCCGAATCAACATTCAATTTAT[C,G]TACAATAACATTGGCAGAAATTCCA | 128,316 | 83 |
| 47. | TGAAGAAAAGATATCGGTTATTTT[T,C]TtAAATCAGTCCTTAATTGAGATCC | 128,408 | 83 |
| 48. | GTGGTTATAGGCAAAGTGATTTCT[C,T]cTTCAGCAGCTACGGGATTTTCAGA | 128,816 | 83 |
| 49. | GAGGAGTTTGGACTTCTTGAACAT[C,T]AGTATCAGAAAAAAAAaTAACATTG | 129,023 | 83 |
| 50. | GCCTGAGCATACTTTTGGATTCGG[G,A]TTAGCATTTGATCGTAGGTGTCCGA | 129,583 | 83 |
| 51. | GTTGTCCGATCCCATCTCAACAGC[C,T]ATTTCGATCATGCATTCCGATAGAT | 129,605 | 83 |
| 52. | CTGCTCCCTTCTTTTATTTCTTTC[A,C]TTTTTCTTTTtCTTCTTTCCTTCCA | 129,891 | 83 |
| 53. | GACTCATTGAAATTTTTGACTTCA[A,C]GCATGACGTATTGAAGTGCACTGTA | 130,161 | 83 |
| 54. | AAAATTTCTTGAGAAAAAaGGGAT[C,T]GTAGGTCAAAATCTTGCTTATCTTG | 130,535 | 83 |
| 55. | TATCTTGGGAATGATTCCCAAGTT[A,G]TACTTCCATCAGCCGTTTTTCAAGA | 130,578 | 83 |
| 56. | GGATCTTGATGGATTGGCTGATGA[T,C]TGTGTTGGGACAGAACTTTTTGAGG | 130,733 | 83 |
| 57. | TTGAGGAATTGCCTCTCATTGCTG[T,C]TTTATGGTACATTGGAGTTGTTGTA | 130,777 | 83 |
| 58. | TGAAGGTTGAATAGCTTCTGGTCC[G,A]CCTCTTGGAGAAGATGGTGAAGGCA | 130,890 | 83 |
| 59. | GAATTATTGTGCTTTCTAATTTAC[C,T]ATTTTTCACAATCTTTTGGGCAAGC | 130,942 | 83 |
| 60. | TTTATGGTTTTTAAACTATGGCTT[G,T]GATGTTAACAGATAATGAAGCTGCC | 132,949 | 83 |
| 61. | TTCATTTTTTGACTCCTTTTTTAA[G,C]CCAGGTTTGCTCATCATTCACTTAT | 133,628 | 83 |
| 62. | ATCTAACGGGGCTAGCCAAACCAA[T,C]GCTCCATCTGAGCTATCTGATCCCT | 134,691 | 83 |
| 63. | TGCAGAAATAAGGTTGGAGTTGGA[C,A]AAAGTCAGAAAGGTGGCACAAAAGA | 135,827 | 83 |
| 64. | CACCATGGCTCAATCGAAGCGCCC[G,A]CGTGCTGAAGCTTTTGAGGGTCGAT | 135,896 | 83 |
| 65. | TTTGTTTTGTAATTTGGATTGGCC[A,G]aTCTTTTGTACCAGAGTAATATTAA | 137,583 | 83 |
| 66. | AACCTTGTTGTATGATGAGCTGAC[T,C]tGTTAGTAGAAAGATTCTTAAGTTC | 137,652 | 83 |
| 67. | CAGCTTGGCTCGACTGGGTCATA[G,A]CTCCAAGCTTATTGAAGGGGTTCTC | 138,012 | 83 |
| 68. | TACATCCCGTACCAAACCATACCA[A,G]TGGGGAGCTGGTCCGATTTAGACTG | 138,124 | 83 |
| 69. | GATTGAACCGATCGGTTCAGTACG[G,A]TATTGGCCCGAACCGTCCGATGTCA | 138,199 | 83 |
| 70. | GTTTGATCCAATTCGGTATGGTTC[G,A]AAGCTGGTTTGATTCGGTTCGGTCT | 138,253 | 83 |
| 71. | GTGGATTGAGTTGGCTTTGCCGAT[A,C]TATGGAGCTTCCGAGGATCCTCTTA | 138,568 | 83 |
| 72. | TCAAATGATTAAGATTTTTAGCTC[C,A]GCCATCAGGGATAAGGGGCTATTCG | 138,637 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 73. | GATTTTGGAGCTTCCAAGGATCCT[T,C]TTATGGGGTTATGCCTCACTTTTTG | 138,927 | 83 |
| 74. | CATCCGCTCAAGATCCATTGGCCC[G,A]ATCCAACCTTGTCTTTAGGCCTTGC | 139,645 | 83 |
| 75. | TATGTTTGTTATCTCCTGCTTTAT[T,C]tGGTGAGATATGTTTGTTATCTCCT | 145,595 | 83 |
| 76. | GTGAGATATGTTTGTTATCTCCTG[T,C]CTTATTTACTCGTGGCAGGTTGTTG | 145,622 | 83 |
| 77. | TTCTGGCTGCATCAACCTTTCAGT[G,A]AAGCTACTATTGCTTTTTtAGTTTC | 146,302 | 83 |
| 78. | TTCTAATTATTTTAGTTTTACAGC[C,T]GCACGGATGTTACCTTTGTTGTTTT | 146,487 | 83 |
| 79. | GTTATTTGCCACTCTTGGACCGAC[C,T]GTCAGTTTTCCATAGTTTCTAGACA | 146,576 | 83 |
| 80. | TCTGTTAGGACTGTTTATGAGCAA[T,A]GATATTTTCTGTGCATTGTCAATAT | 147,611 | 83 |
| 81. | TGGCATTGCGCATGCCCAATTTTC[G,A]TATCCACATGGGCCTCTCTTGAAAG | 147,666 | 83 |
| 82. | AAGTTTGGAAGCTACTTATGGCTA[G,A]GATGTTCCAAATGGCTGTAGCCACT | 147,923 | 83 |
| 83. | ATGGCTAGGATGTTCCAAATGGCT[G,T]TAGCCACTCTGTTTCATGGTAGAAT | 147,940 | 83 |
| 84. | CTGCAGGAATCAGGTGCATATAAT[A,C]aTTATTGAAAGAAGAGACAGAAAAC | 148,413 | 83 |
| 85. | CATTGATTTAGATGAAGATGAAGA[T,A]GACTGCTCAACTGCCTTAAAGGAAA | 149,495 | 83 |
| 86. | ACTTCTTAGAGTATAAATTTGAAG[C,T]GAGTTGTTTTCCTCTCGGGAGATAG | 156,804 | 83 |
| 87. | GGATTATGAAGGAATATGTGATGA[T,G]CTGTTTCTTTGAAGGTTGTTTTCTC | 158,166 | 83 |
| 88. | TGCGAGCTGCTTATCAGGTTCCAC[A,C]TGTGAGCCACAAAGTTAGGTACACT | 158,405 | 83 |
| 89. | GCAAGTGTTTAGATCTACAGAATC[T,A]TGCATCTCTAGCATGTGTCTGGGTT | 158,473 | 83 |
| 90. | ATTGTTGGAATTTTGCTACTGGAA[C,G]TTTTGCTAGaTGCACGGTCTGATTC | 161,181 | 83 |
| 91. | TTTTGCTACTGGAAcTTTTGCTAG[A,T]TGCACGGTCTGATTCACTGAGATTG | 161,191 | 83 |
| 92. | TAGTTTATTCAATATAATAAATTC[C,T]ACGACTTCAACTTCTGCACCTGTAT | 181,615 | 83 |
| 93. | CCACCAAACAACTAGAATTGGAGC[C,T]ATTTATTTTCATTCTCCTTCTACAG | 182,673 | 83 |
| 94. | CTAGGCCTTGGGGACTCTAACTCA[A,G]ACGAGACTGGGATCCCGTATTAGGC | 186,051 | 83 |
| 95. | TACCCCTATTGGCCCACAGAAATC[A,G]ATAGTTGGCTTATTTATGAGTAACA | 186,644 | 83 |
| 96. | AAAAGGCACAAGCACGTCATAGTC[G,A]TAATAGAGGCGTGTCTTCTGCAATC | 186,787 | 83 |
| 97. | CTAGGGTAACGCTCGAACATCAGA[C,T]GCAGATCCAAAAAAaGACTTGAGCC | 187,294 | 83 |
| 98. | TCTTTCCTCACTACTTACTGGCTA[C,A]CGCATTTGGGAGAGTCAACTCCCAT | 187,401 | 83 |
| 99. | CATCGGATAAGATGACGTCCGCCA[C,T]CAAGGTCCAAATAGGGAGGAATGGT | 187,557 | 83 |
| 100. | TTCTCTCAGAATCAACTTCGATCG[G,A]AACTTATTTTGTAGATCACACTGCT | 187,872 | 83 |
| 101. | TTAACTTGGAATTTTTATGTTAG[C,T]AAAAGCAACAAATTTTTCTCTCGA | 188,731 | 83 |
| 102. | TCTCTTCTGCCCCCCTTTGATCCT[C,T]TTGTGTGCTTGCAAATCTCTATCAA | 201,006 | 83 |
| 103. | TTACTTCTTCCATCAACTTGGAGC[T,G]GTTGTCGATCGGTATTTTGCTATCG | 201,220 | 83 |
| 104. | GCATTTCAAAATCTAAATATGATC[C,T]GCAGCGTATACCAACAATGGTTGCA | 202,350 | 83 |
| 105. | GGAATGAATGATTGTTGCTTTTTt[C,T]TTTTtGCATCTAACTTGCATCATTC | 202,626 | 83 |
| 106. | GTGATCAGGGAGGAATTATTCTGA[C,G]ACTACCACCAGGGCATCCTTGCTGC | 203,394 | 83 |
| 107. | ATGAATTCATCATTCGTTTTGTCA[T,C]TTTAAGTTCAACAATGCCATTGGGT | 203,652 | 83 |
| 108. | TTAAGTTCAACAATGCCATTGGGT[T,C]TTTATCTCCTCGATGTTGGTAGCAG | 203,678 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 109. | GGGTTTTTATCTCCTCGATGTTGG[T,G]AGCAGCTTAAATATTTCTTTTCATG | 203,698 | 83 |
| 110. | AGCTTAAATATTTCTTTTCATGCC[T,G]TGAAAGTGGTTGGCAGTGTTTGGTG | 203,726 | 83 |
| 111. | GAAAACATGTTCTATGGTTTCTAT[G,A]TCAGGTTTTATTAGTGTAAGAGAAA | 203,943 | 83 |
| 112. | GGACATCAACTCAGAATGCCAGTT[G,T]GAAGGGTTAATGCTTCTAATAAGCC | 204,699 | 83 |
| 113. | CCCTAAAAGATGAAGGCATGACTC[A,G]GTACAGGATTCATAGACCTTCTTAA | 213,142 | 83 |
| 114. | TGAGCCCCTAAAAGATGAAGGCAT[G,T]ACTCAGTACAGGATTCATAGACCTT | 213,147 | 83 |
| 115. | TTTAAGTGACTTGATTAAGAAATT[A,G]TGAAGCACAGATTAAATCAAGATCA | 213,308 | 83 |
| 116. | ATAAGGAAAGATGACTGTTGTCTG[C,G]ATGTGTCGGACCATCCAGATACCGG | 213,390 | 83 |
| 117. | TCAAATCATCATTAATTTCTATTT[T,C]ATGAATATAATAAGATTAAATCATA | 213,437 | 83 |
| 118. | TTACCTCGTTCATTTTAGATCTTC[A,T]GACTTCGTTAGAAGAATCAACTAAT | 213,500 | 83 |
| 119. | TGATTATTTAAAAATAAATAAAGA[A,G]CGTAAGATCCACTTACCTCGTTCAT | 213,537 | 83 |
| 120. | TTTTTCATATCACACGTGCTGATC[C,T]TTATTTTATAAAAAATATGATTTCA | 213,615 | 83 |
| 121. | AAATATATTCATAAAATCAATGCT[C,T]ATAATAAAATATAATTTTTCATATC | 213,654 | 83 |
| 122. | TTTATATCTTTTTTTtAAAGCATA[C,T]ATATACATAAATAAAAAAaTAATAA | 213,736 | 83 |
| 123. | ATACCCGTTGGCAGGGCTATGTTT[C,T]GTGTGGATGCTAGCTCTGGATGTCG | 213,834 | 83 |
| 124. | CTATTATACCTGTGATAGGGCCAT[A,G]TTTCTTAATCGACAGAGTTCTTAAT | 213,899 | 83 |
| 125. | GATATATTGCTCCCAGATATTCGT[T,G]CTAAGATCACTATTATACCTGTGAT | 213,933 | 83 |
| 126. | AATCATGAATCATAAATCATTCTT[A,G]TCATGTATTCATGTCAAGTTTTGAT | 213,980 | 83 |
| 127. | ATATAAAATAAAATATTTCATAGA[A,G]CATATAATAAAATAAATTATAAACC | 214,063 | 83 |
| 128. | ATATTTAAAAAaTAACAGATAATA[T,C]AAAATAAAATATTTCATAGAACATA | 214,084 | 83 |
| 129. | ATCTAAACCTCATCTACAAAATTT[C,T]CAAGCTTGCATCGCAGATCTCTAAA | 214,264 | 83 |
| 130. | CTAAATCCAAAATCAAATATAAAT[T,C]CATATATCAAAATCCATAATTACTT | 214,338 | 83 |
| 131. | AGCATCTAAATCCAAAATCAAATA[T,C]AAATTCATATATCAAAATCCATAAT | 214,343 | 83 |
| 132. | CCATGATAACACGAAGCCAATCCA[A,T]CATAATCATCCAAAATCCATCAAAT | 214,444 | 83 |
| 133. | ACATAACACGACCATGCTACCGAA[G,A]GATGGAGCCCATGATAACACGAAGC | 214,477 | 83 |
| 134. | AGGGTTGATCTGAGTACGAGAAGT[G,A]TTAACTCTGGAATGAAGTGGGAGGT | 215,375 | 83 |
| 135. | AAGGACATGATAACTTTGCTGATT[T,G]TGATGTTAATTTTTTtGCAAAAAAa | 215,483 | 83 |
| 136. | AAGCATGATGGTCTGAATTAATTA[A,G]AAaTATTAATCTTTTAAATTAAAAG | 215,843 | 83 |
| 137. | AATACGTTAGTTATAAATAAGGAA[G,A]GATTTTACTGATAATAAAAGAATGC | 215,902 | 83 |
| 138. | GAAGGATTTTACTGATAATAAAAG[A,G]ATGCTAGAGAGAAAATCTATCTGAT | 215,923 | 83 |
| 139. | AGTCAACGATATATTAGACCTTTT[G,A]AAATTTTAAGCCGAGTAGGAGATGT | 216,121 | 83 |
| 140. | CACAATGTCTTTCATGTTTCATCA[C,T]TGAGAAAATTTATACCTGATCCAAA | 216,211 | 83 |
| 141. | ATGTCTTTCATGTTTCATCACTGA[G,A]AAAATTTATACCTGATCCAAATAAT | 216,215 | 83 |
| 142. | CATGTTTCATCACTGAGAAAATTT[A,G]TACCTGATCCAAATAATGTGGTAAA | 216,223 | 83 |
| 143. | TAAAATTTTAAATAAAAAAaTATC[T,C]TTCTTATTCTGAAAAAaTTATGACA | 221,260 | 83 |
| 144. | CTTTATGACTTTTGAAAGAAAAaT[T,C]AAGACATTCTGCATGTAAAAGTCA | 221,443 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 145. | AAACCATAGATCATCTCATGACTC[C,A]ATGTGAATACTCCTATCTCACATAA | 221,900 | 83 |
| 146. | CATGACTCCATGTGAATACTCCTA[T,A]CTCACATAAAAACATCTGCTACAAC | 221,916 | 83 |
| 147. | TTAAACTTAATTTAATACCCCCTC[G,T]TGACAGCCTCTAGGCTCTTTCCTCA | 226,490 | 83 |
| 148. | TCTAGGCTCTTTCCTCAATTTCTT[A,T]ACTTATTGTTTTTATTCTTCTTTA | 226,523 | 83 |
| 149. | AGCTTCCTGTATTTGGCCACTCTG[T,C]CTCCTCTAAGCTTCCATATTTGGCC | 229,627 | 83 |
| 150. | CATTATTTTTTCAGAGATCTGCAG[G,A]AAAGGAGAGCACTTGAAAGAGATTA | 229,844 | 83 |
| 151. | TTTAGCAGTTATTTTTTCGATATA[A,G]TCTCAATGCTACAGACTCTTTAGTT | 230,883 | 83 |
| 152. | CAGTTATTTTTTCGATATAATCTC[A,G]ATGCTACAGACTCTTTAGTTTATGT | 230,888 | 83 |
| 153. | AGCCTAGTAAATTATCGAAGTTAT[C,A]TATAATGATGTGGGATGACAACATG | 230,950 | 83 |
| 154. | TGCTTAGTTGTCTTCCTTCTGTAA[T,G]GACCACACATGAAGCACTCCAGACC | 235,235 | 83 |
| 155. | ACATCTGCTCTTCCTATCATGGAC[C,T]GAAAAATTGTCAGCATAAAGACATA | 235,370 | 83 |
| 156. | TCAAGAAAATCCCAGCAAATACAG[T,C]TTTtCTGAAACAATCATAAGATACA | 236,194 | 83 |
| 157. | GAGGAAATGGCTCGACCGAACAGG[G,A]TAGAACAGGGTCTCGCCTTTTCATC | 238,549 | 83 |
| 158. | AGGAAATGGCTCGACCGAACAGGG[T,C]AGAACAGGGTCTCGCCTTTTCATCA | 238,550 | 83 |
| 159. | GAACAGGGTAGAACAGGGTCTCGC[C,T]TTTTCATCAATTTTTCCAACGATCC | 238,566 | 83 |
| 160. | AAGCCATGGGAAGGAGGGAAGGA[G,A]GAGAGGAAGGAGGGCCGGGGCTTAC | 238,638 | 83 |
| 161. | TTCAGATTCGAGGAAATTTAACTG[A,G]AGTCTGAATTCTAATAAGATGTGAA | 239,157 | 83 |
| 162. | TTATTGCAGTTGTATTTGTTGGAG[C,A]CATTGGGGGTATATTTGGAAGTCTA | 239,926 | 83 |
| 163. | TTGTTGTCATTCTTGGATTGTGTT[G,T]ATATACTCTAGACATTAGCTTAAAT | 240,051 | 83 |
| 164. | GTTTCTGACAGGGTCTAATTATTT[G,T]CAGGAAAGGTGCACCTTTCAAGATC | 240,153 | 83 |
| 165. | TCTTGGTCTCCATGAGCACTGTCC[T,C]ACCGTTGGCCGCTCAGGCAACTTCA | 240,283 | 83 |
| 166. | CAACTTCAAGAACTTTCAATGCCC[A,G]CAAGGTCATTACAATGACCTTGCTT | 240,325 | 83 |
| 167. | TATTGAAACAATGTCTCTAGCCAA[G,A]GCTGCAGTGCTCTTCAGAGAGCTTG | 241,225 | 83 |
| 168. | ACTAAAAAAaTCTTGACCCAAACC[C,T]GAGCCAGATGCGAAAAGATGTAAAA | 242,216 | 83 |
| 169. | GTTAAATGAAGTGTCAATGCTCTT[A,C]TGAAACCTGAAATCTGTTTTCTTGC | 242,494 | 83 |
| 170. | TtCTTCTTTTAAGCTATCAAAGAG[C,G]CCCCTCCACAGAGTTTGTTGAGGCT | 244,290 | 83 |
| 171. | ATTCTCCACCAGATAGCTGCATGA[T,C]ATTTCTTGTTGTTTCTGCTTATTGC | 244,369 | 83 |
| 172. | GGACAACAAATTACAAGGTAGAAC[T,A]AGCAAAAATGACTCGACGACTGCCA | 244,511 | 83 |
| 173. | AACCTTCTCAGCTAAGAAAGCAAT[G,A]TTTTTTACCGCCCTAATTTGCCAGA | 244,560 | 83 |
| 174. | CATGCATTTCCAGGTATTTAGATC[C,T]GGAACGGTGGCAGGCACTGCCATCC | 244,685 | 83 |
| 175. | ATTTCCAGGTATTTAGATCCGGAA[C,T]GGTGGCAGGCACTGCCATCCATCAA | 244,690 | 83 |
| 176. | AAAACTAAAAGCATATTTGATTCA[T,C]GATCGAAATTAGAATCAGAATCGAA | 244,802 | 83 |
| 177. | CAACCAAACATGCCTTATAGGAGC[A,G]AGGCAGAGAGAAATTCAGTGACTAG | 245,088 | 83 |
| 178. | TCATCTCTCCTCTCAAACACCCAT[A,C]TCTCTCCTCCCGTTTTGCTGCTTTC | 245,235 | 83 |
| 179. | CCGTTTTGCTGCTTTCCTCCAAAA[G,T]TACAACTTCATCATTTAGTAAATTG | 245,269 | 83 |
| 180. | TATTTTAGAGAGAGTAAGCTTAAG[T,C]GAGAAAGTCTCTTGACTAAAAAGAT | 245,406 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 181. | ATGGAGCTTGATCCTAAGGGGTCC[A,G]ACTGAACAAGTCTCTCATGACTAAT | 245,516 | 83 |
| 182. | GGGGTCCAACTGAACAAGTCTCTC[A,G]TGACTAATCTTCATGAGGATTCGAA | 245,533 | 83 |
| 183. | CAAATTTTTGCTCGTGGTCCCTTT[C,T]CTTTGGCCAATTAACTTATAGCTCT | 245,964 | 83 |
| 184. | CCTTTCCTTTGGCCAATTAACTTA[T,C]AGCTCTCCAAGAATGATGATCTAAT | 245,983 | 83 |
| 185. | ACCAGGTAGAAATACTATTAATCA[A,G]GTAGCCATTTGGTTGTGGATGCCTG | 246,038 | 83 |
| 186. | TAAGAGTTTGTTTATAAAGAGTTA[C,T]CGAATCTCTGCTAGCCATGTAACCA | 246,277 | 83 |
| 187. | CTATGCTTCCTGTAAAAATCATGA[A,T]CTGGATAGCTCCTTGCCCAAGCCTA | 246,339 | 83 |
| 188. | ACCAGATCATCGTCTATTGGTGTT[G,A,T]CTCTTTTTGTGTTTCAAGCTTCGAC | 246,448 | 83 |
| 189. | CTCCAAAGACTCTAAAAAATTCAA[C,T]AGATCAAATGATTTGATTCACCCAC | 246,722 | 83 |
| 190. | GTTACAAGTTGAGTTGGGCCTAGA[A,G]CACACCTTGATTGAGCAGTATGTCA | 246,993 | 83 |
| 191. | TCTGAAGCTTTTAGTGCCCAGACT[C,T]AATCTCAAATAAGCTCTATAGGGGC | 247,056 | 83 |
| 192. | CTCAATCTCAAATAAGCTCTATAG[G,A]GGCGTGTCTTTCCATATCTTAGTAT | 247,078 | 83 |
| 193. | CATATGCATTGTCTAGATATTTGT[T,A]GTATCCTAGAAATATATTTGTCTAA | 247,199 | 83 |
| 194. | GGGTTTTCAAAGACCTATGTTTAC[C,T]TGGTGTAATCAACTAGGATCTA | 247,649 | 83 |
| 195. | TCTGAGCTCATGGCCGGTCATTTT[G,T]CTTCTAATCATTGTCCTTCATTGAT | 247,758 | 83 |
| 196. | TAGGCCTAAACCTTTTTGGTTTGA[G,A]AAATTTTGACTCTCCGAGCACATAT | 247,831 | 83 |
| 197. | ACAAGGAACCATTCTTCTGGTGTG[C,T]GACTTTCTATTGTTCTACATAACAC | 247,912 | 83 |
| 198. | GCCTTAGTTGATGAAATCATTGTC[A,G]CTTAGGTAACTTTTTTTCAAGTTGGT | 247,970 | 83 |
| 199. | CTAATAATAAGTTGGAGTATCTT[C,T]AGTTGAAGGAAGTCTCTTATAGTGG | 248,026 | 83 |
| 200. | TATCTTCAGTTGAAGGAAGTCTCT[T,G]ATAGTGGTTTGCCTCATTAAGATCA | 248,044 | 83 |
| 201. | AGTGGTTTGCCTCATTAAGATCAT[A,T]AGGATTTAACTGCACACCCTTAGGCT | 248,071 | 83 |
| 202. | AAGGATTTACTGCACACCCTTAGG[C,G]TTATAATCTTGACTTGAATCAATA | 248,095 | 83 |
| 203. | CACACCCTTAGGCTTTATAATCTT[G,A]ACTTGAATCAATAAGAAATCTTCTG | 248,107 | 83 |
| 204. | TAGAATTTCGTGGCTTAAGGAAGA[A,T]AATAGTAGTACTAAATTTTTTCGCT | 248,169 | 83 |
| 205. | AAAATAGTAGTACTAAATTTTTTC[G,A]CTACTCTACTATACAGAAGAGAAGA | 248,192 | 83 |
| 206. | TTTTTTCGCTACTCTACTATACAG[A,C]AGAGAAGAGCTACTAAAATTACTAA | 248,209 | 83 |
| 207. | ATTAGATGGATCTAAAGTTGACGA[C,T]GATGTTATGATTCATCAATTTGTAT | 248,268 | 83 |
| 208. | TAAAGTTGACGACGATGTTATGAT[T,G]CATCAATTTGTATTCACTTATTTTA | 248,280 | 83 |
| 209. | CTTAAATGAACTTAGCAGATTGAG[C,T]CACTTTTTGATTGGTTATGTTTGGT | 248,332 | 83 |
| 210. | ATTGAGCCCACTTTTTGATTGGTTA[T,G]GTTTGGTATTACCCATTTTATCTTC | 248,350 | 83 |
| 211. | CAACATGAGCAACTAGTATGCGCA[G,A]TCACTAACAATGAAATTAAGGAAGT | 248,404 | 83 |
| 212. | GATGTTGTTCTTATTGTGAAGGAT[A,G]CTTCACAATATATATCTATGCCATG | 248,543 | 83 |
| 213. | ACAAACTTTTATTACTTGAATCTC[A,T]AAAAAGAATAATCTTATTTTAATTT | 248,602 | 83 |
| 214. | TATTACTTGAATCTCAAAAAAGAA[T,G]AATCTTATTTTAATTTTTGATCCAT | 248,611 | 83 |
| 215. | TAATACAACTTAATCATTGCAAAT[T,G]TTTTTACAAACAAACTACTTATCAT | 248,670 | 83 |
| 216. | ATCATGTCTTCCTTAATCCATCCT[G,A]TGCAAGGTGCCTTTTTTCCTACATA | 248,715 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 217. | ATATGTTTTGATTACCCAAAAGAT[T,C]ATGCATTTCCTTGATGCATGCACCTG | 248,777 | 83 |
| 218. | CATTTTGGCTTTCAACTTGGATTC[A,G]TAAAGTGGGTACAACTCCGTGTCAA | 248,913 | 83 |
| 219. | ACTTGGATTCATAAAGTGGGTACA[A,G]CTCCGTGTCAACTTTATTAATAAAT | 248,927 | 83 |
| 220. | TATAAATGATAAGCTATCTTCTT[G,A]GTATCAAACTACTATGGGCTTAACA | 248,969 | 83 |
| 221. | TCGGCTAGAAATGATCCAACTCTT[G,A]CTCATATTTTTTCTAATTTATATTG | 249,120 | 83 |
| 222. | CAATGGAAGACTCTTTCATTTGCA[T,C]GAAGAGCAATCTTAATGCAATCGAT | 249,387 | 83 |
| 223. | CATTTGCATGAAGAGCAATCTTAA[T,C]GCAATCGATCTTAACTTCTATCCCC | 249,403 | 83 |
| 224. | TTCATTTCCCTTCCTCCATTCTAC[A,G]TATATTAGAGAAGTACTTTTGTGCC | 249,472 | 83 |
| 225. | TCTATTGATTGGCATGGTCTACAC[G,A]TTCTTGCTCAGAGTATTGTTTGTGC | 249,537 | 83 |
| 226. | ATGGTCTACACGTTCTTGCTCAGA[G,A]TATTGTTTGTGCCTCCAAATCAAAA | 249,550 | 83 |
| 227. | AATATTCAGGTCGATATCAGGAGG[T,G]TCAGCTTGTTAAGTTTATTACACCT | 249,903 | 83 |
| 228. | TCAGTCTCTTTGCATAATGTTTCA[G,T]CTACCATATCCTCTTCTACCTCATC | 250,081 | 83 |
| 229. | ATACTATTTGGAGACTTTCGATTT[G,C]TATGAATGTCAAGACTTTTGTTGG | 250,148 | 83 |
| 230. | AGACTTTCGATTTGTATGAATGTC[A,C]AGACTTTTGTTGGAAACCGATTTG | 250,159 | 83 |
| 231. | CTTTTTGTTGGAAACCGATTTGGT[T,C]GAAGCTCCCGACCAAAGAATATCTA | 250,187 | 83 |
| 232. | TATATCATGACAGGAAGGAGGATT[T,G]ACAGTATATTTTTCTCAGTTGCAAG | 250,280 | 83 |
| 233. | ATATTTTTCTCAGTTGCAAGCTTT[C,T]ACTCCTTTGTTGGACACATGTAGTC | 250,310 | 83 |
| 234. | GTAGGAATTTGACAACTTACATCG[G,A]ATACTTGCTCAAGTTTCACCTCTTC | 250,576 | 83 |
| 235. | TAAGTTTGCTAACTCTCTTTGGGA[C,T]CTTTGTGTGCCTCTCAAATTAAGTT | 250,717 | 83 |
| 236. | CTTCTTCGGAAGAAGACTGGAAAA[A,G]ATCTAGGTGGTTGTGTGCTTTGTGG | 250,816 | 83 |
| 237. | GGAAAAAATCTAGGTGGTTGTGTG[C,T]TTTGTGGCCATGGAGAAGAGTCAGT | 250,834 | 83 |
| 238. | CTCAACTTGTTTTTtCTTCTCATC[C,T]ATCTAGAAAGCTGTTTGTTCCTTAC | 250,896 | 83 |
| 239. | CATCTAGAAAGCTGTTTGTTCCTT[A,G]CTTGGGATACTACACCGACAGTCTT | 250,920 | 83 |
| 240. | ACAGTCTTCCTTTGAGGATCAATG[T,C]CTTTCATGGAGAAGAAGGACCTTCT | 250,962 | 83 |
| 241. | AAGAAGGACCTTCTCAAAATATTT[A,G]CAACCAATTATTTTGATGCTATACT | 250,998 | 83 |
| 242. | CCAAGGATGCTTGCTGATGACTGA[T,A]ATGGTGAACAATGCAAACAAATGAG | 251,223 | 83 |
| 243. | GAAGGGGCAAATGGATATGACATT[A,C]CCACTTATGCAGATGGGTTCTCTAA | 251,313 | 83 |
| 244. | AGATGAAAAATTCAGAATAGCCTT[A,C]CAGGTTTACGTGACTTCAGTAAACT | 251,538 | 83 |
| 245. | TTCAGTAAACTAAAAACAGTTTGC[A,G]GCTATCCAAAAAGCGAACCAAATGG | 251,577 | 83 |
| 246. | GATGAGAACAACATCTTTAGTTTC[T,C]CTATTCAATAGTTTCGATCCCAAGG | 251,627 | 83 |
| 247. | ATCCTCAGTGATTGCAGACCAGCT[A,T]GTGAGCATTTGAATAATTCTTAGAA | 251,725 | 83 |
| 248. | TTGAATAATTCTTAGAATCAGGGT[C,T]TTTGCTGTTAGAGCTTCAAACTTGA | 251,758 | 83 |
| 249. | TATCTTCAGCCGAAGATGAGGTAT[A,C]CAAAATACCTAGCTTTTGAGTGATT | 251,919 | 83 |
| 250. | ATAGATGCAGATGGTGAAAAGATG[G,C]CTTATGGATTCTGGATGTAAACAAC | 251,989 | 83 |
| 251. | AGATGGCTTATGGATTCTGGATGT[A,T]AACAACACATTGGACAAACATGAGA | 252,008 | 83 |
| 252. | TCTGTAGTAAGGATTTTGTTGTTT[T,A]GCAGCAACCAAGTAAAAATTTTAAT | 252,086 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 253. | TTTTCTTTGCAAAGATAGACCTGA[T,G]ACTGCCGTCACTGAAGAATTGATAA | 252,161 | 83 |
| 254. | TGCAAAGATAGACCTGATACTGCC[G,A]TCACTGAAGAATTGATAATATTTTC | 252,168 | 83 |
| 255. | GATACTGCCGTCACTGAAGAATTG[A,T]TAATATTTTCTAACAGAGAATTTTC | 252,183 | 83 |
| 256. | TAAAAGATTTCCTCCATGTTCAAA[G,T]ATATATCTTCCCTGAAAGTCATCTC | 252,310 | 83 |
| 257. | GAAAAGATGAAAAGAATTGAAAA[A,T]TTGGATTTCAGTGGCATAATTCCAA | 252,408 | 83 |
| 258. | GGATTTCAGTGGCATAATTCCAAG[C,T]CATTGGTCATCCAAAATGAGATATT | 252,435 | 83 |
| 259. | CATTGCCCAGATTAAAATAAATGC[T,C]CATTGGTCATCCAAAATGAGATATT | 252,490 | 83 |
| 260. | AGCCCTTCCTTTTGTTCTGTTTAG[C,G]AGTCTGTTATGATAGTGCGGCTGTG | 252,575 | 83 |
| 261. | GGAAGACATCTAATATATTGGTAT[C,A]CTACTGAGAACGTGATTAATAAGAG | 252,851 | 83 |
| 262. | AAGTGGAAGTCCCAGGTAAGTAGT[G,A]GGCAATGTTGATAGCTTACAACCAA | 253,007 | 83 |
| 263. | GTGGAAGTCCCAGGTAAGTAGTGG[G,A]CAATGTTGATAGCTTACAACCAATA | 253,009 | 83 |
| 264. | TTGTATCCCAAAAGTGCTGGTAAA[A,G]TGATATTGGAAATCCCTCTGGTCCT | 253,454 | 83 |
| 265. | ATCCCTCTGGTCCTGGTGATTTAT[A,C]CTTGGCCATACTGAAAAGGGCGTTT | 253,490 | 83 |
| 266. | GGCATAGCAAGCTGAAAAAATTTG[G,A]CAACAGAAGTTTAATTTATTTTATA | 261,788 | 83 |
| 267. | CAGAAGTTTAATTTATTTTATAAT[C,T]ATGGATTTGTAGTTATTCATAAATG | 261,816 | 83 |
| 268. | AATCATGGATTTGTAGTTATTCAT[A,G]AATGTTGAGATTCGGGTTAGTACTT | 261,837 | 83 |
| 269. | GTTATTCATAAATGTTGAGATTCG[G,A]GTTAGTACTTACTTTTGGATTTAGA | 261,852 | 83 |
| 270. | ATGTTGAGATTCGGGTTAGTACTT[A,G]CTTTTGGATTTAGATGCTCTGAACC | 261,863 | 83 |
| 271. | CCCATATTGGTTCGATTATTTGAT[A,G]AATAATAGAATTGAATCTTTTTATT | 261,911 | 83 |
| 272. | AATATGGGTTCAGAGCATCTAAAT[C,T]CAAAAGTAAGTACTAACCCGAATCT | 261,919 | 83 |
| 273. | AATTTGGTGTAGATTGCCGATGAT[C,T]CTCCCTTGGTCCTCTATCCAAGCGA | 262,136 | 83 |
| 274. | TGAAAAATTTGGTATTTTGTCC[G,C]CATATTTTAACCAATTTGCTCTGGA | 262,221 | 83 |
| 275. | AACTTGCTCTTTTCTATTACTTTTC[C,T]TTCTCTCTTTGGCTCTTCTCCTCGT | 262,304 | 83 |
| 276. | CTCCCATCTTTTCTATTACTTTTC[C,T]GCCTTTACTTTGTGGATCAACACTT | 262,735 | 83 |
| 277. | TGAGCAACCTTCTGTAAATACCTT[A,G]GACTTCAATAAAAACCGGATGGCAG | 262,794 | 83 |
| 278. | ATAAAAACCGGATGGCAGAATTCT[A,G,C]CAGCCTCCCTTATCCTCAAACAAAa | 262,826 | 83 |
| 279. | AAAAACCGGATGGCAGAATTCTAC[A,T]GCCTCCCTTATCCTCAAACAAAaAA | 262,828 | 83 |
| 280. | TCTACAGCCTCCCTTATCCTCAAA[C,A]AAAaAAAAAAAatGAAGAAAGGCTAG | 262,847 | 83 |
| 281. | ACTGGGATAGCTCAGCTTtTTTAT[T,C]TTTtACATCACCATTCTTTCCCTCT | 263,020 | 83 |
| 282. | AGCTTtTTTATTTTtACATCACC[A,C]TTCTTTCCCTCTGTTAGATGGCTTC | 263,033 | 83 |
| 283. | CTCACTTTGCAGTAGTCAAAATAA[T,A]TTTTGATAGCTTAGTTAAGCAAGGA | 263,086 | 83 |
| 284. | CTATCAGAATAAATAAAACTTCTA[C,T]TCCTATTGCAGGTTGGTACTTGGGC | 263,195 | 83 |
| 285. | AATCCAACAGATTGACTAGCTGGC[C,T]ATGCTTGTGACTTCAATCCTTTGGA | 263,429 | 83 |
| 286. | TCTTTCACTCTATATGCCAAAGAT[A,C]TTGCCTTTTTAATGACTATATTCAT | 263,737 | 83 |
| 287. | CCACTCTTTATTGCAGATGGGCTG[C,T]GTGTTATGGAATATATATTGCAGAT | 263,820 | 83 |
| 288. | TATTACATGGTCCTAATTTTACCT[A,T]ATTTATGTTCGTTATACTTTCAGCA | 264,095 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 289. | TCCGCATTATACCAAATCAGCTTG[A,C]CAATCGTTCGACATTTATTCTTATT | 264,218 | 83 |
| 290. | CGTTCGACATTTATTCTTATTGCG[C,G]TGTTGAGCAACTTGTCTCATATTTA | 264,247 | 83 |
| 291. | TTATTCTTATTGCGCTGTTGAGCA[A,G]CTTGTCTCATATTTATCTTGCTGCA | 264,257 | 83 |
| 292. | TAATTTTTAGCTTATCTAGTGTCA[T,G]CATTCTACGTTTACATGTATGCACT | 265,482 | 83 |
| 293. | TCTCTCTCTCTGTATGTGTGTGTG[C,T]GCGCGTGCGCGCGCGCATGCAATCC | 265,826 | 83 |
| 294. | AGATGGACCATGGAGACTGTTCCC[T,A]CTCTTTCCCCTATTCATGTTCGATA | 265,968 | 83 |
| 295. | ATAGTTATTTATCTGTCATCCCAT[T,C]TGGTGGTTCTGTCAGATTAAACACC | 266,057 | 83 |
| 296. | GATTCTGTCTATAAAGCATGGATA[C,T]GGATGTGACACGATACAGATGTGCC | 266,188 | 83 |
| 297. | GTGACACGATACAGATGTGCCGAT[G,A]TGACAAGTTTGGAGAAGTATGTTAC | 266,217 | 83 |
| 298. | TATGTTTTAAAGAGTGATAGCACG[T,C]ATTATTTGATAAACATAGAGTGATA | 266,461 | 83 |
| 299. | ATTTGAAGTTGAGCTTGACCAGAC[C,T]CAGGCTTGATTAACGTCAGTTAATC | 266,811 | 83 |
| 300. | TTGCTTTTGAGCTCTGACTGATAT[T,G]CTTATTTCTATTTGAAGGGTTTCAT | 267,210 | 83 |
| 301. | AGCTCTGACTAGGTGCAAACAAAA[T,G]TTATTTATTCCAAATGCCTGTGCTT | 267,441 | 83 |
| 302. | TACACATAGTAGTCTGCCTAAAAG[T,C]ATCATGGGCTTTGCCAGTATAATGG | 267,784 | 83 |
| 303. | CATGTGCTAGTATATTAATGAAGA[G,A]CAGATGGTCTCATGCAGGTGGCGAA | 268,130 | 83 |
| 304. | CTGAACCGGGCCTCCAGTGGCTTG[G,T]CAAAAGGAGATAAACATTTGGCTAT | 268,605 | 83 |
| 305. | GAACCGGGCCTCCAGTGGCTTGGC[A,C]AAAGGAGATAAACATTTGGCTATGA | 268,607 | 83 |
| 306. | CAACAAAAATAAAaTAAAaAAaT[A,C]AAATAAAATAAGATCCTTGAATTCA | 268,934 | 83 |
| 307. | AAAATAAAaTAAAaAAaTAAAAT[A,C]AAATAAGATCCTTGAATTCAGCTGC | 268,939 | 83 |
| 308. | TGCTGTCAGAGTCCATTCTACTCA[A,T]CAAGGAAATTACAGTAGATGAATCT | 269,103 | 83 |
| 309. | ATTCTACTCAACAAGGAAATTACA[G,A]TAGATGAATCTCCTCTCCATATTGC | 269,117 | 83 |
| 310. | CTCCATATTGCAGATGCCTTTCAA[A,G]CCCGTGTGACAATCATAATCCCTTT | 269,156 | 83 |
| 311. | AGATGCCTTTCAAACCCGTGTGAC[A,C]ATCATAATCCCTTTCCAAGCAACAT | 269,167 | 83 |
| 312. | CCGGCCACCACTGTAACAGCTCCA[C,T]CCATATTTCTAATCATATAAATTAG | 269,258 | 83 |
| 313. | CTAAGAGTTAAGTCATCTATAATG[G,T]GGGATTTGGTGTAATTGAAGGAGGA | 269,359 | 83 |
| 314. | GGAAAATGCAAGAGTGCATAAAAA[C,T]GTCATAAAGATGATAATTGAGGTGG | 269,733 | 83 |
| 315. | AAGATGATAATTGAGGTGGAAAtT[T,C]TTTTGTAGAGAGGTTGATGCTGTTG | 269,764 | 83 |
| 316. | ACTCTTTGGTTACGTGGCCTTCTA[A,C]AAGGCTATCGAAAGATGTGTCTCGA | 270,299 | 83 |
| 317. | TCATTTTCTGGTCAGGCTGAAATG[T,C]CAATGCCCTCAGTTGTTTCTTCTTT | 270,358 | 83 |
| 318. | AAGCTAAGCGCCATATGTTTCCTT[C,T]CTGGATGAACAAAAGTACTGGAAAA | 272,395 | 83 |
| 319. | CATCTTGCTTCGGCTTCCGGCTCA[T,A]TTCTGAATACTGCCCCCCCATCAGC | 273,088 | 83 |
| 320. | GCAAAATCTCCTGCCACAGATTAG[T,A]TGAAGAATCTGCTAGGGCACTACTA | 273,139 | 83 |
| 321. | TCTATCAAAACTGCTTACCCCATC[A,G]AGCTTCTCAGTTGCAACTAACAAGC | 273,602 | 83 |
| 322. | TTCAAGATACAAGGATGGACAAGA[T,G]TATTCTGAAGCTAACTAAATGATCA | 273,906 | 83 |
| 323. | AAACTTAGCCTCTTATCATTATAT[G,C]AAATGCCAAACTTAGCCTCGCCGTT | 274,316 | 83 |
| 324. | GATTCTCTAATGGAATGATATGCT[T,A]CTCTATTTCGACTAGTCAACTCACC | 274,376 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 325. | AAAAaCAAGTACAATTACCAGTAC[T,C]TAATCAATTCAAGAGTACATAGCAT | 274,586 | 83 |
| 326. | ACAGTAGTTAGAAaTTAAAAAAGT[G,A]CAATTCTGGATGCTAGGTCATTTCT | 274,696 | 83 |
| 327. | AAAGTGCAATTCTGGATGCTAGGT[C,T]ATTTCTGATGTTTGATGATTTATAA | 274,715 | 83 |
| 328. | GTGCATATATAAATTTTTAAACAA[A,C]ACTTAGCGAAAATGAAATTAAGAAG | 274,981 | 83 |
| 329. | ACCTTATCAACCTTAACTACCTAC[A,G]TTTAAAATCCTTATAAGAGCAGGAT | 275,070 | 83 |
| 330. | TTTAAGCCCCATACTAATTTCTCT[G,A]TGTCGTTTATAAACCCATAACCTGA | 275,155 | 83 |
| 331. | TTGAGGTTTATCCTGTGTCACTTC[G,A]TATAGGAGATTATGTTATGCACAAA | 275,692 | 83 |
| 332. | AGCTTAATCACTATACCTCAAGGC[A,G]GATTTATAACAAATGGATTATCAGA | 275,815 | 83 |
| 333. | AACACCAAAAATAAACCATGGGAA[G,A]AAGGCAGCAGCATCTACAGCCTCAA | 275,916 | 83 |
| 334. | TTATGCATATCTAGGTCTTTGATT[A,G]TACAATAACCTATAAAGTATCATAG | 276,097 | 83 |
| 335. | TATAAAGTATCATAGAAGTCCCAA[C,A]ATCATGAATTGAATTGTCTACGAGT | 276,132 | 83 |
| 336. | CCCAGTTTTTGTGCTAACTGCAAA[A,G]AAaGGAAATGCTCCCTGATCCTCCA | 276,667 | 83 |
| 337. | ATAGCTAGACATTTGGCGATCTAT[G,A]GTCGGACTTGAAATCTTATTTTGAC | 276,971 | 83 |
| 338. | GAACAGTCTTATCGGCTGTTAAAG[T,G]GGCATGATGCTGTGCTCCTAACAAT | 277,896 | 83 |
| 339. | GTACTCACACATTTAAAGAGAAGA[T,C]AAGATGGGGAAATATGAGAGGAAGT | 278,554 | 83 |
| 340. | GAGAGATAAGAGAGATAGGGTGGA[C,G]AAGAGTAGAGATACAAAGCCACTTG | 278,613 | 83 |
| 341. | AAAAAaGAAGAATAAAAGGGAGAC[G,A]AGAGAGGGATAGGAGGTGAGAGAGA | 278,666 | 83 |
| 342. | ACCCCTATTTCGAATTGGAGTTCA[A,G]AGGTCCTCCTCCGGCCTCAGCCGCC | 278,867 | 83 |
| 343. | TCCTCCGGCCTCAGCCGCCCTCCG[C,T]TCCCTTGACGCTGGCTCGCCGGTTG | 278,898 | 83 |
| 344. | CATCTGAAGGCCTCCGATGATCCA[A,G]TGAGGTCTCCCCCGCTTTTCTTCCC | 278,976 | 83 |
| 345. | CGATGATCCAATGAGGTCTCCCCC[G,T]CTTTTCTTCCCTCCCTCCACCCTTA | 278,990 | 83 |
| 346. | CTTCCCTCCCTCCACCCTTAGCAA[G,C]CTCAGAAAGAGCTCCGACAGCCACC | 279,020 | 83 |
| 347. | TCGATATGGTTCGACATGGCCTGC[G,A]TCGTCCGATTTGGGATAGTTCAGCG | 279,185 | 83 |
| 348. | ATGATATCAAACATGGTGGACTCT[G,A]AAGTATTTCAAGGAAAAGAAAAATA | 279,747 | 83 |
| 349. | AGTATTTCAAGGAAAAGAAAAATA[T,A]AGAGAAATTCACCAAATCTTGAATG | 279,773 | 83 |
| 350. | TTCAAATAGTTTTCAAGCAAGGTA[T,A]GACACTAGCAAGAAGAATCTCGCAA | 280,334 | 83 |
| 351. | CGGGTCTTGAATTAAGCTTTTAAT[C,G]AACTGCTTAAATGCCCAAAATGGAT | 280,447 | 83 |
| 352. | CTCAACGCCAAACCACTGCAGCAG[C,T]TGTGCCGAAGTAGTTTGTCCAGGTTG | 280,840 | 83 |
| 353. | AGTAAAGATATAACTGTTAAAAGA[C,T]CAGACAAGTTTCACGGTAATTCTAT | 281,259 | 87 |
| 354. | GTTTCCGATGGGAGCGAGAAAGA[G,A]GCCAGGGATTGGGAAGCTACAAGAG | 282,139 | 87 |
| 355. | GGATTGGGAAGCTACAAGAGCGAG[T,C]TACCGGAGTGGGAGGAAACCTTGG | 282,169 | 87 |
| 356. | GATTGGGAAGCTACAAGAGCGAGT[T,G]ACCGGAGTGGGGAGGAAACCTTGGG | 282,170 | 87 |
| 357. | TACTATATTTAGTTGGAGGTGATC[G,A]TATATAGAAATATGATAAAATTTAT | 282,989 | 87 |
| 358. | GATAAAATTTATAAATATATTTTT[C,T]AATATAAAATAATTTTAAAAAAaTT | 283,027 | 87 |
| 359. | TTAAAAAAaTTATACAGATATCTC[C,T]TTAAGTTTATTTCAATTTCATTTAT | 283,066 | 87 |
| 360. | TAAATTAAATCGTCTCAATTAGA[C,T]CTTCCAAATTATCGAAGTGTATCGA | 283,123 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 361. | TTATCGAAGTGTATCGATGTGCTC[C,T]TTCCGTTCATCTTCGTTAACCAAAT | 283,156 | 87 |
| 362. | ATTTTTTtAAAATAATAAAAATAT[T,C]CTTGATTTCAATTCTCAGTCGAGCA | 283,235 | 87 |
| 363. | CGAGCATTAGCCAAAGCGTCAAAA[G,A]GTAAAATCACATGCCTCACGTGAGC | 283,279 | 87 |
| 364. | CAAAAGGTAAAATCACATGCCTCA[C,T]GTGAGCCATTATTTTGGATGCCCTA | 283,298 | 87 |
| 365. | GAGAGAGATCTTCGATCAAGCTAG[C,T]CGTGGTAGAGAAGGAGTCGCCATGT | 283,390 | 87 |
| 366. | AGATCTTCGATCAAGCTAGCCGTG[G,A]TAGAGAAGGAGTCGCCATGTACGCC | 283,395 | 87 |
| 367. | CCGCAGGTGGAGAAGAAAAAATTC[A,G]TGAAAGAAAAaGAAGGTTACCGATA | 283,443 | 87 |
| 368. | TGAAAGAAAAaGAAGGTTACCGAT[A,G]GAGAAAAAAGCAATGAAGGGTTTCC | 283,468 | 87 |
| 369. | GTGGAACCAGATTGCTACTGAGAA[C,T]CTTTGGGACCACCGCAAATCCTGGT | 283,569 | 87 |
| 370. | ACCAGATTGCTACTGAGAACCTTT[G,A]GGACCACCGCAAATCCTGGTCGGCA | 283,574 | 87 |
| 371. | CTTTGGGACCACCGCAAATCCTGG[T,C]CGGCATTTCTTTAGATGCAGAATGT | 283,594 | 87 |
| 372. | TGTTTAACTTCGAATTGTTTGTCA[A,G]GTAAATGGGGGCTCTGGTTCTTCC | 283,696 | 87 |
| 373. | CTGGATTGTTATGCTTTTTTATAT[A,T]ATCGATTTTCTATTTTAAATATACT | 283,883 | 87 |
| 374. | AATTCTTTATGAAATGAAAAAAAa[T,A]TTCTCTAGTTGTTAGCAATGATGGT | 284,020 | 87 |
| 375. | AGTGCTACATTGTTAATGGTACAG[T,C]ATACTTATAAGTTTCGATGAACACC | 284,077 | 87 |
| 376. | ATTGTTAATGGTACAGTATACTTA[T,C]AAGTTTCCGATGAACACCCCTGATAT | 284,085 | 87 |
| 377. | TATACTTATAAGTTTCGATGAACA[C,T]CCCTGATATTTTATTGCTATTACGC | 284,101 | 87 |
| 378. | CCTATAAGAATTTTTTTtGTCACA[C,T]GCATCAAAATATCACAACTTTTAAT | 284,245 | 87 |
| 379. | TACAAAAAATATAAAAAATTTGAC[T,C]GACAAATCACAATGTATCAGTGCAT | 284,302 | 87 |
| 380. | ACATACAAAATACAATGAAGTCCC[A,G]AATATATCTAAAATGGCCTTGATAC | 284,392 | 87 |
| 381. | TCTGAGACAAATAACCTACTGCTG[A,G]CTGGAAGGGAGCTGGTTGGGAGAAA | 284,514 | 87 |
| 382. | GACAAATAACCTACTGCTGACTGG[A,G]AGGGAGCTGGTTGGGACAAAGAATG | 284,519 | 87 |
| 383. | TAGTAGCTTCTGGCTGGGAGGACA[G,A]ATGCTGGAGGGAGCTGGCTAGGAG | 284,583 | 87 |
| 384. | GCTGTAAGGACAGAGGTTGGGAGG[A,G]AACTGGTTGGGAGAATGTACCCACT | 284,646 | 87 |
| 385. | GGACAGAGGTTGGGAGGAAACTGG[T,G]TGGGAGAATGTACCCACTGAAGTTG | 284,653 | 87 |
| 386. | TTTGGTCTATAAAAAAaTACAAAA[T,A]GATAAGTAAATATTTATTAATTTTA | 284,728 | 87 |
| 387. | TAAATATTTATTAATTTTAATATT[A,G]AATATAAATGTACCAGTGATCTCTC | 284,759 | 87 |
| 388. | GCAAGCCCTGGAGTTATGGACCCA[T,C]TGTTGACAATTCTTGCACCTTAAGG | 284,893 | 87 |
| 389. | AAGCCCTGGAGTTATGGACCCATT[G,A]TTGACAATTCTTGCACCTTAAGGAT | 284,895 | 87 |
| 390. | GCCTATGTTGCTTTAGTGTACCAT[G,A]TACTAACAAAATATTCTGCTTCCTT | 285,123 | 87 |
| 391. | ATACATAATAGCTATTACAGCATG[G,A]CAGCATGGGATGCCAGTTAAATCTT | 285,179 | 87 |
| 392. | CAACAAATCTATCATTGTGATGCT[T,C]AATTTCAATTTTGTAGCCTCCTCCC | 285,265 | 87 |
| 393. | CCATGGCCTCTAACTTTTGCTTTTT[C,T]CAATTTCTTTTGAATCTTAGGACAT | 285,331 | 87 |
| 394. | CAATAATATACTTGTTGAATGACT[C,T]GCATATGTTGTTCAAAAGCATGCTA | 285,487 | 87 |
| 395. | AAAGCATGCTAGACTTCCTTCTAT[C,T]GCTGAAAGCATGCCTCGCCCATAGC | 285,526 | 87 |
| 396. | GCCCATAGCTCTGGTGGATGTTGT[C,T]GAAGCCACTGCCATGTTGTCTCATC | 285,567 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 397. | ATAACACTCTTGAAGGTCTCCACA[G,A]GACCCAATAAAAGAATTGAAAAAAa | 285,774 | 87 |
| 398. | TCCACAGGACCCAATAAAAGAATT[G,A]AAAAAAaTAAATTACGTATAAAATC | 285,792 | 87 |
| 399. | AAGAGAATTGAACAAGTTTTTTAA[T,C]AAGATAAATAAACCTTCTGTCTGTC | 285,851 | 87 |
| 400. | TAATAAGATAAATAAACCTTCTGT[C,T]TGTCAGACATAAAGATCCATCCATG | 285,872 | 87 |
| 401. | TCTCTACAACAGCCCATGCAACAG[A,G]AAAAATATTTTCATTTCTATCCTTC | 285,983 | 87 |
| 402. | CCAAAAGAGCCCCTTCAAGTGGCAA[C,T]TGTCCAAACCAATGATAGATCTGCA | 286,057 | 87 |
| 403. | TAGATCTGCAACCTTTGATAAAGC[C,T]CTGCTTGTATGCTGCAAGACAACAG | 286,097 | 87 |
| 404. | AACAGTATAACCTTCTAAAAATGG[G,A]CTGGCTACTCTCATCGACCTACTAA | 286,142 | 87 |
| 405. | CTTCTAAAAATGGGCTGGCTACTC[T,C]CATCGACCTACTAACATCCAACAAC | 286,153 | 87 |
| 406. | CCCTGTGGCTGTCCTAAATAATCT[C,T]CAATGCTCTACTTTGGCCCTATAA | 286,267 | 87 |
| 407. | TTATTTGATAGGTAAGCTCGCTCT[G,A]TACAGAAAAAGTATGAATCTTCCAC | 286,492 | 87 |
| 408. | CCTCCTATATGCTATAAAGCCACA[G,A]CACTTTCTTAAACTGTGTGACATTC | 286,609 | 87 |
| 409. | ATTGAATTCAGGATATTCAGAACC[T,C]CGAATACCAGCATCTGAATCACTAT | 286,712 | 87 |
| 410. | TAGGCTGCTCCTCTCCAAAAAAAT[C,T]AACTCCCTCATGAGGTAGAGAATGA | 286,816 | 87 |
| 411. | GGCTGCTCCTCTCCAAAAAAATCA[A,G]CTCCCTCATGAGGTAGAGAATGATG | 286,818 | 87 |
| 412. | CAGGCAACCGTAGGATTTGAAGTG[A,G]CAGCTTCAATCCCTTTCAATTTCTT | 286,980 | 87 |
| 413. | TTTTCATTACCAATCTCTTTACCC[A,G]AGTTCTTGGTGTTGATGCATTGTAT | 287,059 | 87 |
| 414. | ATACACACCAACAAGCTTTGTTTG[T,C]CTGTTTCAGATAAAGGAACATCACC | 287,143 | 87 |
| 415. | CACCAGCATTTGCTTGGTGCTCAA[C,T]ATATACCTCAACCATATCAGCACCT | 287,189 | 87 |
| 416. | GCATGACATCTTAATTTCCTCAAG[C,T]CATTTTGTAATGTCTGTCATGGCAT | 287,269 | 87 |
| 417. | TCAAGCCATTTTGTAATGTCTGTC[A,C]TGGCATTAGGTAATAAAAATGGTTA | 287,288 | 87 |
| 418. | CTGTCATGGCATTAGGTAATAAAA[A,G]TGGTTACAATTTGTGTATCCTAACT | 287,307 | 87 |
| 419. | ATTAGGTAATAAAAATGGTTACAA[T,A]TTGTGTATCCTAACTAGCTCATCAT | 287,317 | 87 |
| 420. | TTAGATGGTATTTAAAAGATCTAC[T,C]ATAATGAATTTGTACAGTAAATAAG | 287,447 | 87 |
| 421. | AAGTTAGAGTCTATCTCTGCACAA[T,CT]GAATAAGAGACATAGAATACTAAAA | 287,494 | 87 |
| 422. | AGAAGAGAATCTGATCTTTTTCTT[A,G]ATAATTGGGTTAATCTGATATAACA | 287,626 | 87 |
| 423. | ACATGTACAAAAGATAAAGGACAC[T,A]AAAAAATACTAAGTTAATCAGAGTC | 287,685 | 87 |
| 424. | GTGGATCCTATCTGTCATGCTCAC[G,A]TATATCAAAAATAGGACCACAAAAT | 287,840 | 87 |
| 425. | TGGATCCTATCTGTCATGCTCACG[T,C]ATATCAAAAATAGGACCACAAAATA | 287,841 | 87 |
| 426. | CAAAATATATGAGGACAAAGGGAC[C,A]ACAAAAATCAAAGAAAAAAaTCCTA | 287,884 | 87 |
| 427. | GTATCGGTTTACAACCATAAAATC[C,T]TAAAACTATCGGTTGGCCACTAAAG | 287,937 | 87 |
| 428. | AGATGTATTATCGGCAAAAGAAGA[T,C]ATAAGGCTCATCCACAGATAAAAAT | 288,049 | 87 |
| 429. | CACAGATAAAAATAAGGTATTCAA[G,A]AGGCTATCACGCTCGTGCACAAGGG | 288,086 | 87 |
| 430. | TAAAAATAAGGTATTCAAGAGGCT[A,G]TCACGCTCGTGCACAAGGGAGGAGA | 288,092 | 87 |
| 431. | GGATAGCATTATCATTTTCAATTA[A,G]TTTTTATATAATGAATATAATCACA | 288,461 | 87 |
| 432. | ATGAATATAATCACATAACTCTTT[G,A]CATAATGCTATCTTCATCTTAATTT | 288,496 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 433. | AAAAGCTCTTTATTGAATAAATTT[G,A]GATAGACATTAAAACAAATTTAATA | 288,552 | 87 |
| 434. | GATAGACATTAAAACAAATTTAAT[A,G]ATTACATATGTAGCTTTATTGAAGA | 288,577 | 87 |
| 435. | TGTAGCTTTATTGAAGATATTTCT[G,A]TCAGGTATAGATTATCATCATTTAG | 288,610 | 87 |
| 436. | AATTTTTTtATCATTTTTTtATTT[C,T]ATTTTTTATACTAAATATTATAATT | 288,726 | 87 |
| 437. | TGATCACATTTATCAACTTTAAAA[A,C]GTGATTATTTTAGGTATCAAAAATT | 288,915 | 87 |
| 438. | ATTTAAGGATTGAAAGACTTCACC[T,A]TTATTTtGTTTTTGATCAAAGCTTG | 289,120 | 87 |
| 439. | TTTGACTGATTGAATTGGAAACCG[G,A]TTATCTATCCAAAATAATATGAAAA | 289,258 | 87 |
| 440. | AAAAATAATCAAAACTTGGTCAAA[T,C]AGGATGAATCGGATGAACCAATCAG | 289,314 | 87 |
| 441. | GTCCTAAATCTCTCCCTCTCTCCT[T,C]CATCACTGGAATCTAGTGCCTCCCA | 289,530 | 87 |
| 442. | ACTGGAATCTAGTGCCTCCCAACT[T,C]TGCCCTCGAGAGTTTCTCCAAACCT | 289,559 | 87 |
| 443. | AGCTTCTCTCACACCTAGTCTCTA[G,A]GGTTTTGTGGTGCTCAAGGCCTTTC | 289,610 | 87 |
| 444. | CTAGGGTTTTGTGGTGCTCAAGGC[C,T]TTTGGTGGTGGGGAAGATGGAGCTG | 289,631 | 87 |
| 445. | CACTCATGGTACTCACCTCAAGGT[T,C]ATCTATATTGGGTCCTTTCTCATTT | 289,922 | 87 |
| 446. | CGACAACACCACTACTATCCACCA[C,T]TTCATCGCTAGCCCTCCCTCCTTCG | 289,988 | 87 |
| 447. | TCCTTCGTCCCTTCCACCCTACAA[G,T]GACTAAACAAGCCTGCTCTATTGAC | 290,031 | 87 |
| 448. | AGGTGGATAGTGGGGAGCATAAG[A,G]AGCACTTGAGAGTAATAAAGGAGTA | 290,198 | 87 |
| 449. | GATAGTGGGGAGCATAAGAAGCA[C,T]TTGAGAGTAATAAAGGAGTAAGGAG | 290,203 | 87 |
| 450. | TACTGCATGTGATAGTGGGGAGGG[A,G]CATGTGAGATATACAACGGCATTGG | 290,283 | 87 |
| 451. | CATTGGTGGATCAATCAAACTGAC[G,A]TGCACCAACCATGCGTGAAGAGTGA | 290,327 | 87 |
| 452. | GTGAAGAGTGAGGAAGGATGCTTT[T,C]CGAGCATGTGAGATGAGGGCAATTA | 290,366 | 87 |
| 453. | GAGGGCAATTAAATTGGCCAATCA[G,A]ATCGATTAGACTGGTCAACCCAAGA | 290,405 | 87 |
| 454. | TAACTTGATGGTTCACTATCTAAT[T,C]CGATTTTAAAAATATTACTTTTTTA | 290,461 | 87 |
| 455. | ATCTAATTCGATTTTAAAAATATT[A,G]CTTTTTTATTATCTTTTATCGCACT | 290,478 | 87 |
| 456. | TCAAAAATATAACAGGTATCATAT[T,A]ACAACTCCAATGAAAACAATGAAAG | 290,840 | 87 |
| 457. | ATTAATGCGCACATGAGAAGTTCA[C,T]GACTCACAAATCTCAGGAATGGTAG | 290,902 | 87 |
| 458. | AATATTATTTTGGTATCAATGCAA[T,C]AAATACAAATATACAATGAGGAGTC | 291,108 | 87 |
| 459. | ACCTTGAATGGTAGATATTAAATA[T,C]GGATAGGCCAAACAGTGGGGTCCAT | 291,394 | 87 |
| 460. | ACCACATGATGATCACTGGGGCCG[T,C]TAGTTCATTCGATCTTGATAGATCC | 291,719 | 87 |
| 461. | AGATCCGATCCGATCTGAATCAAT[T,C]AAATTTAAAAATTAAAAaTTAAAAA | 291,763 | 87 |
| 462. | GTGAATCAACACCCACTTAATTGA[A,C]ATTTCAAAAGAATCCCCATGCTACA | 292,995 | 87 |
| 463. | GAATCCCCATGCTACAATGGCTCA[A,T]GGATACAAAATCACCACCCGTTGAG | 293,029 | 87 |
| 464. | GTTCCAACATAAAACCCATCAAAC[G,A]ACGCTGAGTTACCCTCCAATTGCCG | 293,078 | 87 |
| 465. | AGATGCCTAATACTCATCACCTGT[A,G]ACAACCAAATTTTTGATGATATTTG | 293,152 | 87 |
| 466. | ATGAGAAGAATATTATGAGAATAG[G,A]TGCAAAAGGCTTTTCACATGGAATC | 293,337 | 87 |
| 467. | TCACATGGAATCTGGAGAATACTT[C,T]TATCAGGAAGATGTGAAAATAGACC | 293,375 | 87 |
| 468. | AAAACAAAATGCCACAATTTTGGT[A,G]TCATATACTGAGATTATATGCTTTC | 293,440 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 469. | TGAATTGACTGACGTAGAAAACA[T,A]AGTATAAGTGGGTGCAAAGGTGGCT | 293,562 | 87 |
| 470. | AGTATAAGTGGGTGCAAAGGTGGC[T,A]ATCTTGGTGCCTTAGGAAGTCTTTT | 293,587 | 87 |
| 471. | AGTGGGTGCAAAGGTGGCTATCTT[G,A]GTGCCTTAGGAAGTCTTTTGCTCAA | 293,593 | 87 |
| 472. | GCACAAAATAGGTGAACATCTTCA[T,C]ATCCCATGTTCCTTCTTCCTGTGTG | 293,792 | 87 |
| 473. | ACATGAGCATATGCTCACCAAAGG[C,G]CAACCTATTTTGTGTGGTTTCAT | 293,909 | 87 |
| 474. | GTTTCATGTGCATTCCATGCAAAA[G,T]TCTTGGACTTTACACAGGGATAGGC | 293,592 | 87 |
| 475. | TGTGCACTCCATGCAAAGTCTTG[G,A]ACTTTACACAGGGATAGGCATGCTT | 293,958 | 87 |
| 476. | TTGGTGCCATCTGCTTTTCCCTTC[G,A]TGTTCTTCATTAGCACAGGCACCCA | 294,075 | 87 |
| 477. | aAAAAAaGACTTAAAGCTCCACC[C,A]TATCACAAATCTCCTTAGCTTCAAC | 294,141 | 87 |
| 478. | ATTCTTTCTTGTTCTAGACCACTC[A,G]TCACTCTATTTCTTTGTTTTCATCA | 294,191 | 87 |
| 479. | TCTGGCTTTACTGAAGAAGTATCT[A,G]ATCCATACATATCACCATTTTGCAA | 296,049 | 87 |
| 480. | CATGGGAAGTGAGTATATGGTTTC[G,A]TTGAAAGCGAGAGGAGACTTTAAAG | 296,795 | 87 |
| 481. | AGCGAGAGGAGACTTTAAAGACAA[A,C]CCAATGAGATCATGACCTGTCAGCT | 296,825 | 87 |
| 482. | CCTCTGGGTAATAATGAAAACATC[A,G]GTCTCATTAATCTCATATGCTCCAT | 296,939 | 87 |
| 483. | CAAGTAAACTTTTCTACCTTCCAA[G,C]ACCTTCAACTGCGGAGGGAAAGGTG | 297,059 | 87 |
| 484. | TTGATTAAAACATACTCTTGTGGC[T,A]GAACACCTTCACCAGAGGCTCTATC | 297,123 | 87 |
| 485. | TGGAATTTGCAATATCACTGTCC[G,A]ATAGACCAAAGCTTCTCATTATCTC | 297,402 | 87 |
| 486. | TAGTAGAATCCTCCTCTGTGGAAG[A,G]AAACACAGGTGGATTTCCAAACTGC | 297,565 | 87 |
| 487. | TTGTCCCGAGCCTTGAACAGCTAC[C,A]GATAATCTACAAGAAATTTCAACCA | 298,363 | 87 |
| 488. | CAATAGCCTGACAAATACAATAAG[A,C]CCCAGCCATAATAATGCTTTCCCTC | 298,444 | 87 |
| 489. | ATCAAAAGATCAGGCTCGCAAACA[A,T]GCTTCGGATTGAGAAAACCAATAAA | 298,497 | 87 |
| 490. | ACCTATCACGGGTCAAGAAAA[C,G]GATTGGGTCACTTTGGTCTACTATT | 299,935 | 87 |
| 491. | CTACAACAAGTCAAGTCATGATGG[T,G]TTGAGCTGCAGTGAATTGGGTTTGG | 300,085 | 87 |
| 492. | CAAGTCATGATGGTTTGAGCTGCA[G,T]TGAATTGGGTTTGGTTTGGTTGCGT | 300,096 | 87 |
| 493. | ATTTAGCAACGTTTATGTTTTGAC[T,C]CAATCCGGCTCATCTTGACCATGCC | 300,272 | 87 |
| 494. | AACGTTTATGTTTTGACTCAATCC[G,A]GCTCATCTTGACCATGCCACCATGA | 300,279 | 87 |
| 495. | ACGTTTATGTTTGACTCAATCCG[G,A]CTCATCTTGACCATGCCACCATGAT | 300,280 | 87 |
| 496. | ttGCCCCCTTATATGAATCAGATC[A,T]GGCATCCGAGAATGTAATCAAGTTC | 300,382 | 87 |
| 497. | AAGAAAGAATAGTTCGGAATGAGA[A,G]TTTGTTCCAAAGTTATGTTGGTCCC | 300,451 | 87 |
| 498. | TTTTTAGCCCACTTGTGGTGTGGA[C,T]GAATGTTTCTTTTAGTAGTTGCATT | 300,509 | 87 |
| 499. | ATCTTGAGTATAAAAGGCTCTTAC[T,C]CTCTTTCCACCTTCGATCCGACTTC | 301,022 | 87 |
| 500. | AGCCAAACCTCCTTCGGTTTCCTC[C,T]TTTGATTTCCTTCTTCGATCCTCCT | 301,236 | 87 |
| 501. | AAGAAGCTGTACTCATCAGCACTC[G,A]ACTATCACTAAGGGAGCCCAAATCT | 301,307 | 87 |
| 502. | ACTCGACTATCACTAAGGGAGCCC[A,G]AATCTATGCCATTTTATTTCTTCTT | 301,327 | 87 |
| 503. | GTATTGCTTGGCACCTCGGTCACT[C,T]GAGATCTAGGATTTTTTTTtCTTA | 301,409 | 87 |
| 504. | GCACCTCGGTCACTCGAGATCTAG[G,A]ATTTTTTTTtCTTATTTTAATGGC | 301,419 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 505. | TTTATTTAGTAAATAGATTAAACA[G,A]ATTGAGTCAGATCAGTTAAACATGT | 302,448 | 87 |
| 506. | GTATTTATCCTCACCCACAGATTT[A,T]GTGCCGTCGAACTTTGGTAGCTGGC | 303,638 | 87 |
| 507. | ACAAACAAACCCATGGCATAGGGT[A,G]CACTTTGCTCTAAATCACCACTCAT | 304,506 | 87 |
| 508. | AATTAGGTATAATTTTCTCAATTG[G,A]TTATTGATTTGAAAATTTTTAAAGA | 314,020 | 87 |
| 509. | GTTGCCATCGATAGAGAATAATAT[T,C]TTAAATTAATTAGTAGTAAAAATTC | 314,126 | 87 |
| 510. | GAATAATATTTTAAATTAATTAGT[A,G]GTAAAAATTCAATCTCTCAATTTTT | 314,141 | 87 |
| 511. | ACTCAACTGATTGTTTTAAAAAAa[T,A]AATAAATTTTATTTAAAATCTAAAC | 316,153 | 87 |
| 512. | CCGGACCAGAAGATCAGCAAACTG[G,C]TCGGCATTGTACACGTTTCGTGTAT | 318,252 | 87 |
| 513. | TAACAATAATAGGAGAAAAATACA[T,A]GAAAACTGGTGCACACTGCAGGCAC | 318,855 | 87 |
| 514. | TGATGAGACGAGGGGACAATAAAT[G,C]CAGTCTACGAATGTATTAAATGGAG | 318,924 | 87 |
| 515. | GGAGAACTTGCTCTTATACCTTGG[A,T]ATTCGAGACTAGACCTTATTTTCCT | 318,970 | 87 |
| 516. | TATACCTTGGAATTCGAGACTAGA[C,T]CTTATTTTCCTTTGACCAATGTAGT | 318,984 | 87 |
| 517. | ATAGAAGATGAAAAATTGGTGGAT[A,G]TTAGAGAGTATTATTAGGCATAAAC | 319,035 | 87 |
| 518. | TAAATCAACCTTAGACATGAACCA[T,A]GGAGGATTCAAAGCAAAGTGTGTTC | 319,171 | 87 |
| 519. | TACCATACTTTAAATACAATGCGA[G,T]GAAAGAGATCGAGTAAAGTTAGCCC | 319,258 | 87 |
| 520. | TTTAAATACAATGCGAGGAAAGAG[A,G]TCGAGTAAAGTTAGCCCTATGAGAT | 319,266 | 87 |
| 521. | TGAACTGGATACAAGGTGGGAAG[A,G]AAAGGAGATGGGTTGATATAGAAAG | 320,075 | 87 |
| 522. | TGGGTTGATATAGAAAGGGGAAGT[G,T]AAAAGGATGGTGGGTAGATAAGGG | 320,108 | 87 |
| 523. | CTTGAATGCTGAATTTGAATGGTA[G,A]TAGCGTCATAGGCTCGCAAGTTTTA | 320,392 | 87 |
| 524. | TGAATGGTAGTAGCGTCATAGGCT[C,T]GCAAGTTTTAGCCTAGAAAGTGGAA | 320,407 | 87 |
| 525. | AGTTTTAGCCTAGAAAGTGGAACT[T,G]GATCAGAGTTTTTTtATTAGAAAAa | 320,435 | 87 |
| 526. | CAGTAACCATCATTGGACTACTTC[C,T]ATGAATTATGGCTTAGGCTTGGAAC | 321,370 | 87 |
| 527. | TTACTTGGTTTCCGGCCATTTTTT[A,T]AACTTGAATGCTGTGGCCATACTCT | 321,452 | 87 |
| 528. | ACTTGAATGCTGTGGCCATACTCT[T,A]AAGAATATCATTATGTTTTtCTGA | 321,478 | 87 |
| 529. | CCATACTCTTAAGAATATCATTAT[G,A]TTTTTtCTGAAAATATATGTGGTGA | 321,493 | 87 |
| 530. | GGTCCATGCATGGATCCAAAACTT[A,T]GGAGCACTATTCCTGGGAAACGTGG | 321,758 | 87 |
| 531. | AATTAGGTTTAAGCCCTTTAAAAG[G,A]GCCTGTGACGAACAGTGAACAGCAG | 324,295 | 87 |
| 532. | TAATCCACGTATTTTGATTATTTT[G,A]TTTTATTTCCTTTTTtCTTCCTGCTG | 324,624 | 87 |
| 533. | GATAAATGGAGCTAAAACCTTTGA[C,T]GCTTATACAAAGAATAACTTCAGTT | 325,487 | 87 |
| 534. | AGAGATAAGCCTAAACCATTGTCT[G,A]GTGCAGAGATTTTAAAGATGCTAGA | 325,761 | 87 |
| 535. | GTCTTTTGGGAGCAGAAATGTGAG[A,G]GCTAGATACAATCAATCCAATACTA | 325,826 | 87 |
| 536. | AGATACAATCAATCCAATACTATT[T,C]TTAATTGGAGGAAAAGAGTATTCT | 325,854 | 87 |
| 537. | ATGCATATTGAAAAAaTATTTAT[G,C]AAAATATTATGGAGACAATAAAGAA | 325,956 | 87 |
| 538. | GTTAAGTAGGTGTGTGAGTGAAAA[G,A]AAGCAAAAATTTTTGATATGAAGA | 326,189 | 87 |
| 539. | ACAAAACAATATCTCTGATGATTT[C,T]TTTTTTTtGGCTTTAGATTCATCAT | 327,134 | 87 |
| 540. | ATCTCTGATGATTTCTTTTTTTtG[G,A]CTTTAGATTCATCATTTGCTTTCAA | 327,144 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 541. | AACTATAATCAAGCCAAAACACAA[C,A]CATACCTTTTAGAATCAGAATAAAT | 327,847 | 87 |
| 542. | TTATATCTTTGCTTGTTTATTATG[C,T]AACAAGTATGCAATTAAAGAATCAT | 327,958 | 87 |
| 543. | TATCTTTGCTTGTTTATTATGCAA[C,T]AAGTATGCAATTAAAGAATCATGAA | 327,961 | 87 |
| 544. | ATGTTTGTTTGATTAATGCTACAT[C,A]CATTTAAGTTTCTATCATTTATATA | 329,332 | 87 |
| 545. | TCATATCTACCACTAGGTCAAAAT[T,C]ATTTTATCAAAAGGAGTATGAAATG | 329,711 | 87 |
| 546. | TTTTATCAAAAGGAGTATGAAATG[A,G]TAAGCTGTTCAAATTGTTGTATTAC | 329,737 | 87 |
| 547. | GTTTACATGTGTCTCTTAATTTTT[C,T]CTCATAAACATATGATAGATGAATC | 329,798 | 87 |
| 548. | AAACTAGATCATAACCTATTGTTG[C,A]AAGGGTGCAGAAGGATGAATAGTC | 330,065 | 87 |
| 549. | TAATCAATTGTTAATTCTCATGCA[G,A]TAAATTTTTCTCATCCAATTTGTAT | 330,205 | 87 |
| 550. | AGGGGCTGGTTATAAGTTAATTAT[A,G]ATTGAGACAGCAAAGACCATTCACA | 330,551 | 87 |
| 551. | AAGAGAAAATCCATGAAGAAAAAA[C,T]ATGTAGATATGCAAGCAAAGTTACA | 330,610 | 87 |
| 552. | TAGTTTGGTTGGCTAACATGATTT[A,T]GTTACACACTATTGGTGTTATGTCT | 330,884 | 87 |
| 553. | TGGTGTTATGTCTCTAATTTAATT[G,A]TCATTTGTTATTTGCTATTCTTTTA | 330,921 | 87 |
| 554. | TGTAATACCCGATCCATTTGGGCC[G,A]TGGATCAGGCCCAAAATCTGAGAGG | 331,052 | 87 |
| 555. | AAATTTAGAGAACGACGAGGATCG[T,C]CAGAGTTTTCTCTCGTGGAAGTCCTTC | 331,261 | 87 |
| 556. | CGAAAACAAAaGGAAAAGGGGCA[T,G]GTCCCTTATTTTTtGAATATTTTTt | 331,608 | 87 |
| 557. | TTTTTCTTTCTCTAATTGCATCAT[G,A]GACCATAGGATGAACTTGAGATGAA | 332,016 | 87 |
| 558. | ATTCATGCAGTAGGTTGGATCTCA[G,A]TCTGATCCTTATTCGAAATTTATAA | 332,093 | 87 |
| 559. | ATGATCACCATTATATATGCTATC[A,G]TTGGTATTGTATCATTGGTTTTGTA | 332,692 | 87 |
| 560. | GCTATCATTGGTATTGTATCATTG[G,A]TTTTGTATTGTTGAATCCGTGATCG | 332,710 | 87 |
| 561. | ATCTGAGAAAGATCATGAATATTT[C,T]GATTCGAGAAAGATTATAAAAGTCG | 333,063 | 87 |
| 562. | TGATAGATAATATCAGAGCTTAAC[A,G]TTATGATCATTAAGGATATGATAGA | 334,092 | 87 |
| 563. | AATATGATTTAAGTGGTATTTGAT[C,T]TTAAGATTATAATTATTCAAAATTA | 334,175 | 87 |
| 564. | TTTAATAATCTTTGGATTAGATTC[T,C]TTATTTATGTAATTCAAATCAAAAT | 334,905 | 87 |
| 565. | TTTATTTATGTAATTCAAATCAAA[A,G]TTAAAATTTCTGAGCTGATCTAAGG | 334,927 | 87 |
| 566. | GTAGTGAAGCTTATGTAATGAGTT[C,T]AAACATAGAAAGGTGGATGAAGATTT | 335,269 | 87 |
| 567. | AGATTTAATTTTGATGTGCTATGC[C,T]TAAGAGATAGTAATGATAAAGAAAC | 335,313 | 87 |
| 568. | GCTATGCCTAAGAGATAGTAATGA[T,C]AAAGAAACTTAAAAaTTTTATCGTA | 335,330 | 87 |
| 569. | GATTATTTTATTGTAGATAATGCC[T,A]AGAAGAATCCTAGACATCTCAAGTT | 335,654 | 87 |
| 570. | AATATGGCACAATATCAAACAAAT[A,G]TCTTTCAGAGCCTCCAGACATATGA | 338,811 | 87 |
| 571. | GATTTCGAGTTGTGTATGGGTCAC[T,C]AGTTTTGAGCTAATTCAATGTTTTC | 338,866 | 87 |
| 572. | ACGTGCCTAATATATGTAAATAAT[G,A]TTCTCAATTACTTTTAAGCATACGA | 339,971 | 87 |
| 573. | ATTTAAGTACTAAAAATTATATCT[A,T]TAAAGTAGCTAAGGTGTAATATAAC | 340,259 | 87 |
| 574. | TACTAAAAATTATATCTATAAAGT[A,T]GCTAAGGTGTAATATAACTATATGG | 340,266 | 87 |
| 575. | CTAGCAACCATGTATAATTCCTTC[G,A]CTAGCAACCAGGAATCCACTTCATA | 340,348 | 87 |
| 576. | CAAGTGATGATTAGGCTATCTAAC[G,A]TGGTAACCATCACAATGGCATAATA | 340,512 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 577. | TAACCATCACAATGGCATAATATC[C,T]ACAGTAGAATAGGAGCATGATCAAA | 340,540 | 87 |
| 578. | aTGCACTAATAGCTTTTGTAAAAA[T,A]TATCGCTAATATGACCTAGGATTCT | 340,690 | 87 |
| 579. | AGAAATAAAGAAGCTAACTAGTTT[T,C]ATCCTACTTATCAAGAAGTTTAGTA | 340,845 | 87 |
| 580. | GAAGCTAACTAGTTTTATCCTACT[T,C]ATCAAGAAGTTTAGTAACATTATAT | 340,854 | 87 |
| 581. | TGATTATGAACTTGTATTGTTATA[T,A]TCCCAATAATGTATGTAGTATATAT | 340,968 | 87 |
| 582. | ATTGTTATATTCCCAATAATGTAT[G,C]TAGTATATATTATCTATTTTTATAG | 340,983 | 87 |
| 583. | AAAAaTTTGGATTTGATTAGAGAA[A.G]AGTTTGGGCTTGAGAATTCTGGATG | 341,085 | 87 |
| 584. | GAATTCTGGATGCATTAGATTTGG[G,A]TATCTCAAGTAAAGCAAGATTGTGC | 341,123 | 87 |
| 585. | GCATTAGATTTGGGTATCTCAAGT[A,C]AAGCAAGATTGTGCCACAGAGTCAA | 341,134 | 87 |
| 586. | TCTCAAGTAAAGCAAGATTGTGCC[A,C]CAGAGTCAACCCTATGAGCTGCTTG | 341,150 | 87 |
| 587. | CCTAAGGGCTGGGCTTATTAACAT[C,T]GAGGGCGACTTAGTTATAGCGGTCA | 341,424 | 87 |
| 588. | CTTCCGCAGGATATTTGAAAAATG[A,G]TGAGAAAGTATTATATATATATATA | 341,504 | 87 |
| 589. | AGAAAGTATTATATATATATATAT[T,A]TTTTGATACTAAGTATGTTATTAG | 341,531 | 87 |
| 590. | AAGAAGACGCTGGGCCGCGCGGAG[A,C]CGCTACCCAAGTGGACCGACGCCGA | 342,246 | 87 |
| 591. | GATTAGGTTTTGTATTGGATGGAT[C,T]TTGATGGGTCTTGTCTTGATTCAGT | 342,477 | 87 |
| 592. | TGTTCATTTTCTTGGTCTTGGCG[T,C]TTTATTTGGGATTTATCTGAGCTTT | 342,661 | 87 |
| 593. | TATCAACAGTTGGATCTTTTGTTT[G,T]GAATGGTCTTATCTATATTGCATTT | 342,768 | 87 |
| 594. | GTGCAAGTACGTTTTCCCAAAATC[G,A]TATTAAAGATGATAGCCTGTGGAAA | 343,039 | 87 |
| 595. | GGAAGAAATTCATAAAGTCCCAGT[T,A]TATTTGACTATGTTCACTAAAAGAA | 343,530 | 87 |
| 596. | TGGACATGTTGCTTCTTATTATTG[C,T]TCATTCTTGACCAGTTATTGTAATT | 343,665 | 87 |
| 597. | CTTTCCTCATAATCAGGGCCTAAA[A,C]ATTTGATTTTGTTTTGGTTTTTCTA | 343,736 | 87 |
| 598. | TTAAGTTGCTAATCAATTAAATGC[A,T]TGAGGTTATAGAATATCATAATTAT | 344,205 | 87 |
| 599. | AGTTATTATCTTTCCCTCTTTTAA[C,T]TCAAGTAATGGAGAGAAAAGTCATT | 344,351 | 87 |
| 600. | GTTGTGCATTTAATTGTCGATACA[T,C]GAAATGACACATATACCATTCCTTT | 344,680 | 87 |
| 601. | CTGCATTTTGATGTGAAATGTAAA[A,C]TTCATGATACACTATTAATATTGAC | 345,208 | 87 |
| 602. | GTAAAATTCATGATACACTATTAA[T,C]ATTGACAGTAAAGGAACCAAACAAG | 345,227 | 87 |
| 603. | ACACTCATATTTCATCAGTGTTGG[C,A]GTTTTGAGATAATAATGCAAAATGA | 345,735 | 87 |
| 604. | AGATAATAATGCAAAATGACTGA[C,T]TTATAAACTGCAAATTTTGGTCTTT | 345,766 | 87 |
| 605. | TGACATCCTTACTAGTGCTTGACA[C,T]TTTTCTTTTAATTACCAATTCTTTG | 345,815 | 87 |
| 606. | TGGAATGGACCTCTTTTCCCTTTA[C,T]AGTTGAAAGCTCTAAGGGAATCAAG | 346,115 | 87 |
| 607. | TATTCAAAGAGCCCACATGGTACT[G,T]TAGCTTTATTACTGTCATACTTCTT | 346,226 | 87 |
| 608. | TGAGTGCAGCACATAAACAGGTTT[A,G]GCAATCATATACTATATTTTGTACA | 346,402 | 87 |
| 609. | TCAATCTGCAGTAATGCTGAGCAT[T,A]AGCATTTGAAAGATAAACCTTTTTGT | 346,558 | 87 |
| 610. | CAATAAAAGTTAGTGCATAGTTCC[T,C]GTGTTTACTCTTTAATGATTATTGC | 347,298 | 87 |
| 611. | TTAAACTCATGAGACCAGAAGATA[G,A]GGCTGTGAATTGATCTGAGATGCTT | 347,762 | 87 |
| 612. | CTGAGTGATCATGTATTTCACAAT[G,A]TATTTAATACTTTTTAGATTTATAT | 347,982 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 613. | TAGATCATTACAATGCTCATTCAC[G,A]AGCAGGAGCATGGGCCACAGGTGTT | 348,176 | 87 |
| 614. | AGTGATGAGAGTTAGAGAGAGTGC[A,G]AGTGAGCCAGATTTTGCTGGCCATG | 348,283 | 87 |
| 615. | AATTTCCCTAATTTGAACCATTAA[G,A]TAATTGGATAAAAAACAGATAATTC | 348,491 | 87 |
| 616. | GGTGTCCAACACTGCTTAAACACA[C,T]AGCTAGAGTGTATCTGCTTGAGTCA | 348,687 | 87 |
| 617. | GAGCCTTTTTTTTtGGTTATGTT[C,T]TTCTCTACTTTGCCATTTCTGTATG | 348,872 | 87 |
| 618. | CATATCCGTCCCCATCCTATATCC[A,G]TTTTGGGTCGAATCAGGTCGAGTAA | 349,156 | 87 |
| 619. | AGAATGGATTGGGTCGGGTCGGGT[T,C]GGGTATCTTCCCTTGCATGGGGTCG | 349,257 | 87 |
| 620. | ATATAGAATAATTGGGAAAACAGT[G,A]GTTACAACAGCAATACATGCTCACA | 349,721 | 87 |
| 621. | AGCAATACATGCTCACAACGGCAC[T,A]ACCCACTTAAACATAAAGGCTACTA | 349,754 | 87 |
| 622. | AAAGATAACCACCCTCCTTACCAA[A,C]AAAaGATTTCACAAATTATGGGGAT | 349,867 | 87 |
| 623. | TATGTTATCCGGTCAGGTTCGAGA[T,C]GGGGCATACTATTATCTGCACCTGA | 350,326 | 87 |
| 624. | GTGTGCCCTTCAGGTGTTATGAAT[T,A]TTCCCTTTTGCTTTTACCTGATTAG | 350,591 | 87 |
| 625. | TCATTAAATTGTGCAGCCAGGTGA[C,A]TTTTGCGCTTAATCTTTGGGAACAG | 151,708 | 87 |
| 626. | CTCTCTCATATATATGCTCGGTAG[G,C,A]CCACGGGAGTACCAGCCCATGCTGG | 351,794 | 86 |
| 627. | CTTTAATTTTCATGATTATATAAT[T,C]TGACTGTTACTCTTGATGAAAGATA | 353,306 | 86 |
| 628. | AAAATCAAAGAAAGCTTCTACTTC[T,C]ACCCCAAAATAAGGAAATCTTTTAC | 353,362 | 86 |
| 629. | TGTGGCACGTACGTGATACGTCCA[A,T]ATTTCGAGATGCCTTTCCAGGGCAT | 353,596 | 86 |
| 630. | TCCAAATTTCGAGATGCCTTTCCA[G,A]GGCATGCAGCTCCTCCAGTGTCATA | 353,616 | 86 |
| 631. | CTCCAGACATGTACCTGTCACCCA[A,T]GTTCTTTGAACTCATGCACAAACTT | 353,685 | 86 |
| 632. | GTTGAGGCAGGCAAAAACGGAACA[C,T]ATATTTAAGCATGCAACCACAACAA | 353,813 | 86 |
| 633. | GTTTATTGGTAAAGAAAGGTCCAT[T,C]CAACCATCCACTAAACTAGGAGAAG | 353,893 | 86 |
| 634. | TATTGGTAAAGAAAGGTCCATTCA[A,C]CCATCCACTAAACTAGGAGAAGGCT | 353,896 | 86 |
| 635. | TCGTTATAAATTCTAACTCTCTCC[C,T]AATTCATGATTACATGTGGAAGGA | 354,013 | 86 |
| 636. | GAAGCAATAAATTATGAGTTGCAT[T,C]CTTTGTGACAAATTGGCCTAGAGCC | 354,061 | 86 |
| 637. | AATTTTATTCTATAAGAAACACTT[C,T]TTTTGAGATATGAAGAAATTGCATA | 354,308 | 86 |
| 638. | GCTTTGTACCCCTAGGTATGGCTT[G,T]TCCTAGAGTTTTGCAAACTGCCAGG | 354,523 | 86 |
| 639. | GAAGTTGCTAAAATGACTAAAAAA[T,A]GAAAAGAGGAGACCTGATGGTGTGT | 354,708 | 86 |
| 640. | AAAAAATGAAAGAGGAGACCTGA[T,C]GGTGTGTTACCATTCTGTCTCATTT | 354,726 | 86 |
| 641. | TACCATTCTGTCTCATTTAAGCCT[A,C]AATCATCCAAAGCTATTTAGGGGTG | 354,758 | 86 |
| 642. | TCATTTAAGCCTAAATCATCCAAA[G,A]CTATTTAGGGGTGCGCCTAGGTTCC | 354,770 | 86 |
| 643. | CGGCGGCCTAATGCGCTAAGGATT[G,A]TGTTGTAAGTAGATATTGGAAAAAG | 354,819 | 86 |
| 644. | CGGCTAGGGTTTCATTCTTTATCC[T,G]ATTATGTTCATCCTTCTCGGTTCCT | 354,917 | 86 |
| 645. | TTCTAGTAAAAAaCTAATATGAAA[T,C]TAAATACATGCTCACACGACAGTCT | 355,168 | 86 |
| 646. | GTCCTAGGTTGTTACAATTATAGT[G,A]AAAATTTTATTATTACACTAAAGGA | 355,283 | 86 |
| 647. | TTTAAAATATTTATTATTAAAAAA[T,G]TATATGATTTGGAGATCCCTACTTA | 355,720 | 86 |
| 648. | GGGATCTCCAGACTGTATGATTTT[C,T]TGATAGTAAATAGTTTAGAGATAGT | 355,856 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 649. | ATCTCCAGACTGTATGATTTTTTG[A,G]TAGTAAATAGTTTAGAGATAGTAGA | 355,859 | 86 |
| 650. | GAAGGCATAGCTTATATATTAATG[C,A]TATCATCCAATTAATTTATGTAATT | 356,240 | 86 |
| 651. | CCTAAACCCATAGGCATGAAGAAT[G,A]GAAATCATGTATTACAGAAGCCTGT | 356,378 | 86 |
| 652. | ACAGATAAGCTAACTAAAAGAGGG[T,C]AAGTCTTTGTTTTTTtAGAAGAAAA | 356,464 | 86 |
| 653. | TCAGGATGATAGATTGTCATCGTC[G,A]TAGAGGGTGACTCTATAACAGTGGT | 356,528 | 86 |
| 654. | TCTATTGTGACTTAGATTTTATGG[A,G]TTTAAAATACAGAAATAGCCTCTTT | 356,900 | 86 |
| 655. | TATGTTTGACCCTCATTTGATCCC[A,G]CAGTAACGAGGGCCTTGTGCATTGG | 356,971 | 86 |
| 656. | ATTTCCTCCACAACACCAAATTTT[G,A]CTTTTttTTTTtCTTTTGAATCTAG | 357,110 | 86 |
| 657. | TATATGCACGTGAACAAATATTGC[A,G]TGCATAGGCATGATCACATGCATGA | 357,332 | 86 |
| 658. | AGGCATGATCACATGCATGAATGC[G,A]CACAGATGTGCATGTACATATTTAT | 357,362 | 86 |
| 659. | CATGAATGCGCACAGATGTGCATG[T,A]ACATATTTATGCATAGACACAAGCA | 357,377 | 86 |
| 660. | ATGTGCATGTACATATTTATGCAT[A,G]GACACAAGCAGGCATGAACAAACAC | 357,392 | 86 |
| 661. | CGGTGCAGAGAAATTATAGCTCTG[G,A]AGTGCGTGCAATTTTGTTTCTTATT | 357,476 | 86 |
| 662. | AAGGATTTGAGGTGTTTAAGTTGG[C,T]CATTCGTAGTACCTAGCAAACAGTA | 357,583 | 86 |
| 663. | TTTCCTACCATGCTTTTCTGAATA[G,T]CCCACTTTTATATGGCGATAGTGAG | 358,143 | 86 |
| 664. | CAATGGGCCCTTGCAAGTCTTCAT[G,T]ATACATATAATTCTTGGTTAATGAG | 359,208 | 86 |
| 665. | GGAGGCTCTCATTGATGGGAATCC[T,C]CCTCCACCCACCAGTGACAGTCTAT | 359,475 | 86 |
| 666. | AACTGAAGCTGAGACATGGAAGAT[C,T]ATGTGTAATAACATTTATGTGGCAG | 359,837 | 86 |
| 667. | TTTCCGAAGGAATCAGGTCATCAG[T,C]GAACATTCTTTGGACCTCATATAAG | 360,112 | 86 |
| 668. | ATTCCATTTTAGCCACATATGCAC[A,G]TACTCATTTTGCGTGAACTCTCGTG | 360,163 | 86 |
| 669. | TATGCACATACTCATTTTGCGTGA[A,T]CTCTCGTGTGTTTTTCATATAAATT | 360,180 | 86 |
| 670. | TTTGCTTGAAGTCACATTGAAGTT[T,G]CCCACTTGATTCAGTTTGCTAAATT | 360,589 | 86 |
| 671. | AAAAGCCGCCTCTCTTTTTCTCCC[A,C]AGAAAAAGAGAGATAGTGGTAGTGC | 362,274 | 86 |
| 672. | ACTTAACACCTTTCATCTCTTTCT[T,G]AAGATAAGAAAGAATATTTTGTATA | 362,390 | 86 |
| 673. | TTTGCCTAGGTCTCTATTGTCACC[C,T]AGTGAATTGTTTGAGACTCTAAAAT | 362,514 | 86 |
| 674. | AAGTATCCTTTAAAGTTTGCACAT[G,A]TCATTCATGACTACATCAAGTAATT | 362,596 | 86 |
| 675. | TCTTCAAAATGCAAATCTATGAAT[G,C]GAGAATTATAGGTGTGCCAGATCGA | 362,652 | 86 |
| 676. | ATAACTCAAAGATAAAATAACCAA[C,T]GAATAACATTGATTATAAATAAGAA | 362,815 | 86 |
| 677. | TTGATTATAAATAAGAATAATTGA[A,G]TATAAGTAATTCTTTAGGGAGATTT | 362,848 | 86 |
| 678. | TTGATTTTCTCCAAGATGGAATGA[A,G]ACATCACATTAGAGAACTATTGATT | 362,946 | 86 |
| 679. | ATAAAACTTTTTCTATGTTGGGT[G,A]GTTAAATATCCATGCATGCATAGAG | 363,047 | 86 |
| 680. | TAGCTCCTCTTAAATAGTTAATTC[T,C]AATATTTGACCACCCAAATATGACG | 363,253 | 86 |
| 681. | TAATATTTGACCACCCAAATATGA[C,T]GTTTTATATACGTGCCAAGTGGCCA | 363,277 | 86 |
| 682. | AAAATAATTATTAATTAAATATTG[A,G]TTGGTATAATAATATTATTCATTTA | 363,354 | 86 |
| 683. | TTTATTATAGTTGGTTGATGGTAA[C,A]TTAATTCATAGGGATAAACATTACC | 363,400 | 86 |
| 684. | TAGTAACATGCATGATCATAGGCA[T,C]CATTTTATGTGGATTGATCATGCCT | 363,617 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 685. | ATGATCATAGGCATCATTTTATGT[G,T]GATTGATCATGCCTATCAACCATAA | 363,628 | 86 |
| 686. | ATAACAAGTCTCTACTCACAGTCC[C,T]CTTATTATTGTTGTCGAGCATATAT | 363,674 | 86 |
| 687. | ACCAATTATAATAATTATTATTGG[T,A]CAAAATAAATTTCAATCTATAATTT | 363,919 | 86 |
| 688. | TTTTATAACCAATTGGATCATTGC[G,C]TCGCAAATATTTGAGTACTTTCAGT | 364,074 | 86 |
| 689. | TCATTGCGTCGCAAATATTTGAGT[A,G]CTTTCAGTTGATCAGCCTTTTCAAG | 364,091 | 86 |
| 690. | TTATTAATTCACTGCTAATTGCGA[A,T]ATAGATCACTTAGGCTCTTTAAGCC | 364,147 | 86 |
| 691. | TGGGGCCATCAAGGAGAGCATATT[A,C]ATATGATCACATATATCAACCATTC | 364,292 | 86 |
| 692. | GATCATTCCCTTCAGAAAGCTTCA[G,C]TTTATTTCATTGCCTTGGAGCTTTT | 364,544 | 86 |
| 693. | AGCTTCAGTTTATTTCATTGCCTT[G,A]GAGCTTTTCTTTGACATTTTATCCT | 364,561 | 86 |
| 694. | AGAATTTCAAAGCTCACTAGTGAT[A,T]GCAATTGAATAACAACAAGAATACA | 364,743 | 86 |
| 695. | AAAGCTCACTAGTGATAGCAATTG[A,C]ATAACAACAAGAATACAAACCCAAG | 324,751 | 86 |
| 696. | GATCTCAATGCCGTTTGCCCATGA[T,C]CATCATGTGACCACACCTGGCCCAC | 365,500 | 86 |
| 697. | CAATCATACATAGCTTCTGATTTT[G,T]ATCATACATCACCTCTGATCCGACC | 365,554 | 86 |
| 698. | CAACTTGAGTGCCCTCCACAGCTC[G,C]GATAGGTCAAGCCTAGAGAAGAAGG | 365,678 | 86 |
| 699. | TCCACAGCTCGGATAGGTCAAGCC[T,C]AGAGAAGAAGGATATTAGATTGAAG | 365,692 | 86 |
| 700. | GCCGCATGGCACTTCACCACTGTC[A,G]TTTGCTCCTCCTCGAGAGCCCCTTC | 365,817 | 86 |
| 701. | CCCCTTCTTGAACCAAGGATCGCA[A,G]AGGATCCCATCGATGGTGATCCTTG | 365,860 | 86 |
| 702. | TTGGGGCATCGGTACTCCCTCCAA[T,C]AGATCTTGCAGTTCATCGCCATCAA | 365,969 | 86 |
| 703. | TTAAGGACGTAAAGAATAATGCTG[T,C]AGGACCAGATGTCGATCTTGGTGCC | 366,050 | 86 |
| 704. | TGGCATTATCGAGGAGGAGGTTCT[T,C]TGGCTTGAGGTCCCAGTGGTAGATG | 366,231 | 86 |
| 705. | CTTGAGGTCCCAGTGGTAGATGCC[G,A]CGTGCATGGCAGTATTTGATGGCGG | 366,259 | 86 |
| 706. | GATTCGTTGGCAGAAGTAGCATTG[A,G]GAGAGGTCCTCAAGAGATGGCCTCG | 366,310 | 86 |
| 707. | ATGCATGCATAGAGCTTGCTATTG[C,T]AGGCGAGCTTGAGGACGAAGTAGAT | 366,364 | 86 |
| 708. | GCGAGCTTGAGGACGAAGTAGATC[T,A]TGGAGCGGGAAGCGAGGACCTTAAG | 366,391 | 86 |
| 709. | TCTTGGAGCGGGAAGCGAGGACCT[T,C]AAGGAAGTGAAGGATGTGGGGGTGA | 366,413 | 86 |
| 710. | AGTGAAGGATGTGGGGGTGATGGA[A,G]GTGGCCGCATTATGGCGATCTTGCGG | 366,443 | 86 |
| 711. | AAGTGGCGCATTATGGCGATCTTG[C,T]GGATGACATTGTGGGCATAGCCGCC | 366,466 | 86 |
| 712. | GGCCCTTGGGGATGGCCTTGAGAG[C,T]GATGCTTTGATTAGAGTAGAGGTTG | 366,527 | 86 |
| 713. | CCTTGGGGATGGCCTTGAGAGCGA[T,C]GCTTTGATTAGAGTAGAGGTTGTGA | 366,530 | 86 |
| 714. | GCATATAATTGTTTAATGAGCCAC[G,A]TGCAGTCACGTGATAGTTATGGACA | 366,624 | 86 |
| 715. | TTAGCCAAATTGGCAAACATGAAA[T,G]TTGGATCACTTGATTGCTAATATCT | 366,731 | 86 |
| 716. | GAAATTTGGATCACTTGATTGCTA[A,G]TATCTCTGAACTTCATTATACAAAA | 366,751 | 86 |
| 717. | TATCTAACTTACACTACAACAAAA[C,T]AAGATATTAGCATAAAAAAAaTTC | 366,826 | 86 |
| 718. | AAATCAAATTTAAAAAaGCATTAG[T,C]ATCACTAATAAATATTAAATTAAATA | 367,132 | 86 |
| 719. | ATCATAATTTCTGACATAAATTTT[T,C]ATCACTAATAAATATTAAATTAATA | 367,180 | 86 |
| 720. | CACTAATAAATATTAAATTAATAA[C,T]GATAAAAATATTTTCATCACTATTA | 367,207 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 721. | GGTTATTTACGATGAAAATATTTT[T,A]ATCGCTATTAATTTAATTAAAAATT | 637,326 | 86 |
| 722. | ATTAATTTAATTAAAAATTTTTAT[G,A]AAAATCAAATTTAGAAAAATATTAG | 367,357 | 86 |
| 723. | AAAATCAAATTTAAAAAaTATTAG[T,C]GATGTAAATTTTACATCTCAAATAT | 367,489 | 86 |
| 724. | TAAATTTTTATCGATAATAAATTT[T,G]tAATTATTTATGATAAAAATATTTT | 367,553 | 86 |
| 725. | TTTTTTATCGCTAATATATTTTTt[A,G]ACGACCAATATTTCATCGAAAATAA | 367,670 | 86 |
| 726. | AATAAATTTATAAATAAATTTTAT[T,C]ATTTTATTATATTAAATTAAAATTA | 367,834 | 86 |
| 727. | TTTTATTATATTAAATTAAAATTA[C,T]AAGAGACCTAAAATAAAAaTAAAAA | 367,860 | 86 |
| 728. | GCATAGATGTCAGTCCTGAATGAG[T,C]GTGAGGATGAGGTAGCAGTGATCCC | 368,153 | 86 |
| 729. | GATCTCATACCAAGCACCTGATCA[C,T]AACTCTCGCCATCTGTGGGTGCGAT | 368,228 | 86 |
| 730. | GCACCTGATCACAACTCTCGCCAT[C,T]TGTGGGTGCGATCGAGCCCTCTGGA | 368,241 | 86 |
| 731. | ATAAAGAGCTCCTAGCACTCCGTC[A,G]TTCACTCTTTTGATCGTCGCTGGTG | 368,400 | 86 |
| 732 | AAaTTGGATGTATAATCTGATATG[C,T]CGGATCCTTGTAATATCGGTATATG | 368,746 | 86 |
| 733. | AGTGATGCTGTCATAGGGCCGCTG[T,C]CGCATTGCCTCCACCTCATGATCCT | 368,813 | 86 |
| 734. | GAAATACAAAGATAAATGAGCATC[T,C]CGCATTGCCTCCACCTCATGATCCT | 368,909 | 86 |
| 735. | CCCTATCAATAACAAATATTAGAA[A,G]AATACTATACTAATTAAATATTCAC | 368,982 | 86 |
| 736. | AAAAGCGTCACGGGGCATAACTGC[A,G]GCATATGATGCCCAGCTTGATCTGC | 369,103 | 86 |
| 737. | AACTGCAGCATATGATGCCCAGCT[T,C]GATCTGCCACAGCTCGTACCATCTC | 369,121 | 86 |
| 738. | GGAGACACTATCTCGGGTACTCGC[A,G]TCTCCAATACTCTAAAGCGAGGTTC | 369,208 | 86 |
| 739. | TCACCTCACTACCGGTGGAGACTG[G,A]CCTGAAACAATAATAAATAAATCAT | 369,275 | 86 |
| 740. | CATCTTTCTCCTGGTGCCATACCT[A,G]CAATTCTTGACATATAAATGAATAT | 369,509 | 86 |
| 741. | CATATAAATGAATATAATATTAAA[T,C]AATAATAATAAAAAaTAAATTATAT | 369,544 | 86 |
| 742. | ATCGCATACCATTATTGCAAGAAA[A,G]GATTGAACAAAGAATATAGATCTAC | 369,612 | 86 |
| 743. | CTCATCGTCATTTATGAACTGATC[A,G]TCGTCCTCTGACTCATCAAGATTAA | 369,739 | 86 |
| 744. | GTTAGACGGTAGATTACGGGTATT[T,C]AAAGGAGTCATTACAAGTTCTTCAT | 369,811 | 86 |
| 745. | AGATTAGCCCTATTTAAAGGAGTC[A,G]TTACAAGTTCTTCATCAACAAGAAG | 369,821 | 86 |
| 746. | AAAGCTTCCTCTTCATGTAAATTT[G,A]AATTTTCATCCATCTCTAATCGGGT | 369,899 | 86 |
| 747. | TTTGAATTTTCATCCATCTCTAAT[C,T]GGGTTGGTATGTCATATACACCTCT | 369,920 | 86 |
| 748. | TTTCTTAAATATTTTtTTTCTAAA[C,T]GAGCTCCGGACTCGGCTTCCCATAG | 370,043 | 86 |
| 749. | CGGACTCGGCTTCCCATAGCCCCC[G,A]CTCCCACGGCGCCGGCGTCGTCACA | 370,958 | 86 |
| 750. | AATAGTTAATTTATGATTTTTTCT[C,T]CAAAAAaTTATGTACATAAAAAaT | 371,958 | 86 |
| 751. | TCTCCAAAAAaTTATGTACATAA[A,C]AAaTATAATTTTGATGAAAAATTTA | 371,979 | 86 |
| 752. | CAACTTCCGCAATGGAATAAGCAC[C,T]ATAGGAGATCGATAGTTTTGAGGTC | 371,066 | 86 |
| 753. | TCTTCTTCTTGGAGTCCCTGTTCT[G,A]GAAGTCGGAGTACTTGAATGTCGCG | 372,136 | 86 |
| 754. | AAGTCGGAGTACTTGAATGTCGCG[A,G]TGATTCTGAGATCGCGAGAGAAATC | 372,162 | 86 |
| 755. | ATGAAAATATTGATAAAATAAGAA[T,A]TATCTTTTGTATTGCGTCTATCTCA | 372,248 | 86 |
| 756. | CTCTCTGAATCCCCGAAGTAACTG[C,T]TGTCCACTGTCCAGGAGCTCTACTC | 372,638 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 757. | TCCCCGAAGTAACTGCTGTCCACT[G,A]TCCAGGAGCTCTACTCCTTCTCTTT | 372,647 | 86 |
| 758. | AAGTTATCCGCGCACCACATCAAA[A,T]GTCAGGCCACACCATAACCCTTCTG | 372,755 | 86 |
| 759. | CAGGCCACACCATAACCCTTCTGT[T,C]CACGGTCACAGCCTTTTAAAGGCTT | 372,782 | 86 |
| 760. | AAGATGATTAATATAAAAAAGCAT[G,A]CCTCATAAACTATAAAATAGACTGT | 373,749 | 86 |
| 761. | TATAAAAAGCATGCCTCATAAAC[T,C]ATAAAATAGACTGTTTACAAATAAA | 373,760 | 86 |
| 762. | ATTTATAATAAAAAAaTTTCATCG[C,T]AAATAATAATCAATTTTTGATTTTT | 373,862 | 86 |
| 763. | ATTTATGATGAAAATAATATTTTC[G,A]TCATAAAAAAaGTCATTTACGATAA | 373,956 | 86 |
| 764. | ATTGATGATCAAAATATTTTTAAT[G,A]TAAATAATCTATTATTTATGATGAA | 374,781 | 86 |
| 765. | AAAATATTTTTAATGTAAATAATC[T,C]ATTATTTATGATGAAAATCGATTTT | 374,791 | 86 |
| 766. | GTTTTTGAAATATTTTAAATTTCT[C,T]ATTTTTTTtCTAGATATTGACGATG | 374,896 | 86 |
| 767. | GCCGACGAAAAAATATTTTTCATC[A,G]TAAATAATTAAATTATTTACGACGA | 374,974 | 86 |
| 768. | ACGACGAAAATATTTTCATCGTGA[G,A]TATTTTAAAATTTAAAATTAAAATA | 375,017 | 86 |
| 769. | AATAAATAATATATTATTTACGAT[A,G]AAATATTTATCATAAATAATTTGTA | 375,063 | 86 |
| 770. | TGCATGTCAGCAAAAACTTGCAAT[C,T]TAAGACTTAATGCGAAGCTGCGGCT | 375,695 | 86 |
| 771. | GGAAGGGTTTATGAAGAAAGTAAA[G,C]CTATTACGCATAGCAAGTAAAAACA | 375,785 | 86 |
| 772. | GGTTTATGAAGAAAGTAAAGCTAT[T,C]ACGCATAGCAAGTAAAAACATTATT | 375,790 | 86 |
| 773. | CATAGCAAGTAAAAACATTATTTG[C,T]TTATCTTTTCTCATGCTACAGCACA | 375,818 | 86 |
| 774. | TGCTACAGCACAAGTAAACCAATG[C,T]AACATACATGCTTCAAGGGGCTGCC | 375,856 | 86 |
| 775. | GTATTAACTTAAAAAGGAACTACC[A,C]AAAAaTTTACAATCTAGAGAGCAG | 376,064 | 86 |
| 776. | TAAATGACAGTGGCAAATTAAATG[C,T]TAAAGCGCCATGCTAATTCCAGTTC | 376,448 | 86 |
| 777. | GATAATCTTCAATAAGATCCAGTG[A,G]CACAAGTCTTTGTAGGCATAAATGT | 376,572 | 86 |
| 778. | TGTTCAATAGAAACAACAGGCAAT[A,G]GGGTATAAATACAAGCACATTAGCA | 376,765 | 86 |
| 779. | AATACAAGCACATTAGCAGCTAGA[T,C]ACAGACAATATTCTGTGATACCCTA | 376,797 | 86 |
| 780. | TCAAATCAATGTGCAATTTAAAGC[A,C]AGATGACTGTGTCACATCCCAGACA | 376,878 | 86 |
| 781. | CTTTACGGGGAAGTAAAAAaTACA[T,C]CATTCTTTTGAATAAGGTATTTGTC | 377,039 | 86 |
| 782. | TAAAAAaTACATCATTCTTTTGAA[T,C]AAGGTATTTGTCCTCATATTGCTAG | 377,052 | 86 |
| 783. | AGACGCATTGGGAAAAAAAAaa[G,A]GTAGCTCAGTGCACAAGGCTTTCAGC | 377,251 | 86 |
| 784. | CTCAGTGCACAAGGCTTCAGCCAG[G,T]GTAAGGTCTGAAGAGACTCCAGCCC | 377,280 | 86 |
| 785. | AGGCTTCAGCCACGGTAAGGTCTG[A,G]AGAGACTCCAGCCCTACCCCTGCAT | 377,291 | 86 |
| 786. | AGAGACTGTTTCCATATTTCAAAC[T,A]GTCACAATGGGCAACTTTAGCATTG | 377,345 | 86 |
| 787. | GCGGTCCAGCTTTATCTTCAGCTC[A,G]GTACATTGCCCAAAGAATTTTGCAA | 377,511 | 86 |
| 788. | GCATCAGGAACCAAAAGAAATGGA[A,G]AAAAAAaTGAAAAGGATGGCACTAA | 377,955 | 86 |
| 789. | AATATGAAGCCAATAAGGAGATGA[A,G]CTACCTCTGCACACATCGGATGCCT | 378,013 | 86 |
| 790. | TCCAACATTCTAAATTAAGAATGA[T,G]GCGAAAAAACTATAGAAACTGAACC | 378,099 | 86 |
| 791. | CTGCACCAATTTCCAAGCTTAAGG[G,A]CCACATGAATGTGAAGTTTCCCTAC | 378,333 | 86 |
| 792. | ATGAATGTGAAGTTTCCCTACACT[A,C]TCCATCCTCAATTGCTATGTTAGAG | 378,362 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 793. | ACTATCCATCCTCAATTGCTATGT[T,C]AGAGAAGCACTTCAATGGTCAATGT | 378,383 | 86 |
| 794. | TTGATCCATTTACTGACAAAACAA[C,G]GTATCAGCTCTAAATCCAGTCTGCT | 378,745 | 86 |
| 795. | AATTAAGAGGGATCATATCATGCC[A,G]ATTCCTAATCTGTATCCAGTCATGC | 378,796 | 86 |
| 796. | TCATGCCAATTCCTAATCTGTATC[C,T]AGTCATGCTCACCATACAAATACAT | 378,813 | 86 |
| 797. | CAGGCATACCAACAGACATAAGTC[C,G]TAATTTCAGTTGACAAATGATATTC | 378,935 | 86 |
| 798. | ATTTCCAAAAATGATCCACCAGAG[C,T]CATTCACTAGCCTAAATTTTGCTTG | 379,228 | 86 |
| 799. | AAATATCTTAATTAAGTTTAATAT[G,C]AAAAAaTAGCTATTCAATTTTATC | 379,711 | 86 |
| 800. | TGCAGTGCTACCAACTATGCATTG[T,C]CAAAGGGTCTAGTACTTGGATTATC | 380,092 | 86 |
| 801. | GTGGGCTCTAACTTCTTAAGTTGT[C,T]GACACAAGGGTCCAAAGGTTTAGGT | 380,171 | 86 |
| 802. | AAGGCATTCATCTTTATATTCATA[A,G]CCTACAAAGCATAATTGCATCTGTA | 380,312 | 86 |
| 803. | TTGGCATGTACATGATTCTTGGTA[T,A]GGGAAGGGTGGAAGGCAAGAATGAA | 380,864 | 86 |
| 804. | GTGGAAGGCAAGAATGAAAAATATG[T,A]GATTTTTTTCATATAGAACTATGGC | 380,896 | 86 |
| 805. | CCATGTAGGAAACAAGAAATTCAT[G,T]CTAATGGGACTATAGAAGCATATTC | 381,109 | 86 |
| 806. | TTTATCTATTCATTGCAAGCTGCT[G,A]TATCCACATTTATCTGTCAGATTAA | 381,455 | 86 |
| 807. | TCCCTACTAAAGTCATATTTTGCC[C,T]GTGAGCATTAAGTCTCATGACCTGT | 381,660 | 86 |
| 808. | ACGAACTGAAAGACTATGAAAACA[A,C]ATCAAAATACGATTGCAACCATATA | 381,824 | 86 |
| 809. | CATCACCAACACGAAGTGCCAGTA[T,C]AAAAATAGGGAGAATTTTTTTTTTt | 381,914 | 86 |
| 810. | TCATCATACCTATGATCTTGAATT[T,C]GGATGAGAAGATCGAACAAGAATAC | 381,991 | 86 |
| 811. | GATCTTGAATTTGGATGAGAAGAT[C,A]GAACAAGAATACAGGGCTTTCAGAG | 382,004 | 86 |
| 812. | TGTCATCTTGGGCTCCATGCCAGC[A,G]TGGAGGCCGAAATGGGGATGCTGAT | 382,067 | 86 |
| 813. | GTGACCCAAGCCAAACCTCAGTCT[C,A]AACCAGACAAGGAAACCTGGGAATC | 382,137 | 86 |
| 814. | TCTCAACCAGACAAGGAAACCTGG[G,A]AATCTGGGATATTGATGGAGGATTG | 382,158 | 86 |
| 815. | ACCAAGCCATCAAAAGGAAGGCCA[T,A]AGCCTAGAAATCGAGAACTGCAACC | 382,276 | 86 |
| 816. | TCGAGAACTGCAACCCATAACAGA[C,G]GACTAATGAACCTATTGAACGACAA | 382,311 | 86 |
| 817. | ACAATCAAAATTTAACATTAATTC[T,G]CCATGTTTTCTTTGAAGCAGATAAA | 382,836 | 86 |
| 818. | AGGAGCGTCCGCCAGCTTTGATTG[T,G]AGAACGGCGACCGGCGACGGCACGA | 382,242 | 86 |
| 819. | ATTCAGGGAGAAGGCTCTCGCACG[T,G]GATCGAAGACAAAGAGTAGGGAGAG | 383,291 | 86 |
| 820. | TGGCGTCAAAGTCCCCTTTTTTTT[T,A]CGATTTTTTCCGCGATTCATGTATCG | 383,833 | 86 |
| 821. | GGCGTCAAAGTCCCCTTTTTTTTt[C,A]GATTTTTTCCGCGATTCATGTATCG | 383,834 | 86 |
| 822. | TATTCCTGTTTTACCTGAATTCCG[G,C]ATCGCTGGATTTGTACGCGTGTGAA | 383,886 | 86 |
| 823. | TCCCTGCAGACTCCATATCTGAAA[C,T]TCCAGGGGATGAAAACTTGAGTAGG | 383,386 | 86 |
| 824. | TACATCCCTCGGTACTATATTTCT[C,T]TTTTtTTTCTATACAGAAAATGTTC | 384,833 | 86 |
| 825. | GTGTAAAATCAGGCCTTAATGCTT[C,T]TGTTGGGAAGGAATCCTCACGAGTG | 384,970 | 86 |
| 826. | CTTAATGCTTCTGTTGGGAAGGAA[T,C]TGTTGGGAAGGAATCCTCACGAGTG | 384,984 | 86 |
| 827. | ATCTAAGAGCGCTAATTCAGGTGA[T,C]GGTGTCAATACCGCAATAAGAAGAa | 385,037 | 86 |
| 828. | CACCTCTGATCGTTCAATCACGAC[C,T]GCAAGCTCTTCTGACCTTCAGATTG | 385,406 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 829. | CAGGGCAAGCTCTTCTGACCTTCA[G,A]ATTGCGCAAAACAATGCATGAACCG | 385,427 | 86 |
| 830. | CAAGCTCTTCTGACCTTCAGATTG[C,T]GCAAAACAAATGCATGAACCGCGCAT | 385,432 | 86 |
| 831. | ACCGCGGCGGTCCACGCGCGATGC[G,A]TGGACTGCGACTTCCTGTGGATGCG | 385,586 | 86 |
| 832. | GACCGTGCTGTGCACCATGTGGGC[G,A]CGCTAGTCTGGGCTGAGCATGTCAA | 385,641 | 86 |
| 833. | TGCGTTGTAGCGAGCTTGGGCGGC[T,C]TGCGGGCCTACGAGCCACGCTTGTA | 385,740 | 86 |
| 834. | TGTAGGCTTGCCGCCTGTGTCTAC[A,G]TGCCTATGGGGCTGGACTTCTCTTT | 385,786 | 86 |
| 835. | ATTCAACAATCTCCACCTCGACTC[G,A]ACATTCGGCCTTCACCTAACTTTAA | 385,871 | 86 |
| 836. | TTCACCTAACTTTAAGAACTTCTA[G,T]ATCATCTTGCCCCCCATGTCTTGGGG | 385,906 | 86 |
| 837. | GCCCCCATGTCTTGGGGCAAATGT[T,C]TGGCTGCTCATGGATGGGCAAACAT | 385,939 | 86 |
| 838. | GCTGCTCATGGATGGGCAAACATG[G,A]GAGTCGAGCCAGACCGCTGATACC | 385,966 | 86 |
| 839. | AGATCTGATCGGGGTAGCCTCCTG[C,T]AGTAATAGAAACTTCATTCTGCGAT | 386,049 | 86 |
| 840. | ATCTGATCGGGGTAGCCTCCTGCA[G,A]TAATAGAAACTTCATTCTGCGATGT | 386,051 | 86 |
| 841. | TTCGTCTCATGCCCAATCCATCTG[T,C]ATCTGGAGCTCCACCTCGTTCTGAG | 386,123 | 86 |
| 842. | AAGCTCTACCTCATGCTGAGCTCT[C,T]TGTCAAGAGGTAATGTTCTCCATAC | 386,189 | 86 |
| 843. | TCTTCCCTTTCATCACAATACCTAC[T,C]GTCGTGCAAGACTTTAGGATTTTTT | 386,240 | 86 |
| 844. | ACTGCTCCATCAAATATCTGTAAG[T,C]TGACAATCTCAATGCCCTTGATCGC | 386,388 | 86 |
| 845. | AaGTAGATACCTCATCAATCACCA[A,G]AAGAACATTATCACTATCTTCTGTA | 386,557 | 86 |
| 846. | GCTATGGGCAATCTCTGACTCGAT[G,A]CCCCAACTCATCATACCTGTAACAC | 386,653 | 86 |
| 847. | CTATGGGCAATCTCTGACTCGATG[C,T]CCCAACTCATCATACCTGTAACACC | 386,654 | 86 |
| 848. | CCTGTAACACCTGATCTTGCTGTA[G,A]TCCCTCGATTTGGATTTGGACCGCC | 386,693 | 86 |
| 849. | GTCACTGCCATTGCCGAGTCATCA[T,C]CTGAACTCGAAGCTCAGTTCTTCCA | 386,790 | 86 |
| 850. | CTTCCATCTGAGAACCTCATTCTG[G,A]AGAAGTGTAGAAGTGACTTCTTTCA | 386,834 | 86 |
| 851. | AAAAACTCAAAaGGAAAAAAAaGT[A,G]ATGAAGGCAAGACCAATGCCTTGGT | 386,922 | 86 |
| 852. | TCAAAaGGAAAAAAAAGTAATGAA[G,A]GCAAGACCAATGCCTTGGTCTTCTC | 386,928 | 86 |
| 853. | GAAAGTTGCTGAGATGCTCCTGCA[T,C]GCTTTGTCCCTCACTCATCTGCAGC | 387,022 | 86 |
| 854. | CTGCAGCTGATAGAACTGCTTTCA[A,G]AGAAAGAGAGCGTTGGTGAGTGACT | 387,065 | 86 |
| 855. | CATCTCGAGCTTCATCCACATCGC[T,C]ATCGAAGAACTGTCGCTAAGCATAT | 387,125 | 86 |
| 856. | AAAAAaTAATACAAGAGGAGATC[A,G]CACACTTTCAACTCTCATAAACTTT | 387,637 | 86 |
| 857. | AGAACCCCTAAGTAGACCCTCTAC[A,G]GCTCCCTCTGCTTCACGGGTTGCTC | 387,730 | 86 |
| 858. | AAATTTTATCAGGACTACCCCCCa[T,C]GTCGACCATCCGATCATGACCGCA | 387,853 | 86 |
| 859. | AATTTTATCAGGACTCAAAAAaT[G,C]TCTGACCATCCGATCATGACCGCAA | 387,854 | 86 |
| 860. | ATGACCGCAAGCTCTCCTGACCCT[T,C]AGATCGTGCAAAACAATGCATGAAC | 387,894 | 86 |
| 861. | GCACTCGTCCGTGCGCACGTGAGC[C,A]GCAATAAACCCTCTGTAGACCGCCG | 388,012 | 86 |
| 862. | CACGTAGCCGCAATAAACCCTCT[G,A]TAGACCGCCGCAGTCCATGCGCGGC | 388,027 | 86 |
| 863. | CGTGCGCCTATGCGCGTGGGCCGC[A,G]CGCTGGATAGGTCGCCCACGCTGTG | 388,098 | 86 |
| 864. | TGGGTGCCTGCAAGCCGGGCCTAG[G,A]GGCTGCACCTGTAGGCCTAGTTCCT | 388,154 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 865. | GGCTACTTTGGGTCGAATTCGAGG[T,C]GCCAAAACTCAACAGCTTCATCATT | 388,238 | 86 |
| 866. | ATACCTACCATTAATCTAAAACCA[T,C]CAGTCTGGAAAGAAGAATTTGGAGG | 388,312 | 86 |
| 867. | TTGGAGGTCACCTTGAAGAAGGA[C,T]AATCAGAGGAATTGTTTGTTGATGT | 388,355 | 86 |
| 868. | GTGTGACTTTAGTGTGAACAGAAT[T,C]CAAGAGCATGTATAAATAAGGAAGA | 388,911 | 86 |
| 869. | GAGACCTTTGTGAGTCGCATGCAT[T,C]GCATGTCCCTGTCTAATAATTTGTG | 389,520 | 86 |
| 870. | AAATCTTGATTCATTGTTTTTGAT[T,C]TCTATAGATTTCTCCCTTTTTCTTT | 390,032 | 86 |
| 871. | AAAAAACACATAGGCTAGCTTATT[C,A]AAAAAGATCCAATTCAGTTCATGGA | 390,551 | 86 |
| 872. | GTAAAGGTTGCTAAGAAATCTGTC[G,A]AGACATTTGCTTGCCATCCATGATC | 391,234 | 86 |
| 873. | GTCTTCAGGATTGAGAACTTGATC[G,A]TCAATTGATGGTAATGTTATGGGTG | 392,029 | 86 |
| 874. | TCTGCATCTCATTCATTTCTCCCT[A,G]TCTGAACATATCTTTCTTCCGAAAG | 392,738 | 86 |
| 875. | AATCACTACTTTCTGTACCTGGTT[A,C]TTTTGCTGACAGTGACTCATGCACC | 392,985 | 86 |
| 876. | CTGTGATGCGGAACTAAGCATGAT[A,C]TATATGGCCCTTTCTGGCTTAAGCC | 393,847 | 86 |
| 877. | AATGATTGGGTAATGATGTTTTAC[T,A]TGCTTTTTGACGCCCATGCATCTGT | 394,038 | 86 |
| 878. | TGCTAGTGGGGTCTGCTTTGGC[G,A]CTTAAACATCAGAAGATAGACCAAA | 394,830 | 86 |
| 879. | TTTATCAGGGACCAGAGTAAATAA[C,T]ATAGGTACTAGTAGTGACAGAATAT | 395,132 | 86 |
| 880. | TTTCCTTACATAGGGATCAATCAT[C,T]GATGTTTTAGCTGATATCAGCCATT | 395,457 | 86 |
| 881. | GGTCAGCTTTACTGGGCAATGTTT[T,C]TCCCAGGGTATCTTTCATGTTTTTA | 396,342 | 86 |
| 882. | ACTAGTTACCATTTTTCACTATGT[G,A]AAATTGTCTCTCACTCTGCCAGCCT | 396,502 | 86 |
| 883. | GTCCTGGTCAATCGTGTCATTTTC[A,G]GTATGGCTGTAATCAGGTTCCATGA | 396,656 | 86 |
| 884. | TGGTTTCATTACTGAGACAAGTCT[G,C]TACTCACGAAAAAATGATGTGATTT | 397,285 | 86 |
| 885. | TTTTGTTAATGTTTTTGCCATGGA[G,A]ATTATGGAAATGGGTTAGGGAAGTT | 397,698 | 86 |
| 886. | CTTCATCTTGTTGCCTCTAGTATA[T,C]GCCTTTTTAATATCATTTAATCACT | 397,983 | 86 |
| 887. | ATGTATATATGTATATATGCATGC[A,G]TGCGTGCATGTGTGTACATATATAA | 398,096 | 86 |
| 888. | TATATGCATGCATGCGTGCATGTG[T,C]GTACATATATAATAGGATTGGACGG | 398,109 | 86 |
| 889. | AAAAATCACAGAAAAGCCCTCAAT[G,A]GAAAAACACTCTCTTTCCATTACAG | 398,180 | 86 |
| 890. | CTCTCTTTCCATTACAGGCCCAAC[T,A]CAAGTATGGCCTAACAAAAACTCTT | 398,213 | 86 |
| 891. | AGTTATGATTTCCTCATCCCTAGT[G,A]TAGCAAAACAAACTAGTAGAAACCT | 398,276 | 86 |
| 892. | AAACCTTGGGCAACGCATGAAATA[G,T]AGCCAAGAAATATAAGAACGTGTTT | 398,320 | 86 |
| 893. | AATTTGAATTATTTTGGTGGACAA[A,C]AATTAGAGAAGAGATGAGACTACTC | 398,447 | 86 |
| 894. | CACATGTTGTAAAGCAACTAAACA[T,A]AACTTTTCCAATATTTACAAAAGCA | 398,511 | 86 |
| 895. | CATGTCCAATGGGAGTATTTGGAC[A,G]GGGGTTAGCATCATCTGGCTGCCTG | 398,859 | 86 |
| 896. | TTGGACAGGGGTTAGCATCATCTG[G,A]CTGCCTGCATGTAAGTCAATATGTA | 398,877 | 86 |
| 897. | ATTACATAAACAATTATCATCAGC[A,G]GCAGCGCATCTTCTCATTCATGATA | 399,072 | 86 |
| 898. | TATTGAGATTCGTTATATTTATCG[A,G]GAGGTCAATAGCTCTATCGACTGGA | 399,146 | 86 |
| 899. | ATTTATCGAGAGGTCAATAGCTCT[A,G]CTGACTGGATGATCTTTTATGTGAC | 399,162 | 86 |
| 900. | AAAAAAaTAAAGTGACATGTGGCC[T,C]GGCACAAAGTCACGTGACCTTGAAT | 399,326 | 86 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 901. | TCCAACAAGCATTTTAGATTATAA[G,A]CTTACACCATGGGCGAGGGAAGTTT | 399,376 | 86 |
| 902. | TCTGGTCAATTTTATTAAAATGTA[T,C]TGTTCCAATATTAAAATTTTCTCGA | 400,348 | 86 |
| 903. | GTGTTCCTTTGATCTAAAAACAGT[C,A]TAATTTTTTGCTACCACAAATATAC | 400,418 | 86 |
| 904. | TTCTTTTACAGAAAAAACTCACGGA[C,G]AATAAGCTTAAATCTTCATGGCCAG | 400,605 | 86 |
| 905. | TATATCGATGGTCCCGGAGGAGTC[T,C]TGATTTAGTACATAACTTCTAAATG | 400,778 | 86 |
| 906. | ACATAGCATAGCATTTACCATAAA[G,A]AACCATGCATCGTTACGTCATCCAA | 401,047 | 86 |
| 907. | GAAGTCTTATGTATGCTTAaGTTTT[C,T]CCTTTAGAATACTTGGAAGGCTTGA | 401,812 | 86 |
| 908. | TGTTCATGCAATTAAGTTACCTTG[A,C]CATATGTGATGCATTAATTACATGC | 402,407 | 86 |
| 909. | GTGTAAATATTAATTGTTCTTATC[T,C]ATTATTGCTTTTCTTAGTGTTTTTC | 402,836 | 86 |
| 910. | CAATACCATAGGTATTTGTTCTTG[C,T]TAGCCATAAAAATATACAAGCATAT | 403,009 | 86 |
| 911. | GGTATTTGTTCTTGCTAGCCATAA[A,C]AATATACAAGCATATGAGGGTAGCA | 403,019 | 86 |
| 912. | TGGTGATGATGTTATCCATAACCT[T,A]ATCAATAATTTGGTTTTGATTTTCT | 403,130 | 86 |
| 913. | ATGTACGTGGGTAGAAGGGACAGC[G,T]TTAACATGAAACATGTGGAAGTTTT | 403,562 | 86 |
| 914. | CTATTTATAGATGAAAGAAATGAA[A,T]AGAAAGAAAAaCTTTAAAAGAAaGA | 403,675 | 86 |
| 915. | TTATAGATGAAAGAAATGAAAAGA[A,C]AGAAAAaCTTTAAAAGAAaGAAAAA | 403,679 | 86 |
| 916. | AAAAAaCTTTAAAATACACCGCA[C,T]GATTAATTTCTTATTCACCATGTCA | 403,725 | 86 |
| 917. | AATACACCGCAACGATTAATTTCT[T,C]ATTCACCATGTCACCTCTTCTATGA | 403,737 | 86 |
| 918. | ACATTTTATATCGAAGATATAGTA[G,A]CACAAACTCCATCCGGCGGTACAGC | 404,131 | 86 |
| 919. | CTCTTAAGAGGAAACCCACATAT[C,T]CGATGCCAATTGCATGCAGTGGAAA | 404,204 | 86 |
| 920. | GCTCCCTTCTTTTCCCTCGGAATT[T,C]GCGGTGTTGGACTTCACCTTCTCTT | 404,277 | 86 |
| 921. | TATCCATTTGTCATGATCTTGTCT[C,A]ATGAATATATGTATTCTGTTCTTGT | 404,924 | 86 |
| 922. | TCTGCAAACGCCGAAATGGACTGC[T,C]GAAGAATGCTTATGAGTTGTCTGTC | 405,325 | 100 |
| 923. | ACGCCGAAATGGACTGCTGAAGAA[T,A]GCTTATGAGTTGTCTGTCCTTTGTG | 405,332 | 100 |
| 924. | AGAATGTTAATGATGGTAGTTTTG[C,G]TCCTCTTCAATTTATTTGCTTCCCT | 405,543 | 100 |
| 925. | CTCCCACCCTGTGCAACTAATTCC[G,C]ACAAAATAAGGGTCTCCATTGTTA | 406,358 | 100 |
| 926. | TGTGCCTCATGACGAGCATTACCT[T,A]TCCATGGTTCTGACACGACATTGA | 407,199 | 100 |
| 927. | CATGGTTCTGACACGACATTGCAT[A,C]CTAGATTTTACTGTGTACGTAAAAA | 407,226 | 100 |
| 928. | ACACGACATTGCATACTAGATTTT[A,T]CTGTGTACGTAAAAAAGCACTGCAT | 407,236 | 100 |
| 929. | GGACTAAGTTTAAACATATAAAAA[T,C]ATTTAAATTTTGAAATATATATGTA | 407,845 | 100 |
| 930. | AATGGATTGGGTCTGGTTGGGTCA[A,G]TGCGAGTCTGCTTTAAATATATATAT | 407,944 | 100 |
| 931. | AATATATATATACATATGGGCATG[G,A]TCAAATCAGGTTAGTTTATATATAT | 407,983 | 100 |
| 932. | CAAAATTTTTGCAAGCATTCAAGT[G,A]GACACAAATCAAGGGCACTAATGC | 408,312 | 86 |
| 933. | TAAAAATAGCATGCATTTTATGAA[G,T]ATAACCTTACTATTATTAGGTAATA | 408,455 | 100 |
| 934. | CGAGATGGAGAGAAAGCACTTCAT[C,T]TCTCATCTTTCCTCTCTAAATAACA | 408,567 | 100 |
| 935. | AGAAAGCACTTCATCTCTCATCTT[T,C]CCTCTCTAAATAACATTTCACTAAG | 408,577 | 100 |
| 936. | TACCATTTCTCATAGAAAAAAAa[C,T]ATTATCTAAGAAGAATAAATTATTA | 408,694 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 937. | CTTGTTGCTATTATAAACCCATG[A,T]CAACAATCAATATGCACTAAAGTTT | 408,807 | 100 |
| 938. | GAAAGTAAGGAAAATTGCTTGAA[G,A]ATTTAGAAGTGCATAAATATAATCT | 408,992 | 100 |
| 939. | GAGGAGTCTTATTTATATTTTGAG[A,G]ATTAGAAAGGGGGAGAAAATTGAAC | 409,048 | 100 |
| 940. | GAACAAAACTTTGATAAATTGATT[G,A]TAAGAATTTTCAAACCTTAAAGCGA | 409,094 | 100 |
| 941. | AAGGTTATCTATATTCATTAATAT[C,T]AtTTTTTAAATTATTGTATATATT | 409,187 | 100 |
| 942. | TTCTTTAAAAGTTAGATTGGTTTC[G,A]TATCCATCATAAATGATAAATGATC | 409,256 | 100 |
| 943. | CTTTAAAAGTTAGATTGGTTTCGT[A,C]CTTATCATAAATGATAAATGATCTG | 409,258 | 100 |
| 944. | AAAATTATTTGACATATAACCTTT[G,T]ATAAGAAATTACATATTAGGATTTT | 409,319 | 100 |
| 945. | ATATTAGGATTTTATGGTTTACTG[T,C]CATATAGTTCTTTGTTTTGTATTTA | 409,356 | 100 |
| 946. | TGATGGCTTATGATTTTtATTTTT[T,C]ATAACATTTATTTTTATCTATAATA | 409,471 | 100 |
| 947. | TTAATGAAAGTGGATTACACGACA[T,C]CTAACTTATATTTTTGAAAATAGAG | 409,536 | 100 |
| 948. | tTTTTAAAATTTAAATGTCATAGG[T,G]TTGAAAAATTCTTACTTGTAAATAT | 409,702 | 100 |
| 949. | ACACTTAGATTGTGATTGTTGTTT[G,A]GCATTGGAAGATCGAGACAATTAAT | 410,005 | 100 |
| 950. | TTAATACCATAAGTGGGATATATA[C,G]TTGCTTAACCCAACATTAAACCAAA | 410,050 | 100 |
| 951. | ATACTTGCTTAACCCAACATTAAA[C,T]CAAAATCACCTCTCGACAATCACAC | 410,071 | 100 |
| 952. | GTGTACTCAAGATAAACATGGATT[G,A]TCAAGATATATATAAGAATAATAAA | 410,129 | 100 |
| 953. | TTTGTTTTTAATTTAATCCTTGT[C,T]TTCTTAAATGACTCAGCTTGTAATT | 410,291 | 100 |
| 954. | ATCCTTTGTCTTCTTAAATGACTC[A,G]GCTTGTAATTTAAATATATCATTAC | 410,306 | 100 |
| 955. | GCAGTAATGTCCATTTGTTGTAAA[T,C]AATATTTGGCAATAGAAAGAAATAC | 410,360 | 100 |
| 956. | CCATTTGTTGTAAATAAATATTTG[G,A]CAATAGAAGAAATACTATAAGGTCA | 410,370 | 100 |
| 957. | TTTCGTATAGTCTATTATAAATGT[A,C]GAATGAAACATAATAGGCTTTTCAT | 410,446 | 100 |
| 958. | AATTATCAAATATCAAAATTAATG[T,C]ACCAATTTTGAGACATCAATATTA | 410,515 | 100 |
| 959. | AGACATCAATATTATAAAGGGATA[C,T]AAGAAACTAACGAGAGTACACTGA | 410,551 | 100 |
| 960. | CTAAGAAACTAACGAGAGTACACT[G,A]ATCAAGAAATGTGATCGACCAGTGA | 410,575 | 100 |
| 961. | ATCGACCAGTGAGGCATGTTGTTT[A,G]TAAATTAATTAGACACGTTTTCAAT | 410,613 | 100 |
| 962. | GAGGCATTGATAAATGGATCACT[C,T]GAAATAAAATTAAGAAAGAATGAG | 410,623 | 100 |
| 963. | TTTATAATTGATAAATGGATCACT[T,A]TTTATTTGCTCTTTATATTTAGACT | 410,686 | 100 |
| 964. | ATTTTCATTACCATAAAaAAAGAT[C,T]GAAAATAAAATTAAGAAAGAATGAG | 410,805 | 100 |
| 965. | GATAAGTTTGATAATTTTAGACAT[C,T]CGCTTGCATAATATGGCATGTTTAA | 410,854 | 100 |
| 966. | TTCATGTTTAATATTAATTTATCA[C,T]GAGAATGCAAAATATATAAAATT | 410,893 | 100 |
| 967. | TTAATTTATCACTGAGAATGCAAA[A,C]ATATATAAATTTTTAATTAAGCTT | 410,906 | 100 |
| 968. | AAATAATAATTAAACTAAGAAAA[T,C]AAAAAATATTTAATAACAATTGGAA | 411,066 | 100 |
| 969. | AATGCATGGAATGATTTCATAAA[G,A]TTGCATTGTACTAAAAGAATTTATG | 411,249 | 100 |
| 970. | TTAATTATACTTTACAATAGTAAAC[T,A]ACCTTTTGAGCAAAATGGTGGTAAC | 411,330 | 100 |
| 971. | TTATACTTTACAATAGTAAACTAC[C,T]TTTTGAGCAAAATGGTAACCCA | 411,333 | 100 |
| 972. | CTAGATAAAGAAGGGGACAGAAA[G,A]AGAGATATAGGGCTCCCGAGCTTAA | 411,422 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 973. | GATAAAGAAGGGGGACAGAAAGAG[A,G]GATATAGGGCTCCCGAGCTTAAGCA | 411,425 | 100 |
| 974. | AAGAGAGATATATAGGGCTCCCGAGC[T,C]TAAGCAACCAAGCAATTCAATATAG | 411,444 | 100 |
| 975. | CCGAGCTTAAGCAACCAAGCAATT[C,T]AATATAGTTGCAACCAATAAAATCC | 411,462 | 100 |
| 976. | AATATAGTTGCAACCAATAAAATC[C,T]GATATGAGCAATATAAATATAACT | 411,487 | 100 |
| 977. | AATATAAATATAACTCACTAAAAG[C,T]CCAAATACACCCAATAAGCCAGG | 411,522 | 100 |
| 978. | AAAGCCCAAAATACACCCAATAAG[C,G]CCAGGTAACCACTAGCCCAAACATA | 411,542 | 100 |
| 979. | CCTCTACCTTCCAAGCTCTAATTA[T,C]TTTAATGCCATTGCAAATCATCATG | 411,642 | 100 |
| 980. | TCTTCTTCTAATTTGGTGTACTAT[C,T]ATTTTCAATGTATTGCAACTCTATT | 411,697 | 100 |
| 981. | TCTAATTTGGTGTACTATCATTTTT[C,T]AATGTATTGCAACTCTATTGCCAAT | 411,703 | 100 |
| 982. | TTGCCAATCGATGCTCCTCCAAGG[C,T]ATCTCTCAAGATCTCATTTGGCTCT | 411,745 | 100 |
| 983. | TCAAGATCTCATTTGGCTCTTAG[C,T]GCTACCACTACCATCCATCCTATTA | 411,775 | 100 |
| 984. | TCTAGATCAATATCAAAATTAATG[C,T]AGCTCTTTTCTCGATACTTTTTGCA | 411,828 | 100 |
| 985. | TCAATGTCCATGCCCATCTTCCAT[G,A]AAAGCTACTTGGCAAACAATCCTAA | 411,978 | 100 |
| 986. | GAAAGCTACTTGGCAAACAATCCT[A,C]ATAGGTTCCAAAAAACCCCACAGCT | 412,002 | 100 |
| 987. | AACCCCACAGCTAAGGACTAAACA[C,T]ACAACCACACGGTTCTCTTATACT | 412,040 | 100 |
| 988. | CTAAACACACAACCACACAGGTC[T,A]CTTATACTCTCTTTATTTAGATTCA | 412,057 | 100 |
| 989. | TCTAGTCAACTGAATCATAACA[T,C]CATAATCAATCCATGGTCAACTCCA | 412,135 | 100 |
| 990. | TGGTCAACTCCAACCATTTATGAA[G,A]CATAAAGATCTTATCTAAAAAAaTC | 412,173 | 100 |
| 991. | ATCAATAAAATACATGCTTGTGC[G,A]GAGATCCTCACAAAAATATTTAGCA | 412,292 | 100 |
| 992. | TCAAATAAAATACATGCTTGTGCG[G,A]AGATCCTCACAAAAATATTTAGCAA | 412,293 | 100 |
| 993. | CAAAAATTAAAAGTATAAGATGAA[T,C]ATAGAATTGATGAATAAAGAACCAA | 412,485 | 100 |
| 994. | ATTGATGAATAAAGAACCAAAAAA[T,C]ATACTGAACTAAAAGAGAGAGTATG | 412,515 | 100 |
| 995. | AAGGTAGAAACCCCACTATGGTAT[G,A]TATAACATAAGAAAGACCGTTATTA | 412,585 | 100 |
| 996. | TCTTAGCTAGCTACTTTAAGGATA[C,T]AACTTTTACACATTCACTCACAAAT | 412,682 | 100 |
| 997. | TTACACATTCACTCACAAATCCTA[G,A]AGATTTAGCAAAAGAGAAAAGAGAG | 412,712 | 100 |
| 998. | GAAAGGCAAGGGAAGAATAGTTCC[T,C]ATAATAGAATTTTCACTAGTTAATA | 412,771 | 100 |
| 999. | TTTGTAGGTAATATATAGGAACTC[A,T]ATTCTTAAACTTTTCAATGTGGGAT | 412,867 | 100 |
| 1000. | TTGTAGGTAATATATAGGAACTCA[A,T]TTCTTAAACTTTTCAATGTGGGGATT | 412,868 | 100 |
| 1001. | AACTTTTCAAAATTTATTAATATC[A,C]AACTCTCCTAACTTAGACAAAAAAT | 413,004 | 100 |
| 1002. | CCATTTTATCTAGATTTAAGATG[C,A]ATAACTTGAATGATAAGATTTTAAC | 413,534 | 100 |
| 1003. | TCATAAAAGGTGGTAATCAAGTCA[T,C]ATTATATTTATCAAAGCACTGTCTA | 413,631 | 100 |
| 1004. | TTTTAAAATTTAGTGAGATGGTTG[C,T]ATTGCCTCCATCTATGACTTAAATT | 413,742 | 4100 |
| 1005. | TTTAGTGAGATGGTTGCATTGCCT[C,T]CATCTATGAGTTAAATTTTTGGATA | 413,750 | 100 |
| 1006. | TTGCATTGCCTCCATCTATGACTT[TA,A]AATTTTGGATAACAAAGCCATATC | 413,763 | 100 |
| 1007. | GGTTAGAAAATGTTACTAAAGGTG[A,G]TTTCATATGATTCTTAATGTCTAAA | 413,891 | 100 |
| 1008. | TTCTTAATGTCTAAAATAGTGTTT[A,G]ACTTTCTTTTCTCTATTTTAGTAA | 413,926 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1009. | CTATTTTTAGTAACCAATGTCAAC[A,G]ACCTTAATGAAGCACTTGAAAAGAT | 413,963 | 100 |
| 1010. | TATTGATAACTAATTGTTACTTCA[G,A]TAACTCATCAAACTATTTTAATAA | 414,062 | 100 |
| 1011. | AATGCAACATGATATATCAATATG[C,T]TTTTCTATTAGACAATTCAACTTCT | 414,145 | 100 |
| 1012. | AGAGATTAATTCTCAAGTAAGAAA[G,A]ACATGGCAATTTAATCTAAAATAGA | 414,336 | 100 |
| 1013. | TAATTCTCAAGTAAGAAAGACATG[G,A]CAATTTAATCTAAAATAGATTTCTC | 414,342 | 100 |
| 1014. | CCATATATTTTTGCCTCATATGCT[T,C]ATCAGTTAAAATTCTTCATGCTCAT | 414,398 | 100 |
| 1015. | ATCTTTTTGTTGTTTGTTCATAGC[C,]TTACATGTATCTTTGAATATTTTGT | 414,488 | 100 |
| 1016. | TGGTTTACAACCTTTCTTTGAGAG[T,C]TGTAAGGGTGTAAAGGGCTAGAGCT | 414,635 | 100 |
| 1017. | GTCATTCCTTATAATGTAAGAGGT[A,G]ATGAAAAGATTTTCTTGCAAATTA | 414,769 | 100 |
| 1018. | CATTCCTTATAATGTAAGAGGTAA[T,C]GAAAAGATTTTCTTGCAAATTAGA | 414,771 | 100 |
| 1019. | CCATAATTGCTTTTCCTCTATTTT[C,T]TTTTTTtCATTAATCCCATATTAGTTC | 414,924 | 100 |
| 1020. | ATATTGTTATGGTGTAGGAGGGA[A,G]GGTATCATTAATCCCATATTAGTTG | 414,967 | 100 |
| 1021. | CTATGAGCCAAAACGGACAATACG[T,A]AATAGCCGAGCCATGAGCTCTTGGT | 415,102 | 100 |
| 1022. | ATACGTAATAGCCGAGCCATGAGC[T,C]CTTGGTTGCAACAGTGGCACACTAG | 415,121 | 100 |
| 1023. | CGAGCCATGAGCTCTTGGTTGCAA[C,T]AGTGGCACACTAGGAAAGGAATCAC | 415,133 | 100 |
| 1024. | ACACAAACTCCTTGACTGGAGGGC[G,A]GTAATAAAAATAAAGATGATGGTACC | 415,213 | 100 |
| 1025. | TGGAGGGCGGTAATAAAATAAAGA[T,G]GATGGTACCTTCCGTCTATCCATAG | 415,229 | 100 |
| 1026. | CAAAAACGGACAATACTTCACATG[C,T]CAAGCCATGAGCTCTTAATCATAAT | 415,451 | 100 |
| 1027. | AGCCATGAGCTCTTAATCATAATA[G,A]TGGAGGGAGGGCATCATTAGTCTCA | 415,478 | 100 |
| 1028. | GGAGGGAGGGCATCATTAGTCTCA[T,C]ATTGGTTGTAAATCAAAGAAGATCC | 415,504 | 100 |
| 1029. | TCATAGTGGCTAAAGATCGAAACT[A,G]ATAATACATCACATATGCGGGAGTG | 415,878 | 100 |
| 1030. | TCATGATTTGTAGTGAGCATTCAT[C,G]TACTATTTTTTtCCAGAACTCATT | 415,973 | 100 |
| 1031. | ATTTATCTCAATTTTCATGTTTTA[A,G]AAGAAGGATAGATCTTGCCCAATAA | 416,026 | 100 |
| 1032. | ATTTATGAAAGTCCTATGAAAGCC[T,C]TATTGTAGTCAGAAAACAAGGTCAA | 416,086 | 100 |
| 1033. | GTCTATGGTTGAGAACTTCAACCA[A,C]TTGACTACGTTGCCTGAATGTTCAA | 416,148 | 100 |
| 1034. | TTATGATAGCAACTCTTCAAAAAa[C,T]CAAAAaTTGTGATGACAAACTGTTGC | 416,327 | 100 |
| 1035. | CAACTCTTCAAAAAaCCAAAAaTT[G,A]TGATGACAACTGTTGCCTAGGCGAC | 416,336 | 100 |
| 1036. | AAaTTGTGATGACAACTGTTGCCT[A,G]GGCGACATGTAAGTGGTTAAGATTG | 4165,355 | 100 |
| 1037. | CTAAAGTAGATGTTGAATCATAGG[C,T]GAACAATACTACTGAACAATACATA | 416,497 | 100 |
| 1038. | GAACAATACTACTGAACAATACAT[A,G]TTTCTTGCATACATTGGCTTGACTA | 416,522 | 100 |
| 1039. | ATACATTGGCTTGACTATTAGTGC[T,C]ATGCACTCTAGGTTCATTTATACTT | 416,555 | 100 |
| 1040. | ATTAGTGCTATGCACTCTAGGTTC[A,G]TTTATACTTCACAAGAGTTTTTATT | 416,571 | 100 |
| 1041. | TGAATAAGAGTTAAGTAAAAGGAC[C,G]TAATTATCATAAGCTATGGAAGACA | 416,673 | 100 |
| 1042. | ATGGAAGACAAGACAAGGGATACT[G,A]CCATTGATACTCTTAGTAAAATAGT | 416,713 | 100 |
| 1043. | CTGCCATTGATACTCTTAGTAAAA[T,A]AGTGTTATAAGTGATAGTAATAGCA | 416,735 | 100 |
| 1044. | GAAATGCATACAAGTTGCGGTATC[A,C]TTTGTGAAAGAGAAAGTATTTTCTT | 416,831 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1045. | CATTTGTGAAAGAGAAAGTATTTT[C,T]TTTTATTTACGTTTAGTCAAAACCA | 416,854 | 100 |
| 1046. | GAAAGAGAAAGTATTTTCTTTTAT[T,C]TACGTTTAGTCAAAACCATATTTAT | 416,861 | 100 |
| 1047. | ATTTGCCATTATACCGCCATTGGT[A,T]AGAACAAAATGCCCTCAATACCAAA | 416,974 | 100 |
| 1048. | CATTATACCGCCATTGGTAAGAAC[A,G]AAATGCCCTCAATACCAAAATAAAC | 416,980 | 100 |
| 1049. | AAATGCCCTCAATACCAAAATAAA[C,T]TGCATTTGCAAGTTATTTGAAAGAA | 417,005 | 100 |
| 1050. | TTGAAAGAAGTGCAACTCTATTAT[T,C]GTGGCATGTTAACGAGCTTTTCTAT | 417,046 | 100 |
| 1051. | CTATGATGGTTATCAAATTGTATA[A,G]CGAAGGCAAAAAACTATGGCTAAAT | 417,117 | 100 |
| 1052. | CAAGGCTCTAAAGAATATACAAAG[T,C]CTTAACTTCTTTACATCCTCAAAAT | 417,330 | 100 |
| 1053. | CTCAAGTATCTGATTGGTGTTGAT[A,G]ATGCTCCATCTAATTAATTCCTTCA | 417,475 | 100 |
| 1054. | CCAAAATACATATATCCTATGAC[T,C]CTTAAAAAGAAAaGGAAAAGAGGAG | 417,526 | 100 |
| 1055. | GATGTAAGCTTTACAATCCAATAA[G,A]AATTTTCACACACCAACACTAATAT | 417,575 | 100 |
| 1056. | GCTTTACAATCCAATAAGAATTTT[C,T]ACACACCAACACTAATATAATAATA | 417,582 | 100 |
| 1057. | TAATAATAATAAATAaAAATAAG[T,C]AATAGTTGTTACTCTTATAAGTCTT | 417,624 | 100 |
| 1058. | ATAATAAAACATGCAAAGAAAGTA[C,T]ATCTTTTTATATAATAAATCATATT | 417,692 | 100 |
| 1059. | CACTGAACTATCACAATCATGTTT[C,A]TGGCTCATGGCAAGATATCGACATA | 417,795 | 100 |
| 1060. | CTGGCTCATGGCAAGATATCGACA[T,C]AGTGGCTAGTCTCCTAAACTATCAC | 417,819 | 100 |
| 1061. | TCTAAACTATCATAATCACATTTT[C,T]AGATTACGGTAAGGATCAATATAGT | 418,017 | 100 |
| 1062. | AAACTATCATAATCACATTTTCAG[A,T]TTACGGTAAGGATCAATATAGTGGC | 418,020 | 100 |
| 1063. | CGGTAAGGATCAATATAGTGGCTT[A,T]TCACACAGACTACCACAACTATATT | 418,048 | 100 |
| 1064. | ACACAGACTACCACAACTATATTT[C,T]CAGCTTGTGGTGGGGCATCAACAAT | 418,075 | 100 |
| 1065. | CAGCTTGTGGTGGGGCATCAACAA[T,C]ATTAATAGCCTAAAGCACCACAACC | 418,100 | 100 |
| 1066. | CATCAACAATATTAATAGCCTAAA[G,A]CACCACAACCCACTATTCAGTTACA | 418,115 | 100 |
| 1067. | ATAACTTCATACAGATCTCTCTCT[A,C]TATATATGTATGTATATATGTATGT | 418,260 | 100 |
| 1068. | ATGTATGTATATATGTATGTGTGT[T,G]TGTATACATACAATTAACAAATAAG | 418,290 | 100 |
| 1069. | ATACATACAATTAACAAATAAGCA[C,T]ATAGCATGCAACTATCAAAAATCAT | 418,318 | 100 |
| 1070. | CATATAAATCAAAATCACTATGCA[C,T]AAAATAATTGTTATATAAATAGATG | 418,365 | 100 |
| 1071. | ATATAAATAGATGATCAATGTCTA[G,C]AAATTTTCGCTCTACGTACTGATG | 418,402 | 100 |
| 1072. | CTAGAAATTTTTCGCTCTACGTAC[T,C]GATGACAAACTTGGTTATAACTATT | 418,423 | 100 |
| 1073. | GTCCATGCCTAGCATGTCCAATCA[A,G]TCAATATAATTTCAGTTCATCCTGA | 418,478 | 100 |
| 1074. | CAATCAATCAATATAATTTCAGTT[C,T]ATCCTGAATCAACCATTAGCATAAA | 418,496 | 100 |
| 1075. | CATAAAAATTAAATAACTTATTGT[C,T]AGTGTTTTAATTTCAAAGCTCTAAT | 418,540 | 100 |
| 1076. | AACTTATTGCCAGTGTTTTAATTT[C,T]AAAGCTCTAATATTCGAATTAATCT | 418,554 | 100 |
| 1077. | TCTATACTTTCTAATTAAAAATTA[C,T]ATAATTAAATAAAAAATTTGGATTT | 418,617 | 100 |
| 1078. | TTACATAATTAAATAAAAAATTTG[G,A]ATTTTATCTTGACTATAAACTAGAG | 418,638 | 100 |
| 1079. | GCATAAAATCCCTTGCTCAGTATT[T,C]CTTAATTGGATGATTGGTCCCATCC | 418,687 | 100 |
| 1080. | TCTTAATTGGATGATTGGTCCCAT[C,A]CAAAATCAAAATCAATAATTAGAAA | 418,711 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1081. | CATAAAATGGTTATCATCGATGGT[A,G]GAAAATTTAGAAGAAGAATATAGCT | 418,765 | 100 |
| 1082. | GGCAATGCTAGTAGCATCCAGTGA[C,T]TAGTGTTAGCCCAATATACATAATC | 418,943 | 100 |
| 1083. | TAGGAATTTGGTGATGATAAAATC[A,C]AACAATGCTTAGCAGGGTCGGGTTT | 419,035 | 100 |
| 1084. | AGGGTCGGGTTTGGAGTTAACTAT[T,C]ATACAGAACAAGTCCAAAACCTTCT | 419,073 | 100 |
| 1085. | AAACCTTCTTCTAGGATCAACATA[G,A]GGTCTACTATCAAGTCTTCAAAATC | 419,114 | 100 |
| 1086. | TATAAGAAGAGAGAGAAAAAGATA[G,T]AGGAAGAAAGCTGGTAGAAAGAGAT | 419,194 | 100 |
| 1087. | GAGAAGGGAGAAAAAaaGAACAAA[C,T]CAAATCTCTCTCTTTCTCTCTTCAT | 419,250 | 100 |
| 1088. | TTTCTTCAAAAAGGGGATTTTCCC[C,T]TTTCTCCCTCTCTTTCTCCTAGCGG | 419,307 | 100 |
| 1089. | GATTTTCCCCTTTCTCCCTCTCTTT[T,C]CTCCTAGCGGATGGCTAAGGCCAGC | 419,322 | 100 |
| 1090. | CCTAGCGGATGGCTAAGGCCAGCA[G,A]TCTATGGTGGTGTCTAGTGGTGAAG | 419,349 | 100 |
| 1091. | TGGTGGTGTCTAGTGGTGAAGATG[C,T]TATGGCCGCAGTGCTACAGCGATGG | 419,378 | 100 |
| 1092. | CGGTTGGTAGTGGTAGTGGGCGAT[C,G]CAATAGAAAGAAAAGGAAATCAAAA | 419,435 | 100 |
| 1093. | TTGATATGATAAGAAGACTACAAG[G,A]TGGTCAGCGGTAATGACAAGCATCC | 419,509 | 100 |
| 1094. | GTGGTCAGCGGTAATGACAAGCATT[C,T]CGCATTAGCTTAACCTCTTATGATA | 419,533 | 100 |
| 1095. | GCATTAGCTTAACCTCTTATGATA[G,A]TTGCAAAGGCAATAATAGCCACAGT | 419,559 | 100 |
| 1096. | AGAAGGTCCTTAGTGCGGCAACAT[C,T]CGACGGTCTTCCAAGAAGATTTCAG | 419,637 | 100 |
| 1097. | GTCCTTAGTGCGGCAACATCCGAC[G,A]GTCTTCCAAGAAGATTTCAGCCAAT | 419,642 | 100 |
| 1098. | TCTTCCAAGAAGATTTCAGCCAAT[G,A]ATGGCTGTATGAAAATAaAAAaGAA | 419,668 | 100 |
| 1099. | ATAaAAAaGAAaAAAaGGTACCAA[T,C]AAGATGGGAGGCCACGATGCCTCGA | 419,707 | 100 |
| 1100. | GGTACCAATAAGATGGGAGGCCAC[G,A]ATGCCTCGATCATCTCTAATGATGG | 419,723 | 100 |
| 1101. | ATACAGTGGAAGCTTGGCTTTATA[A,G]ATGATGGAGGCTAGGGTTTTCTAGC | 419,843 | 100 |
| 1102. | AATGATGGAGGCTAGGGTTTTCTA[G,A]CCTCCGATGAGTTGGAGAAGGAGCC | 419,867 | 100 |
| 1103. | CCTCCGATGAGTTGGAGAAGGAGC[C,T]AGAGTCAAACTCTTTCTTCGACTCA | 419,892 | 100 |
| 1104. | TTTCTTCGACTCAAATAGGGGAAG[G,A]GAAGGTCTTTCCTTCCTTCCCATTG | 419,929 | 100 |
| 1105. | TTCGACTCAAATAGGGGAAGGGAA[G,A]GTCTTTCCTTCCTTCCCATTGTTTC | 419,933 | 100 |
| 1106. | TTTCAAGCCTCTACAACCATATGA[A,C]ATCATAATGTCAAAGCTAGAAAAGG | 420,015 | 100 |
| 1107. | ACAACCATATGAAATCATAATGTC[A,G]AAGCTAGAAAAGGAGATCTATGCCA | 420,027 | 100 |
| 1108. | AAAGGAGATCTATGCCATAATATT[C,T]CAATTCCAAGCCTAATCAAAGAACC | 420,060 | 100 |
| 1109. | GATACCTAAGTTCTCCCTAGCATT[A,G]TCTATGGTAAGAAAATCTATTAATT | 420,135 | 100 |
| 1110. | CTAGCATTATCTATGGTAAGAAAA[T,C]CTATTAATTAAAATTGCATAATTAT | 420,151 | 100 |
| 1111. | AAGAAAATCTATTAATTAAAATTG[C,A]ATAATTATATCTAAATCAGTCAAAG | 420,168 | 100 |
| 1112. | TCTCTCTTTCTTTATCAAAATTAT[A,C]CTCCTTTACCAGGAAACTAATTCGA | 420,230 | 100 |
| 1113. | ATCTTTTGGATCAAAGAATTAATG[T,C]ATTTAATTAGTTTCAAAATAACTCA | 420,292 | 100 |
| 1114. | TAATCTAAATCCATCGATTCCTCT[G,A]GGTTGACTAGGTGAATTCTAACAAA | 420,368 | 100 |
| 1115. | TTCTAACAAAATACCGCTTAATAT[C,T]GGAACCAAGAAGATCCAAAATTTTA | 420,408 | 100 |
| 1116. | TTAAATTAATCCTGACTTCTCTAA[C,T]AGTTGAATTAGACTATCAAGATCAC | 420,611 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1117. | TTAATCCTGACTTCTCTAACAGTT[C,T]AATTAGACTATCAAGATCACCTTTT | 420,616 | 100 |
| 1118. | ACTTCTCTAACAGTTCAATTAGAC[T,A]ATCAAGATCACCTTTTCTCTTGGAA | 420,625 | 100 |
| 1119. | TTCTAACAAGTTAGAAAACTCTAA[A,G]TCAACATTCTTATTAACTTGTTTAT | 420,688 | 100 |
| 1120. | TTCACTACAATTCTTAGTATCAAT[C,T]GACAAACCACATGAACGCCCCTTAT | 420,754 | 100 |
| 1121. | CACATGAACGCCCCTTATATGTTA[G,A]ACATATACAAGTCCACCAGAATCAA | 420,786 | 100 |
| 1122. | TAGACATATACAAGTCCACCAGAA[T,C]CAATTTCTCTACTCAATTAAATATC | 420,808 | 100 |
| 1123. | ATAGCAAGATACTATAGACCTGCT[C,T]ATAAGCCTAACTCTGATTAGAATTT | 420,859 | 100 |
| 1124. | ATAGACCTGCTCATAAGCCTAACT[C,T]TTGATTAGAATTTAACACATCCAACT | 420,872 | 100 |
| 1125. | GATAATTTAAATTATCAAAGATTC[T,C]ACCAAGATGCATATCTCATATCCAA | 420,967 | 100 |
| 1126. | AATTTAAATTATCAAAGATTCTAC[C,T]AAGATGCATATCTCATATCCAATTG | 420,970 | 100 |
| 1127. | TCTACCAAGATGCATATCTCATAT[C,T]CAATTGATAAAATCTAATCCATTAA | 420,989 | 100 |
| 1128. | TGATCTTCTTATAGGTTTGATTCT[C,T]GAAGAATGTTTATTTTAACACTAT | 421,081 | 100 |
| 1129. | TTATAGGTTTGATTCTCGAAGAAT[G,A]TTTATTTTAACACTATGTAATTCT | 421,089 | 100 |
| 1130. | CCTAAACAACTTGCTAGTAAAGTC[T,C]AAAATTTTAATGATCAAACAATTAA | 421,153 | 100 |
| 1131. | ATATTAAGTTTAGAATTTCAAAAA[T,C]ATCTAAGTGACAATTGAGCAAGTAC | 421,238 | 100 |
| 1132. | GTGACAATTGAGCAAGTACACACA[G,A]CATAACACAATCTACCAATATATCA | 421,269 | 100 |
| 1133. | ATACTTAGGTCAAATCTTACTTAT[T,C]GAAATTAGAGACATAACTTATCCAT | 421,346 | 100 |
| 1134. | AATCTTACTTATTGAAATTAGAGA[C,T]ATAACTTATCCATTCCTTTTGTACT | 421,358 | 100 |
| 1135. | CTTTTGTACTCATAATATGCCAAG[T,C]CTTATGCATAAATTTTTATCATAAT | 421,398 | 100 |
| 1136. | TATTTCTACTATGTACATTACATC[C,T]CTAGTGATCACAACTTTAAGTTCAA | 421,479 | 100 |
| 1137. | AAATATCAATTAAGTTATAATCCC[T,A]AATAATCATAACCTAGCTCTGACAC | 421,527 | 100 |
| 1138. | ATGATGGCCGTATACTTTCTAGGA[C,T]AAGATCCTAAAGAATATGCAAGATT | 421,617 | 100 |
| 1139. | CCGTATACTTTCTAGGACAAGATC[C,T]TAAAGAATATGCAAGATTTTAAATT | 421,624 | 100 |
| 1140. | ATGAATATTACACATTAACAAATA[C,T]CAAACCTTGTATAATTTATAAAATT | 421,720 | 100 |
| 1141. | GATCATCTGATTGGTATTGATGAT[A,G]TTCCATCTAATCAATTCTTTCAACC | 421,771 | 100 |
| 1142. | CAGATCCTATAATATTTAGGTGCT[A,G]GGCTCTAAATTATTACAACTATATT | 422,069 | 100 |
| 1143. | GTGGACTATCACAATCACATTTTT[A,G]GCATGAGGTTGGACATAAGCATAGT | 422,158 | 100 |
| 1144. | TCACATTTTTAGCATGAGGTTGGA[C,T]ATAAGCATAGTGGCTAATCTAGAGG | 422,172 | 100 |
| 1145. | ATAAGCATAGTGGCTAATCTAGAG[G,A]GTCATAAGTGCTCAACTCTGACTAC | 422,197 | 100 |
| 1146. | ATTGGGATATCAATAAAATGGCTA[G,A]TTCAGAAAACTACAAGTACTCAACT | 422,269 | 100 |
| 1147. | GGGATATCAATAAAATGGCTAGTT[C,T]AGAAAACTACAAGTACTCAACTCTA | 422,272 | 100 |
| 1148. | CAAAATAGCAAGCCTAGAGCACCA[C,T]AATCCACCATTCAAGGACACAATTC | 422,362 | 100 |
| 1149. | AATAATTTAAGATCATATTTCTTT[G,A]TAAAATTTAATACATAAAATTACCA | 422,416 | 100 |
| 1150. | AACCACTCAAGTTGGGATAAGTGA[C,T]ATGTGATATATAACTTTATACAGAA | 422,467 | 100 |
| 1151. | TATACTTAAGAAATAAATGTATAG[C,A]ATATAACTATCAAAAACTATATAGA | 422,524 | 100 |
| 1152. | ATAGCATATAACTATCAAAAACTA[T,C]ATAGATCAAAATCATTAATTCACAA | 422,544 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1153. | TCTTATCTCTACTAATGACAAACT[C,T]GGTTACAACTATTTTCTTGTCCATG | 422,634 | 100 |
| 1154. | AAACTCGGTTACAACTATTTTCTT[G,A]TCCATGCCTAATATATCCAACCAAT | 422,653 | 100 |
| 1155. | AACTATTTTCTTGTCCATGCCTAA[T,C]ATATCCAACCAATCAACATAATTCC | 422,665 | 100 |
| 1156. | ATTTAAAATTATATAATTAAATAA[G,A]AAATTAAGATTTTATCTTGACTTGT | 422,829 | 100 |
| 1157. | ACTAAAGCATAACATTTCTTGCTT[T,C]GCATTTTCTTATTGGGATGATTGCT | 422,881 | 100 |
| 1158. | CATTTCTTGTTTTGCATTTTCTTA[T,C]TGGGATGATTGCTCTCATCCAAAAT | 422,893 | 100 |
| 1159. | ATGGTGGAAAACTTAGAAGAAGAA[C,T]AGTTGGTCGAATAATAACATCCGAT | 422,985 | 100 |
| 1160. | AACATCCGATGGCCCAAGTGGGTT[T,C]GATCTAGATGCCTTAGCTAGTGATT | 423,025 | 100 |
| 1161. | TCGTCTATGATGGGTTTCGTGGTT[A,G]CTTGATCAAGATCAAGGTGAAGAAG | 423,092 | 100 |
| 1162. | CCAGTGTCAGCCCATCTAGGTGAT[C,T]CAAATGATTAATCTATAATTAAGAG | 423,166 | 100 |
| 1163. | TGATCCAAATGATTAATCTATAAT[T,C]AAGAGCCAAATTATAGCTCAATAGA | 423,186 | 100 |
| 1164. | TAAAATCCAACAATGCCCGGCAAG[A,G]GTCGGGTTAGGAGTGAACAATTATA | 423,249 | 100 |
| 1165. | AATCCAACAATGCCCGGCAAGAGT[C,T]GGGTTAGGAGTGAACAATTATAGAG | 423,252 | 100 |
| 1166. | CCATCAAGTCTTCTAAATCTATCT[T,A]TCTTtCTTTTTTTTtATGCCTAAA | 423,341 | 100 |
| 1167. | AATCCAAGAAGAGAGATAACAATA[A,G]AGGGAGAATGTAGAGAGAGATGTGA | 423,389 | 100 |
| 1168. | CTTCTTTCTTCAAATAGAAGATTT[T,C]CCTTTCTCCCTCTCGTCCTCCAAAC | 423,480 | 100 |
| 1169. | ATGGCAGTGGATGGCTGAGGCCAA[T,C]AGCCTGCGATGGCATCCAACAGTGA | 423,530 | 100 |
| 1170. | CAACCCCAGTAGCAACAATGATGG[C,T]AGCTGGTGGCAGCAGTGGGCAATCG | 423,588 | 100 |
| 1171. | CAATCGGATATAAAGAAGAAGAAA[A,G]TCAAAGCAAAATAAGGCAAGAGGCC | 423,632 | 100 |
| 1172. | GAAGAAGAAAATCAAAGCAAAATA[A,G]GGCAAGAGGCCTTGCTTTGATCCAA | 423,646 | 100 |
| 1173. | ATGGCAATAATGGCCATGGTGGCC[A,G]ATGGTGGATGAATCAAAGAAAATAG | 423,768 | 100 |
| 1174. | ATGGTGGCCAATGGTGGATGAATC[A,G]AAGAAAATAGGGGATCCTTGGTGCG | 423,783 | 100 |
| 1175. | GGTGGATGAATCAAAGAAAATAGG[G,A]GATCCTTGGTGCGGCAAGATCTAAT | 423,795 | 100 |
| 1176. | TCAAAGAAAATAGGGGATCCTTGG[T,C]GCGGCAAGATCTAATGGTCTTTCAA | 423,805 | 100 |
| 1177. | TTCAAGAAGATCTTAGCCAACAAT[G,A]GCTACACGAGGATAGGAAGGAAGGA | 423,850 | 100 |
| 1178. | TAGGAAGGAAGGAGAGAAAGTGCC[C,A]ATGAGATGGGAGGCGATGCCTCATC | 423,887 | 100 |
| 1179. | TCATCTCCTATGATGGTTCAACCA[C,T]GATTGGGCTAAAACTTTTtTCTCCT | 423,932 | 100 |
| 1180. | ACTTTTtTCTCCTCCTTTTTtGAC[A,G]ATGCAATCAATTGATTTCTACCTAG | 423,969 | 100 |
| 1181. | GACAATGGAGGCTAAGGTTTCCAT[G,A]CATCCAATGAGTTTGAGAAGAAGCA | 424,039 | 100 |
| 1182. | ACTCCTTCGACTCAAACAAGGAA[A,G]GGAAGGTCTTTCCTTCCTTCCTATT | 424,097 | 100 |
| 1183. | TGGGTAGGGTATCACAACAGTTTT[G,A]TTTCTAAATTGTCATTATCAGGAAG | 424,187 | 100 |
| 1184. | TACACCACATTCGATGTAGAAAAA[C,T]TGCACCACTCCGCCTAATTGAGCCA | 424,249 | 100 |
| 1185. | ACCACATTCGATGTAGAAAAACTG[C,T]ACCACTCCGCCTAATTGAGCCACAT | 424,252 | 100 |
| 1186. | TATCTTATGGCCATATTATAATAT[C,T]CTGCAATCAAATTATGATTTCTTAT | 424,403 | 100 |
| 1187. | TTATGGCCATATTATAATATCCTG[C,T]AATCAAATTATGATTTCTTATATAC | 424,407 | 100 |
| 1188. | CATTGGAAAACGGTGCATTACATG[A,G]CTCAATCAGATGGCGCGGTGCATTT | 424,705 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1189. | GCGGTGTACAAAGAATTTCTCTTA[C,T]TAGGAAATATCTTGAGTCTAGACCG | 424,769 | 100 |
| 1190. | CTAGGAAATATCTTGAGTCTAGAC[C,A,T]GGCCCATTTGTCATTTAGACCAATC | 424,793 | 100 |
| 1191. | TCAAGGACTATGAATTTTGGTCCA[T,C]AATAAGTATGAGATCGTCATGGGAT | 424,841 | 100 |
| 1192. | CATAATAAGTATGAGATCGTCATG[G,A]GATTGAAAAAGATGGGAAATAACTC | 424,863 | 100 |
| 1193. | GATCGTCATGGGATTGAAAAAGAT[G,A]GGAAATAACTCCTCAGTTTGCCCCT | 424,877 | 100 |
| 1194. | AAAGATGGGAAATAACTCCTCAGT[T,G]TGCCCCTTGACAGCTCACAATTCTT | 424,895 | 100 |
| 1195. | CCAATGCTATCCATATAAAGGTA[T,C]TTGTTTTCTATTAATGTCATTGCAC | 425,010 | 100 |
| 1196. | ACTAATGAAGACAGCTTCAGCAAA[G,T]ATAGAGCAGAAATCCTTTAAATTTT | 425,058 | 100 |
| 1197. | AAGGGAAATCATTGTGGTTCACAG[G,A]TGGGGGTAGAGCATGTAAGATACGA | 425,549 | 100 |
| 1198. | ATTTGTATTCTGTTCTGCCCCCAG[A,C]AATCAGCATAGGCACCATGATGCAT | 425,635 | 100 |
| 1199. | AACTTCAGAATTTTTTGGCCCATC[C,T]AGCTCTTTAATTTGATTTTTGATGC | 425,707 | 100 |
| 1200. | GAGAACAAAACTCTCTTCCTTGTC[C,T]TTGTCTGCTATTTCTTTCTGATATA | 425,969 | 100 |
| 1201. | ACATCTCAACAACCATAACTGAAG[C,G]CCCTTCAAAGCTAAATGCCTGTTA | 426,632 | 100 |
| 1202. | CCATAACTGAAGCCCCTTCAAAGC[T,C]AAAATGCCTGTTAATTTGTTCTTCA | 426,644 | 100 |
| 1203. | AATGGCATTTTTTCCTAGATGTCC[A,C]TACCGATACTAACGGTATTTTGGAG | 426,701 | 100 |
| 1204. | AGTCTCTAAAATTTTCACTTGTTG[T,A]TTCCATTGATTCTATTTCTTTATAT | 426,820 | 100 |
| 1205. | ACAACACTATTCACACCATCAAGA[C,T]CAGACAACCCTTCATCTTGGATATG | 427,075 | 100 |
| 1206. | CAAATGAAAAACCTAAAATGCTGA[A,G]AGGAATCTCCACAATTATGGAGGAA | 427,448 | 100 |
| 1207. | GAGGAATTAGTACTTCTTAGACCA[C,T]GAAGCTAAAACTAGATCTGCAATCC | 427,492 | 100 |
| 1208. | GCCGAGTGTCACCAAAACATTATT[G,C]AAGTTGCTAAGCCAAGCCCTCAAAG | 427,567 | 100 |
| 1209. | TTTTTGCGTGATGCATATAGGCCT[G,T]GTAGATCACCAAAACCAGACTCGCC | 427,721 | 100 |
| 1210. | GTAAGTCCAGGTTTTCCAGTAGTC[C,T]TGTGATTCTTGCCTCCAGCTAATGC | 427,777 | 100 |
| 1211. | CCAGCTAATGCTTTAGCAGACCAT[T,A]GCAAGCAAATCTCTGTCAGCAACTA | 427,816 | 100 |
| 1212. | GCAGACCATTGCAAGCAAATCTCT[G,A]TCAGCAACTATATGGTCACTTGGAG | 427,831 | 100 |
| 1213. | TGCTTGTCTTTTTGCTTATAGCCT[T,C]CAATTTATTTGATATTATAGTATTA | 427,898 | 100 |
| 1214. | GCCTTCAATTTATTTGATATTATA[G,A]TATTAACCCAAGCTCAAGCTCGACT | 427,918 | 100 |
| 1215. | TTATTTGATATTATAGTATTAACC[C,T]AAGCTCAAGCTCGACTCGATGAAAA | 427,927 | 100 |
| 1216. | AAGCTCGACTCGATGAAAAATAGA[C,T]AAAACTCGAGTTGAGCTTGAATATC | 427,958 | 100 |
| 1217. | TCGAGTTCGAGATCAAGTCTTAGC[T,G]TACTAATAAGATATATATATATATA | 428,021 | 100 |
| 1218. | AACTTTGACTCATTTGTATACATC[G,A]TAAGCTTCTAAAGATAGCCATAAGA | 428,943 | 100 |
| 1219. | AAGGAGGGTGGTACCAACCTATCG[G,A]CTGAAGTTTCGTTGGTGAATGTTAA | 429,038 | 100 |
| 1220. | TACCAACCTATCGGCTGAAGTTTC[G,A]TTGGTGAATGTTAATTTTTGCAAAT | 429,049 | 100 |
| 1221. | ATACAAGCCAATGATCTGTATTTA[A,C]TTAGCTCCCAGTTGCTAGATGGAAT | 429,250 | 100 |
| 1222. | tGGATTGAAGGTACTAAAGCATTT[A,G]AAAaTAAAAaTTTCTCACAATCCG | 429,322 | 100 |
| 1223. | ATTAATCAGCAATCACTAGGTCGC[A,T]GGTTTGAATTCGGCAAGTTAGATTT | 429,411 | 100 |
| 1224. | TTATCCTTTAAAATTTTTACATCA[T,C]AAACTTTAAATTATAATTTACAAAT | 429,561 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1225. | TTTACAAATATTTATTTCATTTAT[A,T]ACAACAGAACATATAGCATGAGAAG | 429,602 | 100 |
| 1226. | TTATTTCTCAAAAATGTTTTTGTG[T,G]CAACACATCTAACAATATCATTGTC | 430,072 | 100 |
| 1227. | CTCAAAAATGTTTTTGTGTCAACA[C,T]ATCTAACAATATCATTGTGAAACTT | 430,078 | 100 |
| 1228. | TTTGTGTCAACACATCTAACAATA[T,G]CATTGTCAAACTTTTATATAAAGCA | 430,090 | 100 |
| 1229. | ATTATTCAATACTTTTAATCTTGC[C,A]TTTGCTATGCCGCTTTTAGTTTCTT | 430,550 | 100 |
| 1230. | CTTAACCCCTTTTTATAGATGCTT[T,C]TGATGTAACCGTCGAGCACATATGC | 431,574 | 100 |
| 1231. | TGTAACCGTCCAGCACATAGTCCC[A,G]CTTTTTATGACGCTAAATTATCGGG | 431,602 | 100 |
| 1232. | CGGGCCATAAATATAAAATTAATG[A,G]GGCGTTAATTCTCCTTAATAGCCGT | 431,648 | 100 |
| 1233. | GCTCAGTCGGTCGATGAAGAGTCA[G,A]AACTGCATGTTCAACCGATATGCAG | 431,905 | 100 |
| 1234. | TACCCCAACAGTTACCCCCACTCT[C,T]AAAGTCCAAGGTGAACCGACGTGTA | 431,993 | 100 |
| 1235. | CAGTGTCAGACATCATTTTGGAAA[A,G]TCAATTCGACGTCGGATGATATGAT | 432,212 | 100 |
| 1236. | GACAAATAGATTTGTGCCATATGT[C,T]TGAATGTTATTGGGTCGGATCTGTT | 432,265 | 100 |
| 1237. | AGATGTTGCCACATGTCACATCTG[A,G]TAAATTTTCGATTCAATCACCTTCA | 432,384 | 100 |
| 1238. | CCAACGTCTGAGGTTGTTATTTTC[G,A]TCTTTTTCAGATCAAGTTTCTGTCT | 432,536 | 100 |
| 1239. | TCTCTTATGGCTAGGACTTCTTCT[T,C]TTTACGGTCGGTTGGAGAATCCGAC | 432,635 | 100 |
| 1240. | TTTGCCCCTAGGGCTGATGGTCGG[A,G]TGAATATCCCTTTTTTGGGCCAGGT | 432,788 | 100 |
| 1241. | CCTGGCACAGAAGGAGCTTGTGAA[C,T]GAACAGACCCTTTATGATGCCGACC | 433,272 | 100 |
| 1242. | GACTTTACTTTTCTTTTACTTGTT[T,G]AGTTGTACTGACTTCTATTGTAATT | 433,370 | 100 |
| 1243. | CTCCATCTGCATCGGTTCCTGAGC[C,T]GATCCCGATACTATCAGCCCCGACA | 433,598 | 100 |
| 1244. | TCTGAACAATCTGTGGCTGCGCCA[G,A]TTGCTCCTTCAGCTGGGGCGCAGTC | 433,750 | 100 |
| 1245. | GGGACTGCCGGCAAGGGATCGGGG[G,A]AAAGCTCTGGTGACTTCGACGGAAG | 433,830 | 100 |
| 1246. | TTCACTTCGACCTTCAAGTACCTG[A,G]TGATAAATTGACCCTGGCCAATCCG | 433,904 | 100 |
| 1247. | AATAAGGTGGCAGCCGTCGATGCT[G,A]AGAAAGCGGCCGCACTCGAACAACT | 434,192 | 100 |
| 1248. | GACGGATGCATCGAAGAACTTAAA[A,G]TCGAACGTGGATGTCATTGGGCCAG | 434,411 | 100 |
| 1249. | TTGAGTCAGACAATCAAGGATTTT[T,C]GGAGTTCGAAAGAATTCAAGGAAGA | 434,555 | 100 |
| 1250. | TACCCGAAGCTCGACTTGAGCAGT[A,G]TCGTCCCTCCAAGATCGGAAGATGG | 434,675 | 100 |
| 1251. | AGCAGTATCGTCCCTCCAAGATCG[G,A]AAGATGGGGTTGTTGAAAAAGAAGC | 434,695 | 100 |
| 1252. | TTGGGTAATCAAATACCTATAATC[G,A]GACTTCAGTCCAATTTTGTAACTTT | 434,862 | 100 |
| 1253. | AGTCAGTTTTTATAGTGGAAAGCC[A,G]ACATTAAAAATCAAAATATAATCGC | 435,288 | 100 |
| 1254. | AGTGAAAGCTGAAATAAACTCTAT[G,A]TCGAAGTACAGTCGATAGTTTGGCT | 435,464 | 100 |
| 1255. | ATTGATAGAACTTGACCAAGGTTT[C,T]TGATTATAATACTGAAGATTCTGTA | 435,544 | 100 |
| 1256. | AGGTGATACATCTTCAGATTGTCG[G,A]CATTTCATGTTCAAAAAATTATCGA | 435,630 | 100 |
| 1257. | AGCTTGCTGTCGGAGTTCTGAAAG[G,A]AGATTTAAGTCGGCTCTTCGATATT | 435,893 | 100 |
| 1258. | TTGATGGCAATCCAATCTCGAGCG[G,A]GATCATTGCTTCTGTTCTATAAGCC | 435,979 | 100 |
| 1259. | AAGGATCAAATATGTCGATTCTCC[A,G]TTGTACGAAGGGCTATGGTGCTACA | 436,443 | 100 |
| 1260. | CAATCGATGTCAACTGACTAGCCG[G,A]TTGATGTTGTATATTTACATACCTT | 436,491 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1261. | GATTTATCTCCCAAATAATTTTCA[C,T]AAATCTCTTCATGTACTTCTCTAAG | 436,631 | 100 |
| 1262. | GAATCTCATCAGTCAAGTATTGGA[C,T]GATCGGATCCATCCAGCTTGGTTCG | 436,818 | 100 |
| 1263. | ATCTTTCACTTTCTAAAGATACTT[T,C]ATCATAGTGGGGTCTCAGGCTTCAA | 437,044 | 100 |
| 1264. | CACCCTTGACTTGTCCAACAATCC[A,G]TTGTGAGTCGGTGAAGACCTTCAAA | 437,096 | 100 |
| 1265. | AGAAATGAATCGACTGAGTGCGAC[G,A]ATCCTTCCATTGAGTTACTGTATCT | 437,928 | 100 |
| 1266. | TCGGGTTTAACTTCATCTGATATC[G,A]TCGAAGTGTGCCAAAGGCTTTCTCC | 438,107 | 100 |
| 1267. | CAAAGGCTTTCTCCAGATCTCGAA[T,C]ATGATCTGAAGTTTGGAGACTCTTC | 438,140 | 100 |
| 1268. | CTTCATATTTCATCCAATCTGGGC[C,T]TTGAAGATCTTATTgACgAGCCGTT | 438,213 | 100 |
| 1269. | CTGGGCCTTGAAGATCTTATTgAC[G,A]AGCCGTTGATAAGTCGCTCCGATAT | 438,231 | 100 |
| 1270. | TgACgAGCCGTTGATAAGTAGCTC[C,T]GATATTTTTCAAACTGAAAGGCATT | 438,251 | 100 |
| 1271. | TGATAAGTAGCTCCGATATTTTTC[A,G]AACTGAAAGGCATTACTTTGTAACA | 438,262 | 100 |
| 1272. | GTCGGTTACAAAAGTCGTGTGCTC[C,T]TCATCTTTTAGTGCCATCCAGATTT | 438,324 | 100 |
| 1273. | GTGCCATCCAGATTTGATTATACC[C,T]GACGAAGGTATCCATGAAACTCAAA | 438,359 | 100 |
| 1274. | TATTTTtCATTGGCTTTTCTCACC[G,A]TTACCACATTGGCGAGTCAATCGAG | 438,514 | 100 |
| 1275. | TCATCCGAGTATGGCATTATGAGC[C,T]GAAGGTACTCGAACTATCGTGAACG | 439,078 | 100 |
| 1276. | ATGGCGTCAAGACTCTTCTGAGTC[A,G]TCAGTCGGTAGTCGCATTCGAGAGA | 439,224 | 100 |
| 1277. | AAACTTTTATTATCTACAATAATT[T,C]TTTTtACATCATAATTTGCTATTGT | 439,300 | 100 |
| 1278. | AGACAACAACAGCATCATCATGGG[G,A]AGTTTGAATTCTCCAAACATCCTCT | 439,355 | 100 |
| 1279. | TTGAATTCTCCAAACATCCTCTTC[T,C]GAAAAAATTATTACATTGTTGAGTC | 439,383 | 100 |
| 1280. | AAAAAATTATTACATTGTTGAGTC[G,A]TCGTCGTTTCACCGACTCTTCTTCA | 439,409 | 100 |
| 1281. | TTCACCGACTCTTCTTCAGTAGTT[G,T]CCCTCAAGTCCAGTCGTTCGGAGAT | 439,441 | 100 |
| 1282. | GATATTTTTGAAGTAGCCTCATT[A,G]AATCAGGGCTTCTATCTCATCCCTG | 439,586 | 100 |
| 1283. | TTAAATCAGGGCTTCTATCTCATC[C,T]CTGAGTTGAATGCATTATTCGGTAT | 439,608 | 100 |
| 1284. | TAAATCAGGGCTTCTATCTCATCC[C,A]TGAGTTGAATGCATTATTCGGTATC | 439,609 | 100 |
| 1285. | ATCACGATGGAACCGACAATACTT[C,T]CTTCGATTGCGATTCCTTAATGATG | 439,668 | 100 |
| 1286. | ACGGAGAGCAAAAGAGGAGTGTA[G,A]AAGTCATACCTGCTGTAATTCAGCC | 439,779 | 100 |
| 1287. | GGGCGAAGCTTGCTTATTGGATGG[C,G]GGCCGACTTGATTCAGCCAGAGCTT | 439,845 | 100 |
| 1288. | CTTTTGTTTCTTCTTCTTCTAACC[G,A]TTGCCTTTTGTCGGGCGTCGGCCAG | 439,902 | 100 |
| 1289. | ATTTGTGACGGCCTTCGACTGCTA[C,A]TGAAGTGAGCCACGAAAGAGTGTTC | 440,191 | 100 |
| 1290. | GAGCCACGAAAGAGTGTTCGAGCT[A,G]TCCAAAGGAGTATATACTTTTCGAT | 440,222 | 100 |
| 1291. | CTTTCTGAAGAGTCGCTGGAAAGT[C,T]GATGCACAAGAGGGCGTTGGTCACC | 440,299 | 100 |
| 1292. | TCGATGCACAAGAGGGCGTTGGTC[A,G]CCCCCTGAATCATCATGAGAGCCTT | 440,322 | 100 |
| 1293. | ATGGTCGATCGAATCAGTGGAGCC[G,A]TCATATGGCTCCACTTACAGTATTT | 440,384 | 100 |
| 1294. | AGCCGTCATATGGCTCCACTTACA[G,A]TATTTTGAACTGAGATGGGATCGGC | 440,404 | 100 |
| 1295. | GCTGGAAAACTCTGAGGGTAGAAC[T,C]CCCTGACGAGCTTGAGGGAGAAGCA | 440,593 | 100 |
| 1296. | CGATCATTTTtCCTTCCTAATACG[G,A]TCGAGATGGGAAGGAGAGGAATGTC | 440,654 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1297. | GGGCTCTGGTCTTCGTCATGGTGT[G,A]TATGATCTTTACCCCTTCCTGACAT | 441,058 | 100 |
| 1298. | TCGTCATGGTGTGTATGATCTTTA[C,T]CCCTTCCTGACATACCAATCTGTTG | 441,070 | 100 |
| 1299. | GATGATTCTGGTGTAATCATCGAG[T,C]ACATGATCCTATTTTTTATGATGCT | 441,332 | 100 |
| 1300. | GGGTGTTTATTTTTCTTAATAGCC[A,G]TGACATGTAGTTGATAACCGTTTGT | 441,403 | 100 |
| 1301. | GTGACGGTTATGGTATTTTGAGCA[G,A]ATTAGCCGATCATATATCGGTAGAA | 441,451 | 100 |
| 1302. | CGGTCAGCCGACAGTAAGTCGGTG[C,T]AGTTCGCTTAGTCAGTCGATAAAGA | 441,624 | 100 |
| 1303. | GAATGATTATTATCGTGTAAAAAG[A,T]TTTTCTCTCTCTCTCATTCTCTC | 441,753 | 100 |
| 1304. | TGTAAAAGATTTTCTCTCTCTCT[C,T]CATTCTCTCATTGTGTCTCTCTCC | 441,768 | 100 |
| 1305. | CACAGGTTATTCGGTTGTAGATTA[G,T]ATCTATAAAGGACATAAGTTATGGA | 442,064 | 100 |
| 1306. | TGTTTATTTACTTTATAATTTTCA[A,T]TTTAAATATGATGAATCTGGTAAAT | 442,114 | 100 |
| 1307. | TCTGGTAAATTGGCAATTCACTGC[C,A]CTTGATATTACGGGCAAGAATTACC | 442,154 | 100 |
| 1308. | GGTACGGCATGATTGGATGCACTT[G,A]AGGTTGCAAGATTTTAAAACTATGT | 442,433 | 100 |
| 1309. | TGGATGAGGTCGTGGGCATGGCCA[T,C]GGTGGTTTCAAAAATATTGGGACAA | 442,778 | 100 |
| 1310. | ATGATGGCAATCCAAATGTGCCTC[C,A]TTTTGATGTCTTCGATTTTTtGCC | 443,040 | 100 |
| 1311. | AAAATTGACTACATGATCATTGAT[G,A]GAGAAATAGTTAAAGAATAATTTTT | 443,102 | 100 |
| 1312. | GAAGAGCAACTATAATACTGTCAG[G,A]TGGTACAAAGTTAGAAATCAACGAA | 443,407 | 100 |
| 1313. | GTGCATCATTTTTTATGATTCAAA[C,T]AGAAAACTTGAGTTAAAAAATTTTT | 443,561 | 100 |
| 1314. | CAAACAGAAAACTTGAGTTAAAAA[A,T]TTTTTTtGTTCTTTCGCCAGGATTG | 443,581 | 100 |
| 1315. | AATAAATATAATATTGAACCAGAA[T,G]TTCACTAAAAAaGAAATGTTTATTC | 443,657 | 100 |
| 1316. | GAAAGGATTCAACGAGACATATAT[G,A]GTCCAATTCATCTCCCTTGTGGACC | 443,898 | 100 |
| 1317. | TCTCATATTCTAGCTGAAATACTC[T,C]AGCTCGGATAAAAGTTTCAATAGGA | 444,768 | 100 |
| 1318. | TAAATTATAAATAAATAAAAGTTA[C,T]TTTGGTATTTTTTCATCATAAATGT | 444,058 | 100 |
| 1319. | AGTTACTTTGGTATTTTTTCATCA[T,C]AAATGTTTCATCTTCTAATGAACTC | 444,077 | 100 |
| 1320. | CTCCTGTGTTGTGGTGAAGTCCTT[G,A]GGACTATTTAGACTCGATAAAGGAA | 444,124 | 100 |
| 1321. | AGACTCGATAAAGGAAGATTTGTC[G,A]CTTAGTCCTTAAACCTGTTTGCGAC | 444,158 | 100 |
| 1322. | AGATTTGTCGCTTAGTCCTTAAAC[C,A]TGTTTGCGACCAAATGATACGTTGT | 444,173 | 100 |
| 1323. | TGTCGCTTAGTCCTTAAACCTGTT[T,C]GCGACCAAATGATACGTTGTTACCA | 444,178 | 100 |
| 1324. | CACTTACACCCTATGGGTTTCATT[A,C]CTTCGGGTGAGTCAACCAATGTCCA | 450,527 | 100 |
| 1325. | TCCACTTACACCCTATGGGTTTCA[T,C]TACTTCGGGTGAGTCAACCAATGTC | 450,529 | 100 |
| 1326. | CTGCGCCCCTCTTCCTCTTGAAGA[T,C]CCACTTACACCCTATGGGTTTCATT | 450,553 | 100 |
| 1327. | GATAATTTATTTAACCTGTTTAAC[T,C]TATTTAATCTATTTCTGATCTATTT | 455,693 | 100 |
| 1328. | ATCGAATTTGAATTTTAGATATCT[G,T]ATCCATTTAATCCGTTTAACCCATT | 455,776 | 100 |
| 1329. | ATTTGGGTCATAAATGGATCGATC[C,T]ATTTAATCTATTTAATAATTAGATC | 455,823 | 100 |
| 1330. | ACAGGTTAGGTTTAGGCTAAACA[G,A]ATTTGGGTCATAAATGGATCGATCC | 455,848 | 100 |
| 1331. | ATAAATTTACTGCAAAGGCAATAT[C,T]AGGTTGGATATAATTAGTAAGATAC | 456,464 | 100 |
| 1332. | AAGTTGCAACCATTGTCTGTTTTA[C,T]AAATTTTCATGAGATGGCACAGTCA | 456,713 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1333. | GTAAAATATGTTTAGTTCAATCTC[C,T]TTTGATAAATCTTCTTTTAACTTGT | 456,917 | 100 |
| 1334. | TTACAAAGAAAAATAATATTTCTC[G,A]TTCATTTACAAAAGAAAaTAATATT | 457,512 | 100 |
| 1335. | AGAGAGAGGAAATCTTTTCATACG[G,A]TAATAATCCTTCTCATTTCATTCCA | 457,589 | 100 |
| 1336. | TGAACACACATTTAAATATTCAAA[T,C]ATATTGTAGAATAATAAAATATATA | 457,671 | 100 |
| 1337. | GAATATTTAAATTTATATATAATT[T,A]TATATAATTTTATATAGTATTTATT | 458,384 | 100 |
| 1338. | TGTAACAGGCAGAAGCAAAGGAAC[T,C]GCATACCTTGATCTAAAAGCCTGCT | 460,498 | 100 |
| 1339. | TTTATCTGACTGATGGGATAAGCA[A,T]GGCAGTAAAAACTCAAAGACTTTTA | 460,849 | 100 |
| 1340. | TCATAGAGCCTTGTCTCAGCTATC[T,A]GGAGTTTGCTTAATGGATCCTCATT | 462,136 | 100 |
| 1341. | CCCAGGTTGGTATCAAAATGTCAC[A,G]GGTTCAAATCCCCATTTAGACCATT | 522,806 | 100 |
| 1342. | CTTGAGTCATGCATGGTCCAGGCT[A,G]CATGTGGTTTTAGCAGCATAAGCAT | 522,924 | 100 |
| 1343. | GTATTATGAAGTAATACCAATTGA[G,T]AAAATATTATAAAGTAATAGTCAAA | 523,012 | 100 |
| 1344. | AAAGTACATGTCACAAACATGGTT[C,T]AATATGATTAAAGTAATAGGCAAGT | 523,059 | 100 |
| 1345. | AAGTACATGTCACAAACATGGTTC[A,G]ATATGATTAAAGTAATAGGCAAGTG | 523,060 | 100 |
| 1346. | AACATGACATTACTCTCACATGTA[T,C]GATAACTTTATTCAAAAAAaTAAAG | 523,305 | 100 |
| 1347. | TGTATTTCCATGTTAGATTCCTAT[C,T]ATAAGGAAGCTCGCAAAAAAaTAT | 523,859 | 100 |
| 1348. | ATCATAAGGAAGCTCGCAAAAAAA[A,T]TATGATTTGATGAATTTTTTtCTC | 523,881 | 100 |
| 1349. | GATGATCAGCAAAACGAAATAATA[T,C]GAGGTAAGGTTCAGCAAATTTAAAC | 524,120 | 100 |
| 1350. | GAGCACATTGCTTTTCTCTAGCTC[T,C]ACATGATCATCGATTTTAGCCTCAA | 524,514 | 100 |
| 1351. | AGTATTTCTTAAGAACAGGGGTGG[C,G]AATTTCTGACCCAGACCCCACAGAC | 524,692 | 100 |
| 1352. | TCACCTTAAATAAACAAGTTTCAA[T,G]GATGTGTTTTtATAATAAGGTTTTG | 524,752 | 100 |
| 1353. | AACAAGTTTCAATGATGTGTTTTt[A,T]TAATAAGGTTTTGTTTCAGGTTAAC | 524,764 | 100 |
| 1354. | TTTCAGGTTAACCAAGACCAATCT[G,A]ATTACAACTTGGTCAGGCTTGGTTT | 524,802 | 100 |
| 1355. | AGTACCGGTAATCTAGTTGAGGCT[T,C]AATTGCATGATTAGGGAGGCTATAT | 524,922 | 100 |
| 1356. | TTTCCACTTAATTTCCTCTCTCTC[T,C]GCATGTGTGTGCATTTGGATTCACA | 525,050 | 100 |
| 1357. | TTTGGCCCTATTTCAGTTTTGTTT[A,G]TAAAGGTATATAATTGAAAAGTGAA | 525,116 | 100 |
| 1358. | CAAAATGGGTTTTGACCCAACCTA[A,C]ATATAACCCACCCAATGCCACTGCT | 525,255 | 100 |
| 1359. | CCCAATGCCACTGCTACTCAAGAA[T,A]GAAAATAAGGATATAACAAACCCTT | 525,290 | 100 |
| 1360. | ATAAAAaGACAAAGGTTCATACA[C,A]CTAAAAaTTATCCATATAATCACT | 525,535 | 100 |
| 1361. | AATAATCCATTAGAGAAACAAAGA[C,T]GTAGATAATCACCTTCTTCATGCGA | 525,602 | 100 |
| 1362. | AGAAACAAAGACGTAGATAATCAC[C,A]TTCTTCATGCGAGAGCCAAGAAACA | 525,615 | 100 |
| 1363. | GATTAAGTTTTGTGACTTTTAGCA[T,A]CAGTAGTTCAAAGTAACTATATACT | 525,791 | 100 |
| 1364. | CCAAATTAAGCAAACTTCTGAAAA[T,A]GTGGACTCCATATTAAAGGTGAATG | 525,867 | 100 |
| 1365. | ATTAAGCAAACTTCTGAAAATGTG[G,C]ACTCCATATTAAAGGTGAATGAAAT | 525,871 | 100 |
| 1366. | CTCAAATTCTGGGCTCATAATATT[G,A]AGTTCTCAATCAGCTTGATAACATA | 525,955 | 100 |
| 1367. | GTACTAAGCACGACGCTTTGGTAT[T,G]GCACATGATGTGGCACCAGCTCAAG | 526,158 | 100 |
| 1368. | GCACGACGCTTTGGTATTGCACAT[G,T]ATGTGGCACCAGCTCAAGTAAAACC | 526,165 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1369. | CTCTCATACGTACCTAGTGGTGTT[T,C]GGCCAACCATAAGGAGAGGGAAAGA | 526,454 | 100 |
| 1370. | GCACAAGTTGAGGGAAGCTAAACT[T,C]CTCTTTAATGTAGTTGTATAGATTT | 526,671 | 100 |
| 1371. | ACAAGTTGAGGGAAGCTAAACTTC[T,C]CTTTAATGTAGTTGTATAGATTTCC | 526,673 | 100 |
| 1372. | ACTTGAACTTGTGTTACCCTCTCT[C,A]TCTTTCCAGATGTGAATATGGGACA | 526,755 | 100 |
| 1373. | GGAGGGAAAAaGAAAGGATGGAGT[G,T]TGTGGGAGTGGGACTTGCAGTGTTT | 526,823 | 100 |
| 1374. | CAATGTATTTAGGCATCTATTATC[A,G]TCTAGTGAAACAAAGGAAATGGGAA | 527,090 | 100 |
| 1375. | TAGATGCCATCCCAATAGTAGTCC[T,C]ATGCATATTTAGTCAAGCCCTACGT | 527,150 | 100 |
| 1376. | CCACTAAATACCTAGGTTCCCGGT[G,A]TCTCACTCCTTGAATTAATTTATCA | 527,294 | 100 |
| 1377. | AAGGAAGCAAGAGATGCAGATTTG[C,T]GGGGGACTCAGATGTGCAGGACTGC | 527,384 | 100 |
| 1378. | ATACACAGAAAAAAAaTGGACCCT[T,C]AAACAACCACACCGAATGCTTATTG | 527,830 | 100 |
| 1379. | AGTCTTTCAAAAATGCAACAAAAA[G,A]AAAAaTGTAGATCGTTCAATTTGAA | 528,005 | 100 |
| 1380. | CCCCTTGCAGATCTCCTTCGGCGT[C,T]GGCAGATCCTTCCCTAAATTCGACC | 528,320 | 100 |
| 1381. | TTTGGGCAAGCTTGCCAATGAAAG[A,C]CTAGTTTTGTCTAGCTTCGTATATA | 529,465 | 100 |
| 1382. | CATGATACAAAATAACTATTAGAT[T,C]ACTCGAGAAGATAGGAAAGAATTGT | 530,032 | 100 |
| 1383. | TTTGTTAGGCATCTTTAGAAAAAT[A,G]ACTTTTGTAAGTTAATTTtGTTttA | 530,109 | 100 |
| 1384. | GTTAATTTtGTTttAGTATAAATT[T,A]TGAAACTACTGGCATATTACTCACA | 530,144 | 100 |
| 1385. | ATATAATTTTTtAGACATTAATAT[C,T]TATTCTATTATTATATAAAATTTTt | 530,256 | 100 |
| 1386. | ATATAAAATTTTtATTTtATTGAT[G,A]AATGTATTTATTGATTTTTaTTAAA | 530,293 | 100 |
| 1387. | AATATATTATTTTATCAATATAAA[A,T]TTTAATTTATTAATATATTATTAAT | 530,364 | 100 |
| 1388. | ATCATTAACCCTAACTTATGCATA[T,C]GTAGGATCCAAACCAGATCACCAAA | 530,949 | 100 |
| 1389. | AAACCAGATCACCAAAACCAACTT[T,C]CGGTGAGCTAGTTGGCATCCATTAT | 530,983 | 100 |
| 1390. | TTGATACGCTTtCTCTCTCTCTCT[C,A]TATATATATATATATATTGATCATT | 531,894 | 100 |
| 1391. | GAGTTGACTCATGATTCGATCCAG[T,C]CTGACCCGTTTAGATCCGATCCTAT | 531,982 | 100 |
| 1392. | TGGATCATTTGAATATTTGCATAT[C,A]TCATACTCTCCAAGCATCATCTTCT | 533,135 | 100 |
| 1393. | AAAGAGTCTGGATTGAATTTTATG[A,G]GATTGGACCATTTATATTCTACTCC | 533,781 | 100 |
| 1394. | AGAATGGGAGTAACCCATTCCATT[T,C]CTATTTTAGGCCCCAATTCTCTCCA | 533,871 | 100 |
| 1395. | AAATCGAAATATAATTTAAATAAT[C,T]GGGAAGAGTAGAGAATAGATTTTGA | 533,932 | 100 |
| 1396. | AATCGAAATATAATTTAAATAATC[G,A]GGAAGAGTAGAGAATAGATTTTGAG | 533,933 | 100 |
| 1397. | ATTGAAAATTTTCTCAAAAATTG[G,A]AATGGAAATAGAACTTTCTCTAACC | 533,985 | 100 |
| 1398. | TGCTCGTTCTCATTCCCATTTGAG[A,G]CTCCAACTCCCTTCAACTAGATGTC | 534,053 | 100 |
| 1399. | CTTTCGTTCAGAAAATTTTAACAT[G,A]TTCAACCTGAAAGGAGGTATCCCTG | 534,102 | 100 |
| 1400. | AAAGGCATTCAAGCTGCCATAGCT[A,T]TCTTGCAAGCTACCTCACTAGAGAT | 534,259 | 100 |
| 1401. | ATCACTTGCCTTTATTCTCCTGGG[G,A]CAATTGCTTCCTCTTTGAATCCTTT | 534,335 | 100 |
| 1402. | TCTCCTGGGGCAATTGCTTCCTCT[T,G]TGAATCCTTTGCTTCTGGATGCTTG | 534,350 | 100 |
| 1403. | TTCTTTGAGGAATCCAAAACTTGC[T,G]TTTTTTtCCCATCTATGAAGGAAAC | 534,405 | 100 |
| 1404. | TGGGCCAAAACAGGAGAGACAAGA[G,A]CTCACATTTTAGGTAAAACATACAA | 534,609 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1405. | CCTGAGTTGAAATCAAAGCGGAGTG[C,T]GTATGGGAACCCAATCATGGACTAG | 534,683 | 100 |
| 1406. | CCCCTCTGTTAGATGACAAGAATT[C,A]CTCATTTCGAAGGTTGGATGATGCA | 534,754 | 100 |
| 1407. | TTCTCATTGTCTTTTATTTTTTTt[A,T]TTtAGTTTATTTAGTAGTATTGCTT | 535,138 | 100 |
| 1408. | AAATAAATAACTAAGTAAATGAAG[C,G]TTCGAGGGCCATTTTTTGTGAGAAA | 535,209 | 100 |
| 1409. | AAATAACTAAGTAAATGAAGCTTC[G,A]AGGGCCATTTTTTGTGAGAAAGTTG | 535,213 | 100 |
| 1410. | GTATTTCAAAAGGTATGAAGTTCA[C,G]GTCAGCCCTATACCTATTTCTAGTT | 535,471 | 100 |
| 1411. | CAAAAGGTATGAAGTTCACGTCAG[C,A]CCTATACCTATTTCTAGTTTGTTCT | 535,477 | 100 |
| 1412. | TCTCACCTAAATGGCCTAAAAATA[T,C]TACTCCACTTAACCCTCTTGAAAAC | 535,624 | 100 |
| 1413. | ACCTAAATGGCCTAAAAATATTAC[T,C]CCACTTAACCCTCTTGAAAACCAAC | 535,628 | 100 |
| 1414. | GCTTCCTCACTTATGAGTGCACAC[T,C]ATTGAGAAGGCCTGTTGTATCCTGA | 536,779 | 100 |
| 1415. | CTCACTTATGAGTGCACACTATTG[A,G]GAAGGCCTGTTGTATCCTGAGGGAT | 536,784 | 100 |
| 1416. | TAAAGGATAGAAATGGATCCCACT[A,G]CTACTAGTACCATTGCCGCTAGTTC | 536,950 | 100 |
| 1417. | CCCACTACTACTAGTACCATTGCC[G,A]CTAGTTCCTCCAATGCTACATCCAC | 536,698 | 100 |
| 1418. | GCCATACCGTTGCTTCCTACCATA[C,T]CTCTCACTGCACATGAGGGGTTTCC | 537,034 | 100 |
| 1419. | ATACCAGCAATATAGAGAACTGGA[G,A]GCATGCAAATAAGACGTTGGCCAAC | 537,218 | 100 |
| 1420. | TGAAGATAAGGATATCAAGATGCA[G,A]ATCAACGAGTACCACAAGCTGATAG | 537,308 | 100 |
| 1421. | TATAGCTGGCATGCTGATCGAAAA[G,A]CTGCCCAACTCGTGGAGCGACTACA | 537,398 | 100 |
| 1422. | ACAAGCAACAACTCAAGCACAAGT[A,G]CAAGGAGATGTCGTTGGAAGATTTG | 537,445 | 100 |
| 1423. | GGAGAAGAAACTATTTACTTAGGT[A,G]ACTCAAAATCTACACAAGTTCTTGG | 537,915 | 100 |
| 1424. | TTCTCAAGCTCACCTCAGGCAAGA[T,C]ATTGGCATTGAATGAAGTGCTCCAT | 537,979 | 100 |
| 1425. | CAGAGACTCTTTGTACTTTATATT[G,A]TTGAAGTAATTAATGAAAATGCATG | 538,157 | 100 |
| 1426. | ATAATGCTTGCATGAACAAGTGTG[G,A]AATTTATGCTGAAACCAAAACAACT | 538,320 | 100 |
| 1427. | TTTATGCTGAAACCAAAACAACTA[G,A]AAAAACTTATGCATTTGTGGAAAGA | 538,347 | 100 |
| 1428. | TATGCATTTGTGGAAAGAGAATCT[A,G]AACTTTTAGGATTAATTCATACTGA | 538,379 | 100 |
| 1429. | ATTGATGATTATTCTAGGTATACT[G,A]AGATTATTTATTGAGGAATAAAGA | 538,487 | 100 |
| 1430. | GATTCCATATAAAAACACCGATAA[G,C]ATACCTTTTGAATTGTGGAAGGGTT | 538,831 | 100 |
| 1431. | ATACTGATCATAGTGCAGCATATA[A,G]GTTTCTTGTTTTGAAAAATGGCATG | 538,995 | 100 |
| 1432. | CATAGTGCAGCATATAAGTTTCTT[G,A]TTTTGAAAAATGGCATGCTTGAGTG | 539,003 | 100 |
| 1433. | TTTAGAAATGATTtTtGTATCTAT[T,C]TTATTGATAAAGATCCTGTGTCTTT | 539,204 | 100 |
| 1434. | AGAAATGATTtTtGTATCTATTTT[A,G]TTGATAAAGATCCTGTGTCTTTTTC | 539,207 | 100 |
| 1435. | TCAAAAATGAACTTGATCAATTT[C,T]ACATAATCAAACTTAAGAACTAGTT | 539,301 | 100 |
| 1436. | AACAAAATGTGCAAATTGAGAAAA[T,G]CTTTATATAGTTTAAAACAAGCTCC | 539,659 | 100 |
| 1437. | TTTAAAACAAGCTCCAAAACAAATG[A,G]CATAAGAAATTTGATAGAGTTTTAA | 539,694 | 100 |
| 1438. | GAGTTTTAATGGATATCAGATTTT[C,T]TTCTATTGGAGTAGATAAATGTGTG | 539,735 | 100 |
| 1439. | TACACCAAGACTATTGATAATGAC[T,C]GTGTGATTATCAATTTGTATGTGGA | 539,785 | 100 |
| 1440. | AATTGTGAAAGAAACAAAAGGTTT[T,C]TTAGCCTCCCAATTTGACATGAAAG | 539,865 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1441. | ATGAAAGATATGGGAGAAGCCAAT[A,G]TGATTTTAGGTGTTAAAATCATAAG | 539,908 | 100 |
| 1442. | TATGGGAGAAGCCAATATGATTTT[A,G]GGTGTTAAAATCATAAGAGATATGA | 539,916 | 100 |
| 1443. | CTGTTTGTACTCCTTATGATGCTA[A,G]TACTCAATTAAAAAaGAAGAGAGGT | 540,038 | 100 |
| 1444. | ACATGACCTGATATAGCTTATGCA[G,A]TGTGTAGATTGAGCAGATATACTCA | 540,151 | 100 |
| 1445. | AGATATACTCAAAATCCCAATCGT[A,G]ATCATTGGACTACTTTAGTCAGACT | 540,190 | 100 |
| 1446. | GAGATGAATTTAGCCGATCCTCTG[C,A]CTAAACCTTTGGGCAGAAAATTCAT | 540,685 | 100 |
| 1447. | CCCTTATGAGTGGTGTATTGAATT[A,G]CAGTGTACACTTGATGGAATCACTT | 640,962 | 100 |
| 1448. | TATATATGAGTGCGAAGTGGGGTC[G,A]CTTCTGTAAGATTCTTTGACAAGAT | 541,013 | 100 |
| 1449. | TGATTCATAGCTCAAAAGGCACCA[A,G]TTTCGATGCATTACACTCAGTTGAG | 541,252 | 100 |
| 1450. | CATAGCTCAAAAGGCACCAATTTC[G,A]ATGCATTACACTCAGTTGAGTTAAC | 541,257 | 100 |
| 1451. | TTTTACCAACATCCTCTCACCTAA[A,G]TGGCCTAAAAATACTATCCCACTTA | 541,509 | 100 |
| 1452. | TTATATTATGGCAACAATACTTCG[T,C]CATATTTCAAAAACaGGTAAAAGCT | 542,089 | 100 |
| 1453. | CAATACTTCGTCATATTTCAAAAA[C,T]aGGTAAAAGCTATCCATCTTTGAAA | 542,103 | 100 |
| 1454. | CAGCTTTCTCTGATTGGTCCCCAT[A,G]TGCCAATCGGATGAACTCATCATCC | 542,257 | 100 |
| 1455. | TTCACCTACGTTGCCTCCTTTTAA[G,A]TGGTCGGCATTCGTTTTAAACGGTC | 542,417 | 100 |
| 1456. | CCCCAAAAATAGCTGTTTGTTGTT[G,A]TAGGTTTTCTTGTTCCCATGTACAA | 542,499 | 100 |
| 1457. | CCGGAAGCGACTTAGCTTAGCTAC[A,T]TAAAGATTTTGACCAATGGTGCGTA | 542,761 | 100 |
| 1458. | CCAATGGTGCGTACATCGAAAGCT[T,G]CTGTACCTATAAAGTACAGCTGACC | 542,798 | 100 |
| 1459. | GTTGATTATTGCTTAAAATTGCGG[C,T]TGTGTTGTCATCATCTTCATTATGG | 542,966 | 100 |
| 1460. | TTATGGAATTCATGAGAATGTTAT[G,A]GGAATGCATAATTATATTCATAATA | 543,010 | 100 |
| 1461. | TAACTGATTTTCACATGCAAATAT[C,A]ATGAATTATATATAGATAGCTGGGG | 543,080 | 100 |
| 1462. | CATGCAAATATCATGAATTATATA[T,C]AGATAGCTGGGGAAGAAATGAAAGA | 543,093 | 100 |
| 1463. | GGTTCTGCTAGGTATCGGGAAAAA[G,A]GGGTTCTCGGAATACACCCAAATTG | 543,264 | 100 |
| 1464. | GGTATCGGGAAAAGGGGTTCTCG[G,A]AATACACCCAAATTGTAGAACATGT | 543,274 | 100 |
| 1465. | ATGTATTGGTTGCAAAATGAAATT[A,G]TGACATAGTCATATGTAAATAAGCT | 543,320 | 100 |
| 1466. | TAAGTCATAATTTATGCACCAATG[A,G]CAAAAAATTAGGGTTGAAAATTGTG | 543,418 | 100 |
| 1467. | TGCATAAGCTAGAATATGTATACA[G,A]GCATTTTATGTGTAACTTCAACATT | 543,482 | 100 |
| 1468. | GAATATGTATACAGGCATTTTATG[T,A]GTAACTTCAACATTAAAATTATTTC | 543,493 | 100 |
| 1469. | CGGCAATTTTCTTAGATGGTTATC[A,T]ATAATTAGAACCTCATTTTTGCAAT | 543,544 | 100 |
| 1470. | AAGTATAAAAATAAAATTGATAAC[G,A]TATCAATAACCTGAGTTTATCTATA | 543,633 | 100 |
| 1471. | ATTGATAACGTATCAATAACCTGA[G,A]TTTATCTATACCAAATGCTAAGAAT | 543,648 | 100 |
| 1472. | ATAGCTCGCAACCTTTGCTAAATC[A,G]TTCATTACTCGTAAAAATCTAGCCT | 543,696 | 100 |
| 1473. | TTtCTTGAATATTAGATTTTTTC[A,G]CATTCACATGTTCCACATCAAGAAG | 543,754 | 100 |
| 1474. | CACATCACATGTTCCACATCAAG[A,G]AGGGGATTGTGGATTCTCTACATTC | 543,777 | 100 |
| 1475. | AGGGGATTGTGGATTCTCTACATT[C,G]TTGTCTAAACCGGTTCCTATTAACA | 543,802 | 100 |
| 1476. | AACCGGTTCCTATTAACATCATAT[A,G]CCTTTTTCAATTTACTAGCATAAAT | 543,834 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1477. | TTAAGCTTGCACTGTGGTCATTAG[G,T]TGGTTGGACTGCCCCACTCACACGG | 544,022 | 100 |
| 1478. | TTAGATGCTAACGTGCACCAAGCC[A,C]GCAGCGGCACCACCTCCACAAATGG | 544,075 | 100 |
| 1479. | GGCGATGCGAACCACCGCCGCTGC[A,G]ACGTCGCTGCGCCGCCTGTCGTGC | 544,349 | 100 |
| 1480. | ATGCGAACCACCGCCGCTGCAACG[G,C]TCGCTGCGCCGCCTGTCGTGCCTTC | 544,353 | 100 |
| 1481. | AGCGTCCGGAGGTGTTCGTCGGCC[G,A]TGAAGGCGGTTTCGTTGCAGACACC | 544,566 | 100 |
| 1482. | TTCGTTGCAGACACCGGTGGCGCC[T,C]GTGGAGGTGAGTTGGTTTTtATTAG | 544,601 | 100 |
| 1483. | AATTAATATTTTTGCTGCTTACT[A,T]GGTAATCCTGGCTCTTCCTTCTCGA | 544,878 | 100 |
| 1484. | TTTTTTGCTGCTTACTAGGTAATC[C,T]TGGCTCTTCCTTCTCGAAATTtATT | 544,886 | 100 |
| 1485. | TTTCTGTTGGAAAATTAGAAAGAA[A,C]GAAAAAGTTCCTGTTTCATTCTTTT | 544,952 | 100 |
| 1486. | AAAATTAGAAAGAAAGAAAAAGTT[C,T]CTGTTTCATTCTTTTTTtACGAGCAA | 544,962 | 100 |
| 1487. | AAAAAaTAAGTGAAGTGTCAACA[G,A]ATTTTGGATGATATTTGTCAAAGA | 545,326 | 100 |
| 1488. | AGAACTTTACACCTTTCATTTCTC[T,C]ACTCTGCATTTTCATGTAGTACGCT | 545,698 | 100 |
| 1489. | CATTTCTCTACTCTGCATTTTCAT[G,A]TAGTACGCTTGTAACTGCATCTAGC | 545,714 | 100 |
| 1490. | CTACTCTGCATTTTCATGTAGTAC[G,T]CTTGTAACTGCATCTAGCAAAAGTA | 545,721 | 100 |
| 1491. | AAGTTCATCTTTTACTTGCTCTAT[T,G]TTTCTAGTAGAATCACTACTATTGT | 546,331 | 100 |
| 1492. | TCATCTTTTACTTGCTCTATTTTT[C,G]TAGTAGAATCACTACTATTGTCTAT | 546,335 | 100 |
| 1493. | AAAaaTAATCTAGTGTACATGCAA[C,T]GACAGAAAGACAAGGATCTTGTATT | 546,439 | 100 |
| 1494. | TATTGGACATTTTATCTGTTATTGA[C,A]TGAGACTGACCAATTCTTTAGATGTT | 546,781 | 100 |
| 1495. | CTTAGGACTTCTGACAAGCTGTAT[C,T]CCTGAATTAGATTGATAAATATTCC | 546,912 | 100 |
| 1496. | TCCAAGTAAGTTTGGTTTAGATGT[A,G]AGGTCCAAGATACCCTTGGATCAAG | 547,243 | 100 |
| 1497. | TTTAGATGTAAGGTCCAAGATACC[C,A]TTGGATCAAGGCTGGGTAGGTCTCA | 547,258 | 100 |
| 1498. | ATTGTAAGTTGTTCATGGTGACCG[A,G]CTTAAAAAACAAGATTCATTGATTTG | 547,442 | 100 |
| 1499. | TGTAAGTTGTTCATGGTGACCGAC[T,A]TAAAAACAAGATTCATTGATTTGTG | 547,444 | 100 |
| 1500. | TGAATAAAGTAGTATTCTTCACCT[T,A]TAAAAACAAGATTCATTGATTTGTG | 547,461 | 100 |
| 1501. | GTGATCTGGCTGGATTTTGCTCA[G,A]CTCAACTGACTTGATTGAGTTATAA | 547,868 | 100 |
| 1502. | TGACATATAATGATGATAATATAT[G,A]ATACATATATTATAAAATAGTAAAT | 548,042 | 100 |
| 1503. | GGGTTACGTTTATGAACATTTTT[C,T]TTTGAAAGCTTCCTGAGCATTATTT | 548,210 | 100 |
| 1504. | AACATTTTTCTTTGAAAGCTTCCT[G,T]AGCATTATTTTTACTAAATTTTAGC | 548,225 | 100 |
| 1505. | TGCACATGCATGCATGTAGATGAC[T,C]CTGATTTTTAAGAAAAAaTAAATTT | 548,282 | 100 |
| 1506. | GAAAGGTAGAGAGCACTTTATTTC[A,G]GGGCACAAGGGAAAGAAAAGAGATC | 548,549 | 100 |
| 1507. | TTTTATTATACTTTTtGAGAAGTG[T,C]AATGTATGGCTGCAGGCTTTGCGGC | 548,610 | 100 |
| 1508. | CCCATTGGTTATGTTCTCATTCTT[T,C]TGAGAGTGTTAAGACTCACTCCTAC | 548,885 | 100 |
| 1509. | TTACTGGGATACTGGTTGATAAT[G,A]ATGTTTGCATGTGTGTCTTGATTAT | 548,952 | 100 |
| 1510. | TGCTTGCAGTTATGTTTGCTTGCT[C,T]CCCCTGCTACTTGCTCCTGCACTGC | 549,042 | 100 |
| 1511. | TGCATGTGTTGGTGTGCTTGGAGC[A,G]CTTTTTAAAGTTCATTCTGACTCTG | 549,119 | 100 |
| 1512. | TTAAAGTTCATTCTGACTCTGAGT[G,T]TCAAATTTACTCCTGCAACTAAGAA | 549,148 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1513. | GAAGAAATATTTTACTAGAAACTA[T,G]AATTCACAATGTGTAACACATCCGT | 549,222 | 100 |
| 1514. | AAGTAGATGAATCCTTCTAGTAGT[T,G]GTCACCTTGAAGTTACAAAGTATTG | 549,433 | 100 |
| 1515. | GTCACCTTGAAGTTACAAAGTATT[G,T]CAAGCCATCAATGATAAAAAaTTA | 549,458 | 100 |
| 1516. | TTGGCTCTAAAATGCCACATCAGG[A,G]CACATTCTGGTTGCTTAACTTATTA | 549,662 | 100 |
| 1517. | TTAATCTTTTATTGTTGCCATTAT[A,C]TTTTTTtGTTTtGTTTTAAGTTGT | 549,717 | 100 |
| 1518. | GAAGAACGTTATTCTTAAATCTTG[T,C]TGTTGATTGGCCCAGCTTCGCTTTG | 549,959 | 100 |
| 1519. | ATATCTCTTGACAATCTCCCCATG[C,T]AGAACGTTGCTGCTGTGACTTCGAC | 550,179 | 100 |
| 1520. | TCTTGACAATCTCCCCATGCAGAA[C,T]GTTGCTGCTGTGACTTCGACATCAA | 550,184 | 100 |
| 1521. | GAACGTTGCTGCTGTGACTTCGAC[A,G]TCAACACGCACTCCAATCTACAAGG | 550,205 | 100 |
| 1522. | TTCGACATCAACACGCACTCCAAT[C,A]TACAAGGCCTATGCAAAAGGAGAAA | 550,223 | 100 |
| 1523. | TAGTATATTAAATGTCTAGGAGTA[T,G]GAAAGGGTTTACAAGACCTGATCCG | 550,378 | 100 |
| 1524. | ATATTAAATGTCTAGGAGTATGAA[A,G]GGGTTTACAAGACCTGATCCGAGTA | 550,382 | 100 |
| 1525. | ATGACCCTAGAGTCATAAAAGGAT[A,G]TTATAAGATTTCTATGGTATTTTTT | 550,517 | 100 |
| 1526. | GGCCTCTTTGGCTACAACTGCAGG[C,G]ATAGGTTGGGATTGGACAGCTGGAA | 550,648 | 100 |
| 1527. | TCCTATATATTGGACTTCTAGGAA[A,G]CACATAATCACATTGCTGTCTTTCA | 550,890 | 100 |
| 1528. | GCACAAAGTCCTTCCAGCTTTGAT[A,G]TGCCATAACAACTCCATTTCAAAAG | 551,019 | 100 |
| 1529. | TCCAGATTCATAAGGAGGTCTCAT[A,T]GGTGAAGCCCCATAATGCCAGTCAT | 551,144 | 100 |
| 1530. | AAGCCCTTTAGCATCCACGATAGA[G,A]TGTGAGAGGTCCCTGACAGAGATTC | 551,199 | 100 |
| 1531. | TTGATGAATTCATCCCACATTTCC[A,C]GATATTGTTGACCATTTTTTCTTCC | 551,279 | 100 |
| 1532. | AAAGAATTGGCCATTGACCAAAAA[C,A]ATAGAGATCTGATTTGGTTTCTTTG | 551,960 | 100 |
| 1533. | TTAAACCGATTTCCACAATATTGT[T,G]CATAAACTTTAGATAACTTCTAAAA | 552,053 | 100 |
| 1534. | AGCTGGTGGGATGCTAATTGGTAT[A,G]GTCCCACATTGTGAGCCTCAAGATA | 552,543 | 100 |
| 1535. | TTGATATGGCATGGTACAACACAA[T,C]ACTTAATATTCTGCTCTAGCAATGG | 552,632 | 100 |
| 1536. | GGTGGCTGTACGAGCAATGATAGA[T,C]ATGTTTTGGATGGACCCAGAAGAGC | 552,694 | 100 |
| 1537. | GATATGTTTTGGATGGACCCAGAA[G,T]AGCTATTTTTGATGGTTTAATTATG | 552,716 | 100 |
| 1538. | TAAAGACATGTATTAAGACACAGT[T,A]TCATAGCATGATTATCCTAAAAAAT | 552,964 | 100 |
| 1539. | TGAAATGTACACAATACAATGAAA[G,A]GATAAGAAGTTATTATGTAACATAG | 553,022 | 100 |
| 1540. | AATGTACACAATACAATGAAAGGA[T,C]AAGAAGTTATTATGTAACATAGTGC | 553,025 | 100 |
| 1541. | ATATATGACTAGTAAATCAGGTTT[T,G]AGTGGCTTGTTTCTTTCTTGGTTGT | 553,134 | 100 |
| 1542. | AGAAAAAGAGCAGTTTTGAAGGCT[G,C]ACAAACAAATTTAGTTTCAGGTATC | 553,249 | 100 |
| 1543. | CTTGATACTAGGATTGTCAAATCA[C,T]GATTTATTTACACATCATGGCATGC | 553,298 | 100 |
| 1544. | TCCTTGTGCATGCCTTCAGGAAGG[G,T]GTGCCAACCAGCTTCTCTATGTGAT | 553,717 | 100 |
| 1545. | AGTAATTTTGCACAGCTGCAGAAG[G,T]CTAAACTTATAGGTCTGTTTGAGT | 553,999 | 100 |
| 1546. | GCTTACTTCTATTATTCTGTATAT[T,C]GTGCAACTTACATTACTGAACATTG | 554,174 | 100 |
| 1547. | TATTCTGTATATTGTGCAACTTAC[A,G]TTACTGAACATTGTCATCCTTGAAA | 554,186 | 100 |
| 1548. | CCCTTCAAAGGATAAAATTTATGC[A,G]TTGCTTAAGGATCAAGCAAAGTCTG | 554,352 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1549. | ACACATACATATATATGCAAGTAC[G,A]TAGTAAAAAATAGATCACAATTAGA | 554,808 | 100 |
| 1550. | GTAAGTTTTAACATTCATGTCAGT[T,G]AAAATCAAATGAAGTAAACTTAGAA | 554,956 | 100 |
| 1551. | AGAAGTCCGGAAGAGGAAATTAAA[T,A]CCATTATCCAAACAGAAAAAAGGAT | 555,002 | 100 |
| 1552. | TATTTCCAGTATTTTATTGGAAAA[G,A]ACTGCCATGGTTTTATAAATTTTGA | 555,076 | 100 |
| 1553. | TTTTATAAATTTTGACCTTTGGCT[G,A]GGCAAGTGCCTTTCATCTTATAGAT | 555,111 | 100 |
| 1554. | AAGAGAACTGGCTTTTATTATTAT[G,T]CTCACAACCGGCTCCTTTCTTGCAG | 555,544 | 100 |
| 1555. | TGGATAATGTCAGACTCATTGCTT[A,T]ACCCTGGACGAGCTCGGCTTTGTGA | 555,597 | 100 |
| 1556. | TTACTCAGACAGCAGATATGGCTT[C,T]TCCAAAATTATTCCTAAAGTTCACA | 555,794 | 100 |
| 1557. | TATGGCTTCTCCAAAATTATTCCT[A,T]AAGTTCACACCATACTGCAACACTC | 555,810 | 100 |
| 1558. | TGGCTTCTCCAAAATTATTCCTAA[A,T]GTTCACACCATACTGCAACACTCTA | 555,812 | 100 |
| 1559. | ACTTTTCTCTTCGTTTtCTTTTTt[C,A]CTTTtCCTTTTTTtCATTCAATCTG | 556,254 | 100 |
| 1560. | tCTTTTTtCCTTTtCCTTTTTTtC[A,G]TTCAATCTGTATCATACTTCAACTT | 556,270 | 100 |
| 1561. | CATTGAGATTCATGTTGAAATGTT[C,T]ATATCCTTCATACCCATCAAATGAC | 556,678 | 100 |
| 1562. | ATATCCTTCATACCCCATCAAATGA[C,T]AGCACATTGTTATCCCTCTTGACAT | 556,703 | 100 |
| 1563. | TCAGAAATGCAGCAACCTAGGACT[T,C]ATCTTCTGGCATGTGGAACCTAGGG | 556,752 | 100 |
| 1564. | ATGTGGAGATGGGACTCTTCAGGT[C,A]ATCTTCTTTGGGAGTCTCTTAGGCC | 556,901 | 100 |
| 1565. | AAATCTTGGCAAGGAAAGGCTGAA[G,A]CCTGCCTAGGGGTCATATTTTCTAC | 557,019 | 100 |
| 1566. | CTAGCTATTTGAAGAGAAGATAAA[G,A]CATATGCTCTCCTGCAAAGTTGCCC | 557,069 | 100 |
| 1567. | CCAATTAGAGATGCCTACAATGCG[C,T]GAAGGAACCTAAGGATGCGAAAGGT | 557,215 | 100 |
| 1568. | ATGCCTACAATGCGCGAAGGAACC[T,C]AAGGATGCGAAAGGTTGAGGGCTAT | 557,225 | 100 |
| 1569. | ACTTGCTTTTCTCTTACACATGCG[A,G]CTTCCCTCCCCTATCTCAAAAAATA | 557,485 | 100 |
| 1570. | GACTTCCCTCCCCTATCTCAAAAA[A,T]TAAAAaTAAAAaTAAAAaTTATCCG | 557,508 | 100 |
| 1571. | TATCCGATTTCCTTACCATGTTAT[G,T]GAGTCTTGAAAATTGATTGGTCTTT | 557,552 | 100 |
| 1572. | TGGTCTTTCAATAATCGAACAATT[T,G]CTTTACTTTAATTATGGTTTGATAG | 557,594 | 100 |
| 1573. | TTTCAATAATCGAACAATTTCTTT[A,G]CTTTAATTATGGTTTGATAGAATGG | 557,599 | 100 |
| 1574. | TAAACCATCACACTTTGGATATAG[C,T]TGATAAAACAAGAAGATATGCAGAT | 557,653 | 100 |
| 1575. | ATTCAATTGGTTATGTTATCACCG[G,A]AAGATCCCTGCGGTCGACACTTTAG | 558,021 | 100 |
| 1576. | GGATATCATTATATCAATCACTCT[A,G]TAGTTCCTATGATCAGAGAGAAACTA | 558,280 | 100 |
| 1577. | CGGTCTTCCATTGGCAATGGCTGG[A,G]AAATATTACTAGCTATGATGAACTA | 559,158 | 100 |
| 1578. | AATGTGGACAATTAATTTATGAGA[G,A]AGAAAATTCCCAATTATTCTTGAGA | 559,590 | 100 |
| 1579. | GACGGCACCAAAGTTATGGTTTGC[G,A]ACCCCCCcTCCCGTCAAGGGGGAGT | 560,280 | 100 |
| 1580. | TCAGGGGAGTATGTGTGCATAG[G,A]TAGAAGGCAATCCCATGGACGGCAC | 560,318 | 100 |
| 1581. | ATAAATTATAAAATGTGATGCAA[T,C]TCCAAAACTGGGCAAACACCTCTCA | 560,630 | 100 |
| 1582. | AACACCTCTCATGTGCAGAAAGCC[T,A]TCAACTTAGCTTGCTCTCCACATAA | 560,669 | 100 |
| 1583. | TAAAATTCATATTTCTCTGTTAAT[G,T]GTTAGTTTCAATTAACTTGATTCCA | 561,423 | 100 |
| 1584. | CCATTCTTTTCAGATTCCAACATT[T,G]TGTTAATTCATCCACTTCTGATTTT | 561,470 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1585. | ATCCATGGTGACCCACAGGTTCCG[A,T]TATGCCGTGCTGGCGAAATGCATGC | 562,172 | 100 |
| 1586. | CTTCCCGTTAATTACTTCATCTTC[G,C]TCACACCATAATGAAGAAAATAAAA | 562,390 | 100 |
| 1587. | ATAATTGCTAAAGAAAAAGATGGCG[G,A]TCTTCGTCGCTAGCAATGACATGGT | 562,474 | 100 |
| 1588. | TGCTAAAGAAAAGATGGCGGTCTT[C,T]GTCGCTAGCAATGACATGGTGGTAA | 562,479 | 100 |
| 1589. | TATTGAGTATTATTTTTtCCCAT[T,A]ATCAAAAGAAAAAaCAAGCAGTTCTG | 562,850 | 100 |
| 1590. | AAAGAAAAAGCTTCATAATTTCTC[A,G]GCATTTGATCATTTAGGAAGAGTCT | 563,346 | 100 |
| 1591. | TTGATCATTTAGGAAGAGTCTTGG[A,T]GAACCTAGGAAATTTTGGAGAGATT | 563,375 | 100 |
| 1592. | TTTCTAAGAACTAAAAAAAaaCTA[G,A]TGCCTCCATTCATGGAATATATGAA | 563,436 | 100 |
| 1593. | TGAAATGAAACTGAAGCCTAACCT[T,C]CAGTAGAATTTGAAAGAGCATCACC | 563,638 | 100 |
| 1594. | ACAGAGTCCATGGAAAAGAAAAaC[G,C]CATTGCCTAAACCACTTATGAAAGT | 563,750 | 100 |
| 1595. | CAGAACTGCTCCACCACACTCTCC[T,C]CCTGCCTCTGGAGCCTCCACCCAAT | 564,118 | 100 |
| 1596. | TCTACAAACACACACACACACACA[C,G]AGAGAGAGAGAGAGAGAACACTGCA | 565,190 | 100 |
| 1597. | ATATTAGATTAAGAAGCATGAAGG[T,C]TCCCATGGACTTTTTTATTCATATT | 565,388 | 100 |
| 1598. | GAGTAACTGAGAGAGAAGACTAGA[A,G]GAGATTTATGAGAAAAACTGCATGG | 565,692 | 100 |
| 1599. | ATTTATGAGAAAAACTGCATGGTA[A,G]GCCTGAAGTAAGAGCTCTTCTTTCT | 565,720 | 100 |
| 1600. | ATCTTCCAACTTTGGATTCCATGA[A,C]AAGAAGACTTTAGAAGAGTTGACAG | 565,882 | 100 |
| 1601. | AAGACTTTAGAAGAGTTGACAGGG[A,T]AAGAGGGGAATAAACAAAGAATATA | 565,910 | 100 |
| 1602. | GAATAAACAAAGAATATATTAAGA[G,A]GTGGAATGAAATTAGGATACATATA | 565,942 | 100 |
| 1603. | ATACAGAGAAGATTTTCTTTCTTA[A,G]AAGAGTGGATGTTTGCTTTGCTTGC | 566,073 | 100 |
| 1604. | TCAGTTACATAGATACTCAAAACTT[G,T]TTAAATTTATAACTTGAAAAaGAAA | 566,449 | 100 |
| 1605. | ATGGTAGAAGTTGTTATGGATCAT[C,T]GTAATGCTTATAATTTTATGAATAA | 566,566 | 100 |
| 1606. | ATAACAAATAACATAATTGAGTTA[A,G]AGATATAGATGCTGCAATAACAATA | 566,716 | 100 |
| 1607. | ATAATAACATACTGTTGAAAATGC[T,C]CGTGTCTTTTAAACCCCAATAAGA | 566,775 | 100 |
| 1608. | TTTTAAACCCCAATAAGAATTCT[A,G]CAAACTTCTATTTTGGGGTTAATTG | 566,806 | 100 |
| 1609. | AAAAAAAaTTTAAATAAAAGGATG[T,G]GTATGCCAATTAAATTTGAAATAAG | 566,930 | 100 |
| 1610. | GGTTAATTTCAAGATTCAAAGATA[T,C]GTGGGTCGCAACCTTAAATCATCAT | 566,982 | 100 |
| 1611. | AATCATCATATTCTCTTTTTTtA[A,C]TCACTAATAATTAGGGTTTGGATTA | 567,023 | 100 |
| 1612. | TCATATTCTCTTTTTTtAATCAC[T,C]AATAATTAGGGTTTGGATTATTCAT | 567,028 | 100 |
| 1613. | TTTTTTtAATCACTAATAATTAGG[G,T]TTTGGATTATTCATTGATCTAACTA | 567,039 | 100 |
| 1614. | GAATAAGGTTAATTATTATGATAT[G,A]AAAAGAATCATTTACTATTAAGGTT | 567,119 | 100 |
| 1615. | ATACTACGACGATTCCTATGCCAA[T,G]CTACAAATATTTTTTCTAAGCTTTT | 567,246 | 100 |
| 1616. | TTCTCTCAGAATCTGCATGACAAG[G,A]ATACTACCAATGTGCAGACATGGAA | 567,435 | 100 |
| 1617. | GAATGTTAGGAAAGAAGCTTGGAG[A,G]CAAGGTCTGAAAATGGAGGAAGAGT | 567,482 | 100 |
| 1618. | AAAATGGAGGAAGAGTCTGTATCA[C,T]GGTACTGTGAAGAAATTATTAAACA | 567,516 | 100 |
| 1619. | GAATGGAAGTCATCCATTCCGATT[T,C]TGATTCCAGACTTCCACTCCACCCA | 567,823 | 100 |
| 1620. | TAACTTCAATTTCCTATAATTTTT[G,A]AAGTTTCCCTGACTGTGTCGAGAAA | 567,977 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1621. | CCTATAATTACTTTCTTTTAATAA[A,G]TCTGGGTGGCAATCCTTGCTTCCCT | 568,053 | 100 |
| 1622. | TCCATTAATTTGAAGTAAAGAATC[G,A]GTAGACGAGGGCAACCAACAAAAGT | 568,195 | 100 |
| 1623. | AGCATGCCATGCAAGCTGGTTCAa[G,A]ACTTGCAAAAGGCCTTGTCATGCTA | 568,268 | 100 |
| 1624. | TATCGCCATGTCTCCTCATTATGC[C,T]CATTAGACCATGAGCTGCCATGATA | 568,448 | 100 |
| 1625. | CTATGGCATGCAATGAGTGTGATG[G,A]CCAAGGATCTTTCAACATAGTAAAA | 568,559 | 100 |
| 1626. | GAAAGATTTTGTGTACTCAAAACA[C,G]AGGCTAGAACTCCGAACCAAGCAAT | 568,628 | 100 |
| 1627. | CCTTTCAAGGAATAATTTGCTCAT[A,G]GTTTGGAATATAGATGGCTGTAATG | 568,684 | 100 |
| 1628. | AAAATGCCCATCATGTTGCCATTG[G,T]CACAACAGCCAATATTTATACCATC | 569,071 | 100 |
| 1629. | AACTCTTGAGATTTAGATACATCT[C,G]CTTGTATGTTATTAGTGTTGATTAG | 571,753 | 100 |
| 1630. | ATCGGACGTAGTGGACGGAGAATT[C,A]CGCCTAGCCAAAGACATCACTTTAC | 572,655 | 100 |
| 1631. | ATATGCAAATAAAGATTTTCGAGA[T,C]CAATATAGAAAAATCTAAAAATTAG | 573,296 | 100 |
| 1632. | GAAGACCGGGACAACGGTTTTTCT[G,T]GGTGAGCATCGAGTGCCTTGTGGTT | 573,368 | 100 |
| 1633. | GGCACTGCAGTGATGGCCAGTAGC[A,G]ACTCAAAGGGTGATGCTTTGGAGAT | 575,751 | 100 |
| 1634. | TGATGGCCAGTAGCAACTCAAAGG[G,A]TGATGCTTTGGAGATATCTGGTGAG | 575,761 | 100 |
| 1635. | TTTGGAGATATCTGGTGAGGTATC[A,C]ACTTCTTTCTAGCAGTGGATTTTAG | 575,792 | 100 |
| 1636. | CATGATGGTGCAGTGAGAAACTTG[G,A]GGGAGGTCCGATACATATCCGATTT | 575,976 | 100 |
| 1637. | GGTGCAGTGAGAAACTTGGGGGAG[G,A]TCCGATACATATCCGATTTTAGATG | 575,982 | 100 |
| 1638. | TTCGAGAGGCTACAGGACGGTAGC[C,T]GGTGGAGGAATCTTGAAGGTGCTAT | 576,059 | 100 |
| 1639. | TGAGCCCACAGCGAGATCCAGGAT[A,G]ACGAACGAAGTCTAAGGAGCCTAAG | 576,535 | 100 |
| 1640. | CAGCGAGATCCAGGATAACGAACG[A,G]AGTCTAAGGAGCCTAAGAACAGCCC | 576,543 | 100 |
| 1641. | TATGCATGAAAGAAGGATGGCACG[G,A]TGCATTAGGCGGAGGCCGGTGGTGG | 576,616 | 100 |
| 1642. | AAGGATGGCACGGTGCATTAGGCG[G,A]AGGCCGGTGGTGGCATCGCGAGGCC | 576,628 | 100 |
| 1643. | GCGCACGCAGGTGCGCGCGGCCCA[G,A]TGCGTGaGCGGGCCCAGTGCAGGCG | 576,690 | 100 |
| 1644. | TGCACGATCGGACAGCTCTGGTGC[G,A]AGCCGATCACGATTGAACGGCCATG | 576,965 | 100 |
| 1645. | GCTCTGGTGCGAGCCGATCACGAT[T,C]GAACGGCCATGAATGATTCTAGGCT | 576,979 | 100 |
| 1646. | ACGGCCATGAATGATTCTAGGCTT[G,C]ATTGGGATTTtGTTTTTtAGTGTAA | 577,006 | 100 |
| 1647. | CTAGGCTTGATTGGGATTTtGTTT[T,C]TtAGTGTAACAGTGTTTTAGAGTTT | 577,022 | 100 |
| 1648. | TTTTATTCTCTCATAGTAAAGCTT[A,G]CACGTTCCATGAAGATAGGCTCGAG | 577,252 | 100 |
| 1649. | ATAGTAAAGCTTACACGTTCCATG[A,G]AGATAGGCTCGAGGACAATCCACGT | 577,264 | 100 |
| 1650. | AGATAATAATTATTATAATATTTT[G,T]TTTAGTATTATAATGATCTGTTATG | 577,496 | 100 |
| 1651. | TTTTGTTTAGTATTATAATGATCT[G,A]TTATGACATAAATAACAATTTTTAT | 577,516 | 100 |
| 1652. | ATATAATTTTTATCCAATGAAAAG[T,C]ATATGGAAGATTTCCTTAAATGGTG | 577,654 | 100 |
| 1653. | TACGTCCGGAATGCGATCATGAAT[C,T]TCTATGCCCAACATGGTCCTATTGA | 582,410 | 100 |
| 1654. | ACAGTGGATTCTGGCGATCGAGCT[C,T]TTTTAAAGAGATGGCGATTGCGAAGG | 583,126 | 100 |
| 1655. | AGCAGTCGGTGGAGAATCGCCGCC[G,A]ACAAAGTCTGAGCGGCCCTCCGACA | 584,325 | 100 |
| 1656. | CAAGCAGCTCATAAGGCTCTCATC[G,A]ACAAAGTCTGAGCGGCCCTCCGACA | 584,365 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1657. | CATAAGGCTCTCATCGACAAAGTC[T,C]GAGCGGCCCTCCGACAATCCTTGGT | 584,374 | 100 |
| 1658. | TGGTGATGGGCGGAGGTGGGGTTC[G,A]TGCCAGCCCCACGGACGCTCGCCAT | 584,420 | 100 |
| 1659. | CCATGTCCAATTTTTGCTTTGTAT[T,G]GAGTCTACAAAAATCTTAAAGTAGA | 584,748 | 100 |
| 1660. | TTTCTGCAGTGCATGGACAACACC[G,A]CTGGGAATCCTCTTTGAAGTATGCG | 584,985 | 100 |
| 1661. | TAACAGTTGTCAATACGTGTTGAT[T,C]AGGCAATCCCATCCATCCAAGGTTT | 585,115 | 100 |
| 1662. | CATCCATCCAAGGTTTCACGAAGC[T,G]CCTGAAAATGAATATCGCGTATTAC | 585,149 | 100 |
| 1663. | TGCCTGCCGTGACTGCTGGGAAGC[G,A]AAGATGAGGCGGTAGGGGCAGCAAA | 586,375 | 100 |
| 1664. | GTCAGACGAGAAAGAAGAAAaCAA[G,C]ACATTCAATATAAGGAACTCATATA | 586,440 | 100 |
| 1665. | AAGGAAAAaCAGAAAGCAGCAAAA[A,G]AAaGAAATGGGGAAAAGGCTATGCA | 587,052 | 100 |
| 1666. | ATATGATTATTTAAGACAAGAAAG[G,A]AATAATCCTGGGAAATCATTGAGCA | 587,718 | 100 |
| 1667. | TTCATTAACCTGTATAAGATTGTC[A,G]ATCGAATAAATCCACATCCTCAGAT | 589,369 | 100 |
| 1668. | TGCATCTCATCACTAGTAGCATCA[G,A]GGGAAGAGGGTTGATGACTGTGCGG | 589,803 | 100 |
| 1669. | AGTGGGGGCGTTGGGGTGTCGTAC[C,A]GCCCAAGAAAAAaGAAATCTAAACA | 589,905 | 100 |
| 1670. | AATGACTCTACTGTTAGATGTATG[T,C]CCTAAAAGCCAGATTGGTTGAAACA | 590,055 | 100 |
| 1671. | TTAGTGGTTAATTTCTAAATGCTC[T,C]CGTTCGATAGAACGTCATGGGGACG | 590,270 | 100 |
| 1672. | AAAGTCCAGGTGCTTAATAGAGAT[T,C]AAGAGTACTGAGCGTGACCAACACG | 590,405 | 100 |
| 1673. | GTCGGTGACTTGCTCAAAGTTGCA[G,A]TGGTGTAGATAGTTCTTTAACCTGC | 590,482 | 100 |
| 1674. | AGTTCTTTAACCTGCGATGCCTCA[G,A]CTGCTTACAGCAAGGTTGCTATAGT | 590,517 | 100 |
| 1675. | CTGCGATGCCTCAGCTGCTTACAG[C,T]AAGGTTGCTATAGTTTGACTGCATA | 590,528 | 100 |
| 1676. | CTTCTAGCCATTTGGAGCCTTGAG[A,G]TGTATGTTGGCTACAGTAGATCCAT | 590,588 | 100 |
| 1677. | AGGAATAGGATGAGCATCAAAATG[A,G]AATTTGTCGACCCCGATAGATAGAG | 590,641 | 100 |
| 1678. | TAAAACTGAGTCCTAAAATCCATG[G,A]TCATGGTAGATGAATGATGAAAAAA | 590,710 | 100 |
| 1679. | CAATCCTTCGAAAAGAGTTTCCAT[G,A]ATATTGTTGATAGAGATCACAATAT | 591,014 | 100 |
| 1680. | TTCCATGATATTGTTGATAGAGAT[C,T]ACAATATATCTTACTATCGGATGGA | 591,032 | 100 |
| 1681. | GGGTTTAAGAAAACCCTGCTAGCA[T,C]ATGGTTAAACCCATTTTTtCCTACT | 591,184 | 100 |
| 1682. | CCAAATTGAAGCAAGCTCATTTAG[A,G]ACACCAAGAGTTGGAGTCCTTAAAG | 591,265 | 100 |
| 1683. | TTCTTCGACTAGATAAGAGGCACA[C,T]GCCGGCATGGATAAGATCCATGTGT | 591,366 | 100 |
| 1684. | ATCGAAAACGGAGAGAGTATCCTA[A,G]TCCGAATCCAAACGGATACCTGTAG | 591,997 | 100 |
| 1685. | CTCATTTAAAATTGTTTTAAATTT[C,T]TGATTTTCTTAATCTAGATGCATGA | 592,149 | 100 |
| 1686. | CTGATCTTGATCGGATCGCATGTC[G,A]GATCGAAAAATTTTTGAATTCCACT | 592,221 | 100 |
| 1687. | CTGATATCAGAGCCAGGTTGTACA[G,A]ATCATGCATCTTAAATTAAGATCAG | 592,313 | 100 |
| 1688. | CTTATTAGGACTGATTTTtATGCT[G,T]AATCTAAAGGTTATGATTAAATCTG | 592,512 | 100 |
| 1689. | TCTTAACATAAGTGTTATGTTGCA[T,C]GAGGTGTATTTTGCAAAGGATCATG | 592,612 | 100 |
| 1690. | TGTATTTTGCAAAGGATCATGTCT[A,G]GATCTATTTTGCATGAGATGTAATT | 592,641 | 100 |
| 1691. | CCCTAGATCCAAAAACCCTAGGAT[C,T]TGTTTGTATATGTTGCATTTAAGTT | 593,035 | 100 |
| 1692. | ATGAGTCGACTCAGTTGTGCAGAC[T,A]GAGGCTTACAGGATTTCTGTTCGTC | 593,241 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1693. | AGTCTCGATTGTGATTTTTAATTG[A,G]GATCATGCTTACCTGGCCATGCATA | 593,779 | 100 |
| 1694. | CTCTTCCATGTTGACTGTTCTGGA[C,T]TGGATACAGTGATTCAGTTGCATCA | 594,048 | 100 |
| 1695. | AAGATAGGGTTGGACCTAAGATCT[G,A]TCAGATGAAGATCCAATGACGGTTT | 594,132 | 100 |
| 1696. | GTTGGACCTAAGATCTGTCAGATG[A,T]AGATCCAATGACGGTTTCACTCGCG | 594,140 | 100 |
| 1697. | TGCAATTTACTTGAGAAGCATTGG[G,A]CAAGAGTTGACCACCCATTGGTTGA | 594,274 | 100 |
| 1698. | CATTGGTTGACATATTCACCAAGA[C,T]CTGTCAGGTGAGGTGGTGTGCCAAT | 594,314 | 100 |
| 1699. | GGGAGCTCCGCAGAAATAATGAGA[A,G]CTAAGTTTGTTTCTAAAATAAATTC | 594,454 | 100 |
| 1700. | GCAGAAATAATGAGAACTAAGTTT[G,A]TTTCTAAAATAAATTCTCTAGAATA | 594,463 | 100 |
| 1701. | AAAaTTTCCTCTCTGTAGAATTTT[G,T]TCTCCTTCTAATAGTCTAGCCTGCA | 594,542 | 100 |
| 1702. | TTGTCTCCTTCTAATAGTCTAGCC[T,C]GCATCTTAAAAaTCAACCAATTGTC | 594,564 | 100 |
| 1703. | GATTGGCTAAGGGACTTGAAAaGC[A,G]TTTTGAGTTCCAAGAAGCTAGATTA | 594,630 | 100 |
| 1704. | TCCAAGAAGCTAGATTATGTCTTA[A,G]ACCAAAAaTGTTTATTGGGACCATG | 594,663 | 100 |
| 1705. | ATTGGGACCATGAAGTGTTCAAAA[G,A]ACACCTTTAGAAGGTATGTCGGACT | 594,701 | 100 |
| 1706. | TAAGCAACAGAGCAAAGATTACTG[T,C]TGTTGTCGTAGGGACCTATCTTCTT | 594,868 | 100 |
| 1707. | GTTACTGTGTACCTAATACAAGCA[A,G]AAaTTTGATTTTTATTTCATACTTA | 594,955 | 100 |
| 1708. | TGGTCACTTAATCAACAGTTTCTA[T,C]CATTTGCATGTTGCTGCAGATGAAT | 595,079 | 100 |
| 1709. | TACTAGGTCTGGTACATAGTGATA[C,T]ATGCGGCCTATTTGATGTGCCGGCC | 595,370 | 100 |
| 1710. | AAATTCAGATTTAAGGTAGAGAAG[C,T]AAACTGAGAAATCACTTAAGGTACT | 595,517 | 100 |
| 1711. | TTAAGGTACTTCGATCAGATCGAG[G,A]GAAATACCTAAGTGAAAAATtTCTC | 595,557 | 100 |
| 1712. | ACGCCTCAGCTCAACGGGATTTCA[A,G]AACAGAGAAATCAGACCCTATTAAA | 595,653 | 100 |
| 1713. | ATCCATTCCTACCACACCATATGA[G,A]ATGTCGCATGGTAAGAAGCCGAATT | 595,802 | 100 |
| 1714. | TTCCTACCACACCATATGAGATGT[C,T]GCATGGTAAGAAGCCGAATTTTGGT | 595,807 | 100 |
| 1715. | AATTAGAGACTAGGTCTATGAGAG[C,A]TCGTTTTGTAGGATACCTGAAAAAA | 595,908 | 100 |
| 1716. | AGAAAATGTTCCTCATAGGTGATA[T,C]GATGATCCTAAATCTATGACGAGAC | 596,195 | 100 |
| 1717. | CCTCATAGGTGATATGAACCATGC[T,C]GATGATCCTAAATCTATGACGAGAC | 596,205 | 100 |
| 1718. | TCTTTCACAGCAACTGTACATAGA[G,A]AAAGTGCTGAAGCGGTTCAGCATGG | 596,976 | 100 |
| 1719. | CTGTACATAGAGAAAGTGCTGAAG[C,T]GGTTCAGCATGGAGAATTTCAAGAG | 596,989 | 100 |
| 1720. | AGTCGAATCCAGATGAGGAGCATT[G,A]GATTGCTGTGAAGAATATCCTTAAA | 597,218 | 100 |
| 1721. | AAAGTCTACATCATGTTTTGTATT[T,C]CTGTGTAACGATGGTGCAGTTAGCT | 597,363 | 100 |
| 1722. | ATCGCCGCGTTGGAGGCTGCTAAG[A,G]AAAAATTCTGGTTCAAAAAATTTAT | 597,466 | 100 |
| 1723. | AAAAAATTCTGGTTCAAAAAATTT[A,G]TTGCAGAGCTGGATGTGATGCCACC | 597,490 | 100 |
| 1724. | GTTCAAAAAATTTATTGCAGAGCT[G,T]GATGTGATGCCACCAGATGCCATTC | 597,501 | 100 |
| 1725. | ATTCCACTCTGCTACAACAACAAT[G,A]ATGCCATAACACTCACTAAGAAACT | 597,547 | 100 |
| 1726. | GAGAAGATGAGGCTTAAGTTCATG[G,A]ATGCCATAACACTCACTAAGAAACT | 597,755 | 100 |
| 1727. | ATGAGGCTTAAGTTCATGGTCAAT[A,T]GACTTTAGACCAAGTGAGAGTTTAT | 597,761 | 100 |
| 1728. | TAAATTATCCATAAATCGTTCGAA[A,G]AaTTAACGGATGATGACACGTATTT | 597,930 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1729. | TCGACAGTGTGGAGACACTGAAGC[G,A]AAAGTGTAGGTGCTTGATAGAGATC | 598,122 | 100 |
| 1730. | GTGTAAATAGTTCTTTGACTTGCG[G,A]TGCCTCGGTTGTTCACAGTAGGATT | 598,248 | 100 |
| 1731. | GAGATCCTATATAGTTTATGAAAC[G,A]GAGTCCTAAAATCCATGATCATGGT | 598,431 | 100 |
| 1732. | CTGATGGATTGCCACTACATACTG[T,C]TAGGTGTCACTGATGGATCATAAGA | 598,647 | 100 |
| 1733. | GATAAGAATGAGGAGGTTACATCT[A,G]AATTCAAATTTGAATTTGAATTTGG | 599,195 | 100 |
| 1734. | AGTTGGGCGACAACTACCCTATCC[G,T]TGGTGTACACCAATCTGAATTTCTC | 599,286 | 100 |
| 1735. | AGAGCCCTCCAATCATATCCACGC[A,C]TGTTCTCCCTCTTCTCTCTGATCTC | 599,489 | 100 |
| 1736. | CGGCTCAACAGCGAACCTCAAATC[T,C]ACGATCATCGGATTGCGGAGTTCAT | 599,783 | 100 |
| 1737. | CCATTGTAGCCGAAAGAAAAGATG[A,G]TGCATTAGTCCAGTCAGGAACAATA | 600,172 | 100 |
| 1738. | CAAGCAATTACTGATCATCGATTG[C,T]AGTCCATGAGCAAATATTCCCTCTT | 601,154 | 100 |
| 1739. | AAATTGACAATACAGACTATACAC[T,C]TAAATAACTAACTAAACAATCCCAA | 601,232 | 100 |
| 1740. | ATCAGTTAAAGACAATAAAAAGAA[C,T]AAAGCATTAGTAAAAaTAGCATTCT | 601,922 | 100 |
| 1741. | ATACTAACCATATCATGAAGATAA[C,A]AAATTTTCTTCCTGACAAACATTTA | 602,213 | 100 |
| 1742. | AATTAAGTCAGACTTGTTCAAGGA[G,A]AACAGTCCTTTTTAACTTCTTTACA | 604,520 | 100 |
| 1743. | CCTTTCGATAATAAGGACTAAGAT[A,G]GAGTTTAAAATTTCGCAAGAAATGT | 604,643 | 100 |
| 1744. | TGGTAAAAaTGAAAAGAAAAAaCC[T,C]AATAAGCTAAGTACCAGCTACAAGA | 604,782 | 100 |
| 1745. | CAGGGTTTTAAATCCCGTGGGACA[G,A]GGCAGTTCCAATTTTTTCATGGAAC | 605,107 | 100 |
| 1746. | CGGAATGCACTGCCGTCCTGTCCC[G,A]TCCCAATACTTGGGATAGAGGACGT | 605,156 | 100 |
| 1747. | CACTGCCGTCCTGTCCCGTCCCAA[T,C]ACTTGGGATAGAGGACGTCCCAATC | 605,163 | 100 |
| 1748. | TGGGACGGTCCTGTCCCAACACAT[G,A]GGATGGTACCCCATCCAAGTGTCCC | 605,231 | 100 |
| 1749. | CATCTGAAATTTTGGACATTCATG[A,G]TCAACAATGTGGATGATTGATTTCA | 605,495 | 100 |
| 1750. | ATCTAAAGGGGCCGAAACAAGAAA[A,T]TTTGATCTTTCAGCGTCAGATCATC | 607,187 | 100 |
| 1751. | TGAGAAAACAAAGAAATCAAAAGA[A,G]GACCTGTTAAAGGAGGTGAAAATGT | 607,237 | 100 |
| 1752. | ACATAaAAAACATTTTTTtCAGAA[A,C]CCAGCCACAACACAAACAAACCAAA | 607,441 | 100 |
| 1753. | GAGCGAGAGAGCAATAAATTAGGG[C,T]TCCCAATCTCTGTCGAGAGATTAGG | 607,787 | 100 |
| 1754. | AGCCATGTAACTTTATTCAGTGAT[G,T]TGTGTGTTTTATCTAATATTTTTGA | 608,455 | 100 |
| 1755. | CAACAAAAAAaTAACGAGAGATTT[A,G]TTGTGTGACTAATGCCTCCACATTT | 608,636 | 100 |
| 1756. | TGTGTGACTAATGCCTCCACATTT[C,T]TATTGATAGTCTTGATTATTTATTt | 608,662 | 100 |
| 1757. | ATTATTTTGAAACTTTTAGTTTTA[T,C]GTTGCCAACAATTTGCCCTCTATAT | 608,801 | 100 |
| 1758. | CAATTTGCCCTCTATATCTACTAC[C,T]GTGTCAATCATATTATATATATTCT | 608,834 | 100 |
| 1759. | AAAAAAaTTAATATATTTAACAAT[G,A]TATATATTATATCATGATAGTATAT | 609,035 | 100 |
| 1760. | AATTATTAGACATGCATAAATACA[T,C]AAGCAAAAAATCTCATGTACATATT | 609,126 | 100 |
| 1761. | GTCTGTTTCCTCTTTCTCATTGCC[T,C]TCATCCCCTCGCTCCAGTGGCGTAA | 609,401 | 100 |
| 1762. | ttCTTTGGGGTACAATAAACGAAC[A,G]TTAAAAAATAGGTGGACTTTGCGTT | 609,478 | 100 |
| 1763. | TGGAATACTTGGCTGTCCCCGTCC[T,G]CTGTCCGTAAATAATCATTGCTGAA | 609,555 | 100 |
| 1764. | TTTTCCAAATCGGATCCTATTTTT[T,C]CATTAATAACAAACCCTTGGAGAGA | 609,615 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1765. | CAAATCGGATCCTATTTTTTCATT[A,C]ATAACAAACCCTTGGAGAGAGAAAA | 609,620 | 100 |
| 1766. | ATTAATAACAAACCCTTGGAGAGA[G,A]AAAAAATGCGAAGAGGTAGAATTTA | 609,641 | 100 |
| 1767. | TCCTTTTGGCCAACTAAGTATGAT[G,C]CTGCTACTAATTGGCAGTTTCTGCA | 611,000 | 100 |
| 1768. | ATAGAGGCACTTGATTTTTTATTT[T,C]GAGGGGGAGAGAGAAGGTTCAACGT | 611,687 | 100 |
| 1769. | CTATGGAAACATCTAGTGGATGTT[T,C]TTTACTTGTTGCTTGTTGGTATTTC | 612,132 | 100 |
| 1770. | TTGTTGGTATTTCATTGTGATTGC[A,T]TGCATGTATCTTTTGTTCAAGGAAT | 612,169 | 100 |
| 1771. | ATGAAGTTAACTGGTTAAAATGCA[C,G]AGGTCCAAGAGGAAATTAATGAACT | 612,563 | 100 |
| 1772. | TAAGCATCCAACTCTGGTTCTCTT[T,A]TATGTTCTGCTATTGGGAGTTGCAA | 613,414 | 100 |
| 1773. | TATCTGTTTCCTAGGGTAAGGGCC[C,T]TTTTTATGATTCTATTGAAGCAGTA | 613,509 | 100 |
| 1774. | CTTGCCAAAAATATTATTCTCATA[A,G]CCTGTATGTTAATAGAATTCTTTTC | 613,659 | 100 |
| 1775. | ATCTGTTGTTTCGATGACTGAGTC[G,A]ATTTCTTTCATGGCATCCATATACG | 613,755 | 100 |
| 1776. | CAACATCATTCCCATGCAGCAAAC[T,C]CAGGGAGCTTAAAGATAGACTACAT | 614,128 | 100 |
| 1777. | GAAATCATGGTGCACAATTTCTAC[A,G]AACATATAATAAAGCTGTTGAAAAG | 614,260 | 100 |
| 1778. | TGACATCAACTGGTGTATTTTGCC[A,G]GGTGAATGTGCAGGAACCAATTTAA | 614,780 | 100 |
| 1779. | CTGTCCTTTGAGCCAATCAAACTT[A,G]TACAGTGGAATACATGTCAAGTCTC | 615,082 | 100 |
| 1780. | GTAAAATCGGTTAAGTTAGTTACG[G,A]ATTTGCATGCAGATATGGAGGTATC | 615,605 | 100 |
| 1781. | TGTATATTTTTtATAAGTTGCTG[A,G]AAAAGGTCCATATATTGATCTCTTT | 616,087 | 100 |
| 1782. | CGCACAAGCTGATACACCATCAGA[G,A]GTGAGCCAACTTCTTATTTTACTCA | 616,336 | 100 |
| 1783. | GAGGCTCAAGGAACGTAAGGCAGA[C,A]AAGCCATTGTAAAGCCTCTGATAAT | 617,262 | 100 |
| 1784. | ATCAACACTTTCTTTGTCCTTTG[C,T]TACTTTTAATATTAACAAAACATAA | 628,883 | 100 |
| 1785. | ACTTAGGACCCATGCCAATCCTCC[A,C]GATAATATTTTTCAGACAAGGTTTT | 629,077 | 100 |
| 1786. | GCCTACATCTATTGTGATCCTCAC[G,A]AAATTGATGAGAATGGACCAGAAAC | 629,629 | 100 |
| 1787. | ACATCAATATAGGTGGTTTtTTTT[T,A]AAAAAAAAaaGAATTCATATTTTTG | 629,687 | 100 |
| 1788. | AATTCATATTTTTGTTTGTAAAAT[A,G]CAATTTCAATGGCATTTCATTCATA | 629,723 | 100 |
| 1789. | CTCCTAAGATTTCAAGGGAAAACA[G,A]TGGGGAAGAAACACACACTAGAGTG | 633,279 | 100 |
| 1790. | AGTCAAGAGGAGTCAACGGTCAAC[C,T]GTCGCGGTCAAAGTCAAAGTTTCCG | 633,581 | 100 |
| 1791. | TGTAAAAATATTATTGTACCATTT[C,T]TTTTGTTCTTGAGCAGGTAAATATT | 634,380 | 100 |
| 1792. | TTGTGATGTCATTTGGAAGGTTAA[A,T]GACTAGAGTTATTTGAGTTATAATA | 637,431 | 100 |
| 1793. | TTTGAGTTATAATAAGATCAGGAA[T,C]CCTATATTAGCAAGGAGAAGAAAAG | 637,467 | 100 |
| 1794. | CGAGGATTCTCTGCTAGCAGCTTG[C,A]CCCCGGGATCCAAGAGATAAGGTAG | 638,756 | 100 |
| 1795. | TTTCCTCCATTAAATTGCCTTCAG[T,C]ATTCGATTGTACACAAAGTTATAGA | 638,808 | 100 |
| 1796. | TTGTACACAAAGTTATAGACTTCA[C,T]CCTTGACGTCCAGAAGATCCAGGAC | 638,839 | 100 |
| 1797. | TCAAATATGGAGCTAGGGCTCCCA[A,C]AATGAAGGAAGAATCTGATGAATAT | 639,075 | 100 |
| 1798. | GCCGGAAGGCCTTGATACGGTGGT[T,C]GGTCATGAGCACGGAGTGTAGCTCC | 639,411 | 100 |
| 1799. | ACCGACCTGAATTGGAGGCTGAAT[A,G]TTGATCTGAATTGGAGGCTGAATGC | 639,979 | 100 |
| 1800. | TTTAGCTCATATAAATACCGACAT[G,A]AAGCAGAGTATTACATATATCCGAG | 640,163 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1801. | AACTGGCTACGATCTCACGTACAA[C,T]TGTGCTATAACTCATCCCCAACTGG | 640,331 | 100 |
| 1802. | GCTTACTTACAGCTGGCCTCCAAC[G,A]GCCTAACAAACTCTATAGCTGGCCT | 640,435 | 100 |
| 1803. | CGGCCTAACAAACTCTATAGCTGG[C,T]CTCTAACGGCCTAACAAACTCTTCC | 640,458 | 100 |
| 1804. | CATCAGTCCCTCTATAAATAAAGG[G,A]CAAAGGGATCCTTCAGGTAAGTTTT | 640,516 | 100 |
| 1805. | TCTACTTTTTCTATCTTCTATTCT[C,T]GAGGCTCAAATTGACTTAAGCATCA | 640,673 | 100 |
| 1806. | TCTTATTTTGTAGGATTCTTCGAA[G,A]GAGACTCATATTGGATCACCACAGC | 640,759 | 100 |
| 1807. | TATTGGATCACCACAGCCTCTCCA[A,G]CATGACTTCATCCAATCTCTTCATC | 640,792 | 100 |
| 1808. | CTGAGATTTTGAGCCTCACAACAA[T,C]AGATTGGTGCTAGAGGAAGAGTGAT | 640,841 | 100 |
| 1809. | AAAAAGCACAAAGCAACTCTATAC[T,C]TTGACCGTCTCCCTCTGAAGATATG | 640,921 | 100 |
| 1810. | ACAAAGCAACTCTATACTTTGACC[G,A]TCTCCCTCTGAAGATATGCTGGAAG | 640,928 | 100 |
| 1811. | GCTGTCAACTCATGGTATTAATGG[G,A]GACGGCCCCCACATCCTGTGAGGTG | 641,166 | 100 |
| 1812. | TAAACAAAACTCATAACCTCTCCG[A,G]TAATAAATTCTCAAGCTCTATCTAC | 641,319 | 100 |
| 1813. | AAGAAAAAATCAAAACAAGAATAA[A,G]AAAaTTTATCCAAACGAGATATCTA | 641,418 | 100 |
| 1814. | TATCTATTTGAGGAAACTCAAGAT[G,A]CGATTTGAGATTTTAAGACAATATA | 641,462 | 100 |
| 1815. | GAAAAGAAAAAGAGGAGAAAATCC[C,T]CGGACATAGCCGAAGTCATCTTACA | 641,517 | 100 |
| 1816. | CACCCCATCGGATCGGCATCTTCG[A,C]CACTCCCGTGCGCCTCCTGGAGCCA | 641,664 | 100 |
| 1817. | CCAAGTGCCAAAACATCGTCAGAT[C,T]AGTGACTTCCCTCCGATCGAGACCA | 641,796 | 100 |
| 1818. | CGAGACCATCCGCATGCTCGTGTA[C,G]GTTTGCAGCACCAGgCCCTACCAAA | 641,838 | 100 |
| 1819. | GAGGCCCAGCACTGGCAAATCGAT[C,T]TCCAATCCTGCATCCTGATGGTGGG | 641,940 | 100 |
| 1820. | GGCTCCACTGGATTGACGGCCCCC[G,A]ATGATCTCCAGCTCTCCTCCCTGTG | 641,988 | 100 |
| 1821. | ATCTCTGGCTCTCCTTCCTACATC[T,C]GTGGGTATTTTCGGTGCCGAATCCA | 642,068 | 100 |
| 1822. | TTCCTACATCTGTGGGTATTTTCG[G,A]TGCCGAATCCAGTCAGATCGATTGC | 642,082 | 100 |
| 1823. | AAAAAaaaGAAAAAAAaGAaGAGG[A,G]GAGAGCTTGATCTCCAGCCAAAGTT | 642,559 | 100 |
| 1824. | ACAACAAGCAGTCAAGTAGAACTC[G,A]CAAGTTCTCAAACAACAACTCCTGG | 642,644 | 100 |
| 1825. | ATTCTTAAGCTTCCATTTGTTATT[C,T]TTTCTCTTTTCCTTCTTGCAGGATC | 642,700 | 100 |
| 1826. | AGCAAAAATAAGCTCGAATTGAGA[T,C]AAAACTTAAGTCCAAGCTGcGGCAA | 642,821 | 100 |
| 1827. | GAGATAAAACTTAAGTCCAAGCTG[C,A]GGCAAAGAATAGGAAGGAGTCAAAT | 642,841 | 100 |
| 1828. | AGCTGcGGCAAAGAATAGGAAGGA[G,A]TCAAATATAACTCAGAAGCTCTCAA | 642,860 | 100 |
| 1829. | TTCAATATTCGGATTGGTAGAGCC[T,C]AAATGGAGATAAGATCTCCTCAAAA | 643,364 | 100 |
| 1830. | AGATTGGTAGAGCTCCGAGAGGCA[T,C]AAATGGAGATAAGATCTCCTCAAAA | 643,434 | 100 |
| 1831. | TCCGAGAGGCATAAATGGAGATAA[G,A]ATCTCCTCAAAATCTAATCTCCGAA | 643,447 | 100 |
| 1832. | AAGATCTCCTCAAAATCTAATCTC[C,T]GAATTGGTAGAGTCTCGAAGGGCCA | 643,469 | 100 |
| 1833. | GAGATTATCTTCAGTTCTATAAAA[G,T]TCTAATCTAAAGGTCAAGATTATTT | 643,617 | 100 |
| 1834. | TTTGGATTTCTATCAAATACCGAC[T,C]TCAAGTCAAAGTTATATCAAAATTC | 643,665 | 100 |
| 1835. | AAAGGTCGAGATTATCTTAAATTT[T,C]TATCAAATACCGATCTCAAATCGAA | 643,772 | 100 |
| 1836. | TAACTTGAAATTCTATAAAATACC[G,A]ATCTGAGGGTCGAGGTTATCTTTAA | 643,824 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1837. | CTATCAAGTACCGATCTGAGGATC[A,G]AGGTTATCTTTCAGTTCTATAAAAT | 643,918 | 100 |
| 1838. | TTTTTTAGTTCTATAAAATACTGA[C,T]CTGAAGGTCGAAGTTATCTTTTAGT | 643,989 | 100 |
| 1839. | GACCTGAAGGTCGAAGTTATCTTT[T,C]AGTTCTGTAAAATACCGACTTGAAG | 644,011 | 100 |
| 1840. | ATACCGATCTGAAGGTCGATGTTA[A,T]CATACAGTTCTATGAAATACTAATC | 644,170 | 100 |
| 1841. | GTTATCTTTCATTTCTATAAAATA[T,C]CGATCTGAAGGTCGATGTTATATTT | 644,231 | 100 |
| 1842. | AGATCGAGGTTATCATTCAGTTCT[T,A]TCAAATACTGATATGAGGGTCGAGG | 644,305 | 100 |
| 1843. | GATATGAGGGTCGAGGTTCTCTTT[T,C]AATTCTATAAAATATCGATCTGAAG | 644,339 | 100 |
| 1844. | CTATAAAATATCGATCTGAAGGTT[T,G]AGATTATCATTTAATTCTATAAAAT | 644,368 | 100 |
| 1845. | AGTTCTATCAAATACTAACCTGAA[G,A]GTTGTGATTGTCTTTTAGTTCTATA | 644,487 | 100 |
| 1846. | TCTATAAAATATCGATCTGAAGGT[G,C]GAGATTGTCATTCAGTTCTATCAAA | 644,696 | 100 |
| 1847. | GTTCTATCAAATATGGATTTGAGG[G,T]TCGAGGTTATATTTCAATTTTATAA | 644,735 | 100 |
| 1848. | TATCTTTCAATTCTATAAAATATC[A,G]aCTTGAAGGTCGAGATTATCTTTCA | 644,808 | 100 |
| 1849. | CATTCAGTTCTATCAAATACCGAT[A,C]TGAGTATTGAGGTTATCTTTCAATT | 644,893 | 100 |
| 1850. | CTTGAAAATATCAACCTGAGGGTC[A,G]AAGTTATATTTCAGCTCATATAAAT | 645,057 | 100 |
| 1851. | AGCTCATATAAATACTGACCTCAT[A,G]GTCGAGATTATCTTTCAGCTTATAT | 645,094 | 100 |
| 1852. | TGAGGTTTTACTGACCTCAAGATT[A,G]AGGTTATCCTGCAAAATACAGATCT | 645,319 | 100 |
| 1853. | CCAATCTCCAGATTGGTAGAGCTC[C,T]GAAAGACACAAACAAAGATCAGATC | 645,525 | 100 |
| 1854. | CTATGGATCGATATTATCTTTCAG[C,T]TCGTATAGATACTAGTCGACCTTAG | 645,589 | 100 |
| 1855. | GCTCGTATAGATACTAGTCGACCT[T,A]AGGGTCGAAGTTATTTTATTATTCT | 645,612 | 100 |
| 1856. | TGATCTCCAGATCGAAGTTATCTT[G,A]AAATTCTATTATCGATCTTCGAATT | 645,708 | 100 |
| 1857. | AAATTCTATTATCGATCTTCGAAT[T,C]GAAGTTATCTTGAAGTTCTATTAAA | 645,733 | 100 |
| 1858. | CATCTCAGCTCATAAGAAAGCCGA[C,T]GTGAATCAAAGGCCAAGTTTACATA | 645,967 | 100 |
| 1859. | GAAAGCCGACGTGAATCAAAGGCC[A,G]AGTTTACATAAAGTCGATCTGAATT | 645,982 | 100 |
| 1860. | AGATGTTCAGGGTCCCATATGATA[C,T]TTGATTTCATTTTGGTATTTTATCG | 646,515 | 100 |
| 1861. | CTCCGTCTGAGATTTTGAGCCTCA[T,C]AGCAACAATAATAATATAATATAAT | 647,142 | 100 |
| 1862. | CGAGGTGGTTTAGCTCTTCATGGG[A,T]ATAATAACAAATTGTTTCTAACCAG | 649,436 | 100 |
| 1863. | TCATTCATAATATATCAAAGCAAC[C,T]AGAAATCCTACTGGTTCGGTCCAAT | 649,836 | 100 |
| 1864. | CATGTTAAAAATACCCTTGTATTC[T,G]GCTTAATATAAACTTaTCTCACAAT | 649,909 | 100 |
| 1865. | TTGTATTCTGCTTAATATAAACTT[A,G]TCTCACAATCATTTTTCAGTAAATT | 649,925 | 100 |
| 1866. | TTAATATAAACTTaTCTCACAATC[A,G]TTTTTCAGTAAATTAACAATGATAA | 649,936 | 100 |
| 1867. | ATATGtAGGGGTAATCAGAAGAAA[T,C]GAAaGATGTGTCGGTACTCTGGTGT | 649,985 | 100 |
| 1868. | TCAGAAGAAATGAAaGATGTGTCG[G,A]TACTCTGGTGTCAtgCATATAGAAA | 649,999 | 100 |
| 1869. | TTTTTATTCAAAAAAAaTATTTTT[A,G]TTTGTTTATTATTCTATTTTTCTCT | 650,084 | 100 |
| 1870. | TATTCAAAAAAAaTATTTTTATTT[G,A]TTTATTATTCTATTTTTCTCTGCTC | 650,088 | 100 |
| 1871. | TACAGAATTACCAAAAATTTTGCG[A,G]CCATTTAGTTCTTCTTTCAGTATAA | 650,786 | 100 |
| 1872. | ATTACCAAAAATTTTGCGACCATT[T,A]AGTTCTTCTTTCAGTATAATTTCTG | 650,792 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1873. | ACATGGTGCCTCTTGCAAGTTGAT[G,C]AAAGCCAAATTGACTAGCATTATTG | 650,948 | 100 |
| 1874. | AAAAGCATGAACTCTTACACCATG[C,T]ACTCGATCCTGATTACCAGTTCTAA | 651,003 | 100 |
| 1875. | TTTGATGTGATACCAAAAATGTCA[C,T]GCCACCACTCCCCTCTAATTTAACA | 651,160 | 100 |
| 1876. | ACGGGGTTCACTTGATTCCACAGT[T,A]ATCGTACCCTAGTCTACAGTAGAAA | 654,644 | 100 |
| 1877. | CTTTTTTGTTCATCTTTGATGCGT[A,G]GTAGACACAACTTTTTTGAGAATTG | 655,763 | 100 |
| 1878. | TGATCTTCTCTTTGCTTTCTTGTG[A,G]ACGATATGGAATTTTGATGACAGCA | 655,849 | 100 |
| 1879. | GAAGGAATGGTTCTTTTATGTCCC[T,C]AGAGATCGAAAGTATAGAAATGGTG | 655,916 | 100 |
| 1880. | GACGCTTGTCTTCTACTCTGGGAA[A,G]GCTCCTAAAGGCATACGATCAAGCT | 656,063 | 100 |
| 1881. | TTGAGCTAGCTTTTCATATCTGAT[G,C]TTTTCTCTTAAGTCAACAAGAAGGA | 656,718 | 100 |
| 1882. | ATTTTTCTGTTGCTCTTTGTGAAC[C,T]AAGCTTACTGTTTtAAATTTCTTCT | 656,925 | 100 |
| 1883. | CTTTGTGAACcAAGCTTACTGTTT[T,C]AAATTTCTTCTTCTTCATCATGTCG | 656,939 | 100 |
| 1884. | TTTGCAGACCGAAATCTCGCTCTG[C,T]CGAGTCTATAAAAGAGCTGGGGTCG | 657,331 | 100 |
| 1885. | TCCTCCTCATATTTTtCTTTtCTT[T,G]tCTTTTCCAACAAAGACTGCTGAAG | 657,997 | 100 |
| 1886. | TGTAACTGTGGGTGAAAACTTATT[C,G]TAGATCAGGTTTGTAGTTCGACTAA | 658,049 | 100 |
| 1887. | TTATTCATATATACGTTCTCATCA[A,C]TGAATTTAGGGCATTTTATCATCTT | 658,495 | 100 |
| 1888. | TTCATATATACGTTCTCATCAaTG[A,G]ATTTAGGGCATTTTATCATCTTCTA | 658,498 | 100 |
| 1889. | TTTTATCATCTTCTAGGGTCTCTT[T,C]TGGTTTGGCATGTATTTCCTAAACT | 658,533 | 100 |
| 1890. | TGGCATGTATTTCCTAAACTGGAA[A,G]TATTTCAGATCAGTAGTTGTGAGAG | 658,563 | 100 |
| 1891. | ATTTCAGATCAGTAGTTGTGAGAG[G,C]AGATTCTTAGTCTATATGTGGTATG | 658,589 | 100 |
| 1892. | TACGGCCTAGCTATGTAtaGATCT[G,A]GCGTTGCTTCTCACTTTGTTCACTT | 658,866 | 100 |
| 1893. | CCTTTCTTAACTTGGATATCGTTT[T,G]CTTCTTTGGGCAGTGTTTTAGATTT | 659,156 | 100 |
| 1894. | TCTTTTGGTTCCAGATGTCTTGCT[G,A]AGCTTGGGCAATCTCTTAGGTTAGT | 659,326 | 100 |
| 1895. | TCAAAGATTGCGACGATCGATAAA[T,C]CTGTTCTAGACCATGTTCACTCACT | 659,667 | 100 |
| 1896. | TCGACGAAGAATGGCTTTCGGAGA[A,T]AGCTGATCTACTTCACATGAACTTT | 659,889 | 100 |
| 1897. | ACTTCACATGAACTTTCATTTATG[A,G]TCATCTGATCCAGGTCCAACAGTGA | 659,923 | 100 |
| 1898. | AACAGAAAGAGTATATATGACTGT[A,G]AAACTCTCAATTAGTGAGATTACTT | 660,011 | 100 |
| 1899. | TCCATCTTTATTAGCTCCATGAAT[C,G]ATGCACTATCATCATGTCAATATTT | 660,636 | 100 |
| 1900. | ATTAGCTCCATGAATCATGCACTA[T,C]CATCATGTCAATATTTATTATTGTA | 660,645 | 100 |
| 1901. | AGTTTGAAAAGATGAAAAGAGTA[T,C]CAGAACCAAGAAAAAAaTGAACGAG | 660,739 | 100 |
| 1902. | CAAGAAAAAAaTGAACGAGTCTCT[G,A]AATTTTTAGAATATTTTAGAAGAAG | 660,770 | 100 |
| 1903. | GGCAATTTTAATCAGAAATAAAAA[A,G]AAaTCAAAAATTTGCATGATTATGA | 660,819 | 100 |
| 1904. | GAGAGGCTGCTTCACTTCTTCACC[T,C]GTTCAAAACAATACAGGATATTTTC | 660,946 | 100 |
| 1905. | ACCTGTTCAAAACAATACAGGATA[T,C]TTTCAACTCACACATCTAATTGAGC | 660,967 | 100 |
| 1906. | TCGGGGAAGTTAGACACCAGAAGG[C,A]GAATAGAAATGAATCTCCTATTCTA | 661,063 | 100 |
| 1907. | TATATTTAGGATTATCAGATAGAC[C,T]TTTTTAGGCAACATTGAGCTAGACA | 661,351 | 100 |
| 1908. | AACATTGAGCTAGACATCCAGAGC[C,A]ATGAGAACTCACAGGACGGAACCAA | 661,385 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1909. | GATTTTGGAGCTAGACCTGCAACC[A,T]GATCTACTCCAAGTCCAAATAAGGT | 661,851 | 100 |
| 1910. | TACTCCAAGTCCAAATAAGGTTGG[A,C]CAGATCCTGGCCCAAGCTCAACCCG | 661,880 | 100 |
| 1911. | CAAATAAGGTTGGACAGATCCTGG[C,T]CCAAGCTCAACCCGACTGTTTCCAG | 661,891 | 100 |
| 1912. | AGAGAGAGACAGGGAGAGTTTTGT[G,A]GGATATATCGGTTTTATTTGGTAAA | 661,976 | 100 |
| 1913. | TACCTCATTCAAGAGATGTAATTG[G,A]TCGATGATGTATATAATTATAACAT | 662,029 | 100 |
| 1914. | GAGATTAATGTGCCATGCCATACA[C,T]CTGTGAGATTAACAGTGGATAGACT | 662,111 | 100 |
| 1915. | CTCACTAGTTACATTTGTTTGGCC[A,T]AGGCCCTTGTCAGGCACTAGTAACT | 662,159 | 100 |
| 1916. | CTTGATGTTAATGAGGATCGCATA[T,G]ATAAGCATGGGTAATCACATAAAAT | 662,615 | 100 |
| 1917. | TGATGTTAATGAGGATCGCATATA[T,C]AAGCATGGGTAATCACATAAAATGT | 662,617 | 100 |
| 1918. | ATTTGCTGTTTACAACTCACATTA[C,A]TAAATCACTGTAACAGCTCTCTTTT | 663,349 | 100 |
| 1919. | ATCCATTGTAGAGTCCCACAAGAT[G,C]TCGTACAACAGAGATTTTTTGGTAA | 664,398 | 100 |
| 1920. | TCAACCATGCATCATTGTTAGATA[C,A]TAGCCTATTTAGCCAAGCTACGAGA | 664,591 | 100 |
| 1921. | AACCTACAGTAGCTAATATGCCAT[G,A]ACCAGTGTTTTGTCTTAAAAACATT | 664,778 | 100 |
| 1922. | AAGTGAATAAGAAGAAAAAATGTG[G,A]GAGGAAAACTAACATAATAGGCTGT | 664,878 | 100 |
| 1923. | ATAGGCTGTATAAGCTTTAAAGAG[A,G]CCCTAAGAAATATTGGTGAACATAT | 664,919 | 100 |
| 1924. | CACCAAGGGAACCCCCAATATCAG[C,T]CCCAGGTACCCATCCAAGGAGAGCC | 667,196 | 100 |
| 1925. | TGATTGTAGAACTCTTGAAATTGC[C,T]GTAGAAGAGGCTGGTTGAACCTTAT | 667,291 | 100 |
| 1926. | TTTGGCCCAGACTAGATTGGTCAA[G,C]GCCTCCCCAACAGCCAACCTTGCCA | 668,460 | 100 |
| 1927. | GTTCAGCAAACCCTTTATTGGCTG[C,G]TCCCCAATGGCACAAGCACCACCAG | 668,520 | 100 |
| 1928. | CTTCACAACATTACAATTTCCCCC[A,G]GCTCCCTGATCATGAATACTGATGA | 669,132 | 100 |
| 1929. | GCCTCTCTTCCCTTCTCAATGACA[G,T]GAACCACACTAATAGCCTCTGGAAC | 670,165 | 100 |
| 1930. | ATAAACACACTCTGTCATTCTATC[C,A]TGAACCATAGCTGCAAAATCATTAA | 670,248 | 100 |
| 1931. | CAAGAATTTGTACGCAGAAGAAGA[T,A]TAGGCCTCCTTGATCCCTGGAATAG | 670,894 | 100 |
| 1932. | TAGGCCTCCTTGATCCCTGGAATA[G,C]ATAAAGAAGAGATTCCAGAACAATT | 670,919 | 100 |
| 1933. | GCTCCTTGCCTGGGAGTCCCAGAT[G,T]TCCATGTTGCATGTACCATATTTTt | 691,787 | 100 |
| 1934. | ATGTTTATACAGTTGCAATCTTTC[C,G]TTGAGGATAGAACAAAAACTGTAAA | 691,391 | 100 |
| 1935. | ATTTATGATTTAGCTGCCAGAGAT[A,G]GTGGACAATCTAATAACCTGTTTGC | 692,492 | 100 |
| 1936. | TtTTtCTTTtCTTTTCTCTTTtTT[T,C]GGTTGGTTTAAGATGGGGAGTTCTT | 692,876 | 100 |
| 1937. | GAGCATGTGCAAGAGGGTCTTGTT[A,G]GCTGGGCTGAGAAGGTAAAGAGGAG | 692,946 | 100 |
| 1938. | ATGCAATCCATCAATTGGCCAGCA[A,T]CTATGATACTATAACTTATATATCC | 693,145 | 100 |
| 1939. | CTAGTCAGGTGCTCAATGTTATAT[T,C]GATATCCAAATAGATTCAGATCCCA | 694,257 | 100 |
| 1940. | TTTGAGCAATCAAGAAGAGTGTAC[G,A]CACTTAGCAACAACCCCTACCTTCA | 694,298 | 100 |
| 1941. | AGAAAGAAGACTGGGATGAAGAA[A,G]aAAGTGGTCTCCCTATTTCAAATAT | 699,190 | 100 |
| 1942. | GAAAAGAAGACTGGGATGAAGAAa[A,G]AAGTGGTCTCCCTATTTCAAATATT | 699,191 | 100 |
| 1943. | CTTCCATTTTCTTCTTGTCACTTC[C,G]ACCCAAGTTTTTCTTTCCCCCTTTC | 701,712 | 100 |
| 1944. | TCCTTTTTATTAAAACAACTTATT[C,G]AAGTAGTCTACAAGTACGTTAGGTG | 702,566 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1945. | GGTGCAACTATGACAGTACAATAA[C,A]AATGGCGATGTTCCTTTAAGTCAGC | 704,049 | 100 |
| 1946. | GGGAGTTGACAAAAATACAGGGGG[A,G]AAATGATGGACAAGATATTGGTTGT | 705,206 | 100 |
| 1947. | TAATATTATTAAAATTTTTtAACA[G,T]AATAGTTCACGTAATTTACATATAA | 705,411 | 100 |
| 1948. | CATATAACTCTTCTTATATCTGAT[A,G]TGGTATAGTTCAAGAAAAAAAaaa | 705,454 | 100 |
| 1949. | CTGATGCCGAAACCCTAATTTTTA[A,G]CGATTTTCTTTTGGCAGATATTtCT | 705,635 | 100 |
| 1950. | CAGTCTTAGCTCTCATCCTTATCT[G,A]AAATTTTTTAAAAAAGTTTGTCCTT | 706,275 | 100 |
| 1951. | AGCATAAAACCCGTGCTACATTGT[G,A]GgTTTTAATAAATAGAAGACAGAGT | 706,516 | 100 |
| 1952. | AATTGATGTTCCCTAATCTGAAAA[C,T]ATAGTTGGAAGAATAGAAAATTAAA | 706,692 | 100 |
| 1953. | TAACCCTAGCCCCAACCCTAACCC[T,G]AACCCTAACCTTCAAAAATCTAACT | 707,153 | 100 |
| 1954. | CGATTTTTCTTATCTGCTGCCACC[A,C]TCTTCGATCTTTCTAATCCTCAATA | 707,898 | 100 |
| 1955. | ATAAGATAATCCATGCTTTGGCAT[C,T]AATATTTTTGATTTTTCTCAAAA | 708,098 | 100 |
| 1956. | CAGATCGCTATCTTCTTTTTCAAA[C,T]GAAGCATCATATTTTTtCTACATGC | 708,397 | 100 |
| 1957. | TCATACTACCCCCTTTCTGTGCCT[C,T]CTCCTCCCTTCCATCCGGCTCCACC | 710,065 | 100 |
| 1958. | AGGTGGAGCACAGCGACTAGGGCA[C,T]TGTCGAGGCATCCTTCTTCCCATGC | 711,592 | 100 |
| 1959. | CGGGCGGTAGGGGTACAGTCTTGA[A,G]GGCAcGGGAGAGGGAGCAGGTGGCT | 711,750 | 100 |
| 1960. | GGTAGGGGTACAGTCTTGAAGGCA[C,T]GGGAGAGGGAGCAGGTGGCTCCGAT | 711,755 | 100 |
| 1961. | GCCGATCTTTAGGCGGTTCTTTGG[A,G]TTGTGTTGAGCCAAGAGGTGAAGCA | 711,931 | 100 |
| 1962. | TGGGATTATTGAGATTTTGGCGGG[T,G]GTAGAGCAGAAAATCGAGGCCGAAG | 712,822 | 100 |
| 1963. | TTTGGCCCGAGCCCAGCCTAAATG[G,A]TTTTGAGCCGAGCCCAAAGCTTGAC | 713,397 | 100 |
| 1964. | GTGAAGAAGGAAAATAGACTCTTA[G,A]AAAATTGTGCACTTCATATTTCTTC | 715,214 | 100 |
| 1965. | AGAACGAAAAATTCATCGAACTAC[G,A]CTATTTCTTGGAGAAGTGCCAAAAA | 716,031 | 100 |
| 1966. | ATCCTCGGATCGATCCAACCGACA[C,T]CCGACTCTACCCACCGGACAGACAG | 716,177 | 100 |
| 1967. | CACCTTGTCCGAAGGATGGGTTCG[G,T]ATTATTCTTTCCCTATTGGTAATTC | 717,500 | 100 |
| 1968. | AGAGAAGTGCATAAGGATTGATTC[A,G]TTTGAAGCCAAGTAGGCCTTATTGC | 718,659 | 100 |
| 1969. | AAAGGATTGTCTCAAATGGAGCAC[A,G]TGATTTCACAAAGGTGACTTGTCAG | 721,006 | 100 |
| 1970. | TTCTTACTATTTTGATTCCCTTGC[A,G]TATATAATCTTAGCAATCATTGTAT | 721,146 | 100 |
| 1971. | CTGGAGTAGCAAGAGATGCTGTAC[C,T]GGAGTTACTAGGTTTCTTGGTGGAG | 721,828 | 100 |
| 1972. | CACCCATTTTTAAAAGAGAACATG[A,G]CATTCATAAAATGGGGCAGACAGGT | 722,331 | 100 |
| 1973. | GATGCAGCAGGAAGAAAGAAGAAA[C,A]AAAACAAAaATAaAAAACAATCAAA | 723,920 | 100 |
| 1974. | TTATTTGGAAGAGGTTAAGGTTAA[C,T]GGCGATGATTTATCATCATAAAATA | 731,383 | 100 |
| 1975. | AGCTTCTTGGACAAAGGAAGATCT[C,T]CTTAGAAACTAGTCTTGATTTTCCT | 731,600 | 100 |
| 1976. | GCTTCTTGGACAAAGGAAGATCTC[C,A]TTAGAAACTAGTCTTGATTTTCCTT | 731,601 | 100 |
| 1977. | TATGATCCACTACATGGAATAGTT[T,A]ATGAAGCAAGTAATGAGTATTTACT | 732,394 | 100 |
| 1978. | ACTACATGGAATAGTTTATGAAGC[A,C]AGTAATGAGTATTTACTTCTTAGAG | 732,402 | 100 |
| 1979. | CAAGTAATGAGTATTTACTTCTTA[G,C]AGTTAGAGCAGTGCCGACAATGGAA | 732,425 | 100 |
| 1980. | TCAAACCATAGGAGCGCAGGATAC[G,A]CTCAGCAACGAGACAGCCAACAAAT | 732,587 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 1981. | TAAATTCCTCTCTGACGTGGGACT[T,C]TAAGGTTCTTGCAAACTTGAGTTTG | 734,317 | 100 |
| 1982. | CAAGGAAACTGGTAATCCACTGCT[A,G]TTGAGAAGGAGATAGCCTTCAACTT | 734,505 | 100 |
| 1983. | TCAGTCCAAGAAAATTGAAGATCT[A,T]ATTTTCAACAACATATTATGTGGAA | 734,598 | 100 |
| 1984. | CAGTCCAAGAAAATTGAAGATCTA[A,C]TTTTCAACAACATATTATGTGGAAA | 734,599 | 100 |
| 1985. | AACACAAACTGGGCTCTTGGAGTT[G,T]GAAGAAATTAACATGCAGGCAGTTC | 734,720 | 100 |
| 1986. | AATGGATGGAAAaTAAAAAaTTC[T,A]ATCCTTCCCTCTCAGCCTTTGGCTT | 734,847 | 100 |
| 1987. | ATCCAGAGCACATGTAAATAATAG[A,G]CACCCAAATGCTTGTGTAGGTTCAA | 736,155 | 100 |
| 1988. | TCATGGCACGAAAGGCAACCAAGC[A,G]aCGGTGCACCTACCAGAACAGCGCA | 744,082 | 100 |
| 1989. | GTTAGATTTGAAAAATAGATCCCA[T,G]ATTAGATTAGTATATTTGATATAAA | 744,165 | 100 |
| 1990. | AAAAATTAATTAAAGATGATAATA[T,C]TATCTCAATATTAAAAAATTATTTT | 744,477 | 100 |
| 1991. | GGAGCAGAAGAAGTTGCCGACTTA[A,G]ATTATTCTCCTAAAACATGACCAAT | 744,795 | 100 |
| 1992. | ATTCTCCTAAAACATGACCAATAT[C,A]TAACATCCGAACGCTGGAAATAAGA | 744,823 | 100 |
| 1993. | ACTAACATGAAAGATTTTAGGAAT[G,A]AATTTGCAAAAACCGTTTCTTATTT | 744,989 | 100 |
| 1994. | TTATAGCTATCGTTTTGAATATAT[A,G]ATAAATAAATAAATAAATAAATAAT | 745,092 | 100 |
| 1995. | AATAAATAAATAAATAAATAAATA[A,T]TTTTTATATATAATAAATATAAATA | 745,116 | 100 |
| 1996. | TCTAATATCCAACTGTTTAGCACC[A,G]TTAAATTATTCCAAAATGTTGGAAT | 745,226 | 100 |
| 1997. | CCATTAAATTATTCCAAAATGTTG[G,A]AATTGTGACTATGACGTACCAAACT | 745,248 | 100 |
| 1998. | GACTATGACGTACCAAACTAAATT[C,T]GAATTCGAATCTAATTTTATTCTGA | 745,279 | 100 |
| 1999. | TTAAGTCTCTAAATTTTTtAAATT[A,G]AATAAAAAATCTCTAAAATATTAGC | 745,422 | 100 |
| 2000. | TATTTTTAAATTCCTGTCGTCTAC[G,A]TAGATTGATTACATAGGTCTATGTT | 745,476 | 100 |
| 2001. | ATAGGTCTATGTTTAGGTTACACG[A,G]ATTTATGCTCAAGTTACACAGATTT | 745,513 | 100 |
| 2002. | TAGGTTACACGAATTTATGCTCAA[G,A]TTACACAGATTTATGTTCAAGTTAC | 745,526 | 100 |
| 2003. | CGAATTTATGCTCAAGTTACACAG[A,G]TTTATGTTCAAGTTACACAAGTTGC | 745,535 | 100 |
| 2004. | ATTTGTAGGTATTGTGCAGATGAT[A,G]TTTTGGTCTATGATTGATGGATTTA | 749,100 | 100 |
| 2005. | ACATATAAGCATGAACCTGATACA[A,T]GAGAAACTTAGAATAATGGTACTAC | 749,792 | 100 |
| 2006. | GTTAAAGTCCTTGCTGTTGACATG[T,A]AAATAAATGCTGACTGCTTTGTATG | 752,010 | 100 |
| 2007. | CAGTTCATCAAACTTTTGGACACC[A,G]GTGGTTATAACTTTACAATTCATCA | 752,170 | 100 |
| 2008. | AATTCATCATCCTTGACCTTTTTC[A,G]aTAATTAAATTAATAATTGTAACCA | 752,211 | 100 |
| 2009. | TATTTAGAGCAATTAGTGGATCTA[G,A]TTGTCCTGGTCATTTATGTCAATTA | 756,570 | 100 |
| 2010. | ACCTTGCAGGTACGTGGCATTTGT[T,C]ATGCTTTGGGTTTGAAGCGTGATAG | 756,835 | 100 |
| 2011. | AAAACATTGAGGGCCTATAAAAGC[C,T]CTAAAATAAGGTATGGCAACATTGA | 756,935 | 100 |
| 2012. | ACATTGATCTAACTAAGCCCTGTT[C,T]GGCCAAGGTTGGTTCAGGGGTTTAC | 756,978 | 100 |
| 2013. | GGTTCAGGGGTTTACAATTTTGAC[C,T]GGGTTGGAGTAGATTTTTATTAACC | 757,013 | 100 |
| 2014. | CTTTAAAAATGCTAAAGCATCCAT[G,A]TATAGGCTCTGTTTAGGTAATCTTG | 757,688 | 100 |
| 2015. | TCCATATAAATAGGGGTGTGTACT[A,G]AaTCAGAACAGGTTTTCCTCAAAAA | 757,741 | 100 |
| 2016. | CCCAGTCTTCATATGTTAAATATG[T,C]GGCTTAGTTGGTGATTCGAGCAAAA | 757,861 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2017. | GGTCTCTAATCATCAGATTGGAAG[G,A]AAGAAAATAGAAAGCAAAAATACTG | 758,002 | 100 |
| 2018. | TGATGATATGTGATCATTTCTGTC[A,G]TGACTGTCGAATAGAAATATTTTA | 758,144 | 100 |
| 2019. | ATGGTTTGATTATAATTAATTGAA[A,G]TTTAGAATAAACATAAAAATCCTAA | 758,199 | 100 |
| 2020. | GAATAAACATAAAAATCCTAAAAG[G,A]TTTAGAGTTTTTGGCGTAATTAAGT | 758,228 | 100 |
| 2021. | TTTGGCGTAATTAAGTCTTTTTTT[G,A]TGCTTATATTTTACATGTTGGATTC | 758,262 | 100 |
| 2022. | TCTTCTCTCACAAAAAATCCTTCT[A,G]TCAAAACTTCTACCACAGCATGGAG | 763,780 | 100 |
| 2023. | GTAGGTGAGGAGGAGTTTGGTGGA[G,A]AGGATGGCGTCGGTGTAGAGGCCAG | 764,178 | 100 |
| 2024. | TGCCTTAGCCACCCTAGTTGCCCA[C,A]AAGCCAATAGCAAGCTGACCATGAC | 764,705 | 100 |
| 2025. | TACTTCCCAAGCTTGATCCACATC[C,T]AATGCACAATCCAGAGAAAAGCATC | 766,025 | 100 |
| 2026. | GACTTCCAAAAATTTTCATGGCTT[G,T]TTAACTTGTTTCCAAGAAGATGGCT | 766,218 | 100 |
| 2027. | CAGGCAACTGCAGATATTTAATTT[G,T]TTAACTTGTTTCCAAGAAGATGGCT | 766,390 | 100 |
| 2028. | TTATTTGCATGATGCAATTTCATC[G,A]TCTTGCTTTTTGATGTTAACTTGAC | 766,970 | 100 |
| 2029. | AAAAGCATGCGATTACAATGAGCG[A,T]CTGTCGGTAACAGCCCTTGAATACT | 767,172 | 100 |
| 2030. | ATATGGGAAGCAATAAAAGCATGC[G,A]ATTACAATGAGCGACTGTCGGTAAC | 767,186 | 100 |
| 2031. | AACTTGTTTATTTTGAGAATTTGC[A,G]TAATTGAGATTTGACAGATTAATCA | 768,299 | 100 |
| 2032. | ACGTCCTGTTGGTCTACATTACCA[C,T]TTGAAAATTCCACCCAAGAAAATCA | 768,624 | 100 |
| 2033. | ATATATTCTGAAAGGTTAAAATAG[A,G]CAACAGCAATATTGGTATCTAGCAT | 771,000 | 100 |
| 2034. | AAGTCAATAGTAAAATGACTAAAA[G,T]AGATTTTGAAGTATCATGGCAAAAT | 771,070 | 100 |
| 2035. | GAGGAAGAAGAGAAGAGGAAGGAG[G,A]AAAAAAATGGAGCACTACTTTCAAA | 771,249 | 100 |
| 2036. | AAATGTTAAATGATAGTGTTTACT[A,G]CAACACTTCTTTAATAATATTTTAT | 771,906 | 100 |
| 2037. | CAAGGGGAGTAGAAACTTAGGAAA[T,A]ACATTCAAGGCTTCCGCGGGAGGAG | 772,264 | 100 |
| 2038. | GACGTGGCTGACGTCCGGGCCGAG[G,T]GCTAGGGCTTTAAGAGATTCTAGGG | 772,414 | 100 |
| 2039. | AAGAGGACCTCTCCGGAATCGACG[T,C]GGCTGACGTCCGGGCCGAGGGCTAG | 772,434 | 100 |
| 2040. | CGTATCCATCGGCGGTTCTGGAGG[C,G]GAGCCGTTCGGAGGAGAGGCCGATG | 772,511 | 100 |
| 2041. | CACCCTAGACATCAGCTGCTCAAA[C,G]AAAAGAAAAACAACTCCTAAATTTA | 772,791 | 100 |
| 2042. | TAATTTTTTTTttAAAAAAAAaGA[C,T]AGGTAAAAATTCAAGCAAAGAGGAC | 773,145 | 100 |
| 2043. | ACTACCTTGCATCAATCTCTACTA[C,T]CAAGCCTGAAATAAGCCAATGAAAT | 773,657 | 100 |
| 2044. | TCAATTTTAGTGCCTTACTTCACT[C,T]AGGCGAGCGCTTTTCTGACGCCCCT | 773,770 | 100 |
| 2045. | TTCATGTTACAATAGTTATCACTA[G,A]TTGTTATTTATTTATATATCATACT | 773,834 | 100 |
| 2046. | CCAATGAAGGAAGAGAAGACGAAA[G,C]TGATGACAACTTCGCAAGTGAAACT | 774,151 | 100 |
| 2047. | AAaCCTAAAAGACCGCCCATTTAA[C,T]TTCTCAGCTCCATTACTAACAGGGG | 774,291 | 100 |
| 2048. | TtTTTtAATGACTGAAAAGTGTAA[A,G]AAaCCTAAAAGACCGCCCATTTAAC | 774,316 | 100 |
| 2049. | CACCTCAGACGCTCAAGTGAGGTG[C,T]CAGAAGGGGTCACCACCCCTTGATA | 774,473 | 100 |
| 2050. | AATATATGCCATCAATCCAATGAT[G,A]TCAAAAGTGCCAAAAGGCGCACCTC | 774,517 | 100 |
| 2051. | AATTTCAACTTAAAAAAGTGCCAG[T,G]TACAGAAAGCAAACAACTCAAGGCT | 774,679 | 100 |
| 2052. | TGGCATCTACCTATTTAAAAAGTT[C,T]AGAAGGAAAACCTGCACACAGCCCC | 775,516 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2053. | TATAAATCTCTAATTCTATTTCTT[C,A]ACTTGATCGAGCCCATAAAATTAAT | 775,916 | 100 |
| 2054. | CTACGAATGAATTGGCCCAAGGCC[G,A]GGATGTTGCTAGGCCTTGTCATTAG | 776,126 | 100 |
| 2055. | GAAGGATGGGCCAACCCGTGCTTG[A,C]CTGGAATTTTTATATTGTTCATGAT | 776,218 | 100 |
| 2056. | GACATTTGTACCTCTATATTGCAT[G,A]CTAATCCATGTTGATTCACGTTAAGC | 776,648 | 100 |
| 2057. | CGCTACAAAACAAGCATCTAACAA[C,G]AAGTCAAAAGCAATCAGAAAAAACC | 776,852 | 100 |
| 2058. | ATTTTGTGTGCATGACTCAAACAA[A,C]TGCCCATATTGATCTTCACATCCAG | 776,981 | 100 |
| 2059. | TGATTCGGATTCGGATTTTCTTAC[G,A]ACATTCAGGTTGAGTTCACATTCAT | 777,788 | 100 |
| 2060. | AAATTAAAACAATATGAAATAATT[C,G]TAGAAGTAACAATATCTTTGAAATC | 778,657 | 100 |
| 2061. | CATCAGGAGGCAAACACAACACAA[T,C]CATAATTCCCCTAGTCTGGCTATCA | 778,984 | 100 |
| 2062. | CTTCCCCcTCTCTCTTCCTCTCTC[A,G]TTCTCCCTTCACCCTCTCTCTGTGT | 779,535 | 100 |
| 2063. | TCAATAGTGGTGCAGCAAGCTCAA[C,T]TGCCCTCCGGAGTCCCTCTCTCCTT | 779,596 | 100 |
| 2064. | AGGAGGGGCTCCGCCCTCTTGATC[A,G]AAATAGGGGCTTCGGTCTCTGTTTC | 779,885 | 100 |
| 2065. | AGGAAAGGAAAAGGAGGTTCCCCG[A,G]AGGCCTTTGGAGGGCTAGCAAGGCC | 779,965 | 100 |
| 2066. | CTCAATATAACTGAATATCAGAGG[C,T]GGAACTGCAAACAACAACCTATTCT | 780,454 | 100 |
| 2067. | CAAGCATAATGTCACGTTCATATC[A,G]TGAGATATTAATCACTGTCCTTTGT | 780,627 | 100 |
| 2068. | TCAACAATCACTACATCCAAAGGC[C,A]GGTGCCTTATTTTtCTTCAAGATGC | 780,688 | 100 |
| 2069. | GAGGAAGGTGAGCAGAGCATTCCA[G,A]TTTCTCAAAGGGCAGTTAATATGAT | 780,759 | 100 |
| 2070. | TAACAAGAGTAACACATTACAGCC[G,T]AATGCAGGGCTCATTTAATATCCAT | 780,830 | 100 |
| 2071. | CAGACTTGACATAAGTGCTCTGGC[A,G]CAATAAGGACTCTCATAAATCAGAT | 780,999 | 100 |
| 2072. | ATATTCTCAGTATTGTGGGTGAGG[G,A]AGAGTAAAGGGTCAGACTTGACATA | 781,036 | 100 |
| 2073. | AATTAGTGTTATTTTAAAGCATCC[C,T]TTTTTTGAAGCACAGCTGGTGAGAA | 781,100 | 100 |
| 2074. | TGCTTACAATAAAGTCACTTTAAT[C,A]TGAAGCCATATCTTAGATAAATTAG | 781,144 | 100 |
| 2075. | TGAGTTCAGAAATCAGCATTTGAC[C,T]GTGCATGTAATTAATGGTTTGTGGA | 781,937 | 100 |
| 2076. | CTTTTCTACATTATCTTAGATTAG[A,G]TGGATATGGAAGTGAGTTCAGAAAT | 781,974 | 100 |
| 2077. | CTTGGTTATGTTTTATCCTAAGCA[T,C]ATAGGAACAAAAGTAAGCCAAGGAA | 782,198 | 100 |
| 2078. | GTTTCAGGAGTGTCAGGAAGGAGG[A,T]ACTACAGAGCAAAAATAAAGAAAGG | 782,408 | 100 |
| 2079. | GTCTGAAATAGGAACAAAACTAAC[C,T]TAGTTCTCACCTAAGCATATAATTT | 782,505 | 100 |
| 2080. | TAAAAAGAATAGAGAAAAAGCTTG[A,G]AGTAACGAAAGCAATTAACAAAAGT | 782,624 | 100 |
| 2081. | CAAAAATCCACAAAATGCTTTATT[A,T]GTCTCCCTGTACAACAAAATAAAAA | 782,668 | 100 |
| 2082. | AAGGGACTTGGCCCAATTAAATCA[C,A]TTTATGGAGTCCCTTCATCAGGATA | 782,854 | 100 |
| 2083. | ACAGACCGTGCAGGATCAAGAAAG[C,A]AGAAAAGGAGAAAAGGGACTTGGCC | 782,891 | 100 |
| 2084. | GGAACAAGGAAACCTAATCAGACA[G,A]ACCGTGCAGGATCAAGAAAGCAGAA | 782,912 | 100 |
| 2085. | AGAATCTCACAAAGAGAATACCTG[T,C]GATGCAGCTAGCCACTGGATCATAC | 783,375 | 100 |
| 2086. | TCCAACAGTTATGGAAGACATATT[C,T]GAACAAAGGAATGAGTTGAATCACC | 784,113 | 100 |
| 2087. | AAGTCACCCACTGTCCATCCATGC[A,G]CCAAGGTCCATTGAGTCACCTGATT | 784,265 | 100 |
| 2088. | AGAATGACACTACTCAGACATATC[T,C]TGCACGTCATTTGATGTGCTGTGAT | 784,395 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2089. | GAAGAATGACACTACTCAGACATA[C,T]ATTGCACGTCATTTGATGTGCTGTG | 784,397 | 100 |
| 2090. | aAGAaAAAGAGCTAAATGAGTCAC[G,A]CCTTAGAAGAAATATAAATATTAAA | 784,494 | 100 |
| 2091. | TCCATGCCAGCAGGAAAACAAAAG[C,A]ACGCATCTTATGACTGCCCCAACAA | 784,776 | 100 |
| 2092. | GATGAGCACCATATTTCCATGCCA[G,A]CAGGAAAACAAAAGCACGCATCTTA | 784,791 | 100 |
| 2093. | TGGACAATTCAGCACTTGCAATCC[T,C]ATTAGCAAGCAAGATTTCTTCTCGT | 784,955 | 100 |
| 2094. | GCACTTGCTGCCCGATTTTCTACC[G,A]ACCAAATGGCATCACTTCTGGCTGT | 785,123 | 100 |
| 2095. | GAATTGACAAACCAAAAAGTTGA[G,T]GGAGCCTTCCAACATCACAAAATGC | 785,320 | 100 |
| 2096. | TTATCTGGAGCACATCACTTCCAC[A,G]TGGAGATAGTAGGTCTTAACAGAAT | 785,385 | 100 |
| 2097. | GCCGAACGTAGACGGACTTGACCC[A,G]CTCCTGACCTAACTTGGACCTTGGC | 787,420 | 100 |
| 2098. | ATACCGCGACAATGATTGGATAAG[G,C]ATGCCAAGTGGGCCGAACGTAGACG | 787,456 | 100 |
| 2099. | TCTGTTCTTCCTCGTCGGAGTCAG[G,T]GTCTTCTTCATCTTTCCCATCGCCG | 788,028 | 100 |
| 2100. | AATGATTTCAATGAGATACATTTG[T,G]TGATACCACAATGTAGGAATGTGGA | 788,520 | 100 |
| 2101. | ACACCCCAATTGGAAGGAGAAGGT[A,C]TTGATCTTCTGCACCATTTCGAGAG | 793,935 | 100 |
| 2102. | AGGTCCATTAATTTTCCATGACAT[G,T]ATTtTTTTTTCCCGAAAAATGATAT | 794,054 | 100 |
| 2103. | ATTTTCCATGACATGATTtTTTTT[T,C]CCCGAAAAATGATATCCTAGTTATT | 794,064 | 100 |
| 2104. | CGAGTCATTTCATAGTTTCTGGAT[G,T]ATCTAACTGTTGTTATTCTCGAATT | 794,299 | 100 |
| 2105. | GAGTCATTTCATAGTTTCTGGATG[A,T]TCTAACTGTTGTTATTCTCGAATTA | 794,300 | 100 |
| 2106. | TCATAGTTTCTGGATGATCTAACT[G,T]TTGTTATTCTCGAATTAGGTTAAAC | 794,308 | 100 |
| 2107. | TCATTTTAACAGCTAACCAACTTT[T,C]AAATTACAAACTTATTCTTTCAAAC | 794,499 | 100 |
| 2108. | ATATATGACTTTCTCAGCAGACCC[T,G]CACCATAATTTTCATGCTGCTTCTT | 794,623 | 100 |
| 2109. | ACTCCAAAATTCGTTCTCCTTGGC[A,G]GGGTAGTTTGTTGCCATTACGTGTA | 795,254 | 100 |
| 2110. | AGTTGTTTTTCAGCTTATATCAAT[G,T]AGCAATTTTCCTCCAACATATTAAG | 795,317 | 100 |
| 2111. | TTAATGTATTTACTTACAGTAAGC[T,A]CGTCACAAAAAACCAGGgTTTCATA | 795,430 | 100 |
| 2112. | GTAAGCtCGTCACAAAAAACCAGG[G,T]TTTCATATATGTAGAGAAAAGTGTA | 795,448 | 100 |
| 2113. | CAGGgTTTCATATATGTAGAGAAA[A,T]GTGTACATACAATTCATGGGCATGC | 795,468 | 100 |
| 2114. | TGCATACAAAGTAATTGAATACAT[A,T]TGTGGACAGTATACTGGAGGAAACA | 795,515 | 100 |
| 2115. | TTCTCAATCCTCAATGGCAATTGC[C,T]GCAGATGAGGGGTAATTACCTGTAT | 795,785 | 100 |
| 2116. | GAAATAGGCAACTCAATAGATGTT[C,T]TTGCAAGCATGTTGTAAACATCGCA | 795,945 | 100 |
| 2117. | ATTTATTGAAAACTGCGACCTTTG[C,T]GAGATATATGGGAAAAAaTAAGGAG | 796,033 | 100 |
| 2118. | TTTATTGAAAACTGCGACCCTTTGc[G,A]AGATATATGGGAAAAAaTAAGGAGG | 796,034 | 100 |
| 2119. | AAGCTGGCGCGCAATAGAAATTGC[A,G]GCTCAAATCGGCAGTTGATTGTAGA | 796,169 | 100 |
| 2120. | TGTGTGCCAATCATGGGCAAGAGC[T,C]AAGTTGATGCAtCCTAAGATAATGG | 796,494 | 100 |
| 2121. | ATGGGCAAGAGCTAAGTTGATGCA[T,C]CCTAAGATAATGGCTGAGTCAAGAT | 796,506 | 100 |
| 2122. | TGATAAAAAaGTAGAAAGGTCAT[A,G]TTGCAGGTTGGATCAGAAGGTGAGA | 796,723 | 100 |
| 2123. | TTGCATCACAAAAATGATTTTGTA[T,C]TTCAATTATATGGAGGTTATGGATG | 796,990 | 100 |
| 2124. | TAATCCATATTCAGGACAGTGAAA[T,G]AACAAAAAaGGGAGGGCCTTTATGG | 797,189 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2125. | TTAATCTGTTCAAATATTTTTTtC[A,C]aTGAAATTTTGTTACTTTTAACTCT | 797,587 | 100 |
| 2126. | TTTTtCAaTGAAATTTTGTTACTT[T,C]TAACTCTTTTCTTATTATGTGCTAT | 797,605 | 100 |
| 2127. | TACTTCTGTGAAATTTGACAGGAG[A,G]TTGCGGAAACTGCATTCAGGAATAT | 797,654 | 100 |
| 2128. | AGGGAAGATTATGGAGCATTTAAT[G,A]TGTAGAAGCCTAATTCGAGCTTTAC | 798,126 | 100 |
| 2129. | TGTATGACAAAAATGTCAATGGCC[A,T]CTAAAAGAATAAGCAACAAGCTCTT | 798,383 | 100 |
| 2130. | AATATCTGTATGATAGCTTTTCCA[C,T]GCAACTGTACAGGTCTATCAGTATA | 799,055 | 100 |
| 2131. | TCTTCAATGATTGCTACTATTACA[C,G]TTAGTTTGGTGTCATTATAGAACTG | 799,125 | 100 |
| 2132. | AGTTTTTGAACACATGCAACTTAA[C,T]GATGACCAGGTACGAACAGCTTATA | 799,572 | 100 |
| 2133. | ATATTCATtTTTTTTCTTAAaAAA[G,A]AATACATTGCTTGCTGTTGATGGCA | 799,829 | 100 |
| 2134. | CACTTTCACAGGTTTGATGCCATA[T,C]tGTCCAAGACATTTAGAGATTGTTT | 799,892 | 100 |
| 2135. | GTCCAAGACATTTAGAGATTGTTT[G,A]GATGTCTGGGCCCAAAATCCCATGA | 799,918 | 100 |
| 2136. | TAGGCTTGTATTCACAAATATCTC[C,T]CTATGAGATTCGGGCTGGCCCACTC | 800,013 | 100 |
| 2137. | TATTATTTATCCCCAATCCTAAGG[C,T]GGCATTGTTTCTTCTCAGATTCCTT | 800,377 | 100 |
| 2138. | TGATGCAAATTCTGCCCACACTGA[C,T]GTGCGGTCGTTTGTTTCTAATGGGG | 800,769 | 100 |
| 2139. | GGGATTATGTACATTCTGATGCAG[T,C]aCAAGGACTTTAATGTTGTCATATc | 800,814 | 100 |
| 2140. | GTATCATTCCAACCATATCATCTT[T,C]GTCTGCAAGAAAAAGGATTATGTAC | 800,839 | 100 |
| 2141. | GTATCATTCCAACCATATCATCTT[T,C]CGTATcAAAAAAAaTCTCTACTTCT | 804,008 | 100 |
| 2142. | AGTCCAAATCTTATATGTCGTCAA[A,G]AAATCTTTTGTAATAATATGTTGTT | 804,103 | 100 |
| 2143. | TTGTAATAATATGTTGTTTCACTA[T,C]ATGTCGGTCTTCAAGAAAACGATTT | 804,135 | 100 |
| 2144. | TGTCTGATTAACATATGCAAAGTC[T,C]AAAAATTTATTGACCCCCTCAATGT | 804,223 | 100 |
| 2145. | CCCTCAATGTATGTAGGTGAAGTC[T,C]TTTCTCGCAAATCAATCCAACTTTT | 804,263 | 100 |
| 2146. | ACTTTTATCCATAGTAGAGGCCAA[C,T]GTGAAGAAGGGTCCCTTGGTCTCCTG | 804,307 | 100 |
| 2147. | TCCTGAGGAGGACTCCAAGCTTAA[G,A]GAGTTCATAGAGAAATATGGGACTG | 804,352 | 100 |
| 2148. | ACTGGTGGCAATTGGATTGCCCTC[T,C]CTCACAAGGTTGGTAAGAGAGTGAT | 804,398 | 100 |
| 2149. | ATTGGATTGCCCTCTCTCACAAGG[T,C]TGGTAAGAGAGTGATTGAGATCCTT | 804,408 | 100 |
| 2150. | CTTCTCTACCTGTTTAAGAGGGAA[C,T]AGACATGATCTTCTTTTAATAGGAG | 804,483 | 100 |
| 2151. | CTACCTGTTTAAGAGGGAACAGAC[A,G]TGATCTTCTTTTAATAGGAGAGAGA | 804,488 | 100 |
| 2152. | ACAGACATGATCTTCTTTTAATAG[G,C]AGAGAGAGATTTGGTGTCATTATGT | 804,506 | 100 |
| 2153. | CCTGAGGCCTAACATAAAGCATGG[A,G]GAGTTCTCAGATGACGAGGACAGGA | 804,638 | 100 |
| 2154. | AAAGCATGGAGAGTTCTCAGATGA[C,T]GAGGACAGGATAATATGCAGCCTCT | 804,653 | 100 |
| 2155. | TATGCAGCCTCTTTGCTAGTATCG[G,A]AAGCAGGTGAGAGACAGCCTCTTAA | 804,691 | 100 |
| 2156. | ACAGCCTCTTAATACAATCCAGTT[C,T]TTTCCAAACTCTGTCTCCCTCATCG | 804,729 | 100 |
| 2157. | GATAACAAAAATCAATTAGATAT[A,G]TCTTTTTTtGAGGCTGTAAAACAGC | 804,908 | 100 |
| 2158. | AAGGGTTAAACAGAGATCAAGACT[G,A]GAAGATGGAACAAACTATATATTCC | 805,045 | 100 |
| 2159. | TCATTTGTTCTCTCTATTCGGTTG[A,G]CATCGAAGAGGGAGAGATCGAGAAG | 805,095 | 100 |
| 2160. | ATAAATTATTTACCACGATCCACT[A,G]TCGTGGTAAAAATCGTAGATTATTT | 805,585 | 100 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2161. | GATGATAATTAAGGGATTCGCTAA[C,A]CTTTCTTAATCCACTTGATTGAaAA | 805,826 | 100 |
| 2162. | AAATAGTGCTACCATAATGGCATG[C,A]CTTTCTTAATCCACTTGATTGAaAA | 806,191 | 100 |
| 2163. | GGAAGGTGTCAACAAAACAAGTGC[T,A]TGCATCTAGTCATTTTACACATACC | 806,685 | 100 |
| 2164. | ATTTTACACATACCAAATTAGGAT[T,G]AACAAATTAATTTATTAGTTGGCGT | 806,821 | 100 |
| 2165. | TTACACATACCAAATTAGGATTAA[C,A]AAATTAATTTATTAGTTGGCGTACT | 806,724 | 100 |
| 2166. | TAAATCGATCTGGAACAAAAATTT[T,C]GAAATATATATTCAGACTAAGGAAA | 806,787 | 100 |
| 2167. | ATAAAATTTCTTTATCACTTTACA[A,G]ATAACTGCAATGCCAATTACCAATA | 807,000 | 100 |
| 2168. | AGTATTTTTATATCATCCTCACA[A,G]GCATATTCCCACCATATATGAGATA | 807,142 | 100 |
| 2169. | CCTCACATGCATATTCCCACCATA[T,A]ATGAGATATAAATACATTTACAAAA | 807,159 | 100 |
| 2170. | GCAGAGGTTCGACTCTGAGAGCAA[C,T]TTCCATGCCAACGGCCACAAGTTGC | 807,461 | 100 |
| 2171. | AAGCTTGAAGGCTTCCATGAAGAC[C,G]ACAAGAGACATAGGCGGTATCGGTC | 807,531 | 100 |
| 2172. | TGTAGATAGAaCTGGTTTTTAGAT[T,A]tAGTTTGTGATGCAAGTCTTTATGT | 807,750 | 100 |
| 2173. | ATTAAGTGTTCCTTAATTTATCCT[T,C]taTTGAAAGAGAAGGTGGCTGCCCa | 807,817 | 100 |
| 2174. | taTTGAAAGAGAAGGTGGCTGCCC[A,T]GCCAGTCTCTGTGTCTGAATTGTAG | 807,842 | 100 |
| 2175. | GGAGCTGCACAAGTAATTTTCACA[G,T]AGTGCTATGTGCACATATTTGTTCA | 808,073 | 100 |
| 2176. | TCTCTGATTTATTGACCATAACCA[T,C]TAAATCGGTAGTTCAGGGTATTGTG | 808,133 | 100 |
| 2177. | AAGGTGGATAATTGGAAATATATC[C,T]GAGCTTTGCTTAATTTTCTTCTCAT | 808,494 | 100 |
| 2178. | CTTAATAAAGCATCTCATTGAAAA[G,A]CATATTTCTTAGTATATAATCTATC | 820,377 | 100 |
| 2179. | GGCAGATCTTGGATATTTATACAA[G,A]ACTAATCAATCCAAATAATATCTTC | 820,483 | 100 |
| 2180. | TGAGAATCTCAGAGCTTAAATGGG[G,A]GAGTATGTGAGGACTGTGCAGGTAT | 820,701 | 100 |
| 2181. | TCCAACAAGAAGTTCTATCTTATA[T,C]GATTGAAAATTGGAGAAACTAAATA | 820,997 | 100 |
| 2182. | AAGAAGTTCTATCTTATATGATTG[A,G]AAATTGGAGAAACTAAATAGCATGA | 821,003 | 100 |
| 2183. | ATTCCCTAAAATCTACCCCCAACC[A,G]TCATAACTATTTTAACATATTCTAA | 821,092 | 100 |
| 2184. | ATTCAATGGTATAATTACTATGTC[G,A]AATTATATTATGTTAAATAGAAAAC | 821,238 | 100 |
| 2185. | TTAATATCTAGTACATTATGCATT[T,C]GATTTTATTGGATAGACTAACTACC | 821,302 | 100 |
| 2186. | TTAAATAGGCTGGCCCAAATATGA[C,T]TAAACAATGAATATAGTTTAGGCCC | 825,196 | 100 |
| 2187. | GTCGGCATGCAACTTTGAGTGGAA[A,T]GAGATTTTCACCATATAATCACCAT | 825,409 | 100 |
| 2188. | AGAGATTTTCACCATATAATCACC[A,T]TATTACTGCAACTAATTTTTAGCAC | 825,433 | 100 |
| 2189. | TAATCACCATATTACTGCAACTAA[T,C]TTTTAGCACATGCCACCTTTAATTC | 825,449 | 100 |
| 2190. | AATTATTTTATTTGCAACAAACCT[T,C]ATCGCAGCTTGATTTTCTCAATTTT | 825,563 | 100 |
| 2191. | ATCAAAAACACGGGCAGCATGCTC[A,C]CGGTCGGCACTAATAAAGCAGCAGC | 827,934 | 100 |
| 2192. | AACACGGGCAGCATGCTCACGGTC[G,A]GCACTAATAAAGCAGCAGCAAAGGA | 827,940 | 100 |
| 2193. | TTTTTCTCAGCTTTGTTCGCTTTT[T,A]GGAACCCTATTCGCATCAAAAATTC | 828,487 | 100 |
| 2194. | ATTAATTGTGCACATGTACAAGGA[T,C]GGTGTAATTGCGCACAAGAGTGTGT | 829,836 | 100 |
| 2195. | GCATAGTCTTTCGCACTTTTTTTt[A,T]AAAAAAaTAAATAAATAAACATAGG | 831,203 | 92 |
| 2196. | TTAGCTTCCCGATACGGTACCGAT[A,G]GTTGTTTGTTATTCCACGAAATCTA | 831,536 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2197. | ACGGTACCGATAGTTGTTTGTTAT[T,C]CCACGAAATCTACTCGAATGGTTAC | 831,549 | 92 |
| 2198. | ATCAACCAGGAACTTGCTTGCTTC[G,A]TGATATCATTGCCAAAATTTTGTGA | 833,028 | 92 |
| 2199. | CGCCAACCAGCCCTTTTGGTTGAG[G,C]ATAATCTGACATAAAAAATATATCA | 833,084 | 92 |
| 2200. | ATATTTATCAATAAATATTAATTA[T,C]TAATAAATAATTAATAAATAGAGGT | 833,377 | 92 |
| 2201. | TTAATAAATAATTAATAAATAGAG[G,A]TTAGTTAAAATAAATCTAACATAGG | 833,401 | 92 |
| 2202. | ATTAATTTAAGATATTTATTAATT[T,C]ATTTAAATATATTTTAATATTTGAA | 833,529 | 92 |
| 2203. | AATTTAAGATATTTATTAATTTAT[T,C]TAAATATATTTTAATATTTGAAATA | 833,532 | 92 |
| 2204. | TTTCTGATGCTATTTTATGGAGTG[A,C]TTTTTCTATCAACCATACACAATAA | 833,739 | 92 |
| 2205. | AACATTGCAAGTACCTCCCACTCC[A,C]ATACCTAAATCTATTTAGCCAATTC | 835,834 | 92 |
| 2206. | CAAATATTTATGTAAAATATATCC[A,C]CTCAAAAAGCATAAGAAACAATTTT | 835,888 | 92 |
| 2207. | ATGAATGGACTTGGAGGAAGAAAA[A,G]GATGAGAAGaAAAAATGAATAAGGA | 836,505 | 92 |
| 2208. | GAGAATGATCATGGATAAGGAATA[G,T]GTTAGAGAAGAAGAAGAAGGATAAG | 836,567 | 92 |
| 2209. | GGCTTGAAGAAAAAAAaTGAGGAG[A,G]TAAAGTGCATGGGAAGAAAGGAGAG | 837,072 | 92 |
| 2210. | TTAAAGTAGTAAAAATTGTCAGCT[G,A]GCCAATCATAGTTAACAATTAAACT | 840,743 | 92 |
| 2211. | CACTAGGCTCCTAATTACTAAGTG[G,A]TCATATGTATTTAATCTTATTTTtA | 841,235 | 92 |
| 2212. | CCACATACAGTCGCTAATAATCTC[A,G]CCGTCGCTAATTCCGTCGTAACAGT | 841,920 | 92 |
| 2213. | AGTTTACCACATGACATGTGTACC[G,A]TAGAACTATGTGAGCTGGCTACATA | 842,938 | 92 |
| 2214. | TCTCTTCAATATCTATTTAGTTTG[G,A]ATCATTATCAAAAAAAaTTAAGAAG | 844,223 | 92 |
| 2215. | CATCGACATCCGTCAGTTTTAAGA[C,T]ATCATATGAGAAGAAGTAAAAGAGG | 844,302 | 92 |
| 2216. | AAATTAGATTTGACTTAATTTGAT[G,A]TTAATTAGATTTTATAATTCAAGTA | 846,036 | 92 |
| 2217. | TTGAGTTTTATAATTCAAGTAGGG[C,T]TTAGATTCGAAGTCTAATTGAATTA | 846,731 | 92 |
| 2218. | CAAAGTTATGAACTGAACAAAGAA[T,A]TAAATATTATATGCAGAGAGATGAA | 847,973 | 92 |
| 2219. | TTAGGTCATTAAGAATATATATTA[G,T]GATGTTTTCCTTTCACCTGATATCA | 849,575 | 92 |
| 2220. | ATGTTTTCCTTTCACCTGATATCA[A,T]TTTTTGGAATGATCAAATTGTCTGA | 849,601 | 92 |
| 2221. | GATCAAATTGTCTGATTTGATTAT[C,G]CTAGACAAGGCAATAGCATATTTAT | 849,636 | 92 |
| 2222. | ATATAAAATATCTAAAATAATATC[A,G]TATTATTTTATTTTCTGGTAATATT | 849,799 | 92 |
| 2223. | ATTAGTTTAAAATATATTAAAGTC[G,A]TAACAATTATTGGTGTGGCGCTATT | 849,849 | 92 |
| 2224. | ATATAAAATACATTATTATTGAAA[T,G]ATTGATAAAAATATGGTATTATATA | 849,924 | 92 |
| 2225. | GTATAATAGTAAAAAATATATTTT[C,T]CTTATATATACATATAGTAAAAGCT | 849,989 | 92 |
| 2226. | TTTTTATTATTACTCAACCATATA[T,A]ACCACTAACAAGAAAAATGATATCC | 850,041 | 92 |
| 2227. | TGAGCCAAATAAACATAATAATGG[G,C]TTAGAAAGGGCATCTATATCCATTT | 850,170 | 92 |
| 2228. | ACCTTTGTTGGTCTTGAGTTGTCT[A,G]TCCTTAGCTCATCCTTGGTTGGATA | 850,309 | 92 |
| 2229. | TGCTATTGTCTATCAATATTTTTG[T,C]CCAGCTATCTTAGCCACATCATTGC | 850,599 | 92 |
| 2230. | CAAACAAAAATTGGACAGACAAAC[A,G]GTCCAAATTGAGTTTCAAAAAAaTG | 850-776 | 92 |
| 2231. | GCCCAATTTGCCCACTTGCTAGCG[A,G]GGGGGGCAATTTCTGACATGGCAAT | 851-412 | 92 |
| 2232. | ATGTATACATTCGAAATGGTTGTG[G,T]GTTTAGAACTTGCCATGCATAATTC | 851,571 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2233. | GTGGGTTTAGAACTTGCCATGCAT[A,T]ATTCATGGTCAAGCCAAAATGGGGG | 851,592 | 92 |
| 2234. | AAAATGGGGGAAATAAAGGAAAAA[A,G]TTAAGGAAAAGGCGAAGTGAGTGGC | 851,632 | 92 |
| 2235. | GGGAAATAAAGGAAAAAaTTAAGG[A,G]AAAGGCGAAGTGAGTGGCTTGTTCA | 851,636 | 92 |
| 2236. | AGGAAAAGGCGAAGTGAGTGGCTT[G,T]TTCAGAATCTGTCATGTTTTCTTCT | 851,660 | 92 |
| 2237. | GCGAAGTGAGTGGCTTGTTCAGAA[T,C]CTGTCATGTTTTCTTCTATACTTCA | 851,668 | 92 |
| 2238. | CTTTCAGTTTCCCCGGACAACTAT[A,T]CCTTCAATCCCCTTTTCCTGGCCCT | 851,744 | 92 |
| 2239. | CCATATAAAATAAACGAGCTGGGT[A,G]TGGTATCATTCTTTGCAACTCAATT | 851,844 | 92 |
| 2240. | CAACTCAATTATAAATAGCTTAGG[T,A]ATGAATTAAAGTTTTTGTTTGACTA | 851,884 | 92 |
| 2241. | TCGGAATGAAGCCCAAGGACCTCA[T,A]ATTTATGTCTAGATTTCCACCCAAC | 852,015 | 92 |
| 2242. | CAACCGTGAAACTAGGCCACGCTA[G,A]TTTGGGGCCTGGGGAATCTGAAATT | 852,061 | 92 |
| 2243. | TAGTGGCATGACATTGTAGCTAAC[A,T]CTTTTCTCAAAAACGGGAAAATAAG | 852,222 | 92 |
| 2244. | GGCATGACATTGTAGCTAACACTT[T,C]TCTCAAAAACGGGAAAATAAGAAAA | 852,226 | 92 |
| 2245. | AATAAGAATTACGACCAATGTTTT[G,T]GATAGGAAATGGAGATCGATGGTGA | 852,363 | 92 |
| 2246. | TTAGACATATCTTTAAAAATTAAT[T,C]TGAAATAAATGCTAACTTAAAATTT | 854,149 | 92 |
| 2247. | TCCTTTTACTTATGGAGTTTCCTA[A,G]AAGTGTAGCAATATTAGACTTATTt | 854,347 | 92 |
| 2248. | CTTTTACTTATGGAGTTTCCTAAA[A,G]TGTGTAGCAATATTAGACTTATTtTT | 854,349 | 92 |
| 2249. | TAAATCAGTAAAAAAGTTATTATT[G,T]AATAAATTAAAAaTTAAAAAaTAAT | 854,421 | 92 |
| 2250. | ATCAGTAAAAAAGTTATTATTGAA[T,G]AAATTAAAAaTTAAAAAaTAATAAT | 854,424 | 92 |
| 2251. | TTTTttTTTTGGTACAAACGAACG[G,A]TCATACCAATCTAGTGTAAGAACAT | 854,504 | 92 |
| 2252. | GGTCATACCAATCTAGTGTAAGAA[C,T]ATTTCAAAGAGTCAAAATACAAAAT | 854,527 | 92 |
| 2253. | CTTCATCTCATCCTAAATTCAGTC[A,G]ATGACTGGAGTGGAGTCACCCTCAA | 854,762 | 92 |
| 2254. | GGAGTCACCCTCAATGAAGATCTT[T,C]TCAGCCCACAACTCCTGTCTCGTAT | 854,798 | 92 |
| 2255. | GACAGATTCGGAGGAAGGTGGCTC[T,C]CAGGAAATGAAAGAACCCTTCGAGT | 855,009 | 92 |
| 2256. | GTGCAGCAAGAGAATCCTAAAAAC[T,A]TGAGGCAGCAAGGCTCGGACCAGCA | 855,067 | 92 |
| 2257. | TAAAAACTTGAGGCAGCAAGGCTC[G,A]GACCAGCAGTGTCGAAGTGACAGCA | 855,084 | 92 |
| 2258. | GGCTCTTTACAGTACCCATTGAAT[C,T]GATATAATCTCAGTATCAAACAAAA | 855,152 | 92 |
| 2259. | CTCTTTACAGTACCCATTGAATCG[A,G]TATAATCTCAGTATCAAACAAAAGG | 855,154 | 92 |
| 2260. | AAGGCTATTGTTGGACAGCCAAAC[C,T]TGATAAGTGACATACACCATCCTAC | 855,200 | 92 |
| 2261. | CCCTTGCCATGCTCCGATGGATCA[T,C]GTCTAAGAAGGGAGGAAGCTAAGGG | 855,264 | 92 |
| 2262. | TCCAGCCCGCAAACTAGGTAGATA[A,G]TTAGAACCTCCATACCTCTATCTTT | 855,406 | 92 |
| 2263. | CTTCTAGAGAAAAAGCCTAAACCT[G,A]GGATGGGCAACCATTCTCTAAATCC | 855,492 | 92 |
| 2264. | GAGCCCTCCAACTCCTGTCGTCAA[T,C]AGTGATCGAATTATAAACCCACAGA | 855,719 | 92 |
| 2265. | GAGAGAGAGGCAAACTAGAGATCC[C,A]AGCATCCTGGCTCACATCAATCGAG | 855,806 | 92 |
| 2266. | GCATCCTGGCTCACATCAATCGAG[A,G]TTCTGTCTCCAATCAGCTACTTGAT | 855,832 | 92 |
| 2267. | AGCTGTATGTCTGAAAATCATAGC[C,T]TCTCTCCTGACTAGCAAGGATTGGA | 856,036 | 92 |
| 2268. | AGCAAGGATTGGATTCTAAGACCC[T,C]CATCCCGCACCGGCTGACAGACCAC | 856,073 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2269. | GAAGAGAGCGTTGGCTTGCCAGCC[A,G]TCGAAGCGATCTCAGACTTGCTGCT | 856,293 | 92 |
| 2270. | ACCTTGCATTTCGAACTGAAATCT[G,A]ACTAATGAGCAAGCAGTCATCTGTA | 856,556 | 92 |
| 2271. | TGCATTTCGAACTGAAATCTGACT[A,G]ATGAGCAAGCAGTCATCTGTAAAAG | 856,560 | 92 |
| 2272. | ACCAGAGGGCCTCTCGTACCTCCT[C,T]AGTAGACACAGGGCGAGTTAGAATC | 858,614 | 92 |
| 2273. | TCCAACGTGATTTAAAGAAATACA[T,G]AATCTATCTCCTAATCTCATAATAC | 858,737 | 92 |
| 2274. | AGTAGCTTATGTCAAAGCTCCCTT[G,A]GGTCAAGCTCTTGAAGGCCCCCTCC | 858,947 | 92 |
| 2275. | TTGAAGATATCACCAACCTTCAGT[C,T]GGTTCCATCAGATATGCCTGCGCCG | 859,051 | 92 |
| 2276. | ATCACCAACCTTCAGTCGGTTCCA[T,C]CAGATATGCCTGCGCCGCGCAAACT | 859,059 | 92 |
| 2277. | CGGATCAACATCCTTCAAACATCC[C,T]TAATCAGATCTAGGATTTCGGATAG | 859,139 | 92 |
| 2278. | CATCCTTCAAACATCCCTAATCAG[A,G]TCTAGGATTTCGGATAGAAGGTCCA | 859,147 | 92 |
| 2279. | CAGTGGTGATGAGAAGTGGGCAAC[G,A]GTTCGAAGCAATACTCGGAAGGTGC | 859,264 | 92 |
| 2280. | ACGCTCGATCAATCCTCTCCCAAA[T,C]TCTAGCTGTCCCAAGCCAGTTGTTG | 859,349 | 92 |
| 2281. | CGCTCGATCAATCCTCTCCCAAAT[T,C]CTAGCTGTCCCAAGCCAGTTGTTGC | 859,350 | 92 |
| 2282. | ATACTATCCACATACTGCTTGCCA[C,T]CCATCTTCTCATGGGACTCCACTAT | 859,482 | 92 |
| 2283. | GCCACCCATCTTCTCATGGGACTC[C,T]ACTATATAGTTGAAATCCCTAGCGA | 859,502 | 92 |
| 2284. | CTATAGCACCCTCCGCTCCCTGTA[C,T]TTGGTGCTCGCATATCCTCCGGACA | 859,595 | 92 |
| 2285. | CCGGACAGAAGCCAAAGACCATCA[G,A]TTTGCTCAGATATGACTAACGCCAC | 859,638 | 92 |
| 2286. | ACTCGACGTCTCCCTGAAGCCCTG[A,G]CCCAGTCCTCTCGAGAGCCATCTCC | 860,511 | 92 |
| 2287. | AGTTTGTATATGAGTTAAATTCTG[C,T]TATACTTTCATCATGTTCTGATTTT | 861,047 | 92 |
| 2288. | CACAGTCTTGAAAATCATGTATTT[T,C]ACACCAAGCCTTTGTTCCATATTGG | 861,193 | 92 |
| 2289. | TTTATGGTTCCCTCCTGGGTTCTT[G,T]GGCTTGCATGTGATTTGGGCTACTT | 861,551 | 92 |
| 2290. | TGGTTCCCTCCTCCCTTCTTGGGC[T,A]TGCATGTGATTTGGGCTACTTGGAC | 861,555 | 92 |
| 2291. | CATGGTTTCTCTGGACAATTTATA[T,A]CGAATACCAAGGCAAATGTATCCTT | 861,640 | 92 |
| 2292. | TCCTTCTAATGTCTCAAATTTCAG[C,T]AAAAGTGTTAGGATTGACATTACCT | 861,685 | 92 |
| 2293. | TCTATCTCACACTTAATTTAAATG[G,T]CATGCACAATTCAGGCTTTTGTATA | 861,756 | 92 |
| 2294. | TAATTTGTTCCATCAGCCCCTTTT[T,G]ATGTGCTTATTTTTTtAAGCACCTC | 861,825 | 92 |
| 2295. | ACTGGACTCCCATTGGTAAGCAAG[A,G]AAAAaGAAAGAATTAGACTACATG | 861,935 | 92 |
| 2296. | AAAaGAAAGAATTAGACTACATGC[G,A]TTGTTTTCCTTTTGTCAACTTGTGG | 861,962 | 92 |
| 2297. | AACATGTAAGCTTGGTAGAGTCAT[T,G]AATTTTTCTCCTGGATAATCTGATC | 862,095 | 92 |
| 2298. | TAAGCCAGCGACTCTTTCCGGTCT[G,A]CAAGCACGATTGGTTGGGTTAAGCC | 862,155 | 92 |
| 2299. | GCGACTCTTTCCGGTCTGCAAGCA[C,T]GATTGGTTGGGTTAAGCCACTTTTC | 862,162 | 92 |
| 2300. | TTAGGTCACTTCAATCTTTATAAG[G,T]TTTCAAAAATTGAATCCTAGAACTC | 862,478 | 92 |
| 2301. | CTCGTAGAAACAAAAATGAGCAAT[T,C]ACCTTTTCCGGTTTCTTTGTATCTG | 862,679 | 92 |
| 2302. | ACGGGGGTGAGCAATTACCTTTTC[C,G]GGTTTCTTTGTATCTGCAAGTAACA | 862,688 | 92 |
| 2303. | TTCTTTGTATCTGCAAGTAACATT[C,T]TCTCAACATTCAACAAATATATGAT | 862,716 | 92 |
| 2304. | GTTTTACTTGGATTTGTTTCTTTT[A,C]CTTTCTTTCTCTATCAATATGGTGC | 862,866 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2305. | TGGCTGCACTGAATTTTTAGGCAT[G,A]ATGATAAACCAAAATTTTCAAGCCT | 863,053 | 92 |
| 2306. | TTAAATTAGACTTATTGAAAAAGA[T,A]AATATGCATATTTCTATAATACATC | 863,255 | 92 |
| 2307. | GGTCCAGCCAATTTACTTAATCAT[G,C]CTTGGCTTGTGCGGAACTTGTCCTA | 863,334 | 92 |
| 2308. | ATCTCTCAGTAGAAGAGAGTAAAA[T,G]GCTTGCTCATGAGAATGCGAAAGAC | 863,626 | 92 |
| 2309. | GTTGAGTGTTGTCCTTTCACTTGC[A,T]TGAATAGATATGCCAATATCTAGTG | 863,751 | 92 |
| 2310. | GTCCTTTCACTTGCATGAATAGAT[A,G]TGCCAATATCTAGTGGCATAACAAG | 863,761 | 92 |
| 2311. | TATGCCAATATCTAGTGGCATAAC[A,G]AGAACAATGTTGTTATTGAGGTCAT | 863,784 | 92 |
| 2312. | CTGTTTCATGTTTTTtCTTAGTTT[A,C]TTAGATTTCACTCTGGAGCATTAAT | 863,867 | 92 |
| 2313. | CACTTAAATTCCATTTGCATAGTG[G,A]ATGTTGTTTAGTTATTCCTACCATT | 863,995 | 92 |
| 2314. | ACTTTCATGTGACACTGAATTTAA[C,T]TCTCATTCAATGGATTAATCTCCTG | 864,370 | 92 |
| 2315. | GTTGCAAAGTGCATCACGTTTAAT[A,T]AGGTAAATGCTAGAGTCATTTGAGA | 864,467 | 92 |
| 2316. | GCATCACGTTTAATAAGGTAAATG[C,T]TAGAGTCATTTGAGATAAATTCCAA | 864,477 | 92 |
| 2317. | GTTTTCTTATGTCTTGCATTTGTG[T,C]AACTTAGGTTGTGGGAATATTTGGC | 864,562 | 92 |
| 2318. | GTGGGAATATTTGGCTTCACACAA[G,T]AAGATCATATTGGAAAAATTAGCTT | 864,597 | 92 |
| 2319. | AGTTATTTTAGCTTTCTAGTCTAT[A,G]TGTACAAGGCTTCGTGTGTGTCC | 864,700 | 92 |
| 2320. | CCTAGTTCATTTCCACATCTCTTC[C,T]CTGGAAAGGACCAGCTTCGTTGCTT | 864,856 | 92 |
| 2321. | GCATATGCTCTATAGTAAAGATTG[A,G]CATATCCCCACTAATTAGGTTATTG | 864,972 | 92 |
| 2322. | ACAACACATCTTGTCAAGCAGTGC[C,A]GTGTCATTTCATCCAGTATTAAAAC | 865,497 | 92 |
| 2323. | GTGCCGTGTCATTTCATCCAGTAT[T,C]AAAACATTGAATTGTCAGGATACTT | 865,517 | 92 |
| 2324. | TGTCAGGATACTTCAAATTTCCTC[A,G]TTTTCAAAGTGTCCACTTGTCGCTT | 865,554 | 92 |
| 2325. | TATTAACTGTGCATGAAAATTTTG[G,A]CACAAGTATCCATGTTATCTGTTGA | 865,687 | 92 |
| 2326. | TCTGGAACTTCTTTGCTTGTCCAT[T,G]TGTATGATAAGCAACCAGGAGTTGT | 865,787 | 92 |
| 2327. | ATCACCTGTATCTAATAGTTGATC[A,G]TTATAGCTTGACTTCTTGATCCACT | 865,934 | 92 |
| 2328. | GCCTTTGTGGGAACTATTAGATGC[T,A]CCATCCATCATATATGCATAATTTG | 866,261 | 92 |
| 2329. | TTGTTGGTGTTCCATGGTTCCACC[G,A]GTATGTGCTTTTTAAAAGCATTCTT | 866,325 | 92 |
| 2330. | ATTTAAGGCATTGTGAGCCATACT[G,A]GTAGCAAACTGAAATGGTTTAGACG | 866,415 | 92 |
| 2331. | AGAAGAGGGGAGAGGAAGATAGGA[C,T]GACGCTGTTGGAGGCCAGCGGTGGC | 866,516 | 92 |
| 2332. | GGGGAGAGGAAGATAGGACGACGC[T,C]GTTGGAGGCCAGCGGTGGCCCGTCG | 866,522 | 92 |
| 2333. | GAGGCCAGCGGTGGCCCGTCGAGG[T,C]TGGCCGGAGGGCCACGTTGGCCTCT | 866,551 | 92 |
| 2334. | AGGGCCACGTTGGCCTCTGCAGCT[T,C]GATGTCGCCTGATAGGGCATTTAAA | 866,583 | 92 |
| 2335. | GGAGGGATGTGCAGCTGGCGGAGA[G,T]GTTGTCAGAGGGCACCAGATGACTG | 866,671 | 92 |
| 2336. | GATGAAATAGGGACGATCGCCCTT[A,G]TTTCATGTCCGCGGTACCATAGGCG | 866,885 | 92 |
| 2337. | GCTGGCCAGCACAGGTCCCGATTT[T,C]GATTCCGGTTCTGCCTTCCTTGTTT | 867,138 | 92 |
| 2338. | ATCTACTTTTACATGATTGCTGGT[G,C]GATGATGCGTGCCTTGCTCTTTATT | 867,343 | 92 |
| 2339. | TGCTGATTGGATGACGAGCTGTGT[A,G]ACCAGTCACACTGGGACTACATTAT | 867,428 | 92 |
| 2340. | TATTCTCTTTCTTTGTTGTTTTGT[C,A]ACATGTCTTGGTATGACTAGTTCCA | 868,404 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2341. | ATGTTCCAACCTTTTCCCTTGTAT[T,A]CTATGATATTAGCCTCATTTAGCTG | 868,553 | 92 |
| 2342. | GCTTTAATTGAATCATCATTCTTC[T,C]CTGCTCTTCAGGTATTTAAGTGAAA | 868,708 | 92 |
| 2343. | CATCAGCTATAAAGGACACTGGGG[C,G]CCTGAGCAAGCATTTAACTGTATAA | 869,084 | 92 |
| 2344. | AGCAAGCATTTAACTGTATAACAA[G,A]TTTTCTTCTTTATTTTGTAGATCAA | 869,113 | 92 |
| 2345. | CACAGGCAATCTTCAAAGTCTTCC[A,G]GACATGTTTACTCCTTCAAATTATG | 869,488 | 92 |
| 2346. | ACAACTAGTGAAGGCGAAATATTA[T,C]CTCTTCAAGGTTTAAATTCTTGTCA | 869,586 | 92 |
| 2347. | TGGGAAGAAGGAACATGCTTTATA[T,G]AATGCACAGAAAGGTCAAATTTATA | 869,765 | 92 |
| 2348. | TAACGTGATACTACCACAAGATAT[G,A]TGCGTTGATGTGCCACATCCCTTAT | 869,882 | 92 |
| 2349. | CTCGACTAGGTAAGCACTATGCCA[T,G]GACAAATGGTCAGCAGTACTCTGTG | 869,955 | 92 |
| 2350. | TAGGGAATGAGATCTATAGTAAAT[A,C]AATAATTTTCTCTACATGTTCATCT | 870,056 | 92 |
| 2351. | AATCCACTCTCCATCTATCAACCT[T,C]CTTGATTTTCTTGTAGACGACTACT | 870,186 | 92 |
| 2352. | TCTTGTAGACGACTACTTAAATTT[T,C]TCACTTTACCATTTGAGTATGTTC | 870,219 | 92 |
| 2353. | GAACCTGAATATGAACAGGGGGAG[A,G]CAGGAAGGATGTCAGCAAGTGATCC | 870,322 | 92 |
| 2354. | CCAAAGACATAAAAAATAAGGTTT[G,A]TCTTCTATGTAGCATCCCAATTTTT | 870,401 | 92 |
| 2355. | ATATTTCTTTATGTGTGTTATGTT[C,T]CAATGTTTATTAAAaTTAAGGTGT | 870,451 | 92 |
| 2356. | GTTTTACTTCCCATTGGTTCCAAG[T,A]CTAGGATCAATATCTTTTtCTTTAC | 870,552 | 92 |
| 2357. | TCAGAGTAGGATACTGTTTAGCGT[A,T]TGGAGAATCCTTTATACTGGATGTT | 870,681 | 92 |
| 2358. | GCAGGTTGATTTTTTCCAATGTAT[A,C]ATTTtTTTTTTtGCAAGGCTATGAT | 870,891 | 92 |
| 2359. | GCTCATGAGTTTCTCTAAAATACT[T,C]TAGTCAATGGCGGATGTTCAGTTTT | 870,944 | 92 |
| 2360. | TTTATTTTATAATGTGTTAAAATA[G,A]AATTTGGCTGTTTATAGAGTTCTGA | 871,226 | 92 |
| 2361. | TGTTTATAGAGTTCTGAGGTCCTC[A,G]CTCCTTTTTTtCTTGAAACACATAT | 871,259 | 92 |
| 2362. | TTATAGAGTTCTGAGGTCCTCACT[C,T]CTTTTTTtCTTGAAACACATATCTT | 871,262 | 92 |
| 2363. | TCTCCTCTGTCGACGTAATAATGT[A,G]TTCATTTTAAACTCTTCTTTTGTTT | 871,361 | 92 |
| 2364. | CTTTTGTTTGTGTTCTTCACAACC[T,C]ATTCAACAATTTCTTCTTTACCATT | 871,402 | 92 |
| 2365. | AAATAATCTTTCTCCCCACTCCCC[G,C]TTCCCAACTGATCAATTATGACCTA | 871,697 | 92 |
| 2366. | CCAGAAGGATGTTGGTATTGACAA[T,G]AAATTAACAAAATGCCATGTTTGCA | 871,798 | 92 |
| 2367. | TCCATTCAATATCAAAAAAaTAAA[T,C]ATATAAAAGATAGAAATATAATTTA | 871,906 | 92 |
| 2368. | AAATCTTGATTCTTTCATCAGCTT[C,T]CATGCAACACCATGGTAACCCTGAT | 872,041 | 92 |
| 2369. | AACACCATGGTAACCCTGAGAATC[T,C]GAAAGCAATCCAGTTTTTGGATGAG | 872,071 | 92 |
| 2370. | TGGGTCTGGTTGTGTCCAGGTCAA[C,T]CTTTGTGAAAGCTGAACTAGCCCAG | 872,471 | 92 |
| 2371. | ATACTTTTCTTTGTAGGTAATA[G,C]ATATGCTTTTTCTGGTGGCCAAGAT | 872,609 | 92 |
| 2372. | AAATATATGGCATGAGAGATAATT[T,G]TAGTAGTTCATTTTACTATATTGAT | 872,761 | 92 |
| 2373. | GTTAACTTCCTCCACTGTGGGTAA[G,C]TTATACATGAATAACCTACTTGTCT | 872,948 | 92 |
| 2374. | ACAGGTTTATATATTTTAGTTTAT[A,G]TTTATTCATAAGAAAAAAaTGAAAA | 873,172 | 92 |
| 2375. | TTATATTTATTCATAAGAAAAAAa[T,C]GAAAAACATTCATGAGAACCAATTT | 873,192 | 92 |
| 2376. | ATACTCTTCCTTCTTGCCCCAGTG[C,T]AGGTACTTTGTTGGCACCTGGGATT | 873,337 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2377. | ATCTCTTCCTTCTTGCCCCAGTGC[A,G]GGTACTTTGTTGGCACCTCCCATTC | 873,338 | 92 |
| 2378. | ATGAGATTCATGACTAACAATTCT[A,T]GATTTTTTTtCCCAGATGGTGGAT | 873,421 | 92 |
| 2379. | GGATTAAAATGATCAAACAGCAGA[C,G]TTTTTCTGCTTTACTGATTATCACT | 873,553 | 92 |
| 2380. | CGATTGACACTCAAAATACTTTTT[G,T]GTGTTACACAAGTATTCCTGTTCTC | 873,788 | 92 |
| 2381. | ttCATGTAACAGTGCTTCATAGCA[G,T]GACTGATGGGATTGTGAATGGCTGT | 874,221 | 92 |
| 2382. | AATATAATTTGAAGATATCTGTTC[G,C]CTGTACCTGTTTGGTAACTGGTCGC | 874,429 | 92 |
| 2383. | TATCTGTTCGCTGTACCTGTTTGG[T,A]AACTGGTCGCTGGGTGTAAGTGAAT | 874,444 | 92 |
| 2384. | GTTGCAGTTTTCCACACGCATTCT[C,A]AGCCATTTTCTTACAGGGTATCAGT | 874,498 | 92 |
| 2385. | TCTGTGGGCTTTTCACCAGCTCTA[A,C]TTGGTTGCCTTGAGGAAAAATTGGA | 874,591 | 92 |
| 2386. | AAAATTGGATCATTCTTTATACAA[T,G]GACCGGTAAAGAAAAaTAAAAaTTT | 874,632 | 92 |
| 2387. | TGTAATGAGACCAAGAACCATGTA[T,A]GGAATTTAATTTTTGCTAGCAAATA | 874,779 | 92 |
| 2388. | ACCAAGAACCATGTATGGAATTTA[A,G]TTTTTGCTAGCAAATATTAAAAAaT | 874,788 | 92 |
| 2389. | TCCTCTTTTTCTCTCTCCATTTTT[C,T]TCTTTTCAGTTTTCGTAGTTAGGTT | 875,442 | 92 |
| 2390. | TTTTCTCTCTCCATTTTTCTCTTT[T,C]CAGTTTTCGTAGTTAGGTTTCTCAT | 875,448 | 92 |
| 2391. | CAGGGTTTTTGTTACCAAAAGGAT[C,G]TATCACCACAAAAGGTGCATCTTGT | 876,103 | 92 |
| 2392. | TTAACGTATCATTATATGATTGTT[T,A]ATGGAAAAAATGTGAGCAGTTTTCT | 876,184 | 92 |
| 2393. | TCTTGTTTGTATATGTGAGGCAAT[T,C]TTAGAAATAATTATAAGTTGCACCT | 876,231 | 92 |
| 2394. | TGATTGTTGAAAATTAAAAATATT[A,T]TAAGAAATATAGCATAATACATGGG | 876,537 | 92 |
| 2395. | TAATACATGGGTATTGGAATTTGA[T,C]CTCTCCAACATTAATTTAAAGTTTC | 876,576 | 92 |
| 2396. | ATCAAGAAAGGTTCTGAGTGGCTG[T,C]GCCAGTCACCCAATGGCATACTATG | 876,901 | 92 |
| 2397. | GAGATGTTCTTTTAGTTAATAAaA[A,G]TAaAAAAATGGAGTTAAATGGCATT | 876,998 | 92 |
| 2398. | AATAaAAAAATGGAGTTAAATGGC[A,G]TTGCACCAGCCCATTCCTTGTGCCA | 877,021 | 92 |
| 2399. | CCAGTATTGGACTAGCATGATGAG[T,C]CAAGCTATATTATTGGCACTTATCT | 877,068 | 92 |
| 2400. | ATGAGTCAAGCTATATTATTGGCA[C,T]TTATCTTGAGCAAAAGTATCATCGG | 877,087 | 92 |
| 2401. | TCGGCACTTGAAACCATGATTCTG[G,A]GCATGTTAGATtTTTTTATTCTTTT | 877,133 | 92 |
| 2402. | GCTCTTTGTAAAACTGCTTGATGA[T,A]TTTCTGTTGTACGATATATCACAAA | 877,230 | 92 |
| 2403. | ACTGCTTGATGATTTCTGTTGTA[C,T]GATATATCACAAAGGTAGCCACACA | 877,242 | 92 |
| 2404. | TAGAGTATATTGGCTTTGTGTTTG[G,A]AGTGTTGCTCAAAATTGCGACCAAA | 877,409 | 92 |
| 2405. | TTCAAAATAAGTCCTGCAGTGCTA[A,C]ATATTAAATTCGTAAATCATTGGC | 877,645 | 92 |
| 2406. | TATAGATTTATTTTATTTTTCGTC[G,A]CTTTTTCTCTTAATTTCTTtTTTTA | 877,843 | 92 |
| 2407. | TAGATTTATTTTATTTTTCGTCGC[T,C]TTTTCTCTTAATTTCTTtTTTTACA | 877,845 | 92 |
| 2408. | ACTAAAGCTGGTGTACTGAGGATG[C,T]GTGGTGCTTTTTGTTTGATGATTA | 878,175 | 92 |
| 2409. | AATAAAGAGCCAGCATTACTATTT[C,T]GAGAAACATTTGGTTGATGGTTTAC | 879,200 | 92 |
| 2410. | TTACTATTTCGAGAAACATTTGGT[T,A]GATGGTTTACTATGTTTTGTTCATG | 879,215 | 92 |
| 2411. | GGAAATCTTTCTTAAACAGACAGC[C,A]GGATCATACTCCTTTGATTGTATCT | 879,348 | 92 |
| 2412. | GTTTTTGTCTAGACAGGGAATCTT[C,T]CATATTCTAAATATGGACCTATTCC | 879,558 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2413. | AAGATATGTGGTTCATTCTTGAAT[T,A]AACTGAGCACTTGCAGCTGTTATGT | 879,632 | 92 |
| 2414. | AGCTTCAGCAAGAAGGTTGTTTGT[T,C]CTCCGGGTTCTACTTCTGAGTCAAG | 879,791 | 92 |
| 2415. | TTTATTATTTGCTTCAGGTGATGC[G,A]CTGCACACCAGTCCTGATGGTTGGC | 879,907 | 92 |
| 2416. | GAAGAAGATTTTGCAAAGGCAAGT[C,G]TGGGTTTAGAACTAGATGCAGGTAT | 879,978 | 92 |
| 2417. | ATGTGAGGATCTGATATTATGATA[G,A]TTAATGAACGAGAAGCAGTTCTGTT | 880,305 | 92 |
| 2418. | TTTTGCTTTCACATCTGAACATGA[A,C]AAAGAGGTCAACATAGTTTATTTTG | 880,358 | 92 |
| 2419. | GTTTTGTTATCCAAGCCTCTAGAA[T,C]AGATTTTAGCTGATTCAATCTGAAC | 880,407 | 92 |
| 2420. | AGGAGAAGAGTAGGGTAATGAGCC[G,A]TGAACAATAGTGCACAAGTGAGCAA | 880,509 | 92 |
| 2421. | AGCAACAAGGGATTACTCTATGTT[T,G]AAATAATCAATTTTGAATTGGATCT | 880,554 | 92 |
| 2422. | AACCCTCTAAAAAGGGCAACCATT[A,G]TTAAATAATCATTTCAAGAGTATTC | 880,748 | 92 |
| 2423. | GCATCAGTATGCCCTGTATCCTGC[T,G]ACAACTTAAGTGCCCATGCTGTTAA | 881,061 | 92 |
| 2424. | ACCTTATCAAACTGGTATCTCAGC[G,A]TTTGTGTCACTGTTTCACCCAATTA | 881,350 | 92 |
| 2425. | ATCTGAAAATCTAGCACCTGTGAC[A,C]GCACACATTTTCTGTCAGATTAAGT | 881,416 | 92 |
| 2426. | CTTAAGACTTCATGCTTCAACGAT[C,T]CTCAACATGGCTAAATAAACAATAG | 882,012 | 92 |
| 2427. | AATGCAGTGCATTCATTTTGTTGC[A,T]GCTCCCCTGCAAAATTGGGATTATT | 882,168 | 92 |
| 2428. | TCCTTATGAATAGCATAAAACTCT[T,C]ATGCCACATCGGATGGGTTATTGAG | 882,303 | 92 |
| 2429. | GGCCTAAGTGGTTGCTCAAGGCAC[A,G]AAACCTGCATTCCAGGTCACGTTTG | 880,536 | 92 |
| 2430. | CAAAACCTGCATTCCAGGTCACGT[T,C]TGAATATTTTTGGAATGAATCATAC | 882,559 | 92 |
| 2431. | AATCATACTAATGAATGCTTTCTT[T,G]GATGGAATTTGTAGCAATAAACATC | 882,601 | 92 |
| 2432. | ATCGGGTCCATACTGGTCTTGAGC[T,G]GGAACAGTATGGTACTGGTACAGTT | 882,768 | 92 |
| 2433. | ATCCTTTCCAATCATTGTCAAACC[A,G]CAAATCGCATGCGGGGTTGCGGATG | 883,050 | 92 |
| 2434. | AATCTTTTTATCTTCCAGTTGGCT[C,T]GACTGACAACTGACAAAGTGCAACT | 883,284 | 92 |
| 2435. | TGACAACTGACAAAGTGCAACTTC[G,A]GCTATAAAAGCTATTTAGTTGATTT | 883,312 | 92 |
| 2436. | AAAAAAaaTTTATCTCCACCTTTC[A,C]GCTTTTGAGAAATGGATATACTCAA | 883,427 | 92 |
| 2437. | TTGCTGTTATTATCTTTAAATCAT[C,T]ATTGTTATTATATCTTTATCATTCT | 883,481 | 92 |
| 2438. | TTTAGTTAAGTTGGCTTCTTGCTC[A,C]AATCATTTTTtGTTTTCTTATCCTT | 883,576 | 92 |
| 2439. | AGCTATTCTTCAGGTAAACAAGAA[T,G]CACCTGCAGATGATGCATCATAAGT | 883,684 | 92 |
| 2440. | TGAATATCAAGAGAAATTGCGCTT[T,C]GTACATTGTGATTCAGTTTTTTACA | 883,773 | 92 |
| 2441. | ATGCTTTAGGTGTTCAGATGATTA[C,T]ACTGTCCTAAAACAAAAaTCTTAAA | 883,902 | 92 |
| 2442. | GAGAAGTATATAAAATGTAAATCA[G,T]GCTACAAACTAGAACTAATTTTGCT | 884,971 | 92 |
| 2443. | TTTCATGGTTCTTTTAAAGAACTT[G,T]AGAATAAAATTAGATTTGTAATCATG | 885,034 | 92 |
| 2444. | AATGTTTACGTTTGTTACAGTATC[G,A]ATCGCTCTCCAACCACTCCACATGT | 885,177 | 92 |
| 2445. | TCGATCGCTCTCCAACCACTCCAC[A,G]TGCTTTTGTGGGATCAGGTGTTGAG | 885,199 | 92 |
| 2446. | AGATCCAACAATTGCGAGCACAAG[T,C]CTTGGCCAAAAACAGTGACTTTACC | 885,299 | 92 |
| 2447. | TGGTTGCTCAAGTCAAAATCAGAC[G,A]TCATGCATCAATACATAGTTTAGGT | 885,448 | 92 |
| 2448. | AGCAGTCACTGCAGTGCCCTCAAT[A,G]TGAGAAGATCCAGTAGTTGGAGTGT | 885,500 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2449. | GTTGCTGCCTCTGGACTTAAACCC[A,G]TGCCATTGCACTTGTCAGTGCAAGC | 885,716 | 92 |
| 2450. | TAGGAATTGAACCTACGCCATCAT[G,A]CTTGTCAGCCCAAGTCTTTTACCAT | 885,905 | 92 |
| 2451. | CAGCAATAGCCTCTTTGCAAGGTG[A,G]CAATTGGAAACCTTACCATCAACCA | 885,961 | 92 |
| 2452. | AAATGGGTCATGTAGGCCATTAAG[T,C]CACAATGGATCAGTCCTACTTCAAT | 886,082 | 92 |
| 2453. | TTTGAGTTGTGTTATGGGTTAGGC[C,T]TGAAAGATTTTGGACTGGTTTGGAG | 886,317 | 92 |
| 2454. | GGCCTGAAAGATTTTGGACTGGTT[T,C]GGAGTTAAATACAGAGCCCATATGT | 886,338 | 92 |
| 2455. | AGTTAAATACAGAGCCCATATGTT[C,T]TTTGGGTTGGGCTCAGGTATATCAT | 886,365 | 92 |
| 2456. | AGGCCCAAAATGGAGCTTGAACTC[C,A]AGCATGAAATGGAGTCCAAACTTAG | 886,454 | 92 |
| 2457. | TCTGGTAAATATGTTCTGATCATC[G,A]GATGGTTGCTAACATGAAGCTACAG | 886,569 | 92 |
| 2458. | GGATGGTTGCTAACATGAAGCTAC[A,G]GTATTTTATCAGAAAAAATGTGAAG | 886,593 | 92 |
| 2459. | CTTCAATCGGGTTTGGGCCAGCCC[T,A]ATTTTTATCCCAAATGGATAACTTG | 886,671 | 92 |
| 2460. | TCAGTTGTGATATCTTAATGCATC[G,A]TTGGCATCAATAGGTTATCCAGATT | 887,077 | 92 |
| 2461. | TGCATCGTTGGCATCAATAGGTTA[T,A]CCAGATTGGGCTACATCATGCAAGT | 887,095 | 92 |
| 2462. | TACATCATGCAAGTTTGATTAACC[A,T]ATAAATTAGTTCTTTGTGCTTCTAA | 887,131 | 92 |
| 2463. | TTAGTTCTTTGTGCTTCTAAATGG[T,C]GAGAGCAACTTTTCTGGACAGAGAA | 887,161 | 92 |
| 2464. | TCCAAGAAGACCTTTGTTGATGGA[C,T]GAGCAGAATACATGAGAGGTACAAA | 887,219 | 92 |
| 2465. | AAATCTGTTGTGGAAAAACAGCCC[G,A]GTCACAAAACCTGAAAAATGCTTTA | 887,508 | 92 |
| 2466. | TTTTCCTGATTTTTCCATCAAATA[C,T]ATTTTGCCCAAAATCAAGTTACAAA | 887,578 | 92 |
| 2467. | AAGAAGATAAAAGATCCGGAAATC[C,T]ATTTTGCCCAAAATCAAGTTACAAA | 887,745 | 92 |
| 2468. | GAAGCAATATTTCGGAAGATGGCT[T,C]CTTGGCTCCCTGAGTTGTCAGACAT | 887,800 | 92 |
| 2469. | ATTTATGTTCAATTTTTTGTATTA[T,C]AAATATTTTTCTTGGCATCTCCTTG | 888,137 | 92 |
| 2470. | ATTTTTTGTATTATAAATATTTTT[C,T]TTGGCATCTCCTTGTTCTTACAATT | 888,148 | 92 |
| 2471. | TCTTTGCATGCCCATCCACTACCT[A,G]CCATCTTCTAAAACATCGGTATAAA | 888,266 | 92 |
| 2472. | ATAAAGCCATATGTTTCTAAATGC[C,A]CAATGAAAGAAGCTAAACAGAGATT | 888,311 | 92 |
| 2473. | ATTTGGGCATCATGGGTTCAAACA[T,C]GAAAACAGCCTTTCAGCATACGGGG | 888,428 | 92 |
| 2474. | GGGCAAGACTGCTTACATTTAACC[T,C]TCTCCAAACCCTGCAGTAGTGGGAG | 888,476 | 92 |
| 2475. | GGCCAATTTGAAGTTTGAAACCTG[A,C]GTGGATTATTCTAGATATGCATGTT | 888,601 | 92 |
| 2476. | CTGGAGGCACTTGACAAGATTATT[G,C]GAGATGAAAGTTATAATTTTGATAA | 888,948 | 92 |
| 2477. | AGTAGAATTACTTTTATTAATTCG[C,T]AGTTATTAATAGAGATCCTAAATGC | 888,999 | 92 |
| 2478. | CCTGCAACTATCATGCATCCTAAT[C,T]GCTATTCACAGTTGCTGTGTAGAAC | 889,152 | 92 |
| 2479. | TATTCACAGTTGCTGTGTAGAACA[G,T]GCAAAAAACTGAAACCTATATAATA | 889,179 | 92 |
| 2480. | GAAAGAAAGATGAGAAACCAAC[C,T]ATCCCTCCATAATTGGTTTCTGGTT | 889,329 | 92 |
| 2481. | CACCTTCACACCTTGTCTGCCCCA[T,A]GGCTAGGCGACTTCACTTGGGCATT | 889,609 | 92 |
| 2482. | TAGGCGACTTCACTTGGGCATTCA[A,G]AAAGCATGCCTTTTATATGCCTTGC | 889,637 | 92 |
| 2483. | AGAAAGTACATTGTACTGTTTTT[G,T]ATTAGGAATTTGGTGATTAACCAGA | 889,699 | 92 |
| 2484. | TGGTGATTAACCAGAAGAGAGAAG[G,A]GGGAAAGATATTGTAGAAAAAGGA | 889,734 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2485. | TTCTTTTTCTTCCATTTGATAAAT[T,C]CCTTATTCTTCCTGTTCTTCTTCTC | 889,861 | 92 |
| 2486. | TTTTCTTCCATTTGATAAATTCCT[T,A]ATTCTTCCTGTTCTTCTTCTCTTTT | 889,865 | 92 |
| 2487. | GGCCCTCCTCTGCTGCTGCAACTA[T,C]TGACTGATGCTTCTGTGCTCATATG | 889,959 | 92 |
| 2488. | CAACTATTGACTGATGCTTCTGTG[C,T]TCATATGTATGTGCGTATGCATGTG | 889,977 | 92 |
| 2489. | GCTCATATGTATGTGCGTATGCAT[G,A]TGTACATATATGTATATGTACATAT | 890,000 | 92 |
| 2490. | TTCCACAGCAGCTCAGAAGTTCAG[C,T]AATGATTTAGCATCAAAAACTCTGC | 890,150 | 92 |
| 2491. | ACATTTCAGAAACAAGATATAGAG[T,C]GACATGGTTTAACTGTTTGCTATTG | 890,872 | 92 |
| 2492. | TAACTGTTTGCTATTGATTTTTAA[T,A]GAAAATATATATGAGAAGTTTTTCT | 890,906 | 92 |
| 2493. | AAAATAACAGAAAATTTCAATTAA[A,G]AATATAAGATGTAATTTTAAAATTG | 891,073 | 92 |
| 2494. | GGTGTTTCTTCACGTTTTCACTCA[A,G]GGGGCCAAAGAAAGCATAGACTTCT | 891,150 | 92 |
| 2495. | ATCCTGGCTCTACCCTTGCAATGC[G,A]TACCAAGTCCAGCACTCCAGTTTGG | 891,220 | 92 |
| 2496. | GAACTTAAATTGCAACTAGCCAAC[T,C]ATACTCATGGCAGCTTGATGAATAC | 891,360 | 92 |
| 2497. | TGGCTTGGCCATGCACATCAGAAG[T,C]CTTGTACGAGTGCCTGCTGATCTCC | 891,427 | 92 |
| 2498. | TGCACATCAGAAGTCTTGTACGAG[T,C]GCCTGCTGATCTCCCATACAAAATT | 891,438 | 92 |
| 2499. | ATTGCTTTGGTATTTGGACTCGAC[G,A]TTCCAACTTATAGTTGGCTCTACTT | 891,532 | 92 |
| 2500. | TGAAGTCTCTTCCAGTTGCTACTG[G,A]GGACCAGTTCTCAGCAGGTGGGCCA | 892,041 | 92 |
| 2501. | CCATGCCTTTCTCTACTGAAATGT[T,G]TAAGCTGTAATACTGCTGCTGCTAG | 892,199 | 92 |
| 2502. | TAACCCATTCAAATTTATCGCGGG[T,C]CATGAGATAAACTGCATTTCCTAGA | 892,641 | 92 |
| 2503. | CCACAAAATTCACCATGGGCTGTT[A,T]TATCATCATGGTAGCAGATATTTGA | 892,745 | 92 |
| 2504. | ACTATTCTCATCACTTTTCACGTT[C,G]AGCCTGCACCAAAGAATAAACCTTT | 892,974 | 92 |
| 2505. | CTGTAGGCATAATAGCTTCTTTCT[T,C]ATCTGGTACACAAACTATTTAGCTG | 893,059 | 92 |
| 2506. | TCATGATTCTCAGATTCCCATATT[C,T]CAAGAAAAaCCAAAGCCAAAACAAA | 893,172 | 92 |
| 2507. | GATCGCAGGCCCACTGGAAAATGG[A,T]GCTCAGAAAGGTGTGTCTCAGTTTC | 893,693 | 92 |
| 2508. | TCTCAGTTTCTTTATCAGATCCAC[A,T]GCTCAGAAAGGTGTGTCTCAGTTTC | 893,733 | 92 |
| 2509. | CAAGCGGATCTGCTGCAATTCATG[C,T]TGCATTGGATCCTCTCCATGCCAGG | 893,756 | 92 |
| 2510. | CCATTGGTTTTGGTTTGTTGGGGG[A,G]AACGCCTTATGGCATGTTACAGTAG | 893,871 | 92 |
| 2511. | TAACTTCAGATGATCTGGCCGATA[G,A]AGCACCTTCGTTGTGGTTCTTAATC | 894,029 | 92 |
| 2512. | TGTCAAATGACCGGAAACTTCATA[T,C]GTAGTGCATCAAGAAATGTATCCCA | 894,082 | 92 |
| 2513. | GTCCAGGAAGTTGAAGGTTTTTCA[T,C]AAAGAAAGCCGCCAGTCTGCTTACT | 894,185 | 92 |
| 2514. | TCACTTCCTCCAGGATTATACATC[A,T]AAACTTTTATTCTGTTTTTACAGAA | 894,317 | 92 |
| 2515. | CAAAGATCGCCACTTAAATTAACC[A,G]GCAGTTTTACCTTTCAAGCTTCTGG | 894,446 | 92 |
| 2516. | ACATTTGCAATTTTCTTGCCTGT[T,C]TGAGAGGTTGAAGTTGAAAAGAAA | 894,683 | 92 |
| 2517. | AGGTTGAAGTTGAAAAGAAATCA[C,T]CAGCATTAGCCAGAACCAGTCATAC | 894,712 | 92 |
| 2518. | GTTGGGTAAATTTGATTTCTGCAG[A,C]TGGAGAAACCTGCAAAGCAAATAAT | 894,861 | 92 |
| 2519. | TAAATCTTAACAAAATTTCCTGTC[C,A]AATCACAAACATCACCTATGCAGCG | 895,196 | 92 |
| 2520. | TAAAGATATGAATTCCTACTTTAC[A,G]ATGCCACTCTTATGCACCAGCATCG | 895,348 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2521. | ATGCCACTCTTATGCACCAGCATG[G,T]TCCTGAATGTTCCCATCAGACTTCT | 895,373 | 92 |
| 2522. | GAGCAGGTAATTATCCTCACTTTC[A,G]TCCTFAGGACCAACAAAGCGTTAGG | 895,577 | 92 |
| 2523. | ATCCTCACTTTCATCCTGAGGACC[A,G]ACAAAGCGTTAGGGCATTACATATA | 895,589 | 92 |
| 2524. | AGTGATATTTTTATAGTCAAAATA[G,A]TATACCATCAGGCCAGGCTCATTTT | 895,464 | 92 |
| 2525. | TATAGTCAAAATAGTATACCATCA[G,A]GCCAGGCTCATTTTCTGGCTTAATC | 895,657 | 92 |
| 2526. | TGAGAACTCACCGTCATCTGTGTC[G,A]CCTGAATCCAGAGGGATGCCCTCAT | 895,848 | 92 |
| 2527. | AGCAACAACATAGAAGGGCAGATA[T,C]TAGGAGGGTTAGAGGTCCAATCACT | 895,986 | 92 |
| 2528. | ATAACATATTCAGGTAGTCACTGC[A,G]AAGCAGTTTTTCTCTATCCTGAATG | 896,338 | 92 |
| 2529. | CTAGATCACAGTGAAGCAACCTTA[C,T]AGTTGTGCCATGGCTCATGCTCTAG | 896,730 | 92 |
| 2530. | ATTCCATTGTTGGATGATGGTAAA[C,T]TAGGTGCTTGGTTAAAGCAGCAAAT | 896,937 | 92 |
| 2531. | TGTGCACTGAGGTACACATATAGG[A,G]CCCCATACCAAGATTTAAAGCATGG | 897,084 | 92 |
| 2532. | ATTGTCCCACTTTCAAAAAATCAT[C,A]ATTGCAGTGCAAAAATGGTGTTGTT | 897,927 | 92 |
| 2533. | ACGAAGTTCTTGGGCAACACATGG[G,T]AGCATCAATCGCAACTGGCAGTTTA | 898,138 | 92 |
| 2534. | CTCAACTATGTATATACTGGTACT[A,C]GTAGCATTTGATATGCTTATTTTG | 898,836 | 92 |
| 2535. | ATTTTATGGCATTTTATGGCATAC[C,T]GTAGAATATAATTAAGCACCAAAGT | 899,058 | 92 |
| 2536. | TTATCCCAGAAGGAGGTTACCACT[A,T]TCTAAACAACATGAATTATTGATGA | 899,207 | 92 |
| 2537. | TTAAGAATTTTCATTTCAAGCATA[G,A]TAGCTTCAGCAAGAGGAATAATATT | 899,807 | 92 |
| 2538. | AAATGAATAATTtTTTCTAGTGAT[G,C]ATTATTTTGTATTTACTTACCTACA | 899,912 | 92 |
| 2539. | ATATTTGCACAATCTAACATTATT[A,T]TGAAGGTTGATTGGAATATCTGAAT | 900,482 | 92 |
| 2540. | AAATGGAAAAGAACTAAGCCTCAT[A,G]ATTGGCAGCATTTACAATGGAGCAA | 900,600 | 92 |
| 2541. | TCTACCTGAAAAACTATTAGTTTT[C,A]TACATTCTGGTCCACTGTGAGATAA | 900,768 | 92 |
| 2542. | ATCCTAACCTAAATTTCAATGATC[G,A]GTGTTTCTGCATTTTCACCAAGCTA | 901,313 | 92 |
| 2543. | GCATTTTCACCAAGCTAGAACATA[T,C]TGTCCGCGCAACAGGAAAGAAAATG | 901,346 | 92 |
| 2544. | TTTGGTGCAACACGTAGGGGCACC[T,G]ATTAGCAGAAATCAAAGAACGTCAA | 901,570 | 92 |
| 2545. | CGCTGAAACCCTCCCAACCCATCA[C,T]AGTTAACGAACAAGATATAAATCAT | 901,691 | 92 |
| 2546. | ACCCTCCCAACCCATCACAGTTAA[C,T]GAACAAGATATAAATCATGAACAGC | 901,698 | 92 |
| 2547. | AATCGATGAAAAATATGTGATTAT[C,A]TAAAACTAAAGATCCAGAGCAAGAG | 901,914 | 92 |
| 2548. | ACTCGGAGTCCGGGGAGGTAGCAT[G,A]TAAAAGAGGTAGAGTGGATCCGCTG | 902,292 | 92 |
| 2549. | tGGTAGAAGAGAAGAGCAGTTTAA[C,T]GCAAATAAAATTTAACTCTGGTTAA | 902,729 | 92 |
| 2550. | TCAAGTAATAGCATTTTTTtCTTG[A,G]TCCATTTGTTAGCCATTCATGGTCT | 903,286 | 92 |
| 2551. | AATATATTTATATGAGTTAATAAA[T,G]ATTTTTGAATTAATTATATATTAAT | 903,378 | 92 |
| 2552. | CAAATACAAAAAAAaTAAATATCA[C,T]ATTTCTTGTAGTATTTATTTTATCT | 903,671 | 92 |
| 2553. | AAGCTTAGGGAGTGCATGTATATA[C,T]TATATGGAGCAACATTTAGCATTTAT | 907,042 | 92 |
| 2554. | ATAAATATATAAATATTATGACTA[C,A]ATAAATATATGTATATATGCAGCAC | 907,437 | 92 |
| 2555. | AAaTAAATTGAAATGTAAATCGAA[A,G]TAGAATGACAATGGAATGTGGTGAA | 908,165 | 92 |
| 2556. | ACTTTTTATTTTATATTTTATTAA[T,A]TATTTATTATTTACTATATTACATA | 908,346 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2557. | ACTATATTACATACCTTATGTTGC[G,A]GTCAATCCCTGTAGCGCCTGTCGC | 908,383 | 92 |
| 2558. | TCCATACTAATCGAAATTGTATCC[G,A]ACAGAGATCCTCTGATGCTCAAATA | 908,459 | 92 |
| 2559. | ATGACAAAGTGTTAGCTCAAAATT[A,G]TCTTATCAATACTGTTCGTTTACCT | 908,546 | 92 |
| 2560. | GGCTATAATCATAGAGTTAATGGG[C,T]GGTTTATGCCTATTGATAGTCGTGA | 908,652 | 92 |
| 2561. | AATGGGCGGTTTATGCCTATTGAT[A,G]GTCGTGACACGTAGTCGATGACCAT | 908,670 | 92 |
| 2562. | TAGTAGGTCGACAGTCGTGGAGTT[C,T]CGAATGAGCGTCGATCGATAATTTT | 908,842 | 92 |
| 2563. | ATTTTGATATATCAATGATCATCA[G,A]TCGGATATTCACTGAGTCATCGTGG | 908,887 | 92 |
| 2564. | CGGTTGGTCAACTGATTGTTAGTC[G,A]GAGTATTGTGTTCATAAGGACGATG | 909,969 | 92 |
| 2565. | GTGGTCTGTCACGTTGGACGAAAG[G,A]AGTTGTCACGTGCTGTCTCGAGCCC | 909,106 | 92 |
| 2566. | GAGTTGTCACGTGCTGTCTCGAGC[C,G]CCGACTCGACTGCTGGTATTAATGA | 909,130 | 92 |
| 2567. | ATATGAGAGATCTTCAGCTATTTT[G,A]CTGTTTCGATAGCTGTGAAATCATC | 909,189 | 92 |
| 2568. | TATGAGAGATCTTCAGCTATTTTG[C,T]TGTTTCGATAGCTGTGAAATCATCA | 909,190 | 92 |
| 2569. | CTTGATGTTGCCACGTGTCGATAT[C,T]TGAGGAGATCCAGGTTTGATCGATT | 909,417 | 92 |
| 2570. | GCTTTACTTTGCATTTGTTAACAT[C,T]CTCTTCAACAGAAGGTTCTGCTGGA | 909,519 | 92 |
| 2571. | CCCCAGTACTAGGAGCTCCAGGGT[A,C]TTATTTCTCGCACCATCCTTTGACT | 909,575 | 92 |
| 2572. | ATCCGAACACAATGTTGACTGGCT[T,C]TGGGAGCAGTACCGTATCCCGGAGC | 909,802 | 92 |
| 2573. | ATTTTTCTCCTCTGGGTCTGGTCG[T,A]AATTTAATCGAGGACCTTCGGGTCG | 909,891 | 92 |
| 2574. | GTCTCTGTCCTGCTCAGTTGGCCC[T,C]GAATTCTATCCGGCTAATCATCAGC | 909,992 | 92 |
| 2575. | ATCTTTTATCATCGATCTTTCATC[G,A]TCTATTCATGGATGGAAGAATCAAT | 910,164 | 92 |
| 2576. | TTTTATCATCGATCTTTCATCGTC[T,C]ATTCATGGATGGAAGAATCAATTTT | 910,167 | 92 |
| 2577. | ATCGTCTATTCATGGATGGAAGAA[T,C]CAATTTTttTTTATTTCTTCTTTTT | 910,185 | 92 |
| 2578. | TCCAAGGACTGGCCCTAACGAGAA[C,T]AGTCGGATGGAGGCCAATGATCGAA | 910,266 | 92 |
| 2579. | CTGAAGGATATGGCAGTTTTACCG[C,T]AGTGAGAGCTGATGACCGAATAAGC | 910,330 | 92 |
| 2580. | ACCGCTGATATCCGCTCGCACGTA[T,C]GCTACCAAGAAAAAGGCAGCAGCTG | 910,518 | 92 |
| 2581. | AGATGGTTCCTGAGCCAATCTTGA[T,C]GTTGTCAGCCCTGACAATGCTTCCT | 910,649 | 92 |
| 2582. | ACTCTTTTCGACATTCGGATCTCT[A,G]AGGGTGAGTCAGCCTTGGCCAATCC | 910,969 | 92 |
| 2583. | AGGGTGAGTCAGCCTTGGCCAATC[C,T]GACATTGGCCAAGCGGCTTATCGAA | 910,994 | 92 |
| 2584. | GCCATCCTGAAAAGGCTGGCACTG[G,T]CCAATGCTGAGTTGGCCTCCGCACG | 911,525 | 92 |
| 2585. | AGGGGCTACACCGACTGAAGACGA[C,A]GCACCGACTGCACCAGAAGCTGCTC | 911,785 | 92 |
| 2586. | GAGCAAGGAGATGAAGACAACGAC[T,A]GGTGACAGGTGTAGCATTTTtATTt | 911,855 | 92 |
| 2587. | GTTTGACTATCGAATATCGATCGA[T,C]AAGTTGAATGTTCGATAGTAATTGT | 912,035 | 92 |
| 2588. | TTATTTGATAAACGATAGTAAGCC[G,A]AATATCCTTCGACCAATCGTAGTCA | 912,193 | 92 |
| 2589. | AAGCCGAATATCCTTCGACCAATC[G,A]TAGTCAACTCGGTATAGTTTCAATT | 912,212 | 92 |
| 2590. | CAATTAGAGTCGACTTTTACAGTA[G,A]AAAATTGAGATATAGTCGGTACTGA | 912,326 | 92 |
| 2591. | GTACTGAGATACAGTCGGTATATT[G,A]ATTTTTATAATAAAAATTGAGATAT | 912,369 | 92 |
| 2592. | ATGTATTGATTTTTACAGTGAAAA[A,G]TTAAAATATAGTCGATAAGAATTGA | 912,424 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2593. | TtCTTAGGACCAAATCTCCTGGAT[A,G]GAAGATCTTCGGGTTTAACTTTTGC | 912,743 | 92 |
| 2594. | GGACCAAATCTCCTGGATCGAAGA[T,C]CTTCGGGTTTAACTTTTGCATTATA | 912,749 | 92 |
| 2595. | CTTGAGCTTGTTGTCGAACTTCTG[G,A]AAGTAAGTCTAGATTGACCCTCCAA | 912,837 | 92 |
| 2596. | ATCACTTTTATTCTATAAGCCAGA[T,C]TGAATGGCGATTTTTCCATTGGTAT | 912,956 | 92 |
| 2597. | TTTGAGTCCATACAAGATTATTCG[G,A]TTTGTCACTTTCACTTCACCGTTGG | 913,084 | 92 |
| 2598. | CTTCCATCTTACTTTCTGTGATTT[A,G]TATCAGAGGTCCGACTTCTATCCAT | 913,448 | 92 |
| 2599. | AGCTGACTAGTCGATTGATGCTGT[A,G]TATTTACATATTTTTGGCATGGTTC | 913,615 | 92 |
| 2600. | TTAGCCATTCATCAAAATATATTG[C,T]GAGGCCATCCATATGAGTCATTTAG | 913,860 | 92 |
| 2601. | TGATTAGAGCGTAGATCATTTTCT[T,C]CGCTCTTGAATATCTTACTTCGACA | 914,732 | 92 |
| 2602. | TCTTTCCGATGTGCTAATCTGTTA[T,C]GATCAATCTCCTATAGCGTCCGTCA | 914,885 | 92 |
| 2603. | CCTGCAAAATGAAGTCCACACTGA[C,T]CAAAATTGTATCCAGTGGGGACCCT | 914,948 | 92 |
| 2604. | TGAGGAGTGATGAACAGCAGATAA[G,A]AATATTTGAAATGGCAGAGTGTTAG | 915,014 | 92 |
| 2605. | TCATAACGGTTAAATATGTGGGTT[C,T]CGCATATTCTGGCATTATATGATCA | 915,223 | 92 |
| 2606. | TAGTAGGTCGGTAGTCGTGGAGTT[C,T]CGAATGAGCATCAGTCGATAACTCT | 915,346 | 92 |
| 2607. | TCGTGGAGTTCCGAATGAGCATCA[G,A]TCGATAACTCTGATATGCTGATGGT | 915,360 | 92 |
| 2608. | TCTACATTTGGTTTCTCTTTACTT[G,A]GTATGTAATCGAGATATTCGTTTCT | 916,080 | 92 |
| 2609. | GAATCAGAAATTATCCTCAATAAA[G,A]ATATTACCTTCTTTATGCATTATAC | 916,233 | 92 |
| 2610. | ATAATACATTAAATTAAATGTTTA[A,C]TAAATTATTTATTTTCATTTGATAT | 916,381 | 92 |
| 2611. | TTGTTGTGGCAAATAGTATTTGCC[T,C]CTAAAAACAATTTTCATATATAATC | 917,340 | 92 |
| 2612. | ATCTTTTACCGACTTATCAGTATT[A,G]CCGATATATAGTCGGTTTATCTGTT | 917,858 | 92 |
| 2613. | ATAAAAGGGAGTAAATGAGTAGCA[C,T]CGGATAAGGATAATTTCTGGGTCAA | 918,058 | 92 |
| 2614. | AAAAGGGAGTAAATGAGTAGCACC[G,A]GATAAGGATAATTTCTGGGTCAAGA | 918,060 | 92 |
| 2615. | TCGGAGGATTTTCGTCGGACACAA[C,T]TTCGATCTGTGAGGACTTGATTTTG | 918,161 | 92 |
| 2616. | GAGGATTTTCGTCGGACACAACTT[C,T]GATCTGTGAGGACTTGATTTTGCAG | 918,164 | 92 |
| 2617. | CGTCGGACACAACTTCGATCTGTG[A,G]GGACTTGATTTTGCAGGTGCTCTTC | 918,173 | 92 |
| 2618. | TAGTAATTATTTAATTTAATTTTG[T,G]TGGGCATGAATGTGAAGCTTTACAC | 918,299 | 92 |
| 2619. | CACTCTTGAAGGCTCATGTAAAAG[G,T]AATTAATTACGAGCTTGGCCACTTA | 918,372 | 92 |
| 2620. | TGTAAATTGCACAACTTGTACGTA[A,G]GAGTTATAGTTGAATAGATCAGTCC | 918,901 | 92 |
| 2621. | TACTGTTGTAATGAAAATAACTAA[T,A]ATTATTAGTCAAAAATTGGACTTTT | 918,986 | 92 |
| 2622. | CTTTGTTCTCAAAAGAACATATA[A,G]CTTAAATAATTGTGTTTGTTATTA | 919,161 | 92 |
| 2623. | TGCATAAACTTTTTAGGAAAAAAa[G,C]CAAATAGGATAATAGAGTCACTTTA | 919,736 | 92 |
| 2624. | CAAGGAGAAGCAGCTGAAGATAGA[T,C]AAAGCTTGTGCTACAACACAAAACC | 920,563 | 92 |
| 2625. | TAATTAGAAATGTCAGTTTGATAC[A,G]TTTTAAAATACAGAAAATGTAAGTG | 923,791 | 92 |
| 2626. | TGTAAGTGAAATTGAATTAAAATT[A,G]AGAAGATATTTTTATAATTTTTtA | 923,833 | 92 |
| 2627. | CATCTCCATTTATTATATCACACT[T,C]ACTCTCTCCCTCCCTCCTATTTTTC | 924,159 | 92 |
| 2628. | GCTTTAATATTAGTTGGTGGTTTC[G,A]GTTAAGAAGGTCAAATACTTTGGGA | 927,283 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2629. | GTTCCGAACTCTTCACTTGGAACT[C,T]ATGAATCAAATAGGCTGAGCTTAAA | 930,533 | 92 |
| 2630. | CAATGCTTATFCTACTGCTGAGAC[G,A]TGACTCAGATAACTTGGCTCGGTGA | 930,994 | 92 |
| 2631. | GATAACTTGGCTCGGTGAGTAGGC[A,G]ATTATGAAGTAATGTTGGATTCATT | 931,026 | 92 |
| 2632. | CAATTATGAAGTAATGTTGGATTC[A,G]TTAATCTTGTTCTGAATTTTCTCCC | 931,049 | 92 |
| 2633. | TCCATGTTTAGCTGTAAGTTTATG[A,C]ATAATTCATTTATCAACGAAAAGTG | 931,143 | 92 |
| 2634. | GATCATCCGCTGTTTTGAACAAAA[C,G]AAAGAAACCTTTCAGTATCATAAAT | 431,198 | 92 |
| 2635. | TGTGCTACATGAAAAGAGCTGACT[T,A]ATGCTAAGAAAATTTGAGAGCTTCC | 931,573 | 92 |
| 2636. | TAAGAAAATTTGAGAGCTTCCCAC[G,A]TTCATTTAGAGGAAAATTTCTTGAT | 931,602 | 92 |
| 2637. | TGGAGAGAAGAGTAGGGTCCGAGT[C,G]CAAGCCGTCCCTTCTTCACCCAGGA | 931,940 | 92 |
| 2638. | CTAGCTCATGCATGTGGTGGGCCT[C,A]CTTATTTATACCAGTTCCCACGCAA | 932,777 | 92 |
| 2639. | AAGATAATGACCACATGGACCAAA[A,C]TCCTTATATTGAGTCTGTGTGATGC | 932,957 | 92 |
| 2640. | AGATCCGATCAAATCCAAAAAaTA[A,G]GATTTGATCGGATTTGGGTAAAACC | 934,143 | 92 |
| 2641. | CCAAAAACTGTAGTACGGGTATAG[G,A]TAGGATATGAGTAGTGCTATTTTCT | 934,192 | 92 |
| 2642. | CCTGATCCGAACCTACGGATATGG[G,A]TAATATCCGAATCCATATCCAAATA | 934,261 | 92 |
| 2643. | ATCCAAATATATATGTTTATAATT[T,C]TATTTTGGTAATTCTATTTTGATTG | 934,302 | 92 |
| 2644. | ATATATGTTTATAATTTTATTTTG[G,A]TAATTCTATTTTGATTGATAATATG | 934,310 | 92 |
| 2645. | CTCTTTTCTTATCCGATCAGATAT[A,G]AGGTAGAATTTGGGTATAGAGTATT | 934,607 | 92 |
| 2646. | TATCCGATCCAAACCCTATCCGTT[G,C]CCATCCTTACTCCTCATTGACCCAT | 934,686 | 92 |
| 2647. | TTACTCCTCATTGACCCATTGTGA[G,A]GACCTATATCGATATGTATTTAGTC | 934,717 | 92 |
| 2648. | AATTATTTGATAGGAAGATCTAGG[T,A]TACTTATACAGAACTGAATAATCTA | 934,774 | 92 |
| 2649. | TTGGATAAGATCCTGGATTATTAT[T,A]AATAGAATCAAAGGGATCCGGCTCA | 934,484 | 92 |
| 2650. | GGCTCATAAGTCATCTGGAATGGG[A,T]GATATTATAGCACGGATTCATTGAG | 934,892 | 92 |
| 2651. | GGGGTGGAACCAAGCCGGGCGCTA[C,T]CCCTATCCAAGCCTAGTTCAAAAAT | 934,983 | 92 |
| 2652. | GGTGGAACCAAGCCGGGCGCTACC[C,T]CTATCCAAGCCTAGTTCAAAAATAA | 934,985 | 92 |
| 2653. | CGGGCGCTACCCCTATCCAAGCCT[A,G]GTTCAAAAATAATTTTCAGGCTTCA | 934,998 | 92 |
| 2654. | ATGTGTAAAAATCCAGGCCCGAGC[A,C]CAGGTTCGAATCCATTTGGGTTAGC | 935,069 | 92 |
| 2655. | TTGGGTTAGCTCGAGACATTACTT[A,G]GTTCAAGCCTAGCTCGAGCTCAACC | 935,109 | 92 |
| 2656. | GACATTACTTAGTTCAAGCCTAGC[T,C]CGAGCTCAACCCAATATTAATATAA | 935,123 | 92 |
| 2657. | GTTGGACGAGGCCTCAGGCCACTC[T,C]TTCTGCTACATGTGCTCTGCCATAC | 935,378 | 92 |
| 2658. | TCCCCCTCTCAATCTATGATGCCC[C,A]GTTGTTGTCGCCGCCTAGTCATAGG | 935,518 | 92 |
| 2659. | TTAATAGAGATTTGTTCCTCTTCG[G,A]GCCGATTAAGTAGTGTGCGCTCTGG | 935,648 | 92 |
| 2660. | CTTCGGGCCGATTAAGTAGTGTGC[G,A]CTCTGGAGCCTATTCGATGCCGTAC | 935,667 | 92 |
| 2661. | GCCTATTCGATGCCGTACCTTTCT[T,C]TAGCATGCTCATGAAGAAGAAGAGC | 935,699 | 92 |
| 2662. | GCCTCTCGGAGAAAAACCGCCACC[T,C]TAGATGTTCCCCCTCTGGAGCTTCA | 935,795 | 92 |
| 2663. | CCCCCTCCAGAAGAAACAAAGAAG[A,G]GAAGAAGAATGTGCGAACAGCGGTG | 935,874 | 92 |
| 2664. | GTGCGAACAGCGGTGCTGCAATTG[A,G]AAAATTAAATGAGAAGATTGGAATC | 935,909 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2665. | TAGGATCGCACTTGCAGTCGAGCT[T,C]AGGTTGGGGCAATGGTAGGCCCGAG | 936,071 | 92 |
| 2666. | AACCTACAGTCGAGCCTATCCGAG[T,C]ACATTTTCAGCCTCACATGCGGGTG | 936,191 | 92 |
| 2667. | ACATCAGTTATTTGCTGGAAAGAT[T,C]TTAAATATTTATATAGAATCGAGAA | 936,254 | 92 |
| 2668. | CTGGAAAGATTTTAAATATTTATA[T,C]AGAATCGAGAAATTCAAATAATATC | 936,268 | 92 |
| 2669. | GAAAGATTTTAAATATTTATATAG[A,G]ATCGAGAAATTCAAATAATATCTTG | 936,271 | 92 |
| 2670. | AATATTTATATAGAATCGAGAAAT[T,C]CAAATAATATCTTGTGACTAATCTT | 936,282 | 92 |
| 2671. | ATTCTATAGCCAATCAATAATAAA[T,C]TGTTTGGCATCATTGTTCTTATGTT | 936,403 | 92 |
| 2672. | ATTGTTTGGCATCATTGTTCTTAT[G,T]TTTTTTtCTTTCAACAAATTAATCA | 936,426 | 92 |
| 2673. | TTGGAAGCTCAAAAATTTTACAAA[C,T]AATTTCAAGAAAAAaGAAAGGTTCC | 936,531 | 92 |
| 2674. | GAATCAACACACTAGCTGCCTAAG[C,T]TGAGCTGACTGTCCAAAATGAAAaT | 939,585 | 92 |
| 2675. | GATGGTTTACATAGACTGGATGCA[G,A]TACAGCAAATATCATCCATTAACTT | 939,800 | 92 |
| 2676. | TCATACTGGTTAAAATAGGCTGAT[A,G]TCTAGAATATCATTGAACCTTAGCC | 939,857 | 92 |
| 2677. | AAATAGGCTGATATCTAGAATATC[A,G]TTGAACCTTAGCCAGGCAATGTTCC | 939,869 | 92 |
| 2678. | AAGCTCATTTGCAAATTTACTTCA[T,C]GATTTTTTGATGGATTGATAATAGT | 940,532 | 92 |
| 2679. | TAATAGTTTGCCATAAATCTTTCA[G,A]AGTTTCATATAAATTGGCAACTACA | 940,575 | 92 |
| 2680. | ATCTTTCAGAGTTTCATATAAATT[G,T]GCAACTACAGACAAATTAATGCACT | 940,591 | 92 |
| 2681. | TCAAAATGCTTGCGGCAGAAGAAC[G,T]GAAAGACGTCTTTGGGTGGGTTTGG | 941,002 | 92 |
| 2682. | GTTTTGAACCTAATGGAACAGGAC[T,A]AACCTGAAAAATAAGCCCATTTATT | 941,058 | 92 |
| 2683. | CCATTTATTAAAAGGATAGGTCTC[G,A]GCTTGGGGATTAAAGCTTGGCCCAG | 941,099 | 92 |
| 2684. | TGAACCACGAAAAGCCTGCTAGAC[A,G]TTTCCATTTCTTTTAAAAAAaTAGC | 942,823 | 92 |
| 2685. | CAATATAACAACTTTTCGGCTATA[A,G]AGCTGAACAAAATCACCACTTTTTC | 943,047 | 92 |
| 2686. | CGATACGTGACTGTAAAGGCAAAA[A,G]AAAAaGGTATCACAAAGAATATATA | 943,695 | 92 |
| 2687. | TTTCCATCATCACTAACAACCTAT[A,T]AAATGCAAAAGGCATGGTGTATCAG | 943,839 | 92 |
| 2688. | AATGTATCAGTGACAGTAGTGCCA[G,C]CAACTAGCAAACTGCTGTAGAACTT | 943,919 | 92 |
| 2689. | ACTTTTCTATATGAAAGTTACAAG[G,A]GATTTTGAATGAGGAACAAAATGCA | 943,965 | 92 |
| 2690. | CAACATGCAACCAGTTATGGAAAG[C,A]AGTTGTTGGGAAGGCATATGATCAA | 944,013 | 92 |
| 2691. | ttAAGAAAATAGAGGGGATGAGTG[G,T]CCCCCTAATTGCTCTGACCATTATA | 944,428 | 92 |
| 2692. | AAaGAAAACTCCACCTCCACCTAC[C,A]AAAGCCAGTTTACACCTAATCCATT | 945,112 | 92 |
| 2693. | TGTTGAATGTAGCGGATCACTAAG[T,C]GTAGTCACATTGCAATGGATCGTCA | 945,311 | 92 |
| 2694. | GCTTATGAGTCAACAGTCTTGTAA[C,T]GCAATGACATGTACATAACATCTTG | 945,541 | 92 |
| 2695. | TCTCAAATCTCTCATCTCCCATCT[T,C]TCTTTTtCTTATCCCTAAAGTTCCA | 951,947 | 92 |
| 2696. | CATCCTTCTTTGCTCGGTTCTtCT[T,C]CTCCACTCGTCTCCCATCATCTCCT | 952,043 | 92 |
| 2697. | CCAACACCTCTCACTAAGCCAGCA[C,T]CAATTTCATTGTCTTCTCCTCCCAT | 952,094 | 92 |
| 2698. | AAGAAGAGAAACTGAAAGATAATC[A,G]GAGAAGAAAAAaGAAAAaTAAGATT | 952,193 | 92 |
| 2699. | ATCAATGGTTGTCACATCAGACTT[T,C]CAATGAAAGAAAGCCATCAGAATAG | 952,318 | 92 |
| 2700. | TCAAGGACTAAACTTTAGCTTTTT[A,G]TAATTTAGAGATTTTTTAAGAATAT | 952,403 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2701. | TGATGATTGGAAGGCTTAAATTTG[G,A]CCACTTGTTTATTTATATAAGCGGT | 952,637 | 92 |
| 2702. | GGCTCAACCTAATTTTGCATGAAT[G,A]TTGAAGAACTCATTGTTTGTGGGTT | 952,967 | 92 |
| 2703. | AGTTTAAGTGACTTGTGAATTTGG[T,C]CGTGGACTAAAATGATTCGAGTCTC | 953,104 | 92 |
| 2704. | ACTCCTTTTATATGGGATCAAGTA[G,A]TAGAATTGGCCATGTTTGGAGCAGC | 953,178 | 92 |
| 2705. | TGGAAGAATTGATTCTATTTCTGT[A,G]ACGCATAAGTAGTTCTGCTCAATGT | 953,966 | 92 |
| 2706. | GTTCTGCTCAATGTGCATCACATC[C,T]AAGTATATATCACAAGTATATGGAT | 954,002 | 92 |
| 2707. | AACTAATTGACCCAAAGTTTAACA[A,G]GTAGTACTCTTCAACAATCTATTAA | 954,469 | 92 |
| 2708. | GTGCCTAACATCTTATAAATTTTC[C,A]ATCATGATAATTGTTTATTTTGGTA | 954,540 | 92 |
| 2709. | GTAAAGTACTTATGTATATACACA[T,C]ATAAAATATACAACAAGAGTTGCAT | 954,724 | 92 |
| 2710. | GGCTGTGTCCAAGTAATTTCGATG[T,C]AGCCGTCAGCAAAGTCCAATTTACC | 957,113 | 92 |
| 2711. | AATTTCGATGTAGCCGTCAGCAAA[G,C]TCCAATTTACCTTAGATTGATGGCT | 957,127 | 92 |
| 2712. | GGCCCAAATCTTATAAAATATGAG[G,A]AGGCATTTTTAAACCAAATCCGTTG | 957,431 | 92 |
| 2713. | AAATCCGTTGAAAAATCCAAACAT[A,G]CCCTTGAGAACATGTTTGGATATCT | 957,471 | 92 |
| 2714. | TTCCTTTAAGAAAATAAGAAACCA[T,C]AATAGTAAACAGAAGAAAACTGACA | 957,685 | 92 |
| 2715. | TCCTTTAAGAAAATAAGAAACCAT[A,G]ATAGTAAACAGAAGAAAACTGACAT | 957,686 | 92 |
| 2716. | TGATAGGTTGTAGAATAGATGATG[C,T]AGCTATACAATCATGGCAAAAGGCT | 958,371 | 92 |
| 2717. | GCGAGGAGGAGGGCAGTAAGATAT[A,G]GACAGCGTGGGAGGAGGTGGCGAGA | 958,777 | 92 |
| 2718. | AGGTGGCGAGAGGGTAGAGAAGTG[A,G]GAGGAGGAGGAGGGAGAGGGTGCGC | 958,816 | 92 |
| 2719. | ATCCTATTCTTCCCAAACTGGCTC[C,T]AAAAAGCTCAAAAGGCTTGGCCTGC | 959,110 | 92 |
| 2720. | CTCTACTAGTGTAATATAATAATG[C,T]GAAGATCATGCTAATATAGGATAAT | 960,098 | 92 |
| 2721. | TGTGTAAATGCTGTTTTGCAGGTG[C,G]TCGTTACCGATGACAGAGGACGGGG | 965,263 | 92 |
| 2722. | TAAATAGCGGACGACTTGAGCTGA[T,C]GGTATGACAAAATTATCAACCGACG | 965,339 | 92 |
| 2723. | CTGCTCAACATGCCATACCGTCAC[G,A]AATGGTTATCGACCGCATATCACGG | 965,422 | 92 |
| 2724. | CCACTTTTGATCAGAGCTCTGCTA[C,T]ACTGAATATTCAACAACTACTGTTC | 965,605 | 92 |
| 2725. | AACAACTACTGTTCACCAACTTTT[C,T]TCTCTGACTTAAGCATCGAAGGATC | 965,641 | 92 |
| 2726. | CTTTTCTCTCTGACTTAAGCATCG[A,G]AGGATCCCCGCCGGACACCATTCCG | 965,660 | 92 |
| 2727. | ATGCTGTTTTGCGGGTGCTCGTTA[C,G]CGGCGACAGGCGACGGAGAGTTGGC | 965,720 | 92 |
| 2728. | ATAAGGAGAAAAAaTTCTTCCCA[C,T]ATGAGGTACCTTTTAAAGGACAAAA | 965,969 | 92 |
| 2729. | GTGGACAATACCTCACATGACGGA[T,C]CGAGCCTTTGTCCGCAACAATGGCG | 966,040 | 92 |
| 2730. | CCGCAACAATGGCGCGCCACATTG[A,G]TTGTGAGTCAAGAGAGACTCGCACT | 966,076 | 92 |
| 2731. | ATAGATTCCAAACAGAACCATAAT[A,G]TGACCTTATCACATTAACTTGGGTT | 966,408 | 92 |
| 2732. | CCTTATCACATTAACTTGGGTTTA[C,T]AGTGGAAGAGAATGGAGAGATGGTG | 966,436 | 92 |
| 2733. | AAGAGAATGGAGAGATGGTGAATA[C,T]ACTTCTATCAGAGCAAGGAATAAAT | 966,466 | 92 |
| 2734. | TTATATCCCAATGATATGATATGG[G,A]AATAATGTGCAGGAATAATGGTAGG | 966,551 | 92 |
| 2735. | ATGATATGATATGGGAATAATGTG[C,T]AGGAATAATGGTAGGCATATAAAAA | 966,561 | 92 |
| 2736. | AAGCATTGAAAAAAaTAGTAAAAT[A,G]GAATAAGCAAGCATCGCATATCACA | 966,658 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2737. | GAAACACAAGAATTTATATCAGTA[T,C]AGTATAAAGTTCAACCAATGATATA | 966,713 | 92 |
| 2738. | GATATATGGGCATATTTAACCAAG[A,G]TTTCTTGTACCGGTACCGGTGGCCG | 966,757 | 92 |
| 2739. | AAATCCTAGAATTCCAAGTTCTGT[A,T]TTCTTGTCCGAACACATTCATGCTC | 968,452 | 92 |
| 2740. | GTCAGAGAATATATCAATGCTCAC[T,C]TGTCAAGAACACAAATAATGGTATT | 968,541 | 92 |
| 2741. | TTCACAACCTCTTTCACGAAGCCC[T,C]CTTCTTCCCCTTCAGCGAACTCCAC | 968,610 | 92 |
| 2742. | CTCTTTCACGAAGCCCTCTTCTTC[C,T]CCTTCAGCGAACTCCACCTGAACCA | 968,618 | 92 |
| 2743. | GACCAGCCAAATGAACGTGACTCC[G,A]GCGACGAAGAATGGGTTCCGGTTGA | 968,834 | 92 |
| 2744. | GGAGAGGAATCATGAGGCAAGACG[A,C]GAGGGAAAGAAAGAGAAAATGCGGA | 969,259 | 92 |
| 2745. | TGGGAGGAATTTCTCCAGGTTTTA[C,G]AGTTTGAATCACCAGTAAAACATGA | 969,734 | 92 |
| 2746. | AACGGTCACTAGGATCTGGTTGTT[A,G]TAGACCCCTTATCCTCTCCCACTTC | 969,931 | 92 |
| 2747. | TCTAGTCTTATGGTGAAGGGCAGG[C,A]AGAAAATGTTAGTGCTAGCTTTGTC | 970,020 | 92 |
| 2748. | GAAAATGTTAGTGCTAGCTTTGTC[C,A]ACGAGAGATCATCAAGGAAGAGCCAT | 970,046 | 92 |
| 2749. | TCATCAAGGAAGAGCCATTCTCAG[G,A]GCTGGTCAACTTCGGGGAGCTTGGG | 970,078 | 92 |
| 2750. | AACTTCGGGGAGCTTGGGAAGGTG[C,T]AAGTGCATTCTTTCATTTGGATCAT | 970,110 | 92 |
| 2751. | TTAGGTCAATGGTGCAAAATAAAA[A,G]CTAAAGGTGATGAAAAGCTGACTTC | 972,260 | 92 |
| 2752. | ATGTGTAACAATCGATACTTCAAA[G,T]GTGTCAGAATTTTGGACCATCCAAT | 972,375 | 92 |
| 2753. | AACAATCGATACTTCAAAGGTGTC[A,G]GAATTTTGGACCATCCAATAGCTGA | 972,381 | 92 |
| 2754. | AATGATTCAAACTTGTAGTATTTG[T,C]CAATTGCAAAAGATCACCCTGGTT | 972,486 | 92 |
| 2755. | TGATTCAAACTTGTAGTATTTGTC[A,G]ATTGCAAAAGATCACCCTGGTTAG | 972,488 | 92 |
| 2756. | AAAAGATCACCCTGGTTAGACATG[C,G]TTAGTTTAATCATGCCTTCATTCAA | 972,519 | 92 |
| 2757. | TGCCTTCATTCAACACTAGGGCAG[T,C]GAGCAAAGTATGTGATTGCTCACAT | 972,556 | 92 |
| 2758. | CATGAGAATCATTGCTGATTGTCC[T,C]GTATTTCAAATTGTCATCCAACTTT | 972,711 | 92 |
| 2759. | ACCAAAACAGAGTAACCTTTTGAC[G,T]TGCACACAGTCAATAGAAGGTTTGT | 973,334 | 92 |
| 2760. | CAAAAGAATCTGCAGTAAATTGCA[T,C]GGCAATGAGGAAGACCACTGGCAT | 974,479 | 92 |
| 2761. | CCAGAAATGTGAAATAATTTGCAT[T,C]TGGCAATGAGGAAGACCACTGGCAT | 974,626 | 92 |
| 2762. | AAGAGAAGCTTCATGTATATGTCAT[C,T]ATTCATCTCAATTGTACATTCTGA | 974,729 | 92 |
| 2763. | AACTAATTTAGGTAAATAGTTTGG[G,C]TGTTTGAGTATCAAGTGAGAAATAA | 975,411 | 92 |
| 2764. | TCATTCATAGGGCAGTATGCTGTT[A,T]ACAGCTTATTACATAGACAGTCTGC | 975,509 | 92 |
| 2765. | GAAATAGAATCCATGATTAAAAAT[C,T]AAATTTAAGAACTTGTCGAATTGCT | 1,030,909 | 92 |
| 2766. | GTTAGATGCCATGAAAGATGAAAT[A,G]GAATCCATGATTAAAAATCAAATTT | 1,030,928 | 92 |
| 2767. | GATATTGAGATAAAAGATGATCCA[A,G]TCTCATTTAAGGATACTTTGAATAG | 1,030,996 | 92 |
| 2768. | AACAGACTATCAATGAGCTTGATC[C,T]GATTAAAAATAATCATAATAATGAT | 1,031,136 | 92 |
| 2769. | TGAACCGTATAATATGGTGTTACA[A,G]AAAaTAAAAAAaTCTCTTCCTATTA | 1,031,270 | 92 |
| 2770. | TAGGTTCATTGAGGATGGTGAAAA[T,C]AGTGGAAGTAGTGAACCGTATAATA | 1,031,306 | 92 |
| 2771. | GAAAATCGCTATGTATATCTTAAA[T,C]CGGATACTTAGTAAGGTCGTTTCTA | 1,031,568 | 92 |
| 2772. | ACAGCATAGCATTGTAACACAGTA[C,T]ACTATGTCAGAAAATCTCCAACAAA | 1,031,686 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2773. | AAAATCAATTAGATAGAAAAATTA[T,C]GATTATGAGATCTGATAGGGATGGT | 1,031,798 | 92 |
| 2774. | CTCGCATTGTGGTTATATTTTTCT[A,G]TTGCATGAAAAATTTGAAGCTTTGA | 1,031,878 | 92 |
| 2775. | GATACATACCGATATTTGTGGCTA[T,C]TTTATATCTTATTTTGGAGTGGCAA | 1,031,957 | 92 |
| 2776. | AAaTAAaTTAAAAGATATAAAAAG[C,T]ATGCCACTAGAAGTCAAAAATTCTT | 1,032,013 | 92 |
| 2777. | AAAaTAAaTTAAAAGATATAAAAA[G,A]CATGCCACTAGAAGTCAAAAATTCT | 1,032,014 | 92 |
| 2778. | TAAATTAATAAAAAAAaTTATTTT[A,G]GTTGTTATAGGAATATTGTGCAATA | 1,032,285 | 92 |
| 2779. | CAGTTGGGACCTACAGATTTATTA[T,C]AGATATTGGATTCCAATTAGATCTA | 1,032,432 | 92 |
| 2780. | GCTGCTATTCATGTTTACAACTCA[A,T]TACAGGGATTCCTTTCAAGTCGAAA | 1,032,541 | 92 |
| 2781. | GAAAAGAAGGATATTCTCTTATCA[T,C]TTATTTGTTTCAAAATTAATTTTAT | 1,032,628 | 92 |
| 2782. | ATTAAAATATTTTTTCTATAACAA[G,A]GAGGGACATATCAAGAAGGATTGTA | 1,032,698 | 92 |
| 2783. | CTCATAAATTAAAATATTTTTTCT[A,G]TAACAAGGAGGGACATATCAAGAAG | 1,032,705 | 92 |
| 2784. | AGATTGAAACATGAAGGGGTCCCA[A,G]TTATTCATGTGGTTTCACAGGAGCA | 1,032,817 | 92 |
| 2785. | ATCTCCTAGTGTGTGCAAGAGGAA[A,G]AAAGATTGAAACATGAAGGGGTCCC | 1,032,844 | 92 |
| 2786. | AATAGTTTATCAGATCAAGTAAAG[T,C]CTTAGCTGGTATCTTAATGAACAAG | 1,033,102 | 92 |
| 2787. | AGTTTCACAGCGAGAGATATTAGG[A,G]GATCTGTTTCTGATAACGAATTGGC | 1,033,178 | 92 |
| 2788. | CTTTCATGATTATTAAGAGTTTCA[C,T]AGCGAGAGATATTAGGAGATCTGTT | 1,033,195 | 92 |
| 2789. | GAGCATTCTAATAGATTATCTTTC[A,G]TGATTATTAAGAGTTTCACAGCGAG | 1,033,214 | 92 |
| 2790. | CTTTTACTTATAGTTATGACCCCC[A,G]TTTTACTCTCATCGCATTTTATCTAA | 1,033,394 | 92 |
| 2791. | CATCATGATCGTAATTATGAGCAT[A,G]TTCTTTTACTTATAGTTATGACCCC | 1,033,421 | 92 |
| 2792. | ATGTTTTATAGTTGTATAATAAGT[G,A]TTATTAGCAGAATTGTGTTAGAAAA | 1,033,475 | 92 |
| 2793. | GAATATATAACTAATATGATGGAT[C,T]ATAGTTTAAATATGAATTATATGTA | 1,033,673 | 92 |
| 2794. | AATTACATAAAGATGGAGAATTCT[A,G]CATTCAAAGATGGGAATAACCTAGA | 1,033,753 | 92 |
| 2795. | GACCCAAAGGTTACTGTAATTTGA[T,G]ACAAAATTAATAGCAATAGGTTAGC | 1,033,810 | 92 |
| 2796. | GTCATTGAGGGCTGATGATTTTTT[C,T]TCTCATTATAGTTTTAAAATTACAT | 1,033,881 | 92 |
| 2797. | TATTGTAATATTCAAGTGTATTTT[T,C]GCATAGCCCCAAAGGGCTCGGAGCA | 1,033,954 | 92 |
| 2798. | TATTTGATAATTTTGCTCATTATT[G,A]TAATATTCAAGTGTATTTTTGCATA | 1,033,974 | 92 |
| 2799. | CCGATTTGAGCATTTTTTtGAACC[G,A]TTGGACTCATGATGGCTTGAAGAAT | 1,034,077 | 92 |
| 2800. | GAAATAATTATCTTATAGAAAAGT[C,T]CCTTTTTTGTCTGAGATTTACGATT | 1,034,183 | 92 |
| 2801. | TGACATAGTTTATTACAGAAAAAT[C,T]CCTGAAGTTTTCTGACAGACTTATT | 1,034,235 | 92 |
| 2802. | CCCTGACATAGTTTATTACAGAAA[A,G]ATCCCTGAAGTTTTCTGACAGACTT | 1,034,238 | 92 |
| 2803. | TAAAATTATTTTGCAAATAAACCC[C,T]TGACATAGTTTATTACAGAAAAATC | 1,034,260 | 92 |
| 2804. | CGAACCCATAATAGCCTTTCGGGT[C,T]TTAGGTTTGATCCATTAAGGTTTCA | 1,034,344 | 92 |
| 2805. | GCTTCTTGTCTTCAGTGGCTGGGG[T,G]GGATAGGGGCGGCGCTCGACCGCTC | 1,034,489 | 92 |
| 2806. | CGCGGTGTCTCCGTGTGGCTATGA[A,G]AAATCATGGCTTCTACCATGGCGAT | 1,034,587 | 92 |
| 2807. | CGGCAGTGGGAGCCACCACCGCAC[G,A]CGGTGTCTCCGTGTGGCTATGAAAA | 1,034,610 | 92 |
| 2808. | GGGTCGCCGGCGGAGGGGGAGCTC[C,T]TGCTCCCCGACGGCAGTGGGAGCA | 1,034,645 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2809. | TTAAAATTATTTTTTt[C,T]AAAATAAAATAAGATTTAAAAAaTT | 1,034,827 | 92 |
| 2810. | TTGCATAAATATCAGAGTACGATC[T,C]AGATATAAAGGAATTAAATTATCTA | 1,034,947 | 92 |
| 2811. | AATCATCATATTGGCAAGATGACG[A,G]CGGAAGGTATAGTTTACTTATGATT | 1,035,004 | 92 |
| 2812. | AACTCTTTGGATCAGCCATATATC[A,C]TGAATCAATTATAGTAAGCCTAAT | 1,035,288 | 92 |
| 2813. | ATTCATAATATGATCTAATTATCA[A,T]TTAATCAGATTTAACTCTTTGGATC | 1,035,325 | 92 |
| 2814. | TGATTCATAATATGATCTAATTAT[C,T]AATTAATCAGATTTAACTCTTTGGA | 1,035,327 | 92 |
| 2815. | GGATATAAAAATATTGGATTTGA[T,C]TCATAATATGATCTAATTATCAATT | 1,035,348 | 92 |
| 2816. | CTATCTTGCTTCTTTTTCCTTGTC[C,T]GATGGATTCTACACAAGCCTTTATA | 1,035,475 | 92 |
| 2817. | ACAAGTTAATGAGAATTATTTTTT[G,A]TGTACTATCTTGCTTCTTTTTCCTT | 1,035,504 | 92 |
| 2818. | TAGAACCTGATAAATGTGTCTCTT[G,A]ACTTTCTCAAGATGATATTTAGAAT | 1035,821 | 92 |
| 2819. | ACAAGAGATTATGCGAAAGAATAT[G,A]ACTTTCTACTGAAAGAGAGAGGAAA | 1,036,020 | 92 |
| 2820. | TAGAAAGAATACAAGAGATTATGC[G,A]AAAGAATATGACTTTCTACTGAAAG | 1,036,030 | 92 |
| 2821. | TTCCACCAAGTCCTAGAGATCTTG[T,C]GATATGAAGAGCATCCTCATTTGGA | 1,036,262 | 92 |
| 2822. | CTTGATTCTATGCCCCGAAAGCTT[C,T]TGGAGTACTTGCTGGTTCTTCATAG | 1,036,317 | 92 |
| 2823. | CTGGATGAAGAGTAAGGCCTTCGC[A,T]TTCTTCTTTTTGCACTCCCTATACT | 1,036,379 | 92 |
| 2824. | TATTCTATCGGAGCCTTGAAAATC[C,T]TTTTTTtAAATTTTtCATGCATCTT | 1,036,481 | 92 |
| 2825. | TCCCTCCACAAAGATTGAAGCTTG[A,C]TACAAGTTATTCTATCGGAGCCTTG | 1,036,513 | 92 |
| 2826. | AGCTGGCAACTCTTAAAATTTTTT[A,G]GACAATTTTGCATTCTGGAATAATA | 1,036,656 | 92 |
| 2827. | CAAATTTAGCTGGCAACTCTTAAA[A,T]TTTTTTAGACAATTTTGCATTCTGG | 1,036,663 | 92 |
| 2828. | CCCATTAGTTCATGCAAGGGAGAAA[A,G]GAGATAAATCCTTTGATTCTTCAAT | 1,036,730 | 92 |
| 2829. | GAGGCGAACCTGTTCATTCTTTCC[T,C]CATGTGCTTTAAGAGAGCCCATTAG | 1,036,772 | 92 |
| 2830. | CTGTTTATGCCTATCTTTTTGCCT[T,G]GAGCTTCCAAAAAATTTGGCTTCCA | 1,036,929 | 92 |
| 2831. | TTCTTGCAAATAAAACATTAAGAT[A,G]AGGAATTACCATTTCTTGGGTTACT | 1,036,977 | 92 |
| 2832. | CATTTAAAATGATAATTTCTTGAT[T,C]CATGCCCAAACTTCTTGCAAATAAA | 1,037,013 | 92 |
| 2833. | ATTCTTTATACTAACAATCCCTCT[C,G]AGAAAGATTTGGAATTTTGCATCTT | 1,037,066 | 92 |
| 2834. | ATTTGCTTCATTAGGTTGCCTTTT[A,G]TTCTTTATACTAACAATCCCTCTCA | 1,037,090 | 92 |
| 2835. | CCACACCTCTGCCTTCAACTTATT[A,G]TAGTTTGCCATCTCTAAGCTTGATT | 1,037,292 | 92 |
| 2836. | TGAAGTCATTTTGATCTTAGCAAT[A,G]ACAATATCTTTCTTCTTATCAAGAA | 1,037,483 | 92 |
| 2837. | AAATCTTGTTTGAAGTCATTTTGA[T,A]CTTAGCAATAACAATATCTTTCTTC | 1,037,493 | 92 |
| 2838. | TTCAAGCCTTTATAGTTGAGCTGA[T,C]CATATCTCAAATGCCATAAGTAAGA | 1,037,602 | 92 |
| 2839. | CAACTTCAAAGCCTTTATAGTTGAG[C,T]TGATCATATCTCAAATGCCATAAGT | 1,037,606 | 92 |
| 2840. | GAAGCCCAATTACCATATTTTTAT[T,C]TTTCAACAACTTCAAGCCTTTATAG | 1,037,637 | 92 |
| 2841. | CCAAGCCCTCTTGGAAATGGAAGC[C,T]GATGCAGTTTTCCATAAACACAACC | 1,037,719 | 92 |
| 2842. | TCCAAGCCCTCTTGGAAATGGAAG[C,T]CGATGCAGTTTTCCATAAACACAAC | 1,037,720 | 92 |
| 2843. | GGCCTCCAAGCCCTCTTGGAAATG[G,A]AAGCCGATGCAGTTTTCCATAAACA | 1,037,724 | 92 |
| 2844. | TGGCCTCCAAGCCCTCTTGGAAAT[G,A]GAAGCCGATGCAGTTTTCCATAAAC | 1,037,725 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2845. | GCACTAGCTCTAGCGGAGCTTGTG[G,C]CCTCCAAGCCCTCTTGGAAATGGAA | 1,037,747 | 92 |
| 2846. | TCAACGTGCACTAGCTCTAGCGGA[G,C]CTTGTGGCCTCCAAGCCCTCTTGGA | 1,037,754 | 92 |
| 2847. | ACATCTTCTTGGTATAATCATCAA[C,T]AAAGAGAAGAAAAAATCTTTTTTGA | 1,037,837 | 92 |
| 2848. | TTGAACTGGAAGAAGAAAGAGAAT[G,A]CCTCTGACTTTTGCTCAAGAAAGAA | 1,037,892 | 92 |
| 2849. | GCTCTACAAAAGCTTTGAACTGGA[A,G]GAAGAAAGAGAATGCCTCTGACTTT | 1,037,906 | 92 |
| 2850. | TTTGATGATTGCTTTGCCGCTCTA[C,T]AAAAGCTTTGAACTGGAAGAAGAAA | 1,037,924 | 92 |
| 2851. | GTAGTTCATGAAGGTTCCAAAGGT[G,A]AATTCTCCTCCACGATCTATTCTTA | 1,037,983 | 92 |
| 2852. | GCAACTCCATTTTATTCTGGTGTG[C,T]AGCGGATAGTGAGTTGTCTCTCGAT | 1,038,048 | 92 |
| 2853. | GGCAAGCCTTTGCATTCATCATGC[A,T]TCTAGCCATCTCTACAATTGTGAA | 1,038,110 | 92 |
| 2854. | AAAAATTATTTGGCAAGCCTTTGC[A,C]TTCATCATGCATCTAGCCATCTCTA | 1,038,121 | 92 |
| 2855. | TGCCAAGCTTCATAAGGAGTTTTG[T,C]TCAGCATTGCTTTTGTTGGAGATCT | 1,038,209 | 92 |
| 2856. | ATGCCAAGCTTCATAAGGAGTTTT[G,A]TTCAGCATTGCTTTTGTTGGAGATC | 1,038,210 | 92 |
| 2857. | CAAAGACTTTAAGATGATTTACCT[C,G]AGGCTTTTGCCTATGCCAAGCTTCA | 1,038,247 | 92 |
| 2858. | AGTCAAAGACTTTAAGATGATTTA[C,T]CTCAGGCTTTTGCCTATGCCCAAGCT | 1,038,250 | 92 |
| 2859. | TGATCAAATTTATCTCTATTTTGA[G,A]ATGGAATAAGAGAATAAGCTATGCA | 1,038,299 | 92 |
| 2860. | TACAAGTTCATCAAAGAATACATC[T,A]CGAGAAACAATAAGTTGATTTTTTG | 1,038,417 | 92 |
| 2861. | CCCATTATTATGCTACAAGTTCAT[C,T]AAAGAATACATCTCGAGAAACAATA | 1,038,430 | 92 |
| 2862. | GATGATTTGACTTGAAATGTCTTC[C,T]CTTAATGCTCTCATTGGGCTTGGTT | 1,038,555 | 92 |
| 2863. | TGTAAGCTGCACACCTTTTTTGGG[A,G]TGAAATAGAATCTGTGATGATTTGA | 1,038,595 | 92 |
| 2864. | GTGGTTCACATGAAAAGAAGGCAA[C,T]ATTACAAGATTCATAGATCTCATGT | 1,038,642 | 92 |
| 2865. | TCTTCATCTATGGATTTTAGCCAA[A,T]TCTCATCTTTTCTTGCTTTTTAAA | 1,038,697 | 92 |
| 2866. | AGAGATCAAGAAGCTCCCATGTGC[A,C]ATTTCTTTCGATAGTGATTATTTCT | 1,038,744 | 92 |
| 2867. | CTTTGTGCTTATCGATTGAGTCAT[T,C]TTTtTGAACTTTGTCTTATAGATC | 1,038,825 | 92 |
| 2868. | GCAACAGCAAGAACCATTCTCACT[A,G]TTTCTATACGAACAATAGATGCAAA | 1,038,931 | 92 |
| 2869. | TCATTTGAATTGCAACAGCAAGAA[C,T]CATTCTCACTATTTCTATACGAACA | 1,038,942 | 92 |
| 2870. | TTGCTTTAGGCCATATAATGCCTT[C,T]CGAAGCCGATACATCTTATTTTCTT | 1,039,094 | 92 |
| 2871. | TAGTGAAAATAGCCATCAATTCTG[G,A]TGTTCCATGCATGCGGAGCTTGCTT | 1,039,138 | 92 |
| 2872. | TCAAATCATCAACATATAAGCAAA[A,G]GATTAAGAAATCCTTACCTTGCAAT | 1,039,233 | 92 |
| 2873. | TTCTTCCATTATGATGTCGGTGTA[G,T]ATCAAATCATCAACATATAAGCAAA | 1,039,259 | 92 |
| 2874. | TAACTTGGATGCCAAGAAAATAAT[G,A]CATAAGTCCAAGATCAGTCATTTCA | 1,039,335 | 92 |
| 2875. | TTCTATTGTGATATGCAAATTTTT[T,C]CATTCGACTGAGTAACTTGGATGCC | 1,039,372 | 92 |
| 2876. | CAATTTCCCATATGAAACTTCTTG[A,T]GCAAATCTTCAATATACTTCTATTG | 1,039,414 | 92 |
| 2877. | TGAAATTTCTTATTTTTAGCCAAA[C,G,T]GACTGGCCATCGGCTTGCAATTTCC | 1,039,456 | 92 |
| 2878. | TGTATGTGTGACATAAATGAGTGA[A,G]CCAACTAAACTTCTATAAGTTGTGG | 1,039,535 | 92 |
| 2879. | TTTGCTTGGTTGAATCATAAATCT[G,A]GATAAGAGACTAATCGAAAAAATAA | 1,039,595 | 92 |
| 2880. | GTTCCTAGGCAAAATATGTAGCCT[A,G]ATGTACTTTTGCGATCATCAAAAGA | 1,039,768 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2881. | ACATCAGTAGCTGAAATATATTCT[A,G]CTTCAGTAGATGAAAGTGCCACTAC | 1,039,852 | 92 |
| 2882. | GATATGCTTGGTCCTGTTATGAAA[C,T]ACAAGATTCTTTATCATAGCTATTG | 1,039,994 | 92 |
| 2883. | TGACAAACACTAGTTGAATATCTC[T,C]TTTCTCAACAAGTCTCTGATGAAAT | 1,040,057 | 92 |
| 2884. | AGATGACATTTGGAATTCCCAAGT[T,C]TCTTGAATTTCTTAAGACTATTAAT | 1,040,246 | 92 |
| 2885. | CAGAGTTACAATATGACTCTTAAT[G,A]TTCTAGAACCTGATAAATGTGTCTC | 1,040,308 | 92 |
| 2886. | CAACTCATGCTTCACATCATACCA[G,A]GGGCTCTATTGCCTCCTATTTATAG | 1,040,409 | 92 |
| 2887. | AGGGAAGATATCATAGGAAAGGCC[C,T]CAACTCATGCTTCACATCATACCAG | 1,040,434 | 92 |
| 2888. | GAGGGAAGATATCATAGGAAAGGC[C,T]CCAACTCATGCTTCACATCATACCA | 1,040,435 | 92 |
| 2889. | CATCATCACATACTTGTTGGGTGC[C,T]AGAAAGAATACAAGAGATTTATGCA | 1,040,513 | 92 |
| 2890. | ACACCAAGCCTCTTATTTATCAGG[G,A]TTGAATTCCTGCAAGCCATCAGGCT | 1,040,671 | 92 |
| 2891. | ATTTAaAAAAAAAaTCGATCATGG[T,A]GTATGGTAGAATATTTCAAAGTCTG | 1,040,740 | 92 |
| 2892. | AAAATAATATTTAaAAAAAAAaTC[G,A]ATCATGGTGTATGGTAGAATATTTC | 1,040,748 | 92 |
| 2893. | CTCAGCCCAAGTATTGTATTTTTG[G,A]AAATAAGATGAAAAGAGGGGTAGAT | 1,040,815 | 92 |
| 2894. | TATTCAAAATCGCATGTTCAATAT[G,A]TGGTTTCACCGTATCCGTGCAAACT | 1,040,863 | 92 |
| 2895. | GCACCCCACCTCACCACCCCCACC[A,G]TCCAGCCACCGCCCCCAGCCGCCCAG | 1,041,175 | 92 |
| 2896. | GCTTCATACCAAAGGGCAAGCAGG[A,G]GCTGCAGGTGTGGGCTTCTCCAAGA | 1,042,223 | 92 |
| 2897. | AAAATATCATTATTATTAGAAATA[G,A]AAATAGAAGGTATAATAATATTATT | 1,042,587 | 92 |
| 2898. | TATTTGATTAATAATAAAATATCA[T,C]TATTATTAGAAATAGAAATAGAAGG | 1,042,602 | 92 |
| 2899. | AGAAGGGAAGGGGGTGCTGGGCTA[C,T]AGGGGCAGTAGAGTGCAGCACGGGg | 1,043,225 | 92 |
| 2900. | TACCATAACAAAAAaTTTAAAaTT[T,A]AAAATTTATTTtAAATTTAAAACTA | 1,043,443 | 92 |
| 2901. | TTGATAGGGACACGACGAAACCAC[G,A]TATTGTGGTTTAATATGTGATTTCA | 1,043,524 | 92 |
| 2902. | ACTTGGAGTGAGTTGATAGGGACA[C,T]GACGAAACCACGTATTGTGGTTTAA | 1,043,536 | 92 |
| 2903. | GTGCTGGTTTACGAGCACGTCACC[A,T]TCAAGGCTCTACCGTGACGAACTT | 1,043,929 | 92 |
| 2904. | TGAAAAATCAATAATTAAGCAAAA[T,C]TTTTATATGAAGTCCATTTGATATA | 1,043,994 | 92 |
| 2905. | CTTAAATCAAAGAATAGAATCACT[T,A]GATGTCCCTTAAATGTCTATTATTT | 1,044,066 | 92 |
| 2906. | GCCTAATCATTATTTCTCCGTTGC[A,T]AGAGATGCGTCTCGGTGGCAGATGG | 1,044,569 | 92 |
| 2907. | AATTTATGAAAGATAATGACCCTT[T,G]TTCTTATTTTCTCTTTTTTACATA | 1,044,802 | 92 |
| 2908. | AAGCCTTGCTGATACAAAATTTGG[G,A]TTCAATTTATGAAAGATAATGACCC | 1,044,830 | 92 |
| 2909. | TGATTAAGTCCGGATTGTAACATG[T,G]GGACGACACATTTGTGAAGCCTTGC | 1,044,871 | 92 |
| 2910. | TTGAATCACAATTTAATAATAACT[A,C]CCGCTATGATTAAGTCCGGATTGTA | 1,044,902 | 92 |
| 2911. | AAGGTAGGTTGGCGATTAATTATA[T,G]GCTAAAGAGCAGTAGGTTTCAACCC | 1,045,079 | 92 |
| 2912. | ACACAGAAATACAGACTTCTCTCT[A,G]GTTCTTACTCATGCTGCAGACCATC | 1,045,610 | 92 |
| 2913. | TTCGTGGCAGAATAACAGAAAAGT[C,T]CAGAGATAATAGAAGGGTGAAGAGA | 1,045,663 | 92 |
| 2914. | TAAACATAGTGAAGCTTTGAAAAT[A,G]TACTTCTGTTACTATGCCTTGCAAT | 1,045,712 | 92 |
| 2915. | CTTGTAGTGCATGCCAAGTCTCAA[T,A]AAACATAGTGAAGCTTTGAAAATAT | 1,045,736 | 92 |
| 2916. | GATAGGATAAATACATTGTGAACT[T,C]GATCTATTTCACCTATGAAAGAGCA | 1,045,833 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2917. | ATGTGCAAAACCTTAGAATTACCG[G,C]ATAGGATAAATACATTGTGAACTTG | 1,045,857 | 92 |
| 2918. | ATTTGATGTGCAAAACCTTAGAAT[T,A]ACCGGATAGGATAAATACATTGTGA | 1,045,862 | 92 |
| 2919. | TCGAAATTAAGATTCAGTAGCACG[G,A]TATGGTTATTTGATGTGCAAAACCT | 1,045,894 | 92 |
| 2920. | CAAGTTGTTTATGATCATTTGAGT[T,C]ATAAAATTATCGAAATTAAGATTCA | 1,045,928 | 92 |
| 2921. | TGTCTCTGGTTTTGTTGTGCCACC[A,G]AGTTGTTTATGATCATTTGAGTTAT | 1,045,951 | 92 |
| 2922. | AAAATCATTTTGTAGTCATGCTGA[T,C]GGCACTGTCTCTGGTTTTGTTGTGC | 1,045,981 | 92 |
| 2923. | AAGCAATCCATGTAATGGAATTGA[A,G]CTGCAAGACATCAAGCTCACCTATG | 1,046,044 | 92 |
| 2924. | GTCTTGAGTATTTGTTTCAAGGCC[T,A]GACGTCATAAAACAGTGATGGTGCT | 1,046,766 | 92 |
| 2925. | GTCCTGGCCATGGCATCAGGTAAT[C,T]AAGGGAACATGCATGTATTGCATTA | 1,047,464 | 92 |
| 2926. | TGTACATTACGAGTCCACCAATTT[G,A]AAAAAAGACCATATAATAAATTAAT | 1,052,907 | 92 |
| 2927. | TTACGGGAAAAGTACGTGGAAGTA[C,T]AAGGGAACATGCATGTATTGCATTA | 1,053,273 | 92 |
| 2928. | AGGTCttTtTTTTTTTCCTCTTTA[C,A]GGGAAAAGTACGTGGAAGTACTGTT | 1,053,294 | 92 |
| 2929. | GATTTCAAAAAGAGTGTCTACTGC[A,G]CATTAATCCATTTGGTGAGGCACCA | 1,053,350 | 92 |
| 2930. | GATTATAATAAAAGTGAACATCAG[G,A]CCGTTCATTAACGCCTCACTAATCA | 1,053,684 | 92 |
| 2931. | TTGTCTTCAGTTCTTTCTTTTTCC[C,G]TTGTTGGGTGTAGGCCCCCCAAAT | 1,053,837 | 92 |
| 2932. | ACAAGACAATATTTTCAAAAGTTC[T,A]TATGATAAGTCTGCAGAGGAAAAACC | 1,053,980 | 92 |
| 2933. | ATGGGGGCAGTAATTTTGGTCAAT[G,A]ATGTCTTGCAGTCCAATTCCGGTGC | 1,055,501 | 92 |
| 2934. | TGGCTTGTTTCCGTAGGTAAGCTT[G,T]ATGTCTTGCAGTCCAATTCCGGTGC | 1,055,902 | 92 |
| 2935. | CAACTCGAAGAGTCAGAAGCAACT[T,C]GGCACAACAGAACCAGAGGCAGTAC | 1,055,980 | 92 |
| 2936. | CATTCCATGTCTACTAGAGTAACG[C,G]TTGGACATGGAGGATAAGAAAAGTT | 1,056,097 | 92 |
| 2937. | TATCAATCCATTAAATATTTATTC[C,T]ATTCCATGTCTACTAGAGTAACGCT | 1,056,121 | 92 |
| 2938. | AGACGATTGCATTCCTAATTAGAG[A,G]GATTCAATTTAAAAATTATACAAAC | 1,056,577 | 92 |
| 2939. | TTCTCTAATTAGACGATTGCATTC[C,T]TAATTAGAGAGATTCAATTTAAAAA | 1,056,587 | 92 |
| 2940. | CTAATTAGACGATTGCATTCCTAA[G,T]CAGAGGGATTCAATTTAGAAATTAT | 1,056,649 | 92 |
| 2941. | TGGATGTTTTCGTGGGTATTTATA[T,C]GTACACTTACGGATTATATGTATGT | 1,062,643 | 92 |
| 2942. | CACCAGGATGGTCGCAGGTCCCGG[C,G]GAGCCGCAGGCGGCGTCCCATGCAC | 1,062,871 | 92 |
| 2943. | TGCCCCGGCCATCGATGGTCCCGC[C,T]GGACACAGAGAGACCCTGGACTCCA | 1,063,064 | 92 |
| 2944. | CAATAGGAAAGAAATAAGGATCAA[A,C]TGAAGGACCGCCCGAGGAAACGTAC | 1,063,167 | 92 |
| 2945. | TAAGACGGAGAATAAATTACAATA[G,A]GAAAGAAATAAGGATCAAATGAAGG | 1,063,186 | 92 |
| 2946. | GAATTACGTTATCATATGAGTTAA[G,C]ACGGAGAATAAATTACAATAGGAAA | 1,063,207 | 92 |
| 2947. | AAATAAAATACTGAAGCTACAGCA[G,A]TCATACCTCCTCGTCTTCAGGAACG | 1,064,468 | 92 |
| 2948. | AGCCATTATTTTTtCTTCCTTGAA[G,T]GTACGTTAGCCATTAATTATATGCT | 1,064,653 | 92 |
| 2949. | CAGATAATATCATACTTACCATAG[T,C]TGTGCTAGGGACATGAGGTTAGCC | 1,064,699 | 92 |
| 2950. | TGTATAGAAGTATGGAGCTTCCGT[T,C]AGCACGGTTCTCGAAAAaGAAAAAA | 1,065,057 | 92 |
| 2951. | GTATCAAAAAAAAaTATAATGAA[G,A]TTTAGAAAATGTACTTTTGTTACTA | 1,065,344 | 92 |
| 2952. | TCTCAATCACTTGTACAGTACTTG[C,T]AGTGCATGCCAAGTCTCAATAAACA | 1,065,408 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2953. | GATCACTTGAGTCATAAAATTATC[G,A]AAATTAAGACTCAGTGGCACAGTAT | 1,065,566 | 92 |
| 2954. | TGCAGTGAAAGCAATCCATGCAGT[G,A]AAATTGAGCTGCAAGACATCAAGCT | 1,065,702 | 92 |
| 2955. | TTTCTTTtGTTTTCGATAGAATTC[A,G]TCTGCATCACAAGTGGTCATGAACT | 1,065,757 | 92 |
| 2956. | AAATTGAAAAATTTTTTtGCTATG[A,T]ATTTTTGAGCTTTCATTTTCTTTtG | 1,065,798 | 92 |
| 2957. | GATACAATCCAAGCCCATGCAGAGT[C,G]AGTGGCAACCTATGTCATCTTTTGG | 1,066,133 | 92 |
| 2958. | ACTTTCTTTATGCATGAAGCCATC[G,A]TTGGATTGCACAATGGTCGCTTCAA | 1,066,251 | 92 |
| 2959. | GCAGTCCCCACCAGATTTGGTCAT[G,A]TAGCATTACTTTCTTTATGCATGAA | 1,066,283 | 92 |
| 2960. | TATGCATACTTGTACGAGGAATTC[C,T]TGCGTCAAAAAATTCTTTGGGACCAA | 1,066,433 | 92 |
| 2961. | AACGGAGAAAAGATCACTATGCAT[A,G]CTTGTACGAGGAATTCCTGCGTCAA | 1,066,450 | 92 |
| 2962. | CACCATCCTTCGTCTTCCACTATT[C,A]ATGTGCGAGAATAACGTGAATAAAA | 1,066,639 | 92 |
| 2963. | ATGAAATTAAGTTCATTTGCAGGG[A,G]GAAATGCGTCATATTGGGGTGGGGC | 1,066,702 | 92 |
| 2964. | CCTGCGGTCCTGGCCATGGCATCA[T,A]GTAAGGGAACATGTATGTGTTGCAT | 1,067,110 | 92 |
| 2965. | CACATTGTGATCGATGACTGTCAG[A,G]GAGTGATGGTACAAGGTGTCAAGAC | 1,067,306 | 92 |
| 2966. | TGCAGTCGTTAGCCTTCCATGGCT[T,C]GAAGAACATCATGATAAGTGGGCTG | 1,067,380 | 92 |
| 2967. | TAACTTAATTATGCGATAACTTTA[A,T]TTCATCATTTCTTCATGCAGTCGTT | 1,067,420 | 92 |
| 2968. | CAATTGTTTTCGTCAGAGGATGAT[C,G]AGGTTGAATCGCATTTTAGGATGGT | 1,067,654 | 92 |
| 2969. | ATTTGCCTCTCCAACAATTGTTTT[C,T]GTCAGAGGATGATCAGGTTGAATCG | 1,067,668 | 92 |
| 2970. | ACGACACCTCTTTGATAATTCGGA[C,T]AGTATCTATAGACTCTGCATCTAGC | 1,067,788 | 92 |
| 2971. | ATATATATATATTTCTAAATTTTA[G,A]TTATTTAAAAATTAATTTTTTtATT | 1,067,927 | 92 |
| 2972. | AAGTCCTTAAATTTCTCAATAGCA[G,A]CAGCAATATGATCATATTTTGGAGT | 1,069,271 | 92 |
| 2973. | AAAGCTTGACAAGCTGAAAATGCT[T,A]CAGCCACATACTCTATTTCAGAAGA | 1,070,096 | 92 |
| 2974. | TCTCGGGGATGCTTGCTTCTTCTC[G,C]CAGCCACAAAAACCTCCCAAGATAT | 1,070,959 | 92 |
| 2975. | GGTGGTATCCTGGCCAGACATCCA[T,C]CCAACACCCGTGCCTTCAGAACTCT | 1,071,130 | 92 |
| 2976. | AGGATCTTGGGAGGTGGTATCCTG[G,A]CCAGACATCCATCCAACACCCGTGC | 1,071,142 | 92 |
| 2977. | TTtTCTTTCTTCCTGCTGCATCGC[G,A]TGGTACTGAAAGGATCTTGGGAGGT | 1,071,177 | 92 |
| 2978. | CCCGTGGAGGCGAGCTCTTTTGTG[A,G]CTGATCCACGTATTTTGATTGTTTT | 1,071,242 | 92 |
| 2979. | ACTTCAGGTGAGAGAGAATTGGGT[A,G]TACAAGGGTTGAGGGTGAGGTCTCC | 1,071,330 | 92 |
| 2980. | AAGAGAGAGAGAGCTTTTGTGAGG[A,G]GAACTTCAGGTGAGAGAGAATTGGG | 1,071,357 | 92 |
| 2981. | AAGGAGCAGGAGGCTCCTTGACAG[C,T]GGTCGCCAGGCTCTTCAGGGGTTCA | 1,071,417 | 92 |
| 2982. | ATCTGAGAGCGTGGGTGGCTGGCTCCCG[A,G]TCTTGATCCGACGGTCCAGGGGCTA | 1,071,623 | 92 |
| 2983. | ACCCGGCTCAAGTTTGCTTTGGTT[G,A]ACTAGAATAAAAGTGAACATCAGGT | 1,079,120 | 92 |
| 2984. | CCCCCTCCTTTTCGTCTCTTTTCC[T,C]CCTCTCCTTTTCCCCAAATGAGAAA | 1,079,244 | 92 |
| 2985. | AACTAGGGGTTTTCTCTTTTCCCC[C,T]CTCCTTTTCGTCTCTTTTCCTCCTC | 1,079,265 | 92 |
| 2986. | CGAATGCAAGTTTCTATGATAAGG[C,A]TATATTTTCAAAAGTTTGTATGATA | 1,079,477 | 92 |
| 2987. | GTGAGGGTAAATGGGTCATTTCAT[A,G]TGTTACCACCTACCGTTGCGCCGG | 1,080,311 | 92 |
| 2988. | TTACTATGTACGTAGAACAGCAGT[C,G]AGTGGCAACAATAAAAAGCTGTGA | 1,080,357 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 2989. | ACGACTGCATGGAGAGGAGCACAA[T,C]ATAACATATGGTCAGCTCAATTTAC | 1,080,403 | 92 |
| 2990. | TCGAGTTCCTGAACACTAACGACT[G,T]CATGGAGAGGAGCACAATATAACAT | 1,080,421 | 92 |
| 2991. | CCGTCACCGCCTGGCAGCCATCGA[A,T]CACGATGTGGAACCTCTCGCTATTG | 1,080,502 | 92 |
| 2992. | ATGGCCAGGTCCGCAAGTGACCTT[C,T]TCGATCCATAGGTTCGTCGTGCCAG | 1,080,681 | 92 |
| 2993. | CATCACACGTGTGAGTGTTCCAAC[G,A]TAAGCATCTTATACGCGTGAAACTC | 1,080,781 | 92 |
| 2994. | CCGTTATGTTCATGAGAATACCGA[A,G]CATGATAGAATACGTTATTCTATAC | 1,081,141 | 92 |
| 2995. | TTAAGGCCGAAATTATTATCAATA[A,G]AAAaGACATATCGATCCATTAAATA | 1,081,672 | 92 |
| 2996. | CACCCTTGAGGACTTTTTGGGCAC[T,C]GGACGAATATTGCGTCGTTAATTGG | 1,081,743 | 92 |
| 2997. | GGGCTTGTTTTTGAGTGTAGGCCA[A,G]AATTTTGAACTAAGTTTTCGTCTCT | 1,081,922 | 92 |
| 2998. | AAATAaAAAATATAAAAATAATA[C,T]TTAGTACTTCACATAACATTAAAAT | 1,082,475 | 92 |
| 2999. | TCCTTGATGTAATGATGATCCACT[G,A]GTCTCTCTTTTTTATATTTAGGGAT | 1,082,601 | 92 |
| 3000. | TTAATCCAAAATAAATTGATTAAC[T,G]TACTTTAACCTAATTGATTTTAAAC | 1,083,078 | 92 |
| 3001. | CCACCCTCCTTGCCACATTCTATA[G,T]ATGCCCATTTTCTACATATAAAATA | 1,083,280 | 92 |
| 3002. | GTCCGAGTTGGGAGAGGCGGTGCA[A,G]GCTTTGTCATCCGTGGTCCGGATGA | 1,083,976 | 92 |
| 3003. | AGAACCCCTACCTTAGGGGTTTGT[T,C]AAGATAAAATTTGATGGTAGTGTCC | 1,084,022 | 92 |
| 3004. | TAGGGTTCTATCCATTTCTTGAGA[A,G]CCCCTACCTTAGGGGTTTGTTAAGA | 1,084,043 | 92 |
| 3005. | TCCTTGGCTTGATCCATCAGAGTA[T,C]GGTTGATTGGATGGCTATGGATGGT | 1,084,288 | 92 |
| 3006. | TCGTTCGGTGGGGGTGATTTAGGA[T,A]GCCTGAGTTTTGAGCATTCCTTTAT | 1,084,851 | 92 |
| 3007. | GGGATCTATTCCTTATTGACGAAG[C,A]GGGAGGCTCTGCTTGCCAGACATGT | 1,085,067 | 92 |
| 3008. | AATTTTAAAAAaTAAAAAaTTAGT[C,A]TTTATTTATAATAAAATTTTTCATC | 1,091,438 | 92 |
| 3009. | TTTATTGCCAATAGTTAAAAAAaT[C,T]AAAATTTTAAAAAaTAAAAAaTTAG | 1,091,465 | 92 |
| 3010. | TTTCGTCGTCAATAATATTATTGG[T,C]GATGAAAAATAAAATTGATCATAAA | 1,091,911 | 92 |
| 3011. | TCTTTCACTTCTTCAGGGATCGAT[A,G]GATGAGGTCGCTAGATGAGGACTGT | 1,092,506 | 92 |
| 3012. | GGAGGGATCCGAAAGGAGATCTTT[C,T]ACTTCTTCAGGGATCGATAGATGAG | 1,092,525 | 92 |
| 3013. | AGCTACGGAGGAGTGACGGTGGTA[T,C]TGTGGCTGATAGTGGAGGGATCCGA | 1,092,563 | 92 |
| 3014. | GGCTTACTTGAGCATGAGTTGGGG[A,G]AGCTACGAGGTAAGCTCTTTGAGCA | 1,092,747 | 92 |
| 3015. | AGTGACATCTTCCAACGATTGAG[C,T]GGGTTGAGGCTGATATTGAGGAGCT | 1,092,822 | 92 |
| 3016. | ACTTTTTGTCTTTGAGAGCCTTGA[T,C]GGAGTTTGTCTCCATTGTCCACTTC | 1,094,138 | 92 |
| 3017. | TGACCTTGACCGTCCATTACGATC[G,A]AGGACCGCTGGGGTTCACCCGTGCA | 1,094,263 | 92 |
| 3018. | ATCCAACTTGACCTTGACCGTCCA[T,C]TACGATCGAGGACCGCTGGGGTTCA | 1,094,271 | 92 |
| 3019. | TCGAGCTGGGGTTTCATGGTGAGG[A,G]AGATGCGTGATCGTTTGAAAGATGA | 1,094,870 | 92 |
| 3020. | AAGATCGTATCCCTGCATCGGTGG[T,C]TGGAATTTGCACTTAGGAGTGCTTT | 1,094,982 | 92 |
| 3021. | GGACATGCATGCTTTCAATCTTCT[A,G]GTTTGTATTTTTTtGAGTCAACTC | 1,095,032 | 92 |
| 3022. | AGGAATAGTTTGCAAATGATACAA[C,T]GGACATGCATGCTTTCAATCTTCTA | 1,095,057 | 92 |
| 3023. | ACCTAAATCACATTTTTGAAATAG[G,A]AATAGTTTGCAAATGATACAACGGA | 1,095,079 | 92 |
| 3024. | GACGTTTTGAGATTCTTGTCAAAA[G,T]TGGGACAATTATTTCATTTTTGGTA | 1,095,247 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3025. | TATATATTAAATTATTACTGTACG[G,A]GTGCTTAGCAATATTTTAAGCTCTGG | 1,095,426 | 92 |
| 3026. | ATATATACATATATATTAAATTAT[T,C]ACTGTACGGGTGCTTAGCAATATTT | 1,095,435 | 92 |
| 3027. | ATGAGTTTTAATTTAATTCTTTAA[C,T]ATCATAATATTTTTTtATTTAATTA | 1,095,595 | 92 |
| 3028. | ATATTGATATTTGCATCTATTATT[G,A]TATATTTAGATATAAATTTTTAATT | 1,096,413 | 92 |
| 3029. | GAGTTAGACTATAATTTAAATCTA[A,G]TTAAGGAAACTGATCGTTGGCTGTA | 1,096,830 | 92 |
| 3030. | AAAaATAAAAATTATACATATTCA[C,T]CTCTGCATGAGTTTTTTTTTtGAAT | 1,097,000 | 92 |
| 3031. | GATTAATTAATATTATATAATTTT[T,A]AAAaAATAAAAATTATACATATTCAC | 1,097,025 | 92 |
| 3032. | CATCAAAACCTCCTCCGCCTCTCT[C,T]CTCCTTCCTCATCCCCACAACCATC | 1,098,467 | 92 |
| 3033. | AGTTTTCCCCTACCCAATCTCATG[G,A]CATGGATGAGGATAAGGCCGTGAGA | 1,098,663 | 92 |
| 3034. | TCGACCAAAATAGAGGAAGTTTTC[C,T]CCTACCCAATCTCATGGCATGGATG | 1,098,680 | 92 |
| 3035. | AGAATCGGTCTCATTGGACCTGGT[A,T]AAGCATGAAGCCAGCAAAGATTGCC | 1,098,777 | 92 |
| 3036. | AGGGGGTGAAATTCCAGAATTGAC[A,G]TAGAGATGTCAAATTATGAAGTATT | 1,099,052 | 92 |
| 3037. | TCATAATTATGATGGATCAATATT[G,A]TTGCCTAAAGCCATTACTACCTAAT | 1,099,437 | 92 |
| 3038. | CTATATCTATTTGGTTAGATGGTC[A,C]AAGATATTATGTTTTATCATAAAAA | 1,100,201 | 92 |
| 3039. | TTTATGATTTCTATATCTATTTGG[T,A]TAGATGGTCAAAGATATTATGTTTT | 1,100,211 | 92 |
| 3040. | ATTTGGATTTTGACATCCATAAGG[A,T]AAATGACTAAACTCTTTACAATGTA | 1,100,315 | 92 |
| 3041. | AAGCAATCGTGTAACCAGATTAAA[G,T]TATTTGGATTTTGACATCCATAAGG | 1,100,341 | 92 |
| 3042. | TCACTGGACAGCTCATCATGTTCG[T,C]ATATTGTAGAAGTCCAATTCGGGGG | 1,100,754 | 92 |
| 3043. | CGGCGTCCCATGCATCAAGGAATG[C,A]TTTGGTCGAATCCGTCTCGCCATCT | 1,101,813 | 92 |
| 3044. | ATAATCGGTTGGTGCAACAAGGGT[A,G]CCGTCGATCTGGACGGTGATGTAGC | 1,101,953 | 92 |
| 3045. | TACAATAAGAAAGAAATATGGATC[A,G]AATGAAGGACCGCCCGAGGAAACGT | 1,102,146 | 92 |
| 3046. | AAATGACGAATTACGTTATCATAT[G,T]AGTTAAGACGGAGAATAAATTACAA | 1,102,191 | 92 |
| 3047. | ACCATGTGGTACAGCTCGCTGTTC[C,T]TCGACCTCAACCCACTGATCGTTAC | 1,102,283 | 92 |
| 3048. | TTAAAAATTCCAGCTCAGAAAAGC[C,T]GTAACTTATATATATATACATATTG | 1,103,302 | 92 |
| 3049. | GTTGGCATAATAAGAACAACAAAA[C,G]TGAAAATTTTATTTCGATATATTTT | 1,103,663 | 92 |
| 3050. | ACTTGGGTGGGTTAGATTGGATCG[C,T]GGGCAAACCCCATGCCAACTCAACC | 1,104,572 | 92 |
| 3051. | GCCATGCCTAAGTACCCAAGGCCT[A,T]CCTAAGCACTTTTAACAAAAACTTT | 1,105,060 | 92 |
| 3052. | AATACCTCTCATTGTTCTAAATTT[C,T]AATATATTTTATGATTTAGGGATTG | 1,105,165 | 92 |
| 3053. | TCTTTTtCTTTTATTGACTAGAAT[A,C]GGGAAAGCCTAGCTGAAAACTAAGG | 1,115,335 | 92 |
| 3054. | ATCTTTATTTTCTTTTtCTTTTAT[T,C]GACTAGAATAGGGAAAGCCTAGCTG | 1,115,345 | 92 |
| 3055. | TGGATTCAATCCTACCCGGTGTGG[T,C]TTCAAGTCAAAGATTAGCTTCAATC | 1,115,537 | 92 |
| 3056. | GGCTAACATGATATTTTACTACTT[C,T]AAGTTAAGAAAATCAGAATTTGACC | 1,115,681 | 92 |
| 3057. | ACTGCACCTGCCCCATGTTCTCCT[G,A]GTGAGTTGGTCAAAAGGATGTTGCA | 1,115,753 | 92 |
| 3058. | GATTGCATGCTGGTGAAAAGCTTC[T,G]ACCATAAAATGTCCACAGCTATGAA | 1,116,063 | 92 |
| 3059. | CCCATGGAGAAATGATTGCATGCT[G,A]GTGAAAAGCTTCTACCATAAAATGT | 1,116,076 | 92 |
| 3060. | GTTGTCTATTTCTTCTAATTGTCA[A,C]CCGAGATGATGGAGTAGCTGCAGAA | 1,116,663 | 92 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3061. | TAAAGACGCACCGAAATTTGTATA[T,A]TTTGGTGGAGTCACAGCGTTATTGG | 1,116,962 | 92 |
| 3062. | AAAACATAAGGCAATGACTTATTT[C,G]GCATTTAGGTCAATTTGTCTACATG | 1,118,433 | 92 |
| 3063. | TAGAAATGAAAGTGTTCTGTGCTT[C,A]ATTTGGTTCATGAAAAACATAAGGC | 1,118,471 | 92 |
| 3064. | ACCTGAATACAGTGTATAGTGCAC[A,T]ACTAGTCAAGACTATTCAACATGAC | 1,118,720 | 92 |
| 3065. | CATGGAAAACACCTGAATACAGTG[T,C]ATAGTGCACAACTAGTCAAGACTAT | 1,118,730 | 92 |
| 3066. | TGTCCCTCGAATATTTTTGTAGTT[G,A]CATGGGTGATCTCAATGCCCGAAT | 1,120,076 | 92 |
| 3067. | ATGTTTGCAAGAAGACCATGCCCG[C,T]CGATTTTGATAGGTGAGCTTAATAT | 1,120,196 | 92 |
| 3068. | AGGGCATTCGAGTGTCGGCTTGAG[C,T]AGGCCAATGCACATACTACCCAATA | 1,120,335 | 92 |
| 3069. | GAGTCATTTAGAATAATCAAAAGA[C,A]AAAGAAAAGAAAGGTTCAAGGTGAT | 1,120,869 | 92 |
| 3070. | CAAAGAAAATGTTTCTCGTCCAAA[A,G]ACAAAAGTCAAAAAACAAAGATGTT | 1,121,150 | 92 |
| 3071. | GATAGATCTCAAATTAGATGCTTC[C,T]AATTTTATTCTCTCTCTATAAATTT | 1,121,651 | 92 |
| 3072. | GTTGATTAAAAAGATATTTAAGAA[A,C]GAAAAAGGTGGCTGGAGAATATTGA | 1,122,173 | 92 |
| 3073. | ATTTGGGTGGTGGTGAAACGGTCG[G,C]GCCAGGTGCAGCGGAGCTGGGCTTC | 1,122,409 | 92 |
| 3074. | CGCCATTTCCATTCCCCTGAGAGA[A,C]AGAGAGACAGAGAGAGATTTGGGTG | 1,122,450 | 92 |
| 3075. | CACAACTTTGGATACACCAAAGCC[C,T]TCTATCACCTTTTCAGGAATACAAG | 1,122,799 | 91 |
| 3076. | CTCAGTCTTCGAAATTAAACTATA[C,A]TCTTCCCAACCAGTTAGCCCTGAGA | 1,122,886 | 91 |
| 3077. | TTGTCTTTAAATTTGCTGGTACAT[C,T]TAGTAACAAAAACTTAAACTCGACA | 1,123,029 | 91 |
| 3078. | ACATTGAAGCTAAGCAATAATGGC[A,C]TGACAATGCAGCAAAGCATCATTTA | 1,123,240 | 91 |
| 3079. | ACACATTTTCCATAAAAAAGATTG[C,T]AACACCTCAGTAATTAGCTTCTTTT | 1,123,318 | 91 |
| 3080. | TGCCAGAAAGCATCCCTTAACTTA[C,A]AAGAAACTTGATAATTTTTCCTCTA | 1,123,407 | 91 |
| 3081. | GAGCAAATGCAAAAATAGAATAGG[C,T]AGACAAAATCTGTGGGATTGCCAGA | 1,123,450 | 91 |
| 3082. | CTAAATGAGCAAATGCAAAAATAG[A,G]ATAGGCAGACAAAATCTGTGGGATT | 1,123,456 | 91 |
| 3083. | ATCGAAGATAAAAGACCGTGTTTC[C,T]CAATATTGACCCATTCATATATAAA | 1,123,508 | 91 |
| 3084. | CATAATTTTTGAGTATCGAAGATA[A,G]AAGACCGTGTTTCCCAATATTGACC | 1,123,522 | 91 |
| 3085. | GCTGGTTCATAATTTTTGAGTATC[G,A]AAGATAAAAGACCGTGTTTCCCAAT | 1,123,529 | 91 |
| 3086. | TGCAATAGATCCGACAAAACGATC[G,C]AAAGATATAAAACACAGAACATATA | 1,123,591 | 91 |
| 3087. | ACAGATCTCATAGAATCCAGCATA[C,T]GCTGTAAAACCTGGCATACCTGTGC | 1,123,678 | 91 |
| 3088. | CTTTTGCCTTGTGCCTGCACTTCC[A,T]ACAACATAACAGCCATGTAGCTTTG | 1,123,801 | 91 |
| 3089. | TATCTCAATTAAAACAACTAATCC[C,T]AAGCACGCATGCGCGCGCGCACA | 1,123,909 | 91 |
| 3090. | TTATCTCAATTAAAACAACTAATC[C,T]CAAGCACGCATGCGCGCGCGCAC | 1,123,910 | 91 |
| 3091. | ATAGACTAGATGCAATAAACTAAG[C,T]CACGACTAGAAAAATTAAGATCCTC | 1,124,094 | 91 |
| 3092. | TAAAATAGCTTTCTAAGAACCCTA[C,G]AAGAAGAGAGGGTTGATAGGCAGAA | 1,124,314 | 91 |
| 3093. | CAGGTTTGGGTCATATTTTGCCAA[C,T]TACCATGATACAAGGGTCTATGGAC | 1,125,265 | 91 |
| 3094. | CATTACAGGAGTTTCAGAATATGA[T,C]CATTTCTATCAAGATAAAATGACAA | 1,126,245 | 91 |
| 3095. | AGCTCATTACAGGAGTTTCAGAAT[A,T]TGATCATTTCTATCAAGATAAAATG | 1,126,249 | 91 |
| 3096. | GCAATATACACCACAACCAATGTA[C,T]AAAAATCACATATTATCAGCTATTT | 1,126,428 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3097. | TTGCAAACACTGTACATAACTGAG[T,A]CAAACATGTTCGAACAGCACTCTAA | 1,126,750 | 91 |
| 3098. | ACGGTCAACCATTGCCACCCCAGC[T,G]AATAAACAGCATATGCTTCTCCTTA | 1,127,553 | 91 |
| 3099. | AGAATTGTTTTCTTTTtGGTTTTA[G,C]CAACTTAAAAGACACTTTTGCCAAA | 1,129,764 | 91 |
| 3100. | TACAAGAAAACCATTCGAGTCTCT[C,A]CTCCAACACCAATATCTATATATTA | 1,129,874 | 91 |
| 3101. | CTCAATTTGAATTTGATCCTACAA[G,A]AATAGTATCCTATCATTATCCTTTT | 1,130,004 | 91 |
| 3102. | CAAAAATGACTCAATTTGAATTTG[A,G]TCCTACAAGAATAGTATCCTATCAT | 1,130,013 | 91 |
| 3103. | TCATAAAAATATATTTTTTTTtA[A,T]CCAACAAAAATGACTCAATTTGAAT | 1,130,042 | 91 |
| 3104. | ATATTTATTTTACTCTTATATTTG[A,G]AAAAGATGTTGCTAAGCATATATCA | 1,130,307 | 91 |
| 3105. | ATAAGGAAGTACCATTTGCGAGCC[A,C]AAAAACGCATATTATTGAATAATCA | 1,131,515 | 91 |
| 3106. | CCATCAAATCACAGCAACTTGTAT[G,A]CACAATTATTGAAAGGAAAAAaGaA | 1,131,595 | 91 |
| 3107. | TCAATCGAATAGGTTAGAATTAAC[C,T]TCAGAAAACGCCAATCACTTCCACC | 1,131,643 | 91 |
| 3108. | CAGATIATTTGGCCCGGACCCTCA[A,C]ACAGAAAACGCCAATCACTTCCACC | 1,131,898 | 91 |
| 3109. | TTACAGATTTAAATTAAGAGGACA[T,C]GAAATATAGTCAACTTGCCTTGACG | 1,133,875 | 91 |
| 3110. | ATGAACCTTAAATAAGGCAAAAAG[A,T]CTATAGTACTTAAGCTGTCCTTACA | 1,133,920 | 91 |
| 3111. | TCGAACATAGAAACCTGGATACAA[G,T]AATTCATTGTAAGTCTATATGAACC | 1,133,963 | 91 |
| 3112. | TGTGCTATGTATGTGAGAGGCAGG[T,G]AAAACTGCATCTCATGAATTGCAAA | 1,135,068 | 91 |
| 3113. | AGAAGTAAAATTTCACTTCAGGTC[T,G]GCAATATTCCATGCAAAACATTTCA | 1,136,142 | 91 |
| 3114. | TTTGCTATGGTTATGATTCTTAAG[A,G]AGTAAAATTTCACTTCAGGTCTGCA | 1,136,164 | 91 |
| 3115. | GAAGAACTAAATTGAACCGACGTG[G,A]ACCCATGAAAGAATAACATAAAACA | 1,136,245 | 91 |
| 3116. | TGAGACATGTTCTAATAGAGGAGG[T,C]GGAAAGCAATTGGAGAAAAGTTTCA | 1,136,308 | 91 |
| 3117. | TTACCATCGGATGGGATGATGCCC[T,G]GCTTCATGATTAAGTAGTCAACGTG | 1,137,548 | 91 |
| 3118. | CCAGACACTATGTGGGTGGTGCAT[T,A]CTAAAATGAAGCTATTATGACTTTT | 1,143,835 | 91 |
| 3119. | GAACACCATAAAGGAAATTCTGCT[G,T]GCATTATCCAGACACTATGTGGGTG | 1,143,867 | 91 |
| 3120. | ATAACATTTAAGAAAAACAGATAG[G,T]TCAATAACATTAATTCTGAGTGTTG | 1,144,335 | 91 |
| 3121. | AATTTACAGTGTCATAATTTCATA[A,T]TCTTAATAAAACCATCTTAACTAA | 1,144,384 | 91 |
| 3122. | CTTTTCTCAACATTAATTCTTGTC[A,C]AATAGATGAATAGAATCGAAGCAAA | 1,144,634 | 91 |
| 3123. | GGTGTAAGAGGGAATCAGTGTTGT[G,A]AAAAGCAAAGAACTTTTCTCAACA | 1,144,672 | 91 |
| 3124. | GATTTTGGATACCCTAGCCCTAGA[T,C]GATTATCATAATTTTGTTCAACACC | 1,145,105 | 91 |
| 3125. | TACTACAATTTCTTAGGAGATTTT[G,T]GATACCCTAGCCCTAGATGATTATC | 1,145,123 | 91 |
| 3126. | CAATGTTTAAGAGTCATGGGACAG[T,G]TAAAAaGAAAAaGTTAGTTGCTGCA | 1,145,813 | 91 |
| 3127. | ATGTATTTCCATATCAATTTCAAT[C,G]TTTTGGGGGTTATTTTGGATACAAT | 1,145,859 | 91 |
| 3128. | TTCTAGATGATCTAGGATTTTGGA[A,C]TCCATTAATCACAGGATGGAATGTA | 1,145,904 | 91 |
| 3129. | ACATTAGAACACTATGTTCATATC[T,C]ACATTTCCTGTTGTTTATGAAGGGA | 1,146,946 | 91 |
| 3130. | TCTTGTTGGTGATAGACATTAGAA[C,T]ACTATGTTCATATCTACATTTCCTG | 1,146,961 | 91 |
| 3131. | GCCTCGGTTCAGATGACAAAGATT[C,T]AGGTAGAGAGAAACAACAAAATCTT | 1,147,007 | 91 |
| 3132. | TTTTTGCAGCAAGAAGAACATTTC[G,A]AAAGAGCATTGATGTGTAGAAGTTA | 1,147,202 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3133. | TCGATGCAAAGAAACATGCTACTC[G,T]AAAGAATATGAAGGTGAAAACCATG | 1,147,360 | 91 |
| 3134. | CAAAAGAATATAAAGGTAATCGAT[G,C]CAAAGAAACATGCTACTCGAAAGAA | 1,147,379 | 91 |
| 3135. | GCATTCCTTGGAGCTTTACTATGA[C,T]GGACATATCATAGAAAACATAATTT | 1,148,200 | 91 |
| 3136. | CAAGCTTCAAAGAAAGCATTGTCA[G,T]GAGATCAAAATGGACCCATGCAATA | 1,148,283 | 91 |
| 3137. | TATTCACATCCAACTCCAACATGA[C,T]AAGCTTCAAAGAAAGCATTGTCAGG | 1,148,307 | 91 |
| 3138. | AAGAAGAACAAGTTTTCCTTCTAT[T,G]CTCTATACAAAGGGCACTGATCAAG | 1,148,441 | 91 |
| 3139. | TACATACGTAAGCATGTTATTATG[C,T]TGTAATTTGTCTGAATCTATTTGTT | 1,149,365 | 91 |
| 3140. | AAGACAGGCAGACATAGTGCACTC[G,A]TTCAGATGCTATCATGTACTCAGGG | 1,150,477 | 91 |
| 3141. | ATATGTATTCCAACCATATATTAA[A,G]ATAGAAGGATATATAAGTACACTCT | 1,151,559 | 91 |
| 3142. | GTATATGATGAAAGTGGAAAATAT[G,A]TCAGCCTTCTTTTtCCTTCTTTTCT | 1,151,650 | 91 |
| 3143. | GAAAATATGTATATGATGAAAGTG[G,A]AAAATATGTCAGCCTTCTTTTtCCT | 1,151,658 | 91 |
| 3144. | GGAGTATTTCATGTAGGCATTTTC[A,G]ACATACTGTAAGAAAAAAaTGAATG | 1,151,772 | 91 |
| 3145. | TGTGTCTTTCCACCATCCCTGTTT[G,A]GCACAAGTGGCATATGTTTTGTCCA | 1,151,898 | 91 |
| 3146. | GAAGCTTAAATGTGTCTTTCCACC[A,G]TCCCTGTTTGGCACAAGTGGCATAT | 1,151,908 | 91 |
| 3147. | GCTTAAGGATGTCTTCTTAATTAG[C,A]AAAAGAAAAaGGAAAAAaGGAATTG | 1,152,940 | 91 |
| 3148. | CAAAGAGTTAGTGGATGGATGGAG[A,G]TTTTTATCAAACCTATTTATTAGAA | 1,153,071 | 91 |
| 3149. | GAGTTTTGTATTAGATAAAAGACC[T,A]ATTTTGATTCAAAAACAAATCAACA | 1,153,379 | 91 |
| 3150. | ACAAGAATACATCATAATTTTCAA[A,G]CATATGTTGTTGAAAGAAGCTTATT | 1,153,683 | 91 |
| 3151. | CACCTGCCCATATTGCATCACTAG[T,A]ATCCTACAAAAGGGGTGCAAGTACA | 1,153,902 | 91 |
| 3152. | ATATAATCTATTATAATATTATTA[C,T]ATTATAATAATACAATATAACATAA | 1,158,751 | 91 |
| 3153. | ATTATAGTATATATTATATTTATAT[G,T]ATATGATAATAATATGATACAATAA | 1,158,845 | 91 |
| 3154. | TAATATAATAATAAATTAATATTA[C,T]GATATATTATAAATATATAATATAA | 1,159,079 | 91 |
| 3155. | CATCCTTCCAATGGTGGAACTTTA[C,T]GATATATTATAAATATATAATATAA | 1,159,669 | 91 |
| 3156. | TAAGCTCGAGGAAATTCTTATATC[T,C]GCCCAAAGTAGTTTCAAACCCAGCC | 1,159,746 | 91 |
| 3157. | ATCGGCTGTGGTGCTAGTTAGCTG[C,T]TGCTGTTCTCTTCTTGAGAGGTTCT | 1,159,818 | 91 |
| 3158. | TAAAAACTGCAAAAGGAACCAGCC[A,T]GAAGATATCGGCTGTGGTGCTAGTT | 1,159,849 | 91 |
| 3159. | CGTGAGTCTTTGACTTCTTTTGCC[G,A]TTTCTTTCACTGTATCCTGTAAAAA | 1,160,444 | 91 |
| 3160. | AATTTAGTTCAAATGCTCATGACG[C,T]TAAAAAAGCAAACAGAAGAAGTGAA | 1,160,598 | 91 |
| 3161. | GTTCCATATGGTGGGATTCCCATA[T,A]ACTTACACATATTAACCAATCTTGG | 1,160,846 | 91 |
| 3162. | AATAATTTTCTTCGAAGCATAAAC[C,T]GCAAATAATTATCTGTTCCATATGG | 1,160,885 | 91 |
| 3163. | GGATGATGCATTTTCTTTGAACTT[T,C]AAAAaCATATAACCTACCAAAATAA | 1,160,930 | 91 |
| 3164. | CGGGCAAGCCATGGGCTGACCCTG[C,G]TCAGTGTGCACTCCTAAGTGAGGTG | 1,161,113 | 91 |
| 3165. | CAACCCATACCATAAAAATATTGG[C,T]CCAACCTTCTTATGATGTATGCTGG | 1,161,164 | 91 |
| 3166. | CTCATAAATCATTGGCCCAAGCCT[A,G]GCCTAATTTTAGTTGGGCCAAAACT | 1,161,228 | 91 |
| 3167. | ATATATATGCCAACTGTACATATA[T,C]GTGCTATAGAAGTATTGCCTCAGGC | 1,161,295 | 91 |
| 3168. | AACTTTCCAGCTTTTTAGAAATCT[G,A]AAAGCACTTCTTAATATTTTACCAA | 1,163,216 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3169. | TCCAAAATAGAACTTTCCCAAGTA[G,T]AACTTTCCAGCTTTTTAGAAATCTG | 1,163,241 | 91 |
| 3170. | CTTCCAAACATCAGTCAAGTAGGG[C,T]TCTTGAGAAAATCTCCAAAATAGAA | 1,163,279 | 91 |
| 3171. | TATTATAATATAATGTCATTATGT[T,C]GCTACGAAATTTTCATTAAAAaCA | 1,163,336 | 91 |
| 3172. | ATATTATTATAATATAATGTCATT[A,G]TGTTGCTACGAAATTTTCATTAAAA | 1,163,340 | 91 |
| 3173. | ATCTCCTTTATCACAGAGTGAAAG[G,T]TTGAGAAAGTACTTTTGGTATGACA | 1,163,969 | 91 |
| 3174. | TATTCAAGTATAATGTCACAATGG[A,G]TTTTTTAACTAGAAGTATCTCCTTT | 1,164,010 | 91 |
| 3175. | TAATACGACATATTTTATCAAAAG[C,G]AATGGCAATTAACTATGCAAACAAC | 1,164,175 | 91 |
| 3176. | AATATTCAATATCAATCTCCCAAT[T,C]TTTGCACATTATTTCACATCATGAA | 1,164,281 | 91 |
| 3177. | CCTTCCAGACCTCCAAAGAATAAT[A,G]TTCAATATCAATCTCCCAATTTTTG | 1,164,302 | 91 |
| 3178. | ATAATAACTTGGAGAGCTTAGTAA[C,T]ATTGATTTCTATAATATTGTGTTTA | 1,164,422 | 91 |
| 3179. | TCACAACATATAATAACTTGGAGA[G,C]CTTAGTAACATTGATTTCTATAATA | 1,164,431 | 91 |
| 3180. | TGTCTGCTTAAGAAACACAAACAA[A,G]CATCACAACATATAATAACTTGGAG | 1,164,458 | 91 |
| 3181. | TGCAAAAAAGAGGTCACATTCATA[T,C]GTTACAATGAATCACAAGTAATATT | 1,164,604 | 91 |
| 3182. | ACACAATATAACATGGAGATCATC[A,G]TCACTAGGCACAATCATCTAAATAT | 1,164,701 | 91 |
| 3183. | CATGGTACCAGTACAGGTCTGGTA[C,T]TGAGATTGTGAACATTGACTAAATG | 1,164,860 | 91 |
| 3184. | CATCGTCCTAATTTTACCACCTAG[C,T]ACCGTCATATTAACTAGCAAGATTC | 1,165,022 | 91 |
| 3185. | ATCATGTAGTTACAATCTTCAAAA[G,C]CAGCCACTCTTATTACCTCTCTCTT | 1,165,373 | 91 |
| 3186. | CTTCTGAAGTATGTGTTATCTTCC[G,A]AGGTCCTTCAAGCTGCAGAATCTGC | 1,165,686 | 91 |
| 3187. | CTTCCATGCAAAAGGGGGTGGTC[T,G]GCAAACTATGCCACTTTAACACCAT | 1,165,858 | 91 |
| 3188. | GTGGATCATTATCAAATTCAGATT[T,A]TATATATATATATATAAAGCCCGGA | 1,165,914 | 91 |
| 3189. | AGACTGAATTCTAGACAAAGAGAG[T,C]TGAAATTAATTAAAAGAAGCAGTGA | 1,165,984 | 91 |
| 3190. | CATGCTTGCCTAAGTTCACATTCT[A,G]AAAGAGATTCTACACCCTCTGCCTG | 1,166,136 | 91 |
| 3191. | GGTCCCTACATGCTTGCCTAAGTT[C,A]ACATTCTAAAAGAGATTCTACACCC | 1,166,144 | 91 |
| 3192. | CAGGCATAAGAAAACTTTAAGAGA[C,T]TTGTTTTTAATTGGGTCTATCATTT | 1,166,274 | 91 |
| 3193. | ATAAGCAAAGAATTTCCTTAGTAC[A,C]GGCATAAGAAAACTTTAAGAGACTT | 1,166,297 | 91 |
| 3194. | ACAGTAGACTCTAGAAATGCTATT[A,T]AGTATAAAGAAAATAATTGCAGTAA | 1,166,497 | 91 |
| 3195. | AGGTGAGGACGTCAAATCAGACTC[A,G]AGTATAAAGAAAATAATTGCAGTAA | 1,166,569 | 91 |
| 3196. | TCTAAGAAATGACATCCAAATTAA[T,A]CAGGAGGAAACAACATATATTTaaa | 1,166,801 | 91 |
| 3197. | TATTTCCAGAAACAGTGAAAGCTC[T,A]AGAAATGACATCCAAATTAATCAG | 1,166,823 | 91 |
| 3198. | CATTAATCTCCCAATACTGATACT[A,C]AACAAATAAGGTAATGATAAAGGAA | 1,167,054 | 91 |
| 3199. | TTACATTTCAAGCTTATGCAACTA[G,C]GAACAGCATTCTAAGATAAACTTGA | 1,167,235 | 91 |
| 3200. | AGCAAATCATCAAGACCATTGGTT[A,T]ACCTGATGTCAATCCCTAACAAATT | 1,167,343 | 91 |
| 3201. | CCAGTAGCAAACAATTTAACATAA[T,G]TAACTAGACCAATAGATATGAACCA | 1,167,476 | 91 |
| 3202. | TAGAAACATGCTTTAACAATTGCA[C,G]TCATACAACATTGGCTTGCTAATGA | 1,167,565 | 91 |
| 3203. | AGTAGAGTGCAAGATTATACAGAT[C,T]TACTCACAATTAATTCTGCAGGAAA | 1,167,632 | 91 |
| 3204. | TATGATCATCTAGTCTTCCAATGT[C,T]TTGATTTATGTTGTCTGCTTCTACA | 1,167,713 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3205. | ACTGAAGTTTAGACTTTAAGTCTT[T,G]GAGACTAATAATGTTTTGCATTAGA | 1,167,787 | 91 |
| 3206. | TGAGCATGAGAACATCTCGTGACA[C,G]TACAAAGATAATAAGAGCTAAATAG | 1,167,974 | 91 |
| 3207. | AATCTGACCTAATAATCTGGAGCT[G,C]GATACACTCACTCATACAGGAAAAT | 1,168,175 | 91 |
| 3208. | CAATGAAATCACATCATCTATCAT[T,A]TGCGCCACAGTGAATTTGAATTCAT | 1,168,326 | 91 |
| 3209. | AACAATATCAAATCACATGCAAAC[A,T]GTTTTCGAGTTTGATACATGAAAGA | 1,168,395 | 91 |
| 3210. | GCTGAAGCTAGAACAGCTAATGCA[C,T]GGCTGATTTTACAGAGGTCTTCTCT | 1,168,849 | 91 |
| 3211. | TTAACAAGACTCAAGAACTCTTGA[C,T]GCTCCCTGCTGACAGACTGCAAGGT | 1,169,005 | 91 |
| 3212. | AAGATGAAATATACCTCTTTGTTA[A,G]CAAGACTCAAGAACTCTTGACGCTC | 1,169,026 | 91 |
| 3213. | GGTCAGTATTCTCCCTGACTGCAC[T,C]ATATGCTTTCTTAGCTGCTTCTCAT | 1,169,252 | 91 |
| 3214. | AAAAGCATGCGGAGAAAATGTCAA[T,C]ACCATTTAGTTAAATATGTTTCCAA | 1,169,407 | 91 |
| 3215. | CATGGTGCACATTTGCACATACTC[A,G]GTATATGGAAGGGTTGTGATAGGAA | 1,169,462 | 91 |
| 3216. | GTTCTAGAAAATAAGAAAAACATA[C,A]TGAAAACAAGGGATTTGTAATTGGT | 1,169,601 | 91 |
| 3217. | AATTCTCCCAAGAAACTTTATAAC[T,C]GATACTGTTACATCCACCTTAAGAA | 1,169,705 | 91 |
| 3218. | GCATTATATAATCCCCTATCCCCC[A,G]AAAGAAGTATCGAAGGAAGAAATAT | 1,169,855 | 91 |
| 3219. | AACAAAAaGCAAAGAATAATTACC[T,C]GTCAAGTAGCTGCCAGCAGTTACCA | 1,169,979 | 91 |
| 3220. | GAATAAAGTTTTAGTAGATAGGCC[G,A]ACTAAGTTGTGGAACAACTGAATAG | 1,170,233 | 91 |
| 3221. | TTCATGATATAACACCAAAAACAA[C,G]AAATATAGTTGTTTTAAATTCGAAT | 1,170,279 | 91 |
| 3222. | CATAGAGTFTCTGAGGGAAAAAGC[G,T]AATCTGCATAAAATATTCATGATAT | 1,170,319 | 91 |
| 3223. | GAAGTAGCATAGAGTGTCTGAGGG[A,G]AAAAGCGAATCTGCATAAAATATTC | 1,170,326 | 91 |
| 3224. | AGAAAAACCAAAGAGGCAAAATTA[A,G]AAAGTGTCTTGGTCTACAGCCATGT | 1,170,383 | 91 |
| 3225. | TCATAGAGTGAGAAATTTCAAATA[C,T]GGAAAAAAaGAAATCATCAGTTACA | 1,170,483 | 91 |
| 3226. | ATGGCTGCAGCTGCAACCTCTTCT[G,A]GTGTCACTTTGCCATCATGATCACT | 1,170,555 | 91 |
| 3227. | GCAATCAACCTCTATCCCTAGAAA[T,G]GTTGCTGATGAGTTCCTGGACATCC | 1,170,632 | 91 |
| 3228. | TCTGTTTCATCTCCATTGGCATCA[T,G]CTATTTGACTGCCTAGCTTGACTAT | 1,170,823 | 91 |
| 3229. | CAATTGTATTACCAACGACTGAAG[T,C]TCTGTTTCATCTCCATTGGCATCAT | 1,170,848 | 91 |
| 3230. | ACTATCTTATATAACCACATATAT[A,C]CATAGGTTATTTTGACCAGGCCACC | 1,170,952 | 91 |
| 3231. | CCCTAGAAAAAAaTAAAAaTAAAA[A,G]GATGAATAAACTGAACATGGGTTCA | 1,171,221 | 91 |
| 3232. | TCAGCCAAAACAACTAACAGCTAC[A,G]ATGCATGCAATAAATATGGGCCCC | 1,171,268 | 91 |
| 3233. | ATATCGTTAGCTAATCAGCCAAAA[C,A]AACTAACAGCTACAATGCATGCAAT | 1,171,282 | 91 |
| 3234. | GACATTGGACAGAAACGGCACTCC[G,C]AGAATTACGCTAACAAAATGCTGCA | 1,171,472 | 91 |
| 3235. | CCAAAAGACATTGGACAGAAACGG[C,T]ACTCCGAGAATTACGCTAACAAAAT | 1,171,478 | 91 |
| 3236. | TCACAAATAAATGTAGGGTCATGC[T,C]GAACCGGCATATCTCCAAAGCCTCA | 1,171,696 | 91 |
| 3237. | GCTCATTCTATTTGTAATGAGAGT[G,T]GGAGAAAACTTTGGGTTGGTTACCG | 1,171,786 | 91 |
| 3238. | TCAAAGCCCACAGCTATAATGCTT[A,G]ACTGAAGCTTAATGCCTGCGAGTCT | 1,171,879 | 91 |
| 3239. | ATCTCAAGGTCGAAAGATGAATAC[A,G]GAAAAGAGACAAACTACTCTCGGAA | 1,171,949 | 91 |
| 3240. | ACAAAACCACAAGATGGACTGGTT[T,C]TCAAATCTCAAGGTCGAAAGATGAA | 1,171,978 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3241. | AAGACCAATCCACCAACCCACTGC[T,A]AGTTAACACTGGTGAATTGGAATGG | 1,172,031 | 91 |
| 3242. | TAATGGAGAGCACAAGAAGACCAA[T,G]CCACCAACCCACTGCTAGTTAACAC | 1,172,047 | 91 |
| 3243. | AGCGAACGGATGAGAGGAAATTCT[T,C]AATGGAGAGCACAAGAAGACCAATC | 1,172,071 | 91 |
| 3244. | AATAGAGAGCGAATCTCCTGTTCA[G,A]TTGGAATCCTAGGGAGACAAACAGG | 1,172,133 | 91 |
| 3245. | TAACTCAGCAACGTCATAGTAACT[A,C]AAATGGAGTCTTGTTCCAAGAATGT | 1,172,262 | 91 |
| 3246. | AAGAACCATTCCGACATCCTAACT[C,T]AGCAACGTCATAGTAACTAAAATGG | 1,172,281 | 91 |
| 3247. | TTGCATTATGttTTTTTTTTTtCA[G,A]ACCAACTAGAGGAACGCTATAAATC | 1,172,348 | 91 |
| 3248. | ATCGTCTAATATGTGTTATACAGC[C,T]CATATTGCATTATGttTTTTTTTT | 1,172,377 | 91 |
| 3249. | AGCCGTTCTTTTTATCGTCTAATA[T,C]GTGTTATACAGCCCATATTGCATTA | 1,172,390 | 91 |
| 3250. | ACTACATAACCCTCGCGTCTTTTT[G,A]GAATGGAGATCAAGCTACATCTCGT | 1,172,495 | 91 |
| 3251. | AGAAAGGAAGATGAAAGTAAAGGG[A,T]AaGTTCGATATTTTTtAAAATAAGA | 1,172,837 | 91 |
| 3252. | ATTCCATCGAAAACCTTCCGCACA[A,G]TCTCCAAATCGCCGTTGTTTATAAA | 1,173,372 | 91 |
| 3253. | AGAAACTATATCTCTTAGCCATTC[C,T]ATCGAAAACCTTCCGCACAaTCTCC | 1,173,392 | 91 |
| 3254. | TCAGCCCATATCTCGCATACCCAT[C,T]AACCATAATGCTCCAAGAAACTATA | 1,173,432 | 91 |
| 3255. | GTTATACAGCTCATATTGCATTAT[T,G]TTTTtATTTTTCAGACCAACTAGAA | 1,173,642 | 91 |
| 3256. | GTCAATAAAGAATGCCAAGAAAGT[G,A]TTATAGTTCGGACACTGATGGTAAA | 1,173,893 | 91 |
| 3257. | TTAATTTATGTCAATAAAGAATGC[C,T]AAGAAAGTGTTATAGTTCGGACACT | 1,173,902 | 91 |
| 3258. | GTCAATAAAGAATGCCAAGAAAGT[G,A]TTATAGTTCGGACACTGATGGTAAA | 1,173,902 | 91 |
| 3259. | AAATATCAATGAATTCTATGAAAA[C,T]TGATTCCTCTTGGGCATTGCATCAA | 1,174,776 | 91 |
| 3260. | GAATGAAGTCAAAAAAGGGACCAG[A,C]aGTTAATTACCTATTATTTTTGTTC | 1,175,255 | 91 |
| 3261. | CGGAGTCCATTTTCTCTTTTATGT[A,T]GAAGGAAAGGGAGGAACGAAGGAAA | 1,175,439 | 91 |
| 3262. | AGGGAGAGCAGCCTCCAACATAAC[C,T]GACACCTTGTGGAGAAGAACAAAGA | 1,175,539 | 91 |
| 3263. | CCATTCCATCGAAAACCTTCCGCG[C,T]AGTCTCCAAATCGCTGTTGTTTATA | 1,175,923 | 91 |
| 3264. | AGAAACTATATCTCTTAGCCATTC[C,T]ATCGAAAACCTTCCGCGCAGTCTCC | 1,175,941 | 91 |
| 3265. | TCCACGCTACCATATCTCGAGTAC[C,T]TGAATATCAATGAATTCTATGAAAA | 1,176,078 | 91 |
| 3266. | AAAGGTCCAAGGCTTCCTTGAACC[G,A]GCCATTCTGTGTGTATCCCGAGATC | 1,176,191 | 91 |
| 3267. | ACCACTAAAAGAATGCTTACAAGC[G,A]TGATTTATTTGGTGCCACACCTGC | 1,176,258 | 91 |
| 3268. | GCAACCACTAAAAGAATGCTTACA[A,G]GCGTGATTTATTTGGTGCCACACC | 1,176,261 | 91 |
| 3269. | TAGAGCCCGAATCAAGGATCAAGTC[C,T]ACTTCCATACCCATCTATCCATGTA | 1,176,351 | 91 |
| 3270. | CACTAGAGCCGAATCAAGGATCAA[G,A]CTGATAATTCTCTATGCTTGAGCTT | 1,176,354 | 91 |
| 3271. | CTATGCTTGAGCTTTTCAAAGATG[C,T]TAGCAGCATCCTCAATGCAGCCACA | 1,176,419 | 91 |
| 3272. | TATGTTAATTTAATTGTGTACCAA[G,A]CTGATAATTCTCTATGCTTGAGCTT | 1,176,455 | 91 |
| 3273. | ACTGTGTACTATATTCATTTAATT[G,A]TGTACCATATTTAGTTAACTGTGTA | 1,176,548 | 91 |
| 3274. | GTTACTTTAACTGTGTATATTATT[T,C]ATTTAACTATGTGCAGTGTTCATTT | 1,176,599 | 91 |
| 3275. | GTATCATGTTACTTTAACTGTGTA[T,C]ATTATTTATTTAACTATGTGCAGTG | 1,176,606 | 91 |
| 3276. | TATATACCATAGTTAATTAACTGT[G,A]TGCCATGTTAATTTAACTGTGTATA | 1,176,735 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3277. | CATATTTATTTAACTGTGTACTAT[A,G]TTTATTTAACTATATACCATAGTTA | 1,176,770 | 91 |
| 3278. | ATATAGTATTTATTTGACTATGTA[T,C]tATATTAATTTAACTATATACCATA | 1,176,899 | 91 |
| 3279. | ACTATGTATATTATTAATTTAACT[A,G]TGTACAATATTTATTAAATTGTGTA | 1,177,198 | 91 |
| 3280. | CGGAGAAACGTGTCTATATAAAAA[T,A]AATAATAAATTAATTaAAAAAATTA | 1,177,943 | 91 |
| 3281. | TTTCTTTCCATTTCTTTATGTATG[A,G]TAAAATGATGGGAGGAGGATTGAAA | 1,177,993 | 91 |
| 3282. | AAGTTGGGGGAGTTGGCCAAAAGG[C,T]CAGTGGGGgAGGGTGCAAGCTCAGA | 1,178,386 | 91 |
| 3283. | GAGGATGTTTGGAAGATTGGGGTA[T,C]GGGTGAGGGCCAGTGAGAAGGGATT | 1,178,517 | 91 |
| 3284. | ATGCCAAGTATATTGAGGATGTTT[G,A]GAAGATTGGGGTATGGGTGAGGGCC | 1,178,531 | 91 |
| 3285. | TATGTATCATTTGGCAATATGGTC[A,G]CACTCGGGCCCGATCAAATGGTAGA | 1,178,844 | 91 |
| 3286. | CAGCCCTCCAACTCTGTCGTCTAT[G,A]TATCATTTGGCAATATGGTCACACT | 1,178,865 | 91 |
| 3287. | CTGCATGCAATGGCTCAACTCTCA[G,A]CCCTCCAACTCTGTCGTCTATGTAT | 1,178,887 | 91 |
| 3288. | TCACTATGGCTTCCACCTTTACAG[T,C]CCGAGTGTCGCCCTCTGCATGCAAT | 1,178,926 | 91 |
| 3289. | TGCCATCTTCATACTTGGATAACC[T,A]GTTCCCATCCGACTCTCACTATGGC | 1,178,966 | 91 |
| 3290. | GGCGTCCACATGGCAAGCCAAGAT[C,T]ATAGGCCCCACCATGCCATCTTCAT | 1,179,004 | 91 |
| 3291. | AAGAAAAGCATCTAAGCTAGGTCT[G,A]GACAAACCCTTAATTATAATTTTAG | 1,179,116 | 91 |
| 3292. | CCTATGGGAAGAAAAAAAaCCTCT[G,A]TGAGTCTTTTTCTTCTTCTTGCAAC | 1,179,169 | 91 |
| 3293. | GCCTCGCCTCCTTCCTCCATTACC[G,A]TCTTTATTATTTCGTCTTTCTGACG | 1,182,789 | 91 |
| 3294. | AAGGGTCGGACCGCTCACTGACTG[T,C]GGCACGAGCGGGACGGCGCCGTCGT | 1,183,067 | 91 |
| 3295. | GGTGGTGGAAGACTTTCGCGGCTC[C,T]GACACATATCGGGAGGAACTCCTGG | 1,183,297 | 91 |
| 3296. | TTAGAGTCGTAGAGTCGTAGACCC[A,G]ACATGCCATGTTAGGTCACTCGGTA | 1,183,798 | 91 |
| 3297. | CGAAGGTTAAAGTCGAATGTGCGT[C,T]GTCCCGACATGAGTTGGGCACGTTC | 1,183,993 | 91 |
| 3298. | ATGGCGTCCGACACGTTTAGTCAG[G,A]AAAATGATGACAAGTCGAGTTTCCA | 1,184,188 | 91 |
| 3299. | CGGGGCTCGTACTTCCTGGCGAGC[G,A]CCGACCCACAGTCGAAGAGTCGAGA | 1,184,542 | 91 |
| 3300. | TCGAAGAGTCGAGATTCCAGACTC[C,T]GAGATTTTGAAATTGAATTTGTATT | 1,184,578 | 91 |
| 3301. | CATCTTGTAGGGTCCTTCCCAGTT[T,C]GGAGCTAGCTTCCCTCGGTCTAGAG | 1,184,751 | 91 |
| 3302. | CCATACGAAGTTACGCCTCGCGTC[A,G]AAGTTCGGACAAGAGGTCTAAGTTG | 1,184,903 | 91 |
| 3303. | CGATCTCCAGCGGGATCATGACTT[T,C]CGTTCCGTAGGCTAAGTTGAAGGGA | 1,185,014 | 91 |
| 3304. | ACACCTCCGAACCAATTCAGCCGC[A,G]TCCTTCTTCATAGTGAGCCAGTAGT | 1,185,576 | 91 |
| 3305. | AGGATTTGCCCCCCAAGTGATTAC[T,C]GCAGATCCCTTCATGTACTTCTCTG | 1,185,653 | 91 |
| 3306. | CAGGCACTTCAGCAAGGGAAGAGA[G,A]AACGATCTTTTGTATAGTCAGCCAT | 1,185,729 | 91 |
| 3307. | GAGAGAACGATCTTTTGTATAGTC[A,G]GCCATCCACCATCACATATTGGGAA | 1,185,749 | 91 |
| 3308. | CGGATCCATCCAATTTGGCTCTGT[C,T]GCCAATTGCAGCACCTCTTCGATCT | 1,185,870 | 91 |
| 3309. | TTCCAGACTTTTTATGAATGTCCG[A,G]CTCAAGGTGCCGTAGTCGGATGTCG | 1,185,936 | 91 |
| 3310. | CTTTTTATGAATGTCCGACTCAAG[G,A]TGCCGTAGTCGGATGTCGCGAGCCT | 1,185,943 | 91 |
| 3311. | TCGCGAGCCTGGAGAGTACGTCGG[C,T]CCGAGCATTTTCCGCCCTGGGGATG | 1,185,983 | 91 |
| 3312. | CGCCCTGGGGATGTGAAAGATCTC[A,G]AAGTATTTGAAGGGTGCTACGAGAT | 1,186,020 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3313. | GACGAGCGCCTCATATTCGGCTTG[G,A]TTGTTGGAGGCCTTGAAGTCGAACC | 1,186,209 | 91 |
| 3314. | GTTGTTGGAGGCCTTGAAGTCGAA[C,T]CGGAGGGCGTGCTCGGTAACCACTC | 1,186,233 | 91 |
| 3315. | TTGAAATTTATGTGAATACCCCTC[T,A]AAATTGATATTTGTATATCCTCAAA | 1,196,408 | 91 |
| 3316. | CATATATACTTTTATAAAATACTT[G,A]TTTTGCATGAATAACCTtTTTTTTT | 1,196,679 | 91 |
| 3317. | GCCAATTATTGCTCAAAGTGATAA[G,A]CTGGGCTTGTTTTGGTCAAGATTGG | 1,196,915 | 91 |
| 3318. | GAACATCATGGAATTTGTGGCCAA[T,G]TATTGCTCAAAGTGATAAGCTGGGC | 1,196,934 | 91 |
| 3319. | GGAAAGGAGTGAGGAGATCAGGAG[G,A]AATGCAAGGAAGTGGAGGGAGTTGG | 1,197,021 | 91 |
| 3320. | TGGAGAGGTGTGTGAGGGTGGTGA[T,C]GGAGGGGGAAAGGAGTGAGGAGATC | 1,197,052 | 91 |
| 3321. | CTAAGTATATCGAGGATGTGTGGA[G,C]GATCGGGGTGCGAGCGAGGGCCAAT | 1,197,130 | 91 |
| 3322. | TGTGGCGCCGATGGTTGGAGTGCC[G,A]CAATGGACGGACCAACCGATGAATG | 1,197,180 | 91 |
| 3323. | CCCTAAGAACTTCATAGAGGATTT[A,G]TCCTCGGAGCGAGGGCTAGTGGTTT | 1,197,327 | 91 |
| 3324. | TCACTCTGTATTCTATCTCGTGCT[T,G]tGCCTCTATTCATGTTGCTGGATTT | 1,198,502 | 91 |
| 3325. | CATTTGCCTCGCATATAAAATCCC[G,A]GCCCAATTATTGGCGAATTTTCGTC | 1,198,734 | 91 |
| 3326. | TAATGAAATGATCATCCCTCGGCA[T,C]TTGCCTCGCATATAAAATCCCGGCC | 1,198,756 | 91 |
| 3327. | GCAGTAACTGAATTCAGATTACCA[C,T]cATGGTCGAGCCACCTTCGATAATG | 1,198,801 | 91 |
| 3328. | TTGGCAAAGATTGGGACACGTTTA[C,T]TTTTCTTTTtGTTTATAACAAATTT | 1,199,193 | 91 |
| 3329. | TGTTTCCTAATTTAGTGCAATTGT[T,C]TGGCAAAGATTGGGACACGTTTACT | 1,199,217 | 91 |
| 3330. | AATTTTAATTACTTCCAGTGAAGT[A,G]CAAATTCTATCTTGACCTGGGAACC | 1,199,412 | 91 |
| 3331. | TGAGCCTTTTCCATGCATCATATT[A,T]ATTTTCAAAAGTTACACGAAGCCTC | 1,199,573 | 91 |
| 3332. | AGCTTGaGTTGTTAAGGATTCAAT[A,T]TGAGAGCAGAGATGAGCAGGAGTTT | 1,199,692 | 91 |
| 3333. | AAGAAAAAAAAaTCTTATAGCTTG[A,G]GTTGTTAAGGATTCAATATGAGAGC | 1,199,710 | 91 |
| 3334. | GATCCATCATCCCCCTCCTATCTT[C,T]TTCCATCTCTCTTTTTCTCTCTTTT | 1,213,581 | 91 |
| 3335. | AATGTCcACACTCCCTTGGCTgCT[C,T]TTCAACAATCGgATGGCTCTCCCAA | 1,213,638 | 91 |
| 3336. | TTTGGCTACTGGATTCATCTCACT[C,T]TCCCCCTCTCTTTCTCTATCTGTAT | 1,213,752 | 91 |
| 3337. | CATCTTGCAAGGAGATGGCATGCG[G,A]CCATTCATCTTTGGCTACTGGATTC | 1,213,782 | 91 |
| 3338. | TCTCCCCCcTTACCTCTCTTTCTC[T,C]CTCTCTTACTCCTCTAGTCTCCCTC | 1,214,058 | 91 |
| 3339. | CgTGATGACTTTAATTATATACAA[C,T]TCATCAGAAGCCTTTTAGAGAGAG | 1,214,330 | 91 |
| 3340. | ATTGTTCATATATTATTTTCAGCC[G,A]TGATGACTTTAATTATATACAACTC | 1,214,353 | 91 |
| 3341. | CAATAGCATATAAATATCAACTTC[C,T]TATATTTTCTTCGATGGATATTTCC | 1,214,427 | 91 |
| 3342. | ATCATCAGATTTACAGAAGTAAAT[C,T]AATCAATCAGTAGATTGATAAATTA | 1,214,560 | 91 |
| 3343. | AGGATTATTAACTTCTTTAGCACT[A,G]GTTCAAGTGCATATGTCATATCTAC | 1,214,610 | 91 |
| 3344. | TTTGAATAATTATATCTTTGCCAA[C,T]AATGATTTGAGTAGGATTATTAACT | 1,214,647 | 91 |
| 3345. | TATAGTTTTATGCACTATGCCATC[C,A]TTTATATTAAATACAAATTTTCAAA | 1,214,720 | 91 |
| 3346. | ATATATAtaTATTAGATTTGATTT[A,G]AGGCTTAAAATAATTATTTTTATAA | 1,214,850 | 91 |
| 3347. | TCCAGTGTGTGGGGTCGCCTTCCT[C,T]AAAGGAGCAGCCTCCACCCACTTTG | 1,215,495 | 91 |
| 3348. | TCCGATGGGTGCTAGTATCCATGT[C,T]GACACTTTGGCACCAAACTATAAAC | 1,215,605 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3349. | CCACATCAGAGCTCCCAGCCTCCG[A,G]TGGGTGCTAGTATCCATGTCGACAC | 1,215,625 | 91 |
| 3350. | AGCTGTGGTTCCACATCTCATCAG[T,C]CGAAAAAATATAGGGAGAAAAAAAa | 1,215,704 | 91 |
| 3351. | CATCATGCAGAGAATGTTTGGGTC[C,T]AATGTTTTGATTATAGCTGTGGTTC | 1,215,743 | 91 |
| 3352. | GCACCGCATCCATCATGCAGAGAA[T,C]GTTTGGGTCCAATGTTTTGATTATA | 1,215,753 | 91 |
| 3353. | AAATAGTTCAAACCAAGGCCATGA[G,A]CTAATACAAATTTACCCAAACAATG | 1,215,826 | 91 |
| 3354. | TTCATCCTTATAACAAATTAATTG[T,A]ATCAATCAAATAGTTCAAACCAAGG | 1,215,858 | 91 |
| 3355. | GCCTCACCTCCATGTTCAGCACCA[T,C]CTTGGATTAAGCTCTTGAAACCTAA | 1,216,033 | 91 |
| 3356. | ACATTTGCCTCTGCCTCACCTCCA[T,C]GTTCAGCACCAtCTTGGATTAAGCT | 1,216,045 | 91 |
| 3357. | CACGATCATTTGCTTCCCCTGAGG[T,C]AGCTCCACCACCCACATTTGCCTCT | 1,216,083 | 91 |
| 3358. | ATGGAGCACGATCATTTGCTTCCC[C,T]TGAGGTAGCTCCACCACCCACATTT | 1,216,089 | 91 |
| 3359. | CAATCGAAACTTAAGAAACCCTTC[T,C]AGAACATGGAGCACGATCATTTGCT | 1,216,119 | 91 |
| 3360. | CTCTAATCTCTCTCATTGTGCTCT[C,T]GTTTCTCACATATCTCTAAAAAAAa | 1,216,316 | 91 |
| 3361. | TCAGAAAAAGCAATTGGAACCTT[A,G]GAGACCTCTCTAATCTCTCTCATTG | 1,216,348 | 91 |
| 3362. | ATTTTTtAAAATTAATATTTAATT[T,A]TATTTATTTTCTGAAGATCTGACCC | 1,216,519 | 91 |
| 3363. | TATAACCTATGTGGTGTAATTTTT[T,G]AAAATTAATATTTAATTTTATTTAT | 1,216,537 | 91 |
| 3364. | AGTTTTATCATGCAAGAGCATTAA[T,C]CATAGAAGCATATTATGCACGCTTG | 1,216,866 | 91 |
| 3365. | CATATCCAGTTTCAAGAGTAATCT[G,A]ATTTTACTGAGTAGACTAAATTCAA | 1,218,151 | 91 |
| 3366. | GGAGCAGTGAGAAAGTTGGGTGAG[A,G]TTCGTTGCATATCCAGTTTCAAGAG | 1,218,183 | 91 |
| 3367. | GCATACACATGATGGAGCAGTGAG[A,G]AAGTTGGGTGAGATTCGTTGCATAT | 1,218,196 | 91 |
| 3368. | TGAATTGAGTTGTGCAATCAAAGG[T,C]ATTGGGATAATCAGCTTGCATACAC | 1,218,238 | 91 |
| 3369. | GATTTGTATATGATCTTTGATGAG[G,A]TATCTACTTCTTTTCTTTAGTGAAT | 1,218,372 | 91 |
| 3370. | GCGGCAAAAGATCGCAAGATAGGC[G,A]GTCCAGGTCCAAGTCGAGGGATTGG | 1,218,545 | 91 |
| 3371. | GATCACTTCTATACTTTTTCAGAA[C,T]GAGATTCTCAGACGTGAGAATTGAG | 1,218,624 | 91 |
| 3372. | TATCTTAGCAACTTCTAAAAGGTC[T,C]tCACTGAACTCCTTAGTATTGGTGA | 1,218,785 | 91 |
| 3373. | TCTCACCAATGCTCTCTTTCTCTG[A,G]AAGTAGTTCTACCAGTTGTGGATGA | 1,218,858 | 91 |
| 3374. | TGCTTAATGAGACTTCTCTGACGG[C,T]GATATGATCGAAGCTCGAGAAGATG | 1,218,922 | 91 |
| 3375. | GGAGCTGAATCGATCAATTTGAAG[G,A]TAAACAGGTGAAGAACCAGCAGTAA | 1,219,883 | 91 |
| 3376. | TATTTTAAATATCTATGTACGCAT[A,G]CTAGTATCATTACTTAATAAACCAT | 1,220,262 | 91 |
| 3377. | CTTTGTGTGAGAAGTTCTGGTATT[T,G]TAAATATCTATGTACGCATACTAGT | 1,220,282 | 91 |
| 3378. | CGATAACTTTTTTtATGTTTCGAT[A,G]ATAGCATTTGTCACCAGTGATGTTT | 1,220,474 | 91 |
| 3379. | GATCGGTAAGCCAAGAGTGATGGC[A,T]aTATTTATAAAAAATCGATCTTGTa | 1,220,690 | 91 |
| 3380. | AACAGTAATATTTGTTGTTTAGGA[C,G]GAAAaAGATATTAAATGCATGATAA | 1,220,821 | 91 |
| 3381. | TCTAGTTCCTATTCAGTCTAATTT[C,T]TTTAGTTCCATGCAAATCCTCTTCT | 1,221,070 | 91 |
| 3382. | TGAGACTATGTCAGTGAAAACTTT[G,A]TCAGTTCTTGAATAAGGACTCTAGT | 1,221,114 | 91 |
| 3383. | GCTCACTTATAGCTGCCTATAACC[G,A]TCTAACAAACTCCTCTAATGGCCTA | 1,221,256 | 91 |
| 3384. | AATTTATTTCTGGATCAGATCGAT[A,T]GAATATCGATTTGATTCAATTCAAT | 1,221,564 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3385. | TCTCTGGCACATGATAATATTAGA[A,G]AGAATTATTTGAGAATTATATTGAT | 1,221,617 | 91 |
| 3386. | AATCTAAAGGTCAAAAGTTATATG[C,T]AAGTGACCCGACTTGCCCACTTCGA | 1,221,697 | 91 |
| 3387. | GAGGAAAATCTAAAGGTCAAAAGT[T,C]ATATGCAAGTGACCCGACTTGCCCA | 1,221,973 | 91 |
| 3388. | GAAGATATGCCCTCAAAGAGGAAA[A,G]TCTAAAGGTCAAAAGTTATATGCAA | 1,221,990 | 91 |
| 3389. | CATTTGATGTGAAGCACCTCCATC[T,C]ATGGGCTGGACTTTGCAACATCGGT | 1,222,074 | 91 |
| 3390. | AGATGAGATGAGACACCTGATCTC[C,T]GgATTGGACCATACAAATACTTATT | 1,222,146 | 91 |
| 3391. | AGTCAATAATACTCCCAACCAAAT[C,T]AGGATAACTTGAAGTGAGGCACCTG | 1,222,224 | 91 |
| 3392. | AAAAGCTGATCAAAGTCAATAATA[C,A]TCCCAACCAAATCAGGATAACTTGA | 1,222,237 | 91 |
| 3393. | CCTTCTTTCCCATGTAAGGCAAAA[C,T]CATGAGGCCCAAAATGACCATGGCC | 1,222,464 | 91 |
| 3394. | TATGAGGGAATAGCTAGTTTAGTT[C,T]CATATCGGTTGTGAGTCAAGAGGGA | 1,222,536 | 91 |
| 3395. | AATAATTTTCAAGTCCTGTATAGG[A,T]TAGTTAAACTTAGATCGGGCTATGA | 1,222,615 | 91 |
| 3396. | TAcACATTGGATTTATTAGTATCG[A,G]TTTgTTCTTAATTAACCAATCTAAT | 1,222,765 | 91 |
| 3397. | ATATTTCTTAAAATGTCTATCATA[C,T]ACATTGGATTTATTAGTATCGATTT | 1,222,787 | 91 |
| 3398. | ATCGGACAGAGATATTTCTTAAAA[T,C]GTCTATCATAcACATTGGATTTATT | 1,222,798 | 91 |
| 3399. | GAGAAAATCATCTGATATATGGGG[G,A]ATCCAATCTATCCACGACGACATCG | 1,222,844 | 91 |
| 3400. | TTCAAGGTTGACCTCATAAGGCAT[T,C]AACTTGACAAGTTTTGGCTCAAATT | 1,222,940 | 91 |
| 3401. | GGACCTGAGTTCTGATTAAGACTA[T,C]AACGTATTCAAGGTTGACCTCATAA | 1,222,971 | 91 |
| 3402. | TTTCAATATAGCCATCAACCAGTT[C,T]ATCAAGATGAACACCACATTGATGA | 1,222,072 | 91 |
| 3403. | TCAGAAGCAGTTTCACCTCCACTT[T,C]AATATACCACAGAGTAGCAATTAGA | 1,225,200 | 91 |
| 3404. | CTCCATCTGATTTTTGACTTATTT[T,G]ATAGATTTTTTtGAAGCATTTCAAA | 1,225,431 | 91 |
| 3405. | GCATCGAAGGGTTAAGAACTGGAG[A,G]ATCTCCATCTGATTTTTGACTTATT | 1,225,458 | 91 |
| 3406. | TAAAAATAGAAAATCAGGGATCCT[T,C]CAATAGTTAGTTTAAAATCCTAATT | 1,225,667 | 91 |
| 3407. | CTAACGGTCTAACAAGTTCTGTAA[T,C]GGCCTCATCAATCcTTCTATAAAAA | 1,225,711 | 91 |
| 3408. | AGTTCACTTACAGCTGGCTATAAC[C,T]GCATAACAAACTCTTCTAACGGTCT | 1,225,751 | 91 |
| 3409. | TATGTTACAACTTATCTCTAACTG[A,G]CACGTACAGTTAAGTATGATCTCAC | 1,225,829 | 91 |
| 3410. | AGAATTATATTGATCAAAATCTAC[T,C]TCTGGATCAGATCGGTTGAATACCG | 1,226,036 | 91 |
| 3411. | CCCATCTCTGGCACGTGGCAATAT[T,C]AGAGAGAATCATCTGAGAATTATAT | 1,226,076 | 91 |
| 3412. | GGATGAGGGTAACGAGATTAAATA[T,C]ATAGTAACTGTTGTAAGGGTTATAC | 1,226,280 | 91 |
| 3413. | AATTAGATAATTTGGTACTTAGGA[T,C]GAGGGTAACGAGATTAAATATATAG | 1,226,301 | 91 |
| 3414. | TAATATTTTTtATATAGGCAGCT[T,C]TGATGTTATGGATACGGAAATGAAA | 1,226,404 | 91 |
| 3415. | ACCCGTGGTCAAGTGATTTTTTTt[A,T]AAAATTCCCTTAATATTTTTtATA | 1,226,439 | 91 |
| 3416. | GCTTCGACTtACAACACAGCCCCA[G,A]CATCAATCTCTGCATGCAATGGCTC | 1,227,935 | 91 |
| 3417. | TCAGACTCTCACTACGGCTTCGAC[T,C]tACAACACAGCCCCAGCATCAATCT | 1,227,951 | 91 |
| 3418. | CATATGGCGAGCCAAGATCATAGG[T,C]CCTATGGTGCCATCCTCATACTTGG | 1,228,015 | 91 |
| 3419. | ATGGATTTCTATTCTATTATAGCC[C,T]AGCTTTGCAGCAATTGAGGATTTTT | 1,228,204 | 91 |
| 3420. | GAACGTGTTCTTAGATAATTTAAG[C,T]TAGCTAGGTCAATAGGCCCAATTCT | 1,228,844 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3421. | GGTCTTGTATCAACCAAAATACAA[G,T]CTAGTTTAAATCCTAGAAGGAAAaA | 1,228,964 | 91 |
| 3422. | AGTGTGGTCTTGTATCAACCAAAA[T,G]ACAAGCTAGTTTAAATCCTAGAAGG | 1,228,969 | 91 |
| 3423. | TACTACTAGAGGACCGGTGCCTCG[C,T]AAGGATGAAGAAGAGTTCCGCTTGA | 1,229,157 | 91 |
| 3424. | AAAGTTtGTTGGATAATGAGTGCG[A,G]GTTAACTAGGTACATCCTTAACTAC | 1,229,294 | 91 |
| 3425. | TATAGCAGAGATAGAGTAAAAGTT[T,C]GTTGGATAATGAGTGCGaGTTAACT | 1,229,312 | 91 |
| 3426. | TAAAACTTTGTTGGATAATGAGTG[C,T]GAAAAACTTATGACTTAGGTTGTTA | 1,229,374 | 91 |
| 3427. | TGTGTTAGAGCAGAGATGAGTAAA[A,G]CTTTGTTGGATAATGAGTGcGAAAA | 1,229,394 | 91 |
| 3428. | CTACTTTTtGTTTTtAAATGTGGA[G,T]TAGCCAATGTATTTGAAAATCTTAT | 1,229,465 | 91 |
| 3429. | TTTGGACTACGGTTCATGTGGGTC[C,T]TGGATCTTCATGCGATCCGAGATGA | 1,229,559 | 91 |
| 3430. | AATTTAATTTCTTTGAGTAGGTTA[T,G]TAAAGGATTTGGACTACGGTTCATG | 1,229,591 | 91 |
| 3431. | ACTATAAAATTATTAAATATTATA[G,A]AATTATAAAAATTAATATTTTGAGA | 1,231,148 | 91 |
| 3432. | GTCCACATTGTGACCTATTGAAAG[G,A]AATTCTAGATTTCATTTTAATACGT | 1,231,201 | 91 |
| 3433. | TAATTATTTTTTtAAGATCGATA[G,A]TATTTGTGTTCAATAGGTTTTTGGA | 1,231,280 | 91 |
| 3434. | CAAATCTTAATTGTTTGCAGTCGG[G,A]TACGATGAAGTGAATGACAGTATTT | 1,239,773 | 91 |
| 3435. | GATAATGTTTTCAATTGGAGATCG[G,A]CCATTAGGCTATTTTATAACAAATT | 1,239,983 | 91 |
| 3436. | AAAATTAAGCTATTAGACGACCTC[C,T]GTATGATGGTGTTTTCAATTGGAGA | 1,240,012 | 91 |
| 3437. | AATTAGTGGGAAGGATAGACATGA[A,G]ATTTTCAAAAATTAAGCTATTAGAC | 1,240,044 | 91 |
| 3438. | TTTTCTTTCCTTTCAAATTTCATC[G,A]AAACAAAAGTCCCAAGCAAAATTAG | 1,240,088 | 91 |
| 3439. | TCGTACAGAATAAAGTCATTCATC[T,C]ATAGATACAAATCTCAAAGTACTAC | 1,240,138 | 91 |
| 3440. | ATCTATCCATTTATATAGATCGTA[C,A]AGAATAAAGTCATTCATCTATAGAT | 1,240,157 | 91 |
| 3441. | TATCCTCTATCATTCATCAATTTG[T,A]ATGAAATTTAAAATATTATATTTTC | 1,240,210 | 91 |
| 3442. | AATATTCTATTCTCTATCATCTAT[C,T]TATTTACATACATCTTAAATCACTC | 1,240,396 | 91 |
| 3443. | TTTgAAGTACTTCATCCTTTGTCA[C,T]CCATCTCAAAATATTCTATTCTCTA | 1,240,430 | 91 |
| 3444. | CATTGATCTATCTACACAGATTTT[G,A]AAGTACTTCATCCTTTGTCACCCAT | 1,240,451 | 91 |
| 3445. | ATCGATTTGCATGAATGTTGATGC[G,A]TTCCATCTTCTATCATTGATCTATC | 1,240,489 | 91 |
| 3446. | ATTTGTCTATACAGATCTTAAAAT[A,G]CTTCATTTATAATTTATTTATCTAT | 1,240,745 | 91 |
| 3447. | CATTCATTTACCTACATATATCGC[T,G]AAGCATTTTGTCTGTAATCCATTTG | 1,240,790 | 91 |
| 3448. | GCGAGCATAGATCGTGAAGTGCTC[T,C]AGCTTCAACCATCCATCCGCATATA | 1,240,867 | 91 |
| 3449. | AATCTTAAAATACTGCATCCTTTA[T,C]CATTCATTTGCGAGCATAGATCGTG | 1,240,901 | 91 |
| 3450. | ATTTACATAAATCTTAAAATACTG[C,T]ATCCTTTATCATTCATTTGCGAGCA | 1,240,910 | 91 |
| 3451. | ACTCATTTAACTATTCAATCCATT[C,G]TCCTTCGTATGTTCTTTACTTGTAT | 1,241,148 | 91 |
| 3452. | ATGGCATGAGGACTGTTCCATGCT[T,C]GTTTGTTTATTTTATTCCTTGAAT | 1,244,429 | 91 |
| 3453. | GGTCGGCTGTTTCCTgACGCACTG[T,C]GGATGGAATTCAACTATGGAGGGGA | 1,244,890 | 91 |
| 3454. | TTGGGTGGTGAGATCCTCGGAAAC[C,T]TCTAAGCTCCCAGAGAACTTCATGA | 1,245,010 | 91 |
| 3455. | TATGCTTGGCCCCGACCAAATGGC[T,G]GAGCTTGCATTCGGTCTTCTCAATA | 1,245,076 | 91 |
| 3456. | CCGCAAAATTAATTCTATTTTTtA[A,T]ATTTTtAGTTTTGAAATTAGAAAGA | 1,245,359 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3457. | AGCTACAATATTAAAACTTAAGAT[A,G]TAGCCGCAAAATTAATTCTATTTTT | 1,245,387 | 91 |
| 3458. | TATTTTTAGTTTCATTAATTCTTC[C,T]TATCATCCACGATTGCAATTAGCAA | 1,245,850 | 91 |
| 3459. | TCTCTCTTTGCCATAATTCCATTT[A,G]TTACCCACTAAAAGACTTAGTTTGA | 1,245,994 | 91 |
| 3460. | ACAGCTTGGAATATTTTGTACTTG[T,A]CTCTCTTTGCCATAATTCCATTTAT | 1,246,018 | 91 |
| 3461. | TTGTGACAGCTTGGAATATTTTGT[A,T]CTTGTCTCTCTTTGCCATAATTCCA | 1,246,023 | 91 |
| 3462. | TGTTTCTGACTAGGAATAGTCATA[C,T]CTTCACCCAACAATATTCTATATCT | 1,246,394 | 91 |
| 3463. | ACTTAGATCTCAATGTGAGATGTA[G,A]TTCTAGCAATGATTTGATAAGCATT | 1,246,997 | 91 |
| 3464. | CATGCCCCTCTCCCTGAGAAGTGT[T,C]TGAGTAAAGAGACAGTCCTAGGCAA | 1,266,011 | 91 |
| 3465. | CGGATGAGCGACAACTCTCCAAAT[T,C]TAGGCAGCCTCAATCCGTCTAGAGA | 1,266,086 | 91 |
| 3466. | GTTGAGTGATCTTTTATACTCTCA[G,A]CTGAAAGTATCAACAGCAATGAGAT | 1,266,274 | 91 |
| 3467. | GGCCAATGAGATAAAGGAATGCTC[A,G]AAATCCAAGCATCCTGGATCACCCC | 1,266,368 | 91 |
| 3468. | CAAGAAATTGCGAAACTGCTGCTC[T,C]AGCCTTCTGACACAAGCCACGGGGA | 1,266,736 | 91 |
| 3469. | ACGCACCTCGTTATTCAAAATCCT[A,G]TTCTCCTACGCAGTAATACAGACCA | 1,267,910 | 91 |
| 3470. | CAAATTTTTGATAAAAATTTAATG[A,T]TTCACCACCTCCCTCTTATTCATTT | 1,275,287 | 91 |
| 3471. | GTACCACTTTGCCCAAAAAATACA[G,C]AGGAAGATGGACTATACAGATGTAT | 1,275,369 | 91 |
| 3472. | TCTCATCCCTTCTCACAATCCCAC[T,G]CTCATCTACTCTTGCTCGCACTCCC | 1,276,186 | 91 |
| 3473. | TGAAGCTAAAGTTATGGTCTTCAG[G,A]TCCTTTTAGTTGCTACTCTAGCTA | 1,276,371 | 91 |
| 3474. | TTCTGATGACAAGCAGCTTCCAAC[A,G]AGTCATCATAAACTTCATGTTACAT | 1,276,467 | 91 |
| 3475. | GAGCTTGCAGAAATGCCCTTTTCT[G,A]ATGACAAGCAGCTTCCAACAAGTCA | 1,276,487 | 91 |
| 3476. | TCTCAAGATGACTCATCCTGCTGA[C,T]TGTTAGAAAACTACGCAATGTTAAG | 1,276,568 | 91 |
| 3477. | AAAATGCTAATATTGAAGGTGTTC[G,A]CATCACACTAAGCACCGATCATGCA | 1,276,706 | 91 |
| 3478. | AAGGTGCTGAAAGACATTCATTAT[A,G]TTCTTCTTCTTCTTCTTATTCT | 1,276,912 | 91 |
| 3479. | CTCCAGTTCTACAAGAAACAATCT[G,C]TGCTTATCCTTGTCCTTTCTTCTTT | 1,277,099 | 91 |
| 3480. | TGAGGTTCTCCAGTTCTACAAGAA[A,T]CAATCTGTGCTTATCCTTGTCCTTT | 1,277,106 | 91 |
| 3481. | GGGAAATATCATAATGCCAGACCC[G,A]gAACATAGTATAGCAGAATTAGCAC | 1,277,239 | 91 |
| 3482. | CATCTTTTTGGTCAGGGAAGGTCT[G,T]GTACTTCGCTCATACCTTATTCAAA | 1,277,351 | 91 |
| 3483. | TTTACATCTTTTTGGTCAGGGAAG[G,A]TCTGGTACTTCGCTCATACCTTATT | 1,277,355 | 91 |
| 3484. | GGGGTTTATGGTGCAATCCAAGTT[A,G]CAGCAAGAGAGCCTTTCTCTGAT | 1,277,475 | 91 |
| 3485. | TGAAGGGGTTTATGGTGCAATCCA[A,G]GTTACAGCAAGAGAGCCTTTCTC | 1,277,479 | 91 |
| 3486. | TTCATAGGCTCATTGCCAAGGCTC[C,T]AGAGATGTGAAGGGGTTTATGGTGC | 1,277,511 | 91 |
| 3487. | TGGCGGAtGCGTTGTCATTAACGA[C,T]GCTAAAAaGCGCCGTTAAAAGTTAA | 1,277,752 | 91 |
| 3488. | AAACTGTCAACGCCGACGCTTTTA[G,T]CAAAAGCGTCGTTAAATAAAGAAAA | 1,288,154 | 91 |
| 3489. | TGCATGGCTGTTGGCTACCAAAGC[T,C]ATTGAGAAAAGCCAAACGTCTGAAC | 1,288,690 | 91 |
| 3490. | TTGCTAAACTGATGCGTTTTCTT[A,G]GGGGGTTTATAAAGCGATCGAAAGA | 1,288,863 | 91 |
| 3491. | AATTAAATAGTCAATTTGATTGTA[G,A]GTAGCTCAAATACTTGAAGATGTTG | 1,288,910 | 91 |
| 3492. | ATGCTCAGAATGTCCTCTACCTTG[A,G]CTCCAAGGCACATTTAACCTTCAAA | 1,289,146 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3493. | ATTGAACTAGAGAGATCTGATACA[T,A]AATCACTAGCCCTCTGTGTCTTGCA | 1,289,355 | 91 |
| 3494. | CATTGAGGTCATCTGGAAATTGAC[G,C]ACCACTTTTGATAGATGAGAGTTGG | 1,289,423 | 91 |
| 3495. | TTACTTGCAAACAGGGACATGGCA[T,G]GGAGGTATCATCTAAAGAGCAATTA | 1,289,564 | 91 |
| 3496. | CAATTACTTGCAAACAGGGACATG[G,A]CATGGAGGTATCATCTAAAGAGCAA | 1,289,567 | 91 |
| 3497. | TTCTAATACAGAAAAGATAGTGTG[G,C]CATCAATCCAGTACAAATATCAGGT | 1,289,653 | 91 |
| 3498. | ATATAAATCAATGAAATTTAACGA[T,C]GAAAATTTGCTTAGAATAAACCAAT | 1,289,702 | 91 |
| 3499. | TAAGAAATTAAGAATATAAATCAA[T,C]GAAATTTAACGATGAAAATTTGCTT | 1,289,715 | 91 |
| 3500. | CACTTGTTATCATCTAAGCTTGAT[A,G]CTTTACAAGTCTACATTTTGCCTTC | 1,289,842 | 91 |
| 3501. | GATCATAATTTAGCAAAATCAGTG[C,T]TGTATTATACTGATGTTTTTCCCTC | 1,289,911 | 91 |
| 3502. | CATCCCACCATACGTGTGGGCCCC[C,T]AATGAAACCAAGCCCCACGCTAGTG | 1,290,538 | 91 |
| 3503. | GTGCCCACCGCATCCCACCATACG[T,C]GTGGGCCCCAATGAAACCAAGCCC | 1,298,548 | 91 |
| 3504. | GTCCGGGATCTGCCTGCGAGAGAA[T,G]GACACAAGCTGTGCCCACCGCATCC | 1,290,583 | 91 |
| 3505. | AAGGCATGGACAACGGACTCATTT[A,G]TTTGTTATGGTTGTGCAATTTGTTA | 1,294,974 | 91 |
| 3506. | ACGGACTCATTTATTTGTTATGGT[T,G]GTGCAATTTGTTATGGTGATAAAAA | 1,294,986 | 91 |
| 3507. | AAGAAATTTGTTCTTCACTTGCTT[G,C]TCATGTCACACACATTTTCAGTCCC | 1,295,175 | 91 |
| 3508. | ATCCTAAATTTGCATATCTGCATC[T,G]ATGGACACATGTTAAGAGGCAATAA | 1,296,045 | 91 |
| 3509. | CTATCCCTTATTCCTCGTTCTAAT[T,C]TTTATTGTTGTACATGTAGTCATTG | 1,296,105 | 91 |
| 3510. | CCGCCATTTCTCAGTTTGCAAGAC[T,C]CGTGTCCCAGGTGGTTGTGCACATT | 1,296,374 | 91 |
| 3511. | CAAGAAGGAAGAACTGAAATGGAA[C,G]CTGTTGGTCAGCAAAGTGATGGCAG | 1,296,649 | 91 |
| 3512. | TAGGTTGCCAAaGCTTGTTGCACC[G,A]TGACGGTGCCACCGTATGTAAAGAA | 1,296,855 | 91 |
| 3513. | TGTATTCTGGTGACTGTAACAATA[T,A]GGTGGAATTGAACAAAATTTTGTAT | 1,297,006 | 91 |
| 3514. | AGCTTGAGGATTGAGTTGGGAGAG[A,C]ACAGATTAGGGTTATCACGACCATG | 1,297,188 | 91 |
| 3515. | GGAGAGAACAGATTAGGGTTATCA[C,T]GACCATGGTTATGAATCGCTTTTGT | 1,297,206 | 91 |
| 3516. | GAGAACAGATTAGGGTTATCACGA[C,G]CATGGTTATGAATCGCTTTTGTCT | 1,297,209 | 91 |
| 3517. | ACAGGTAACCCCAGAGAATATCAA[T,C]TGGTGAGCAAAAATGAGGTAACAAC | 1,297,354 | 91 |
| 3518. | TGCTACTCTGCATTTTGAGTTTCT[A,T]CAATTGGCTCAAATTTACTGTCTGG | 1,297,408 | 91 |
| 3519. | TTGTTCTTTCTCTCTTTTTTTTt[A,T]TTTTGGCTCCCATCCTCTCGTTTTC | 1,299,247 | 91 |
| 3520. | GCTCCCATCCTCTCGTTTTCAGAG[C,A]AGAAAATACGAGTCTTAAATCACTC | 1,299,277 | 91 |
| 3521. | AAAATACGAGTCTTAAATCACTCC[C,T]TGACGCACTGTTCTAATCTCATTTA | 1,299,304 | 91 |
| 3522. | CTTGGTGTCATCATTTTGTCTTTC[T,C]TCCTTTCATCTGATGGTTCCCAGCT | 1,299,599 | 91 |
| 3523. | GGTTCCCAGCTATGCCATCCAGAG[A,T]CTCACTCCCTGTTCGTACTCCATTT | 1,299,638 | 91 |
| 3524. | CATCCAGAGACTCACTCCCTGTTC[G,T]TACTCCATTTAACTCACCCGGCGTT | 1,299,653 | 91 |
| 3525. | AATTTCTCCATATTTAATATTAT[G,A]TAAATTTTtCTTTTCCATCTATCC | 1,301,403 | 91 |
| 3526. | CACATCCTCCCTCTCCCTCCGATT[G,T]AGGCCATGAACTAATAACTGACCAG | 1,301,487 | 91 |
| 3527. | AGTTCCTTGTTCTCTCTAATTTTG[T,C]TTGTCCTAGTTTAGGATCTTTTTG | 1,301,767 | 91 |
| 3528. | TGTGGAATGAGATAGAGATCCTTT[T,A]TTAATTTTTtAATTGATATTCTTTG | 1,302,537 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3529. | TTCAATTAAATTTGAAAGGTTGCT[G,A]TTTTATTGTGCTTCTGCTATGTGCA | 1,303,432 | 91 |
| 3530. | TATCAGCAAATATGCTTTATGCTA[T,C]GGTACCTAGACTCTCTATTTTTAAG | 1,303,928 | 91 |
| 3531. | TTAACATATCTTTTTCCCAGTGG[A,G]ATGTAGGGGAACTCTTAGTTTTAAG | 1,304,087 | 91 |
| 3532. | TTTAAGTGCTGGATACCTTCAATT[T,A]GAATATAAAGTTTTCAAGGTTTTGT | 1,304,131 | 91 |
| 3533. | CATATATATATATATGTCTATACA[C,T]GTGTATATATGCATACATAAATGCA | 1,304,562 | 91 |
| 3534. | TTACCGTACCATATGGTGTACCGA[C,T]ATCGTAACAGGATGGTACTGAGACA | 1,304,784 | 91 |
| 3535. | CCGTACCATATGGTGTACCGACAT[C,T]GTAACAGGATGGTACTGAGACAGTG | 1,304,787 | 91 |
| 3536. | TTATTCTAAACGTGAAAAACTATC[C,G]TGCAAGCACAAACTGAATAACCAAA | 1,305,022 | 91 |
| 3537. | ATAGAAGGATGGACGGAAATGATT[T,C]CCTCCTTTGTTTGGTATAGGAAAAA | 1,305,491 | 91 |
| 3538. | TCTATCCTTCCAATTTCATCCATA[A,C]ATTTTCTAATGACTCCAACAAAACA | 1,306,155 | 91 |
| 3539. | TTCTAATGACTCCAACAAAACATA[A,G]GGTAATTTTCACCGTAAGAAACGAA | 1,306,183 | 91 |
| 3540. | ACATTGTTGATTTAAACTAAAGCT[A,G]AAGTAAATATTTTTAAAGGGGAACT | 1,306,279 | 91 |
| 3541. | TTTTTAAAGTAATTAGTGACTTCT[C,A]CAAAATAGAAGCCCATTAACTAAAA | 1,306,364 | 91 |
| 3542. | ATGATCAAATCTGTTTCTGTATCT[A,G]GTTCGGATCAGATTTGAATAGAGAT | 1,306,721 | 91 |
| 3543. | TTGGATTTGAATATAGATATTAAG[g,A]TTTTTTtGGATCCAGATGCAGATAG | 1,306,868 | 91 |
| 3544. | CCTCTTAGGAGCCTCCAACTGTCA[T,C]GGATGAGAGGGTGTTGAGCCGCTCC | 1,307,273 | 91 |
| 3545. | TAGAATTCTCCTCAATCATCAATC[A,G]ATTGGCCCTTAGGACCCCTTGCATG | 1,307,358 | 91 |
| 3546. | GTCGAAGTTGACCTTTAGAAATCT[G,A]GGGGATGGGGGCTCCCAAGTGAGAA | 1,307,548 | 91 |
| 3547. | GCTCCCAAGTGAGAAAACTCATCG[A,G]GACACTACATGAGCGTGAGGGGGGT | 1,307,583 | 91 |
| 3548. | GCACCCTAGGAAGAATAGTGGACA[G,A]CCGCTAGATGTGCGTAGCTCTCAAA | 1,307,882 | 91 |
| 3549. | GGTATGCATGAAGACCACCATATC[T,C]TGGTGCCAGGGCCACTGTGGACAGG | 1,308,168 | 91 |
| 3550. | ACAAAGGTCAGACACCAGCACAGC[G,A]GAAGGTCAACTACTCACGAGTCTCG | 1,308,347 | 91 |
| 3551. | TGATCGAGAGCCCATCCCCCACCC[A,G]CCAAGAAGTCAGGGCCAACACCTCA | 1,308,405 | 91 |
| 3552. | GTAGTTTAGGATTCATATTTGGCA[C,T]GCATCATCGTACTCCAGGGGTTGCT | 1,308,521 | 91 |
| 3553. | TGCCAAGCGATCAGAGCCTTGTGC[T,C]GAACCACTAGGATCTTTATGCCTAG | 1,308,596 | 91 |
| 3554. | ATTGATCGGCTGACAAATAACCTT[C,T]CATGCTAGAAGATGTACCCCATTTC | 1,308,655 | 91 |
| 3555. | ACCCCATTTCCTCCATGGTGCGAA[C,T]CACATAGGAAGTTCTTGAAGAGTTG | 1,308,695 | 91 |
| 3556. | ATATTTTAAAAATCTTTTTATTTA[A,T]AATATTCAAAAATACCAATAATGTC | 1,308,925 | 91 |
| 3557. | TTTAAAATATTCAAAAATACCAAT[A,G]ATGTCAATATATTCCTAATTTGTAT | 1,308,945 | 91 |
| 3558. | TTTATTTAAAAATAGATGATTCAT[G,A]ATTCTTTTTATTTATGCTGCAATTA | 1,309,008 | 91 |
| 3559. | TGGATATAACTAATACCGGACTTG[A,T]ATCCATATTTGTATTCATTAAAAAA | 1,309,387 | 91 |
| 3560. | TGGAACCAAGGTTTTAAATCTCTT[A,G]GGACGAGACTGTTCCGATTTTTTCA | 1,310,016 | 91 |
| 3561. | TAGGACGAGACTGTTCCGATTTTT[T,C]CATGGAATGGGATGCGCCGCCGTCC | 1,310,039 | 91 |
| 3562. | ATGGGATGCGCCGCCGTCCCGTCC[C,T]GTCCTGATACTTGGAATAGAGGATG | 1,310,070 | 91 |
| 3563. | GATATCCCAATCGGGACATTGGA[T,C]GCTAGTGGGACACTGTATCCCAACA | 1,310,126 | 91 |
| 3564. | GACATTGGGATGCTAGTGGGACAC[T,C]GTATCCCAACACATGGGATGGTATC | 1,310,140 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3565. | AATTTGGCAATTTTGCTAGTAAAA[G,A]GTCATAATATTTTTTTCAGAGACAT | 1,310,311 | 91 |
| 3566. | TTGCTAGTAAAAGGTCATAATATT[T,C]TTTTCAGAGACATGTAAAATAAAAA | 1,310,323 | 91 |
| 3567. | GATGCACCTCTTTGACACTTCATC[T,C]TGAAAAGATCTCAACTACTATGAGG | 1,310,488 | 91 |
| 3568. | CATGCACCTTTGTTTTAAAGTTCT[C,T]TATCCACTATGTTGATAGAGTGGTG | 1,310,573 | 91 |
| 3569. | AGCTAGGCCCGCAACAATTTTGGC[T,C]GGGTTCGGGCCTAAACATAGGGTCC | 1,310,817 | 91 |
| 3570. | GGGTTCGGGCCTAAACATAGGGTC[C,T]GTTTGTCTTTCGGGCCGGCTCAAGC | 1,310,842 | 91 |
| 3571. | TCTTTGGTCCAGCCCGGGCTCGGC[T,C]TGGCTCGAGCCCAAGCTCGAATTCC | 1,310,895 | 91 |
| 3572. | TCGTGCCGTGCTTGGGAGAAGCCC[T,C]TGTGCTCTATCCAAAACCCTTCAAT | 1,310,964 | 91 |
| 3573. | TCTCTTCATTCCCCGACGGCGTGC[T,A]AACCCTTTCCTTCCCCTCCCACCGC | 1,311,029 | 91 |
| 3574. | TCCCCGACGGCGTGCTAACCCTTT[C,G]CTTCCCTCCCACCGCCACCTCGTC | 1,311,038 | 91 |
| 3575. | CAGTACATGTTTTGCTTTTTCTCA[C,T]AGCCAAGGACCGTCGAACCAGAATC | 1,311,327 | 91 |
| 3576. | GTCGAACCAGAATCAGAGCTCGTG[C,T]TGGCCGGTCGGCGATACGATTCAGT | 1,311,363 | 91 |
| 3577. | GATTCAGTATGGGTCTGTACTATT[C,T]TGTGCGGGGCCGAACTGATAGGGTA | 1,311,405 | 91 |
| 3578. | GAGGGCCTCCGGCAGGTGCTCTCA[A,G]GTCCCTTGGCGTGGGCTCGTCGGTC | 1,311,505 | 91 |
| 3579. | GTGGGCTCGTCGGTCGTTGGAGAC[A,G]TCATGGTGGCAGTGCCATCCATCCG | 1,311,540 | 91 |
| 3580. | CATCCATCCGGAGGCCTTCGACGG[T,C]CTCCAGACATCCAGTAAGACTCTTC | 1,311,580 | 91 |
| 3581. | TAGCCCATTAGGAGGATACTCATG[T,C]CGTGCTTAAGAGAAGCCCCTGTGCT | 1,311,886 | 91 |
| 3582. | GCCATGCTCCTGCCGTCGTTGTTC[T,C]GCTCCCTCTCTTCTAGCCTCGCTCG | 1,312,026 | 91 |
| 3583. | ACCGGCATCTTTCTTCCCCACCTT[G,A]TTGCCGCCATGGTGTGCCCTTCCTT | 1,312,104 | 91 |
| 3584. | GGGCCTTAAATTTTAAAATATTTT[C,T]GAACCTAAGCTCGCCTTGACGTCTG | 1,312,228 | 91 |
| 3585. | CCTTAAATTTTAAAATATTTTCGA[A,G]CCTAAGCTCGCCTTGACGTCTGAAA | 1,312,231 | 91 |
| 3586. | TTTTCGAACCTAAGCTCGCCTTGA[C,A]GTCTGAAAAAATATTTCGGACCGGG | 1,312,248 | 91 |
| 3587. | ACCTATTTCCAGCCCTATTTCTCC[C,A]TGGAATAGGATGCCCCACTGTCCCA | 1,312,329 | 91 |
| 3588. | AACAAGACAGGACAGCTGGGACGC[C,T]CCTCGTCCTGCTGGGACGTCCCCTG | 1,312,650 | 91 |
| 3589. | TGCCTCTTAATACAATTTGGCTCA[C,T]TAACGTGCATACATGCTATATGTG | 1,312,770 | 91 |
| 3590. | CCTCTTTCTCTTTCTCCCCCCTTT[C,T]CCTCTCTCTTTCCCTTCCATTTTGT | 1,313,334 | 91 |
| 3591. | GATACCAACTACCTCACTAGAACC[C,A]AAAGAACCTATTGGTTGGTGCTATT | 1,313,790 | 91 |
| 3592. | TGGCAAGGTTCTAAATACTAGCCC[T,A]AATAGGACATGCCTTTACTGACATA | 1,314,210 | 91 |
| 3593. | TCTGGTGGTATACTGAACCCTGGT[G,A]CCATACCAGCACTGTGCCGACTGGC | 1,314,303 | 91 |
| 3594. | GTGGTTTCATTCTGTTGTAACTGC[C,T]GAGCTTTATTCCTTAACTGCAGCGA | 1,314,823 | 91 |
| 3595. | GAGCAGATCACACTTCAAGATACT[T,A]TGGATGGCACAGGATATTCGACATT | 1,341,901 | 91 |
| 3596. | AGAAACAAATGTTATGAACCCCAA[G,A]CTGATGCGCAAAACAAAAACAAAAA | 1,315,726 | 91 |
| 3597. | TTGTTAAATATTCCAATCTTCCTT[C,T]TTCTTGTTATTTGAACTTCAGAATA | 1,316,345 | 91 |
| 3598. | AACTTCACTGAGAAAGGAGGCACT[T,C]TATGTTACTGAATCTTCTTTTGATT | 1,317,496 | 91 |
| 3599. | AAGGACACCAGTCTTGAGGATAGG[G,A]CCGACACCGCCACCCCCAAAGCAG | 1,318,228 | 91 |
| 3600. | ATTCCCGTTTGTATGACATCCATG[T,A]ACCAGCTGTTATTGTAAAGCCTATC | 1,318,458 | 91 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3601. | TATTGTGAATCCTGATTCTAGGAC[T,C]ATGGTCAGAAGTCATATATGTTACT | 1,319,112 | 91 |
| 3602. | TCCCCTTTGCAGTGCAATACGGCA[A,G]CAACTGATAAATGCTGAAGATATAC | 1,319,211 | 91 |
| 3603. | ATGCTTTCATTATAAAATCAACAT[G,T]GTGGTGAATTACCAAGTTCATTATT | 1,319,418 | 91 |
| 3604. | ACTTCTTTACAATAATATGCATCA[C,T]GTGGATTTCCACTTAGATCCTGTCA | 1,319,718 | 91 |
| 3605. | TACTATCTCTATATTGCTTACACA[C,T]CAAAAATCTTGTGATTTGGAGAGCT | 1,319,825 | 91 |
| 3606. | ATTTAATGCAAACATGTAAGAAGA[G,T]GCCTGTTCAAAGATCATGTGTTAAA | 1,321,390 | 89 |
| 3607. | CAGATGTTAGTAAAGATTTATACT[T,G]CTACAGAGGTATATAGGTATATGTG | 1,321,443 | 89 |
| 3608. | CTTATTTCAGCCGTAGTCAATTAA[A,T]CATAACTAACCGTGTTCTTTCCCAT | 1,321,862 | 89 |
| 3609. | CTATGAAGTTCATGCTCGCATCTT[G,A]TTATCTATATACTTTCGAGTTGTCT | 1,321,986 | 89 |
| 3610. | CCTTCATTTCTTCTTCAATTGGTT[A,C]AATTGTTATTCTTCTCCAATGTATT | 1,322,116 | 89 |
| 3611. | TTTGTGTTCTTTTCCCTGTGTTAT[G,A]AGTCATCTCTATCGATCAGAATTTG | 1,322,395 | 89 |
| 3612. | TAGTTTGAGAATTTGATCTAGTTT[G,A]ATGTTACGTTGTTAACCCTTCATGA | 1,322,453 | 89 |
| 3613. | TCAACTAATGGCAATAGATTAAAC[G,A]TGCATCCCTTTAAGGAAATTTTGGT | 1,322,946 | 89 |
| 3614. | TGATTGACGACTATATGTTCCTTA[A,C]GTTGGAAAAATAATAAGTGTACCAC | 1,322,289 | 89 |
| 3615. | TCTTAAAATTGTCTTATTGAGAAT[C,T]AAATGACAACAGAAACAGCAATTTG | 1,323,401 | 89 |
| 3616. | CTCTAAACTTCCCACACACCAAAA[A,G]TCATTTGACTTGAAGACCTTTAGCC | 1,323,586 | 89 |
| 3617. | GCATGCTCGTGATACTATTTTGTA[G,C]GCTCAAGGAACAAAGTGTTATAGGA | 1,324,584 | 89 |
| 3618. | GCTGGTCCTCCCGGACAAGGTAAC[C,T]TCCTCAACTTGTTGTTTCATTTATG | 1,324,983 | 89 |
| 3619. | TTGCAAGCAACAAAAATGTTTTTG[A,G]GTTAAATATCTCATAATCATATGTT | 1,325,302 | 89 |
| 3620. | ATCATTATAGTTATCTAATTTGCT[T,A]TGGTGAGGAAGGCCGACATGCTGCA | 1,325,506 | 89 |
| 3621. | TGCACGGAAGCATGTGTATTGCGC[T,C]GTTTCTGTTTTGTCTGTCCATGTG | 1,325,727 | 89 |
| 3622. | ATTAATTATAGAAGTTTATGATTG[T,A]GGATTTCAATGCTGATCATTATCTG | 1,326,298 | 89 |
| 3623. | GGAGAACACTAAAAGAACCAGCAT[G,A]TGCTGGAATATGTTTTTCATATAGA | 1,326,421 | 89 |
| 3624. | ATTTTAGATGCTTTATAGCACCTT[C,T]GTTGGTTTCAATCCTGCTATCAGGA | 1,326,656 | 89 |
| 3625. | TGTTGGTATTCTGTGAAGTTAACT[G,C]GTCTTCATGTTCCTTCAATCAGAAA | 1,327,172 | 89 |
| 3626. | TGCTCCTGTAAACCGCCTGACACC[G,A]GAGACTGAATCAGAAAGTTGCTTT | 1,335,468 | 89 |
| 3627. | CATATGTCTGGTATTCTAGAGAA[T,A]TTGAGTACAAATGTCAGGAGATGTA | 1,336,079 | 89 |
| 3628. | CATTGAATTAACCCATTAAATTTC[A,G]TGGATAATTGTTCTCTTTTGGCCCA | 1,336,346 | 89 |
| 3629. | GTTCCAGCTACAGAAGAAGAAGCA[C,T]GCCGGGTACTTGAGCGCATTGATGC | 1,336,478 | 89 |
| 3630. | CTGAGACAATGTTTAGTTAATTCA[T,A]AATCTAGCTATCTTCTTTAGTGAAA | 1,336,527 | 89 |
| 3631. | AATCCTTTTTTtCGTTGAGCCTC[T,G]ATAGGAAATATTCCTGGCAAGGGCC | 1,337,115 | 89 |
| 3632. | CCTGGGATTGAACCTCCGACTTCT[T,C]GTATTGCTTGTCATGTTAAGATTAC | 1,337,170 | 89 |
| 3633. | TCTTGTATTGCTTGTCATGTTAAG[A,G]TTACTTTGTATTGCTCAAGTACCTC | 1,337,191 | 89 |
| 3634. | TTCTTCTCAGGGAAAGCGTTGGTT[G,A]GTGACTGGATTCCATGCATTACCTG | 1,337,446 | 89 |
| 3635. | GGAAAGCGTTGGTTGGTGACTGGA[T,A]TCCATGCATTACCTGTGCCTAATCT | 1,337,456 | 89 |
| 3636. | GCAATCAAGCATATTTATGCTCCA[G,A]TAGCCTGGTTGGCTTCTAAACACTC | 1,337,586 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3637. | CTTCTAAACACTCGAACAAGTATA[A,T]TCACATTTTGATTGTTTTGTGTAAT | 1,337,623 | 89 |
| 3638. | GATTTATCCGCTGCCTTCGGTGTG[A,G]TGTATCAAATTCATGAAAAATGAAT | 1,338,259 | 89 |
| 3639. | GATTTATCCGCTGCCTTCGGTGTG[A,C]AGTTACCCTATGATCAAGTCATCGA | 1,339,420 | 89 |
| 3640. | AAGTTACCCTATGATCAAGTCATC[G,A]AAAGGATCCCATCCATCATTTCTAA | 1,339,444 | 89 |
| 3641. | AATTAAAACTGTTATTAAGGCAAG[T,C]CTATCCTATATATCAAATTCATTGA | 1,339,494 | 89 |
| 3642. | ATCCTATATATCAAATTCATTGAT[A,G]GTTCATAACCTCAAATTTGCAACTA | 1,339,521 | 89 |
| 3643. | CAATAGCATGTCATAGTTATAATC[A,C]GATGGAAAATCTAAATCTACTTGTT | 1,339,603 | 89 |
| 3644. | CATAGTTGTTTTATAATGACTTGG[G,C]AGATTGTAGTTGTTTCAAGTCATCT | 1,339,776 | 89 |
| 3645. | GACTTTGTATGGTAGTGGTGGACC[T,G]CCATATAACTTTAATCAGAATGTAA | 1,339,884 | 89 |
| 3646. | CCAGGTTTTGTTTAAACGGGCCGT[A,T]CCCATTTAGTCGCGCCCGGCACGGC | 1,340,096 | 89 |
| 3647. | TTAATTTTTATATCATTGCATGTC[C,T]GGTCATGCAAGGTCAAGCCTAAAA | 1,340,371 | 89 |
| 3648. | GCAAAGGTCAAGCCTAAAAAGCAA[G,T]CCATACAGGAGCGTGCGGCCATTAG | 1,340,402 | 89 |
| 3649. | TCATTGATTTTTATGTTTCCTTT[T,C]GAATCTTTTCTATGAGGCATGCTTT | 1,340,514 | 89 |
| 3650. | ATTGATTTTTATGTTTCCTTTTG[A,C]ATCTTTTCTATGAGGCATGCTTTCT | 1,340,516 | 89 |
| 3651. | ACTCATAACAATGAGCTGCACAAC[T,G]GAAACTTGTTCCAAATTCTGCACAT | 1,340,962 | 89 |
| 3652. | TTAATGATCTCGTCCTCTGCCTTC[T,C]TTAAGAACCCACTCATAGCATCATG | 1,341,577 | 89 |
| 3653. | CCTCTGCCTTCTTTAAGAACCCAC[T,A]CATAGCATCATGAAATTGCTGGCTA | 1,341,590 | 89 |
| 3654. | ACACCCAAGGCCAGCGACAGCTTG[G,T]AGGCCAAGCTTTCTGCACTCAAGGT | 1,341,774 | 89 |
| 3655. | GCCAGCGACAGCTTGGAGGCCAAG[C,T]TTTCTGCACTCAAGGTCATCTCGTA | 1,341,783 | 89 |
| 3656. | CTGATTGAATTTTAATGATGACAA[A,T]TGCAAATTCAACAGCACTGAACTT | 1,342,238 | 89 |
| 3657. | TAGAAATGGAATGTGTGGGTGAGA[C,T]GAAAACTAGGAGGACATGGAAAGTT | 1,342,358 | 89 |
| 3658. | TTTGCAATTCAAATAGGATATTGT[G,A]AAATTTATTCTCATAATCAAGTGTA | 1,342,480 | 89 |
| 3659. | GTGAAATTTATTCTCATAATCAAG[T,G]GTAAAGTTGTTGATATtCTTTTTTA | 1,342,502 | 89 |
| 3660. | ACTCAAATGTACTTGAACATTTTG[T,C]CGATTGTTCAAATTATGAAAGAAAG | 1,343,291 | 89 |
| 3661. | CTGTCTTTAGTAAATAAGCCATGA[A,C]CGCTGCATGATATATGACATTACTT | 1,343,454 | 89 |
| 3662. | GTCACATGGAAGAATTGCAAAGTA[C,T]ATACATAAATAAAAATTTGCCATAC | 1,343,547 | 89 |
| 3663. | GGAAGAATTGCAAAGTACATACAT[A,C]AATAAAAATTTGCCATAGTATCATA | 1,343,554 | 89 |
| 3664. | TTTAAACCACTACTTTATCTACTA[T,C]TTTACTAGTGATTGACATGCGATAG | 1,343,741 | 89 |
| 3665. | ACTATTTTACTAGTGATTGACATG[C,T]GATAGTTCACTTTTTTCCTATCCAG | 1,343,761 | 89 |
| 3666. | TAGTGATTGACATGCGATAGTTCA[C,T]TTTTTTCCTATCCAGAATAGAATTG | 1,343,771 | 89 |
| 3667. | TAGATTTACCTCAAGAGTTTCAAA[C,T]GATTTCTTAAGATAATTGACCTCTG | 1,343,841 | 89 |
| 3668. | CGCATCCACTCTCTTAAAAGCAAA[C,T]GGTATATCAAGCACTGCCTTGAGAA | 1,343,916 | 89 |
| 3669. | AATCAACCACAAAAATACCAGTAA[A,G]AATAACTTCATTTGAGTTAAAATTG | 1,344,115 | 89 |
| 3670. | AATCAACCACAAAAATACCAGTAA[A,G]AATAACTTCATTTGAGTTAAAATTG | 1,344,129 | 89 |
| 3671. | ATACAGAAGACTTCAACAACTGAA[T,G]GGGCTAAAACAAATGGTTCAGAAAAT | 1,344,181 | 89 |
| 3672. | GATACTTGATATTGCATTTCATTA[T,A]GCATGACCAAAAAAAGAAGATTAA | 1,344,367 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3673. | TGCATGACCAAAAAAAGAAAGATT[A,G]AACAGCTACAATTGATACATGACAG | 1,341,391 | 89 |
| 3674. | GCATATAGATTGCTACCGAACAGC[T,A]TTTTTATTTTACTATCATTTTGACT | 1,344,673 | 89 |
| 3675. | ACAAAACTCTAGTTAATATCTTGC[G,T]GCCATTGGGATTAGGAAGCTCACCG | 1,345,087 | 89 |
| 3676. | CTTGCGGCCATTGGGATTAGGAAG[C,T]TCACCGAAACAAAAGAAGCAAACTG | 1,345,106 | 89 |
| 3677. | AGGCCAACAAAGAAAGAACACCTA[A,T]CCCTTGGCTAAAATATAGAACAATA | 1,345,201 | 89 |
| 3678. | ACCTAACCCTTGGCTAAAATATAG[A,G]ACAATAACCTTTTTGGAGGCAAGTG | 1,345,220 | 89 |
| 3679. | GCAAAGGGGACAGATGGTTACATG[T,C]AAACTCCAAAGCACCATACCTCACC | 1,345,270 | 89 |
| 3680. | ATCTATTTTCCAACATACACCGAG[A,G]TTGAGGGAGAGTTTATACGTGAATA | 1345,419 | 89 |
| 3681. | CAGTTCATAACGGTGATCAAATCT[G,A]ATTAGGAAAAAATGAGCACTGGCGT | 1,345,557 | 89 |
| 3682. | AAGCATTTTTATCACAATATTGGT[A,C]ATAAAGTTCAAAAAGAGAAAGAGAT | 1,345,910 | 89 |
| 3683. | GGAGAATAACAGCAGGAAGAGAAG[C,G]AAGAAGAAGGAAGGGACTGGCATAT | 1,347,534 | 89 |
| 3684. | TTCTTTTCTTTTCTTCTCCATTTT[C,T]CCTTTTTTTTTTtGTTGCCTCCT | 1,347,691 | 89 |
| 3685. | AAGGAGACGAGAAGATCATAGTAG[C,T]AGAGCAAGACTAAAACAATTAATTA | 1,347,767 | 89 |
| 3686. | AAGGCCGAGAAAACATTGTCGGCC[G,A]GAGAGAACAAAAATGTGGCGGAGAT | 1,352,528 | 89 |
| 3687. | ATATAGATATATTGATATTTATTT[C,T]GTATTTGATCTATTTTTGATCTCAA | 1,353,125 | 89 |
| 3688. | CAATGTACTTATTTTAAATTGGTA[C,T]GAGCGGCTGTTTGTATAGAAGAAAA | 1,353,172 | 89 |
| 3689. | TACTTATTTTAAATTGGTACGAGC[G,C]GCTGTTTGTATAGAAGAAAAAAATT | 1,353,177 | 89 |
| 3690. | CCCCGCGTCTGGATCTCTGGGAAA[C,G]GACAAGAGAAACGGGAAAGCGGAAG | 1,353,391 | 89 |
| 3691. | CGTGAAACGGGAATCGCGGCCTGG[A,G]GTGGTTGCAGCATGTGCGCGCCCCA | 1,353,460 | 89 |
| 3692. | GATTCTCCTGGGAGGTTCCAGGGG[A,G]GCGACGTCAGCGGGTCTGCGAGGCG | 1,353,528 | 89 |
| 3693. | TGGTTGGATAGATATCAAGTCCAC[A,C]GACCAGTGAGATTTTTTTTTTTt | 1,353,808 | 89 |
| 3694. | AAGTATCATTCTATTCTTCTCTCT[C,A]TTGCTTGATCTGGTATAATACCCGA | 1,354,139 | 89 |
| 3695. | TATCATTCTATTCTTCTCTCTCTT[G,A]CTTGATCTGGTATAATACCCGATGA | 1,354,142 | 89 |
| 3696. | TTTAACACATTTGAAGAAAAATTT[A,G]CATTTAGAAGTTCCATGTTAAGATA | 1,354,318 | 89 |
| 3697. | AAGATAATCGATGGCAATTCATGG[C,T]GTATGGCCTTAATTAAAATGAGTGT | 1,354,362 | 89 |
| 3698. | ACCAAGTAACTTCCTTGATTTTGC[A,C]TCTTCTTTCATTGTGGTAGTACCCA | 1,354,891 | 89 |
| 3699. | ACCAAGTAACTTCCTTGATTTTGC[T,C]AGGTGGTCTAAGATAATTAAAGGTC | 1,354,943 | 89 |
| 3700. | TATATTGGTTGGGTGATTTACACA[C,T]GATGAGCCATTTTTTAAGAGGAAGA | 1,354,003 | 89 |
| 3701. | TGAGGTGATAAATGCAGTATATAT[G,A]AAGATCAATTGCGGTGATAGCACTT | 1,355,097 | 89 |
| 3702. | GCAGTATATATGAAGATCAATTGC[G,A]GTGATAGCACTTACATACAACATCT | 1,355,110 | 89 |
| 3703. | TCCTCATACTGATATTCTTTTTCC[C,T]GTTGAATGCATGAAACTATTGGTTT | 1,355,165 | 89 |
| 3704. | CAAATCAAAATTTTATATAATAGA[A,G]ATTTTATATCAATGATCCAAATTAT | 1,355,290 | 89 |
| 3705. | TTATTGAATACAATCTACCATCTC[A,C]AAATTACTTACACATAAAATATCAT | 1,355,336 | 89 |
| 3706. | ATGTATCAAATAGTAAAAAATTGA[G,A]TAGTCTAAATAAAATTGAATTATAT | 1,355,408 | 89 |
| 3707. | ATTTTTAGATTATGATAAGTTAGA[G,A]ATTTTCAGATCATATGATTTTTGAT | 1,355,460 | 89 |
| 3708. | ATTTTTGATATGTAAGTAGTTTTG[A,C]GACAGTAGGTTACATTCAATGACTT | 1,355,501 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3709. | GAAAGTTAAAAATTTTCTGGCCAA[T,C]TTATTTCTGTTTGTTGATTTTTAA | 1,355,654 | 89 |
| 3710. | TTTGTTGATTTTTTAAAATAAAAA[A,G]TAATATGATCAGGTAGGTCTTAAAT | 1,355,688 | 89 |
| 3711. | ATCAGGTAGGTCTTAAATCTAAAC[A,T]TCACGTTGCTGTTAGATTCTAATTT | 1,355,720 | 89 |
| 3712. | AATTTAATGATCCAATCTTTTCTC[T,G]GGAGCTTCTTATTTTATTGCATGGA | 1,355,765 | 89 |
| 3713. | AACCGCCATTAACAATGCAAGAAA[G,T]GTATCATTTTTATATTATTATTACT | 1,355,887 | 89 |
| 3714. | TTACTGGTCGTAATCTATTTGTTT[G,A]CATGTTTGTTTAATCTTTTATGGAC | 1,355,932 | 89 |
| 3715. | CCAGTGCGAATATGTTTGAGTTTC[T,C]GGGGGACATTAATAATTATTATGAT | 1,356,053 | 89 |
| 3716. | ATATTATAAAATATTAATTTGAAT[T,C]TAATTTATTAAATTAATTTAAATTA | 1,356,356 | 89 |
| 3717. | CAAGAGAGAAAGTCTCTGTACACC[A,G]TAATAAAGTTGACGTAAAACGTATC | 1,356,771 | 89 |
| 3718. | TTAATATCATTATCATCTTTATCA[T,C]TAGCTATTTAAGTAATATAAATAAA | 1,357,494 | 89 |
| 3719. | TATCATTATCATCTTTATCATTAG[C,T]TATTTAAGTAATATAAATAAAATTA | 1,357,498 | 89 |
| 3720. | GTAGGGGACAGGGAATGGATGCTA[G,A]CAAAAGATCTCTTTCCTTCTGGAAA | 1,357,630 | 89 |
| 3721. | CTAGCAAAAGATCTCTTTCCTTCT[G,A]GAAAAATTAATCCACTTTCACACGT | 1,357,651 | 89 |
| 3722. | CATTAAAATTGATATCCATATCTC[C,T]CAAGTTACTACTCCTCTGTCTAAAA | 1,357,725 | 89 |
| 3723. | AAATTGATATCCATATCTCCCAAG[T,A]TACTACTCCTCTGTCTAAAATCATT | 1,357,730 | 89 |
| 3724. | GCAGGTAGATGGGGATGCAGGGGT[G,A]GGGACAAAATATTATGATGTTGCAA | 1,358,232 | 89 |
| 3725. | TCAATTCTGAATTTTTAATGATAA[C,G]AGCTCAATCATGGGCTCCAAGAACA | 1,358,469 | 89 |
| 3726. | GGAAATATGGTAGAATCTTATAGC[T,A]AAGGAGCTTTGCTGACAATCTAAGA | 1,358,564 | 89 |
| 3727. | TCTTATAGCTAAGGAGCTTTGCTG[A,G]CAATCTAAGAAGAAGGTTGAGTAGT | 1,358,579 | 89 |
| 3728. | TTGAGTAGTGATGGAAGGCAAAGG[G,A]CCCTGCAAATAGGCAAGAGTAATTT | 1,358,620 | 89 |
| 3729. | TAGTGATGGAAGGCAAAGGGCCCT[G,A]CAAATAGGCAAGAGTAATTTTATTC | 1,358,625 | 89 |
| 3730. | GCAAGAGTAATTTTATTCTAAACA[G,T]GTAAATAATTACAGATACACAAGGC | 1,358,657 | 89 |
| 3731. | TTTCATGTTTGGGGAAAAAATTCT[A,T]GTACTGAAATTATCTAAACTAACTT | 1,358,899 | 89 |
| 3732. | TCTTACTTAAAACTAGTCTCTCTT[G,A]GAAAAGAAAAAAaTCCTACTTAAAT | 1,359,028 | 89 |
| 3733. | GCCATGAAGCCCAATTTATGCTTA[A,G]GGGCCTCCATATAGATATGTTGACA | 1,359,133 | 89 |
| 3734. | GCCAACACATTTATTATTTACAAA[G,A]GAGAAAATATAGCTCAGCACCCGTT | 1,359,214 | 89 |
| 3735. | CATTGCGCATGGATTCTATGTCAG[G,C]TAATTGATCATTTGTTTAAGAAaAA | 1,359,291 | 89 |
| 3736. | ATTTATACTTGTAAATGAGCTTCA[T,A]TGCCATTCTTTAACCGTACAATGCT | 1,359,410 | 89 |
| 3737. | AAGTGAGCTTTAAAACTATCCTTT[A,C]ATAACATAATGTTTTCGCTTTTAGC | 1,359,476 | 89 |
| 3738. | TTCGCTTTTAGCTAGTATGGTATT[G,A]TAGGTTGATTTTGATCTAAATGGTA | 1,359,514 | 89 |
| 3739. | GTGAGAATGTATTGTTTATGTAGA[T,C]AACTTAACTTGCTAATGAATTTtTT | 1,359,571 | 89 |
| 3740. | GCATGGAGTAAATCAATTATATCG[G,A]TCTATGATTTAAAATAAATATTAAA | 1,359,842 | 89 |
| 3741. | AGAGAATTATAAAAAAaTAATTAT[A,G]AAAAaTATTAAAAAaTATATAAATT | 1,359,907 | 89 |
| 3742. | ACAAATAATCTCTATTCTAATTTT[C,T]TTCTTATGTCTCTCGTACACTTTTA | 1,360,018 | 89 |
| 3743. | GTCTCTCGTACACTTTTACATCCA[A,G]AGAAAACTCTAATGATTCTTTTAAA | 1,360,050 | 89 |
| 3744. | ACTCTAATGATTCTTTTAAATAGA[A,G]CATTATATAGATGAAAGTTTAACTC | 1,360,080 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3745. | TAAAAAATTAAAAaTTTATTAAAA[T,C]ATAAATTTTAATAATTTTTAGAAGG | 1,360,140 | 89 |
| 3746. | AAATAATTAAATGGAGTAACATTG[G,A]AAATAGAATCTTAAAGTTATTAAAA | 1,360,190 | 89 |
| 3747. | AAAACTAATCATCAACTAAAAATA[A,G]AATTCTAAATGAATTGAGACTTGTT | 1,360,236 | 89 |
| 3748. | GTGCTGGAAAATCTGAACCTAATT[A,G]GTGGTTAATATCTCAATTCAAATTT | 1,360,316 | 89 |
| 3749. | ATTTTtAATTTTTTTtAAGGGTAA[G,T]AACCCACAGGCATGTTTAAAGCGAA | 1,360,494 | 89 |
| 3750. | CTACTGGAGATCGGGAAACACAGA[A,T]GAGTTCATGTTCATTTCTAAATTTC | 1,360,550 | 89 |
| 3751. | TTATAACACCAAATGGAGCAATCA[T,A]GTTTAGTTGATGTATATATACAACA | 1,360,718 | 89 |
| 3752. | CTTAATTAGCATTCTTTTGTAGAA[A,G]ATGGGCAATGACTGCTTCATGATGG | 1,360,863 | 89 |
| 3753. | TGACTGCTTCATGATGGAAAATGT[G,A]GCTGTTATTGATCCTTTTATTGTTC | 1,360,896 | 89 |
| 3754. | GCTGCTTTACGGATGGATTTGTCC[G,A]TCGGCTCAACAATGAATAATTAATA | 1,361,166 | 89 |
| 3755. | ATTACAATAATAAATAAAAAaTTT[A,G]TGATAAAATTATCATTAGAATCTAC | 1,361,256 | 89 |
| 3756. | AAAAaTTTATGATAAAATTATCAT[T,G]AGAATCTACATGAATCTCTAGGCCC | 1,361,272 | 89 |
| 3757. | TCTCTAGGCCCTTCAGCTGTTCAT[A,G]ACCATGCAAAAACTCCACTAATTAG | 1,361,311 | 89 |
| 3758. | TCTAGGCCCTTCAGCTGTTCATAA[C,G]CATGCAAAAACTCCACTAATTAGCT | 1,361,313 | 89 |
| 3759. | CACTGAGATTATATAAGAAAAATT[G,A]GAATTATATAAACTTGTACTATTAA | 1,361,413 | 89 |
| 3760. | AAGGGAAGTGTGACTTGCCTTTCC[C,T]TCTCCTTTTTCTTTACTCTTTAATA | 1,361,589 | 89 |
| 3761. | GATTCCTGGGCCAGTGAATTATGA[A,T]GCTTTGCATGAACTATAAATGATCC | 1,361,689 | 89 |
| 3762. | TCCCTTGCTAAAACTTTTGGCACA[A,G]GTAGAAAAGCTCTAAAACCTCACAT | 1,362,199 | 89 |
| 3763. | CGAATTTATAATAAAACAACAACT[A,C]AATTACAACTTAATTTAAATATTGG | 1,362,537 | 89 |
| 3764. | TCCACTACGAACAGAACGCATGTT[A,T]TGTGATGCTTGTCTCATGGGTCACT | 1,362,88 | 89 |
| 3765. | TAGGAAGGAAAAAAGATAGCACTT[A,C]CATACTGCTCCATACTCCTTTTGTT | 1,363,074 | 89 |
| 3766. | TTCGGTTTTATCACAAGAGGAAG[G,C]AATGAAAAGCAGTACTTTTGGATGT | 1,364,985 | 89 |
| 3767. | TGTCAAGTGTCAAGATTAAAGAAA[C,T]TTTTAGACTATGATGAGCATCACCT | 1,365,064 | 89 |
| 3768. | AAATGGAGGGGAAAATCATCAATA[A,G]TACACATAAAGTGTTATGATCTCCA | 1,365,405 | 89 |
| 3769. | CCATTTTTTCGATAAAACTATGA[A,C]ACTTATTCACCGTCGACTTTATTAA | 1,365,452 | 89 |
| 3770. | AATATTTTACAATTTAATATCATT[A,G]ACGAAATTCAATCATTAGCCTCTTT | 1,365,541 | 89 |
| 3771. | TTCATATTGGCAATTGATTCTTTC[G,C]TGGGCCAACCTGATTCCCCACCCAA | 1,366,194 | 89 |
| 3772. | GGCCAACCTGATTCCCCACCCAAT[T,A]GTTTAAACCAATTGTTGTGCCCTAT | 1,366,221 | 89 |
| 3773. | CTCAACCAATGGGCTAGCACCAGC[C,A]ACAGCAGTAGATAATGTCCCAAACT | 1,366,431 | 89 |
| 3774. | TTAGGCCATTGTTTCAGAGTACAC[A,C]AATTTACACACAAGGGAGCAGAATG | 1,367,082 | 89 |
| 3775. | TTTCATGAAACATTTATATGAAGA[A,T]ACGGCTGTCTAGGTACAACTGAGGT | 1,367,504 | 89 |
| 3776. | TGGCAAATAGGCCATCACACGACT[A,G]TGGTAGGTAGGTCGAATTAGGAGAT | 1,367,617 | 89 |
| 3777. | CTTGGTCCCAAAATTCATGGCAAA[T,C]CATCCAAATTACTATTCCAATGGGC | 1,367,791 | 89 |
| 3778. | CATATGGCCTTTCATCATTTTGAG[C,T]ATTTTCTGTCACCTAGTATATATTA | 1,368,071 | 89 |
| 3779. | CAACTAATGTTATCAAAGTTTCCA[G,T]GTCAATTGCAACATCCGTTTGTGT | 1,371,479 | 89 |
| 3780. | ACCGCAATGCAGAAAGAAAGCATA[T,C]AGGTGAATTGGGTGCACCTGCATGT | 1,371,536 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3781. | GGTGCACCTGCATGTCCTCATGTG[G,A]AAGATATCATTGTCCAACAATAAAA | 1,371,571 | 89 |
| 3782. | AATAATAATGCCTAATGAACTTGT[A,G]CATTTTCATTTGCTAGCCCTTTGGA | 1,371,967 | 89 |
| 3783. | CATGCTGCAAATAGGAAACGATGA[T,C]TGAGGTTCTTTGGAGTTTAGAGTTG | 1,372,170 | 89 |
| 3784. | TTCTGAGAATGGCAGTCCTTAATT[C,T]GATGGCCTCATGAATCGAAGGTCAT | 1,373,513 | 89 |
| 3785. | AATATGTAGAGAGCAAATAATGC[T,C]ACCATGCTTGCCATTTTATTGTTTC | 1,374,208 | 89 |
| 3786. | TGTGGGATGGAGAATGAGATTGCT[T,G]CACAATCTTCATCATGACTTCACAA | 1,374,261 | 89 |
| 3787. | ATGACTTCACAAGGAAAATCTGGT[G,T]GCATATTACTGAGATATTGTCATTT | 1,374,299 | 89 |
| 3788. | TAATCACAGAAACATGCTCTAATA[G,A]TGATTATTCTATGAGCTCTCTATTT | 1,374,645 | 89 |
| 3789. | TTTGCCAGCATGGCACGTACTGTG[C,T]GATGCATTGACATACAACATGCACC | 1,375,874 | 89 |
| 3790. | ATTTTTCCAGGTTTTATTTTTTTT[A,T]AACTTTGACATTTGAACTTCGTCCT | 1,375,985 | 89 |
| 3791. | GACATTTGAACTTCGTCCTAGTCC[G,A]GTTAAGAGTTGCTCACAAAATTAAA | 1,376,016 | 89 |
| 3792. | CAAGTTAAACTTATTTTGATGAAA[C,T]TTGAAACGTTGACCATTTCTATCAA | 1,376,663 | 89 |
| 3793. | TAGGAAAAGCAACTTATCAATAAC[A,G]AGCATAAGAGGAAAGAAGTTCTAAC | 1,377,079 | 89 |
| 3794. | TCTATTTTTCAAACTCATCATATG[C,A]TAAGGTTGATTGATCACATGACCAT | 1,377,213 | 89 |
| 3795. | GATCAGTGTCACCAAAAGAATGTC[G,A]AGTTCAAATTTGTGCAGGCAGATA | 1,377,376 | 89 |
| 3796. | TAAAGAGTGGGCCTTGGTGCAACA[A,G]TTTGGTTGCTTCATTATGACATGGG | 1,377,619 | 89 |
| 3797. | AAGAAAAGTAAACTAAAGGCAAAC[C,A]ACACTTATCTCTATCTAAACTTAAT | 1,377,799 | 89 |
| 3798. | CATGTAATCAGTATGAATAGATTA[C,T]CACAAAATCTGAAGTTTTAATGAAC | 1,378,234 | 89 |
| 3799. | TTATTTGTCAGAGTTATGATGAAA[G,C]CATGGAAAATGTAGCTAAAATTTAG | 1,378,409 | 89 |
| 3800. | TCAGAACACGTAAATGTAGGTTTT[G,T]CTGGATATATTTGAAGGCACCAAGC | 1,378,949 | 89 |
| 3801. | TCTTTGTTCCTAATCCATCTGCAA[T,A]AATGATAAAAGTACATAACTAATTC | 1,379,070 | 89 |
| 3802. | CTTTGAGCACTTGCTTACCTTGCC[A,G]ATTAACATTACATCACCAATAAAAT | 1,380,653 | 89 |
| 3803. | TTACATTATTTAAGATAAGGGATA[G,A]AATAGCCAAATTATTTGCATATATG | 1,380,951 | 89 |
| 3804. | AGCAGACTAATTATCACTAATACA[T,A]CATCCAATCATTCATATGTCCATCC | 1,381,031 | 89 |
| 3805. | CCAAATTGTTTAGTTTACTCTGTC[G,A]GCAGTAACCCTAAAATGGTAGCTCA | 1,382,247 | 89 |
| 3806. | ATTGATAAGAAACCCAACTGAAAC[C,T]GGGGTTCCAATTGTTCAAAATTATT | 1,382,297 | 89 |
| 3807. | CAACTGAAACCGGGGTTCCAATTG[T,C]TCAAAATTATTTTCCTAATACAAAA | 1,382,311 | 89 |
| 3808. | GATATGTTAGAGGCAACAAATGGG[C,T]CTATTTACACCGAATTATCATGGCC | 1,382,671 | 89 |
| 3809. | TAAGTTCCATTTTTTAAAAAAAa[C,T]ACTTTAGATTAAATCAAGATGTTTG | 1,382,798 | 89 |
| 3810. | TAAAAAAaCACTTTAGATTAAAT[C,A]AAGATGTTTGAGGATTGAAGTCATT | 1,382,813 | 89 |
| 3811. | AAATATATCTCTTCTTTCTGTTTT[G,C]TCGAGACATGGTCTAAAAATCAGAT | 1,383,026 | 89 |
| 3812. | AAGAAGGAACAAGGGAAAAAAGAA[C,A]AAGGAGGAAAGAAAGGAAGGGAAAA | 1,386,486 | 89 |
| 3813. | CGTTAAAGAGATGGAGGGTACCTA[T,C]GGGACAGGATAGAATAGCGGGCAT | 1,386,588 | 89 |
| 3814. | TCCCGTAACTTTCAACAAATAAAG[T,C]GAAATAATATATTGGTGAAAATGATA | 1,389,152 | 89 |
| 3815. | GTAACTTTCAACAAATAAAGTGAA[T,C]AATATATTGGTGAAAATGATATGAG | 1,389,156 | 89 |
| 3816. | AAAATGATATGAGATTGTTAGTTG[T,C]CAATTACAGTTGGTCTTGGAATTGA | 1,389,193 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3817. | TCATGACTCTATTTCTGCATTTCA[G,A]GAGAGGAAATGAGAGGATTAGATGT | 1,389,764 | 89 |
| 3818. | TTGATTTGAAGCATTCATATTTTG[G,C]GATCATGGTGTTTGTGGGGCTTTA | 1,389,940 | 89 |
| 3819. | CTTTACCTATCAAAGCTACATCCC[A,G]TGTTGATTTTAAGCATACATGGTTT | 1,389,985 | 89 |
| 3820. | TTAAGCATACATGGTTTGGCATTA[T,C]ATGTTACACATCACAGTGTTTGTGT | 1,390,018 | 89 |
| 3821. | GTACACTTTACATATCAAAGCTAC[C,A]TACTCTGTTGATTGTATGCATACTT | 1,390,139 | 89 |
| 3822. | ATAATAAAAATTAAACCTTATCA[A,G]CTAGTATGCATTATATGTTACATAT | 1,390,220 | 89 |
| 3823. | CCCCGTCACCCCTCTCTTTACCAC[G,A]TCTCTGGTCCCCTCTTTCTCCCAT | 1,391,647 | 89 |
| 3824. | CGTTTTCTCGAGCCCCCGATCGTT[C,G]GATCCCATCTTTCAGAGCCCCCAAC | 1,391,737 | 89 |
| 3825. | ACTTGCAATGCCTTATTTTCCAAT[A,G]GCAGATTTGAGCCTTTTTCTTTTCC | 1,393,454 | 89 |
| 3826. | TTTTtATTTtATTTTTtAAAAAAA[T,A]TTTCAATGGATTCGGGTCAAGCTTG | 1,393,554 | 89 |
| 3827. | CATCACAGTAGGTAAGTTAAGTAG[T,C]TGAGCTCGTTGTCGCTCATTCAGCT | 1,393,970 | 89 |
| 3828. | TAATTAGGTTTAAGTCAGAAGAAG[G,A]AGATATAGAGGTCAAATCAATCTT | 1,394,048 | 89 |
| 3829. | TGATGTCGGGGTTGATAGGGAGGT[T,C]AACGGGCTCCCACTCAAAAAGGGCA | 1,394,970 | 89 |
| 3830. | CGGGCTCCCACTCAAAAAGGGCAG[T,G]CTCGCCAACCTCGCCGACGGCAGCT | 1,394,997 | 89 |
| 3831. | AGGGCCGGCTCATCGGACCTCGTC[G,A]ATGGTGGCTGGGGGCCGATGAGGGG | 1,395,192 | 89 |
| 3832. | CATCGGACCTCGTCGATGGTGGCT[G,A]GGGGCCGATGAGGGGGGCTAGCGCG | 1,395,202 | 89 |
| 3833. | GCCAGAATATCTCAGCTCAGCTCG[G,A]CTCATTTTTAGGGCTACATGGGTTG | 1,395,555 | 89 |
| 3834. | CAATCGAGGAGAGAGCTCTCAAGC[T,C]GCCAACTCGCATTCTTCTGCACTAT | 1,395,642 | 89 |
| 3835. | AGAGAGCTCTCAAGCTGCCAACTC[G,A]CATTCTTCTGCACTATACGTATTAC | 1,395,651 | 89 |
| 3836. | GATGTGGAGTCACCAGTGACCCCA[C,T]AGTCACACAAAGCCGCATCCGACTC | 1,395,783 | 89 |
| 3837. | AAAGCCGCATCCGACTCTCAGAGT[C,T]AGATGCATGGTAGAGGATCTGTCCG | 1,395,816 | 89 |
| 3838. | GGATCTGTCCGGCTCGCGGCACCT[T,C]CAACTCGATCGGAGGATAAACAGCT | 1,395,855 | 89 |
| 3839. | TCACTTTAAAGTCTAACATTTATT[G,A]TTCAAAATAAATTTTGCAGCGCATT | 1,395,966 | 89 |
| 3840. | GCTAGTGAATGAGTTCTCCAGTAA[G,A]CCATTGGGGCTCGTGATGCAGCCT | 1,396,073 | 89 |
| 3841. | TTCTCCAGTTAGCCATTGGGGGCT[C,T]GTGATGCAGCCTTAGAGATATTCCT | 1,396,086 | 89 |
| 3842. | TCGTGATGCAGCCTTAGAGATATT[C,T]CTGATAAATCAAAAATATTTAATTT | 1,396,109 | 89 |
| 3843. | CCACACATCAGTTTAAAAGAATTG[A,G]TGATTACTTAGATCCTCATTCTCGA | 1,396,675 | 89 |
| 3844. | CTCAATGATCCAGACGTGGGTTGA[C,G]GCACATGATGGCAGTAGCGACAAAA | 1,397,051 | 89 |
| 3845. | AAGCTAAGAGGAAATAATTCAAAT[A,T]TAGAAAGAGTGGAGACAATACATAA | 1,397,503 | 89 |
| 3846. | AATTGGCCAGTTTGACGTAATTCG[A,G]CTAACCTTGCTTATGTATGCAAGAA | 1,397,610 | 89 |
| 3847. | CTACTTACCAGCTGCAAATGCAAA[T,A]TTTTAAACTATGTAGAAATGATATA | 1,397,664 | 89 |
| 3848. | ATAAAATTTTGAAATTGTTTGTTG[T,C]GACAATTAATGAGCATTGCTTTGGT | 1,397,762 | 89 |
| 3849. | AATAGAAATCTCTATTGATAATTT[G,T]GTTCATCAATTACAACAATGACCTC | 1,397,820 | 89 |
| 3850. | AAGAAAAAGTTTCATGCCTTATAT[G,A]ATTTCAGCATTTATTTCTTGCTCTT | 1,397,898 | 89 |
| 3851. | ATAACCATAGAATATGTGCCATAT[A,G]TGCCATCATCATGTTTGTTTTAGCA | 1,397,973 | 89 |
| 3852. | ACATATATTATTTTTATTTATTT[A,G]TCGAGGTAAATATATACATCACATT | 1,398,143 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3853. | TATATTATTTTTATTTATTTGTC[G,A]AGGTAAATATATACATCACATTTTC | 1,398,146 | 89 |
| 3854. | CTTCATCTAATAATTAAATTAAGA[C,T]CTGCACTCTTTGATTGTCACATTAT | 1,398,258 | 89 |
| 3855. | ATTAAGACCTGCACTCTTTGATTG[T,A]CACATTATTATTGCTTTATTATAGT | 1,398,275 | 89 |
| 3856. | TATCATCCTTAAAATAGCTAAAAT[C,T]TTTTATGCTCGTGGGATGTGAACAT | 1,398,467 | 89 |
| 3857. | TCCATGCCGATAGACCATTCCTTA[A,G]ATATGAATTAGAAAAATCTTTATAC | 1,398,747 | 89 |
| 3858. | TGAATTAGAAAAATCTTTATACCG[C,T]CGTAGAAAAGATATGCTTCCAATTA | 1,398,775 | 89 |
| 3859. | AATTAGAAAAATCTTTATACCGCC[G,A]TAGAAAAGATATGCTTCCAATTAAG | 1,398,777 | 89 |
| 3860. | ATATCAACATATTTAGTTTATCTT[C,T]ATATCGTATCAACATAGACAAAATG | 1,398,899 | 89 |
| 3861. | GTGGATAGAATGTTGATTGTATGT[A,G]TTTGATGTGTATAATATTGAAATTC | 1,398,971 | 89 |
| 3862. | AAaTAAAAATTTGGTAGATGATTG[G,A]AATTGTATGGATGCCAGGGCGCTGG | 1,399,596 | 89 |
| 3863. | ACTTGAAATTATACAATTTTAAGT[A,G]GTCGCACCCATGTTTTCACCCTTTT | 1,399,867 | 89 |
| 3864. | TTAAGTAGTCGCACCCATGTTTTC[A,C]CCCTTTTTTATGGCTCTACCCACGT | 1,399,885 | 89 |
| 3865. | TTTCCGGATCCTGCGATGCGAAAG[T,C]ATATTCCCTCGCATGAGTCCACGGC | 1,399,937 | 89 |
| 3866. | TCGCATGAGTCCACGGCTCACCAT[G,A]TTAACTCCATCTCCGGGTTTCCAGA | 1,399,970 | 89 |
| 3867. | AACCGAAAGTTCCACCTAGCGTCC[G,C]CATACAACTTGTATGCGCTCTCTCC | 1,400,038 | 89 |
| 3868. | CCCGACAATTATAAGATTCCCCAG[T,A]TGGAAAGGGGAAAGGAGAGAGAGAG | 1,400,192 | 89 |
| 3869. | TTTCTGTCTCCGATCCCCTCCCTT[T,C]TCTTCTGGCGTTCTTTTGATTCTCT | 1,400,450 | 89 |
| 3870. | TGGATCTAATTCGGTCCGATTTGG[A,T]ATTCTATCTGGAATTCTAATGAATC | 1,400,513 | 89 |
| 3871. | TTTTGAAGGATTTATATGCAGTTT[G,C]GGTGCTTAATTCGTTCTTGACATGA | 1,400,788 | 89 |
| 3872. | GAAGACAGGAGGTGACAACCATGG[A,T]GGTTTTTAAGAAAAAAATGGAATTA | 1,400,994 | 89 |
| 3873. | TGCAACAACAATAGAATTATGCTT[C,A]GGGTTTGTTTGGTTGGGGTATGTCA | 1,401,056 | 89 |
| 3874. | ATGTCAGATTACGAGGTAATCTGA[T,C]GATTTCTGAAAATTATTTATCCGGA | 1,401,100 | 89 |
| 3875. | ATGATTTCTGAAAATTATTTATCC[G,A]GAAAAATTATTGTGGAAAATAAAAT | 1,401,123 | 89 |
| 3876. | ATTTACCACATTTGGATGGTGGAA[T,A]ACTAGCTCTGAAAAATGGCATTGGA | 1,401,171 | 89 |
| 3877. | TTTATTGGAGGTAATCTTATATCG[A,G]AATATTGTCAAATTTTCAATAATAC | 1,401,233 | 89 |
| 3878. | ATACCTGTAAATGGATAATTCAAG[G,T]AATAGCATTTTCTCAATCCATTTG | 1,401,279 | 89 |
| 3879. | TTTAATTTTTtATAAATTAATTA[T,G]ACATATATTAGAGAATATATTGTAT | 1,401,427 | 89 |
| 3880. | TTTATTATAAATAAATTTCAGTAT[G,T]CTTTGTAATATAAATAAATATATTA | 1,401,498 | 89 |
| 3881. | GTATAAATATATTAATATGTTAAA[T,C]ATATTATTATTTATATAATAATTAA | 1,401,626 | 89 |
| 3882. | ATGTATTTATAATATTAATATAAT[C,T]AATATTAATTAAATCATCTAATTA | 1,401,686 | 89 |
| 3883. | CATAATAGATTACCCCCAACCAAA[G,A]GTACCCCAAGTAGAGGAATAATTAG | 1,401,960 | 89 |
| 3884. | ACCCCAAGTAGAGGAATAATTAGC[G,T]AATAAGGATTCATAAAGCTATTGTT | 1,401,987 | 89 |
| 3885. | CTTTTCCACTAATTGAATAAGTTT[T,C]TCCCTTTTCCCCACTTCTCCTACC | 1,402,177 | 89 |
| 3886. | TTTTCCACTAATTGAATAAGTTTT[T,C]CCCTTTTCCCCCACTTCTCCTACCT | 1,402,178 | 89 |
| 3887. | TCTTTTATTTAATTATTTGGTTTG[T,A]TATTGTTTGCAATAAATTAAGTTTG | 1,402,278 | 89 |
| 3888. | TGAATTGCTTTATATGGTTTTCTT[A,G]AGATTGTGTTAAGAAGGCCAATCTA | 1,402,326 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3889. | AATCTATAGTTCTCTTCTTACTCT[G,A]TGGTTTATATGCAGTCTTGTGGTTG | 1,402,370 | 89 |
| 3890. | TTTTTTtAATGCTTATTCTGTTGG[A,G]GTAGATATTGTTATTTTGTATGTG | 1,402,450 | 89 |
| 3891. | TTtAATGCTTATTCTGTTGGAGTA[G,T]ATATTGTTATTTTGTATGTGTGGC | 1,402,454 | 89 |
| 3892. | TATAGGTAAATGAGGAATTGTTGT[C,T]ACGACTATTTTCTAATTAATTTTGT | 1,402,557 | 89 |
| 3893. | AGGTAAATGAGGAATTGTTGTCAC[G,A]ACTATTTTCTAATTAATTTTGTATT | 1,402,560 | 89 |
| 3894. | TTTTGTATTTACCTTTTTGCCCTC[G,A]ACTTATTATTGTTTGTTCTTCTTGT | 1,402,601 | 89 |
| 3895. | TCTTTTTATTTCATCAATTGTAAG[G,C]ATGCATCTTGTTTATGGATAAATTA | 1,402,725 | 89 |
| 3896. | AGTGGTATTTTAATTTTTTTTtGC[G,A]CAGTTGAGAAATTTGTGTTATGTGA | 1,402,948 | 89 |
| 3897. | ATTTGTGTTATGTGACCATGCTAC[G,A]TTTGTGATATCATTATATGTTGTGA | 1,402,983 | 89 |
| 3898. | TTGTGTTATGTGACCATGCTACGT[T,C]TGTGATATCATTATATGTTGTGAAT | 1,402,985 | 89 |
| 3899. | GTGATCTATCGCATTGTACCTCCA[T,C]CCGAGCGATATGAACAAGAACTGCT | 1,403,227 | 89 |
| 3900. | TAGTCTCTTCCTTGTCAAAGACAT[A,G]TTGGGGTTGCATATGGATTTCTGAA | 1,403,284 | 89 |
| 3901. | ATTTGAATATGAATGTAAATATCC[G,A]CTCTTGAATATCTACCAGGAATCAT | 1,403,434 | 89 |
| 3902. | CATATTTCCCTCATCTTGGACCAG[G,A]TCCCCATTTGTTTACAAGGCAGGTT | 1,403,591 | 89 |
| 3903. | TCTTTATCTCTTATTTCTTTACCC[G,T]TTTTCCTTTATTTCTTTtCTTTCAT | 1,403,701 | 89 |
| 3904. | GTCGATCCTGTGCGGCTTCTTGGT[G,A]ATGATCATGGTGATGATTTGGATAG | 1,442,156 | 89 |
| 3905. | TATACTGACACAAGGAGAGCGGAC[G,A]AGGGAGGGGACAGGGAGAGTGAGG | 1,442,316 | 89 |
| 3906. | TCAGATGGGAGGAAAGGTATTCAT[A,G]AGTGATTTCTATCAGCTAGATTTTG | 1,442,497 | 89 |
| 3907. | GCAGAACTTGTTGTGGACTTTAAT[C,T]TCGGTGATGTTTATTTCCTCCTCAT | 1,442,807 | 89 |
| 3908. | AAGTTAGTTCTTGCCATTTGTGGG[G,A]CCATGTGGGAAGAAAGAAACAATAG | 1,442,960 | 89 |
| 3909. | TATACTGTTATATTTTtCTTTTGC[T,C]GAACAGGTTTGGAGAACTTTGAAGG | 1,443,251 | 89 |
| 3910. | TGAVAAGAATGAGGGGACTATAAA[C,T]CATATACTGTTATATTTTtCTTTTG | 1,443,278 | 89 |
| 3911. | TTAAGGGCCATGGCCCCCTCCATC[T,C]ACCCATGTTTGCTGATGTTAACTTT | 1,443,896 | 89 |
| 3912. | AAGATTTGATAAGAACCACATGAA[G,T]TCTCTAAGGAATGATCTTTAAATTA | 1,443,975 | 89 |
| 3913. | CCATAAGAGCTTGATTTATCTTGG[G,A]GAGAATGAAGGGCAGGCTCTGAAAG | 1,444,112 | 89 |
| 3914. | TCACTCTGTGGATAATACGTTATT[A,G]TTCTTTGAAGCTGATTGTGCACGTA | 1,444,223 | 89 |
| 3915. | AGGAATTAGACAGGGAGACCCTCT[A,T]TCTCCATTACACTTTATTCTCTCCT | 1,444,367 | 89 |
| 3916. | ATAAGATGGCTGTTTTAGTCAATG[T,C]GCAGCCCAGAAACTAGATGAACTGT | 1,444,422 | 89 |
| 3917. | AGGGGATTTCCTTCACAGTGGATT[A,C]TGGATCAACTCTAGAATTACCACAA | 1,444,472 | 89 |
| 3918. | ATTGCTTACCTTGCATTAGTCACC[A,C]AAAAaGAAGCTATCAGTGCATCCAA | 1,444,789 | 89 |
| 3919. | AGATTCTTGCATCTCTCCAACAG[C,A]TTCTTTGTAGGAAACTTTGATGCGA | 1,444,849 | 89 |
| 3920. | TGCTCTAGGAGGGACAAGTCACC[A,G]GGGCCGGTTGAATTTCCTGTGCTAT | 1,444,930 | 89 |
| 3921. | GAATTTAAAACTGTGATCTTTGCT[C,T]TAGGAGGGACAAGTCACCAGGGCC | 1,444,950 | 89 |
| 3922. | CAGTGTGAAAAGAAAATCATTTTT[G,T]GAATAATGGAAACTATTGACATACT | 1,445,326 | 89 |
| 3923. | AACTGCATCTTTTTAGAAGAACTC[A,G]ACATATTTAGATTTGAGAAGTGGTG | 1,445,539 | 89 |
| 3924. | TCTGCTTTTATTAGGAGGCATAAT[C,A]TTTTGGAAACTTGTTTAAAAGAAAG | 1,445,709 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3925. | GAAGCAACACAGAATAGTACAGAC[T,C]GTCTAGAGACATTTAATTTGTGAAC | 1,446,145 | 89 |
| 3926. | TCAGCATCATTTAAATTCTTATTC[G,A]GTTGTTTGAATACATGCTAGTACAG | 1,446,987 | 89 |
| 3927. | GCATCTCCTTATTCAGCTTGACGA[G,A]TGCATGCTCCTGGCTTTCTTGAAGT | 1,447,825 | 89 |
| 3928. | TCAGTTTGTGCGGTTGATGTATGA[A,G]GAGAATTGTGAAGATATATGGGCAG | 1,447,921 | 89 |
| 3929. | AAAATATTTTGTGGATCAGTTTGT[G,A]CGGTTGATGTATGAAGAGAATTGTG | 1,447,936 | 89 |
| 3930. | CAGAATCTTGATGTTCTGCAGACT[G,C]TGGAAAATTTTCTTGAATATGTACC | 1,448,052 | 89 |
| 3931. | GCCACAAAGCCTCATTACTTCCAG[A,G]ATCTTGATGTTCTGCAGACTGTGGA | 1,448,073 | 89 |
| 3932. | TTATTTTtCTTAAATATATAATTT[A,G]ATCAATAAAAATATTTAAATTGATG | 1,448,753 | 89 |
| 3933. | TAATATTGACATATTGGCCAATAT[C,G]TTCCAACAATGATTGTTATTTTtCT | 1,448,793 | 89 |
| 3934. | ATAGTTGTTTCATATTATTTTTCG[G,T]ACGTATCTGTACCAAGGCTTTATCT | 1,448,961 | 89 |
| 3935. | TAGTAAAGCCCCACACCCACATGGC[C,T]ACATCCTCTTCTATAGTTGTTTCAT | 1,448,998 | 89 |
| 3936. | AAAATTTCTTTTCAGCTCATTCTC[A,G]AGGACATAAAGTAATAGGCATTGTA | 1,449,275 | 89 |
| 3937. | AGTTCTAGAGAGATCATTTCTGTT[A,G]GACAAAAATATTTTAGAGAGGTACC | 1,449,447 | 89 |
| 3938. | TTTACACTACAAGATGTCTTTAGT[A,G]CTTGAAGAATAAGTCCAGCTATGGC | 1,449,558 | 89 |
| 3939. | CAGTATCTGTTGGTTTTTGTCTTC[A,G]TATATTCATTAATGCTTTTACACTA | 1,449,599 | 89 |
| 3940. | AGAAATATGTTTCTTTTCTTCCTA[A,C]TGGTACTGTAAATACCCAGTATCTG | 1,449,640 | 89 |
| 3941. | CCAAGAAATATGTTTCTTTTCTTC[C,T]TAATGGTACTGTAAATACCCAGTAT | 1,449,643 | 89 |
| 3942. | AGACCAGAAAAAGCTGGGCACGTT[A,G]TTGCAAAGAAATGCTACATGCTTGA | 1,449,893 | 89 |
| 3943. | AGTTGTTTTTAGAGAAACCAGCAT[C,A]TGATGACAGTGGGGATGGAACTGCT | 1,450,165 | 89 |
| 3944. | GGAGATGGTGCAGTTGTTTTTAGA[G,C]AAACCAGCATCTGATGACAGTGGGG | 1,450,176 | 89 |
| 3945. | CCGAAAAATTTGTTACCCTTCTTT[C,T]CTTCTTTCTTTTTAGGAAATCTTGA | 1,450,847 | 89 |
| 3946. | CGGCACTCTTAGTTCTCTACTCTC[C,A]CGAAAAATTTGTTACCCTTCTTTCC | 1,450,871 | 89 |
| 3947. | GACCGAAGGCCACCGGCGATTTTT[G,C]CTCTCCTGCGCTGAAGGTCGTTAGG | 1,450,923 | 89 |
| 3948. | CGAGCCGTTTACTTCCTGAGCCGG[G,A]TTCGAACATGGTCGGGTCTCGCACC | 1,451,020 | 89 |
| 3949. | AAGAGCTGTGCAGAATCTGTCATG[G,T]TAGCCACAAATATCAAATTTCTTGT | 1,456,272 | 89 |
| 3950. | GTGATACTCACCTTCAAACGTATT[A,G]GTATTACTTAATTTATGCATTCCTC | 1,456,456 | 89 |
| 3951. | TTGGCAACAAAATACCTTGATAGA[A,T]ATGATCAACAATTACCATGAAGGAT | 1,456,667 | 89 |
| 3952. | ATCTGAAGTTCATACACGCACACA[G,T]ATCTTTGGCAACAAAATACCTTGAT | 1,456,696 | 89 |
| 3953. | CGAGTCTAATGGGTTGCTCATGGA[A,G]AAGAAACATTATCTTTCACTCCTAA | 1,456,900 | 89 |
| 3954. | CTGGAACGGTCCTTAAACTCTTGG[T,C]CACCTCTAAAATTTATTGGTTGCAT | 1,457,039 | 89 |
| 3955. | GAAAACAAGATTGGGATGCCATGT[A,C]AATTAGCAGGATAGAGTTTACAAAT | 1,458,382 | 89 |
| 3956. | ATTTTTGTACAAAAGAATCTGTAT[G,A]CTGAAAACAAGATTGGGATGCCATG | 1,458,409 | 89 |
| 3957. | TCAGCAGATGAATTACAGAGCGCA[G,A]AATGCATGTGCATATTGTGCAGCTT | 1,458,563 | 89 |
| 3958. | TGCTTCTCAACTGTATTGTGCACC[T,C]AAACACCTTTGGAACAGGGAAATGA | 1,458,971 | 89 |
| 3959. | AATTGATACTGAACCAAGCTAAGT[A,G]GTCCACATTTCTTATTGATATTCTC | 1,459,026 | 89 |
| 3960. | ATCTAACTTGTCACGTTTTGGACC[A,G]GTAGAGTGGACAAAGCTAACAAAGC | 1,459,465 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3961. | GGCTTATCTCACCTTTGGATTTAG[G,C]TTTGAGATCCAACTACCATCCTTGA | 1,460,102 | 89 |
| 3962. | CAGTATTTGTTAAGGAACTGTATA[A,G]CTAATGTTCAGTAGATGCTAGATC | 1,460,614 | 89 |
| 3963. | CGTAGATTTTCCCAGTATTTGTTA[A,G]GGAACTGTATAACTAAATGTTCAGT | 1,460,626 | 89 |
| 3964. | TTTGATGATGATTTGCATGACATC[G,A]TAGATTTTCCCAGTATTTGTTAAGG | 1,460,649 | 89 |
| 3965. | TAGATACATATGCAGGCTCAAACA[G,A]GCACACATGCTTGGTCGACAGCCAT | 1,460,703 | 89 |
| 3966. | TTCAAGATAAACATACTTTGAAAT[A,T]ATTGTTGTAGGCAAAGCGACTTCCT | 1,461,260 | 89 |
| 3967. | ATTAGTTGTTCGGTGGAAAAAGCT[C,A]TAGAATTTCTCAGATATTATTCTGC | 1,461,333 | 89 |
| 3968. | CAGGTTACAATAAAATAGAACGAG[T,C]TGTTTATGAATATTTGTGGATGAAT | 1,461,457 | 89 |
| 3969. | GGTTCCCCTTTCGTCTTGTCTTCT[A,G]ATATTTGATTATATATCTAAAACTT | 1,461,707 | 89 |
| 3970. | TGTCTCTGGTTCCCCTTTCGTCTT[G,T]TCTTCTAATATTTGATTATATATCT | 1,461,714 | 89 |
| 3971. | ATACATACATGCATACAAGTGTAT[A,G]TCTGTGCAGGTCTGTCTCTGGTTCC | 1,461,751 | 89 |
| 3972. | TAGAAATAGATACATGCATTATCA[G,T]GGCTATTCTATTATTTTTATTTGTT | 1,461,899 | 89 |
| 3973. | TGACTTGTAGAAATAGATACATGC[A,G]TTATCAGGGCTATTCTATTATTTTT | 1,461,906 | 89 |
| 3974. | GGACACTTCATTTTAAGGTTTCTG[G,A]AAGTGTTGGCAGTTGGCACTTTTAG | 1,462,379 | 89 |
| 3975. | TTAAGTCTAGAAATGTTCTGGTGT[G,A]CCATGTGAAGCAGCAGATATTCTTC | 1,462,457 | 89 |
| 3976. | TTTCTGCAGTTCTGTTCTGTGCTT[A,T]AGTCTAGAAATGTTCTGGTGTGCCA | 1,462,479 | 89 |
| 3977. | TTTGCAAAATATGCATGATTTCTT[C,T]ATATGCCCCTTTCCACTTTGTTGGT | 1,462,529 | 89 |
| 3978. | TTAATCTCATCTGCGAAAAACATC[A,G]TGCAGATTTTGATTTTGGCCGATGA | 1,462,808 | 89 |
| 3979. | CCGCCGGCACTTGGAGAGTCTGCC[T,A]CTAGAATCATTTGATTCTGTAAGTT | 1,462,948 | 89 |
| 3980. | ATGTTTAAAAATAAAGCTAAATTA[C,T]TTTGACTTTCTATTCAAGTTTCTTT | 1,463,300 | 89 |
| 3981. | TCAGCGTATCTTCCAAAAGTTCTC[T,C]TTGAGATCATTGTGTTTAATTTGTT | 1,463,824 | 89 |
| 3982. | CTTTTATTGCCATTGTATATCTTT[C,T]TTCTGTTCCTTTTTTCCCATTTGAT | 1,463,899 | 89 |
| 3983. | AAAACAAAATTCACCCATAATATA[T,A]TATATTCTTTGCATAAATGATCATG | 1,464,050 | 89 |
| 3984. | TAAGATCTATTATCAAGTTTGACC[A,C]AGAAAGAAAAATAAACAGAGGGCAA | 1,464,680 | 89 |
| 3985. | GTTATATGTTCATCTTTTATCTAT[A,G]CATTCTTATGGTCTTATATTGCATA | 1,466,368 | 89 |
| 3986. | TTTAAATGCACCACTGTAATGGGC[T,C]ATTGAAGTTGCAAATGGTGACATGG | 1,466,979 | 89 |
| 3987. | CACAAGTATACATATTATGGCAGG[T,G]TGGTTTATTACTAACTGTTAACAGA | 1,467,083 | 89 |
| 3988. | TAATCTACAATGTGCTTACCTCAC[A,G]GATCACAAGTATACATATTATGGCA | 1,467,111 | 89 |
| 3989. | GGTTTAATATTCAAGATTTCCTTC[C,T]CTGGGACCTTAATTGTTTATTAACT | 1,467,418 | 89 |
| 3990. | TCATCAGGCTATTGCATATGCTCC[C,T]ATTCATCCATTTGATTTCCAATGTT | 1,467,483 | 89 |
| 3991. | TGAGTTTTACATCAAAAGATGGCC[C,T]GAGTTGGATGGAATGCAATTTGAAG | 1,467,868 | 89 |
| 3992. | TGTGAGTTTTACATCAAAAGATGG[C,T]CCGAGTTGGATGGAATGCAATTTGA | 1,467,870 | 89 |
| 3993. | TCCCCTCTTCTATTTTTATTTTGC[A,T]ATATTAATGTTTTTTTTtGAACTTC | 1,468,784 | 89 |
| 3994. | TTACGTTGCTGGTAAAAAATTGAC[T,G]GTAAGAATAAATTTGAAGCAGAACA | 1,468,935 | 89 |
| 3995. | GTTGTGGTTGGATTTCCTTGCATT[T,A]GCTGGGTGGTCTTCCTGCTTAGCTA | 1,469,073 | 89 |
| 3996. | TTTTTCCTGTCTTTTTTTGACAAG[C,A]AACTTCGTTTGTGTTTTTCTTTGT | 1,469,121 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 3997. | GGAATGCGGACCAGGTACTGTTT[T,G]GGGCCTTTTGGCAATACCTTTGAAT | 1,469,465 | 89 |
| 3998. | GGTCCTAGCTGAAGATGGAAATGC[G,A]GACCAGGTACTGTTTTGGGCCTTTT | 1,469,481 | 89 |
| 3999. | CAGGAACGATAGTTTAAGATTTTC[G,A]CATCTTTCTTCTTAAAAGATATGAT | 1,470,094 | 89 |
| 4000. | ACAAGTATCTATATGATCGTGTTT[C,T]TATATGTTTATTATGGAATCTTTTG | 1,470,359 | 89 |
| 4001. | GGATTTATTTTCATATTTCTGCAC[A,G]AGAATAGTGAGGTGGCAATAGAGGA | 1,470,972 | 89 |
| 4002. | GTGCCTCGGGAAACCACGACCACA[A,G]CTAATGTGCCTTGCCCAAGCCATTT | 1,471,331 | 89 |
| 4003. | ACCATGACCCTAACTGATGTGCCT[C,T]GGGAAACCACGACCACAATAATGT | 1,471,349 | 89 |
| 4004. | AAGTAACTAACCAATCAAACATCA[T,C]TCCCTCTTCTTTCTCTCACAAATCT | 1,471,406 | 89 |
| 4005. | GAGAAGCAGTAGTTCAGGGTTCCC[G,A]TGGATGAGAAAAATCATTGATGTGA | 1,471,626 | 89 |
| 4006. | TTCACTAGAAATTGGGCGCGCGTG[T,G]CGCGCGCACACAGAGAGAGAGAGA | 1,471,672 | 89 |
| 4007. | AATCTTACTAGTTCTTAAACAATA[T,C]ACCAGCATTCTGAAACAAGAAAGTT | 1,471,720 | 89 |
| 4008. | ATTGTTATCCAGTATGAAAAAAAa[T,A]ATATAGATGCGAAAATGTATTTGGT | 1,472,609 | 89 |
| 4009. | GAAATCTTGATGTTTTACTTGCAT[C,A]AATATATTGTTGTGTTTTGTGAAC | 1,473,911 | 89 |
| 4010. | GCCATAACAACTGAAATAGATATG[T,G]CATGATGGATCCTCATGGCTTTGAT | 1,473,977 | 89 |
| 4011. | TGCTGGATTGATTAATCTCCTAAC[C,T]ATGCTGAGAGCATATGATTTTTCAT | 1,474,237 | 89 |
| 4012. | CCTCCCCAGCCCTCGGTCGGCTCT[A,C]CCATTTCGATTTCCATTTCCATCTC | 1,485,539 | 89 |
| 4013. | TATCATCAGAATGATGAAAAACTT[T,C]GAATTAGTGCATGTGGAAAGGCACG | 1,486,274 | 89 |
| 4014. | CATATATGGTACTTCCTTTGCCCA[G,A]TAATGCGGGTGACTTATGAAAGCCT | 1,486,564 | 89 |
| 4015. | TAAATATTATCTAAAAAATACRRA[C,T]CTAGGAAAATATAGATTTTCAGATA | 1,486,640 | 89 |
| 4016. | TAATGCAAAAGAACATAGGTAACA[G,T]ATTTTGAAGCCACTTTTCTATACAT | 1,486,719 | 89 |
| 4017. | TTTTTtAAAACTAAAAAaCATAAA[G,A]GATATTATGGAAAAATATGGATAAAT | 1,486,794 | 89 |
| 4018. | TGTAGAGTGTGAATCATATTCACA[C,G]GAGTTTTAATGTTCTTTTGGCTAAA | 1,487,135 | 89 |
| 4019. | TGCACCAACACTGTAATAGAATGA[T,C]ACTGATACGAGATTTGGTACCGAGA | 1,487,693 | 89 |
| 4020. | TCCATCTCCTTTTGCTGAGTTCTT[A,G]CATCTAAATTTTCCTTTCTTGTTTG | 1,488,084 | 89 |
| 4021. | TTGCAAGATGATGTTGAAGTGTCA[T,A]GGTGGGGAAAACTTTAAAAGATTA | 1,488,502 | 89 |
| 4022. | TACATCATTTTCTAGATCTTCCTC[A,G]AGTCTGTATGGTCTCTCATTAAGGA | 1,489,014 | 89 |
| 4023. | TCCAAATCTTTCCATTCCCACTTC[A,G]GCCGCTCTCGGAACAGTGCTGCGAA | 1,489,607 | 89 |
| 4024. | GCAACCTGATATAGGGCTCCAAAT[C,T]TTTCCATTCCCACTTCAGCCGCTCT | 1,489,624 | 89 |
| 4025. | TACTTGATAAGCAAACCTTCAGAG[G,T]AGAGGCCCGGAACATGCAAGTCCCT | 1,489,774 | 89 |
| 4026. | ATACTTGATAAGCAAACCTTCAGA[G,T]GAGAGGCCCGGAACATGCAAGTCCC | 1,489,775 | 89 |
| 4027. | CAGGTTTTTTTtAAAaAAAAATG[G,T]ACTCGAAAACAGTTACAACAGCTGA | 1,489,949 | 89 |
| 4028. | AGAGCAACGGCTAACCCGTGCTTC[A,C]CACTAGCAGTATAGCCGTTACAAGA | 1,491,268 | 89 |
| 4029. | TTTGGAAAATATTGGTCTTTGGTA[A,G]GCACTTGACACTACAATCCTACATGC | 1,495,583 | 89 |
| 4030. | TGTTGTTACTTACCCTTTTATTTG[G,C]CTTTCGTTTGTTCGTGACCATCCAA | 1,495,745 | 89 |
| 4031. | GCCACCATTGTTGGCACATCTATA[T,G]GTGTTATATATTTCATAAGGCTTTT | 1,496,725 | 89 |
| 4032. | GCGAAGAAAGGTGGAGGCACTCAT[C,T]AAGAGGGAAAGAGCTCTGGCCTATG | 1,497,322 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4033. | TTACACCTTTCTATTCAACAAAAA[G,A]AAGAAGAAGAAGAAGAAGAAGAAAG | 1,497,613 | 89 |
| 4034. | ACTTTTTTATTTCTTGACAGCTTA[T,C]AGGGATGGTACCTATGTAACGAAAT | 1,498,164 | 89 |
| 4035. | TTGGGAGTTGTATGGATAGATCCA[A,G]TATTCTTGTCCAATATAACTCTCAA | 1,498,248 | 89 |
| 4036. | GATGTGCAAGAGGCCATTTTGGGAG[T,C]TGTATGGATAGATCCAATATTCTTG | 1,498,265 | 89 |
| 4037. | TCTGACATATTCTATACATTCTTC[A,G]AAATATAATTACATGCATGCTCACA | 1,498,557 | 89 |
| 4038. | CCTCTTTCTTTTAACATAGACTCA[T,G]ACTTGTGGGCCTTTTCTAGGGTTTA | 1,498,620 | 89 |
| 4039. | ACTATCCAATATAGTTAATTCTGA[C,G]CTTTTAACCCTGTTTTAGACTTTCA | 1,499,153 | 89 |
| 4040. | TCTTACATTGGAGCTTTTTTAAGC[A,G]GTGACTGAAAGTCTCATTTGCAACA | 1,499,223 | 89 |
| 4041. | GACATTCCTCAGGAGGCCTACATC[C,G]ATGGAAGGTTCAACTGTAACTTACT | 1,499,698 | 89 |
| 4042. | TCAAAGCTTATCAATGGTAATGTA[C,T]ATATAAATTTGCAAAGCAAAAAGTG | 1,499,982 | 89 |
| 4043. | CAAGTGGATGGATTAACTTTGGTT[A,C]GGAATGAAAAGAACTCTCTGAGGGT | 1,501,043 | 89 |
| 4044. | TTGGAGAGATGTTCAGAACAAGT[G,C]GATGGATTAACTTTGGTTaGGAATG | 1,501,062 | 89 |
| 4045. | TGTCTCCATCTCTTCCTCCAGTGC[A,C]aTAGGTTTAGCTTTGGAAGTAATTC | 1,502,094 | 89 |
| 4046. | CCTGGTTCCTTGAATGAGAAAAAa[G,A]AAAAAAGCATATAGGATATAATTTT | 1,502,205 | 89 |
| 4047. | TTCTATAGCATGTGAGTCCACTAC[A,G]TACTAAAATAACCACACCATGTCTA | 1,502,737 | 89 |
| 4048. | TACCCATTAAAGGGCAGACACTTT[G,A]CCCTTTCTATAGCATGTGAGTCCAC | 1,502,766 | 89 |
| 4049. | TCCCCCCCTAAGCTAAGGGGTCAC[T,C]AACAGGATGAAAGAGTAGTGGATCT | 1,502,885 | 89 |
| 4050. | AGATAATAGTTTATGCTTGAGGCT[A,T]GACAATGGAGATGATGGCCTACAAG | 1,503,044 | 89 |
| 4051. | TGAGGCACCTcGCATTTAGTGCCA[C,T]ATTTAGATTTTCAACCCCAAATCTC | 1,503,371 | 89 |
| 4052. | CCAGTCTCAAATTTGAGGCACCT[C,T]GCATTTAGTGCCAcATTTAGATTTT | 1,503,385 | 89 |
| 4053. | TTTGAAATGATTGTTACTACAACA[G,C]TTACACTTTTAGGAAGTAAACTTG | 1,503,455 | 89 |
| 4054. | TTATTTGCAAGTAGTGTTGTAAGT[T,A]tGTGAAAATTTAAGAAGATTTTTCC | 1,503,553 | 89 |
| 4055. | TAGcTTTATTTGCAAGTAGTGTTG[T,C]AAGTTTGTGAAAATTTAAGAAGATT | 1,503,558 | 89 |
| 4056. | AAGAATAGCTCCATTGTATGATAG[C,T]TTTATTTGCAAGTAGTGTTGTAAGT | 1,503,579 | 89 |
| 4057. | GAATGGTATTCCAGTGTATTTTTC[A,C]AAAAAAaGATACAACTAATGGTAAa | 1,503,650 | 89 |
| 4058. | GGTTGGCACCCttCTCTTTATAAA[G,T]CATTACGAAAAGCTTCTGGACTTGA | 1,503,707 | 89 |
| 4059. | ATGTAGTATTACTTTATAATAATG[C,T]AATATTATTTTATAATAGTATAGTA | 1,508,198 | 89 |
| 4060. | ATATTATCTTATAATAGCATAATA[C,T]TGTTTTACAACTACAAAGATAATTA | 1,508,309 | 89 |
| 4061. | GTTTTACAACTACAAAGATAATTA[A,G]ATCATTTCATCCCATTTGAGTAGTT | 1,508,335 | 89 |
| 4062. | TTAAAGCAATCTCAGGAACTTTTC[T,A]GTGATTTTTCCAAGTTACCGTAGCA | 1,508,547 | 89 |
| 4063. | AAAaCATGGATCTAAAAGTGTACA[A,G]ATATAAAAATTAATTTTGAAAACAC | 1,508,691 | 89 |
| 4064. | AAGAATAAGCACACTTTATATGCA[G,C]GTAATTAGGTTTACTTTTGCACACT | 1,509,495 | 89 |
| 4065. | TAGTTTTATTCAATGAACTTTGTA[C,T]ATAATCATATAGAGGAACATTAGAA | 1,509,548 | 89 |
| 4066. | ACAATAAAGAACAGAAATTCTTGA[T,C]GATACCGAGGCTTGGCCCATCATAT | 1,509,929 | 89 |
| 4067. | ATCCATGATTTTTTGCAAACATAG[T,G]TTtGCAGAACTGCATTTGTAGCATT | 1,509,997 | 89 |
| 4068. | TTGATCCTCTTTCAAAACAAGCAA[T,G]GAAGATAAAAAAACTAGTGCAGAAT | 1,511,084 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4069. | ATACATAGGAAGCAAAGTGGACAA[A,G]GGAGATGAAAATGAAATGCAAACCT | 1,511,132 | 89 |
| 4070. | TCATTGCATGCTGACACATTACAT[G,T]gAGATTTGTATCCTTCCGTGCAGTG | 1,512,640 | 89 |
| 4071. | AGGTTGACTTGGATATAGTTAACC[T,C]GATCAGCATTACTAGGCAGTAGGCA | 1,513,223 | 89 |
| 4072. | GGTAAACTTCACAAGATAGATCTA[A,G]AACAGAGATGTACATACTCGCAGAA | 1,523,346 | 89 |
| 4073. | AATTATTTAGCTACTAATATTCAG[G,C]TGAAAAACTTCCTTACTACATAATG | 1,523,712 | 89 |
| 4074. | TCTAGCATGCCATGCAAATGCTTC[G,A]TGATGCACTGACATAATGTGATCAA | 1,524,730 | 89 |
| 4075. | ATATGAAAAATAAATTTAAGTGGT[T,A]GAAACACATGACAAAGTACTTAAAC | 1,525,372 | 89 |
| 4076. | GTAAAAATCAAGGTTTGCCATCTC[G,A]ATACCGGACCCcGTACCGGTAAAAT | 1,525,440 | 89 |
| 4077. | GTTTGCCATCTCGATACCGGACCC[C,T]GTACCGGTAAAATTCTGCTTAATGT | 1,525,452 | 89 |
| 4078. | CGGTACGTGGTTCAGTACGGTACA[A,G]TAATGTCAGTACGCTCCGAGATAGC | 1,525,502 | 89 |
| 4079. | GCGATACAGTATTCCATGGTAAAA[A,G]CTAaAAAACAAAACATTACATCACT | 1,525,605 | 89 |
| 4080. | GAGAAGAAACTGAGATAAAAATAT[C,T]AAAAAAAaGGAAAACTCCCCAAGCA | 1,525,977 | 89 |
| 4081. | TAGTCACCTAAACCGCTTTTGTTC[C,A]CcACAAGTAATTATTGCATAAGGAT | 1,526,792 | 89 |
| 4082. | ATGGATAAAAGGAGTCATGATTTG[C,T]GGGCTCCAGATATCAAAATCTCTTT | 1,526,987 | 89 |
| 4083. | TGAAACAAGACATCTATATAAGCC[T,C]TtGACTGGTAAGCAAGCAGCAACAA | 1,527,643 | 89 |
| 4084. | CCAATAAGTCAGGAAGCTTAAACT[T,A]tAGCCACAGGCAAGCAATGCATATG | 1,527,745 | 89 |
| 4085. | CATAGCCATCTTCCTTGAATTCAG[C,T]GCACTAACTAAATGAATATCATCAA | 1,529,092 | 89 |
| 4086. | ACTCAGAAAATGCTGGTCAAATAC[G,A]CTGCAGCTTATTATCTTGGATTGGA | 1,529,163 | 89 |
| 4087. | GTGTCAGTCCTAATCAAAATTTTG[G,T]TTATGCATTGCCCAGATAGATCCCT | 1,529,218 | 89 |
| 4088. | ATCTAATAGAGAGAAAAGGGATGA[C,A]ACTAGTTAAGCGGTAGACTAGTGAT | 1,529,585 | 89 |
| 4089. | AGAGGACAGCAAGAGGAGGCCTTG[T,C]tATATATTTCAGGAGAGAAAAGGAA | 1,529,847 | 89 |
| 4090. | AGGAGAGAAAAGGAAAAGGCATCA[C,A]CTTTACAAATCAAGTCACCTTAGAT | 1,529,882 | 89 |
| 4091. | CACTTCTTAGGCTCCATTTTTGGG[G,A]gAGCCAGAAAGTACTTTCTAGCCCT | 1,529,954 | 89 |
| 4092. | GCAATAATATATTATATTATATTA[T,C]ATTATAATAATATTATGCTTTGTAT | 1,530,355 | 89 |
| 4093. | GTCGAAACTTCCCTTTTTATCTTA[T,A]AAGAAAGCCTCAGAATTTTCAACCA | 1,531,566 | 89 |
| 4094. | TGGAAACTAAATTATCTACCCATC[G,C]AAGAATTGCTGTTTTCTCAAACAAA | 1,531,661 | 89 |
| 4095. | GAGAGAAAGCCGACGCCCGCGGGG[C,G]TCTAGGGTTTCTTTTGGGCGGCTTT | 1,531,989 | 89 |
| 4096. | GTGCCATCTTTTGCCGGACTGGGC[T,A]TGTTCTCGCTCGTCGTTGCGTTCGA | 1,532,259 | 89 |
| 4097. | ATGGACCCAACGACGTTACCAAGG[A,G]TGACTCTTTCCCATGTGGCACTAAT | 1,532,332 | 89 |
| 4098. | CACGTGGTTCACGAACGGTTTTGC[T,C]CATTCTATCACCCATGGTCCCTAAA | 1,532,669 | 89 |
| 4099. | TTAAAAaGATTTATTAGCTGTGAT[C,T]TTTAAAAAATTGTAAGTGTTtTTTT | 1,532,952 | 89 |
| 4100. | TACCTTCTCCTTTTGTCAAGATGG[A,G]AGGGACTCAAATCGAAAACACTAGT | 1,533,172 | 89 |
| 4101. | TATTTTACTAACTTTACCAACTTT[G,A]TTATTTAGCTTCCTCAAATTGATCA | 1,533,225 | 89 |
| 4102. | GTGGGGGGCGATAGAGACTAAACC[C,A]ACAGAGAAGTGTTCAATCATAGAAA | 1,542,453 | 89 |
| 4103. | ACTTAAAAGGCTCCTCAGGGCATG[G,A]CAAGAATATTATTCTGCCTGCCAAC | 1,542,521 | 89 |
| 4104. | ATCATGTTATCACATCTTTAGGGT[C,T]TTATGGCTTCATGAGGATGCTGCTA | 1,542,644 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4105. | AGCCTTTACACGGATCGCAGACCC[G,C]AAGTCAGTGGCCgACATATTGTTCT | 1,542,954 | 89 |
| 4106. | ATCGCAGACCCgAAGTCAGTGGCC[G,A]ACATATTGTTCTTTAAGCTTCTTTT | 1,542,967 | 89 |
| 4107. | TATCCCATTCCGCCTGCATATTCT[C,T]TTCAGCGTAGTTTGACAAACTGACA | 1,543,599 | 89 |
| 4108. | TAGAATTACTTCACTAATATCCAT[A,T]TCATCTTTAGGTCCACAATATTTCT | 1,543,809 | 89 |
| 4109. | ACCTCATGATCCTTGTCGTGGTCT[T,A]GGTAGGATATTACACCATAAGCAAA | 1,544,216 | 89 |
| 4110. | TATATATCACAAGCTATAGAACCT[A,G]TATGACAACCATGATGAATTTTCAT | 1,545,240 | 89 |
| 4111. | GCATCCTTTTTCAGTTATCTTTAT[G,A]TTACTTGGTTAGTTTTGGAGGATGT | 1,545,406 | 89 |
| 4112. | TTTATGTTACTTTGGTTAGTTTAT[A,G]GGATGTGTTTTTTACTTCCTACATT | 1,545,425 | 89 |
| 4113. | GATGCAAGGGCTACAGTTTATAGC[C,T]CTAGGTAGCTAGAACCATATTGTCA | 1,545,534 | 89 |
| 4114. | GTGTGATTAAGATCAGCACCTGAC[T,C]TGGATGAGCATCTCCTTGTTTACCA | 1,545,908 | 89 |
| 4115. | TGTGATTAAGATCAGCACCTGACT[T,C]GGATGAGCATCTCCTTGTTTACCAG | 1,545,909 | 89 |
| 4116. | GTAACATGTGTGCATGACAAATGG[C,T]TCTCAAGACATCCAATATCTCTGTG | 1,546,580 | 89 |
| 4117. | AGAAACATTAAGTATTTATTGGCA[T,C]tAAACCTATAATTGTTATATCTATC | 1,546,889 | 89 |
| 4118. | TATAATTGTTATATCTATCACAAA[C,A]AAGAATCTTCATGTATTCATTCTAC | 1,546,920 | 89 |
| 4119. | TTCTACATGCTTGTGTAACTAGGA[A,G]CATGTAAATAAATACATTGACAGAC | 1,546,964 | 89 |
| 4120. | GACAAAGATATCCATGCATATGCA[C,T]GCAGGCAGTGGCTACATTTATGATG | 1,547,011 | 89 |
| 4121. | TATCCCTGCACCTGAGGATTCCTT[A,G]AACAAAGACAGTGCCTTGAGCAATC | 1,547,758 | 89 |
| 4122. | TGCACCTGAGGATTCCTTAAACAA[A,G]GACAGTGCCTTGAGCAATCTCTCAG | 1,547,764 | 89 |
| 4123. | CGGTGGACTGCAGAGTTCAGTGAA[C,T]GTATTGATAGCCTTCTGCGCTGAGT | 1,548,136 | 89 |
| 4124. | AAACCAGCTCGTTTTCCTCTAGCT[C,T]ACAGTGGATATTCCATTCTCTTGCT | 1,548,270 | 89 |
| 4125. | TCTAGCTCACAGTGGATATTCCAT[T,C]CTCTTGCTCGACAAATTAAACCTTG | 1,548,287 | 89 |
| 4126. | CTTGACATAATACCTCCCTCCAAC[C,A]GTAAAAACCAGACCTTTTACTGAAG | 1,548,333 | 89 |
| 4127. | CAACTAGCTCAAGGTCGAATTGGA[T,C]CCTGAACTTTCCCTATCAAATTGGA | 1,548,487 | 89 |
| 4128. | GACAACGATGAACTAGCTCGATCC[A,C]GTCCGGACCCAGCGAAAGGCCCAAC | 1,548,544 | 89 |
| 4129. | GCAGGGTTGTCTCTGCCATGCTCT[T,A]GTACTGGATGTTCCCCTATACATCC | 1,549,448 | 89 |
| 4130. | ATTGCCTTGTATTGATAGGAAAAA[T,C]TAAGAGCTGCTGCTCAATGATGAAA | 1,549,532 | 89 |
| 4131. | TATGGTAAATGCTGTCACCTCCT[A,G]AATTAATCAAGCAATACAAGTAAGG | 1,550,218 | 89 |
| 4132. | GGTGGATTGCACGCCGTCGCGTCT[T,C]CCTGTAAATACTGGGTACTTGGGTG | 1,550,609 | 89 |
| 4133. | GTGCACCAGCCTTCAAGCACAACA[A,C]CATTGCCATAACATCATGTCAATAT | 1,550,656 | 89 |
| 4134. | GTTTACTAATTTAGTTCTCTTGAT[A,T]GGCGAGATTTGTTGAATTGATTAAG | 1,550,771 | 89 |
| 4135. | TTCCTTGTTGAAATCGGCGGAACT[T,C]GCTGATCTGACACAAAATACTTGCT | 1,550,821 | 89 |
| 4136. | GGGGCTCCGGTGATTTATATAGAA[A,G]GCTGTCAAACAGCTAATTATATAGC | 1,565,285 | 89 |
| 4137. | TGAGATTGTACGATCCTAAAATTG[C,T]GGGGCCATTGGACATATCATTGTGG | 1,565,337 | 89 |
| 4138. | GAATCCGAAACGTCAAGAGACAGG[C,T]CAAAAATATCGGAGCATCCGGTGCA | 1,565,676 | 89 |
| 4139. | TCAAGAGACAGGCCAAAAATATCG[G,A]AGCATCCGGTGCACAGATACAATCT | 1,565,688 | 89 |
| 4140. | TATTTCGGAAAATCCAGATCTAAT[G,A]GATAACATATTGCATCTTATCTATC | 1,565,756 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4141. | GAGTTGGCTGGGGTTGGGCAGACA[A,G]CGTTAAAGGTTGGCAGAGGGGAAAC | 1,568,567 | 89 |
| 4142. | CCAGAAGTTTTTTATGCAAAATTT[A,G]ATCTTCAATATGTTGTTTACATGTT | 1,568,775 | 89 |
| 4143. | TTGGTTTGTTTGCATGAAACAAGC[G,A]TAAGTATGTATGTAATGAACATAAA | 1,568,922 | 89 |
| 4144. | TACACACTAGGGACTAAAAGTTAC[A,G]AGGAACATGGTTGGGCTTGACATGA | 1,569,005 | 89 |
| 4145. | CCCATTTTTTGGTCCCTTTTTAGC[T,C]GGAGTGCTCATATCCTAAGAATTGA | 1,569,087 | 89 |
| 4146. | AGATCAATATCCATGTGACACACA[A,G]TATTGTCAGCTTCAAAGATTCTAAA | 1,570,116 | 89 |
| 4147. | ATCAAAGAAAGAAAGAAAATGAC[A,C]TTTCATCCCCTAAGCTATCCAAAAA | 1,570,197 | 89 |
| 4148. | CTGTGTGCTTGCTAAAGTTGTCGA[G,T]TTAAAAACCACTTCCCCCACCAAGC | 1,570,648 | 89 |
| 4149. | AAAAACCACTTCCCCCACCAAGCC[C,G]CAGAAAGGGGAAAAATGAAAGGAA | 1,570,675 | 89 |
| 4150. | GGCATTCAACTTGTTAAAAATAAC[A,T]TTTGGAGGGGAATTAATTAACTATT | 1,570,776 | 89 |
| 4151. | AACAATAGTGAATCTGACTGAGGA[G,A]TTGGAATCCATAGATACTAGTCTAC | 1,570,955 | 89 |
| 4152. | AATCTCACAGGCAAGGTTTAATAT[A,T]ATTATAACCTGTAATATAATTATAA | 1,571,498 | 89 |
| 4153. | GTTTCTGTGTCATACTGGATTAAA[G,C]CTTCTGCTTACAACACAAAGCTAAT | 1,571,853 | 89 |
| 4154. | TTCTGAGGCTGTGAGCAGCCAGGA[G,A]ACAAGATTTACCAATCCATTTGATT | 1,571,971 | 89 |
| 4155. | ATCATTTCAGAAGTTGCACAGGCC[A,T]TGCCATTCAGTACAAGGTCACCTTG | 1,572,139 | 89 |
| 4156. | TGAGAAATCTATGGGTGAGGAAGC[G,T]GgAATTAAAGCAGCTACAATTGAAT | 1,572,432 | 89 |
| 4157. | CAGCCTCCCATTCATAATTGAGAC[T,C]GTTATGGTGAATCTGGCCGATATAA | 1,572,754 | 89 |
| 4158. | ACTCCATCAATGATTAATTATTGG[G,A]gTAGTTGAGTATGGGGACTCATACA | 1,572,863 | 89 |
| 4159. | TTGGGgTAGTTGAGTATGGGGACT[C,T]ATACAAAAAAGATGTTATAGGAGGT | 1,572,883 | 89 |
| 4160. | AGACTGCAAGTAGTGGAAGATGTT[A,G]AuCTTAGTATTTTCCTGAATAGCCT | 1,573,185 | 89 |
| 4161. | TTGCAAGCACATCTACATCTATCT[T,A]GGGAGACATTTAACCTTTGTGGTTC | 1,573,292 | 89 |
| 4162. | CAGGTCATTTAAGTTTTCACGTAC[G,A]gTTTTTTTtCTTGAAGGAATAAGA | 1,574,513 | 89 |
| 4163. | TTTTCACGTACGgTTTTTTTtCT[T,G]GAAGGAATAAGAAGGATATCTCCAT | 1,574,526 | 89 |
| 4164. | atCGCACCGATGCTCCTCCGGTGC[C,A]GTATGGCACGGGGCTCTCCATGGGT | 1,582,566 | 89 |
| 4165. | AGTAGTTCCGTAATTCCCAATgAs[T,C]CGCACCGATGCTCCTCCGGTGCCGT | 1,582,589 | 89 |
| 4166. | AAGTGATGCCAAGCACGTCTTCCA[C,T]ACTTAGCTTCGAGCAACCTTCTACC | 1,582,657 | 89 |
| 4167. | CAGGATCTGTCACAAATTGTAATA[G,A]AATGTTGATGATCGGCAAAATCTAG | 1,584,707 | 89 |
| 4168. | GAAGAAATGAAATTCTCAGAGGGA[C,T]GGATACGAAAGAAACTTACATCTCA | 1,585,012 | 89 |
| 4169. | AAGGAGAGACGAGCGGTGTTCACC[G,A]GCAACCTTGACATCTGTATTCATGT | 1,585,706 | 89 |
| 4170. | CTCATCAGGTAGGGATACATAGGT[A,G]GCATGGGAAGAATCAGAGACCTTAA | 1,585,802 | 89 |
| 4171. | TTGCCATTCGCTGCTTGTTTCGAG[A,G]GTGCAGAGCTTGACTTACTGAGCAG | 1,586,173 | 89 |
| 4172. | CGAGGAACCTGCAAGTTTGAATAA[G,A]TGAATAAATAAAGAATAAGATGTTC | 1,587,387 | 89 |
| 4173. | TAGAGACAAACTTGACTAAGCTAG[C,A]GAGATTAAGATTGTTAGTAGCCTCT | 1,587,581 | 89 |
| 4174. | TGTTATATATGTGCTATGATGATA[G,A]TTATAAGCTAAAAATAGAAGATACA | 1,587,805 | 89 |
| 4175. | GACAGATAGTAAAAAAAAaTGACA[T,C]AATTGTTATGTCTTTGCCTTTAAAG | 1,592,169 | 89 |
| 4176. | TAAGAATTAATAGTTTTGATATGA[G,T]AGAAGAGTATGCAGAATTTATTTTT | 1,592,460 | 89 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4177. | TGAAGCATTCGAGGGTAATTAGCA[C,A]GTACCATGGATGGGGAATAAGAATT | 1,592,502 | 89 |
| 4178. | TGTAGACTTAAAACGCCGGGCTGC[G,A]TCCACTCCTCTTAACCCACATCCTC | 1,593,096 | 89 |
| 4179. | CCCACCATCCATGGACGACTTGCC[C,A]AGTCTCCGTGGATGTAGACTTAAAA | 1,593,133 | 89 |
| 4180. | CACCGGCGACTCCGGGACCCACCA[T,C]CCATGGACGACTTGCCCAGTCTCCG | 1,593,150 | 89 |
| 4181. | ACAGATGGGCGCTTTGGTATCCAA[C,T]CGTGGAAATATTAGTCACCGGCGAC | 1,593,190 | 89 |
| 4182. | CCTTGTAAATGAACTGACTAACAC[G,A]GTACCTAATGACAAAACAATTTTGG | 1,597,621 | 89 |
| 4183. | ATAATTTACTGCGAGTGTTTGCTG[C,T]AGAATGGATTAAACCGATCTATCGT | 1,597,765 | 89 |
| 4184. | ATTGGCTCCCACCCTAGCATCAGC[A,T]GCCTACAAGATGGCACTGATTTCCT | 1,599,476 | 89 |
| 4185. | ATGGGTGCATATAAAAAATGGTA[A,C]CTGAAAATGAAAATTGAAACTAAAC | 1,601,193 | 89 |
| 4186. | GTTTGCAGGGATTGGTTATGGTCG[C,T]AGACACCCCTACTCCTCAAAATTAG | 1,601,507 | 89 |
| 4187. | GAGTTTGCAGGGATTGGTTATGGT[C,T]GCAGACACCCCTACTCCTCAAAATT | 1,601,509 | 89 |
| 4188. | CCGGCTAGCATGGATTCCGGTTCT[C,A]GTTCCGCGGTCCTTGATCTAGGTCA | 1,601,726 | 89 |
| 4189. | TAGGCAAGAACGCTACAGTGATTT[A,C]CCTGCCACACTTCAATCCCTACATA | 1,604,187 | 89 |
| 4190. | TTAGTGAAAAGAATTAGGCAAGAA[C,T]GCTACAGTGATTTACCTGCCACACT | 1,604,201 | 89 |
| 4191. | AAAAACATTTGTGGCAAATTATCC[G,A]TTAATCTTTAGTGAAAAGAATTAGG | 1,604,233 | 89 |
| 4192. | TTAATCTGACTACCGAAAGTTGAT[G,A]ATGTTTAAGAAACAACAATGTTG | 1,605,145 | 89 |
| 4193. | GTCTTTACCAATGGATGGTAACCT[G,A]CAGGACAAGAGATTCTAAGTTCTTC | 1,606,417 | 89 |
| 4194. | CAAAAGAAGCACGAAGGTTGGAG[T,G]GTCATGATTTCATTAAGCAACCAAG | 1,606,610 | 89 |
| 4195. | CGAAACCTTGGTTAGTGGACGTCT[G,A]ATAAAATAAAATCCCGTATATACTG | 1,606,669 | 89 |
| 4196. | TATGCAAGTCAATCTGCCTGTAGT[T,C]TGAAACGACTACAGAAATCCCTAGA | 1,606,719 | 89 |
| 4197. | CTTTTCCCCAGATAACATTGGACG[C,T]AAGTTACATATAACATTGAACATTT | 1,606,789 | 89 |
| 4198. | CAGAGAGGTCAAAATTAAACTCTC[C,T]AGTCCAAAATTTTTTAAGTTtCTTT | 1,606,835 | 89 |
| 4199. | CTTTATCGTGCATGTCACTTTCAG[T,A]AACCTTCCTCCCTGATGTTTGCTAG | 1,606,888 | 89 |
| 4200. | TTGTAAGGAAAAAGATGTAGGAAT[G,A]CGTGAAAACATGCAGTCAAGGTACA | 1,607,032 | 89 |
| 4201. | ACAATGGTAGGATTAATAATTGAA[A,G]ATATTGTAAGGAAAAGATGTAGGA | 1,607,060 | 89 |
| 4202. | CCAACATTATATAGATGGTTATAT[A,T]CGGCTGTACAGGTTACATGATGCAT | 1,613,951 | 87 |
| 4203. | TTATTGCTATGGATATCATGGATA[C,T]GTACAGTTGGTTTAGGCATCACAGT | 1,614,239 | 87 |
| 4204. | GAAAGGAAAGAAAGGAAGGTAGA[G,A]GAAAAGAAAGAAAAGAAGAGAGAGA | 1,614,509 | 87 |
| 4205. | CACCGGAAGAGATGAAGAAAGAGG[A,G]TAGAAGGAAAGGAAGGAGAGATGAA | 1,614,609 | 87 |
| 4206. | ACCCATCCACACCGGAAGAGATGA[A,G]GAAAGAGGATAGAAGGAAAGGAAGG | 1,614,618 | 87 |
| 4207. | ATCAAGCCCTTCAACATGGCCCGG[G,T]ACATGGCTATACACATGGGGAATG | 1,614,786 | 87 |
| 4208. | TTTTTACAAATAAAAGAACAATAT[C,T]ACATTAAATAAATCAAAAGAGAAAA | 1,615,088 | 87 |
| 4209. | ATGTGATTAAGGGTGGGAAAAATC[A,G]GATATGCATTGCAAACAGTGGATAG | 1,615,313 | 87 |
| 4210. | TGATGACAAAGGATATGTGATTAA[G,A]GGTGGGAAAAATCAGATATGCATTG | 1,615,327 | 87 |
| 4211. | GAATGAAAAAATATGAGCAGGTT[G,T]CAAAGGATGATATTTAACACAGATT | 1,615,480 | 87 |
| 4212. | AGTGAAATTTTGCCTAGGATGCCA[G,T]AAGAATGAAAAAAATATGAGCAGGT | 1,615,507 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4213. | CTCCCACAATCTTGAAAAAGGGGG[A,G]AAAAAaCCTTGGAATAATGGAACGG | 1,615,570 | 87 |
| 4214. | AATAATTGGGTCAAGGGGGTCTCT[C,T]CCACAATCTTGAAAAAGGGGGAAAA | 1,615,592 | 87 |
| 4215. | ATAAATGTAACTCTGAGGCCCTTT[T,C]GGTGTTAGGAGGATGAAACCAAGTT | 1,615,837 | 87 |
| 4216. | TTTAGATTGCATTCAACTAGGGTC[C,T]GGGTTTCTGGGTCTCAGGGATGACC | 1,615,983 | 87 |
| 4217. | TTTATCAAATCTGTCTGAGTGATT[C,G]TTCAACTCTAGGTGGGAACAGTTTG | 1,617,499 | 87 |
| 4218. | CCACTACATGTGGAGAGGCTATTT[C,T]CATGTTTCAAGCCCGTGAGAAATTT | 1,618,241 | 87 |
| 4219. | GGCAGCCCAGCTGCACTAGGCTCC[T,C]GCCACTGCAGGGTCCGGAGAGGGTC | 1,618,308 | 87 |
| 4220. | TTTATAAGATTTCTGAAACCAGGT[T,C]AGGTTTTTCAATTGAAGCAGGGCAG | 1,618,353 | 87 |
| 4221. | ATTAAGAATTTACAAAAGCATCAC[G,A]CATACCATCCCCGAAATATATGCCA | 1,618,413 | 87 |
| 4222. | ATTAAGGTCAAATTGCAGAGAACC[T,A]AAAAACTTCAAAAATCCTTAAATAC | 1,619,009 | 87 |
| 4223. | ACTTCTACTACATAAAAGTCAGCC[T,G]GTTATGGTACACTATTGATCACTAG | 1,619,076 | 87 |
| 4224. | TCTAGCTTCTAGCCTCCAGCAAAA[A,G]GTAAGGGTTTCCAGCTTTATCGCTT | 1,619,307 | 87 |
| 4225. | TTCCTATTCAAGGTTAGTACCAAA[G,C]CAACCCACAAAAAAGGCATGGCACA | 1,619,944 | 87 |
| 4226. | TTTACGTGCTCTTCAAAGGGTAAG[C,T]GTGCTAAGTCATTAGCACACTAAAT | 1,619,996 | 87 |
| 4227. | CCCACACCCTACGCCCGAGCCCAC[C,G]CCCGCACCCCACCACCTCCTTCTCC | 1,620,106 | 87 |
| 4228. | TGCAGACCGATCACCCACACCCTA[C,T]GCCCGAGCCCACCCCCGCACCCCAC | 1,620,119 | 87 |
| 4229. | GGGAACATTCCTGTGCTATTCTGC[G,A]ACACCAAGGCTTACTCAAGATCCAT | 1,620,311 | 87 |
| 4230. | ATCATGAAGGGCTATGTCAATGCC[T,A]GGAATTCTGTCCCTGTCCTCACTGG | 1,620,493 | 87 |
| 4231. | GTGATTTCCAATTCTGATCTTTAG[A,G]AAATAACCATGTCAAATGAACAAGT | 1,620,803 | 87 |
| 4232. | TAAGTCATGATAAGAGTAGAACAA[G,A]ATAAGAAAAGGAATGAGTATAACTG | 1,620,888 | 87 |
| 4233. | TCAGCAGATGAGTGTCATTATTGG[G,A]ATAGAATCGGTCATTGCAAACAAAA | 1,621,313 | 87 |
| 4234. | TGATTCTAATATTATATGCATGCA[C,T]CATATTTAAGTCTGTCTATTATACT | 1,621,413 | 87 |
| 4235. | ATGATTGTGCCCGAAATAAAATTT[C,T]GGATGGAGCAATAGGAAGTACAGAT | 1,621,713 | 87 |
| 4236. | CAAATGAGTTTGAACTTTGAATGT[T,G]GTCAGAATCAGGAGCTTTGAGTTTT | 1,621,787 | 87 |
| 4237. | AGATACCATTATATAATGACTGTT[G,A]ATTATCCTTATATAACACCTCATTG | 1,621,906 | 87 |
| 4238. | CCAAGGCTTGCGCATCACTTGCAG[T,C]AGATGGGATTTTCAAGTTCTGTCGG | 1,622,560 | 87 |
| 4239. | GGAAAACTGATAGCAAGAAACAC[C,T]ATAGTGATTATATTGACATGATCTG | 1,622,965 | 87 |
| 4240. | CCCTAAATATAACTTTAGAATGTT[C,T]TATCATAGCTTCATTTGCTCTTCAG | 1,623,039 | 87 |
| 4241. | ATTTGTGAAATTGTAATACCTTTG[C,T]TCTTGCTATTATTTGCAAGAGCATT | 1,623,276 | 87 |
| 4242. | TTTTTAAAAAATTTGTGAAATTGT[A,T]ATACCTTTGCTCTTGCTATTATTTG | 1,623,286 | 87 |
| 4243. | TTATTCAAGCTGACGGGAATTTCA[A,G]TAGTATAGAATTATTGAACGATCAA | 1,623,562 | 87 |
| 4244. | TGTACACAAATTTTTGAATTCAAA[C,A]AAAATTTCTTTtATTTTTCCACTTT | 1,633,772 | 87 |
| 4245. | ACACTTGTATCACTGTAAGGTACA[C,G]TTCAAATGTACACAAATTTTTGAAT | 1,633,803 | 87 |
| 4246. | GAAATGAAAGTGGAGATCATGTAC[A,C]CATGCATGCATTAGTTTCATCTGTA | 1,633,884 | 87 |
| 4247. | TAAGTTCAAGTTTCGGCAATGACC[A,G]TGATTTTCCAACTATCAGAAATGAA | 1,633,926 | 87 |
| 4248. | TATGTAGTTTAGATAATAATTTTA[A,G]CTGTGCTCTCCTTTTTTAATAAGTT | 1,633,970 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4249. | CCAATCAAATATAAAAAGTATAAA[T,A]TTTTCATCCAATGAGAGGGTCAAAA | 1,634,689 | 87 |
| 4250. | ACCTACAGCATAACCAAAAAAATG[G,A]TGCTGGTAATTGTTAGATCCTTTAC | 1,634,963 | 87 |
| 4251. | AACCAGCAATAGGATTTTGGCAGT[T,G]GATGAGATAAAAGTTCTTCCAGACA | 1,635,187 | 87 |
| 4252. | ATTTGATGAAGTCAAAAAGGATGG[T,C]GGAGATAAAAGGGGTTTATCTAGTA | 1,635,869 | 87 |
| 4253. | TAGCTCTTTTATCCTTTTGTAATT[G,T]GGTGGTCCACTTGGAGACAGGAAGA | 1,635,959 | 87 |
| 4254. | GGAAGTGCCATCCATTTGGCAATG[G,A]GGTGAGACAATGCATTGGTTTCAGA | 1,636,199 | 87 |
| 4255. | AAGATTGATCGGCTCAGCTATAAA[A,C]TAAAGATTGCATTTATAGTAACTAT | 1,636,378 | 87 |
| 4256. | GAAGTTCTAAAATGCAAGCTAGCA[A,G]GAATAAGAAAGTAATCACAAGTACA | 1,636,691 | 87 |
| 4257. | TCTATAACATTCAAAATCCTAAAA[A,G]CCAACAATAATCTCCCGTGAGGTTT | 1,636,971 | 87 |
| 4258. | CACATGCGTGCTGCAAGACACATG[T,G]TAAGCTATACAAAGCTATATAACTT | 1,637,034 | 87 |
| 4259. | TCACCCCTCTATCTCACATGCGTG[C,T]TGCAAGACACATGTTAAGCTATACA | 1,637,048 | 87 |
| 4260. | GCTAGCTGCTTTGCCTCACCATGG[C,T]TGGCAACCTGCAAGCAAATGGCTCC | 1,637,430 | 87 |
| 4261. | CAAACTGAAGTGTGTACATTCCCC[G,A]TTCCCACTTCCCTCTTCCTCTTCCC | 1,637,533 | 87 |
| 4262. | AATGCCATTTTTAGAGCATCATGT[T,C]TATTTTATATATAAAAAAAaGATAT | 1,638,363 | 87 |
| 4263. | ATTTTGTGTTATATAGGTTCCCTG[T,C]TTGCATAGTTCTGTCAAATTATAGA | 1,638,623 | 87 |
| 4264. | AGTCATAAAAAATTCAaAAAAAAT[C,A]GAAGGAGAAGAAAAGAAAACAAGAA | 1,638,695 | 87 |
| 4265. | GCTGGCTCCATAAAGTTTCCATTT[T,C]GGCAGTTTCAGTGATTTTGTAAGTT | 1,638,774 | 87 |
| 4266. | ATGTTGAAATAGTAATTGCATATG[G,A]AAATTAGTGGTAGCTTCAATTTGAA | 1,639,005 | 87 |
| 4267. | AAATAACTATAATCTGAACAATGA[C,T]GACACTGACAGGCTGAGCTGGTAAA | 1,639,673 | 87 |
| 4268. | CCTTTTTTtATTTACCATTATCA[C,T]TAGATAAGCATGCTAGAAAACAAA | 1,639,809 | 87 |
| 4269. | TCAAGCCCTGTTACCTTTATAGAT[G,A]CTCTCCCCTTAAATCTACTGTAACA | 1,639,867 | 87 |
| 4270. | GGCATCAGCCTGAACAGTTAGTCA[A,C]TTTCATTTTCTAAGGTTGCCACATG | 1,639,956 | 87 |
| 4271. | ATTCCTCAAATAGGACACGCTACA[G,A]GCATCAGCCTGAACAGTTAGTCAAT | 1,639,980 | 87 |
| 4272. | CAGTCACCTTTTCTGGTAGGATAG[A,G]AAGGCCATGAGTTAATTCCTCAAAT | 1,640,019 | 87 |
| 4273. | TCTCATAAGGAAGCCAAAAGAAAG[A,G]AAAATCTATTCAAATACGAGGTTGC | 1,643,151 | 87 |
| 4274. | GAACTTGGGCTGTGTTGCTTATGA[T,C]AAGGTGTAACTCCTACATTCCATCT | 1,643,419 | 87 |
| 4275. | CATCCAATAATTTCTCGCCAGGCC[A,G]GGGCCCCACCTGATTTATTTGGATA | 1,643,611 | 87 |
| 4276. | TTCACTTGCGCCTGGTGCATCCAA[T,C]AATTTCTCGCCAGGCCAGGGCCCCA | 1,643,628 | 87 |
| 4277. | CATACCGTGAAACTGTTTGCTGCC[T,G]TCTATGGCGGGCTTTTGTCAAGGCA | 1,643,810 | 87 |
| 4278. | GTGTGCGTCGACCATACCGTGAAA[C,A]TGTTTGCTGCCTTCTATGGCGGGCT | 1,643,822 | 87 |
| 4279. | CGATTTATTTGAAGGCATCGGCGG[T,C]GCAAAAGCCCTATAACAGATCTGGC | 1,644,152 | 87 |
| 4280. | TTGATAAGATAGTACAGAAGTTGC[T,C]ATACTGTATCAACCTTCCTTGTTAA | 1,644,960 | 87 |
| 4281. | TCATTTAACTGACCAAAAAAAAAC[A,C]CAGTGATGGCATTTTATTAAAGAAA | 1,645,014 | 87 |
| 4282. | TGTTAATTGCCATGTAATATCCTT[T,A]ATCACAGGGATCCGCATCATGTACG | 1,645,330 | 87 |
| 4283. | CTAGACAGTGAGCAAACAAAATGA[A,C]CCAAAAAAAaGGTGAATCAAAAACA | 1,645,464 | 87 |
| 4284. | AATCATTTTGAAAGTACAAAGCAA[A,G]AACATTTATCCTGAATGATTTCTCC | 1,645,845 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4285. | ACATATTCATGGGACATTGGCTGG[T,G]GCACACCTAGCCCATCGCCCCATCT | 1,646,022 | 87 |
| 4286. | ACAATTACCTCAAAATAAGATGTT[C,G]TCGATGACTACATTAGGCATGAGAA | 1,646,721 | 87 |
| 4287. | GCATGCGGGATAAGGTTGTGCAC[G,A]TCCAGACCCCACAATGGCGAAAGCC | 1,646,807 | 87 |
| 4288. | TCAAAATACGTAAACAGCCTCTCC[G,A]CATGCGGGATAAGGTTGTGCACGT | 1,646,831 | 87 |
| 4289. | CGAAATTAGTTGCCTAAGAAATTC[G,A]ACAGGTACTTGCAAAGCTACCTATG | 1,647,719 | 87 |
| 4290. | ATCTTGTTTGCTGAACAGAAAGTG[T,C]AAACCTAGTTATGGCATATCTGAAG | 1,648,270 | 87 |
| 4291. | ATTAACGTTTAAGTTGGAACAACA[A,T]TCATATATGTCACCGATTATATGTG | 1,648,545 | 87 |
| 4292. | AAAACATTAGACCCAAGAACCAAC[T,C]GCTGGTAAGTTGGATGACCAAAAAA | 1,648,606 | 87 |
| 4293. | TACCATTACACCAGGTGTAAAAGG[T,A]AACTGGTGATAAGCAGGCAAACAAA | 1,649,651 | 87 |
| 4294. | TCAGTATGATCCAAAATATGCCAA[C,T]GATCATCCAAATATAATGTCAGCGA | 1,649,897 | 87 |
| 4295. | ATGTTAAGGTAGCAGAACAGCATT[C,T]CAAATACTAACATAAATAAGGATAA | 1,650,173 | 87 |
| 4296. | TGCATAATGTAACTGAATTGCATT[G,A]ACCTCATCAAACACAAAAAGTTGCA | 1,650,329 | 87 |
| 4297. | TATGTACTTAGTACTTTAGGCTTA[T,A]GACTTGAAGTTTTAACTTGTAGGAG | 1,650,399 | 87 |
| 4298. | TCAGACTGCCTGTAATTAGAAATC[A,G]GACTTGAAGTTTTAACTTGTAGCAG | 1,650,637 | 87 |
| 4299. | GAAAGCACTATCAGTCGAAGAACC[G,A]TCCGTCCTGGACCTCTTCACATCTC | 1,652,345 | 87 |
| 4300. | CTTTCCTACTGCCACGCACCGAGC[A,G]TGGCAAACGGGAGTTCCACCTTTGG | 1,652,558 | 87 |
| 4301. | GGATGGCGGAGGAATTGCCAGTTG[T,C]GGTACCACAGCATTAGTTGATTGCT | 1,653,038 | 87 |
| 4302. | ATTGACCTACTTTGCTTCATTATG[A,C]ATCATAATATTTCTACTGCTTTTCA | 1,654,508 | 87 |
| 4303. | AATTCACAATGAGGAATCTTGTGC[G,A]CCCCTCATTGTCGGGATAAGAATA | 1,655,827 | 87 |
| 4304. | TGATTTCTCTATTAAGATTTGACA[C,T]TGAGGCGACCGGTTTAAGCACGTCA | 1,656,187 | 87 |
| 4305. | TTCCTCTATTTGATGGGATTCCTC[G,A]TATCCATCGGAGATTAGAGCGGGAA | 1,656,593 | 87 |
| 4306. | CTCTCCTCATGACAAGCGCATAAC[T,C]TTCGCAAACGTGTTTGTAAATAGCC | 1,656,828 | 87 |
| 4307. | ATGGCATATCAAAATCCAACTCCA[G,A]ATTCTAAAATTAATATCTGCAGTAC | 1,657,314 | 87 |
| 4308. | TGCCTACGATGGGAATAGTTACAC[T,C]AGAAATTGTTCCAATTTTTGTTTGG | 1,657,628 | 87 |
| 4309. | TATTAGGCTGGATTTGGATCGAGA[A,G]AAAGATAAAAATAGCAAAACTTATG | 1,657,676 | 87 |
| 4310. | CCATTTTATGAGAACCACTTTTGC[A,G]ATACAATCTTTTAAGGCACCATTGT | 1,658,010 | 87 |
| 4311. | ACTGATTATAGCTTTCCTCCTCTT[G,C]CCTGCCTCTCCTAACTCAAGTTCAA | 1,658,358 | 87 |
| 4312. | GGTAAGGTTTTGCCCATTACCATA[A,T]TTCTTTTATTCACATAACTATTAAT | 1,658,611 | 87 |
| 4313. | TCTTCCCCACAGCCTCCTTTGCTC[A,G]GCCACCTTATGCATAGTGGTAGCTT | 1,659,494 | 87 |
| 4314. | ATTTGGCATGGAATTGTTTCATCT[G,A]GAAACTCGACCTTACGAACTCCACT | 1,660,372 | 87 |
| 4315. | TAGTTGCTTCCGGGTCTCCTTCCC[C,T]TGTCCACCTTCTTGCCCTTTGGTGG | 1,660,502 | 87 |
| 4316. | TAGATTAGCCTTCAAGACATTGAC[G,A]AGTCAAAGAAAACTCATCTGAGCAC | 1,660,641 | 87 |
| 4317. | GGGCATGCCATTGATGCCGATCTC[G,A]ACATACATCAAGGTCCTACCTCCCA | 1,660,704 | 87 |
| 4318. | AAAGTTGTATCAAGGCAAGAGCAC[C,T]ATATTGAACTACCTCAAGAACTCCA | 1,660,982 | 87 |
| 4319. | TCCTTGCTTGCATCGTAAAAAGAA[G,A]CTTGGTACCTAAATTGGGTTTGGTC | 1,661,073 | 87 |
| 4320. | GGTTTTGCAGCTCAAGCCAGGCAC[A,G]GCCCATAAGGGCTTGGGCTAGCACG | 1,661,824 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4321. | GTCGAGGTAGTTGTGGAATAACTT[G,C]TTCATTAAGGTGCTAAATGTAGCTG | 1,662,429 | 87 |
| 4322. | GCCATCCAAATACACCACTACAAA[C,T]TCGTCGAGGTAGTTGTGGAATAACT | 1,662,456 | 87 |
| 4323. | AAGTGCTCCACATGCTCCTCCAAC[A,G]TCTAGTTGTATATGATGATGCCATC | 1,662,500 | 87 |
| 4324. | ATTCAATCTCTTCCCAGGCAAAAA[G,A]GCATGTAGAAGGAAACTGCAAAATT | 1,662,565 | 87 |
| 4325. | GTCTCCACACCCTCAAGCAGTGAA[C,T]TACCACTACATTCTCCTTATCATGA | 1,663,022 | 87 |
| 4326. | GCAAACATTTTCCAATGGTCACTC[G,A]AAAATGAATAGTGGTTCTAGCAACT | 1,663,598 | 87 |
| 4327. | CCATTCCGATTCCGATTCCAGACC[T,C]CCCACTCCCCCCAACCAAGCACCCC | 1,663,977 | 87 |
| 4328. | GAAATCGGAATAGATATCAAAATG[A,G]ATTGGAATCAGAATCGAAATCAGAA | 1,664,203 | 87 |
| 4329. | GGTTCGCAACCGGAATCAAAATCG[A,G]AATCGGAATAGATATCAAAATGAAT | 1,664,226 | 87 |
| 4330. | AATGGGCTCCAACTGGTCGCCTCG[A,G]TCTTCTGTAGATTGTAGGAGAATTG | 1,664,325 | 87 |
| 4331. | ATTGTGTAACTTGCAAGTAGCCTT[C,G]TATTGTGAGGGCAATATTTTTACAA | 1,664,585 | 87 |
| 4332. | AACAAATAAGGCCATTGTGTAACT[T,C]GCAAGTAGCCTTCTATTGTGAGGGC | 1,664,598 | 87 |
| 4333. | GACGAAGCTCTCTTGGATTCACCT[C,A]GACCAAGGTCATCTAGCTCTCCATA | 1,664,765 | 87 |
| 4334. | CCGCTCCATCACACCACACAGTCC[G,A]CCAATATATATTCCACCTCCTTGTC | 1,664,834 | 87 |
| 4335. | AGTTTGAATACATGCAAATGTCAC[A,T]ATTTCAACGATTAAAATCCCCCTAG | 1,665,184 | 87 |
| 4336. | CATATCGAAATATTTAGATGAAAA[G,A]AAAGAAAACCATGAACGTTTTGGGA | 1,667,536 | 87 |
| 4337. | TACTCAACACTCTTGGCACTCATG[C,T]CAAGTGTCTTCATAACATGACCACA | 1,667,584 | 87 |
| 4338. | TTAACTAAGAACAGTAGTCGACAA[T,A]CTAAACTTTTTTACATCCCGTCACC | 1,668,936 | 87 |
| 4339. | CAGATGGAAATCAAAGATGAACCC[C,G]CTTTTGCGCTTCTGATGGTCGGTCG | 1,669,033 | 87 |
| 4340. | AAAAAaaTCCCTAGACGCAAAAAT[C,G]GCAACCAAACTCCCGTGGAACCAGA | 1,669,079 | 87 |
| 4341. | CAATCCAACGCTAACCCGCCCGGG[C,G]CCCAGCCAGGCAAGATAAAACAGCC | 1,670,180 | 87 |
| 4342. | ATTAAATACGGGCCAAGCCCAATC[A,G]GTGGTGCACCCTTGTGCAAAGAAAA | 1,670,430 | 87 |
| 4343. | GCAAATTTATTTGCTTACGAAGCA[G,A]ATAAATAACTATTAACTTATTAGGC | 1,670,589 | 87 |
| 4344. | CGAGGCTTTGCCTCCGAATGTCTCG[G,A]TATCCATGGAGGTCATTGAGCCTCA | 1,670,922 | 87 |
| 4345. | ATCGCCTAGTGGGTGAGTAGGCTG[G,A]CGGCTTGAGATCGGGGCAAAATCGA | 1,670,969 | 87 |
| 4346. | TGAATCAAGATTGTTAGACGTAGA[T,A]ATCAACTGTGGATTATGCTCATGTT | 1,671,045 | 87 |
| 4347. | GAGGCGGTGGAGTTGTGCGCTCTC[A,G]TTTTTGCCATCTTCTCTtTTTTTTT | 1,671,404 | 87 |
| 4348. | CACTAGTCTTCCTTCCTCAAGCTC[T,C]GATAGGAAGGTGACCGGCAGAGAGC | 1,671,645 | 87 |
| 4349. | TTTAATCCCCTACCCCCTAAAAAGT[C,T]GGAGATCATATTGATGACATCAACT | 1,671,865 | 87 |
| 4350. | TGCCGACTAGCTATGAGAGGTCTT[C,T]AGAGGATTAGCTCCATCGCTGTCAT | 1,672,334 | 87 |
| 4351. | TCTGCTCGACTCATCCCTAGACAAA[A,G]GAGCACTAAGTGGCCAAAGGGATCC | 1,672,447 | 87 |
| 4352. | GGATGAGGAGCACTAGATTGCTAT[G,A]TAATGTCCTCGAAGAGTTAGCCCCA | 1,672,515 | 87 |
| 4353. | TATGCGGCAGCTGTCATGATCCTT[A,G]GCTCGCAAACTCGCATCAGGGACAT | 1,675,378 | 87 |
| 4354. | GATGATTGATGAGATGCTTTGTAT[G,A]CTTGTGGAGAAAGTATCCATGAGTA | 1,675,426 | 87 |
| 4355. | TTTATTTTAGATTGAAATTTATT[A,G]AAGTTAATGTAAGATCATTTGAATA | 1,675,574 | 87 |
| 4356. | AATTTTGATACTTTTATTTTAGAT[T,G]GAAATTTTATTAAGTTAATGTAAG | 1,675,586 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4357. | AATTAAATTTCGAACTGATGAATTA[T,G]ATATGCTTATTTTTTATAAATTATT | 1,675,781 | 87 |
| 4358. | ACCGCAAGATGATACATAGCTTAT[A,G]GTAAGATGATACGCAATATGATCAT | 1,675,972 | 87 |
| 4359. | ATCCTGTCAATTGAGGCTAATACG[A,T]TGACAATTATTAGTCCGAAAGATTT | 1,676,175 | 87 |
| 4360. | GATGACTTGAAACTCTCTGCTTAAC[C,T]ATGTGGAGGATCCTGTCAATTGAGG | 1,676,209 | 87 |
| 4361. | CCACCATCAATATGCATTTTCATA[C,A]TTATTCATACTCTTTCTAATGTTGG | 1,676,641 | 87 |
| 4362. | AAACACCTTGTCAATTAGACAACA[G,T]ATTTGCATTATCCAAGTCTTCATCG | 1,676,936 | 87 |
| 4363. | ATTGAATCATCTGTATGGTAATTC[G,A]GTCATGATTTGATTAAATCATCTGA | 1,677,147 | 87 |
| 4364. | TGTGGTTTCTAAGCATCATACTGG[C,T]ACTCATCTTAGTCAGATCATGTACC | 1,677,223 | 87 |
| 4365. | TTTGAAACCCACCAACTCTAGCCT[C,T]CTATCATCATCGAAAAAGTTATCTT | 1,677,917 | 87 |
| 4366. | CGAGGCCTTTGCACAGATATTGAA[G,A]CAGCATTAAAAAAAaTTTGGCCAGC | 1,678,096 | 87 |
| 4367. | AGTGACTATTAGATAAACTATACC[A,C]CCCTAGCCTATAGGAGCCTAACCCC | 1,678,163 | 87 |
| 4368. | TCCTAGATAATTTAACATAGGGTA[T,C]AAATTTATTTtTTCTTGATGAGTGA | 1,678,208 | 87 |
| 4369. | CATGATGATAAACATGTCATTCAC[T,C]AAGAAAAATTAATAAAATAAAATAA | 1,678,263 | 87 |
| 4370. | TCATATGATTTTAACCAATATTTT[C,T]GTTTCTATGTTATTCCTTCTCATAT | 1,678,322 | 87 |
| 4371. | AGAGGATTATTTCTTTTTACCAAC[A,G]TCTAGATCTATAATCATATGATTTT | 1,678,360 | 87 |
| 4372. | TATCAAAATATAGACAATTAGTGA[T,C]CAATATTCTGTGAAAAACTAATGTA | 1,678,688 | 87 |
| 4373. | GCGTATCAAAATATAGACAATTAG[T,C]GATCAATATTCTGTGAAAAACTAAT | 1,678,691 | 87 |
| 4374. | CAAAGGTATGTTGTGAGCGTATCA[A,G]AATATAGACAATTAGTGATCAATAT | 1,678,707 | 87 |
| 4375. | GGTTAACTGCTAGAGCAATTTTTA[T,C]CGACAAGATACTTTTGAGAAATGAT | 1,678,888 | 87 |
| 4376. | ATTGAATTGGCGCATTATTTAAGT[A,G]TTATCAATAAGGATTTGAGTAGTAA | 1,679,007 | 87 |
| 4377. | AATTTTGAAACTTGAGAGATTTTA[T,C]TTTAAATTGAGGAGATGTCTATTAT | 1,679,244 | 87 |
| 4378. | GATGTTCGATAGAATTTTACAATT[A,G]TTAAGTATAATAATTTATCTCCTAA | 1,679,386 | 87 |
| 4379. | ATGATATCAATAATAAAATTTTTC[C,T]GCATTTTGATGTTCGATAGAATTTT | 1,679,418 | 87 |
| 4380. | CACCATGCTATTCCTCATCAGTCA[G,T]ATATGGTAAGCTATGTAGGCTATTT | 1,679,552 | 87 |
| 4381. | ACTCGTCCGTAGGGTATCCCCAGT[A,G]TGTTCAGCAACATAGGCGGCTATCC | 1,680,120 | 87 |
| 4382. | ATAAACATGTGATGGATAATTTAA[T,C]ACATATGGTACAAATTAATTTAGCT | 1,680,276 | 87 |
| 4383. | ACTATGATGGTAAACATGTCATTC[G,A]CCAAGAAAATTAATAAAATAAAATA | 1,680,323 | 87 |
| 4384. | TGTTAATATGATATTTTTCAAACA[A,G]TACATGATCAATCCTGCTGAATTTA | 1,680,512 | 87 |
| 4385. | ATTTTGATGAATTCCATTTAGTTA[C,T]AAATATAATAGGTTGCTAAGCTTAT | 1,680,565 | 87 |
| 4386. | AGCTTGAATAAGAAAGTTATGGTC[A,G]AAATAATAAAATTGTATTAGGATAT | 1,680,740 | 87 |
| 4387. | AATTCGAACTACTTCAACTACATC[T,C]ACCTTTAAGTTAATTTCTCAAAACA | 1,680,809 | 87 |
| 4388. | CTTAAGGAGAGATGGGTGAGTGCT[A,C]TTTGCCAAAAGCATTTAAGAACAAA | 1,681,014 | 87 |
| 4389. | TAAATGCTAGAGCAATTTTTATCG[A,G]CATGATGTTTTTAGAAATAATCTT | 1,681,088 | 87 |
| 4390. | TACTTGAAATGAAAGTTAAATGCT[A,G]GAGCAATTTTTATCGACATGATGTT | 1,681,104 | 87 |
| 4391. | TATGTTGGCTACTTGGATAGCAGT[T,C]CCTCTGATTGCATCGTTCTGATATG | 1,681,706 | 87 |
| 4392. | CATTATTAGCGATAAATTTTTTGC[A,G]TCACTAATACCCTATTCTGTTGTAG | 1,682,167 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4393. | TTCATCGCTAATAATTTTTATCGA[T,C]GAAAATTCATTATTAGCGATAAATT | 1,682,199 | 87 |
| 4394. | TGATTCATTGTAAATAATCATTTT[A,G]TTATTAGCGATATAATATTTTATCA | 1,682,422 | 87 |
| 4395. | AGAAGAGATTGAATATTATGGTGT[G,A]CTGATAGATATCATAGAACTGAAT | 1,684,647 | 87 |
| 4396. | ATAATATAGATGCTGATGATCAAT[A,G]TAGGAGAAAATTTGCAAATGATTT | 1,684,981 | 87 |
| 4397. | GTTCTAAATAATTGTAAAAAAaTT[A,G]AAGATTTCATTGACTAAGTACCATC | 1,685,131 | 87 |
| 4398. | CAATCATTCAGATCGTAACGCAGA[T,C]CGTGAATGGGATGATAATGAACTGA | 1,685,273 | 87 |
| 4399. | GAATTGCAGAAAATAGAAATCCAA[T,C]CGGAGTTGCATTTAGTTCATCGAGG | 1,685,987 | 87 |
| 4400. | AAAAAGTAAAAGATAGTACAAAAG[C,T]TTATCTTGAATTGCAGAAAATAGAA | 1,686,019 | 87 |
| 4401. | AATTTGAAAAAATATCGGGTACTT[A,G]CAAGCGAAAGTGTATTGAAGCTGAG | 1,686,205 | 87 |
| 4402. | TTGATGGTAAGTTCGATCGACGTC[T,C]GCCACCCAAGGAGTTAAGTAGAGCA | 1,686,292 | 87 |
| 4403. | CTAGTAATCACTCTTGGAGGACCC[A,G]TTACAATCAATACTTTGATGGTAAG | 1,686,331 | 87 |
| 4404. | TGATGTATATCTACGACAGTTAAT[C,T]GATGTTTTGAAGGAGCTATGGGAAA | 1,686,595 | 87 |
| 4405. | TCACCTTGAAAGTACATGAAAGAA[C,T]CATTTATTTTTATATCACTATTGAT | 1,686,675 | 87 |
| 4406. | ATTGCTTCATATTAAAATCGTGAA[T,C]CGATGGAGTCAGAAGTCATTTGATC | 1,687,242 | 87 |
| 4407. | GTATAGACAAGAAGTATAGTCGCT[G,A]GATATGGTATGGAGAGGGTCATTCG | 1,687,574 | 87 |
| 4408. | ATGGTATAGACAAGAAGTATAGTC[G,A]CTGGATATGGTATGGAGAGGGTCAT | 1,687,557 | 87 |
| 4409. | ACAGTGCTAGTCGGATAAAGTATC[C,T]ATGCAAAGATGTGTCAATATGGTA | 1,687,667 | 87 |
| 4410. | GTTGTTAGATGGATATCAACAAAA[G,A]TTGGATAAATATCAGAGATATTTTT | 1,687,775 | 87 |
| 4411. | GTCGAAATAATAAAACAATATTAG[G,A]ATATTAAAATATTTGATAAGATGTC | 1,692,796 | 87 |
| 4412. | TTAGATTTCAAACTTGAACTACTT[C,T]AACTATATCTAACTTTAACTTAATG | 1,692,896 | 87 |
| 4413. | GATTTTATAAATGCTAGAGTACCA[T,C]GATACACTTGAAATGAAGGTTAAAT | 1,693,210 | 87 |
| 4414. | TGCATGTTTGTATGTTTTGGGAGG[A,G]GGAGAGAGAGTTAGTGAGCGAGTGG | 1,693,502 | 87 |
| 4415. | TGGCAGAATTTTGCAATTGTTAGG[A,T]ATGATAATTTATCTCTTAAAGAATT | 1,693,702 | 87 |
| 4416. | TCCTATCTTCTAATGATGATATCA[G,A]TAATAAAATTTTTCTATATTTTGAC | 1,693,755 | 87 |
| 4417. | CCCTCTAGTTGCATCGTTCCTCAT[G,A]CTCTAATATATATAAGCATAGTGAT | 1,693,8147 | 87 |
| 4418. | GCACCATCTGGACTCGAATACCAC[A,G]CTATTTCTTACTAGTCAGATATGGT | 1,693,892 | 87 |
| 4419. | GTGAATCTCGTCGAGCACCATCTG[G,A]ACTCGAATACCACACTATTTCTTAC | 1,693,906 | 87 |
| 4420. | TATAGGTGGCCATCCAGTCTGCCA[C,T]TGTGTTAGCCTCCCTGAAGACATAT | 1,694,412 | 87 |
| 4421. | ATTTCAAACTCGAACTACTTTAAC[T,A]ACATCCAACTTTAAGTTAATTTCTT | 1,695,134 | 87 |
| 4422. | CTTTGACAATGTGACCACAAACTG[T,G]GGTTCCTTTATATGTGTATATGTAG | 1,696,167 | 87 |
| 4423. | AGGAGGAGAATTAAAATTCTCGTT[G,A]TCGAAGTAAGCGGAGAGCAAGTCAT | 1,697,212 | 87 |
| 4424. | CCTAGGAAGACTGAGATTAACATC[T,C]AGCACCTGTTTGACACCTACTAAAA | 1,697,644 | 87 |
| 4425. | CAAGACACATGGATTATGATTCT[T,G]TTTACCTAACAATCATCCTAAGGGC | 1,697,815 | 87 |
| 4426. | GCATGTAGTGGTGAGATGCACAAT[A,C]AAGGAAGAGTCACAAATTGCAAATT | 1,698,462 | 87 |
| 4427. | TTACAGATAATGATGAAGAGATAT[T,A]TGAAAGGCATCTGATAGGGGTGGAT | 1,698,525 | 87 |
| 4428. | TGGCATATTGACTTTTTATTCATC[G,A]ACTGATTATGTGAGAAAGCATAAAC | 1,698,610 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4429. | TGTATCTACAAACAAGCTACAAAG[C,T]ACATCAACTAGAAGAGGTGCATGTG | 1,698,737 | 87 |
| 4430. | ATTAGTTTTCTCAGTAAATATTCC[A,T]GGTAAATAAAATCAATTCAGTTGTC | 1,700,288 | 87 |
| 4431. | ATTGAAATTTAACAGATCAAATGA[C,G]AAGTGCATTGCTACTAGATTCTTCA | 1,700,782 | 87 |
| 4432. | AATTGGAGATCCTTGAACATATAC[A,G]GTAGCTTCTAAAACACCACTATTTT | 1,700,885 | 87 |
| 4433. | TTATTGTTATCTGATGGGCCCTCC[G,C]CCCTTTTGTTCTGATAAGTCATTGG | 1,701,721 | 87 |
| 4434. | ATAGTTTCACCAAGACAAATTCTG[A,T]ATCAATAAACCAACGATATATAATG | 1,702,011 | 87 |
| 4435. | CAATTATGAAATTAGAAAGTTATT[T,C]TCTATGCTTGAAGTTCTCTAGTTTC | 1,705,974 | 87 |
| 4436. | ATGTTTGAGGAAAACAAGTAGTCC[T,G]ACAATTATGAAATTAGAAAGTTATT | 1,706,000 | 87 |
| 4437. | TGTACCACCAAGTTGCATATAACT[T,C]TAGAGTCAAGTCTAATCTGTATGTT | 1,709,089 | 87 |
| 4438. | TCTTGTCCTGATAATTTCCTTTAA[C,G]ACGTTAATTCCAGCAATTAACTACC | 1,706,507 | 87 |
| 4439. | TCAGCTCACATCGTCATGGTACG[A,T]AGGTGGTGTAGAAGCCTTCTCCAAT | 1,706,729 | 87 |
| 4440. | AGTCAGCTCACACTCGTCATGGTA[C,T]GAAGGTGGTGTAGAAGCCTTCTCCA | 1,706,731 | 87 |
| 4441. | ATATAAATCCATAACAGTTTAGGA[T,C]GCAGAATACTCTTGATGCCTGGGCA | 1,706,843 | 87 |
| 4442. | GTCTATTGCGAAAAGTGGGTCAGT[C,T]AGATGGAATTGAGAAAACATTTGAG | 1,706,928 | 87 |
| 4443. | CCAGGTCAGCCTGTCTGGTTGTGT[C,G]AATCCAAATAAAAGATTTGATGTAG | 1,707,048 | 87 |
| 4444. | AGCACGTCCAGGTCAGCCTGTCTG[G,A]TTGTGTCAATCCAAATAAAAGATTT | 1,707,055 | 87 |
| 4445. | TAAGGTTTCTGAGCTTCTTGTTAC[T,A]GTTTGTATTTCATTTCCTAAAATGG | 1,707,122 | 87 |
| 4446. | GCTTTAGCTAATTATGCTATATAT[T,A]TTTTtAGATTAACTGTTGATTCTTG | 1,707,191 | 87 |
| 4447. | AATCCAGTTACCATGTTTTTGAGA[C,T]GTGCTATTGTAAAAGTTGAGGAAAA | 1,707,479 | 87 |
| 4448. | TTCCATTGATGATTGGTCCATCAT[A,T]CAAGATTGTCTGCTCGTGCATATGC | 1,707,970 | 87 |
| 4449. | CAGTTGGGCTACATTGGTCTTGGC[A,G]TAGAGTTTTATCTCCATTATACTCT | 1,708,567 | 87 |
| 4450. | ATTTTGTGGATAGTGAGGGATGGG[G,A]AAGCCACTCTTGTATGAGATTTGGG | 1,708,829 | 87 |
| 4451. | TGTGCTGAGGTTGGAAGTCATAAT[G,T]TTGCGACTGATTACGCAGTCTTGGG | 1,709,305 | 87 |
| 4452. | GAAAGCTGTGTTGATTTGGAAAAA[A,T]TTCCTCTAAAGAGATTCTTTTTATC | 1,709,396 | 87 |
| 4453. | ACCTCAATCAGCCAATTCGATTTA[C,T]TGTCTGGAAGATAAGAATGTGAAAG | 1,709,441 | 87 |
| 4454. | TCCGGACAATTTTGTTGGATGAGA[G,T]ACTTGCACAACAGCCATATATTTAG | 1,714,587 | 87 |
| 4455. | TTTGTTGGATGAGAGACTTGCACA[A,C]CAGCCATATATTTAGTTATGTTGCC | 1,714,597 | 87 |
| 4456. | AAGCTAAAATAGATATTTAGATCA[G,A]TTAACTGCTCGCAACCGATGGCGAA | 1,714,657 | 87 |
| 4457. | TTAGCTATTGTAGGCTCAAATTTA[C,T]GGGCAAGCTGGGTGCATGGCATGA | 1,714,892 | 87 |
| 4458. | ATGCCCATCTCCTCTTGGAATTTC[A,G]TCTGGCAACGAGCATTCCCCACCAT | 1,715,211 | 87 |
| 4459. | ATCGGGGTCGCAGGTATCTGTGTC[C,G]GGGCACCCGCAAGCACAGGAGCTGC | 1,715,757 | 87 |
| 4460. | GTCCATGGTTGGTGGTAAGAGGGT[A,G]CCATTCTTACAGCAATAAGGTATCT | 1,716,105 | 87 |
| 4461. | GTTACTCGACTTTTCAAAACTGTG[G,A]ATCTTATTTAACTATACCTCTAGTC | 1,721,227 | 87 |
| 4462. | CTTATTTAACTATACCTCTAGTCA[T,C]CAAAGTGGTCCACATAAAATTTGAT | 1,721,254 | 87 |
| 4463. | AACTATACCTCTAGTCATCAAAGT[G,A]GTCCACATAAAATTTGATGATTCTC | 1,721,261 | 87 |
| 4464. | GGTGAGCTTCACAATATGCCATGT[A,G]TCCCTTAATACTAATCTTAAAGTAT | 1,721,402 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4465. | CATTTTAAAGATCTTAGCTCCCTT[C,A]TGTGAAGTTGAAGTTGGTTGATTGC | 1,722,661 | 87 |
| 4466. | TCTAGATCCGATCCTTCTTATCTC[T,C]CCAAAATTTATCTAAGTTTTCACTA | 1,723,087 | 87 |
| 4467. | GAAACACATATAGTGTATGACTTC[C,T]ACGTTATTACAGATTCTAATTGAGT | 1,723,351 | 87 |
| 4468. | TCATTATCTATTGATCTCTGGTTT[G,A]ATGGTGGATCAGCATTACATGGGTT | 1,723,854 | 87 |
| 4469. | AATCTGAATTACTACGTTTGATAT[A,G]TTTTTTTGGATGGTAATCCAGATTA | 1,724,043 | 87 |
| 4470. | TATATTTTTTGGATGGTAATCCA[G,A]ATTATCTTAATAATTTAATTGAAAA | 1,724,064 | 87 |
| 4471. | GCTAATTATACTTTCGTCCTTTGA[G,A]ATTTTTTATTGTATGAAATTTTTA | 1,724,468 | 87 |
| 4472. | CACCAAGCTAGTAGACCAATTAAA[C,T]TTGAAAGCAACACTACCCTAGCTCC | 1,724,534 | 87 |
| 4473. | CTATATCTAATGACTAATAGTTTC[A,G]AGGCATATTTTAACAAGCTCAAGA | 1,724,726 | 87 |
| 4474. | CTTTTGATAAAAACTTGTAGGCTC[G,A]CAAGGGCCTATTAAGATGACTAGTA | 1,724,810 | 87 |
| 4475. | TATGTTGAAACCGAATATCCACCA[A,C]GGCTTACATAAAAATTAAATGGCAC | 1,736,030 | 87 |
| 4476. | TTTGCATCATTTGATCATTCCTAC[T,A]GTGTTCTGGTGATATCCAGTGGGGG | 1,736,416 | 87 |
| 4477. | CTCTTTGACTTCAATCTGTGCTTC[C,A]GAGATGAAACGAAAAGGTCATCATA | 1,737,193 | 87 |
| 4478. | GAAAAGGTCATCATATATTAAACATC[A,C]ATTCTTAATCTCCACCTTTCCAGGT | 1,737,228 | 87 |
| 4479. | TTGGAGGATTGCTCGCCAGTAGCA[T,C]GAGTACCTGGAAGGAAGATCTTCTT | 1,737,289 | 87 |
| 4480. | CTAGACATAAGAGCTCAACTTACT[T,C]ATTACCACATCCGAATCCGCTCCAT | 1,737,545 | 87 |
| 4481. | AACCTGGACGAATCATACTAATCC[G,A]AAAGGCTGAGATCCCATATGGATCA | 1,737,648 | 87 |
| 4482. | AAAATTTAACAGAGACTAAAGATG[A,C]CCCAAAACAGTGGACATTGACTTGA | 1,737,948 | 87 |
| 4483. | ATTACAGCCAAAAGAAGACATACC[G,A]AAGCTTCCAGAAGCAGGTAGTGGCA | 1,738,040 | 87 |
| 4484. | GAGCAAAAATTCTTCTACATCAAC[G,A]ATCTAATGGTGGTGCAACCTGGAAA | 1,742,280 | 87 |
| 4485. | CCAGAACAACCATTTGACAATTTA[C,T]CATGAGAAAGTTATTTGCTGATCTC | 1,742,608 | 87 |
| 4486. | TCTCAGAAAACTCTAAAGAAAGCC[A,G]AaTATAAATTTTAGACCTAGATTCA | 1,743,060 | 87 |
| 4487. | ACGTAATTCGGTCAGCAACTCTGC[G,A]CTTGTTTCAGCATTGTTAGGACTGG | 1,743,358 | 87 |
| 4488. | AAGATTTACTTTGTCAACTGGGAA[A,T]ATGCCATGAACAACATATACACCTT | 1,743,569 | 87 |
| 4489. | TTTTGTTGTAGTTCAAGCATGATG[G,A]GATGGGTTTCAAAATGAGTCTCAAC | 1,743,821 | 87 |
| 4490. | AaGGTATGAGCCATTATTGAGTTA[C,T]AAATGAGCCACAAATCAAACAGATC | 1,744,027 | 87 |
| 4491. | TAAGCTTCATGCATCAGCTCAGAT[A,G]AAGGAACCAAGGAAAAGAATGAAAG | 1,744,167 | 87 |
| 4492. | GAACAGACGTACAGTTGGTAGCTA[A,T]GCATTATATTGTGGCAATGAAGGAA | 1,744,566 | 87 |
| 4493. | TGCTTACAAGTTGAGCCTATAGCA[T,A]GAATGGATGCAACTCTACTCTACCA | 1,746,019 | 87 |
| 4494. | ATTAGCCGACAAATATTAATTATT[A,C]TGAGACCGGCATATAAGAAGTCTAA | 1,747,911 | 87 |
| 4495. | GCAGATATGGAAGACTGATCCAAG[T,A]ACcGCTAAAACCAGATCATTCGAGT | 1,748,046 | 87 |
| 4496. | GATATGGAAGACTGATCCAAGtAC[C,T]GCTAAAACCAAGATCATTCGAGTAGA | 1,748,049 | 87 |
| 4497. | GTAAGTTCCGACCACTCACCCTG[A,C]AAAAAGGTGGCAACTTTGAGATGCT | 1,748,288 | 87 |
| 4498. | CTATGCATTGACAATATGAAATTA[C,T]TACAGATGTGTTTCGATTAACAATG | 1,757,258 | 87 |
| 4499. | TTTATCCATCCGTTGTTTGGTTTG[G,A]CTTTACCATCGAGTTCATCTATTCT | 1,757,837 | 87 |
| 4500. | TTGAAAAGCAAAAATAAGGCACTC[A,G]GACATGATAATAATATTATCATTTA | 1,758,074 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4501. | ACGAACAAGCACCGATAGATATTT[T,G]AGTGTAAACATGCTCATGTCATGTT | 1,758,152 | 87 |
| 4502. | TTGTTTTGTGGGAGAAAAGGCTTT[G,C]CATCTGAGCCTGACCTTTCATCTGC | 1,758,355 | 87 |
| 4503. | TCTTTGCCTTTATCCTTGGATTTC[T,A]GCTCTACTTAAATGGTCTTACTAGA | 1,759,719 | 87 |
| 4504. | TGTAATATATTTCTATTGCCCCCC[G,A]TGTATTTGTTACATGATGGACAAAT | 1,760,495 | 87 |
| 4505. | AAACACTGAAAATTAAATCCCAAG[T,C]AGACCGTTAGCATCTACTGGATATC | 1,766,861 | 87 |
| 4506. | GATAGTATACATCTTTTTCCATAT[A,T]CCTAATAATTAAATGAACATTTCTC | 1,771,974 | 87 |
| 4507. | ACACAGTCTTTATATTCTTTCCTG[C,G]TCATTACTCTGTTATATTTCTTTAC | 1,772,033 | 87 |
| 4508. | TAATGTTAAATCCCATATCTGTGA[G,A]ACTTGTTATGACAACAATCGAACCC | 1,772,152 | 87 |
| 4509. | ACACCATCAGTTGCAAAACTGAAA[G,A]AAATTGAGTAACCATTGAGGGTTAG | 1,772,334 | 87 |
| 4510. | AATCTTTGTCGCTGCCTTGGGATG[T,C]TTTAGCACGAATCCTTCGTCCATCA | 1,772,414 | 87 |
| 4511. | TGCCTTGGGATGTTTTAGCACGAA[T,C]CCTTCGTCCATCAAGAATAGCATGG | 1,772,426 | 87 |
| 4512. | TAAATAACCAGACATCCAAGAAAA[C,T]AGAAATCTCTTCAAACCCATCCAAA | 1,772,536 | 87 |
| 4513. | TTATAAAAAATTTATATCCATATC[C,T]GATTGGATCGGATGAAATTTATTTA | 1,773,207 | 87 |
| 4514. | AGATCTTATCTTCTAATTTTGTTC[A,G]TCTGTCTTTTGCTTTCGTTGATTT | 1,773,531 | 87 |
| 4515. | TTTTTTtATAGGAGTCTCAATCAA[G,A]AAGAGGTGTGAAACTTTTTtGGTTT | 1,773,612 | 87 |
| 4516. | CAAGACATAGGAAGTCATAATAAA[C,T]CGATAAAATATCATATAAAAATACA | 1,774,443 | 87 |
| 4517. | TATATTAGCTCGGCTATATCGCAC[A,G]GTTGGAATGATTGTCACCACATGCA | 1,775,021 | 87 |
| 4518. | TTCCCAATAATAGACTCCAACCCC[G,A]TTCTATATATAAGAGCGATTCGAGG | 1,775,114 | 87 |
| 4519. | ATAGTTTGGATTTTAGCAACAACA[C,T]ATCTCAACAAATGGCAAGGATGGTC | 1,775,304 | 87 |
| 4520. | TGACACTCTATCTATCCATCTGCT[T,C]ATCCGTAAAATCCAAGCCATAGTCAA | 1,776,580 | 87 |
| 4521. | ATCATCGATTTCTTTCTTCTCTTG[A,T]CCTTCCAACAAATTTTATATGTAGA | 1,779,615 | 87 |
| 4522. | TCCATCTTCTATATCAGTTCGAGT[G,A]ACAATATTAAATTTTAAAAATATGA | 1,779,684 | 87 |
| 4523. | TTGCTGCGTACTCTGATTTTAATT[T,C]ATCAAATTATATAAGTCTATTAAAG | 1,779,957 | 87 |
| 4524. | AAAAACTCAAGCCAACATCCTTAA[A,G]TAgAATCAACTTGATTATTTCTTAT | 1,780,304 | 87 |
| 4525. | TTGACTTGAATAATTAATACACCT[C,T]ACCATCTTCAACAATCACAAGAAAA | 1,780,487 | 87 |
| 4526. | ATCAAGGAATCATATTCAGAATAT[G,A]ATATTTTGAGTAACCAAAGATTTCA | 1,780,718 | 87 |
| 4527. | AGACCAAAACAATAATGTAATTTT[A,G]AAATATTACATGGCTATTTTAGAAA | 1,787,842 | 87 |
| 4528. | TTTCCATTTTCACTGGATGAAAAC[A,G]GTGGAGGATTATGTTAGGCTGACAG | 1,788,406 | 87 |
| 4529. | CCTTCATCTGCAAGAAAAAAGTAA[C,T]CTATGATAATTAACGTGTTAATGCA | 1,789,793 | 87 |
| 4530. | AAAGTAACCTATGATAATTAACGT[G,A]TTAATGCATAATGGTTATGGTAGCA | 1,789,810 | 87 |
| 4531. | AAAATACTAAGAAATCCCATTATT[T,G]TTTAACAAAAAAaCAGCTGCGCTTA | 1,789,929 | 87 |
| 4532. | TTCGTTCCAGAAAATTATGTTCCT[A,C]GAGAACTTTTTCTTCAATGCTAACA | 1,790,225 | 87 |
| 4533. | GACGGCAACTGTATAACGCTATAA[A,C]ATAAGAAAATATAACAAAGATAAAC | 1,790,331 | 87 |
| 4534. | AATATAACAAAGATAAACAAATGC[T,C]CCACATCCACAGAAAgAGAGAGAGA | 1,790,363 | 87 |
| 4535. | GACGCGGTCTGAGCCACTCGTTAC[A,G]AGAGAGAACAAATGAGAACCTTTTG | 1,790,538 | 87 |
| 4536. | CCGACAATCTATTCAGATAATTGA[C,T]AATTTAAAATAGACTTATCAAATTA | 1,791,054 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4537. | TTTTCCTGCGGTGGCTATCATGTC[A,T]ATAACTTCTAGATGCTGTTTTCTTA | 1,800,705 | 87 |
| 4538. | CTTCCTTTCACTAAGAGATGCAGT[T,C]GGCTGTTTTCCTGCGGTGGCTATCA | 1,800,735 | 87 |
| 4539. | GTGCTCTGTCAGCTTCACTTGCAG[C,T]cTTCTCTGCCTCCCTTTGGCACTGC | 1,801,372 | 87 |
| 4540. | TTCCTCAGATCGAAGAAGCCTTTC[A,G]TACCACCAATCACCATCTTTTTCCT | 1,801,614 | 87 |
| 4541. | AGACCAATTATACGTGCCTTCTGC[A,G]TACCACCAATCACCATCTTTTTCCT | 1,801,659 | 87 |
| 4542. | ATAGTATAACATAGATGTGAAGCA[T,C]AGACCAATTATACGTGCCTTCTGCa | 1,801,684 | 87 |
| 4543. | TTCCAATAGCATAGCATCAGTTGA[T,C]GACATCTTTCGCAATTAATGTTATG | 1,801,785 | 87 |
| 4544. | AAACTTATCAGGTTATAAAGAATT[A,G]AaGATTGAAGTTTCTTTTAATGCTT | 1,802,612 | 87 |
| 4545. | AACTAGATGTCATTCTCACCAGTC[A,G]CTTTGAGATGTGAAGCATTATCTGC | 1,804,403 | 87 |
| 4546. | ATTTAGTCGAAAGCTGTATTTCAT[T,C]ATAACCTAATGACAAAAATGAATCA | 1,805,534 | 87 |
| 4547. | CCAATTCTATACCAGTAtACAGTA[C,T]AGGAGGCGAACCAACACTCGGTACG | 1,805,766 | 87 |
| 4548. | TACCGTACCAATTCTATACCAGTA[T,C]ACAGTACAGGAGGCGAACCAACACT | 1,805,773 | 87 |
| 4549. | ACATGTTACACCACACCATACCGA[T,A]CCATGTGGTATGGAACCTACCGTAC | 1,805,815 | 87 |
| 4550. | CAATGTGCATTGGAGGTTCCTTTA[A,G]GATTCCTCCAGAAACAGGAATATGG | 1,806,013 | 87 |
| 4551. | ACTCCACATTTTGTTATTCACAcT[C,T]ACTAGCGAATATCAGCAAATCAGGT | 1,806,206 | 87 |
| 4552. | TAACTCCACATTTTGTTATTCACA[C,T]TcACTAGCGAATATCAGCAAATCAG | 1,806,208 | 87 |
| 4553. | GATGGGCAATTGCCTGCTCACCCA[T,C]AGTACATGAAACTTGTAGATATGCA | 1,807,608 | 87 |
| 4554. | GGTTCTCACTAATCAAGATTGTT[A,G]TACGGCCAACCAATTATAGAAGGTA | 1,808,014 | 87 |
| 4555. | TCGAGTGACTATGAGCGTAATTGG[T,G]AAACCTTCGTCCTTATCCACAGCAA | 1,809,638 | 87 |
| 4556. | TCaCATCATTTTATGTTCTTTTCA[G,A]GAAAAGTATATGGTTCAGGCAAAAG | 1,810,035 | 87 |
| 4557. | AaTACATGGGCATGGAGCAAGATC[A,C]CATCATTTTATGTTCTTTTCAGGAA | 1,810,057 | 87 |
| 4558. | AATGCAATTGTTCTTAGGCAAAAa[G,A]AAAAaTACATGGGCATGGAGCAAGA | 1,810,085 | 87 |
| 4559. | CATACTGACAAAGAAACAACTTGC[A,C]aTATAAATTTAGTGTGCTTTATTGA | 1,810,147 | 87 |
| 4560. | TCCCCCCAAGAAACTTATAGAAAT[C,T]cGCTATCTAGATGGGATATTTTAAT | 1,810,238 | 87 |
| 4561. | TAGTGCTTGATATTTATTTTAAAA[C,T]TTATATTATAATTTAATGTTTAACA | 1,810,313 | 87 |
| 4562. | TTGTTTATATTCAACCTCAAAAAC[C,T]TAGCTGATGTATAGATCATTTATTA | 1,810,929 | 87 |
| 4563. | ATTTTtATTTAGATAATAATAAT[T,A]ATTATTTTTATTTCTAGCTATGTCA | 1,811,018 | 87 |
| 4564. | TATTTATTGTAATAACCATCATCA[G,T]CCTCATATCATCACCACCGTCATCA | 1,811,406 | 87 |
| 4565. | TGCGCGCGcgcGTGTGTGTgtg[T,A]GAGAGAGAGAGAGAAGATCAAATAT | 1,811,453 | 87 |
| 4566. | AGAAGGGGATAGAAGAGGGAGTGA[C,T]GGGGGTCCATGGAAGCCAAaTGAAT | 1,811,513 | 87 |
| 4567. | AAAGAACAACAGTGAGTGAATTTG[C,T]GACAGAAGGGGATAGAAGAGGGAGT | 1,811,541 | 87 |
| 4568. | CCAATTCAGTTTGTTTAATTTTGA[G,A]CCAGCTCGAGTTTGGTCCATGTAGC | 1,811,636 | 87 |
| 4569. | ATCATCTGTGCATAGAGGAGGTCT[C,T]GGGCACTTGAGCAAGGCAAAGGACC | 1,811,946 | 87 |
| 4570. | CAAGCAAACTATCATCTCATACTT[C,A]GGTATTGAAACTGAGAACAGCGATA | 1,812,346 | 87 |
| 4571. | TGTCTTCACGAATTACTTATGGTC[T,C]AGCATATGTCTATTATGTTGAGTCC | 1,812,414 | 87 |
| 4572. | GATGACGATGATAACAGAACTTCA[G,A]TGCACCTAAAAATATGGATAAACAT | 1,813,044 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4573. | AAGTAATAATGTAATAGATCCCTG[T,A]AATGCATCAGGCAATTAAAATCAAG | 1,813,181 | 87 |
| 4574. | AAAATAATATTATATGCCTGGCTT[A,T]CATCTATCACAGATAACTAATTAAA | 1,813,298 | 87 |
| 4575. | CCAACTAGCATCCAGAAAACGTAA[T,C]GACATATGCAGTTTGCAAAGTTTAC | 1,814,046 | 87 |
| 4576. | GACcACAAAATTATACAAGTTAAG[T,G]TtGCATTTAGCTCATTGTCAGAAAA | 1,814,109 | 87 |
| 4577. | TGTCAAAAGTGAGCACCACAGAC[C,A]ACAAAATTATACAAGTTAAGTTtGC | 1,814,130 | 87 |
| 4578. | GCAAACTTTCTGGACAGAAAGCTT[A,C]TTGTTTGTTCTGAACCCTAGGATCT | 1,814,292 | 87 |
| 4579. | CCATTAATTATATTAGCTCATCCC[T,A]AAAAACATCAAATATTCTACCTAAC | 1,814,384 | 87 |
| 4580. | CTTGGTATGCCTCAGCACAAAAAG[C,T]GGTACAAGATGGTACGGGGCCTGTA | 1,815,917 | 87 |
| 4581. | CTAAAGTACACTTCTAATTTGGTG[C,G]cTCAAACTCATAAAACTCTTTCGCA | 1,816,277 | 87 |
| 4582. | ATGAAGGTATAATAGCATTAAAAG[A,G]GTTTTGGCAGAGTTGTAAGTGTAAG | 1,816,826 | 87 |
| 4583. | TTACAAAAAAaGGGTCCTTCATC[A,T]ATGGAAAACAAATTGTAACAACCTG | 1,817,617 | 87 |
| 4584. | TCCCAGTTGGTCTTGGTTTCTACC[A,G]aGCATCACATGGACTGAACCAGCCA | 1,817,917 | 87 |
| 4585. | ATAGAATTTTAGTAGACCATGTTC[A,G]TATTCCTAAGGTCTTGCCAAGTTAA | 1,819,010 | 87 |
| 4586. | AAAgAATCAGTATTTCTGTTAAAa[C,T]cATATACGGAAGTCTGACAAGGAAG | 1,819,075 | 87 |
| 4587. | AATATTCTTCTCTAACAAGAAAAA[G,A]AATCAGTATTTCTGTTAAAaCcATA | 1,819,096 | 87 |
| 4588. | TGATGGAACTAAGGGAACTGGAAG[C,T]GAAATAGCAACTCATATAAATAGCA | 1,819,268 | 87 |
| 4589. | tAAAAAGCACATATTTTGGAAAAC[T,C]tAAAAGATTACCAGCAGAgAGTAGA | 1,819,652 | 87 |
| 4590. | AAACGGAACGATGTTTTAATTAT[T,C]TtAAAAAGCACATATTTTGGAAAAC | 1,819,678 | 87 |
| 4591. | CTTAACCATCAATCTGACATAGCT[A,G]CTAGAGAAACAGAAGAAAGAAGTT | 1,819,841 | 87 |
| 4592. | CTGCCAATGAAAGAATATGAGGTG[A,G]ACAAGCACAAAGGATTTACAGGTGAC | 1,819,897 | 87 |
| 4593. | AAGAACAGATCTGACTTATCAGCA[C,G]TATATTTCTTTATTCTTGCATTATT | 1,822,088 | 87 |
| 4594. | GTGGTTAAGACCTTAGAGATCACT[G,A]TGGTTTCGATTTCCATGGTTTCGAT | 1,822,311 | 87 |
| 4595. | CTGTGATTGTCTGTAGAAAGAGGC[C,T]GAAGAGAGTCGAGAATTTTATATTT | 1,822,561 | 87 |
| 4596. | ATAATAAGCACATCGTGCATCACA[A,G]GAATCTGAAAGGGTATTGTTTTGAA | 1,822,881 | 87 |
| 4597. | ATACgAAAAGTCAGTATATCCAAA[T,G]ACAAACAGAAGAAAAAGAATAATGA | 1,822,937 | 87 |
| 4598. | ATGCAATGATGCCAAGAATGATAC[G,A]AAAAGTCAGTATATCCAAAtACAAA | 1,822,957 | 87 |
| 4599. | AAAATTACATATAACAGACACAAA[A,G]TCCAAGTTATATATAAGTTCATGGG | 1,823,210 | 87 |
| 4600. | CATATACGAATAAAATGAACAAAG[C,T]ATATAAAAATGTGACCATAGAATAA | 1,823,534 | 87 |
| 4601. | AAAACTAAGTATGGCATGTACCgC[G,A]gTACACCTCCATACATACTCATGGT | 1,823,970 | 87 |
| 4602. | TCAAAACTAAGTATGGCATGTACC[G,A]CGgTACACCTCCATACATACTCATG | 1,823,972 | 87 |
| 4603. | ATCACATCATGACTGTGTTAGGCT[T,C]GTTCAGTTTAAATAACCAAGTGGTG | 1,824,164 | 87 |
| 4604. | CTGCATTTCCTACAACGCCTTACC[A,G]TTCTAAGGAATTACATCTCATGCTA | 1,824,275 | 87 |
| 4605. | TATTTAAACTCATGACTTGGTCTA[A,G]ACAATTTAGCCAAGTGTCAGTAACT | 1,824,574 | 87 |
| 4606. | TAaTTGAGGCATCTCATGTGTCCC[C,T]TGACAACAATCACATGCACCCATTA | 1,824,633 | 87 |
| 4607. | GAGCTTCAAGCTGCACAAATTGCT[A,T]aTTGAGGCATCTCATGTGTCCCcTG | 1,824,656 | 87 |
| 4608. | GTTGAATCCAAATTgCATATCTGT[G,C]TCCATGCCTCAAAGACCATGATTAG | 1,824,745 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4609. | ATCTACATATGTTGAATCCAAATT[G,A]TCCATGCCTCAAAGACCATGATTAG | 1,824,755 | 87 |
| 4610. | GGAAAAGGTGGGAACTAGTAATAT[C,T]ATATCACATTTTTTATAGGAATTGC | 1,825,267 | 87 |
| 4611. | GAAGATACGaCCAAGTCTTGCCTA[T,A]tCACCATTGCTCCACTGCACAAAGA | 1,825,463 | 87 |
| 4612. | CTCGCAATCTTCTCTGAAGATACG[A,G]CCAAGTCTTGCCTATtCACCATTGC | 1,825,478 | 87 |
| 4613. | CACATGCTACACATGATAGTTATA[A,G]GCCATTGTAATGATACATCATCTGC | 1,826,046 | 87 |
| 4614. | TGAGAACATGAGTAAGTTGGTCAA[T,A]AAAAAAGTTGACCAACTATCCCATG | 1,826,253 | 87 |
| 4615. | ATGAGGAAGTAACTTATCCATCCT[T,G]AAAAGTATGAGAACATGAGTAAGTT | 1,826,285 | 87 |
| 4616. | TAAAGATATATTAAGAATGAATTA[C,T]AGAGGTTATTTTTTCGATTGATGGA | 1,826,399 | 87 |
| 4617. | TTCTATATTATATTATATTATTAT[C,A]TAATAATATTTATATAATATATTAT | 1,826,493 | 87 |
| 4618. | GTAAAAGATTTTGTATTGCTAAGC[G,A]TAACATGGTATAAGCATCACTAAAA | 1,834,430 | 87 |
| 4619. | AAACATACTGTCAACACCAGTCCC[G,A]GATTTTTCATTCCTTTTTGATACTT | 1,835,096 | 87 |
| 4620. | ACCTGACCTATCAGTGCATACTGA[T,C]GATTTTTCATTCCTTTTTGATACTT | 1,835,155 | 87 |
| 4621. | GAAATAAAGGAAGTTCACAAACTG[C,T]TTAGTCTGGTCTAACATCCTTTTTC | 1,835,871 | 87 |
| 4622. | GCAAAATGCAAAGGGTGACCTCTT[A,C]TCCTCAAATCTAATATGCCTATATG | 1,836,268 | 87 |
| 4623. | AACATATTAGAAAATAGTTTGCAT[C,T]ACAAAAATCCTCAGGTTCGTTACAT | 1,836,788 | 87 |
| 4624. | CTTATAATTAGCCAAAAAAAAAAa[T,A]CTTAAGAATGATAACATGCCAGTAA | 1,837,586 | 87 |
| 4625. | TAGAAGATGCACAGCCTAATTATC[T,C]TGATGAGATCCATTAGATAAATTAA | 1,838,522 | 87 |
| 4626. | GTGGGATAAAGGCATAAAGCTGGT[C,T]GAACCATCAGTTTACAATTGCAATT | 1,838,574 | 87 |
| 4627. | TCTCCGAGGTAGAGAAGAGTGCCA[T,C]CAATGTGGGATAAAGGCATAAAGCT | 1,838,603 | 87 |
| 4628. | TCGTAACAAGCGATTAGCATAGGA[A,G]AATTTAGAATTCTCCGTTAGCGTAA | 1,838,693 | 87 |
| 4629. | TTCGTAACAAGCGATTAGCATAGG[A,G]AAATTTAGAATTCTCCGTTAGCGTA | 1,838,694 | 87 |
| 4630. | CTTTATCTCCTCACCTTGTTAATG[T,C]GGAGAAATTGGTGAAAGGAATTCCT | 1,838,896 | 87 |
| 4631. | TTTTTACCGAGCTTTGAATTAGCT[T,C]TATCTCCTCACCTTGTTAATGTGGA | 1,838,918 | 87 |
| 4632. | GCGAACCAGAGAGAAACTAGAAAC[C,A]AGTGGATTCCGGTGAGAGTCCACCG | 1,842,855 | 87 |
| 4633. | ACATCAAAGATTAGCATGAGATGC[C,A]GCTGATTGTTTTCAGCCGTGGTTCA | 1,843,255 | 87 |
| 4634. | ACAAGTCCAGATAATTTATGCCGC[T,C]CCTTCAGCCAGTACAGCATAATCTA | 1,843,493 | 87 |
| 4635. | GTGTGTGTGTGTGTGtaTGTATGT[A,G]TGTGTGTGTGTTTGTGCAGAAAGCA | 1,846,206 | 87 |
| 4636. | aGGTTTAATTAAAGTAATTAGAAC[C,A]TCAACAGTTAAAAGAAAAAGGGGAA | 1,847,598 | 87 |
| 4637. | ATAAAGAACATGTAGCTCTCTCTC[A,G]AaGCAGATGGGCAGCATGTTCGACC | 1,848,084 | 87 |
| 4638. | TAATCCTATTGACTTCAAGATCTT[C,T]CcAATTAAAGGATTCAAATGCTAAA | 1,849,179 | 87 |
| 4639. | GGAGACATCATCTTCTAGTGGCTA[C,A]TATCCTGTGCAATTCGGAGCGTCTT | 1,850,297 | 87 |
| 4640. | TAGCAGGAGTCAGAGCTTGAtGAG[C,T]cAGAATCGTCTCCACGACCTGCCAG | 1,850,912 | 87 |
| 4641. | TCAGTAGCAGGAGTCAGAGCTTGA[T,C]GAGCcAGAATCGTCTCCACGACCTG | 1,850,916 | 87 |
| 4642. | CCAACTACGAGTGATTTTATTAAT[G,A]AAGATGAAGATCCGATGATCGGATG | 1,850,975 | 87 |
| 4643. | CAAATGTATTGAGAAGGAAGTTCA[G,A]ACTGAAGTACTCAGATCCAACTACGA | 1,851,015 | 87 |
| 4644. | CTAAAATAGGAATGCCATAATGAT[C,A]TTGTGTACGTGCATTATAATTTGAG | 1,851,074 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4645. | GGATTCGCATGAAATTTGAAAGAC[T,C]TtGCCATCAAGATCCTCTTCCAGAC | 1,851,194 | 87 |
| 4646. | GTTCAATGATATTTATTAACTTAG[C,T]TGTATCTTCAACAGCTAAGATTTTA | 1,851,443 | 87 |
| 4647. | GAGGGGAGCAATGTGGAGAGCTTA[G,A]TGACGAGACAATCAGCAGATCGTGA | 1,851,917 | 87 |
| 4648. | TATATTGAGACCAGAGATGTCACA[A,C]GATTTGCTATTAATTATATAGCACT | 1,851,055 | 87 |
| 4649. | GAATCCTTGATGCCAAAATTGATG[T,A]AGAAAGGTACTAGCAACAACAATCA | 1,862,549 | 87 |
| 4650. | TCCCCCATGACTGATACTTTACAT[T,C]TTTTATGGGCTGCAAACACTTTTAT | 1,864,734 | 87 |
| 4651. | GCATGGAACGTGTTGCGAGGAAAA[T,A]ATATACTTTTCAGGATGACAATGAG | 1,864,816 | 87 |
| 4652. | TATATAGTTCAGCATGGTATGAAA[C,T]AGCATATCGACGATCGGCGTGGTAC | 1,865,003 | 87 |
| 4653. | TTTCTTTGATTTTTTTAATCCTTT[T,C]TtCTAACCAAAACTCTGAATCTTGA | 1,865,202 | 87 |
| 4654. | GCTCTTTTTAAGCATGACATCAAT[A,G]CTCACTATCATACAGAGTCATTTCC | 1,865,820 | 87 |
| 4655. | ATGCCAACAAGATATATTGCCATG[T,G]AAAGGAAAATATGAATGTAAGGGGC | 1,869,037 | 87 |
| 4656. | AAAGGTATTCAAACATTTAAGGTA[C,T]cGTTATAAGAAAAGTTCATATCATA | 1,869,270 | 87 |
| 4657. | CTATCATCAGAAAACTGATTAATG[A,C]TATGCACCAAAAGGCTACCAAAAAG | 1,869,930 | 87 |
| 4658. | CAGATAAATGCTTAAAAAGCAAAA[A,T]TACTAATTCTGGTACTCACGAATCA | 1,870,000 | 87 |
| 4659. | GGATAAGCATTCTGAATCAGAGCT[A,T]CCAGAAGCGGGTCCAGGTATGGCGA | 1,870,963 | 87 |
| 4660. | ATGTAGAAATATTAAAAAGCTGGC[G,A]TTGGCAAATACACAGTGTGCTACAT | 1,871,040 | 87 |
| 4661. | CAACATGTGATTTGAAGCTTGGTA[T,C]GTTGTAACGGTTTGTTCATTTGCAT | 1,871,278 | 87 |
| 4662. | CATTCTCCATACAATAGCATCAAC[T,C]GTTGTAACGGTTTGTTCATTTGCAT | 1,871,599 | 87 |
| 4663. | ATAATGCATGAAGGCAGCATGTGA[T,A]TAAACTATCACCACAATCATAGCAT | 1,871,833 | 87 |
| 4664. | AATGCTCTGGTACTATATAAAAAG[T,G]GTCTGAATTTACTAAGATGAAGTGA | 1,872,511 | 87 |
| 4665. | CGATCCTTGATGCGTCAAGAATAG[T,G]CCGCTCAATAGAGCATGGATTCATA | 1,872,605 | 87 |
| 4666. | ATACCAAGGCACGATCCTTGATGC[G,A]TCAAGAATAGTCCGCTCAATAGAGC | 1,872,616 | 87 |
| 4667. | CGGGAGTTCCAACGAGCATATGCC[T,C]GTCACTGGTATGTGGTCCTATGATC | 1,872,871 | 87 |
| 4668. | CTCCAAAGCTATACCCGGGAGTTC[T,T]AACGAGCATATGCCTGTCACTGGTA | 1,872,886 | 87 |
| 4669. | AAGGTAACAAAGATCTTTGAGCAC[T,C]AGTAGAAGAGTATTTTACAGCTTAG | 1,873,097 | 87 |
| 4670. | ACCATGATATCAAAGGCAACGATG[G,T]GGAGAGAAGGTAACAAAGATCTTTG | 1,873,128 | 87 |
| 4671. | TTTAGTTTACATGTTTGGAAGAGG[T,A]AGTCAAAAGTCAAGACCATGATATC | 1,873,167 | 87 |
| 4672. | TAAAAATTTTTGAAAATTGTTACA[G,T]ATTACTCCCTTTTTCTTCGTTCAAT | 1,874,274 | 87 |
| 4673. | TTTCCGGACTTTGGGCAGAGACTT[C,T]CCATATTATTTTGACTTCCCAAATC | 1,874,372 | 87 |
| 4674. | GTATGCAATCAAAATGGTTAGCTG[G,A]TTGGTTTCCGGACTTTGGGCAGAGA | 1,874,401 | 87 |
| 4675. | AAGGTTTTGTTTTTGGGCTGCAGC[T,A]ACTTTTCCAATTTATTGATGGCGTT | 1,881,662 | 87 |
| 4676. | TGAAAGGTTTTGTTTTTGGGCTGC[A,G]GCTACTTTTCCAATTTATTGATGGC | 1,881,665 | 87 |
| 4677. | TCTTGTGCCTAATATTTTTACTTC[G,A]ATATACACTAACTTCTATAACCCAA | 1,882,276 | 87 |
| 4678. | ATTCCTTTTTtCTTGCTGTTTTGC[A,G]TGGGCATGGAGTAAACTGTGTGAAT | 1,882,706 | 87 |
| 4679. | TCTTATTCTTCTGTTAGTTTTGAT[G,T]GACAGCAGACCTTACCTGTTTGAAA | 1,882,802 | 87 |
| 4680. | AAACATGTTTGTCCCACTCAGATT[T,G]TTTATATAATAGAGACCACTTTTCT | 1,884,074 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4681. | GCAAATTTAATTTTATTATGCACT[T,G]ATCTGACCAAATCAATGGTTAATTA | 1,884,440 | 87 |
| 4682. | AGTAATTAATTGAGAATAGGAAGA[C,T]GAGCGTTAAAATCTTGAAGGCGAGC | 1,884,765 | 87 |
| 4683. | ACTTTCTTTAACTTCTCAATTTTC[C,T]ATATGTTTAGAATTTATATTTTGTT | 1,884,831 | 87 |
| 4684. | GCACCTTGTTATGTGAGTAATCAC[A,C]TTTCCTTCCCTCCTTTCTTGCTtTT | 1,885,151 | 87 |
| 4685. | TAACTCTGCCTCCTAGTCGGCACC[T,C]TGTTATGTGAGTAATCACATTTCCT | 1,885,170 | 87 |
| 4686. | AGCCCTTAACTCTGCCTCCTAGTC[G,A]GCACCTTGTTATGTGAGTAATCACA | 1,885,176 | 87 |
| 4687. | TCATACAAACTAATGACCTCAAGG[T,C]TAAGTCCTCTAAACCCAACAGCTTG | 1,885,267 | 87 |
| 4688. | CATTCGACCCGGTAAATTATAGAC[A,G]TATGATAGATAGTGAAATGTCTCAA | 1,885,320 | 87 |
| 4689. | TGGTCATCCTTATAGAATGATGTC[T,C]AGCATCCTTCGAAAATAATTTGCAT | 1,886,343 | 87 |
| 4690. | CTATCTATTTGAGTCAAACATCCA[A,G]CTTTGTGTACAGATTAAGACCTGAA | 1,886,662 | 87 |
| 4691. | GATCTTGACACAACACTCAAATTC[A,T]TATAGATCATACGCAACCTCTTTCA | 1,886,755 | 87 |
| 4692. | ACCTGACCCTATATTAATTGGCAC[G,A]AGGCTTGATGAATATGATTATGGCT | 1,887,158 | 87 |
| 4693. | ATAAGCTTGACTTAACATCAGGGG[C,A]AGCAGCCCTCAATATTAATCTTGTG | 1,887,222 | 87 |
| 4694. | AGGCAAGTTTTTGCTCAAGAATGT[A,G]GGAAGAGGAGGTGAAGGCCTTTGGT | 1,887,304 | 87 |
| 4695. | ATTCTAGAGGAATCACAGGAGCTG[C,T]ATAAATTAAGGCTAAAGTGATGGAA | 1,887,412 | 87 |
| 4696. | AATGAGCTATTCTAGAGGAATCAC[A,G]GGAGCTGCATAAATTAAGGCTAAAG | 1,887,420 | 87 |
| 4697. | TTTATAGAATGGCCACAGGGCTTC[T,C]AATGTTGTATGGTTTAGAAAGATGG | 1,887,564 | 87 |
| 4698. | TCATGTGATTGATGTATGCCTTGG[C,T]TACTTAGCTGAAGATTTTATAGAAT | 1,887,604 | 87 |
| 4699. | TAGGTATAGTTGAATTATGAGAAT[C,T]TTGTGAAATTTGTTTTTATGTGCAA | 1,887,802 | 87 |
| 4700. | CAGCTAAATGGTGCTAACTATTAT[C,T]GAGCCTTCTGAAGAATATCAGTAGT | 1,887,887 | 87 |
| 4701. | TTTTATTGTACAAAGCAACTTATG[C,T]AGGTTCTTTATGATCAGACCATTCT | 1,888,079 | 87 |
| 4702. | AGCATCTATGAAAGCAAGGCAAAG[C,T]GTAAGAAAATGGAGACTGAAGGAGA | 1,888,317 | 87 |
| 4703. | TTTTTGAGAAAAAGAAAGCACATG[A,G]CTCCTCATTCTAATCAAAATTTCGG | 1,890,054 | 87 |
| 4704. | AAAACCATCACCTGAAATCCAGAA[T,G]TGCATATCTATATAAATGAGCTTCT | 1,890,417 | 87 |
| 4705. | GGAGACTCATTAGCATTTTAAGTT[A,C]GATGGGAGAAATGAAACGGAAAAAG | 1,890,595 | 87 |
| 4706. | AAAAaCAAAaTGATGCAAATCCTC[T,C]AGAAATCACCAACTCTACCTACAAT | 1,890,664 | 87 |
| 4707. | AAATAAAATAGCTCCCAACATCCC[A,T]ACTTAAAGAAAAACAGAAAAATTTT | 1,890,931 | 87 |
| 4708. | GTGCGGGATTTGGTGCCGGTATTT[T,A]AAACCTCAGTAGGAATTTCATAAAA | 1,891,074 | 87 |
| 4709. | GATGGAAAGATAGTGCGGGATTTG[G,A]TGCCGGTATTTTAAACCTCAGTAGG | 1,891,086 | 87 |
| 4710. | TGATGGAAAGATAGTGCGGGATTT[G,A]GTGCCGGTATTTTAAACCTCAGTAG | 1,891,087 | 87 |
| 4711. | AGCATGTACCATCGATACTTGTAC[C,T]GCAGTGATACGTACCATTTTGATGG | 1,891,131 | 87 |
| 4712. | CTTTGCACATGATATACCATCTCA[A,G]CCAATTCTCCATCCCTTTAACCTCA | 1,891,623 | 87 |
| 4713. | TTTTtCAATAATTGCTATCAAGAT[A,T]TACCTTTGGTATTTCTTCAAAATTT | 1,891,784 | 87 |
| 4714. | CCAATTATTGCAAATATAATCATA[T,A]GTATTCTATCAAAATTATAACCATA | 1,891,881 | 87 |
| 4715. | AAGCAAGGTTCATTCTTCATCCTA[A,G]AAAAAaGCAGGAGGGAACAAAGTAC | 1,891,978 | 87 |
| 4716. | GAACAGCAAGGCAGAGGGGTAGAC[A,C]TGATTGGGCATATATTATAACTAGG | 1,892,262 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4717. | TAGCCACTTCTAAGGAAATTCACA[T,C]CCAAAAATAAGCCAAATCAAACAAC | 1,892,699 | 87 |
| 4718. | TAAGCAGACCAAATGGATTCTTCA[G,C]TCATCTAAAAAGGACCAGGAAAATA | 1,893,241 | 87 |
| 4719. | GCCTGGGCTAACAAGCTAGAAACT[A,G]AATGAAAAGAATCTATATATTTGG | 1,893,423 | 87 |
| 4720. | ATATATATATATTTCTTGATAAGA[A,T]GAAGGGCAGACCCTCTACAATCTGG | 1,893,494 | 87 |
| 4721. | TATTTTCAATTACAGCAAAAGGAA[G,C]AGAGACAGGAGAGCAACAATTATAA | 1,894,862 | 87 |
| 4722. | GCCATGGCACATCCATTTTCTGTC[A,G]TCCATGAATTTCTTTGTTATAGAAT | 1,895,129 | 87 |
| 4723. | GTGACAGGCTCACATGAATCTTAT[C,T]ATCATCACGTGACTCGACAACTATC | 1,895,567 | 87 |
| 4724. | GCTGGAAACATATTGTCTGGAAAT[G,A]AATAGGGCAACTTTGGAAAATGCAA | 1,895,659 | 87 |
| 4725. | ATAGCAAATTGGAAGTTGCCACAG[C,A]ATATCTACCAAAAATTACCTTTTAC | 1,896,410 | 87 |
| 4726. | GTTCTCGAAATTACAGACCATATT[C,T]CATATTTTGAAAGAGTTAAAATAAA | 1,900,973 | 87 |
| 4727. | CATCTCACTCATAAAATTGGCACT[G,A]AAGTATTTGCGAAATGGGGTGATGA | 1,901,084 | 87 |
| 4728. | ATTTGGTGGCCTAAAAGCCAACTT[G,A]AGTTTCTATGAGATGGACATCTCAC | 1,901,126 | 87 |
| 4729. | TTTTAGAAACTTCATACGTAATTA[A,T]AAGATTGTATATAATATGCAAACAA | 1,901,859 | 87 |
| 4730. | CTCTTTTGTCCAGGCATCTTTCTC[G,A]ACCATTACTTCAGGAACAGAAAAGT | 1,902,441 | 87 |
| 4731. | GACCAGAAGAACCAGAAGGATACC[C,T]CCAATCCTCTTTACTTTCATTCAAC | 1,902,660 | 87 |
| 4732. | CATCGCAAAATAATGGACAGGAAG[G,A]GGTTTGGTTGGTATAGGCTAGGCCG | 1,902,897 | 87 |
| 4733. | ATAGAATTCATAAGGACATTGGCC[A,G]GGTAGGATTTATGTTCGTAGCATTC | 1,903,024 | 87 |
| 4734. | TTCTAAGATTGAAAATAGTCAAAA[C,T]AACTTGATGGTCTATTTGAATAATT | 1,903,086 | 87 |
| 4735. | ATGAAGGAAGATGAATCATTCTTT[G,A]GTGCGAAAGATACACGTCTGATATG | 1,903,159 | 87 |
| 4736. | ATTACCCTGCATGTGAGATTGGGA[T,C]AAGCCATGGATGGATAAGAAAGTCT | 1,903,579 | 87 |
| 4737. | TTTCACATGCATTACCCTGCATGT[G,C]AGATTGGGATAAGCCATGGATGGAT | 1,903,608 | 87 |
| 4738. | AACTAGGCTTTCAAAGCTCCATAT[A,T]GAAGGGCAACTTGGTCCCAATGAAC | 1,903,106 | 87 |
| 4739. | ACCCATTTTTCTAATCCGACACGC[C,T]GAGGATGGGTAGTACTGGCAACATC | 1,904,669 | 87 |
| 4740. | ATAAAGAGAAGAGGACCAGCCTG[G,A]GCGCGAAACTACTAAAATGCCCCCC | 1,907,286 | 87 |
| 4741. | CCTCGCCCCGACCAACATCGACCG[T,C]TGGAGCACCGTACCCACCACCGCCA | 1,907,500 | 87 |
| 4742. | GAAGCAGATAAAAATTAAGACCAA[C,T]GTGCGTCTTGTAGTGCAGACATTCC | 1,907,844 | 87 |
| 4743. | TTTTTTGCAAATATTCACAAAAAC[A,C]GTCCATTCGAAGCAGATAAAAATTA | 1,907,877 | 87 |
| 4744. | AAATCCAAAGAAAACAGAAATTTC[A,C]CGTTGCTACACCAGATAAAAATAA | 1,907,988 | 87 |
| 4745. | AATGCAAAAAATTATGCAAATCTC[A,G]GTAAGCATTTTAAACACACTTCAAA | 1,908,413 | 87 |
| 4746. | TAATGAAACTGGAGGAGGATGAAT[G,T]GCCAAAAAaGAAAAAGCAGCTATAT | 1,908,492 | 87 |
| 4747. | AGATGATCACACCGAATGTCACTT[T,C]GGAACAAACTCTAATATACAGCTCA | 1,908,820 | 87 |
| 4748. | AAGCATGTTTTTAGTCATTGGCTC[A,C]TAAAAACTTTCACTAGTTTTCCCCG | 1,909,032 | 87 |
| 4749. | CAAAAAaGTTCCTATAAACTTTAA[C,T]GCAGCATGGCTACATCAACAGCCAA | 1,910,986 | 87 |
| 4750. | AAAACTTAAGAAATCAAAAAATTA[G,T]TATAGCAGAATCAGTTCAATAAGAA | 1,911,191 | 87 |
| 4751. | ACCTTTCTAGTGAAATGATGAATG[A,C]AGATCAGGGGAAACAAGAAAACACA | 1,911,477 | 87 |
| 4752. | AATGTTACAGTTGTAATAGTTGAA[C,G]GATACGTAAGACACCTTTCTAGTGA | 1,911,514 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4753. | GAAaaAAAAAAaGAAAAGCATGAA[T,C]GTTACAGTTGTAATAGTTGAACGAT | 1,911,536 | 87 |
| 4754. | AAGAAATTAAGTGGGCTTAGCCAAC[A,G]AAGGCTGCAAAAACAAACTAGCATA | 1,911,610 | 87 |
| 4755. | AGGAAAAAaTGGAAAGAATTAAGT[G,A]GGCTTAGCCAACAAAGGCTGCAAAA | 1,911,623 | 87 |
| 4756. | AGAAAGGAAAAAaTGGAAAGAATT[A,C]AGTGGGCTTAGCCAACAAAGGCTGC | 1,911,627 | 87 |
| 4757. | CCAGAAAACCATTTGAACTTTTAA[T,C]TTTAAAATCACTGAAAATAAAAaTA | 1,911,731 | 87 |
| 4758. | ATGGGAGGATGCCATATGGATCTT[A,G]AAACAGTAAATCCCAGAAAACCATT | 1,911,768 | 87 |
| 4759. | CATATAAAATAATCGATAAAGTAA[T,C]GGGAGGATGCCATATGGATCTTAAA | 1,911,791 | 87 |
| 4760. | ATTGTGAACACATGATACCTACAT[G,A]TACTTTTTAGAAAGTAACAGATATT | 1,911,949 | 87 |
| 4761. | TGCTATATGGCAAATTAATTCAAC[A,T]AAAaCCATAGTTTTCAAGAATAAAA | 1,912,297 | 87 |
| 4762. | ATGCATGCAGCACGAGAGAGAGA[A,G]AGAGAGAGAGATCAAAATGCATAGG | 1,912,404 | 87 |
| 4763. | GGACATTGACATTGTCAAACATGC[A,G]CATGTATGCATGCACGCACGAGAGA | 1,912,434 | 87 |
| 4764. | TCCCCTTTTATGTGAAAAATAAGC[A,G]TATGCCTGGTAAGATGCCCTTTTTG | 1,912,870 | 87 |
| 4765. | AATGCAAAACCGAAGCGTGGGAGG[T,C]TTATAATTTTTAATCGAGTTATGGA | 1,912,968 | 87 |
| 4766. | AGCAAAAACTAAGCATTAACAATA[G,T]AATCTAAATTTTACATTTAGGTCCA | 1,913,037 | 87 |
| 4767. | CAAGCAAAAACTAAGCATTAACAA[T,G]AGAATCTAAATTTTACATTTAGGTC | 1,913,039 | 87 |
| 4768. | ATGAAAACATTAAGGATACTAAAa[C,T]AAAAAaTATATCCTGAAACCTGATA | 1,913,128 | 87 |
| 4769. | AGGATCATATATTAAACAAAATCA[A,T]GACAAACAATTTATATAGAAGGGTA | 1,913,304 | 87 |
| 4770. | ATTATAATCCAATTAGTAAGTGGG[G,A]GTCCTATTATTGGAATTCTCGTTGA | 1,926,205 | 87 |
| 4771. | TGGGAGGTGTTTTTGTGTTAAGCT[C,T]GGTCATTTTCAGTGTCGGGATTTTA | 1,926,272 | 87 |
| 4772. | TTGTGGAATTGAATGGGAGGTGTT[T,C]TTGTGTTAAGCTCGGTCATTTTCAG | 1,926,285 | 87 |
| 4773. | GTTTCATGCATTTTTTTtATAATT[C,T]GATTGTGGAATTGAATGGGAGGTGT | 1,926,312 | 87 |
| 4774. | CAACATGTACATACCCATATCAAG[A,G]CATTAAAACAAGCCAATCAATTAAT | 1,927,461 | 87 |
| 4775. | CATCCAGTTATATATTATCATCTA[C,T]GGTTGAAAATATGCATCATAAAACA | 1,927,591 | 87 |
| 4776. | ATATTACGTTGGGAGATAAGAAAA[C,A]CTGTGTACCTCTAAGATAGATAACA | 1,927,648 | 87 |
| 4777. | AACTTTATGATCTATCTCATCGTA[T,C]TTTAAAATTAGTTAAAAGTGCAACC | 1,927,808 | 87 |
| 4778. | CGTATTTTACATAATATTTAAAAG[G,A]TAATATTAACTTTATGATCTATCTC | 1,927,840 | 87 |
| 4779. | TCTTTTACAATATCAACAATTGGG[T,G]CGTATTTTACATAATATTTAAAAGG | 1,927,865 | 87 |
| 4780. | TCGTTGCTGTCGGAGTGGCTCTCA[A,G]TGCTGAAACGCTCGCGGTGGGACGA | 1,928,057 | 87 |
| 4781. | ACCATCATCATCCGCTCGCAGTCC[T,G]CCAGCTCCATTGGCGAGGGATCCAC | 1,928,142 | 87 |
| 4782. | ACGAAGAAAAGAAGGGCAAGAAGG[A,G]AGGAGACGACCTGTCAAGAGCCGAC | 1,928,245 | 87 |
| 4783. | ATCTTGACTCGAATCCCAAATCCA[C,G]CCAAAAACCCACAGAACGGAATCAA | 1,928,414 | 87 |
| 4784. | ACAGATTGATACTTATTTTGTTAC[G,C]AACATTTCTCTAATCATAACCCAGA | 1,928,554 | 87 |
| 4785. | ATATAACCACTAAAGATAAGAAAG[C,T]AACCGAGAAAGAAAACTTTCTGTAC | 1,928,624 | 87 |
| 4786. | GTATCGGAATGGAAAACGTCCTTG[C,T]AGAAAGTTTGCACCAGGCCCACGCC | 1,928,681 | 87 |
| 4787. | CACGTATAGTTGCAGCAAGTCTCA[G,A]AGTAACTATAAATTTGCAGCAAAAA | 1,928,735 | 87 |
| 4788. | GTTACCAACGCATTAATTAGAAGA[C,T]GATCTAATTTCATTCCCAAGATGCT | 1,928,810 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4789. | TCCGACTGAGTAGCATATATTCTC[G,A]TGAACAAAGAGGGGAAAGAAGCAGA | 1,929,025 | 87 |
| 4790. | TGAATCCGACTGAGTAGCATATAT[T,C]CTCGTGAACAAAGAGGGGAAAGAAG | 1,929,029 | 87 |
| 4791. | AAATTATACACACAAATGACAGTC[T,C]TTTAGATGTTTGAATCCGACTGAGT | 1,929,064 | 87 |
| 4792. | ATAAGAAAATTATACACACAAATG[A,G]CAGTCTTTTAGATGTTTGAATCCGA | 1,929,070 | 87 |
| 4793. | CCGTACTAATAAATCATATTAGAT[T,G]CAATGAAAAGGAACATAAGTGCCCT | 1,929,407 | 87 |
| 4794. | ATCCACCAGAACTACTGGTCTTAG[T,G]CCAGTGCATAAACAAAGTATGTCTG | 1,929,562 | 87 |
| 4795. | ACCTCCTGGGCAAGGCGAAGTAGT[A,G]AGCAGAGGTCCTCTTGGAGTTTTGG | 1,929,627 | 87 |
| 4796. | CACTATCTAATACAACTTCACTAA[A,G]AAGCCTATGAGATTTCCATAAGACA | 1,929,850 | 87 |
| 4797. | AGGAAAAAATCTACATGTTTCTTT[T,C]TGTCTTCCATAAATCTACAGGAGGG | 1,929,974 | 87 |
| 4798. | ACATGATATCTACGCTTAAGGAA[A,C]AAATCTACATGTTTCTTTTTGTCTT | 1,929,993 | 87 |
| 4799. | TATAGAAGATATCCTCTTATTTCA[A,T]TGAGATTTTTTtCTTTTACTTTCC | 1,930,408 | 87 |
| 4800. | TAaAAAATAACAAATTTATAGAAG[A,T]TATCCTCTTATTTCAATGAGATTTT | 1,930,424 | 87 |
| 4801. | CCAACTCATACTCTCTCACCCTCA[G,C]CCCCCAATCTTGTTCTCTCTTCATT | 1,931,314 | 87 |
| 4802. | TAATACCTCTATCTCGTACTCTCT[C,G]ACTCTCTCTTTCCCTTGCTCTGTTT | 1,931,364 | 87 |
| 4803. | CCTATTATACCTCAGAGGTAACCA[A,G]TTAAAAGTTGCTAAGTACTCAAATC | 1,931,504 | 87 |
| 4804. | TTTTGATGCAAATATCCAGCCTGG[G,T]GGAAACCTATTATACCTCAGAGGTA | 1,931,534 | 87 |
| 4805. | CTTAAATGTTTAAGTTTCTACTGT[T,A]TCCAAAACCAATTTTGGAGTGTAGG | 1,932,053 | 87 |
| 4806. | CTTGGTTCTATCTTAGCTCTGTATA[A,T]TAAAAGACTAAATCAGAGCTTATCA | 1,932,195 | 87 |
| 4807. | TGGAACCATCACTACCCTCTCCAAT[A,G]GAGCACTTGGTCTATCTTAGCTCTG | 1,932,225 | 87 |
| 4808. | GAAAACCGGGACACCTCTGTCCCA[T,C]GAGATTTAAGACCTTAGTCTTTAGC | 1,932,306 | 87 |
| 4809. | ATTAGATCGCATGATCAGGACTGC[A,T]ATCGAGACAAGACTAGACAGTGGGG | 1,932,371 | 87 |
| 4810. | aAAAGAAaGAAAAAAaGAATTAGG[G,A]GAGAGAGATGGAGGATATCTATTAG | 1,932,416 | 87 |
| 4811. | AGAAAaGAAAAAaAAGAGAAAGGG[G,A]TAAGGAAAGAAAGAAAAAaTAAAGG | 1,932,477 | 87 |
| 4812. | GAGAAAACGGGACTGGGACAAGGT[T,C]GGGACTCCGAAACCCATCTACACAA | 1,932,642 | 87 |
| 4813. | GACAGGGGGTGTCCCGGCCGTCCC[A,G]TCCGTTCCTATGAGAAAACGGGACT | 1,932,678 | 87 |
| 4814. | GGAATAACGAAGAATAACAGCAAG[G,C]CTTCTCTAAACTAAAACAAATACCG | 1,932,794 | 87 |
| 4815. | TAACATCTACTCTATCTCATGGAT[A,T]AGTATTACCTAGTTTTTGTCACCT | 1,932,854 | 87 |
| 4816. | AAAGCACACATTTCTCTTTTTCTT[T,C]CATCTGAAATTCTAACATCTACTCT | 1,932,891 | 87 |
| 4817. | ATGGTATTTAGGCATGCATAAGAA[T,C]CATAAAATCAATAAAATTACAATGG | 1,933,066 | 87 |
| 4818. | CTTTATATGGTATTTAGGCATGCA[T,A]AAGAATCATAAAATCAATAAAATTA | 1,933,072 | 87 |
| 4819. | GGGAACTATCTTCTAGCATGGATG[T,C]TACTTAGCTTTAACAAAAAaTGTT | 1,933,207 | 87 |
| 4820. | ACCAAGGGAGGCTGGCTCAAACAA[T,A]TAGAAAAGGCAACACTCAACACAAA | 1,933,319 | 87 |
| 4821. | GGGAATCCTTAACCAAGGGAGGCT[G,C]GCTCAAACAATTAGAAAAGGCAACA | 1,933,330 | 87 |
| 4822. | TTTATAATTTTGGTTGAAGTCAGC[A,T]ACAGGAGGCCCTCTCTTCCTCTCCC | 1,933,605 | 87 |
| 4823. | GAGGGCCTCTACCCTCCTCTCGTG[C,T]GAAACAGGGATTCAATCTTATTTTG | 1,933,724 | 87 |
| 4824. | GGAGAGGGAGAGGAAGAGAGGCGC[T,C]GGAGGCCACCGAAGGACCTGAGGGC | 1,933,788 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4825. | TGCTGGTCGGCTGATGGTATGGTT[C,T]GGTACAGATTTGTAACGTTCTGTGC | 1,933,909 | 87 |
| 4826. | AAGCAAGGACCACTAAATCGGAAC[C,T]GGTACAGATTTGTAACGTTCTGTGC | 1,933,948 | 87 |
| 4827. | ATAGAAGCCATAAAAGCAAGGACC[A,G]CTAAATCGGAACCGGAATCGGAGCT | 1,933,961 | 87 |
| 4828. | TAAGATAAGGTCTTGAAGAAATTA[G,A]ATATAAAGTTTTACTAAGTACTTAA | 1,934,020 | 87 |
| 4829. | TCATTAACAAGCTAGAAGAATTGC[A,T]TCATGAAATAAGATAAGGTCTTGAA | 1,934,053 | 87 |
| 4830. | TTAGACAACTCCATGCACTTCCCA[G,A]GGAAAAAAaTAAATAAATAAACACT | 1,934,200 | 87 |
| 4831. | TCTGCTGATAAGACGTACTATTAG[A,G]CAACTCCATGCACTTCCCAGGGAAA | 1,934,220 | 87 |
| 4832. | CTGCTGCTGTGAGGCAAGGCTTGA[C,T]GATATATGCTCAGCAAATTCTTTGA | 1,934,550 | 87 |
| 4833. | GAAGAACTAGCTGCTGCTGTGAGG[C,T]AAGGCTTGACGATATATGCTCAGCA | 1,934,560 | 87 |
| 4834. | ATGAAAATGATTTTTGGACTTGAC[G,A]AAGTTCTGATGCATTTTCGTTCTCC | 1,934,724 | 87 |
| 4835. | CAATCACTGGCTTTACCATGGGAC[C,A]AGGTACAATAGGTAGAACACCTGCG | 1,934,796 | 87 |
| 4836. | CATACATAAAAAAACTAGTAAAGG[C,T]GCCTCATTGGGAGGGGAGATTACCC | 1,934,971 | 87 |
| 4837. | TTAATTTGTTGAAAAGAATCTGTA[C,T]GTGAAAACGCACAACTGCATGTCTT | 1,935,031 | 87 |
| 4838. | CTTTAATTTGTTGAAAAGAATCTG[T,A]ACGTGAAAACGCACAACTGCATGTC | 1,935,033 | 87 |
| 4839. | ATGACACAATTCCTCCTCTGAGAG[G,A]AAAAGACAAATTACCTGTCAGATCA | 1,935,151 | 87 |
| 4840. | GTGTTGATGACACAATTCCTCCTC[T,C]GAGAGGAAAAGACAAATTACCTGTC | 1,935,157 | 87 |
| 4841. | TTTACAAAGAAAAGCAACAAAATA[T,G]GGTCCTCAAAATCCACTAATCGATG | 1,935,274 | 87 |
| 4842. | AGGCGGCCTATTTAAGAGTATGAC[G,A]GGTTTCTGGAACTTGTTTCTTCTAA | 1,935,470 | 87 |
| 4843. | GAGATGCTGAAGTTTCAGAATGTC[T,C]GCATTATTACATGAGCCATGTAAGA | 1,935,892 | 87 |
| 4844. | TAAGAACAGATTAGGAAGAGATGC[T,C]GAAGTTTCAGAATGTCTGCATTATT | 1,935,909 | 87 |
| 4845. | TCCTCCTGGAGCTTTGGGCTAAGT[G,T]TTCCCTTTCTGTATGTACATTAATA | 1,936,183 | 87 |
| 4846. | TATAAACAAGACAACGAACCTTAG[T,G]ACTTCATCCTCCTGGAGCTTTGGGC | 1,936,214 | 87 |
| 4847. | TCCGATGTCATGAACATAGGTTGT[G,T]AATCCATCATAACCAATATATTTTT | 1,936,458 | 87 |
| 4848. | CATATAGATGTCTATTGTGCGGCA[G,C]GCATAAATATTGTTATATTTATCCC | 1,936,571 | 87 |
| 4849. | ACATATAGATGTCTATTGTGCGGC[A,C]GGCATAAATATTGTTATATTTATCC | 1,936,572 | 87 |
| 4850. | TACTTCATCGATTAGGTTTAACAT[A,G]TAGATGTCTATTGTGCGGCAGGCAT | 1,936,592 | 87 |
| 4851. | TTTTTtCTTCATTTTTTCTGTTGG[C,T]TCTGATTTTCTATTGGAAGCTTAT | 1,936,977 | 87 |
| 4852. | TTTTTTTtCTTCATTTTTTCTGTT[G,A]GCTCTGATTTTCTATTGGAAGCTT | 1,936,979 | 87 |
| 4853. | AGATTTCGAGCTGCGAGACTTATT[A,G]TCTTAATCTACCAACTACTACATGT | 1,937,277 | 87 |
| 4854. | GAAAATCCCGACAGAAAAGTTTGG[A,G]TCGGGTCTCAATTGCCCGACACCGA | 1,946,522 | 87 |
| 4855. | AGCACAGTCTCCCTCATTTTCGCG[G,A]TCGTCCAAGTTCCTTCGGCCTACAA | 1,946,822 | 87 |
| 4856. | CGTGACGGTCGGTACCGAACCACG[A,G]CAAAGCACAGTCTCCCTCATTTTCG | 1,946,850 | 87 |
| 4857. | CGGCTACCGACTGATCGACTTAGT[A,G]GGGTCTCCACGCCCTTGATCGGCTT | 1,946,942 | 87 |
| 4858. | TTACTCGATCTTCTCCCGAATGCG[G,A]CTACCGACTGATCGACTTAGTAGGG | 1,946,964 | 87 |
| 4859. | CGACAAATATTTTGTTTTACTCGA[T,C]CTTCTCCCGAATGCGGCTACCGACT | 1,946,980 | 87 |
| 4860. | GTTGATAACGGAAGTTCGACAAAT[A,G]TTTTGTTTTACTCGATCTTCTCCCG | 1,946,996 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4861. | TGTAAAACGAATTTTTGTTGATAA[C,T]GGAAGTTCGACAAATATTTTGTTTT | 1,947,012 | 87 |
| 4862. | GTGATTACCTTCTCAGAAGACGAC[A,G]TTCGGGGCATCCAGACTCCCCACGA | 1,947,101 | 87 |
| 4863. | GGACGTCTACAGGGGGGAGCCGA[C,T]GAAAAAGCCGCGCCCGGACGACGTG | 1,947,148 | 87 |
| 4864. | AGTCATCAACATGATCTCCAAGCG[A,G]CTGGGATCGGGGACGTCTACAGGGG | 1,947,183 | 87 |
| 4865. | GGCGCCGACTAACCAGCCGACGGC[G,T]GGAGTCATCAACATGATCTCCAAGC | 1,947,210 | 87 |
| 4866. | TTTCGAAAAGGTCCGCCGACCCGA[T,C]CGGCTGCCGATCGATGCCCCCAGCC | 1,947,269 | 87 |
| 4867. | CGAGCGATGCATCCAGTTGAAGGA[C,T]GAGATCGAAAATCTCATCCGCCGGG | 1,947,333 | 87 |
| 4868. | GAAGAATACCTGCGACGGCCTCCG[T,C]CTCTGAAGGCAAAGGGCCTCGACCA | 1,947,425 | 87 |
| 4869. | TCACCCCGCCGACAAACTCCGAGG[C,T]CGGTGCGTCCCAGGTATGACTCCTA | 1,947,524 | 87 |
| 4870. | GATCCAAAAATCACCCCGCCGACA[A,G]ACTCCGAGGCCGGTGCGTCCCAGGT | 1,947,534 | 87 |
| 4871. | ACCCCGACAGATCCAAAAATCACC[C,T]CGCCGACAAACTCCGAGGCCGGTGC | 1,947,543 | 87 |
| 4872. | GGAGCCCGCCGAACCAAGCAGGCC[T,C]CCGGCCAATAGTCGGCTTTCTCCAC | 1,947,591 | 87 |
| 4873. | AAGCATTGATGCGAAATCAATTAGC[C,T]TGACCACGATCCAAGTTTGGTAGGA | 1,949,701 | 87 |
| 4874. | ATACAATAAATAGAGAGATTGATG[A,T]GGAAAAGAGTGTATTGGAAAATGGA | 1,950,032 | 87 |
| 4875. | ACACAAATTTGTAGGTATGACATA[C,T]AATAAATAGAGAGATTGATGAGGAA | 1,950,053 | 87 |
| 4876. | TTCCATCAAATCATGCCATTACTA[A,G]GAACTGGTCATTAAATCAGATAAAA | 1,951,384 | 87 |
| 4877. | ACTTTAATTGTTGTTTTCAAAAAT[A,G]TTGACGAAAAATTCTAATACAATTC | 1,951,431 | 87 |
| 4878. | ATACGTGGTAAGTCATTGGGCCAT[A,G]TTTTTTCGACCTCTCCCTTCCAACC | 1,951,484 | 87 |
| 4879. | CATGATCCAACAATCCATATTTTG[G,A]CTGCTGACTTCTCTATCAATGGCCG | 1,951,802 | 87 |
| 4880. | ATCATTAATCCTCGTATCAGCCGC[C,T]GACCTAAACATAATTTTTTGACTTC | 1,951,870 | 87 |
| 4881. | AAATCAAAAGTATATTAATTTTG[G,A]CAATACTATTCAATAGACATGCCAT | 1,952,373 | 87 |
| 4882. | AAaTTTtTTtATTTGAGCTTGAGT[T,C]CTACTGTGCACCGTAAAATATGA | 1,952,563 | 87 |
| 4883. | ATCCCTTTTTAGCTGGTTACCAAA[A,C]AAAaTCCCTCTTTAGCTCCATTGAA | 1,952,720 | 87 |
| 4884. | GAGCCTCCTGCTCCTTCTCTCTCA[G,A]CGAGTAGTCTCTCTCTCTTCTCGAG | 1,956,642 | 87 |
| 4885. | GATCTCTCCCTCAACTCTTATACA[T,C]CCAATTTTTCTCTCCTGAAGTTCTC | 1,956,759 | 87 |
| 4886. | GAGGAGATCTCTCCCTCAACTCTT[A,G]TACATCCAATTTTTCTCTCCTGAAG | 1,956,764 | 87 |
| 4887. | GGGTGAAAAAATTTCTTACAGGGT[C,T]CTTTCAGAGCCAACATCCAAGCTTG | 1,958,168 | 87 |
| 4888. | GTAGATCCAAAAATATTGCGCTTG[G,A]CCACAAATAGAATTGTAGATTCAAA | 1,958,726 | 87 |
| 4889. | ATAAATCCAAGGAAATCAACTTGT[A,G]TAGTATCAGATCTTATGCTTGGCAA | 1,959,185 | 87 |
| 4890. | GGATATGACGGTCAAATTCAAATA[T,G]ATAAATCCAAGGAAATCAACTTGTA | 1,959,210 | 87 |
| 4891. | CTTAGAGGAGTTTGTGGGATATGA[C,T]GGTCAAATTCAAATATATAAATCCA | 1,959,226 | 87 |
| 4892. | ATTTGTCAGAAACTCGTAGTATAA[A,G]AAGGATTATTCACTTCCCATGAAAT | 1,959,324 | 87 |
| 4893. | AGTCCAATGCTTCATAATGCATCAG[C,G]AAAAATCAATCCAATAGTGTATACT | 1,959,418 | 87 |
| 4894. | AATATCCCAGCAATTTCGTAACTT[T,C]TTTtATTTTCCAAAATTTGCCATGT | 1,959,493 | 87 |
| 4895. | ATGTGAATACATCTTATGCATACA[C,T]ATACAATATCCCAGCAATTTCGTAA | 1,959,522 | 87 |
| 4896. | GTTCATAATGTTGAGTTACTTTAT[G,A]AAGTATGGAATGTAGTCTATGCATT | 1,959,608 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4897. | CAAAACATATAGGATGCGAATGCT[C,G]GCGATAGACATAGCCAGAATATGTG | 1,960,192 | 87 |
| 4898. | CTTCGACTGCACATAATCCATACA[A,T]TGTCATTAGCTACATTAAAATGTAG | 1,960,492 | 87 |
| 4899. | GAGATTTCACAGTTAGAAGACTTC[G,T]AGTGCACATAATCCATACAATGTCA | 1,960,512 | 87 |
| 4900. | ATGACAGGCAATTAAATGACAGTTC[A,G]GAATAAGACACTTGATTATAAAGAA | 1,961,140 | 87 |
| 4901. | TAAAGTAGAATCCATAAGATCCTGC[A,G]AGACATACCATGAAAAATCATATAC | 1,961,190 | 87 |
| 4902. | TTTACCAATAGCTTTTATACGCTC[T,C]ACGCTCTTGTACCTTAAAGTAGATC | 1,961,229 | 87 |
| 4903. | CCATCTACTCTTCAAGGATACAGC[A,G]TGATAATTAAGACGATVAAGTAAGAT | 1,962,031 | 87 |
| 4904. | AATATATAAATGTGAAATTGAGGT[C,A]ATTGTATAAGAAAGAGGGGCCACAT | 1,962,244 | 87 |
| 4905. | TGCAAGTACAATAATGTAATCTAA[C,T]AGAATCTAACAATGGACCATGGTAA | 1,962,292 | 87 |
| 4906. | TATTAAAAATGATAAACAGACTCCF[T,C]AAAAAAATGATTTGTCCTAGGAAAA | 1,962,734 | 87 |
| 4907. | AACAACTCTAGCTAAAATATGCCT[T,A]TATTATATGTCCAAACCCTATAACA | 1,963,564 | 87 |
| 4908. | AATATTCACCCTATTCTTCCTCAA[G,A]GTAAAGGAGAGACCGAAAATGGTAC | 1,963,678 | 87 |
| 4909. | GTAAATATTCACCCTATTCTTCCT[C,A]AAGGTAAAGGAGAGACCGAAAATGG | 1,963,681 | 87 |
| 4910. | TAATACTTTCATTGTCTTTGATTA[G,A]TTGTTCATTGACGACTTATATCAAT | 1,964,785 | 87 |
| 4911. | AATTGGTAGAAGGATTTAAAGAGT[T,A]ATCGGCATATGATTTTCATTGGCCT | 1,965,924 | 87 |
| 4912. | ATTATATTAGTATATTAACAATGA[A,G]AAAGCATCCGAATATATGGAGTGTT | 1,966,369 | 87 |
| 4913. | AAACCGCAAGGACGATGGCTGTTC[G,A]ACAAATGAGGGGTTCCAAAGGGTGC | 1,967,159 | 87 |
| 4914. | TGGTATATTGGAATTATTTGCATC[A,G]GTGATCTCATCAAGTTGGTTGGCAG | 1,967,224 | 87 |
| 4915. | GCAAATCCAAAATAAAACCCGTCAA[C,A]AACGGCATCATCGTGACAACAACTA | 1,967,877 | 87 |
| 4916. | AAAGGTAGCGGTCCTTCTTCTCGA[C,T]TCATAGGAGTTTGGATCGGGGCTTG | 1,969,458 | 87 |
| 4917. | GAGCAGAAGGGGGTCTTGGTCCAG[G,C]CCAGTTTTGAGGATTGCGGCATGGA | 1,969,572 | 87 |
| 4918. | GCAGCGACCGCATCTCTCTCAGGC[G,A]TTTCACCAAAAACCCATCCGGCATC | 1,969,967 | 87 |
| 4919. | AGCTCCAATGCACCCAACTGAGAG[C,A]AAGCCGATAGAACACAAACGACAGT | 1,970,210 | 87 |
| 4920. | CAAAATTCCAGCCACCTTCTCTCC[T,A]AGGGTCAAGTTTCCAATGGATCTTAC | 1,970,742 | 87 |
| 4921. | TTTTCCCCTAGCACTCACTGCCTT[T,C]TCCCATTTCCCGAATGAGGCATAAA | 1,970,841 | 87 |
| 4922. | TTTTTCCCCTAGCACTCACTGCCT[T,C]TTCCCATTTCCCGAATGAGGCATAA | 1,970,842 | 87 |
| 4923. | TCTGAGGTTCTTCACAACTCGTAT[T,C]GTCGTTCCTGGTTTAGTTGAGATAA | 1,971,147 | 87 |
| 4924. | TTACAGTTCCACAGGTTTTGCATA[T,C]CTGATCAATCCACTCAATCTTTCGC | 1,971,462 | 87 |
| 4925. | TGAAATTCAATTACAGTTCCACAG[G,A]TTTTGCATATCTGATCAATCCACTC | 1,971,472 | 87 |
| 4926. | ATGAACAACATTGTTATCACATAC[A,G]GTAAGGTTCTTGAATGAAATTCAAT | 1,971,511 | 87 |
| 4927. | AAGCAATTGATGAGAAAAGTATTT[C,T]ATGACCCATATAACAGCAAATGGAA | 1,971,582 | 87 |
| 4928. | CATGCGTGGTGCAAGCAATTGATG[A,G]GAAAAGTATTTCATGACCCATATAA | 1,971,594 | 87 |
| 4929. | TCAGTTAAGTTGGATGTTTGAAAC[G,T]GTAACTCATACTTCATATGCATGCG | 1,971,638 | 87 |
| 4930. | ACGTTCACTGTATTCCTAACACCT[A,C]TAAGATCCTAGGCATCCAATAGGTG | 1,971,868 | 87 |
| 4931. | CACACGTTCACTGTATTCCTAACA[C,G]CTATAAGATCCTAGGCATCCAATAG | 1,971,871 | 87 |
| 4932. | ATTTTTAGGTACAAGATTGGTCAT[C,T]TGGTATTTAGTATTTGGGTCTTATA | 1,972,878 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4933. | AGCTCGTTTTTAGTGCTTTGAGT[G,C]ATTGAGTGCTTCAATAAATATCACA | 1,972,957 | 87 |
| 4934. | CTTAACTTCTGAATAATGAATACT[A,G]AAAGAGTTCAGAAGTAACAAGATTT | 1,973,591 | 87 |
| 4935. | GCAGATTCATGGAATGAGAATGCAA[A,G]AGTCTTAACTTCTGAATAATGAATA | 1,973,619 | 87 |
| 4936. | GATCTCATCTTTAGGTAGAAAGGA[T,C]GGAAAAGAGGACCATAAAAACCTGG | 1,973,704 | 87 |
| 4937. | TGGATTGACTAGGGGTGACAGAAA[T,G]CAGCAAAGCTGAGGTGACTGTGTGA | 1,973,752 | 87 |
| 4938. | ATAAGCTTTTCATCAATATGCAGT[G,A]GGGCCTATTTTTGAATTGATCTTAT | 1,974,047 | 87 |
| 4939. | GGTCCATAGCGAAGTTGCTGGATT[C,T]GATAAATATAAATTAAGATTTATGC | 1,974,219 | 87 |
| 4940. | GGTCTGAGCTGGGGAGGAATGTCC[A,G]GTACTCTGCCTGCAATGACTTTTTG | 1,974,628 | 87 |
| 4941. | ATATTTTTtCCTATCCGTGATTA[T,G]TTTGGTAGGGATTGCTGAAATGAAA | 1,975,364 | 87 |
| 4942. | CTACAGCACCACGTAAGTCCAAAT[C,T]CAACTAACCCATTACATGAGTTTTG | 1,984,239 | 87 |
| 4943. | CACATTTTCAGAACACCTTAGAAA[T,A]AAATTCTGAAAAAaTGTCACTACCC | 1,984,693 | 87 |
| 4944. | CATTGGATTGTGAATGAGAAAGCT[T,C]TGAACCCAACAGTAGGCTTGAGACT | 1,985,210 | 87 |
| 4945. | AGCTTTGAACCCAACAGTAGGCTT[G,A]AGACTAGAGAATTTTCACTACCAGA | 1,985,230 | 87 |
| 4946. | CATTGGACGTCCTCAGTTGTGGAC[A,C]ACTGCTAATCATGGAATTCAGCTTT | 1,985,323 | 87 |
| 4947. | GACGTCCTCAGTTGTGGACAACTG[C,A]TAATCATGGAATTCAGCTTTATATA | 1,985,328 | 87 |
| 4948. | CTAATGTCCTCGTGTTGGTTACCC[T,C]CTTTGTTTTTCTCGTTTGTTTAGGC | 1,985,494 | 87 |
| 4949. | ATTTTATGTCTAGGAGCTTTAGTA[G,A]GTTGTAGCATTTTGTTTGATAAGCT | 1,985,544 | 87 |
| 4950. | CCTTCCTCCTGGCAAATGTAGTTG[A,G]GCCTGATTTTGGCATCCTAATGTGA | 1,986,564 | 87 |
| 4951. | TATTCTGCTTCTTTCATGCTGAAG[C,T]GTATAGGAGGCCTTTCCTTGCTTCC | 1,986,660 | 87 |
| 4952. | ATTCCAAAATGGTTGGACTGGAAT[G,A]ATTAAATTCTATCTTGATTGCATAC | 1,986,789 | 87 |
| 4953. | ATCTGCCCAATTAAAATGAGAAAA[C,A]AATATAAAATAATGACAAATTAAAT | 1,987,169 | 87 |
| 4954. | GATGAATAAAAATATAGACCAATG[A,G]aTTGCAAAAAGGTTCAACCGGAAAT | 1,987,381 | 87 |
| 4955. | GCTTGAAAGTAAAAATAAAATATA[A,G]ATCAAAGAAACCATTTTAAGTAGAA | 1,987,666 | 87 |
| 4956. | CTATGGATCATAATAACCCAAGTA[T,C]TAATTTGTCCATATATGTATCGAAA | 1,987,816 | 87 |
| 4957. | ATAACCCAAGTATTAATTTGTCCA[T,C]ATATGTATCGAAAAATAGGTTTCGC | 1,987,828 | 87 |
| 4958. | ATATATGTATCGAAAAATAGGTTT[C,T]GCATCTAGACTCGATAATGATCCTA | 1,987,851 | 87 |
| 4959. | TATATGTATCGAAAAATAGGTTTC[G,A]CATCTAGACTCGATAATGATCCTAA | 1,987,852 | 87 |
| 4960. | ATAGGCTGTCTTGCAATGATTTTT[T,C]TGAAAAACAATTAACTATTGGATCA | 1,988,086 | 87 |
| 4961. | ATTAACTATTGGATCAGCCTTAAA[A,T]TTAAACTTGAATAAGTCGAACTGTC | 1,988,120 | 87 |
| 4962. | GAATCAATAGTAATCACATGGATT[G,A]TAGTGAACGGTACAGAGCCAATAAA | 1,988,357 | 87 |
| 4963. | CAGAGCCAATAAACTGGGCACTTAG[T,G]TATGAGAAACAATTACGTGGATTAC | 1,988,394 | 87 |
| 4964. | TCTAACCATTTAATGTGATCGAGT[A,G]TGGCAAATCATTGGCACCCGCGAATT | 1,988,500 | 87 |
| 4965. | ATGTGTGCAAAAAATTCATTTCCA[T,A]CACTCTTCTTGATTGAAACTCCTCT | 1,988,707 | 87 |
| 4966. | GTGGTCAAATCTTTATCTATCTGC[A,C]TCCCACTGAACTTAGGATGGGACCT | 1,988,825 | 87 |
| 4967. | ACCTTTGTATTTTGCAAGCATGAG[T,C]GAACCTGACATAAACGTCTTGGTTG | 1,988,871 | 87 |
| 4968. | GGCCTCCCACTGACATGAATAGCC[A,G]AGTAATGAAAAGACTAATGCAACC | 1,989,404 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 4969. | CTTCTATAGTGGCAGACCGGCAGG[T,G]TATCTGACGTTCTTGCATTAATGAT | 1,989,498 | 87 |
| 4970. | TGCCACCTTGTGTTTTCGTTTCAT[T,C]GGAGTTGATTCAGATTTTCTTTTGT | 1,992,003 | 87 |
| 4971. | AAATCATCTCATTGATATTGTGAA[A,C]TGAAGATCTCAAGTTTAAGAATCAa | 1,992,174 | 87 |
| 4972. | TGAAGATCTCAAGTTTAAGAATCA[A,G]AAAAGGAGAAAAAAAaGCTTTCTAA | 1,992,199 | 87 |
| 4973. | CCATTCCACCAGATAGGTATGAAG[A,G]GAAAGTTTCATTATGCTTTCCACTC | 1,992,375 | 87 |
| 4974. | CAGTTTTTTGGGATTGTGTGCTCC[A,G]TACCTGGCCATATAAAGTATGAACA | 1,993,969 | 87 |
| 4975. | TCATATTATTTTCTGTTTTATATC[T,C]TTCTAATATTTCATTCCCATTTTGC | 1,995,369 | 87 |
| 4976. | TCTTTCCTTAAATAACTGACTGAG[A,G]CTCCCATTCTTTTGCTGGGTCTCTC | 1,995,423 | 87 |
| 4977. | ACTTATATTTTTACTGACTAATTG[T,C]TAATCAAAATGCTGCTGATTAATTG | 1,995,831 | 87 |
| 4978. | TGGAGCTGTTGGAGATGGAGTGAC[G,A]CTTAACACTAAAGCATTTCAAAATG | 1,996,198 | 87 |
| 4979. | AGGGTAAAGAAGCATTTCATCGTT[T,G]TCAAGGTTGACATCTGATCTGCAAAT | 1,997,344 | 87 |
| 4980. | GAGGAGAGGCTTTACTGGAACTTT[G,A]TCATGAACATTGTTCTATATCACAA | 1,997,657 | 87 |
| 4981. | TTTgTCATGAACATTGTTCTATAT[C,T]ACAATTTGATCCAATCAGTGGATT | 1,997,678 | 87 |
| 4982. | CAAAGATGCTATTCTTAGCTTTGT[G,C]ATATGTTTTCTTATAAAAaTATAGC | 1,997,765 | 87 |
| 4983. | AGCTTTGTGATATGTTTTCTTATA[A,T]AAaTATAGCAGAGAGTCTTTTTAAA | 1,997,781 | 87 |
| 4984. | tCCTACCTTTTTTtACTGTCCATT[T,G]ACAAAGCCAGAAGTTTTTCTTCGC | 1,997,875 | 87 |
| 4985. | CAGGTTTGTTGATTTTAGCCAGAC[G,T]AAACTTGGAGGTACTCTAGCCATTG | 1,998,050 | 87 |
| 4986. | ATTTTATTGTTAATAAGGCAGGGC[G,A]TGCAAGTATTGCTCATTGTGCCTTT | 1,999,056 | 87 |
| 4987. | TCCAGAATCTTCTTGCAAATCGAA[G,C]gTTATATTCCAAATGGGTGTGTGAG | 1,999,122 | 87 |
| 4988. | ATATGTATATGCATGGCAAATAGC[A,G]TTTTCATAATTATTCTGGAAGTAAG | 1,999,527 | 87 |
| 4989. | TTTGTAATAGATTAAAGATTTTTC[A,T]GTCTCATCTAATGCTCTAGTAGTGT | 1,999,641 | 87 |
| 4990. | AGAAATATTTTCTATTTTGACGT[C,G]GTTCAAGTTCTGTTTATTGAGAAAG | 1,999,801 | 87 |
| 4991. | GGTGGGTGGTGTTTGGGGAGTTGC[A,C]AATGTAGTGTTAGCAATACCTCCCA | 1,999,872 | 87 |
| 4992. | TCATTATTATGAAGAGTTAGGCCT[G,T]gTGCTTGCAGTGATGACACCAGATC | 2,000,065 | 87 |
| 4993. | AACTTCTCTAACAATGAGTGAGTT[G,A]AACTCTTCCAACATGGAGTTTACTC | 2,001,265 | 87 |
| 4994. | TAGATAATGTTTAAAGGTAGAAAT[G,A]TGTAATTTAGTTAAACTTATATGTA | 2,001,505 | 87 |
| 4995. | AATCCAATTCTCATATTCGTTACC[C,A]TGCAATGCAGATGCTACATGAATTA | 2,001,602 | 87 |
| 4996. | GAGATGTATGAGGGTTCTACTTCC[A,G]AGCCATCCTAGTAATGGGAGAATTC | 2,002,024 | 87 |
| 4997. | ATCAGAGGTTGAAATGGAGTTGTC[C,T]AAGTCCTAAAGAATGTTAGATATAT | 2,002,188 | 87 |
| 4998. | AATATCTTGTATTTCAAGAGAGTA[G,A]TTCCCATTTTTtGGTTTTGCTAAT | 2,002,582 | 87 |
| 4999. | AGAGGTCTCACTTGTGACTTGTTT[C,T]GGTATTTCAAGTTTTCTTTCTCAGC | 2,002,700 | 87 |
| 5000. | ATTTTCCATGGTAAAACACTTTAG[G,A]TACCATAGATGGACCACAAAAAATT | 2,003,373 | 87 |
| 5001. | ACCACAAAAAATTGTTGATCATAT[A,G]CACATTGATTATGCCCCTAGATCT | 2,003,410 | 87 |
| 5002. | TCTAAGCAGTTGCTAATTTTCTTT[C,A]aTTTGTCAGTTTATAGAATTTAAAA | 2,003,457 | 87 |
| 5003. | CTAAGCAGTTGCTAAATTTTCTTTC[A,C]TTTGTCAGTTTATAGAATTTAAAAA | 2,003,458 | 87 |
| 5004. | GTTTATAGAATTTAAAAAAaGTTT[A,T]TGTCCATAGCCTTTTAAAATGTCT | 2,003,490 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5005. | CATGGAAGTTGTTTTAGTTTTCCT[G,A]TCAATACTGACTTGATGTTATTTTA | 2,003,819 | 87 |
| 5006. | TTTCATGTTTACTGCTCTGATGGT[T,A]TAAGCATTAGTCCGTTTGAGATCCT | 2,008,533 | 87 |
| 5007. | AAACCAAGAGATGGATAGATTGAC[A,C]TGCAACTTTTTATAGCGTTTCCATT | 2,008,787 | 87 |
| 5008. | ATTAGATGCCCTCCGTAGAATAAT[T,G]GAAAGGTTGAGAAAATAAAAGTTTC | 2,009,507 | 87 |
| 5009. | TGATTTTGAAATTAGATGCCCTCC[G,A]TAGAATAATtGAAAGGTTGAGAAAA | 2,009,517 | 87 |
| 5010. | ATTGATTTTGAAATTAGATGCCCT[C,T]CGTAGAATAAtGAAAGGTTGAGAA | 2,009,519 | 87 |
| 5011. | GACGAAGTGTGGTTGTTAGACTAT[T,C]GTTGAAGATGGTTTCTGACTTGAAG | 2,009,634 | 87 |
| 5012. | TGCATTTAATGTTGAAATATGACT[A,G]CTTATAAAATAGTTGTTACTTCCAA | 2,009,705 | 87 |
| 5013. | TTTCTCTGTGTTTTATGAAAAAC[C,T]GTGATACATGTTAACAGATATGATA | 2,009,768 | 87 |
| 5014. | ATGTTTGAGTGAAGGTGGATTTGC[C,T]GATCATTGTTTGAGTGAAGTTTATG | 2,009,899 | 87 |
| 5015. | TTTTTCTGTCAGGTACGGAAAACA[C,A]CTGTTAATTTTTGGAGTGCTATTT | 2,010,160 | 87 |
| 5016. | GAAAGCGCTGCTGTGCCCTTATTA[T,C]CTGGATGACCAGAACCAGCTCTGAT | 2,010,274 | 87 |
| 5017. | TTAACGATTTTATTGAGTGAGTTC[G,A]TCGACATTATCATTGAAAGTCATTA | 2,010,396 | 87 |
| 5018. | AAAGGTGAAGATTTCGGGGATCTA[G,C]CGTTGGAATTTGGAAACTGCTTCCC | 2,010,468 | 87 |
| 5019. | TTGAAGAATGGATTTTTCATGTTA[T,C]GTGCTTGTCTACGGTAGGTATTAG | 2,010,563 | 87 |
| 5020. | TCTTCATCCTTTGAAGAATGGATT[T,G]TTCATGTTATGTGCTTGTCTACGGA | 2,010,573 | 87 |
| 5021. | TTACTTACTGATGTTCTAAGGGGA[G,A]GCAAAATATTCATAATTCAAGCAAC | 2,020,656 | 87 |
| 5022. | AGTAATATGTGATGCAAAAGCTCA[G,A]ACATGATATGCAACCTTGGAAATCA | 2,020,709 | 87 |
| 5023. | AAATACAAGGTTATCATAATATAA[A,C]GTAATATGTGATGCAAAAGCTCAGA | 2,020,733 | 87 |
| 5024. | ACAATTTCTAATTGAATAATGTTG[T,C]ACTTCATCTCTTACCATATGGAAAA | 2,020,780 | 87 |
| 5025. | CAATCATTTGTAATATTATAAACT[A,G]ACACTTCTTTTTGGGTCCTCTTTTC | 2,020,843 | 87 |
| 5026. | AGGCATAGGGCCCATGGCCTCACC[T,G]ATTATGAGAGACAAAAGGCTAGCGC | 2,020,911 | 87 |
| 5027. | AGATTTAATCTAGTATATAACTGG[C,T]CAAATAATATAACAGGCATAGGGCC | 2,020,949 | 87 |
| 5028. | TTAGGTAGAAATAATCTAGTACTT[A,G]TTTTGCATGTCATGTAGGGATTAGG | 2,021,000 | 87 |
| 5029. | ATTAGGTAGAAATAATCTAGTACT[T,C]ATTTTGCATGTCATGTAGGGATTAG | 2,021,001 | 87 |
| 5030. | GCTTATCTGTGGATGGATTAATGG[T,G]ACATTCAAACAACCACTTATTGCCA | 2,021,156 | 87 |
| 5031. | ACCATTTTAAGACGGTTGACAGCC[A,C]CTAATCATGGCTTATCTGTGGATGG | 2,021,190 | 87 |
| 5032. | TTCCTTTCCCTCACCATTTTAAGA[C,G,T]GGTTGACAGCCaCTAATCATGGCTT | 2,021,202 | 87 |
| 5033. | CCGGAATTAGGAGTGCTTGGAAGC[C,A]CCTCTCAATCGGTTCCATTGTTCCT | 2,021,247 | 87 |
| 5034. | GATCGAGTCTTTACCTTAGAAAAC[C,T]GGAATTAGGAGTGCTTGGAAGCCCC | 2,021,270 | 87 |
| 5035. | AAATATCGAGCTCTTTAATCCCTA[T,A]AATTTAGAGATAAGGAAAAACACCT | 2,021,324 | 87 |
| 5036. | TGGATGCCCATCTAATTTATACTT[C,T]GTATATTTCCATTTCTGGATAAAGA | 2,021,420 | 87 |
| 5037. | GATTTAGATGTTTTCCTAACTA[T,C]TTTAGTTTCATCCCTTTCTCTTGGG | 2,021,477 | 87 |
| 5038. | TATCCGTATGTTTCTTCATGTGC[T,C]CAAAGTCATCTAGTTTTTCTATTAT | 2,021,557 | 87 |
| 5039. | TTTTTAAACAATTGTATTTCTATC[C,T]GTATGTTTTCTTCATGTGCTCAAAG | 2,021,577 | 87 |
| 5040. | TAGATAATCGCTTTCATTTCACGA[T,C]GTATCATGCCATTTGTATCGGTTA | 2,021,743 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5041. | TGTAGATAATCGCTTTCATTTCAC[G,A]AtGTATCATGCCATTTTGTATCGGT | 2,021,745 | 87 |
| 5042. | TTTAAATATGTCCCTAAAGTGATT[G,C]GATTTTTTCAAAACCAATGATTGGC | 2,021,849 | 87 |
| 5043. | GAACCTGAGAGTCCAACAACTTGA[T,A]TATATATGCACATACTATATCATGT | 2,022,087 | 87 |
| 5044. | ATTCTAGGATCTGATTTCACATCA[G,T]ATTGAAGTCGAATATAGCGATATCA | 2,022,145 | 87 |
| 5045. | TGTACAAATAATACCCGAAAACCT[G,A]ACAATTCGACTCGATTATTTTGTAA | 2,022,250 | 87 |
| 5046. | TTGGACTTTGTGGCCTTCCACCCG[T,C]AGAATCGAGAAATTTGTTTATGGAT | 2,022,648 | 87 |
| 5047. | AATGAAAATGTTCACCTCTTCTAC[T,A]TTTTGTTGTTCTGAAAAAACATAGA | 2,022,724 | 87 |
| 5048. | ATGCTAAGCCCCATGAAACGAGAA[T,G]AATGAAAATGTTCACCTCTTCTACT | 2,022,749 | 87 |
| 5049. | AATTACATGCTAAGCCCCATGAAA[C,T]GAGAATAATGAAAATGTTCACCTCT | 2,022,755 | 87 |
| 5050. | CTAAAGTCTAAAACATTCTAAGAC[C,T]GCCTTTTAACTAAAATGATTATACT | 2,023,121 | 87 |
| 5051. | AAGCTTACACCTGGGTTTAAATAA[T,G]AGGCAGCATGTTTTTATACTCACAC | 2,023,373 | 87 |
| 5052. | TCTTCATTCTCTCTTTGATAAGAT[G,A]ATTATAAGCTTACACCTGGGTTTAA | 2,023,403 | 87 |
| 5053. | AATGGTTCCCTTTTGATAAACAGG[G,C]CAGGTATGTGGGTCAGGTAGTCAT | 2,024,082 | 87 |
| 5054. | GTTTTCTGCAGGGAAACTGGAGTT[G,A]AATATAATTTTATGTTGGCAGGGTC | 2,024,197 | 87 |
| 5055. | ATAAATAGCATTTATGTTGAGGGT[A,C]ATGTTTTCTGCAGGGAAACTGGAGT | 2,024,224 | 87 |
| 5056. | ATGATGGACTTATTAACGTGAATG[T,C]TGGTGTCTTTGGGAAGCAGGAAGTA | 2,028,739 | 87 |
| 5057. | CCATCCTCCACAAGGGGTGGCTGA[A,T]TGCAAGCTCTGGCTGTGCTATTAGA | 2,028,804 | 87 |
| 5058. | GGTGGCTTTTCTTCTTCCGTCTA[C,A]CCCCATCCTCCACAAGGGGTGGCTG | 2,028,831 | 87 |
| 5059. | GGAAGCTACCATTACGGATTGCTA[C,T]AGTATTTAAGATACAACATCATCCT | 2,028,908 | 87 |
| 5060. | CAAGATCTTAATGCCAcGCACcGA[A,T]TGAAAGGAAGCTACCATTACGGATT | 2,028,938 | 87 |
| 5061. | CAGCAAGATCTTAATGCCAcGCAC[C,T]GAaTGAAAGGAAGCTACCATTACGG | 2,028,941 | 87 |
| 5062. | AATGTCAGCAAGATCTTAATGCCA[C,T]GCACcGAaTGAAAGGAAGCTACCAT | 2,028,946 | 87 |
| 5063. | CATATGGTATCGACCcAACTTTTC[G,A]gCCTCCCTGTCAGTATTACTAAGAA | 2,029,198 | 87 |
| 5064. | TGAAAAGGCGTTGGTGCATTTTC[G,A]TAATGTGTATTTTTTGTAAGGCAT | 2,029,245 | 87 |
| 5065. | GAAAGATGGGGCATGAGGGGGAGT[A,G]GCTGAGAGCCTAATAAGCTTTGGAA | 2,030,025 | 87 |
| 5066. | TTGACTAGAATAATTTAATTTCCT[A,T]TAAGATCATTCTATGTTGAAACCTT | 2,031,957 | 87 |
| 5067. | TAGTATATGGTGCAAGGTCCTCAA[G,T]TACAAAAATATAGTTTGTGATTCAG | 2,032,348 | 87 |
| 5068. | ATTCCGTAGCTTTTTAACAGGGCC[G,A]ATGTTACTAAATTTTTGTTAGTTGC | 2,032,511 | 87 |
| 5069. | TATTGAATGAGCTCTCAGTTTTTT[T,G]GGCATTCTTAAATATGGAACGTATG | 2,034,835 | 87 |
| 5070. | GACAAGTATTGTAATGTTTTAGTG[C,T]GAAACTGGCACAAGTATGGGCATTG | 2,035,103 | 87 |
| 5071. | GATCTAGGGGGTGTATCAAATATC[T,G]GTACACTGAACTCACCGTCCAACCG | 2,035,275 | 87 |
| 5072. | GAGGTAGTCAAGGCCAACATCCAA[G,T]CCTGTGATTCCAATGAAAAGATTGA | 2,035,574 | 87 |
| 5073. | CTTTTGTAGTTGGAGGTAGTCAAG[G,C]CCAACATCCAAGCCTGTGATTCCAA | 2,035,586 | 87 |
| 5074. | CCTAGGTTATGATAAATTTCCTTT[C,T]CcTCTTGTTCAATCCAATCTTATCA | 2,036,345 | 87 |
| 5075. | ACTTCATGTTAACTTCTCTTTATG[T,C]GTAAAAATTTGTTTCTTCTAGTTAC | 2,036,587 | 87 |
| 5076. | CCCCcACCTCATATATATATATAT[G,A]TATGTATGTATGTATGTATGTATGT | 2,039,241 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5077. | TTTGAGTGGAGATCTACTCGAGTG[T,A]AGCCCAATCCCCCCcACCTCATATA | 2,039,276 | 87 |
| 5078. | TGGTGAACCGAACTGGCTAGAAAT[T,C]GGGAAGTTCGATTAAGCATCAAGTG | 2,039,606 | 87 |
| 5079. | AAACCAGAATTGATAAACCACAAA[G,A]AAGCCATAAGCTTCGAAACTGAATA | 2,039,811 | 87 |
| 5080. | ATAACTTCCACAGATTTTATTGTC[G,C]TGATGAGACTGACTTGATCAGAAGA | 2,044,519 | 87 |
| 5081. | CTAATGTTGTTCCCACTTCCCACT[C,T]TCTTTGTGAAGGCAACTTTATCACC | 2,044,910 | 87 |
| 5082. | CCAGTTCTGCAGGTTTGAATTTCT[T,G]GGCAAATAAATATCTGAGAACACCT | 2,045,433 | 87 |
| 5083. | TTGCTCCTGCTGTTATCAATGCAT[T,G]CTCTCACATGCCGTTCAACATTGCA | 2,047,624 | 87 |
| 5084. | TTCTAATTATACCATTTTGTATCC[T,C]CTATTTTTTGAGTCTTCAAAAAACT | 2,048,459 | 87 |
| 5085. | TGATTCTGCTGATGATTAAGTTTG[T,C]tCTCATCGTAAGAGTCAGAATATCA | 2,048,866 | 87 |
| 5086. | TGTTGCTGTCCATTTTATCTGTGG[T,G]TCTTCACTTGCATGATTATCTGATT | 2,048,911 | 87 |
| 5087. | TATATTGTGGATCGTTTCTATTTC[T,C]AACAGTAAACATCACCGTGATCCAA | 2,049,484 | 87 |
| 5088. | ATGGTTTCTTGGGTAAAATGCAGT[C,G]TCACATTTATATTGTGGATCGTTTC | 2,049,516 | 87 |
| 5089. | CAGGTTTCTCTATATCCTTTCTAA[C,G]AACTTGGGTTTTTCTTGGTCCTCGT | 2,049,641 | 87 |
| 5090. | CGAGGTGGGCTTATAATTGTAACA[T,C]GAGTTTATCTTTGTGATTCAGGTTT | 2,049,684 | 87 |
| 5091. | GGATCATTTGTGGTTCTTTCTTT[G,A]CTAGAACTCATTCAATTTTATGAG | 2,049,737 | 87 |
| 5092. | AACCTCGATGGTTTTGGTGGAACC[A,G]TGGAAGCTTTCTCATTCTTACGGAT | 2,049,841 | 87 |
| 5093. | GATTTCATCATTTCCGAACAAAGC[C,T]GAAGATCTTTAACTGTGCATTAGGA | 2,049,967 | 87 |
| 5094. | ATTCACCTTTGGTCCCTTTGAAGT[T,G]GATATCTAATTCTCAAAATTATCTA | 2,050,384 | 87 |
| 5095. | CTCAGTTTATAGCATGATCTCCAT[T,G]CGATCACCATGTAGGGAATGAAAAG | 2,050,557 | 87 |
| 5096. | TATAAATCTCTAAAAATTTATTAt[G,A]TAAGCAACAGATCTGCTTATTCAAA | 2,050,900 | 87 |
| 5097. | TTATAAATCTCTAAAAATTTATTA[T,C]gTAAGCAACAGATCTGCTTATTCAA | 0,050,901 | 87 |
| 5098. | GCCTATTTAGTGATTCTTCTCTCC[T,C]CAAAATCTTCAATCATAACATTTAT | 2,050,947 | 87 |
| 5099. | CTTTTTTCTTGATTATTTATCTTT[T,G]TTTTTtAATTATTTAACTTCTCTT | 2,054,056 | 87 |
| 5100. | ACCTCGAGTGCCTCACTCACCTCA[A,C]TGTTGGTGCCTTTTTTGCACCTTGA | 2,055,263 | 87 |
| 5101. | CCTAATTTATGATAATCCAGCTGC[C,A]AGACACAAGTGAAGCGCACCTCGAG | 2,055,305 | 87 |
| 5102. | ACCCATAGAGTTTTGGCTGTTTTG[T,C]CGTTCTTTTCTCATCCTAATTTATG | 2,055,344 | 87 |
| 5103. | AGGGTTCCGGGAGTCCGATGGAGG[G,A]CTTTGACGATTGGGGTCTAAGCGCC | 2,055,785 | 87 |
| 5104. | TGGAATGAAAATAGGGTCGAAATT[T,C]tAAAACTCATTTACACAGCGAGAGA | 2,056,546 | 87 |
| 5105. | GGTATATTGATCTTTTGGTAATTC[C,T]TTTTATCAAAAAATTATGTCAATTG | 2,056,774 | 87 |
| 5106. | ATCCTTATAAACTAGTCGTTTATG[A,G]TCATTGGTAAAGGTATATTGATCTT | 2,056,810 | 87 |
| 5107. | GTGCTATCATAACAAGATCTATTT[A,G]TACTAATAACTAGAAGCGAAAATAG | 2,057,128 | 87 |
| 5108. | TCACCATCCAAAATTAAATTTAAT[A,G]aTTGTTTCATTAAAGAAACACCAGC | 2,057,924 | 87 |
| 5109. | AAAAAATATCTCTAAATTTTTATT[A,G]aGAATTGAATTACTTGTTATTCGAA | 2,059,926 | 87 |
| 5110. | TCAGTATTTTATTTTTAAATACTA[C,A]ATCATTACTTATTATTATAATCAAA | 2,060,707 | 87 |
| 5111. | TACCCATGAGGTGGTCAATTCATC[G,A]TGCAACCTCTTGAGATATGATCAGT | 2,060,752 | 87 |
| 5112. | TGGAACCTTGCAATTGAAGATGGC[A,G]GTACATGCAAGTGAGTTGCTTGCAA | 2,060,896 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5113. | CATGATATAATATCTACTATAGCA[A,G]TTGTTGCTGCTAAATATTAAAAATA | 2,061,431 | 87 |
| 5114. | GAGAGCCAGAACTGAGGGAAGTGT[A,C]AGAAGAGAGGCAAAGGTAACCCAAC | 2,062,208 | 87 |
| 5115. | AATCCCTACATGCTTGGAGAGATA[C,T]GAGATAAAATCTGAACAAATTATAC | 2,062,318 | 87 |
| 5116. | AACATAAAAGAAAACATCCACAGG[G,A]ATCTTAAATCTTCGGACAAGCAATA | 2,062,625 | 87 |
| 5117. | AGAATTAAAaAATATATATATAGT[T,G]TtAACAGTGCTAAAAGCCTACCTTG | 2,063,381 | 87 |
| 5118. | AAACCATATCAAAAAGAATTAAAa[A,T]ATATATATATAGTTTtAACAGTGCT | 2,063,395 | 87 |
| 5119. | CAACAAAAGAAAGAAAAGTAGCAA[C,G]CcACATGCCACAGAAATAGGGAATT | 2,063,789 | 87 |
| 5120. | CCCATTCGTACTGTCTGCATCTCT[G,A]TTTAGCCAGAACGAGAATACCTTGT | 2,065,527 | 87 |
| 5121. | TGGAACATAGGTATGTTCTCCCTT[G,A]AAATGTCTTGGATCAACACCTCCAA | 2,065,590 | 87 |
| 5122. | TACAAGCTTGAAGGAACATACAGT[A,T]GGCCCTGCAAGCAAGGAAGTTCCAG | 2,065,954 | 87 |
| 5123. | CCTAGTTGGCATGATTATCCATCA[T,C]AGCTTTATCTTAAAGCAAGAGAAAA | 2,066,200 | 87 |
| 5124. | ACAAAGACAGCATCTTTGCAAAGA[A,C]AATACCTAGTTGGCATGATTATCCA | 2,066,229 | 87 |
| 5125. | AGGAAAAAGATATAGTGAGTTTGG[A,C]ATACTCAAACATGAAGTAAAGAGGA | 2,066,410 | 87 |
| 5126. | TGCTGAAGTGGGCCTCAGCACCAG[A,G]CCAAGTGCCAAGCAGACAGGCCCT | 2,066,502 | 87 |
| 5127. | ATAAAAATTTAAGAAAATTGAAAT[T,C]CATAACTCCGTAATTATACCACCGT | 2,067,047 | 87 |
| 5128. | TATTTGGGCGACTATGGTCTGAAA[T,C]GATTAAAAGGATCAAATATAAATTT | 2,067,345 | 87 |
| 5129. | GTATCAACTCTCCATACTGTTTAA[T,C]GACCTCTTTACATTCCATGCTCACA | 2,067,421 | 87 |
| 5130. | ATTATCTCCTTACCTCTTCTGGAG[T,A]TAGGCTGAAAGTTTTATTGGCTATT | 2,068,130 | 87 |
| 5131. | AGTGATTAAGCCTAATATATTATC[T,G]CCTTACCTCTTCTGGAGTTAGGCTG | 2,068,148 | 87 |
| 5132. | TTCATTGTGATGTAAAAAGGGCGT[C,T]TGAGCCCAAGCAGGGCTAGAGTGGG | 2,068,961 | 87 |
| 5133. | TAAGCTTCCCGGTCTTCATTGTGA[T,C]GTAAAAAGGGCGTCTGAGCCCAAGC | 2,068,975 | 87 |
| 5134. | AAGAAAATAAGTAGGTAGCAAGTC[A,G]ATTGATAGAGAGGAAGGACACTT | 2,069,390 | 87 |
| 5135. | AAAGTATTAATCCTGCAATGCGGA[C,A]GAGCTAGAAATATCTCAAAGTTTAT | 2,070,431 | 87 |
| 5136. | ACCCCGCCCAAATACCCACACGTC[C,T]ACCGGCACTTCTCCCCTACCTTATC | 2,075,030 | 87 |
| 5137. | CTTCGACACGTGTCGAGTACGTAA[C,G]CTCGAAGTCTCCTATTTCCTACGCA | 2,075,158 | 87 |
| 5138. | GACATGGTCCTGGAATATAGGCCA[G,T]GGCGCATGAATCAAGTGGCTGATGC | 2,077,325 | 87 |
| 5139. | TTTCTGGCAGAGTTTGACATGGTC[C,T]TGGAATATAGGCCAGGGCGCATGAA | 2,077,340 | 87 |
| 5140. | ACACAGAAGAAGCTATCTCCCAAA[T,C]AAGCCCGTTGGCAAGATTTTCTGGC | 2,077,382 | 87 |
| 5141. | GCTGCGGTTGCCAGATCATACACT[G,A]CCATTCGAAGTCCACACTGATGCTT | 2,077,638 | 87 |
| 5142. | CACGGTTTATTACGGGTTATTCCC[A,G]TCGTGCTGCACCCTTGACGGAGTTA | 2,077,774 | 87 |
| 5143. | AACATTTACTTTTATTCTTTTAA[T,C]GATGCTGATTTTTCCTATGATGTTA | 2,078,081 | 87 |
| 5144. | CTTCCTTGTTTGGATCATCCTTTT[T,C]GGATGTTGTGATCTCCTTCTTCATC | 2,079,748 | 87 |
| 5145. | GGGCCTCGTGCGGACAATCTCGAT[A,G]CCATCCGAAGTGGGGTATGTGCGAG | 2,080,066 | 87 |
| 5146. | ATCTTATCTTCATCTTAGCCCTTC[T,G]GGGCTTACCAATCCGGAGATCGGGT | 2,080,858 | 87 |
| 5147. | ATCGGATTTTGGTCTTCTCAGGA[A,T]TGATCCGAAGGTCGATGTTTAGGTC | 2,081,308 | 87 |
| 5148. | TTTATGAGATTTAATCCAGAGATC[G,A]GATTTTTGGTCTTCTCAGGATTGAT | 2,081,329 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5149. | TCCAATCCGGAGATCAATTTTTCT[G,A]CATAAAATTTTAGTGAAGTCCACTC | 2,081,433 | 87 |
| 5150. | TATCTTTTCGAGACTTGCGAAGTC[C,T]AATCCGGAGATCAATTTTTCTGCAT | 2,081,455 | 87 |
| 5151. | AGGGCATTTCACATGAAATTTTAA[G,A]CTAGAATTTATCTTTTCGAGACTTG | 2,081,488 | 87 |
| 5152. | CCAAGAAAAAGTTTTCAACTTGT[C,T]CGATGTGGCAAATCTGTACCATTTG | 2,081,645 | 87 |
| 5153. | GATCGGCTTTATGATGACATCAGC[T,C]TTCCGATAAGGTCGGCTTTATGATG | 2,081,862 | 87 |
| 5154. | GGCCTTATGATGATCTCAGAGTTT[T,C]GATAAGATCGACTTTATGATAATCT | 2,082,061 | 87 |
| 5155. | ATAAATCTTTTTTATGTCATATTA[C,A]ATTTATATGAACAAATTGAACAAAC | 2,083,116 | 87 |
| 5156. | CTCATCTGGGATGTCTGGACCTCT[C,T]TTCGTCAAACTGTTGCAGTTAGAGT | 2,083,414 | 87 |
| 5157. | GTTTGGATTCAGAGAGGTGCTAGG[C,T]AGCTCGAAGCCCATCCTCTCATCTG | 2,083,456 | 87 |
| 5158. | TGATGGGAGACTTATAGTGGCTGG[T,G]GGCTCCCACCCCTTTGAGCCTTCTG | 2,083,610 | 87 |
| 5159. | AGGGACAGGAGAGGTGGAGCAGGC[T,C]TTGTTATCCATGGCCCTGATGGGAG | 2,083,651 | 87 |
| 5160. | AACTTTGATGGCTGTGTCAGGGAC[A,G]GGAGAGGTGGAGCAGGCTTTGTTAT | 2,083,669 | 87 |
| 5161. | CGTGATGATCTCAGATCAGAGGGA[C,T]ACTTATATCCATATCTTTTTGGAAT | 2,084,900 | 87 |
| 5162. | ACAACTAATACCTATCCAAAGTGG[C,G]TGACAAAAAGAATGTTAGCTTCTGA | 2,085,871 | 87 |
| 5163. | AAAATAGGCACCTTCACAAGAGCC[G,A]GTGGGTAGGTAGAGTAGGATAAGAA | 2,085,962 | 87 |
| 5164. | TCTGAAAGTCCTCGTTGGTTACTC[A,G]CAGCCGCACAAGCATCCAATCTCTA | 2,086,579 | 87 |
| 5165. | GAACAAGGAGATGGTACGTCGAGA[T,C]GATCGCCTTGAGGGCGTTCAATCCG | 2,088,651 | 87 |
| 5166. | ATCTCCGCGCATCTCTCCGATTCC[A,G]TTTTTGGTCGGGAACCGAACAAGGA | 2,088,692 | 87 |
| 5167. | GATCTCCGCGCATCTCTCCGATTC[C,T]ATTTTTGGTCGGGAACCGAACAAGG | 2,088,693 | 87 |
| 5168. | TCCCTCGACTCGTCGCTTTGAGCG[A,G]AGATTTGGAAGCATCGTCGGGCGAG | 2,088,748 | 87 |
| 5169. | TCCAGCTTGTCGATCGTCAGAGAA[T,C]CCCTCGACTCGTCGCTTTGAGCGAA | 2,088,772 | 87 |
| 5170. | CGAGCCTCGTTCTTCCTCCTCCCG[T,C]TGGTCCAGCTTGTCGATCGTCAGAG | 2,088,800 | 87 |
| 5171. | GGGATCGCCTCGAGCTACTCGGCC[A,G]GCGAGCCTCGTTCTTCCTCCTCCCG | 2,088,826 | 87 |
| 5172. | CTCCTATCGGGATCGCCTCGAGCT[A,G]CTCGGCCAGCGAGCCTCGTTCTTCC | 2,088,834 | 87 |
| 5173. | CAAATATGTCGGCATTGGCCGTCA[A,G]CAGCTCCGTCAGACGGCGTCGTTCG | 2,088,930 | 87 |
| 5174. | GATGCCCGACATATCTGCTGTCGA[T,C]CAAGCAAATATGTCGGCATTGGCCG | 2,088,959 | 87 |
| 5175. | CGGGGATGCCCGACATATCTGCTG[T,C]CGATCAAGCAAATATGTCGGCATTG | 2,088,963 | 87 |
| 5176. | TGAGTCGGTGGGTTATTATTTCTG[C,G]GGGGATGCCCGACATATCTGCTGTC | 2,088,987 | 87 |
| 5177. | GGAGCGAAGGACCTCTTCTTCTGC[T,C]TCACCGGTCTCATCGTCGGGTCGAT | 2,089,039 | 87 |
| 5178. | CTGCCTTTCTGGAGCGAAGGACCT[C,T]TTCTTCTGCTTCACCGGTCTCATCG | 2,089,049 | 87 |
| 5179. | CTTTTTTGACCATGACAACATTGG[C,G]GAGCCAATCGGGATACGTGGATTCT | 2,089,149 | 87 |
| 5180. | GAAGTGGAGGATCTGCATCGACTA[C,T]ACCGACCTCAACCGAGCCTGCCCAA | 2,089,156 | 87 |
| 5181. | CTGCATCGACTACACCGACCTCAA[C,T]CGAGCCTGCCCAAAAGATAGCTTCC | 2,089,168 | 87 |
| 5182. | GTCGATGCAGATCCTCCACTTCCC[A,G]TTGGCTTTTTTGACCATGACAACAT | 2,089,178 | 87 |
| 5183. | CATCCACCAGCTGGTCGATCTTGG[A,G]AAGCGGGAAGCTATCTTTTGGGCAG | 2,089,248 | 87 |
| 5184. | GCATCCACCAGCTGGTCGATCTTG[G,A]AAAGCGGGAAGCTATCTTTTGGGCA | 2,089,249 | 87 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5185. | ATGAAGCTGAGCAGTCGAAATCCG[A,G]ACGTCGCATCCACCAGCTGGTCGAT | 2,089,279 | 87 |
| 5186. | AGACGAGGAGCACACCGCGTTCGT[G,A]ACTCCCAAGGGCCTCTACTGTTATC | 2,089,321 | 87 |
| 5187. | GCTCCTCGTCTTCAGGCACCATCC[A,G]GATCTGATTGTACCCGACGAAGGCG | 2,089,332 | 87 |
| 5188. | CACCGCGTTCGTGACTCCCAAGGG[C,T]CTCTACTGTTATCGGGTGATGCCCT | 2,089,333 | 87 |
| 5189. | AGGTGGCACCGGCGTTCTTCAGTC[T,C]GAAGGGCATCACCCGATAACAGTAG | 2,089,410 | 87 |
| 5190. | ATTGACAAGTCGCTGGTAGGTGGC[A,G]CCGGCGTTCTTCAGTCTGAAGGGCA | 2,089,427 | 87 |
| 5191. | CTGGTCTTTGAAGACCTTATTGAC[A,G]AGTCGCTGGTAGGTGGCACCGGCGT | 2,089,445 | 87 |
| 5192. | AATGAAGCTCAACCCGACCAAGTG[T,C]GCTTTTGGGGTGACCTCAGGGAAGT | 2,089,555 | 87 |
| 5193. | CATTCGGTGTCGTCGAAGGGTGCG[G,A]AAGGTCTCCTCGAGATCCTAAACAT | 2,089,559 | 87 |
| 5194. | CTTCCCTGAGGTCACCCCAAAAGC[A,G]CACTTGGTCGGGTTGAGCTTCATTC | 2,089,604 | 87 |
| 5195. | TGGCCTCAATCCCTCTCTGAGAGA[T,C]GAGGAATCCGAGGAACTTCCCTGAG | 2,089,644 | 87 |
| 5196. | ATTGGCCTCAATCCCTCTCTGAGA[G,A]ATGAGGAATCCGAGGAACTTCCCTG | 2,089,646 | 87 |
| 5197. | GAGGATTGCCTTTATTTTCTCAGG[A,G]TTGGCCTCAATCCCTCTCTGAGAGA | 2,089,670 | 87 |
| 5198. | TCGACTAAGAGCGACAATTCTTTC[G,A]TTCAGCTGTTGGACCTCCTTCTTGG | 2,089,739 | 87 |
| 5199. | AATCGACTAAGAGCGACAATTCTT[T,C]CGTTCAGCTGTTGGACCTCCTTCTT | 2,089,741 | 87 |
| 5200. | AGAGATGAATCGACTAAGAGCGAC[A,G]ATTCTTTCGTTCAGCTGTTGGACCT | 2,089,748 | 87 |
| 5201. | GTGGCGCAGAGTTTTGAAGAACGG[T,G]AGGCACCTTTCAGCTGATCGAGAGA | 2,089,793 | 87 |
| 5202. | CGGCGGGGAAGCCAAGTACTTTTT[T,C]AGGTCTTCGAAGGCCTGTTGGCATT | 2,089,868 | 87 |
| 5203. | TTCCCCGACCTGCGGCTTTACGAG[T,C]AGCGGCGGGGAAGCCAAGTACTTTT | 2,089,895 | 87 |
| 5204. | CTCAGGAGATGTGGCCAAGTAGAG[A,G]TACAAGGTTTCCCCGACCTGCGGCT | 2,089,928 | 87 |
| 5205. | CGAGTACCGAACTGATCGCCTCAG[G,A]AGATGTGGCCAAGTAGAGATACAAG | 2,089,947 | 87 |
| 5206. | CGAGAAAATGAGTGCCGAACCCAT[C,T]AGCCTATCTACTACACCAGCAAGGT | 2,089,949 | 87 |
| 5207. | CACTCATTTTCTCGGACGAGTACC[G,A]AACTGATCGCCTCAGGAGATGTGGC | 2,089,963 | 87 |
| 5208. | TCGGCACTCATTTTCTCGGACGAG[T,C]ACCGAACTGATCGCCTCAGGAGATG | 2,089,967 | 87 |
| 5209. | GATAGGCTGATGGGTTCGGCACTC[A,G]TTTTCTCGGACGAGTACCGAACTGA | 2,089,982 | 87 |
| 5210. | GGCGAAAATCATCTTTTCCGTCTC[T,C]GAGTACCTTGCTTCGGCCCCGTGGA | 2,090,051 | 87 |
| 5211. | CGCGCAACGACTCCGTCCATACTT[C,T]CAGGCCCACGCCATAGTGGTGCTCA | 2,090,062 | 87 |
| 5212. | TCGGCGCAGTATCGCCCTCAGGGG[T,C]TGGTTGGTGAGCACCACTATGGCGT | 2,090,144 | 87 |
| 5213. | GCTTCATCGCCCACTTCGCGAGTC[A,G]TCCAGATGTGTCGGGTCGGCGCAGT | 2,090,184 | 87 |
| 5214. | TCGGTACTGAATGTCGAACTCGCT[A,G]AGCTTCATCGCCCACTTCGCGAGTC | 2,090,210 | 87 |
| 5215. | TGACAGAGCTCATTCAATAATTTT[T,C]GAAGATCATGGATGATGAGATGTAT | 2,096,183 | 87 |
| 5216. | AAGCCGTTTCCGGATAAATCCCTG[A,G]ACGAAGAGGGAAATTTCAATGACCC | 2,096,914 | 87 |
| 5217. | CGTTAACCAGACCCGTTCGATCTC[A,G]TCTCAGTGGCTCCAATTTCGTGTTT | 2,097,200 | 84 |
| 5218. | CTGGTGGGAAGCGAAGGTGGTGCC[G,A]CGCCGGGAAGTGAACTCGAGAAACC | 2,097,965 | 84 |
| 5219. | TTCAGACACTACAGTTATAGGCTA[G,A]AGGTGAACCATTGCATTAAGAACAA | 2,099,347 | 84 |
| 5220. | GAAATTGCATGCTTCAAAGCATTT[A,G]CCTTTCCATTTACAAAAATCAACAG | 2,099,551 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5221. | AAAATTATTTAAGAAAACTTAGGG[T,C]GAGGACCACTTGACATCAAATGCTG | 2,099,639 | 84 |
| 5222. | ATAATGTGAAAATCAGTGTAGTGA[G,A]AAGTAAATTATAAATAACTAGTGTA | 2,099,773 | 84 |
| 5223. | ACACACACACACACACACGTAT[G,A]TATTAACATAATGTGAAAATCAGTG | 2,099,805 | 84 |
| 5224. | GTTATTAGAATTCCTGTTCAATGA[T,G]ATTCTTTTTCCAAAGAACCCTAACA | 2,100,008 | 84 |
| 5225. | CCCACCCAATGAGTTATTAGAATT[C,G]CTGTTCAATGATATTCTTTTTCCAA | 2,100,020 | 84 |
| 5226. | TTTTTTCAGAATACAAGGAATCCT[T,G]AGTTTACTTCCGCCAACTCATACCA | 2,100,196 | 84 |
| 5227. | AACAAACATTCCGGAACATGAACT[C,T]GTGCTATATAATTGACTTGAAAAAT | 2,100,376 | 84 |
| 5228. | CCAAGTCCCAAGTGTTTGGCATTA[C,T]AAAGAATAGAAGATAGACTCTAGCA | 2,100,629 | 84 |
| 5229. | TCCATAAAGTAGAATATTCAAATG[C,T]CAAATAGCATAAGCATATGACAATT | 2,100,855 | 84 |
| 5230. | CATGAATAATAGGCCAATACCTTC[A,G]AAAGAAGAGTGGAGGGAAATCGTTA | 2,105,126 | 84 |
| 5231. | TCCAATAGGGATGGAAGTCAAAAT[C,T]CGAAAGAGCCTCCTTCATGAAGCGC | 2,105,533 | 84 |
| 5232. | ACTCCAAACGTATGCCATAGTCCA[A,G]TCTATCCAATAGGGATGGAAGTCAA | 2,105,562 | 84 |
| 5233. | ACAGCACGAAGAGCTCGCGAAAGG[A,G]CATCAGCACATATAATAAAAAGATA | 2,105,699 | 84 |
| 5234. | AAAGCCAATAGCATTCCAGAACGT[G,A]GCCCATCCCAACAGCAAGCAATCAT | 2,105,823 | 84 |
| 5235. | CGTTATGCTCGGCCACACCTAACC[G,A]ATCTCGAATCAAGTGCTGCAATTGC | 2,105,962 | 84 |
| 5236. | ATCCCCAAATACTGAAGAACCCCG[T,C]TATGCTCGGCCACACCTAACCGATC | 2,105,984 | 84 |
| 5237. | ATAATGTTCGAAAGTAAATAAACA[G,A]GCATAGAAGTGAGAATGGACCTCAT | 2,106,152 | 84 |
| 5238. | CATGCTAGCAGATGTACACCACCA[T,C]CCCTTTAGATTTGGAACGCCACAAG | 2,106,250 | 84 |
| 5239. | TACTAGTTGGCAGACCATATCTCA[T,C]GCTAGCAGATGTACACCACCATCCC | 2,106,272 | 84 |
| 5240. | CCTTCTATACTAGTTGGCAGACCA[T,C]ATCTCATGCTAGCAGATGTACACCA | 2,106,279 | 84 |
| 5241. | ATCATGCTCTACATCGACTCAGGG[T,C]CAAGTAGAAGCTTGGCAGTATGTCG | 2,106,379 | 84 |
| 5242. | CGCCGCATCATCATGCTCTACATC[G,A]ACTCAGGGTCAAGTAGAAGCTTGGC | 2,106,388 | 84 |
| 5243. | AGGAACACATTAGGGGCATGCACA[C,T]AGATCTCCTACCATATAACTGAAGC | 2,106,486 | 84 |
| 5244. | TGAAGGAACACATTAGGGGCATGC[A,G]CACAGATCTCCTACCATATAACTGA | 2,106,489 | 84 |
| 5245. | TAACATCCGAGCCATGATGAAAAG[G,A]TGTAGGAATCCTCAGTACTCATCGG | 2,106,737 | 84 |
| 5246. | AAAGATTAACTCTCGGGTGCACTC[C,T]GAGCCTCCAAATCCATCCACCATCC | 2,106,869 | 84 |
| 5247. | CGCAAATAAGACCTGATCGAAAGA[T,C]ATCTCCAAGCTACCTTCCACAAGAA | 2,106,918 | 84 |
| 5248. | CTAGCTGGTATCCAAATCTCTCTC[A,G]CGCAAATAAGACCTGATCGAAAGAT | 2,106,943 | 84 |
| 5249. | CGTCTCCTCCTCCCTAGCACAGCA[G,A]GAACACTCTAGCTGGTATCCAAATC | 2,106,975 | 84 |
| 5250. | CACCCCCTACTCTTGATCTTAGTC[G,A]GTCTAAGAAGGCCCCAACAGGATCA | 2,107,108 | 84 |
| 5251. | GCAGCATTGATAACTACATTGTGG[A,G]ATAGAACACCCCCTACTCTTGATCT | 2,107,139 | 84 |
| 5252. | TGTGGCTCTCTTCAAAATGAACCA[T,A]GCCGAGGTCATTCTGGATTCAAAAA | 2,107,230 | 84 |
| 5253. | TTCACCTTAAAGTACCTCGGAGGA[A,G]AGGACTCCCAAATGATAAACACCTT | 2,107,361 | 84 |
| 5254. | AGAGTACAAAACCTGCACCTCCAA[A,G]CCTGCCGTGAACGCTACCATCAAAG | 2,107,411 | 84 |
| 5255. | ACGTCGCAACCTAATCAACTATATAC[C,A]GTTGGCCTTCCGGAGAGCATGTCGG | 2,107,704 | 84 |
| 5256. | AACCTCGGATCAGTCTCCAAAAAT[T,C]CATCGGAGTGTTCCACAACGAACGT | 2,107,750 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5257. | CAGAAAGTGAAACATCCTTGAAAG[A,G]CCAAGGAATCAACCTCGGATCAGTC | 2,107,785 | 84 |
| 5258. | ATACGGAAATCAAACATCCACGGT[C,G]TAGGGTGACTCTACGAGTCCAAATA | 2,108,077 | 84 |
| 5259. | GAuGTTCTAGAAAGGTAATAAACT[T,C]GTTTTGAAATATGCCGAGAGTACGA | 2,108,395 | 84 |
| 5260. | GAAAGAATGAGGTAGAAAAGCATT[T,C]CTTGAAAAGAAAGTTCTTTCTACCA | 2,108,459 | 84 |
| 5261. | TCGATCTGATAGATCGCTACAAAT[T,C]GATTTATGAATAATGATAAATTTTC | 2,108,724 | 84 |
| 5262. | GAATGTACAATTCTGCGGTTTCCT[T,A]AGTCATCAATTGTGGGCATTTTTTT | 2,110,260 | 84 |
| 5263. | AACCTTCCCATCCTTCGTTGTAAG[C,A]AGTCTTATTGTTGTATATGAATGTA | 2,110,303 | 84 |
| 5264. | ATAATTTGATTCCTAAAGCTTCCC[C,T]AGCAGCACCTTTCATTCATGTATTA | 2,111,002 | 84 |
| 5265. | TATTAATCTCATCTGAATGGTATC[G,A]TGTAAAGATTAGATTATATCAACAA | 2,111,990 | 84 |
| 5266. | TGGCCAAACGTTAGCAGAACCCTA[C,T]CAGTTGCCACCCCTATACTGTGTGC | 2,112,476 | 84 |
| 5267. | GGCTTTCGGATGGATATGGCCAAA[C,T]GTTAGCAGAACCCTACCAGTTGCCA | 2,112,492 | 84 |
| 5268. | TGGATATGGATGTAGGATTATAGA[T,C]AGGGGTTGGGTCTGACATATGTACT | 2,112,544 | 84 |
| 5269. | CACTGTTTTACAAGTAGTGTTCCA[A,G]CAATCCTAACTTGTATGCCTTATCA | 2,114,922 | 84 |
| 5270. | TGACTTCGGTTGCCTCTTCTTCTA[C,T]GTGGATTAACTGATGCAAAGTGATC | 2,115,107 | 84 |
| 5271. | CATGCTTTGGCAGTCATCTGACTT[C,T]GGTTGCCTCTTCTTCTACGTGGATT | 2,115,125 | 84 |
| 5272. | CAAAAGCTATTCTCTTTAGCTTGC[G,T]GAGGCATCATTACTTTTCCTCTTCA | 2,115,436 | 84 |
| 5273. | CATTCAAGTGTATAATAGTTCCTT[T,C]TGTAGTTTCTACAAATCTCAGGATC | 2,115,584 | 84 |
| 5274. | AACTAATCTCTCCCTCTCTCTC[T,C]AACAAGTCCATTTAACATTTTAATT | 2,116,191 | 84 |
| 5275. | AAATATTCGATGTCATACCAGATT[T,C]TCTACCATCATAATACAAAATAATG | 2,116,329 | 84 |
| 5276. | CACTTCTGGCCTTATAGTTTGAAT[A,G]TTGTGGGAATAAGGCCTTATAGTTT | 2,116,395 | 84 |
| 5277. | TGGTACCTGTGAGATTCTCCAAAA[T,C]GTATCCTCTTAGTTTATATTAGCTC | 2,116,444 | 84 |
| 5278. | ATTTCATTCCGTGATTGCACTCCT[A,G]CTCTTCTTATCTGAAATTCGAAGAT | 2,118,327 | 84 |
| 5279. | ACCAAAGAAATAATGAACACCGAT[A,T]AGAGTTCTAGATATCGAGAAAAGGA | 2,118,444 | 84 |
| 5280. | TCATTACTGTCCATCATGGAATAC[T,C]ATACCGTCCCATACCGCCCGTAGCA | 2,118,655 | 84 |
| 5281. | AACCAAAATTATATGATACTTTCT[C,A]ATAGTTTAGAACAGAAAATACTACA | 2,120,420 | 84 |
| 5282. | TGAGCCAAATCACATGTAGAGAGG[C,T]AAGTGGTTGCGGGTGCTGGGGACTT | 2,120,476 | 84 |
| 5283. | GCAGTTGTAGAATATATGAAAGAA[G,T]GGTGCATGTAATTGTTGTAAGCTTG | 2,121,161 | 84 |
| 5284. | CTTTTATGGAATTTCGGTTGAATC[G,A]TGATACAGCACAGCCTTCTGCACTT | 2,121,232 | 84 |
| 5285. | TTTGGAGGATTATTAACTTGTCTA[A,G]TCTTTGACCACAACTTGGTGGAAAG | 2,121,312 | 84 |
| 5286. | CATAAGGGCATAGCATTCCAACAA[C,T]TATTTATACTTCAGAATTCAGGTGG | 2,121,868 | 84 |
| 5287. | CATCCACCTGTTCATTTTCGGTAG[T,C]TATAATTCCACCAAAGAATTGATAT | 2,122,435 | 84 |
| 5288. | GCAGAGATTGGTGATTGTTAGACT[T,G]ATCACCATTTTGCACTTCAGCTTCT | 2,122,730 | 84 |
| 5289. | TTGGGTAGCCAAGATCAACCAATT[A,G]TAAGTGGGTGGGGTATGGATTTGAC | 2,124,017 | 84 |
| 5290. | TTATATTTAGTGTTAATTCATTAT[A,T]GTTGTTCTTGAACTTTTTACTGTTT | 2,125,059 | 84 |
| 5291. | CCGGCCGGCACGAGTTCCAATACC[G,A]AGTCCGCGAATCTTGATTCAATATT | 2,125,202 | 84 |
| 5292. | GAGCGCCCTTGTTTCATGCTTGCA[G,A]CACCACAGGTATCAAGTGCGCCGTT | 2,125,433 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5293. | GCTATCGAAGGGCGTCGGGTCGCT[G,A]CCGTGGCCACCGCCCACCGGGCAGC | 2,125,685 | 84 |
| 5294. | GATCGTATTGGAGGGAGGAGCGAA[C,T]GGTGGAGGAGCTATCGAAGGGCGTC | 2,125,719 | 84 |
| 5295. | AGAGAGAGAGGGAGAGCGATCGTA[T,C]TGGAGGGAGGAGCGAACGGTGGAGG | 2,125,736 | 84 |
| 5296. | ATCACGACGCCGTCGGAGGCCGAC[G,A]GTGGCCTGCTGTGGCCATCAGAGGG | 2,125,844 | 84 |
| 5297. | TCAAAAGAATGGCAATCTAATAT[A,G]ATCATTCAATACATAAAATTTCGTA | 2,126,026 | 84 |
| 5298. | GCTTTTTGTACTTTATGCCGACAA[C,T]GTTGTGGATGACTCAGTAAGGTGTG | 2,127,146 | 84 |
| 5299. | GGGATTACTAACACTTCAAAGGAA[C,T]CTTAATGAACTCTCCTTAATTTAGT | 2,128,887 | 84 |
| 5300. | CATTTTCTATGCTCTCAAGGGCAT[T,G]CTGGGATTACTAACACTTCAAAGGA | 2,128,914 | 84 |
| 5301. | CCTATACCTGGTCATGTCCTTTTC[G,T]CAATAAATTATAACAAGCAAGAGAC | 2,130,403 | 84 |
| 5302. | GGAGTTTTGGAAGGAGAAATAAAC[A,G]TACTCTAGGGGAAGGTCAAAGGAAC | 2,130,583 | 84 |
| 5303. | GTTGAATATATGACTTAAAGACAA[A,T]ATCTGGAACAAAAAAaGAAAAaTG | 2,132,387 | 84 |
| 5304. | CAATCTGGCACAACCTGGTCTTCT[A,G]CTCTATTTGCACCTTTCTCTTCAAA | 2,132,513 | 84 |
| 5305. | ATCCACCAAGCTAGCCATCTTGGA[C,A]GAAGAAACATAGATCAACACCATTC | 2,133,229 | 84 |
| 5306. | TAATTCTTCCTTCTCTTGTGGCTA[G,A]ATAGTTTCTCTGCTAATATGTTTGT | 2,133,507 | 84 |
| 5307. | GTCCCCTTATTAAAGAATCATTAA[G,C]GTTAAAAAAATGCAACTCCGTTCGG | 2,133,841 | 84 |
| 5308. | TCTCGTTGCTGGTAGGCTTTGTGT[C,T]CCCTTATTAAAGAATCATTAAGGTT | 2,133,863 | 84 |
| 5309. | CCATCCCGCCTCTTCTCTCCCTGC[C,T]GTCGGCTCGGCTGCCGTTCTCTCTT | 2,134,491 | 84 |
| 5310. | ACTTGAGCTATCCGAAGAGAAACA[A,G]TTTTTCTTTCCTTCAAATTAAACTA | 2,136,184 | 84 |
| 5311. | TTTCTTATAGCGTCTGGCATGTAT[A,G]CAAAGTAGAGGATCTGCACATCCAG | 2,136,348 | 84 |
| 5312. | TTGCGAAGATCGAAGTTTATCCTG[T,C]TTTCTTATAGCGTCTGGCATGTATA | 2,136,373 | 84 |
| 5313. | GGTGTCACACCAGTATATCTTCTC[C,T]CTCGTTTGATTGGGTTGCGAAGATC | 2,136,412 | 84 |
| 5314. | TGAGTTAGGAGTCCTATATTTATT[G,A]GATCATGGGATTCATCTATAAATAG | 2,137,204 | 84 |
| 5315. | CTCTTATGGGCCGACCAACACCTG[G,A]AAGCTTCCTTATTGTGGACGTCCCA | 2,137,358 | 84 |
| 5316. | ATTCGAATCGGACCCATTTTGGAT[G,A]AAGCTTCCTTATTGTGGACGTCCCA | 2,137,419 | 84 |
| 5317. | TAAAATTGACAGCCTTTCGAAATT[G,A]TTTCGAACCAGCTTCGAATTGAATT | 2,137,466 | 84 |
| 5318. | GTACTAATTAATTTTAGATTATAT[T,C]TAAATTAATTAGACTTAATTGGATC | 2,137,558 | 84 |
| 5319. | ATATGATCTATGGAGTATATGAAA[T,G]ATTGGATTTAAGTACTAATTAATTT | 2,137,594 | 84 |
| 5320. | CACATGAGGTTCAAGTTCGATCAC[G,A]GAGATGAACAGTTTTCGATATATGA | 2,137,638 | 84 |
| 5321. | GAGAATTAAGTTATGGATCGAATG[G,A]GATTGAAGAGTTGACTATGTCTAGC | 2,137,696 | 84 |
| 5322. | AGTCACACACACAAGTCAAACACC[A,G]TAGGAAAGAATTAGCTTATATTTAT | 2,137,798 | 84 |
| 5323. | AGTACAGAAGTCGGTTCCTGTGCT[G,A]CTGGCTTAGTATTTAAACCTATGGA | 2,137,847 | 84 |
| 5324. | GTATAGATTTTGAAATATTTTTTT[A,G]TGATAATTTGACCTATTTGGACGTC | 2,137,926 | 84 |
| 5325. | CAGGGTCAAAAGAATGAATTATAC[G,A]GTAACCATGTGTATAGATTTTGAAA | 2,137,961 | 84 |
| 5326. | AATCTGAAACCATCCTAGAGCATT[C,T]AGGGTCAAAAGAATGAATTATACGG | 2,137,985 | 84 |
| 5327. | ATTGACAGTTAATCTGAAACCATC[C,A]TAGAGCATTCAGGGTCAAAAGAATG | 2,137,995 | 84 |
| 5328. | CTTAATCAGGATAATCTATGAGAT[G,A]GATTTGAAAGGTTGAAATACAATGT | 2,138,061 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5329. | ATATGTAGATCAAAATGGGATTGA[T,C]CCCTTCAGATTATTGGAGTTGATGT | 2,138,137 | 84 |
| 5330. | TATAGTTAAGTACTTGTGAAGTCT[A,G]TATGTAGATCAAAATGGGATTGATC | 2,138,161 | 84 |
| 5331. | AAGTATCTTTCAGTTCTAAGATCA[T,C]CATAGTGACTTGCAAATAATTCTGT | 2,138,264 | 84 |
| 5332. | CAAGGACTGTGGTGACACTGATAT[A,G]ACATACAGGTGTGATATAGGAGTAC | 2,138,386 | 84 |
| 5333. | TGATACGTCATTATAGAATGCTAA[C,T]ATTTATCGAGTGGAAGTCATTGTGT | 2,138,463 | 84 |
| 5334. | AGTCCTTAGAACTATATTAGTGTA[T,C]GATAAAGAGAGAATTTATCGTATAG | 2,138,537 | 84 |
| 5335. | TGAACTCTTGTATTGTGATGAAGT[C,T]CTTAGAACTATATTAGTGTATGATA | 2,138,558 | 84 |
| 5336. | TGATAAATGAATAAAAATTATTCT[G,A]ACATTTTTTCATCACAAAGTTATAT | 2,138,614 | 84 |
| 5337. | AATGGAAGATGGGTATAAGATACT[G,A]CCCCGATTGACTTTAGTCCAAGTTG | 2,138,732 | 84 |
| 5338. | CCGACCCCTTTACTAAAGCTCTCG[G,A]GATCAAAGCGTTCGATGACTTCAAA | 2,138,780 | 84 |
| 5339. | CAATAGAAAGGAGAACCTAGCCGA[C,T]CCCTTTACTAAAGCTCTCGGGATCA | 2,138,800 | 84 |
| 5340. | GCATCAGATATTGCAAAATATTCT[A,G]CATCGCTATTACTTGGTGCGAGAGA | 2,138,884 | 84 |
| 5341. | TCTGTATGCAAAACAGAATACAAT[G,A]CTGCATCAGATATTGCAAAATATTC | 2,138,911 | 84 |
| 5342. | AAGAATTTCAAGCAACATACTGTG[A,G]TCGATTCTGTATGCAAAACAGAATA | 2,138,941 | 84 |
| 5343. | TAATGGAGGAGCTATTTGTCAGAA[G,A]AATTTCAAGCAACATACTGTGATCG | 2,138,963 | 84 |
| 5344. | TTATGATGACAGCAGAAGCGTGTC[A,G]AGCTATGTATTTATCTTAATGGAGG | 2,139,004 | 84 |
| 5345. | CGGCAACTCCTGAGGAGAGAGCGC[A,G]TATGAGTACAATACCATATACTTTG | 2,139,272 | 84 |
| 5346. | ACTCTTTTCAAAAAGATTGTCCG[G,A]CAACTCCTGAGGAGAGAGCGCATAT | 2,139,294 | 84 |
| 5347. | AGGGATAAATTTAGAAGATTGCTT[G,A]GATTATCCTAATCCATGTACATCAA | 2,139,411 | 84 |
| 5348. | GAATGAAGATCTATAGGGATAAAT[T,C]TAGAAGATTGCTTGGATTATCCTAA | 2,139,425 | 84 |
| 5349. | AGTGTAAAGCTATAGTTATCATCA[T,C]AGTTTTTCATGAAGAACTTGGGAGA | 2,139,492 | 84 |
| 5350. | TATGTGGATGATATACTGTTACTA[G,A]AAAATGACATCCCGACTTTGTAGAG | 2,139,540 | 84 |
| 5351. | TGTACTATATGTGGATGATATACT[G,A]TTACTAGAAAATGACATCCCGACTT | 2,139,547 | 84 |
| 5352. | CTTTGCGTCTACAAGTGGGCTTCC[G,A]ATTCTGTAGTCATCTTTCTTGTACT | 2,139,591 | 84 |
| 5353. | ACAAGCTAAATAGGTCTATTTATG[G,A]ACTTAAACAGGCGTCTAGAAGTTGG | 2,139,698 | 84 |
| 5354. | CATCCATAGATGAGTCGAAAATGT[A,G]CAAGCTAAATAGGTCTATTTATGGA | 2,139,722 | 84 |
| 5355. | CTGGAAGAAGAGGTGTATATGATA[C,T]AATCTGAAGGGTTCACATCCATAGA | 2,139,762 | 84 |
| 5356. | TCCTGTGGCAATGCTCAAGTCCAT[T,C]CGAATTTTGTTTGCTATCGCTGCAC | 2,139,868 | 84 |
| 5357. | TATAAAGCTCGTCTAATTACTAAG[G,A]TTTACCATCAACATTATGGTATTGA | 2,139,936 | 84 |
| 5358. | GTATGGACACTAATTGATCCATCT[G,A]AAGGGATAAAATTCATAGGATGTAA | 2,140,032 | 84 |
| 5359. | GAGATGGAGTCTATGGAGATCCAT[A,G]GTGTATGGACACTAATTGATCCATC | 2,140,059 | 84 |
| 5360. | GGGCCCGACTCTCAGAAATGGCTT[G,A]AGGCCATAAAGTCCGAGATGGAGTC | 2,140,098 | 84 |
| 5361. | TGGATAGATACTATGATTTTTTtG[G,A]TCCAGAATGATGATTCCATTAAATT | 2,140,183 | 84 |
| 5362. | AATCAAATCTGGAGCCAATAGAGG[T,C]GCTATTAAGGAGATCCGGTAGAGTA | 2,140,243 | 84 |
| 5363. | TTGATTGATGAATCAAATCTGGAG[C,T]CAATAGAGGTGCTATTAAGGAGATC | 2,140,253 | 84 |
| 5364. | GACACACACAGAATTGAATTTGAT[T,C]GATGAATCAAATCTGGAGCCAATAG | 2,140,272 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5365. | AGTTCTTTAGTGAAAGAGCTAATG[C,T]CTGTAAAATTGAATTTGATGAAGTT | 2,140,339 | 84 |
| 5366. | GTTTGCAGTTGGACAGTCTTTTTG[G,A]AAAAAGAGTTCTTTAGTGAAAGAGC | 2,140,370 | 84 |
| 5367. | CGATAAAACTCTATATGAGATATG[G,A]ACTTGGCGTAAGCCGGTGCTCTCAC | 2,140,561 | 84 |
| 5368. | TAGAGATATGCTCTTGAAACTGCC[T,C]GTTATATTTTGAATAAAGTGCCGAG | 2,140,620 | 84 |
| 5369. | CACAACATAATGCGATATCTAAAA[G,A]GAAAAATCAAATCTTGTTAGATATG | 2,140,712 | 84 |
| 5370. | CTCTTGGAGCACCACAACATAATG[C,T]GATATCTAAAAGGAAAAATCAAATC | 2,140,724 | 84 |
| 5371. | GAAGTAGAGAAATAGATTGGAAAG[G,A]GTATTAAGACCCTTCGGTCAGACCG | 2,140,845 | 84 |
| 5372. | TATTTGAAATATTCAAATGATTTC[A,G]TGCTGAAGTAGAGAAATAGATTGGA | 2,140,874 | 84 |
| 5373. | GATGACCTATCGAGGTATGAGTAT[G,A]TCTATCTTATGAAGCATAAATCAAA | 2,140,926 | 84 |
| 5374. | TTTACAGATGACCTATCGAGGTAT[G,C]AGTATGTCTATCTTATGAAGCATAA | 2,140,932 | 84 |
| 5375. | TAATACATACTGATGTATGCGGAT[G,T]TATGAACATAAGTGCCAGAGGAGGA | 2,141,000 | 84 |
| 5376. | GATCTAATACATACTGATGTATGC[G,A]GATCTATGAACATAAGTGCCAGAGG | 2,141,004 | 84 |
| 5377. | CTACTTGGTAAGATGACTAAGTCA[T,C]CTTTTAAGAGAAAAGGTGAAAGAGC | 2,141,067 | 84 |
| 5378. | TGAGATAGATGATTGTGAATCATT[A,G]CCAACCTACGAATCTCGTCTACTTG | 2,141,110 | 84 |
| 5379. | ATATCCTAAATTAGATAATGTCAG[C,T]GAATCCTACCTTTGGCATTGTAGAC | 2,141,212 | 84 |
| 5380. | CACGACCTGTTAGTATAATGTACA[G,A]CCAACAAATATCCTAAATTAGATAA | 2,141,244 | 84 |
| 5381. | GATTTTTATGATATCATTATGAAT[A,G]ATACTGCAATTATGTGTGGATAAT | 2,141,317 | 84 |
| 5382. | TTTATAATAAAGGATGATTTTTAT[G,A]ATATCATTATGAATAATACTGCAAT | 2,141,332 | 84 |
| 5383. | GCCTTTTGGCCAAACTTAGTTACA[A,G]GTTTATAATAAAGGATGATTTTTAT | 2,141,358 | 84 |
| 5384. | AATATCATCTCTGTAGGCCTTTTG[G,A]CCAAACTTAGTTACAAGTTTATAAT | 2,141,374 | 84 |
| 5385. | CAGCTTGTCTTCTAATCCAGTAGT[G,A]TCATGTTAGATAATTATCACTATTG | 2,141,440 | 84 |
| 5386. | TTCAGTTCTAGTCTTGAAAACTTT[A,G]CAGCTTGTCTTCTAATCCAGTAGTG | 2,141,465 | 84 |
| 5387. | GAAAaGATACAGAAATCCCATGC[C,T]ACCGATCCTAAGCAGAGTAAATCAT | 2,141,821 | 84 |
| 5388. | AAAaAGAAAAaGATACAGAAATCC[C,T]ATGCCACCGATCCTAAGCAGAGTAA | 2,141,826 | 84 |
| 5389. | AGGAGTTAGTGAATTAGTGAGAG[G,A]ATTATCTACAGGACATCGATCCTTT | 2,141,885 | 84 |
| 5390. | CAGAAGGAGTTAGTGAATTTAGTG[A,G]GAGGATTATCTACAGGACATCGATC | 2,141,889 | 84 |
| 5391. | GAGGCTTTAGTCACCAATCATGTA[C,A]TGTACATAATTGAGCAGATTGAATA | 2,142,111 | 84 |
| 5392. | GCAGCTATGAATGACAAACTTAGT[C,T]GTAAGTTCAAAGATGCGCAGGTAGA | 2,142,258 | 84 |
| 5393. | AAACCTACAGTCAATGCTCCTCGT[G,A]CCGTGAGAGATACTTACATGAAGTG | 2,142,345 | 84 |
| 5394. | AGAATTAATGTAATTTTCGAATTG[G,A]AGGTAGAGGCTATCAATTCATAAAA | 2,142,623 | 84 |
| 5395. | TCTAGTACCCACTAAAGAATTAAT[G,A]TAATTTTCGAATTGGAGGTAGAGGC | 2,142,638 | 84 |
| 5396. | CACAGTCAGATCCGAATGCAGTCT[G,A]TGTGGATTCTAGTACCCACTAAAGA | 2,142,670 | 84 |
| 5397. | GGGGTAAAACCTAATTGCTAGAAA[T,G]TATTTGAAAAAATAATTGATTATGA | 2,142,753 | 84 |
| 5398. | GCCTGGGGTAAAACCTAATTGCTA[G,A]AAATTATTTGAAAAAATAATTGATT | 2,142,757 | 84 |
| 5399. | CTCAGGTTGATCGAGCCACACTCG[A,G]ATTTGAATATCCATTTGTTAGATAC | 2,142,882 | 84 |
| 5400. | CATTCATCATATGACCATCATGAT[A,G]TACTTTCAGATCAATACTCAGGTTG | 2,142,923 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5401. | TTGATCATAGCCTCCTATTAAGGT[G,A]CGTGATAATGAGTCGAATATTTCAA | 2,143,024 | 84 |
| 5402. | CTATATAACTTGATGAAGTTAGTG[A,G]GAGGATTTGCAGCTTGTAGGTCATC | 2,143,153 | 84 |
| 5403. | TTTGATTAGGTCACTAGTCTATTC[G,A]TGCAGACCCATGCTATTAAGGTGAA | 2,143,251 | 84 |
| 5404. | GATCATGGCTCCGTGGTTGAGCCC[G,A]AATCTTCTGATGGACCAAATCGAAA | 2,143,451 | 84 |
| 5405. | CATGATCATGGCTCCGTGGTTGAG[C,T]CCGAATCTTCTGATGGACCAAATCG | 2,143,454 | 84 |
| 5406. | TTGATCAAGTCCATATGTTTGATC[C,T]AATAAATGGATCATGATCATGGCT | 2,143,491 | 84 |
| 5407. | CAAAGGATTAGTTTGAATCAGATC[T,C]TTTTAATGGGTTAGACCTAGGGTTA | 2,143,640 | 84 |
| 5408. | ACAGATTAAAATACATGTTTGACA[C,T]AATTTTGAATTAAGCTTTGAATGAT | 2,143,738 | 84 |
| 5409. | GATCATACCTATATATGTTTAATT[G,A]TTGAACATATTATAAAAATTTATTT | 2,143,842 | 84 |
| 5410. | TTATCATGATGCATGAGATGTATG[T,A]ATGAAGTTTAGATCATACCTATATA | 2,143,877 | 84 |
| 5411. | GAACAAATTTTTATATATTATTTT[A,G]ATCAAAATATATTTAGATTAGATTT | 2,144,030 | 84 |
| 5412. | TCTCTTTTATCTATTCGATGGGTT[C,T]TCTTATGATGTGTAGGGGTGTCATT | 2,144,109 | 84 |
| 5413. | ATCATAGAGATTAATTTCTCTTTT[A,G]TCTTATTCGATGGGTTCTCTTATGAT | 2,144,125 | 84 |
| 5414. | TTGATGAGATCACTAAACCATCCG[G,A]TCATAAGAGATCATAGAGATTAATT | 2,144,159 | 84 |
| 5415. | TATAATTAATAAGATCAAGGATAT[G,A]TTCATGACATAAAAATTATTTTATC | 2,144,276 | 84 |
| 5416. | AATATTTTATAATCAGTATAAGAT[G,A]TGTTTCAGATTTGATATGATGTATC | 2,144,351 | 84 |
| 5417. | CGCAAAAATAGATTTTATCAGAAA[T,C]TTATTCCTCATACATTCATGTTTGC | 2,144,439 | 84 |
| 5418. | AACCCCTCTCCAGTGTCAAAGTCT[G,A]AGTCCCCTCCTTCAATGATTTTAAT | 2,156,359 | 84 |
| 5419. | TGCTCCCGTAACTCTATATCGAAC[G,A]CCCACAACCCCTCTCCAGTGTCAAA | 2,156,389 | 84 |
| 5420. | GAGACATAAATACATCAGGCATCT[C,T]AGTCCATAATGAGTTTGAGTCTGCT | 2,156,435 | 84 |
| 5421. | TCTAATTTTTATAGTAATTTCTGT[T,C]TAGTCAATTTGGTGAGGAGTTGATG | 2,156,495 | 84 |
| 5422. | TAATATTTTGACTCTAATTTTTA[T,C]AGTAATTTCTGTTTAGTCAATTTGG | 2,156,508 | 84 |
| 5423. | CAACCACCATGTTTATCTCATAGG[C,A]ATCATTGTGAGAATTATGGAGAAAT | 2,157,685 | 84 |
| 5424. | ATATATTTTACATGTATGAAAAAT[G,A]TCTTCACTTATCGATCTATTAATCC | 2,157,829 | 84 |
| 5425. | ATACTAGATTATTGTAGAAAATA[G,A]AAATATTTATTCACAACAATCCGAG | 2,158,169 | 84 |
| 5426. | TTCTTTTCTTTAATATACTATATT[G,A]TCTTTTATTGCATTTGAACTTTTAT | 2,158,315 | 84 |
| 5427. | TATAGCACTAAATTGGGTCCATCT[A,T]GATTTAATAGGGTCAAAATCCATTT | 2,158,524 | 84 |
| 5428. | ATAAGATATTTGATAAAAAATTTA[A,G]TGCTTTATATTATGTTTGCCCTACC | 2,158,630 | 84 |
| 5429. | GTGGGTCTACTTTCCTTCTCTCAG[T,C]GGGAAAAATTTTGGTAGATCTTAAA | 2,158,750 | 84 |
| 5430. | TTTAGTGATATTTGCAATTCAAGT[G,A]GGTCTACTTTCCTTCTCTCAGTGGG | 2,158,772 | 84 |
| 5431. | CTTGAGTGTTACTAACATTCTATT[G,T]CTATAAACTTCATTTATTTTAGTGA | 2,158,814 | 84 |
| 5432. | TTTCTTTAAACTATTATAAGAAAG[C,T]GTTAGAGTAATAGATGCTCTTGAGT | 2,158,857 | 84 |
| 5433. | TATTTAAAAACACTTTTGATCAAA[C,T]ATTGTTATATTATATATTTTTATA | 2,158,910 | 84 |
| 5434. | GTGTCAACCAACAATTAGCTTCTA[G,A]AGCACATATCTAACATAAAATTTTT | 2,159,007 | 84 |
| 5435. | GTATAAAGTTTTGTTCTGAAATTA[T,C]AAAATGTGTCAACCAACAATTAGCT | 2,159,037 | 84 |
| 5436. | TTAATTTTTAAGACAAATCATGGA[C,T]ACATAAATATAATTGAAATAAAAAT | 2,159,117 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5437. | AATTCTCAACATCTTGAGAATATA[C,T]AAAAATTATTTTTATTAATTTTTAA | 2,159,156 | 84 |
| 5438. | GATTCTTTAATTGAGAGCATTTAG[A,G]AACTAACCATTAATTAATGCATGTC | 2,159,209 | 84 |
| 5439. | TCACTATCCCTATGACGATTCTTT[A,G]ATTGAGAGCATTTAGAAACTAACCA | 2,159,225 | 84 |
| 5440. | TGCACTCTCATCCCAGTGTCTCTA[T,C]ACCGCAGATCTGAGACTTATCTATC | 2,159,316 | 84 |
| 5441. | GGTCACGCTCAGTGCAAGTTGTTC[C,T]CTAACAACCACTGGCCTGCACTCTC | 2,159,357 | 84 |
| 5442. | AATATATACAGCAAGAATCCGAAT[G,T]GCTAGAGACCAAGAAAACGTACAGT | 2,159,527 | 84 |
| 5443. | CAAACAGCAAACCTGAACCTACTG[T,C]AGTCAATATATACAGCAAGAATCCG | 2,159,556 | 84 |
| 5444. | ATAATCCATCAGTGCACACCTAGCA[A,G]TATGTAGTGACAATTCAATAAAATA | 2,159,874 | 84 |
| 5445. | AATAGGATTTCAATAAATTCTAAC[A,C]CAATTACAACTTCACAAGTCTAATT | 2,160,101 | 84 |
| 5446. | CTTTCTTGATTCCAAATCATTATC[C,T]AATCAGGCTAAAAAGATTAGATCTT | 2,160,707 | 84 |
| 5447. | CTAAGAGACCATCTTCTTAAATAG[G,A]CCTTTCTTGATTCCAAATCATTATC | 2,160,733 | 84 |
| 5448. | TTAAAATTCAATCTTTTAGAATCC[T,A]AAGAGACCATCTTCTTAAATAGGCC | 2,160,756 | 84 |
| 5449. | AGAAGAAGGAGAAAGGATGAGGCA[A,T]GGAGATATGGCAGGACGAGTTTAGA | 2,160,810 | 84 |
| 5450. | CCCTTGGGCATAGGAAAGAGAAGA[A,G]GGAGAAAGGATGAGGCAAGGAGATA | 2,160,828 | 84 |
| 5451. | TCTACAGATATCCACTAAGATCAA[T,C]CTTGAATCTTTCTTTCCATGGTAGA | 2,161,034 | 84 |
| 5452. | TCATCACTATCGATGATCTTAGAT[C,T]CGAAAGTTCTTGAGCCGTACACGTG | 2,161,091 | 84 |
| 5453. | AAAAATAAAATAAAAGATGAGAGT[G,A]AATCTCTATACATTTATGTAGGTTA | 2,161,145 | 84 |
| 5454. | AATCTAAAAATAAAATAAAAGATG[A,G]GAGTGAATCTCTATACATTTATGTA | 2,161,150 | 84 |
| 5455. | TTTAAAGTGTTAGAAAAATCAGATA[A,G]GATGTATGCATAGATTTCAAAAATT | 2,161,301 | 84 |
| 5456. | TACTAATTAATTACTATTTAATCA[G,A]AAAATATTATCCTCATAAGGTACTA | 2,161,421 | 84 |
| 5457. | TCATTGTGGGCTGAATCTCGAGGC[A,G]TCAAATCCTAACAATGATAAATAGT | 2,161,497 | 84 |
| 5458. | CTCATTGTGGGCTGAATCTCGAGG[C,T]ATCAAATCCTAACAATGATAAATAG | 2,161,498 | 84 |
| 5459. | TTACATACATATTTAGTGATTAAA[T,A]ATTATCATTGCAAAAAATCTAAATC | 2,164,896 | 84 |
| 5460. | GCATGCAAACTTCACTATGAAAAA[G,A]AAATTTTACAAGAGGAGACCTCACC | 2,164,896 | 84 |
| 5461. | ATATTTATTTTTAAAAACTTACAT[A,G]CATATTTAGTGATTAAATATTATCA | 2,164,914 | 84 |
| 5462. | ATCAATGTGTCTAGCTGAAACCTC[G,A]TTACTTTTAAAATTTATTAGATATA | 2,164,968 | 84 |
| 5463. | ATATATTTAACCTATTAAAAAAaT[G,A]TTAAATATAAATAGGATATATAACA | 2,165,018 | 84 |
| 5464. | GAAGTTTAAAATAATATATTTAAC[C,T]TATTAAAAAAaTGTTAAATATAAAT | 2,165,031 | 84 |
| 5465. | TATTTATCTGACATGATCGACCAC[G,A]TAACTATTTAGTAAATAGGATTGGC | 2,165,086 | 84 |
| 5466. | ATAAATTAATTGTAATGCATCATT[G,A]GTGATTCAGTAATCATTAATGTATA | 2,165,196 | 84 |
| 5467. | AGTAAGTACAATATATTAATTATG[T,C]ACCCTTCTATATTAATAAATTAATT | 2,165,235 | 84 |
| 5468. | AACTTTAAGTTTTCTTATATTTTT[C,A]ATACAAATCATGTAGGATTAGTGTT | 2,165,556 | 84 |
| 5469. | TATTATATTTTATATAAAAAACTT[T,G]AAGTTTTCTTATATTTTTCATACAA | 2,165,575 | 84 |
| 5470. | TAATATTGAATATTTTTAATACTT[T,C]ATATTATATTTTATATAAAAAACTT | 2,165,601 | 84 |
| 5471. | CTTTTTAAAATATAGGAGGTGTAA[T,G]TGAAATCGAACTAAAATCGAAGGAT | 2,165,706 | 84 |
| 5472. | AAGGTTCATTTGACACTTTTTAAA[A,G]TATAGGAGGTGTAATTGAAATCGAA | 2,165,721 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5473. | ATTAAAATAGTTTGTTAAATAGAA[A,G]GGTTCATTTGACACTTTTTAAAATA | 2,165,744 | 84 |
| 5474. | TATCATGTCAAGGTCACATGATAC[A,C]ATTTCATTAATAGAAATAGATAGTA | 2,165,801 | 84 |
| 5475. | ACTTTTATATATATTTATATTTTT[A,T]AATATGTGAAAAATTTTATATATAC | 2,165,966 | 84 |
| 5476. | ATAGAACACTTTTATATATATTTA[T,C]ATTTTTAAAATATGTGAAAAATTTTA | 2,165,973 | 84 |
| 5477. | TTTAACCTCATTCAAACTTACTCG[T,C]GTAGCCAAATTAATTCACAATGAAT | 2,166,189 | 84 |
| 5478. | TTGTGGTTAGGTCCTTGATGCAAT[G,A]GATCTTACTTTTTAACCTCATTCAA | 2,166,224 | 84 |
| 5479. | ATACTATATGAGAAAATTGTGACC[T,C]TTAGAAGTTAGGGTTTGTGGTTAGG | 2,166,263 | 84 |
| 5480. | TTTGAATGCTGAAAAGGAATACTA[T,G]ATGAGAAAATTGTGACCTTTAGAAG | 2,166,281 | 84 |
| 5481. | AATTTTATATGAAATGACTATCAA[A,G]AAAGCAATTTTATGGTACTCAGCTA | 2,166,350 | 84 |
| 5482. | TTCAATTATGAAGTATTGGGCT[A,G]TTATAATTTGACCTTTATAAATAGT | 2,166,413 | 84 |
| 5483. | AGGTCTATTTAGATATCCGTATAA[T,C]GATCATGGATTGGGACATCCAGATA | 2,166,478 | 84 |
| 5484. | GCTATATGTCAAATTTTATTTTtTT[T,C]TATTtTTTATATTTTTTAAATAAGA | 2,166,875 | 84 |
| 5485. | CTATCTATATAATAATTATAAAGC[G,A]ATATACGGATATTAGAGATGATATT | 2,166,965 | 84 |
| 5486. | TACGTAAAACATCTCCTCCCTTTG[A,G]AATGGAAATTGATGCATGGACAATG | 2,167,083 | 84 |
| 5487. | GAATTAGTTGGGCAAGGAAGGATG[T,A]CTTGTACATAAATATTTCCAAGAAA | 2,167,238 | 84 |
| 5488. | CCCTGGTGGCTTCTTCCAATCCGT[G,A]CCCTATGCTTCCACCATGGCCACCC | 2,167,883 | 84 |
| 5489. | TCGTAAAGGTTTTCCTTTTTCCTT[A,G]CTGCCTTTACGAGTGGGACTATGAT | 2,168,301 | 84 |
| 5490. | TGTGTATAATTAGCTGAACATCAA[A,C]TACTAGTCAAAAAAAAAaaGCAGC | 2,168,393 | 84 |
| 5491. | AGTTCTTAGCCTTGTACATACTTA[T,C]TCACAACTTGTAACCAAAGACACCAA | 2,168,514 | 84 |
| 5492. | ATCAGGGCTTAGTCAAAAATTTTA[T,A]GTGGGATTTCTAAAGCCTAAAACTG | 2,168,835 | 84 |
| 5493. | AATTTCCTCCGGTTGTTAGTCACA[G,A]ATTGACAGATGCCTCATTTATTGCC | 2,169,188 | 84 |
| 5494. | ATCAACAGTTGAAAATTTTTCCGT[T,G]AATCTTCCCTTATTATGTATTTCTG | 2,169,393 | 84 |
| 5495. | CATGGAACGTGGTCAAACTAGCAT[G,A]CAGAACTTCGGACATTCTGGTGCTG | 2,170,204 | 84 |
| 5496. | ATGACATTAGTTAGGTTGTGGCTT[C,T]TCTTGCAAAACAGCAAACGTGACAT | 2,170,938 | 84 |
| 5497. | GCCCGAACCGTCTTTCTTTCAAAG[A,T]CTCCAATCCTCTCTCTCTCCTCTTC | 2,172,125 | 84 |
| 5498. | TCCCTCCCCTGACGACGTGTCCCT[A,G]TCAGGCGACGTGGTGCTCCACGGAG | 2,172,447 | 84 |
| 5499. | TTTTTTTTtGGTAGAAGTTTGGA[T,A]AACTTATTTAAAAGAAGAAAGTCAT | 2,172,797 | 84 |
| 5500. | GAAAAGATTAATTCTTTACTATAG[C,T]TGTCTTTAAGAAAACAGAAAACACA | 2,172,931 | 84 |
| 5501. | GTCCACCTAATAGTAATTTATTCT[A,T]CCATACATAATTAATCTAGTTCACC | 2,173,099 | 84 |
| 5502. | GAATTGATAAGTCCACCTAATAGT[A,T]CCATACATAATTAATCTAGTTCACC | 2,173,109 | 84 |
| 5503. | TAGATTCTCATCTAGAAAATGTTG[T,A]GCTTTATATCAACGTCATGAAATAT | 2,173,176 | 84 |
| 5504. | ACGTGCGCCTCATGGCTCTATCCA[A,T]GACTTTAATAGGAAAGAAGGCTCTG | 2,173,794 | 84 |
| 5505. | CTCCCACAAGTGCCCAAAAATGGA[C,G]TTATTGGTTGTTTTATTTGTTGGCA | 2,175,171 | 84 |
| 5506. | AGCTGAAGTCTTAGATTATTGCTC[T,C]GAGAGGTGTAGTGATGGAACCGAAA | 2,176,993 | 84 |
| 5507. | ATAGAAAGAGTTAAATGATAGGGA[C,T]ATATTGAAATATCAACAATGCTTTT | 2,177,070 | 84 |
| 5508. | CATATGTATAGAAAGAGTTAAATG[A,G]TAGGGACATATTGAAATATCAACAA | 2,177,077 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5509. | CTTCCTTGAAATTAGCTTTATTAT[G,A]ATGGTAACTAATATTTCTGAAATAT | 2,177,202 | 84 |
| 5510. | TCCTATGAACATGCCTATAACAAGG[A,C]TGCCATTTCTAAAAAGGGAAAAAGA | 2,177,356 | 84 |
| 5511. | ATCTTGAAATTATATGACATCGTT[C,T]TGGTGCTCCTATGAACATGCCTATA | 2,177,387 | 84 |
| 5512. | TCTCATAGACTATAAACCAGTGTA[A,G]GATTATATATGATAATCCGGGCCAA | 2,177,436 | 84 |
| 5513. | AACATTTTAGCATGCGGTCCATCA[A,G]CCATGATTTTTTtAATTTTtGATCT | 2,177,841 | 84 |
| 5514. | CAAAAATGAGTGAAATACATAGGA[A,G]TAGTATGGAGTATAATTCATAAAAA | 2,178,055 | 84 |
| 5515. | TTTGTGTTCCTTTGAGCCATCGTC[G,A]TGAGAAAATATTCACAGCAACGGTG | 2,178,148 | 84 |
| 5516. | GGCTGCCAAATGCTGGAAAGACTT[T,A]AAGACCCTTTTACATAAAAGTTTTA | 2,178,253 | 84 |
| 5517. | TTCATCTTTTTCACAAGAAAGATA[C,T]AGGTATGATTACAACCTTTATAAAT | 2,178,911 | 84 |
| 5518. | ATTAATGATATAACAAACTACTCA[T,G]GGATAATAATTCTCAAAAGAAAATA | 2,179,071 | 84 |
| 5519. | TATTAACTAGTATAAATAAATAAT[G,A]AAAAAATTAAAATTTTACGAGAGAT | 2,179,495 | 84 |
| 5520. | GATGATTTAAAAATAAGGTATATA[C,T]CACTTATTTATAATCGCAAGATCGC | 2,179,604 | 84 |
| 5521. | CATTAAAAATTATAGCAAGCATGC[T,A]TCTTGACGGTTACACACCTCTATCT | 2,180,510 | 84 |
| 5522. | TTCATGACAAGCCATTAAAAATTA[T,C]AGCAAGCATGCTTCTTGACGGTTAC | 2,180,522 | 84 |
| 5523. | CGATGTGATGACCATTTCTGATGG[G,A]CACTTGATGGGTCATTAACTTCAA | 2,180,588 | 84 |
| 5524. | AGAAATTCTTGGCAATCCTAAGTC[G,T]TTGAACAAGTAGTCACATTTGTTTT | 2,180,880 | 84 |
| 5525. | ATATCTTTGGCCAAATGGATAGGT[C,T]AGGCCATGAACTAAAATTAACAGGC | 2,181,006 | 84 |
| 5526. | AATTAGAGAGTCAGAATTAGAGAG[C,T]CGACTTTCTTTGAGAGGCAGTCCAA | 2,181,049 | 84 |
| 5527. | CATCCAATCAGAATTAGAGAGTCA[G,A]AATTAGAGAGCCGACTTTCTTTGAG | 2,182,060 | 84 |
| 5528. | TTTATAAGTGGCATCCAATCAGAA[T,A]TAGAGAGTCAGAATTAGAGAGCCGA | 2,182,071 | 84 |
| 5529. | TAGGAGTAATTTAAGAATTAATAA[A,G]AATTATTAATTCTTAGGATGATTTT | 2,182,251 | 84 |
| 5530. | CACTTGCACTCTCGCTCATTATTC[C,T]CACACTGTAGACTAAAAACTCGTCT | 2,182,370 | 84 |
| 5531. | CCACTTGCACTCTCGCTCATTATT[C,T]CCACACTGTAGACTAAAAACTCGTC | 2,182,371 | 84 |
| 5532. | TGATCGCTCATTTGATCACACTCA[G,A]TACCGATGTTCTCTAACAACCACTT | 2,182,415 | 84 |
| 5533. | AAACTACTCACACCACTACAGCAT[T,C]GAGACGATCATTGACGAGTGAGAAA | 2,182,474 | 84 |
| 5534. | CAAAAACTACTCACACCACTACA[G,A]CATTGAGACGATCATTGACGAGTGA | 2,182,478 | 84 |
| 5535. | TTGCTATGGCCACAAACTTAAGGA[C,T]CCAGCCTCTCAAATTTCATAGTACT | 2,182,696 | 84 |
| 5536. | ATTTAGTTTCTCTATCATGTGTCC[T,C]GATAGGATGGAGGTTATGAAAACTC | 2,182,834 | 84 |
| 5537. | TTGGATTGCAACATTTATAATTAG[A,G]TCCTCCTAGCTAACAATTAGCTGAT | 2,183,196 | 84 |
| 5538. | TTCAATCTCAATCCAATTCGAATC[G,A]AATTCGAGTCCAACCTGATCCAGAC | 2,183,375 | 84 |
| 5539. | GGTTTGGGTTCAATCTCAATCCAA[T,G]TCGAATCGAATTCGAGTCCAACCTG | 2,183,383 | 84 |
| 5540. | TCTCTAGGGTGATCGACCAGGAGG[A,G]GGTGGGCATGTGGATTAGGGTGGA | 2,183,791 | 84 |
| 5541. | TCTCCCTTTCTTTCTTTATTTTTC[T,C]CGCTGATCTCTCTCTTTCCTTCTCT | 2,183,836 | 84 |
| 5542. | AGGTACTAGCTCTCTTGTAGATCT[T,C]ACTCCTTCAAGTTTAGATCTAATCT | 2,183,982 | 84 |
| 5543. | AGGCTAAAGTAGATCAAAGCATCC[A,G]AGATCCCCGAGGTACTAGCTCTCTT | 2,184,016 | 84 |
| 5544. | GAAAAATAAAATGAAAGTATGCAT[A,C]TAATTTTAAAATAAAATAATCAAAA | 2,184,188 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5545. | CATATGAACCCGTGACTCTGATAC[T,C]ACTATTGAATTTTGAGGTGTCATGC | 2,184,352 | 84 |
| 5546. | TTATGCCAAGACAATCTTATAGCA[T,C]ATCGATATCGAACTAATTAACATAT | 2,184,589 | 84 |
| 5547. | AAATATATCATAAATCTCATACAT[A,G]ATTGTAGATTAAATCTAAAATCGTT | 2,184,682 | 84 |
| 5548. | TCGACTTGATTAACTACAACTATT[A,G]TTTTAATCCTGAGAACTCTTGATCT | 2,184,955 | 84 |
| 5549. | TTAACATATAGATATCAATCGACT[T,C]GATTAACTACAACTATTATTTTAAT | 2,184,973 | 84 |
| 5550. | TTTGGGTCAATCGAGTTAACATAT[A,G]GATATCAATCGACTTGATTAACTAC | 2,184,988 | 84 |
| 5551. | CTTACAATATTTAGTGCCTCTAGC[A,G]TCTTAAATTAAATATTCATCACCAC | 2,185,133 | 84 |
| 5552. | TAATAAAATAATATTAATGATTAC[T,G]TACAATATTTAGTGCCTCTAGGATC | 2,185,156 | 84 |
| 5553. | AAATAGACTAGATAGCATTAAATT[T,C]TTAATAAAATAATATTAATGATTAC | 2,185,182 | 84 |
| 5554. | ACTCTCGATTACCTGTAAAATAGA[C,T]TAGATAGCATTAAATTTTTAATAAA | 2,185,199 | 84 |
| 5555. | TTCACACTGAAATAAGAGCTGATT[A,G]CTTGGTTCACTCAAATCTGAACCAA | 2,185,280 | 84 |
| 5556. | CTTGCTGCGCCCGATGGTGGATGT[G,A]TCTCCTTGAATCCTTCATTTTTCTC | 2,185,801 | 84 |
| 5557. | AACCAAGTTGATCTTCTTGCTGCG[C,T]CCGATGGTGGATGTGTCTCCTTGAA | 2,185,816 | 84 |
| 5558. | CTTTTCATTAATCTTATAAAGAAG[C,T]ATACATAAAAAAAAAAAaTTACGAT | 2,185,878 | 84 |
| 5559. | AATAGTAAATTATTCTAATCTATA[A,G]AAAGTAGTAAATTGCTAGGTTATAG | 2,186,320 | 84 |
| 5560. | ATCTATTTATGAAGTAGAAAATCT[C,T]TAATTATATAAAAATAGTAAATTAT | 2,186,357 | 84 |
| 5561. | ACAGTTAAGAATAAAAGGTAACTA[T,C]GTAATCCAAATAAAAGGCTAAGAAT | 2,186,410 | 84 |
| 5562. | TAACTACTTAACTATGCAAATAAG[G,A]TAATCTCACAGTTAAGAATAAAAGG | 2,186,442 | 84 |
| 5563. | ATAGTAAATCACTAAGAATAATAG[G,A]CAATAATAAATAAGATAACTACTTA | 2,186,482 | 84 |
| 5564. | TTTTAGGATAATAAATTATTCTAA[G,A]CTATAGAAAATAGTAAATCACTAAG | 2,186,516 | 84 |
| 5565. | AAGATCAAGTGATTCTAACTAAAT[A,G]AAAAGTAAATCATACTAAGATTAAA | 2,186,610 | 84 |
| 5566. | ATTAGATATTAGAAGATCAAGTGA[T,A]TCTAACTAAATAAAAAGTAAATCAT | 2,186,622 | 84 |
| 5567. | TTAAGYAGATTTTAAAATTTAATT[G,A]ATTTATTTATATTAGTCAAGTGTTA | 2,186,751 | 84 |
| 5568. | TCTGAAGATTTATATCATCATTCTTG[G,A]TCTCTTCAGGCTCTCCAGGTATGTACA | 2,194,296 | 84 |
| 5569. | TGGCCCTTTTGCCATATCCCACAA[T,A]ACATAGCTTGGTCATTTTTTCTTAA | 2,194,932 | 84 |
| 5570. | TTTTCTTTGAGATAACTCAAAAAA[G,A]TTTTACTAAAATATTCTCCTCTTCA | 2,195,199 | 84 |
| 5571. | AGAAGGAGTCCATTATAAGACTAT[A,G]TCATTTTCTTTGAGATAACTCAAAA | 2,195,227 | 84 |
| 5572. | AGAATCTTATTTAGTAAATAAATC[A,G]TGGTTAGTAGAGCATAACCCTAAG | 2,195,373 | 84 |
| 5573. | GTAGAAATAGATTTAGAGAGAATC[T,C]TATTTAGTAAATAAATCATGGTTAG | 2,195,391 | 84 |
| 5574. | TATCTCATATGATATAGTAGAAAT[A,G]GATTTAGAGAGAATCTTATTTAGTA | 2,195,407 | 84 |
| 5575. | TAGCCTCTAACTTGTCAGCCATTT[G,A]TCTTTTCACATAGGCTGGACATCTC | 2,195,486 | 84 |
| 5576. | TGGACCTAGCCTCTAACTTGTCAG[C,T]CATTTGTCTTTTCACATAGGCTGGA | 2,195,492 | 84 |
| 5577. | AGCAAAAGTAGTATCATATTGATT[C,T]TTTAGGATACCTTATGAAGCAAGCT | 2,195,546 | 84 |
| 5578. | CGTGTCTGACTCACAATTACATTAT[G,A]ATCGTCTGAAAAGCAAAAGTAGTAT | 2,195,582 | 84 |
| 5579. | ATTTTTCTAGAAACATAGCGTGTC[G,A]ACTCACAATTACATTATGATCGTCT | 2,195,600 | 84 |
| 5580. | TAAATTATTTTTCTAGAAACATAG[C,T]GTGTCGACTCACAATTACATTATGA | 2,195,600 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5581. | TAGATCCTCTGTAAGCATACCTAA[G,A]TACCTTTCAAGAGGACAGGAGATCC | 2,195,779 | 84 |
| 5582. | ATGATCCTTATCTCCTACGAAGAA[T,C]ATTTCTTCTAGATCCTCTGTAAGCA | 2,195,812 | 84 |
| 5583. | TCTTTTCTTGTAGTGTCTCCATGA[T,C]CCTTATCTCCTACGAAGAATATTTC | 2,195,832 | 84 |
| 5584. | TTATGATGAAAAATAATTTTTATC[G,A]TAAATAATTTATTATTAGCAATAAA | 2,195,958 | 84 |
| 5585. | ATTAACTTTTCATCATAAATACTT[T,C]TATTATTTATGATGAAACTATTTTC | 2,196,129 | 84 |
| 5586. | TATGTCAAAAATTTAATTATTATC[A,G]TCAATACTCATTATTTATGATGTAA | 2,196,571 | 84 |
| 5587. | ATTTATGTCAAAAATTTAATTATT[A,G]TCATCAATACTCATTATTTATGATG | 2,196,574 | 84 |
| 5588. | TCATCGCTAATACTCCATTATTTA[C,T]GACGTAATATTTTTATCACAAATAA | 2,197,001 | 84 |
| 5589. | CAATGAAAATTGATGTTTCATCGC[T,C]AATACTCCATTATTTACGACGTAAT | 2,197,018 | 84 |
| 5590. | ATTGACAATGAAAATTGATGTTTC[A,G]TCGCTAATACTCCATTATTTACGAC | 2,197,023 | 84 |
| 5591. | TATGCACATATTATTTTTAAAAA[T,C]TATCTAATATTTATTTTTATAAATA | 2,197,219 | 84 |
| 5592. | TTGTCTAGGATTGATTTTTGATTT[T,C]CATAATATTTTGGATCCAACCATTC | 2,197,390 | 84 |
| 5593. | GGCCTATTTTACTATTGTCTAGGA[T,C]TGATTTTTGATTTTCATAATATTTT | 2,197,404 | 84 |
| 5594. | GACAAGGAACCAGATCATCAGTTT[C,G]GGATTTTTTAAATTAAAATTTTGAT | 2,197,651 | 84 |
| 5595. | ATGTAAGTATTTTCTAGGCTTCG[A,G]AACCATGAATTAGACAAGGAACCAG | 2,197,688 | 84 |
| 5596. | CTTGCTGTTCAAGAATGTCGGCAA[C,T]AGAAGGTAATTCTTAGACGTTGTTG | 2,197,870 | 84 |
| 5597. | AAGATGGAGATGGATAGAATAAAG[C,T]AATTATAAATATAAAACTCTTTTTC | 2,197,931 | 84 |
| 5598. | TACGAAGATATTTAAAAGTTTCAA[A,G]AAATAATATTAAAGCATACAGCTTG | 2,198,007 | 84 |
| 5599. | GATACGAAGATATTTAAAAGTTTC[A,G]AAAAATAATATTAAAGCATACAGCT | 2,198,009 | 84 |
| 5600. | TTACCTTATCAGCGGACGCGACTG[C,T]GATGGCGACGGTGATCGAGGATGGC | 2,198,575 | 84 |
| 5601. | TCGGTTCACGATTTTAGTATGAAG[C,T]AATTTTATCAAAAATTTTAACTTGA | 2,202,190 | 84 |
| 5602. | CTTTATAAAATAATATACAGTCAT[T,C]TTTGCAGGCATGTATAAGAATATAG | 2,202,359 | 84 |
| 5603. | TTATCAAATTTCGGACATTCAGTT[G,A]CTTATTCATTATCTTTATAAAATAA | 2,202,396 | 84 |
| 5604. | TAATGTCATCTCATTTTTTCAGCT[A,G]TCTTTATGGACATATATAACCTTTG | 2,202,528 | 84 |
| 5605. | GATGGCTAAGTATATTCTCCTCAG[G,A]AAGTCACTACTCATAATGTCATCTC | 2,202,566 | 84 |
| 5606. | TCTTTCCATACTAAAGAGTCGACC[A,G]GATGGCTAAGTATATTCTCCTCAGG | 2,202,591 | 84 |
| 5607. | GACCAAGTCGAGATATTGTGGGAT[C,T]ACTCGCAAAGTATGAATGCTTTGCA | 2,202,647 | 84 |
| 5608. | AGGTGACACATTATATACAACTAG[T,C]ATCACAGGCCACATATTATAAAAGG | 2,202,736 | 84 |
| 5609. | TTCATTACCTGGTGCTTTCGGATC[C,T]GGAATCAACTGTGACATAAAAATAA | 2,202,808 | 84 |
| 5610. | TATACATCAATTTCATTACCTGGT[G,A]CTTTCGGATCCGGAATCAACTGTGA | 2,202,819 | 84 |
| 5611. | TATATACATCAATTTCATTACCTG[G,A]TGCTTTCGGATCCGGAATCAACTGT | 2,202,821 | 84 |
| 5612. | GTTGTATATATACATCAATTTCAT[T,A]ACCTGGTGCTTTCGGATCCGGAATC | 2,202,827 | 84 |
| 5613. | GACCTATGAAATATATTTTCTGTC[T,C]GTGCTTTAAATATAAAGAGGATGCA | 2,203,058 | 84 |
| 5614. | TCCTTAGGTGGCGAACATCGGTCG[G,A]ACTTACCATCAAAATATTGGTTATA | 2,203,149 | 84 |
| 5615. | ATTAGACATTTTCAATGACTTCAA[A,G]TTGTTCTAAAATTTTTGCTCCATTT | 2,203,202 | 84 |
| 5616. | TTTGTCCAATTCAGCTCAGCTTCA[G,A]TATGCTTCCACTTGCGAGTACCCGA | 2,203,263 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5617. | TAGTTCGAAAAAGATGCTTCACTT[T,C]GTCCAATTCAGCTCAGCTTCAGTAT | 2,203,285 | 84 |
| 5618. | ACCGATGATATTATCATAAATATT[T,C]TTTTCAATGTGTATTACATCGAGAT | 2,203,366 | 84 |
| 5619. | TTTTTCTAGATGTTCAATACAGTA[C,T]CGATGATATTATCATAAATATTTTT | 2,203,389 | 84 |
| 5620. | GCAACTTCGATCGGATTCTCATTT[C,T]CTGCAAATCAAGATGAGCTTTTGTA | 2,203,450 | 84 |
| 5621. | GATTTTAAACCATCCACAGAAATT[T,C]TTCTTTTCCTCACCAAACAGTGAAT | 2,203,546 | 84 |
| 5622. | TAATTTTTGACAACACAGTTCTCG[G,A]AAGAACACTCCCAGCTCAATCAATG | 2,203,753 | 84 |
| 5623. | TTCTAACTTACAAAGAATGAGTAC[G,A]ATATCCTTCTCTAATTTTTCAAGTA | 2,203,813 | 84 |
| 5624. | ATCCAACGATAATGTACCGGTCCG[A,G]CCAAAAGTGCTTTCTTTGGAAGATA | 2,203,912 | 84 |
| 5625. | GGATACATCCAACGATAATGTACC[G,A]GTCCGACCAAAAGTGCTTTCTTTGG | 2,203,918 | 84 |
| 5626. | GGCACGGTCTGTCTCGTCCGATTC[T,A]CCGTATTTTTGGCACATCTCTCTG | 2,206,064 | 84 |
| 5627. | AAAaTTAAAAATTACCTACCATGT[A,G]CTCCATGTGACGAGCGAACGATCTC | 2,206,129 | 84 |
| 5628. | CAATTTGAGAATTAATTAAAAAAa[T,A]TTTAAATAACTAAAAATTATATGCT | 2,206,184 | 84 |
| 5629. | CATCTGGATCTGAAGCTGCTGATA[T,C]TTATCGACGCGTGCAGCCAACTCCT | 2,206,399 | 84 |
| 5630. | CATCTGGATCTGAAGCTGCTGATA[T,C]TTATCGACGCGTGCAGCCAACTCCT | 2,206,677 | 84 |
| 5631. | CTATCCACTCTATCATCTGGATCT[G,A]AAGCTGCTGATATTTATCGACGCGT | 2,206,690 | 84 |
| 5632. | GACATCTAGAGAACGAGCTGGAGA[C,T]GGAGAGCACTTGACGGAGCTCGAAC | 2,206,785 | 84 |
| 5633. | ATATTAAATTAAAATTATAAAAAa[T,A]TTAAAaTAAAAAaTATATCAATAAG | 2,206,847 | 84 |
| 5634. | TATATATTTATTAAAAAATTAAAT[C,T]ATGTTAGTAAAATATATTTGACGAT | 2,207,064 | 84 |
| 5635. | TAGCGATGAAAATATTTTCATCGC[C,T]ATTAATTCTAAAGTTTTAGCGACTA | 2,207,304 | 84 |
| 5636. | ATATTTATGATGAATTATACCATC[A,G]CTAATAAATAAAAAaTTAATAGCGA | 2,207,348 | 84 |
| 5637. | CATAATTTTCGTCACTAATATTTC[G,A]TCACCAATAATCGCATCGTTGATAA | 2,207,493 | 84 |
| 5638. | TACAACAAAATAGGTTATTAGCGA[T,C]GAAAAATTTTCATCGCTAATAATCG | 2,207,570 | 84 |
| 5639. | TTCACCTCGAGCCTAGCTTTATAG[G,A]TCTCTACTTTACCATCTATACCTAT | 2,207,791 | 84 |
| 5640. | GATCTCCATCACTAGATGTGAAAT[T,C]CTTAGGCTATTCCATATAGAAATCT | 2,208,000 | 84 |
| 5641. | CTATATATAAATCTTTACAGCTTG[C,T]AGACTTTATGATCTCCATCACTAGA | 2,208,034 | 84 |
| 5642. | GAAGCTTGTTTTAATCTATATATA[A,G]ATCTTTACAGCTTGCAGACTTTATG | 2,208,049 | 84 |
| 5643. | TCGTTGAAATGAATATTCTAACTT[T,C]GAGAAGCTTGTTTTAATCTATATAT | 2,208,076 | 84 |
| 5644. | TGTCATCCACGTACAGTACGAAGA[A,C]TGTGACAGCACTCCCACTGATCTTC | 2,208,180 | 84 |
| 5645. | AAAAATGTAATTCCCAATAAGGAG[G,A]ATGTCATCCACGTACAGTACGAAGA | 2,208,206 | 84 |
| 5646. | CAATCATCTTTTGATCAAAAATGT[A,C]ATTCCCAATAAGGAGGATGTCATCC | 2,208,222 | 84 |
| 5647. | ACTTCCCCTATGTACATTTTCTAT[G,A]AAAAACCAAGCATCCTTTTGGATCT | 2,208,341 | 84 |
| 5648. | ATCCAGTACTCTTCGTCCAGATTC[G,A]ACTAATAACTGCTCATGACACTCAC | 2,208,581 | 84 |
| 5649. | CACAGCTATCCAGTACTCTTCGTC[C,T]AGATTCGACTAATAACTGCTCATGA | 2,208,588 | 84 |
| 5650. | CTGAATTAATATATCCTTCGAACC[A,G]CAGCTCTGATCCTCCGTCAAAGATT | 2,208,683 | 84 |
| 5651. | CACCATTGCATACAAACACACAAT[T,C]TGATATAGATCTTCTATCATCAAAA | 2,208,746 | 84 |
| 5652. | TTGGAACTCTTCCACCTGGTAGCT[T,C]CACCATTGCATACAAACACACAATT | 2,208,771 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5653. | TATCATTACACTAAGTTCTGCGAT[G,A]AATTTTTTATACCAGAAAGCTTCCT | 2,208,883 | 84 |
| 5654. | TAAAGTAATGGCATCCAATATCAT[T,G]ACACTAAGTTCTGCGATGAATTTTT | 2,208,901 | 84 |
| 5655. | AGTGCTATGGTGTCATTGTTGTCG[T,C]AGTATAAAGTAATGGCATCCAATAT | 2,208,930 | 84 |
| 5656. | TAGACTCTTTAGTGAGTGCTATGG[T,C]GTCATTGTTGTCGTAGTATAAAGTA | 2,208,944 | 84 |
| 5657. | TTTGTATATGACTCCATAGGTTCT[A,G]TTCTGTCTGGTAGTGAGATATTGTC | 2,216,699 | 84 |
| 5658. | GATGCTGAATCGACGAAGAAGGTA[G,A]TGTGGGAGAAGTTTCTGTCATGACT | 2,216,699 | 84 |
| 5659. | CTTGGATTCATAAATTCAATTTCT[T,G]TCATCATTGTACATCAGGTTTCTGA | 2,216,699 | 84 |
| 5660. | AGTTGAGGAAGCCTTGGGTAACGT[G,A]CTTCATCTCTGCTTGAGCCACTTGT | 2,216,699 | 84 |
| 5661. | TGGGTAACGTGCTTCATCTCTGCT[T,C]GAGCCACTTGTATAAAAATCATATA | 2,216,699 | 84 |
| 5662. | ATATGATTGTTACAGTGTCAGGCT[T,G]GCCAGCCCTGGCTTTGGATTGGGCC | 2,216,699 | 84 |
| 5663. | TTGGAACTCTTCCACCTGGTAGCT[T,C]CACCATTGCATACAAACACACAATT | 2,216,699 | 84 |
| 5664. | CACCATTGCATACAAACACACAAT[T,C]TGATATAGATCTTCTATCATCAAAA | 2,216,699 | 84 |
| 5665. | CACAGCTATCCAGTACTCTTCGTC[C,T]AGATTCGACTAATAACTGCTCATGA | 2,216,699 | 84 |
| 5666. | ATCCAGTACTCTTCGTCCAGATTC[G,A]ACTAATAACTGCTCATGACACTCAC | 2,216,699 | 84 |
| 5667. | ACTTCCCCTATGTACATTTTCTAT[G,A]AAAAACCAAGCATCCTTTTGGATCT | 2,216,699 | 84 |
| 5668. | CAATCATCTTTTGATCAAAAATGT[A,C]ATTCCCAATAAGGAGGATGTCATCC | 2,216,699 | 84 |
| 5669. | AAAAATGTAATTCCCAATAAGGAG[G,A]ATGTCATCCACGTACAGTACGAAGA | 2,216,699 | 84 |
| 5670. | TGTCATCCACGTACAGTACGAAGA[A,C]TGTGACAGCACTCCCACTGATCTTC | 2,216,699 | 84 |
| 5671. | ATCATTTTGTCTGCAATATGTTTG[A,G]CAGAAGAACAAATCATTTGCAGGCC | 2,216,699 | 84 |
| 5672. | AAGGCGCAAATGCGAGAGTAATTA[G,T]AATCTACTGGGGCTATTTATATATA | 2,216,699 | 84 |
| 5673. | GAGGTACAGAGCCACCATTTGTTC[C,T]GGAAGCTCTCTACCATTGCAGTGCA | 2,216,699 | 84 |
| 5674. | TTCCGCCTTCGCCACATTCGAATT[C,T]CATCGCAAATTCGCCTCCAAGTCCA | 2,216,699 | 84 |
| 5675. | AGGTCCTCCTAGCTAACAATTAGC[T,C]GATCCAATGCTTGTAACTTTTACAA | 2,216,818 | 84 |
| 5676. | ATTGAATTGCAACATTTGCAATTA[G,C]GTCCTCCTAGCTAACAATTAGCTGA | 2,216,841 | 84 |
| 5677. | AGAACTTGGTTTTCTAATTTGATC[T,C]CATCAAATTGAATTGCAACATTTGC | 2,216,872 | 84 |
| 5678. | AGGTCAAGCCCAAACTAATTAGGC[T,C]TGATTTAATTAATTAGAACTTGGTT | 2,216,911 | 84 |
| 5679. | GGCCGACTAGATGGAGGTGGGGTG[C,T]GTGGATTAGGGTGGAAGCGACGAGA | 2,217,436 | 84 |
| 5680. | TAGAAGAAGACTCGCGGATCAACA[A,G]GGCTGAAGTAGATCGAAGTGTCCGA | 2,217,570 | 84 |
| 5681. | CCGACCTCTACACGTATCCACACA[A,G]GGCTGAAGTAGATCGAAGTGTCCGA | 2,217,693 | 84 |
| 5682. | AGGTTCCGTTGAAACCGCACATAC[A,G]TCCGACCTCTACACGTATCCACACA | 2,217,719 | 84 |
| 5683. | AGTTCATATGATGAAAAACAAGAT[G,A]AAAACATGCATCTGATTTCAAAATA | 2,217,853 | 84 |
| 5684. | CTAGTTCATATGATGAAAAACAAG[A,G]TGAAAACATGCATCTGATTTCAAAA | 2,217,855 | 84 |
| 5685. | GAGTGAGACTTCCGCCAAATGAGA[T,A]AAATTTGCTTTTCCATATTATAAGT | 2,218,048 | 84 |
| 5686. | ATCCAATTTCTTGATGACCCAGGA[C,G]GAAAATTTATATAGGGACATGAAGC | 2,218,131 | 84 |
| 5687. | CGCCAAAATGAAACATTTAAGCCA[C,T]TACCAACCGTATATTTAGTTTTGTT | 2,218,487 | 84 |
| 5688. | TTTTACCACGGCAACTATTGAATA[T,G]ATTTGGAAAAGAATTTTCAGTGGG | 2,218,558 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5689. | TGAAGACTTGGGTCTCCATGATTT[C,T]AGTATTTGTGCTTAACATCCTTTGG | 2,218,558 | 84 |
| 5690. | GAAGACTTGGGTCTCCATGATTTC[C,G]GTATTTGTGCTTAACATCCTTTGGA | 2,218,558 | 84 |
| 5691. | ATCTGAGAATGGAGAGAAGACC[C,A]GCTTTTTCGTGCTGCACTAATGGAG | 2,218,674 | 84 |
| 5692. | ACATCTGAGAGAATGGAGAGAAGA[C,T]CCGCTTTTTCGTGCTGCACTAATGG | 2,218,676 | 84 |
| 5693. | CCAATCTTTATTAATAAAGAGCTA[C,T]ACAAGAGTAGGATACAGATAAGCTT | 2,219,472 | 84 |
| 5694. | AGTTAGGCTTGATCAGAAGAACAC[G,A]AGATAGGTGAAGGGGAAGAAAAATT | 2,219,726 | 84 |
| 5695. | ACAATACTGATTCCTGGAGATACT[C,T]ATAGTTAGGCTTGATCAGAAGAACA | 2,219,753 | 84 |
| 5696. | CTACAAAAATACTAACACAACTAC[A,C]AATGCAAAGACAACCTTCTTCCTTG | 2,219,870 | 84 |
| 5697. | ACAATACTGATTCCTGGAGATACT[C,T]ATAGTTAGGCTTGATCAGAAGAACA | 2,219,870 | 84 |
| 5698. | AGTTAGGCTTGATCAGAAGAACAC[G,A]AGATAGGTGAAGGGGAAGAAAAATT | 2,219,870 | 84 |
| 5699. | TAGGAAGAAAACTACAAAAATACT[A,T]ACACAACTACAAATGCAAAGACAAC | 2,219,881 | 84 |
| 5700. | GCTGGCAATGTGCACAGGCTACAC[A,T]ACACAACTACAAATGCAAAGACAAC | 2,20,085 | 84 |
| 5701. | ATTCCTCAATGCTGGCAATGTGCA[C,T]AGGCTACACAATTCTGTCAGGTTGG | 2,220,095 | 84 |
| 5702. | TTGTTAGTTGGCTCTCAAGCTGCT[G,A]CTATTCCATTGCCTTCAACTTTGCA | 2,220,200 | 84 |
| 5703. | CTTATTCAGTTGTATTAAATACAA[T,C]TTATTCATGCTGTATAATTTAACTT | 2,220,200 | 84 |
| 5704. | TAGGAAGAAAACTACAAAAATACT[A,T]ACACAACTACAAATGCAAAGACAAC | 2,220,200 | 84 |
| 5705. | GATTCGAGTGGTGCGACGCCAGAG[A,C]TCTTGGGTTGCCATCTCAGGTCTTG | 2,223,894 | 84 |
| 5706. | AGAATGTAAGATAACAGTTCACAG[C,A]AAGATTTACCGCAAAATCATCTAAT | 2,224,178 | 84 |
| 5707. | TTGTCAGATACATAGAGAAGTTCA[G,A]AACAACTAAAAACTAATTGTACAAT | 2,224,681 | 84 |
| 5708. | AGAAAGGGAAAAGTTATCTGGATT[G,A]AGTAGATATACATTTTGAACTTTGA | 2,226,007 | 84 |
| 5709. | CACTTGAATCTAGGAGGGAGATCA[G,T]TTTATTATTGGATTACTTCTTCCCC | 2,226,133 | 84 |
| 5710. | CCTCTGATATGTTTCAAAGCCAAC[G,A]AAACCCTTTACATGTTACCACACTT | 2,226,573 | 84 |
| 5711. | AAAAAAATCTTAAATTGAATCAAT[C,A]GAAAAGCATAGTTTTACCATAGCCG | 2,226,706 | 84 |
| 5712. | AAGAAATAATAGTAAGCAAATGAA[A,G]GTTATCAATTGCTGGATTAATTTTC | 2,226,893 | 84 |
| 5713. | ATTTTAGACAGGAACTGGTACAAT[G,T]CTAAAGTTACAATTCTAAGTTTCAC | 2,226,893 | 84 |
| 5714. | CACTTGAATCTAGGAGGGAGATCA[G,T]TTTATTATTGGATTACTTCTTCCCC | 2,226,893 | 84 |
| 5715. | AGAATGTAAGATAACAGTTCACAG[A,C]AAGATTTACCGCAAAATCATCTAAT | 2,226,893 | 84 |
| 5716. | CAAATTTCATATCCTTTTTCTCTA[A,T]GAGGTCCATTTTATGCCATGGTTGT | 2,226,893 | 84 |
| 5717. | GCTTGCTCGGACACACTTTAATTC[C,G]CAAATATTACTCATGTTGTtTTTTT | 2,227,219 | 84 |
| 5718. | AATATTAGGGGTTAGTTCTATCAA[T,C]CCTTATTCGTTGAGCCTTCCCATTA | 2,227,326 | 84 |
| 5719. | TTTAAAACCTTGGTCCTAAATATT[A,C]GGGGTTAGTTCTATCAATCCTTATT | 2,227,344 | 84 |
| 5720. | GAAACTCAAAAACTTGAAGATAAC[T,A]ATTAAAACCGTTGAAACGGCTGAAA | 2,227,431 | 84 |
| 5721. | TTATTTTGTAAATTTATCGGCTG[T,G]TTTCCCGAAACTCAAAAACTTGAAG | 2,227,462 | 84 |
| 5722. | TTTATTTTTCTCTTATTTTGTAAA[T,A]ATTAAAACCGTTGAAACGGCTGAAA | 2,227,474 | 84 |
| 5723. | GCATCAAAAGAATCTCACAAAAAC[C,T]GTGGATTCCTGTCCTCTTTAGTCCT | 2,227,553 | 84 |
| 5724. | CTATGAAGAGACTGTAAAGAAGTA[T,C]GCCAAGCTATGAAACATATACTTGC | 2,227,777 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5725. | ATCCTTCAACCACAGGGAGAAAAG[C,T]ACTTCTGTCAACATCTAGGGTTACT | 2,227,865 | 84 |
| 5726. | GCATCAAAAGAATCTCACAAAAAC[C,T]GTGGATTCCTGTCCTCTTTAGTCCT | 2,227,865 | 84 |
| 5727. | GAAACTCAAAAACTTGAAGATAAC[T,A]ATTAAAACCGTTGAAACGGCTGAAA | 2,228,720 | 84 |
| 5728. | TCTCCACTAAATTTTTCACCTCAT[C,T]ACAAAGCTGTTATGAAGTTGGCCTT | 2,229,240 | 84 |
| 5729. | TCTTCTCGATTCCTTCGTAACATT[T,A]GTTGTTGACATAGAAGATGGTGCTA | 2,229,248 | 84 |
| 5730. | TAACATTATCTTCTCGATTCCTTC[G,A]TAACATTTGTTGTTGACATAGAAGA | 2,229,319 | 84 |
| 5731. | CACCTTACCAATTAAAATCCTCAA[C,T]CTCCATTAAAACCCTCTCCACCAAC | 2,230,789 | 84 |
| 5732. | ACCCAACAACCATGCACAACATAC[C,A]ATCATTATGTGTTTGTTCTACAAAA | 2,230,822 | 84 |
| 5733. | TACCCGGTCTTCCCTTTTACCAAC[G,A]CAACCCAAACCCAACAACCATGCAC | 2,230,969 | 84 |
| 5734. | AATCCATCATTCAAACTAAAACAA[T,C]GCACCCAGGTTGCTCGGAAATTATA | 2,230,973 | 84 |
| 5735. | TGCGAATCCATCATTCAAACTAAA[A,C]CAATGCACCCAGGTTGCTCGGAAAT | 2,231,217 | 84 |
| 5736. | GCCAGCATGAAGTAGGAAAACAAA[T,C]CTAGCCATGTCTTGGAAGAAAATTC | 2,231,248 | 84 |
| 5737. | AAGACAAATAGGTCGGCCAGAAAC[C,A]ACTTTAGCCAGCATGAAGTAGGAAA | 2,231,261 | 84 |
| 5738. | ATAGGAAGGAACCAAGACAAATAG[G,A]TCGGCCAGAAACCACTTTAGCCAGC | 2,231,574 | 84 |
| 5739. | AAGGAaAAAAAAAaTAGTCCTCCT[T,G]GTCTTACCTTTCTCTGATTCAAAAG | 2,231,574 | 84 |
| 5740. | AAGACAAATAGGTCGGCCAGAAAC[C,A]ACTTTAGCCAGCATGAAGTAGGAAA | 2,231,574 | 84 |
| 5741. | TGCGAATCCATCATTCAAACTAAA[A,C]CAATGCACCCAGGTTGCTCGGAAAT | 2,231,574 | 84 |
| 5742. | AATCCATCATTCAAACTAAAACAA[T,C]GCACCCAGGTTGCTCGGAAATTATA | 2,231,574 | 84 |
| 5743. | ACCCAACAACCATGCACAACATAC[C,A]ATCATTATGTGTTTGTTCTACAAAA | 2,231,574 | 84 |
| 5744. | TGATCTTTGTCTGTTATTTTGATG[G,A]CAATGCATTTGTTTTGTGGTCTGTT | 2,231,574 | 84 |
| 5745. | CACCTTACCAATTAAAATCCTCAA[C,T]CTCCATTAAAACCCTCTCCACCAAC | 2,231,574 | 84 |
| 5746. | TCACCAAAACATGCTGCCAGGTAC[A,G]ATTCTTCTGGATAATCCGTCCTCTC | 2,232,075 | 84 |
| 5747. | TTCGTGTACGAGCTCGTCTCGCCA[A,G]AAAAGGTTACGGGAAGGCTCAAGGT | 2,232,124 | 84 |
| 5748. | TGCTATCGGTTTCGTGTACGAGCT[C,T]GTCTCGCCAAAAAAGGTTACGGGAA | 2,232,134 | 84 |
| 5749. | GAACATCATCTCCGTCTCCAGCGA[C,T]GATGACAGCGTCCATCGACCGAACT | 2,232,189 | 84 |
| 5750. | CTAGAAGAGAAGAGGTAGCTGGGG[G,A]CTAGCTCTGCTTTGAAGCCCAAACC | 2,232,322 | 84 |
| 5751. | CAGCAACCATGTGGGCATGCGTTA[G,A]CTGGCTTTTTTAATGGTTTAGGTAG | 2,232,417 | 84 |
| 5752. | GGTCAGCCAGTGGACTTCACACCA[G,A]CAACCATGTGGGCATGCGTTAGCTG | 2,232,439 | 84 |
| 5753. | AAGGTGGCCTTCCCACCCCCACCA[C,T]ATACCATTATTCCATTCAACTCTCC | 2,232,638 | 84 |
| 5754. | GCTTTATTGGGGACCGGATGAAGT[C,T]ATACCATTATTCCATTCAACTCTCC | 2,232,968 | 84 |
| 5755. | GAAGATCTTCTCATCTTAAGGCCA[T,A]TGCTTCAGGTGCATACCAAATCTTA | 2,232,968 | 84 |
| 5756. | GGTCAGCCAGTGGACTTCACACCA[G,A]CAACCATGTGGGCATGCGTTAGCTG | 2,232,968 | 84 |
| 5757. | CAGCAACCATGTGGGCATGCGTTA[G,A]CTGGCTTTTTTAATGGTTTAGGTAG | 2,232,968 | 84 |
| 5758. | CTAGAAGAGAAGAGGTAGCTGGGG[G,A]CTAGCTCTGCTTTGAAGCCCAAACC | 2,232,968 | 84 |
| 5759. | TCACCAAAACATGCTGCCAGGTAC[A,G]ATTCTTCTGGATAATCCGTCCTCTC | 2,232,968 | 84 |
| 5760. | TAGCACCCCAAGCTTGAAGCAAAT[T,C]GCTGTCTAGACTGCAGAGAAGAACA | 2,241,530 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5761. | GTAGAAGCATAATTTGTTTGTGGC[T,C]GACCAAGCCTCAAAAGGAGTAATAG | 2,241,530 | 84 |
| 5762. | CAGGCTCTTTTTTCTCTCATTTCT[A,T]TGTTCTTCCCTAGACTTTCTGAAAG | 2,241,530 | 84 |
| 5763. | GGTTAATCCTCAGGTTATTTTTAG[A,T]ATTAAACCAGAAATTCTTCCATGCA | 2,241,530 | 84 |
| 5764. | ATGCAATTTGTGATCTATATATGC[G,A]TATAAAGTAGCATCAGTGGTAGTGT | 2,241,530 | 84 |
| 5765. | CTACTACTTTGTACCTTAATCGCC[G,A]TGCTCCTAAACTATAAACAAGAACA | 2,242,318 | 84 |
| 5766. | TACCTCCATATAAGTACCCAAAAT[C,T]TTTTCAACAAATCATCCATGATAAA | 2,242,489 | 84 |
| 5767. | CAGTTGAAAGGTATTATTTGAGTT[T,C]CTTACCTCCATATAAGTACCCAAAA | 2,242,516 | 84 |
| 5768. | TTTTCGTGTTTAAAATTTCAAATT[T,C]ATATAGATCCATTCATAAATATTAT | 2,242,655 | 84 |
| 5769. | CAATCCTAAATTTTTTAAGTAAAT[A,C]ACTAATATGAGATAAAATACATGCT | 2,242,723 | 84 |
| 5770. | ATTTGAATACCACGTTCAAAAAAA[C,T]TAATCAGAAGATATTATTCAGATTT | 2,242,788 | 84 |
| 5771. | ATTAAAAAAAaTCATCAAAAAAAa[C,T]CTTTGTGGGTATCTATAGTCCAAA | 2,242,869 | 84 |
| 5772. | TAGTTGATTTGAATAAATTTGGAT[C,T]CTTAGCTTGATGTGAACGTCAGGAC | 2,243,768 | 84 |
| 5773. | TTTGTCATGGAATTTATGATACTT[T,A]TAGTTGATTTGAATAAATTTGGATC | 2,243,793 | 84 |
| 5774. | ATCAGAGAGGATTTAACATATAGC[A,C]TATATGGACTAGGGATACTATAACA | 2,243,880 | 84 |
| 5775. | TTGAAATGATATCAGAGAGGATTT[A,G]ACATATAGCATATATGGACTAGGGA | 2,243,890 | 84 |
| 5776. | CAATTTTCCACATTAATTAATCTT[C,T]AATACAATTTGTGAATCCCTTTTGT | 2,244,671 | 84 |
| 5777. | CTGACGGTGCATCATACCGTACGC[G,T]AAGATTCCAGAGGGTGAAAAATTAG | 2,245,411 | 84 |
| 5778. | CTACTCAGCCTTTAAGACCACACA[A,G]GGACATCTATTTGCTCGTAAGAGGG | 2,245,562 | 84 |
| 5779. | ATTTCTTCCCTCTTCCCATCTCTC[G,A]CTTCCTTGCTACTCTCTCTCTTTCT | 2,245,616 | 84 |
| 5780. | CTACTCAGCCTTTAAGACCACACA[A,G]GGACATCTATTTGCTCGTAAGAGGG | 2,245,616 | 84 |
| 5781. | GCTCTTCTTCTTGAAGCCAAGAAA[G,T]CCGAGCAAACATTTCTTCCCTCTTC | 2,245,651 | 84 |
| 5782. | TGGACCAACAATGCGGGAAGAGC[T,A]ACTGGCGATGGGAAAATGGACTATG | 2,245,855 | 84 |
| 5783. | GGTGGACTGAGTTACATAATGAAA[A,T]CATGGCATAGGTGGACCAACAATGC | 2,245,891 | 84 |
| 5784. | GCAAGCTGAAAAATTTAGTGGCTG[T,G]GGTGGTGGAGTGCGATGGTAGAGTT | 2,246,737 | 84 |
| 5785. | AAGACAGCCTTCTTTCGTACTAA[C,A]ATGTCCTCTGCCCTTCTGTGTTGTA | 2,247,093 | 84 |
| 5786. | AAAAGTTTGGTATGGTAATGATGG[C,T]GGTTTGTGAGTGCACTCCAAGTAAT | 2,247,168 | 84 |
| 5787. | TTTTAATGAGAAAAATATTTTTTT[T,C]tCTTTATGATTCGTAGAAGAAAAAT | 2,247,284 | 84 |
| 5788. | AAAAGTTTGGTATGGTAATGATGG[C,T]GGTTTGTGAGTGCACTCCAAGTAAT | 2,24,284 | 84 |
| 5789. | ATAGGATGTCAGAAAAAAaGAAGA[G,A]ATATTTTTtATTTAAAAATTTTAT | 2,247,338 | 84 |
| 5790. | CTCAAATTATAATTTTCTGTATAA[A,G]ATATCATAATTTTTTCATAGGATGT | 2,247,379 | 84 |
| 5791. | ATAGGATGTCAGAAAAAAaGAaGA[G,A]ATATTTTTTATTtAAAAATTTTAT | 2,247,379 | 84 |
| 5792. | CCTACGCTCAAATTATAATTTTCT[G,A]TATAAAATATCATAATTTTTTCATA | 2,247,385 | 84 |
| 5793. | TTTtCATTTAAAATTTTGAATGAT[A,G]AAAATATTCTTCTTCTTCTGAAAAA | 2,247,466 | 84 |
| 5794. | CCTACGCTCAAATTATAATTTTCT[G,A]TATAAAATATCATAATTTTTTCATA | 2,247,466 | 84 |
| 5795. | GTCGTCAATTTTATTTTtCATTT[A,G]AAATTTTGAATGATAAAAATATTCT | 2,247,481 | 84 |
| 5796. | CTCTATCTGATTGGGTCATATAGT[T,C]ACTGTTTTTCGATATGTATTTAATG | 2,247,530 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5797. | GAGATTCTTTGTACAACGCATGTG[G,T]TGTAGGAAAAATATACCACTCTATC | 2,247,573 | 84 |
| 5798. | CTAGGGATTTAATTAGATATTGGG[G,A]TGTAGGAAAAATATACCACTCTATC | 2,247,603 | 84 |
| 5799. | CTTCCAGTCTGCCAGACCCACTAG[G,A]GATTTAATTAGATATTGGGGTGAAA | 2,247,623 | 84 |
| 5800. | TTAGAGAAAAGATCAATCACTTTG[T,A]GACCAAGGGGCTCCCCTAGTTATCA | 2,247,749 | 84 |
| 5801. | CTGAGGTTTGAATCTGAAATCTCT[A,G]TTGAATTTTCTTCTCTTTTGGAGGG | 2,249,204 | 84 |
| 5802. | TCTGAGGTTTGAATCTGAAATCTC[T,C]ATTGAATTTTCTTCTCTTTTGGAGG | 2,249,205 | 84 |
| 5803. | CGAAAGATTCCCAGCAAGCCGTAC[A,T]TCAATACCTCATTTTTCCAATCTGT | 2,249,278 | 84 |
| 5804. | TTTTAAAGTCTCCATGTGCTTGCA[A,C]TTGGATATTAATTCATAGGTAGGAA | 2,249,837 | 84 |
| 5805. | TGGCATCCAACACGTGAAATGTCC[C,A]CCTAATTTCGGAAGACCTTTGCATC | 2,249,895 | 84 |
| 5806. | GGAGGATGGAATGAATCTAATACC[T,C]CCCTCTGTCTGTATATATAGGGGAA | 2,250,070 | 84 |
| 5807. | GACCATTGTAACCGCCTCAAGAGC[G,T]TGAGTCGTGGTTTCTGGGCCTTGAT | 2,250,398 | 84 |
| 5808. | ACATCATGTAACTTCACAAAGAAA[A,G]CGGGAAAGAAAAATGATACATGAAT | 2,251,125 | 84 |
| 5809. | CTTGTCCATTTTGTGGGACATGAA[T,C]ATAAAAAAACTATATGCATGCTATG | 2,251,727 | 84 |
| 5810. | AAGCCAAGGATCCACTTAAGTTTA[T,C]TAACTCTGTAGAGCAAGATTGGAAA | 2,251,839 | 84 |
| 5811. | CTTGCCCCCAATCACATCCCTCTT[G,C]TTAGCAATCAGAGGTTATTAAAAAA | 2,251,996 | 84 |
| 5812. | TAATAGTAAAAGGATATTGTGTGC[T,G]ACGTCTTGCCCCCAATCACATCCCT | 2,252,025 | 84 |
| 5813. | TCGGACAACTAGCATTCCATGGAT[G,A]ATTGTTAGGGGAACAATCTATAGA | 2,252,137 | 84 |
| 5814. | TAATAGTAAAAGGATATTGTGTGC[T,G]ACGTCTTGCCCCCAATCACATCCCT | 2,252,137 | 84 |
| 5815. | CTTGCCCCCAATCACATCCCTCTT[G,C]TTAGCAATCAGAGGTTATTAAAAAA | 2,252,137 | 84 |
| 5816. | AAGCCAAGGATCCACTTAAGTTTA[T,C]TAACTCTGTAGAGCAAGATTGGAAA | 2,252,137 | 84 |
| 5817. | CTTGTCCATTTTGTGGGACATGAA[T,C]ATAAAAAAaCTATATGCATGCTATG | 2,252,137 | 84 |
| 5818. | ACATCATGTAACTTCACAAAGAAA[A,G]CGGGAAAGAAAAATGATACATGAAT | 2,252,137 | 84 |
| 5819. | GACCATTGTAACCGCCTCAAGAGC[G,T]TGAGTCGTGGTTTCTGGGCCTTGAT | 2,252,137 | 84 |
| 5820. | TGCTAGCATTGGTCGTTGTACCCT[T,C]TGCTGCTGCCATTGTAAAACTAGTG | 2,252,137 | 84 |
| 5821. | TTTTAAAGTCTCCATGTGCTTGCA[A,C]TTGGATATTAATTCATAGGTAGGAA | 2,252,137 | 84 |
| 5822. | CGAAAGATTCCCAGCAAGCCGTAC[A,T]TCAATACCTCATTTTTCCAATCTGT | 2,252,137 | 84 |
| 5823. | TCTGAGGTTTGAATCTGAAATCTC[T,C]ATTGAATTTTCTTCTCTTTTGGAGG | 2,252,137 | 84 |
| 5824. | CTGAGGTTTGAATCTGAAATCTCT[A,G]TTGAATTTTCTTCTCTTTTGGAGGG | 2,252,137 | 84 |
| 5825. | TTAGAGAAAAGATCAATCACTTTG[T,A]GACCAAGGGGCTCCCCTAGTTATCA | 2,252,137 | 84 |
| 5826. | CTTCCAGTCTGCCAGACCCACTAG[G,A]GATTTAATTAGATATTGGGGTGAAA | 2,252,137 | 84 |
| 5827. | CTAGGGATTTAATTAGATATTGGG[G,A]TGAAAGAGATTCTTTGTACAACGCA | 2,252,137 | 84 |
| 5828. | GTTACAATTAAGATAATATGTGCC[G,C]AACAATATTAACTCGGACAACTACG | 2,252,174 | 84 |
| 5829. | GTACTATATGATTGCTAATTGGGT[T,G]ACAATTAAGATAATATGTGCCGAAC | 2,252,196 | 84 |
| 5830. | ATAAACAAATGTTTCATGCATTTA[G,C]ATTGTACGTCATTATTAGCCGGATC | 2,252,448 | 84 |
| 5831. | CATTAATATTAATTGATTCTTACC[A,G]ATTACAAACGAAAATTTTGTTTATA | 2,252,645 | 84 |
| 5832. | ATGTCTCCATCGATCTCTACGCAG[T,C]ACTCCTTTTAATTTTTATGTTAAAT | 2,253,020 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5833. | AAATGGTTTCTTCTCACTATAGCA[G,A]TGATTCGCTAGCTGGCTAGATGTCT | 2,253,064 | 84 |
| 5834. | GCTTGACTTGTCCTATATATATGT[G,T]CATGGTTGCTTTTGTGGTTAGGCTC | 2,253,184 | 84 |
| 5835. | GATTATGAGTTGATTATTGGCTCT[A,G]AGATGCATATCTAATCAGTCTTAAA | 2,254,302 | 84 |
| 5836. | TTGGACGTACGTACGTACGTACCC[T,C]AACGGACTAGGAAGACGGGATTCTT | 2,254,445 | 84 |
| 5837. | GATTATGAGTTGATTATTGGCTGT[A,G]AGATGCATATCTAATCAGTCTTAAA | 2,254,445 | 84 |
| 5838. | ATGCCATGGCTTCTTGACATTATC[C,T]ATCCCTTTATTCGTGGCTGAACCAG | 2,254,445 | 84 |
| 5839. | GCTTGACTTGTCCTATATATATGT[G,T]CATGGTTGCTTTTGTGGTTAGGCTC | 2,254,445 | 84 |
| 5840. | AAATGGTTTCTTCTCACTATAGCA[G,A]TGATTCGCTAGCTGGCTAGATGTCT | 2,254,445 | 84 |
| 5841. | ATGTCTCCATCGATCTCTACGCAG[T,C]ACTCCTTTTAATTTTTATGTTAAAT | 2,254,445 | 84 |
| 5842. | TGACAAAATCATCAAAGTCTGGCA[C,T]TTTATGATAATTCTCTTTGTGGTTC | 2,254,445 | 84 |
| 5843. | CATTAATATTAATTGATTCTTACC[A,G]ATTACAAACGAAAATTTTGTTTATA | 2,254,445 | 84 |
| 5844. | GTACTATATGATTGCTAATTGGGT[T,G]ACAATTAAGATAATATGTGCCGAAC | 2,254,445 | 84 |
| 5845. | GTTACAATTAAGATAATATGTGCC[G,C]AACAATATTAACTCGGACAACTAGC | 2,254,445 | 84 |
| 5846. | GAACCATCCAAATCTCGATCAAGA[A,T]AGGTATGTGGTGGATAATAGGATGA | 2,255,146 | 84 |
| 5847. | GACCAACCTGCATACCTTAATTCC[A,G]TCCAGCTACTTGGATGAGTTTTCTC | 2,255,379 | 84 |
| 5848. | ATATATAAGAGATCGACGATGATC[G,A]ATCTAGCTTGCAGACATATTGACAC | 2,255,577 | 84 |
| 5849. | TCAGCCAAATATATAAGAGATCGA[C,A]GATGATCGATCTAGCTTGCAGACAT | 2,255,585 | 84 |
| 5850. | CTATAGATGGAGCTTTTCTATTCC[C,T]TCTCTTCCTCCTCTCCATTTTCTAT | 2,256,565 | 84 |
| 5851. | ACTATAGATGGAGCTTTTTCTATTC[C,A]CTCTCTTCCTCCTCTCCATTTTCTA | 2,256,566 | 84 |
| 5852. | GGCTCAATGTGGACCAAATTTTAA[A,G]GTGTATTTCCTAACAAGCATGCATA | 2,256,636 | 84 |
| 5853. | GGAACTTACCACTCAATCGTTGTA[C,T]AAGAGTCTCTCAAGAAAAAATCCCA | 2,257,371 | 84 |
| 5854. | TGAGAGAATAAAATAAGATCAATA[C,T]AAGAGGAACTTACCACTCAATCGTT | 2,257,400 | 84 |
| 5855. | AAAGAAGAAACAAAATAAGAAACA[C,T]AATACAAATACGTGGATCGATCTCA | 2,257,483 | 84 |
| 5856. | CTCGATCCATCACCGCTGCAGCCTA[C,T]ACTCTGGCACCACCTTGCTCTGATA | 2,257,582 | 84 |
| 5857. | CTTGTTGGATGAGCACGTCTTTCA[T,C]CCTTGCCTGCCACAAAGAGAAATTG | 2,257,950 | 84 |
| 5858. | GCACGCTCTATCCCTCAATCATCC[G,A]CAGTTGATAAAACTGCCTCCATCGA | 2,257,950 | 84 |
| 5859. | CTTGTTGGATGAGCACGTCTTTCA[T,C]CCTTGCCTGCCACAAAGAGAAATTG | 2,257,950 | 84 |
| 5860. | CTCGATCATCACCGCTGCAGCCTA[C,T]ACTCTGGCACCACCTTGCTCTGATA | 2,257,950 | 84 |
| 5861. | AAAGAAGAAACAAAATAAGAAACA[C,T]AATACAAATACGTGGATCGATCTCA | 2,257,950 | 84 |
| 5862. | TGCATGCCGAATCTAAAATCCACT[G,A]CTGGAAAGAAGTAGATTCCTCGTCA | 2,258,463 | 84 |
| 5863. | TCACCAGAAAATTCATTAAACTTC[G,A]ATCCCTCTGATTAGTCCATCCATCT | 2,258,463 | 84 |
| 5864. | AGATCCAAAAATTTCTTTCCCACC[G,A]ATGGCTCCATGGCAGAGCAACAAAA | 2,260,135 | 84 |
| 5865. | GATCATCATGTCCATCGTGAAAAC[G,C]GATCAAAGTCTAGACAATACCTTTC | 2,260,406 | 84 |
| 5866. | AGATCCAAAAATTTCTTTCCCACC[G,A]ATGGCTCCATGGCAGAGCAACAAAA | 2,260,406 | 84 |
| 5867. | AGTCATACCAGCCATGATGAAATT[A,T]GTTGCATTATCGGTAATTACTTGGA | 2,260,406 | 84 |
| 5868. | CCATGATGAAATTAGTTGCATTAT[C,T]GGTAATTACTTGGACAACATTTGCC | 2,260,406 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5869. | AAAAATAAGACACAGATGAATTAT[C,T]AAGAAGGAGACCAAACAGCAATCAA | 2,260,750 | 84 |
| 5870. | GGATGGCAAAAATTTTATTTGCCA[T,A]AGATGCATCAAAATTTTATAAATTA | 2,260,979 | 84 |
| 5871. | ATAGAGATTAAAAAGCAGTCCAAG[G,A]TCTAAGAATATTCGTTACGACTGGA | 2,261,026 | 84 |
| 5872. | CAGATGTTATCTTTAGTACTGTAC[C,A]CTATAGAGATTAAAAAGCAGTCCAA | 2,261,053 | 84 |
| 5873. | ATGACATAGTAAGGTTCAAATAGG[T,C]GGAGTTGGAATGGGAGAGTCTTCAT | 2,261,112 | 84 |
| 5874. | TAGAATTCAAACAAAAGATGACAT[A,T]GTAAGGTTCAAATAGGTGGAGTTGG | 2,261,129 | 84 |
| 5875. | TGATTTTACCTGGTGGGTTACCTG[G,T]CTGGGCTATTTACCGTCCTTCCGTG | 2,261,447 | 84 |
| 5876. | ATGCGCTCCCAACATGATTTTACC[T,C]GGTGGGTTACCTGGCTGGGCTATTT | 2,261,461 | 84 |
| 5877. | GCAATTTACCATCCAGATACATGC[G,T]CTCCCAACATGATTTTCAATGGTGG | 2,261,481 | 84 |
| 5878. | AAAAAAaTTAAAAaTAAAGTCGA[G,A]AGGAGGGAGAGTAAGAGAGCCCAAT | 2,261,549 | 84 |
| 5879. | TAGAATTCAAACAAAAGATGACAT[A,T]GTAAGGTTCAAATAGGTGGAGTTGG | 2,261,549 | 84 |
| 5880. | ATGACATAGTAAGGTTCAAATAGG[T,C]GGAGTTGGAATGGGAGAGTCTTCAT | 2,261,549 | 84 |
| 5881. | CAGATGTTATCTTTAGTACTGTAC[C,A]CTATAGAGATTAAAAAGCAGTCCAA | 2,261,549 | 84 |
| 5882. | ATAGAGATTAAAAAGCAGTCCAAG[G,A]TCTAAGAATATTCGTTACGACTGGA | 2,261,549 | 84 |
| 5883. | GGATGGCAAAAATTTTATTTGCCA[T,A]AGATGCATCAAAATTTTATAAATTA | 2,261,549 | 84 |
| 5884. | ATTTTAAACAAATGCAAAAACAAT[T,A]TGCAATGTAGAATTAGAAATTAGAA | 2,261,549 | 84 |
| 5885. | AAAAATAAGACACAGATGAATTAT[T,C]AAGAAGGAGACCAAACAGCAATCAA | 2,261,549 | 84 |
| 5886. | GGTGGTGGTGGAGGCGAAAGAGGC[A,G]TCGCTGTGAGAGATTGAATGGCTTT | 2,261,994 | 84 |
| 5887. | GTGATCTTGCCATCGCCATCGACA[C,T]GGTTGAAGACGGCGAAGAGGTCGAA | 2,262,176 | 84 |
| 5888. | TTCGTTTAACTTGTGGAATCTCCC[C,T]AATATCTTCCAACATTAGATCTATG | 2,262,176 | 84 |
| 5889. | AAAATAATTCATTTTTTTCATAAT[T,C]GAATCCGGACTCACCCTAATAAAAT | 2,262,440 | 84 |
| 5890. | TAAATATACATTTTAAGCCCCACT[G,A]GGGTCCAACGCATCTTATATTTTCG | 2,262,645 | 84 |
| 5891. | AAAATAATTCATTTTTTTCATAAT[T,C]GAATCCGGACTCACCCTAATAAAAT | 2,262,645 | 84 |
| 5892. | GCCAAGTGGTGATGTGTTTTGGTC[C,T]GCGGTCACCTTGCACGATGTATCAA | 2,262,758 | 84 |
| 5893. | TCTTTGTGTGGCTCTCGTGGACAC[C,A]AAATATTTTTATATATGTTTGCACG | 2,262,830 | 84 |
| 5894. | GATGACCATGTCCGCACTTGATCT[G,T]AGCCAAAAGGCTGAGAAAGGTATAC | 2,263,024 | 84 |
| 5895. | CGGACAATTGATTTGATTATAGTT[G,A]GTAAATAAGATGTTATCGGTGATGA | 2,263,069 | 84 |
| 5896. | TCATTTAAAAGCCGAAATTAATGA[T,G]GCTTAAGATGCTTGAGGATGTATCT | 2,263,444 | 84 |
| 5897. | TTGAACAAAAGAGGAGTAGGTGTA[G,A]AACCCTTTAGCAGGGCAGGCACTAT | 2,264,187 | 84 |
| 5898. | TCATTTAAAAGCCGAAATTAATGA[T,G]GCTTAAGATGCTTGAGGATGTATCT | 2,264,187 | 84 |
| 5899. | CAAGTACACATGCATGCATGCATG[T,C]ATGTATGAATCCAAGGTTGATGTAT | 2,264,341 | 84 |
| 5900. | AGTTGTAGTTCCTGCCAGGGTCCA[T,A]TGTTTTGAGCTATACAATTAGAGCA | 2,264,792 | 84 |
| 5901. | CTACCAGAAAAGTAGATAAATACG[T,A]AAACCAAGGCCATAGGAATTGCAGA | 2,265,400 | 84 |
| 5902. | TATTTAGTAAAGTGTTTGGAGAGA[G,T]AGGAAGTATTTTTTGTCTTTCAAAA | 2,266,061 | 84 |
| 5903. | AGAGCTTGAAGAATTATCTGATTT[T,C]AAAAATAAAATATTTTTTTtGGATA | 2,266,238 | 84 |
| 5904. | AAACTTTCATATCGATCAATCATT[C,T]TGAAACTTAAATAAAAGATTTTGGA | 2,266,328 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5905. | TATTTTTCAAATAATTGGAACATA[C,A]ATTTGAATAAACTCTTTTTCGAAAA | 2,266,380 | 84 |
| 5906. | ATCTTGCAATCGAGTCAACTCAAA[A,T]TTTTTAAAGAAATTTAGAAAAaTAA | 2,266,779 | 84 |
| 5907. | TCACAGAAAGAGAGTCATTTTGCT[G,A]GATGATCTAGTCGAGGAAAAGCAAA | 2,266,828 | 84 |
| 5908. | AAAGGTAGTTAGCCTCGATATTTA[A,G]AGGACAATTTACTTAGATTATGTTC | 2,267,067 | 84 |
| 5909. | AAATTTCAAATTTTCAATGAATCC[T,A]ACAGGCATGGTGGAAGATGTCTTTG | 2,267,203 | 84 |
| 5910. | CTTTAAGCTTTTGATTGTACTTGA[C,T]GTACACTAAATCACTAAGCTTCTTT | 2,267,203 | 84 |
| 5911. | GTACCAATCAATCATTTATCAAAA[T,C]TTGTTTAAAAATATAATATTACTAT | 2,267,203 | 84 |
| 5912. | CTACCAGAAAAGTAGATAAATACG[T,A]AAACCAAGGCCATAGGAATTGCAGA | 2,267,203 | 84 |
| 5913. | CCTGTTCAAACACACTCCAATTAC[G,A]CTCACAACCAGATGCACACCATTCC | 2,267,203 | 84 |
| 5914. | AGTTGTAGTTCCTGCCAGGGTCCA[T,A]TGTTTTGAGCTATACAATTAGAGCA | 2,267,203 | 84 |
| 5915. | TTTCGCGTAAAAGATACAACCTAC[A,G]TCCATAAAGAACCAGCTCCTCAAGG | 2,267,577 | 84 |
| 5916. | CTAATAGTTATGGCAACCAATACT[C,T]ATCCAAATTTGCTTAGATTTAAAT | 2,267,758 | 84 |
| 5917. | CATATTAATTTTGCTAATAGTTAT[G,T]GCAACCAATACTCTATCCAAATTTG | 2,267,771 | 84 |
| 5918. | TATGTATGCATACCCTCACGTGAA[A,G]CCATCATGTGCCCCTTGTATGTATG | 2,267,919 | 84 |
| 5919. | CATCTTTGGTCTGTGAAAGGCTTC[A,G]CCAATTATGTATGCATACCCTCACG | 2,267,949 | 84 |
| 5920. | ATGAAATAATGAGGTAGGCGAAGA[C,T]CGATATAACCGCCATTATACCGTTA | 2,268,109 | 84 |
| 5921. | ATCTTTTTCTTTTGGAGTGCAAAC[G,A]TAAATAGGTCAAAATTTAAGGAATA | 2,268,381 | 84 |
| 5922. | AGATTGGTGGGAGAAAGTCGATAA[T,C]GGGTGACAATTGGGAGGAAGATGGTG | 2,268,656 | 84 |
| 5923. | GGGCGATGGCAGCGAAAAGAGCAG[G,A]GAGGAGGTCGATGTCTCTCTTTTTC | 2,268,880 | 84 |
| 5924. | TCAAAACTCAACACGTGGTTTGAT[A,G]GAGATTTTTAAGAATAaAAAAAATC | 2,269,154 | 84 |
| 5925. | TATTTTTCCTTCCTTCTCTAACAC[T,C]TGCTGCCCTAGCTACTGCACCCCAT | 2,269,154 | 84 |
| 5926. | GGGCGATGGCAGCGAAAAGAGCAG[G,A]GAGGAGGTCGATGTCTCTCTTTTTC | 2,269,154 | 84 |
| 5927. | TTTTAGAAGTTTCTTGATTTTAGC[A,G]TGATCAAAACTCAACACGTGGTTTG | 2,269,182 | 84 |
| 5928. | GCAACATAAATGTTCTTTTTAGAA[G,A]TTTCTTGATTTTAGCATGATCAAAA | 2,269,198 | 84 |
| 5929. | ACACATTATCTATTACGATGGGCC[G,A]TCACCATAACTCCTATCATCATTAT | 2,269,380 | 84 |
| 5930. | TTTTAGAAGTTTCTTGATTTTAGC[A,G]TGATCAAAACTCAACACGTGGTTTG | 2,269,380 | 84 |
| 5931. | AAAaGTTATGTGGAGCTTGATCAC[A,G]TTCAAGCTCAGATAAGCTCAAGCTC | 2,269,570 | 84 |
| 5932. | GTGTTCATATATAATCAATTGTTA[C,T]ACTAAATGTAGTGACTGCCCTTCAT | 2,269,882 | 84 |
| 5933. | TAAGTTTGGTGGCTTTGAATGTGA[A,G]GTTGAAGCTGCTGTTGATCTTGATC | 2,270,882 | 84 |
| 5934. | TAATGGTTTATCTCAAAACTAGCC[G,A]CCCATCAATATGGCCACAATCATGC | 2,270,189 | 84 |
| 5935. | TAATTATTGGATCAACACTCATCT[C,T]TCTATTTAAGTAAAAATAATCCAAG | 2,270,240 | 84 |
| 5936. | AAAAaTATTCAAATATTTTATATT[T,C]ATCAAAATTAATTATTGGATCAACA | 2,270,273 | 84 |
| 5937. | TGTGGCTTCTTCCATCTTTTTTTt[A,G]CACTCTATAACTTGGCATTGATGAA | 2,270,394 | 84 |
| 5938. | TCAATCTCTTCTTCTGAACTAGAA[C,T]GAATCTCTTCATGATTTAAGTTTGG | 2,270,394 | 84 |
| 5939. | GTCAGCTCTTGACTTTTTTCATTT[G,A]ATTTCTCATGATGTGGCTTCTTCCA | 2,270,430 | 84 |
| 5940. | TTGTATATTTCTGAAATTTATGCA[G,T]AACTAGCCATAAAAGTTGTTAACCG | 2,270,755 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5941. | ATTGTATATTTCTGAAATTTATGCA[G,A]CTTGATTATTTTTCTTAACTAACAA | 2,271,266 | 84 |
| 5942. | TCCTCAAACCATCCTTAAAAATTT[T,C]ATTATGATTTTTCCTCAGATTATAG | 2,271,291 | 84 |
| 5943. | TATTTATTCCTCAAACCATCCTTA[A,G]AAATTTATTATGATTTTTCCTCAG | 2,271,298 | 84 |
| 5944. | AAAAGTAAATAATAAGACACAAG[C,T]AAATACAAAAAAATTTATAGTGATT | 2,271,369 | 84 |
| 5945. | ATTGTGTGTGTGTGTGACAAAA[A,C]AGATTAGCAATGCAATGTCTAGAAC | 2,271,713 | 84 |
| 5946. | ATCTTCCATCTCCTTCCCGAAATA[A,C]AaGGAAAATTAAGGTAAAAGAAAGC | 2,271,936 | 84 |
| 5947. | CAAGAAACAGCACATTGGCTGCTA[A,T]ATTGTTCCAAACGAAGGAAGTTCTA | 2,272,047 | 84 |
| 5948. | GGTTGCTTTATATATATATATATA[T,C]ACAAGCGATCAAATTGATCCTTTTG | 2,272,119 | 84 |
| 5949. | TACGGGAAAAATATAAAACATGA[G,C]GTTGCTTTATATATATATATATA | 2,272,143 | 84 |
| 5950. | TCTGCCAATTAGTTTGTATACGGG[G,A]AAAAATATAAAACATGAGGTTGCTT | 2,272,161 | 84 |
| 5951. | TAAAATTTAAAATTTGGATGGCTA[T,C]GCCTCCTGTTACATCGGGAAACAAA | 2,272,373 | 84 |
| 5952. | TTCTTCAATAATGTTGTGGGAAAC[T,C]GTATTCTATTTTAGTTTCCCTCCCC | 2,272,506 | 84 |
| 5953. | CAAGAAACAGCACATTGGCTGCTA[A,T]ATTGTTCCAAACGAAGGAAGTTCTA | 2,272,506 | 84 |
| 5954. | ATATGTGTAGCTGCCCTCTGGAAC[A,G]GAATGCTTTGGTAGAGCATAATAAG | 2,272,625 | 84 |
| 5955. | TGGGTGGGAGTGAGGGTGGAGCTG[A,T]GGTGGTGATGGACTTGGTGGGAGGT | 2,272,840 | 84 |
| 5956. | TTCTCACAAACCCCACAATCATGG[A,C]ATTCCACGATACACGGTTTCTCTGA | 2,273,379 | 84 |
| 5957. | AAGCTTGTTTCTCACAAACCCCAC[A,T]ATCATGGAATTCCACGATACACGGT | 2,273,387 | 84 |
| 5958. | TGTGGTGGTVVTVSYYHVSHVSVS[C,T]ACAGCCACCTCTATCAATTAGATTT | 2,275,059 | 84 |
| 5959. | AAAACTGTTGTTTGCAAGAAAGAT[T,A]CCCTGCTGCCAAATTGGGCAGCTGG | 2,275,332 | 84 |
| 5960. | AAGCTTGTTTCTCACAAACCCCAC[A,T]ATCATGGAATTCCACGATACACGGT | 2,275,332 | 84 |
| 5961. | TTCTCACAAACCCCACAATCATGG[A,C]ATTCCACGATACACGGTTTCTCTGA | 2,275,332 | 84 |
| 5962. | GGTACTAGGCGCTGAAAAAGCGAA[A,C]ACCTGATTGAAGTCAGATGCCATGT | 2,275,332 | 84 |
| 5963. | CACCTGCACACCATAAGCTGAAGG[T,A]TGTCCTACCAATTTGAGCTTCACAA | 2,275,443 | 84 |
| 5964. | AATTTTTAAGCCTGGATTGGTACT[T,C]ATTTTTGGGCTATTCTATCTTGTAC | 2,275,594 | 84 |
| 5965. | CACTACTAACTATAGGATATCGGT[A,C]AAGTTTATTATGCAATTCTCCTGTT | 2,275,650 | 84 |
| 5966. | TTTCCATTTGGAGGGGTGAGATCA[C,G]GGGGCAAACGCCCTGCACTACTAAC | 2,275,690 | 84 |
| 5967. | GCAAGGGAGGGAGACGGTACCTGT[T,G]GGAATTACCTAGAATTGAAGATTGA | 2,275,771 | 84 |
| 5968. | AAAATAAAAGCAAGGGAGGGAGAC[G,A]GTACCTGTTGGAATTACCTAGAATT | 2,275,780 | 84 |
| 5969. | TGATCAAAATTGGTCTCGAGGAAA[G,A]GGAGAGGGATGGTGGCTTCCAAGAA | 2,276,364 | 84 |
| 5970. | TGTCAAATCAAGAAGTTGGAGCTC[T,C]TGATGCAAGAGGAGAGCTAAATGAT | 2,277,100 | 84 |
| 5971. | AAATGGTGGTACTTGTGAGCCCAT[G,T]ATTGTCAAATCAAGAAGTTGGAGCT | 2,277,127 | 84 |
| 5972. | ACAGTTACAGTAAGAGGGACAACC[A,T]GCTCAAAATAGTTTTGTGGCTTTCT | 2,277,525 | 84 |
| 5973. | TGATCAAAATTGGTCTCGAGGAAA[G,A]GGAGAGGGATGGTGGCTTCCAAGAA | 2,277,525 | 84 |
| 5974. | ATAAGGAGGGAATGGTATAATGAA[C,G]AGGAGACAGTTACAGTAAGAGGGAC | 2,277,555 | 84 |
| 5975. | GAGAGAATCGAAGCAAAAGACTC[G,A]TGAGGGCAATTATTACGCAAATATA | 2,278,007 | 84 |
| 5976. | AGTGGCCAAAAAGGAAGTGTCTAC[T,C]AGAAAATTGAGAGAGAATCGAAGCA | 2,278,042 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 5977. | GCAAGAAAAACCAGAGCGAGCAAA[A,C]AGGGTAGCAATGAAGCAGAACATGT | 2,278,316 | 84 |
| 5978. | TCCCATGTGTtTTTTTGCAAGAAA[A,G]ACCAGAGCGAGCAAAAAGGGTAGCA | 2,278,332 | 84 |
| 5979. | AATGGTTTGGCGAGGCCCAAAAAA[T,A]ACATTTTAGCCTGATTGGGCCAGA | 2,278,873 | 84 |
| 5980. | TTCTAACACACCTTCGTAGAATAT[A,C]GATCAAAATTAACGCAATTAAATCA | 2,279,223 | 84 |
| 5981. | TCTTATCTTTGTAGCCCACAGACT[C,T]TAGCTGAAAGCAGAAAGAACTAATG | 2,279,454 | 84 |
| 5982. | ATATTTGTCGCTTTTGTTGTCCAT[A,T]ACATTATTGTGGGGTGCAAATCTTT | 2,279,741 | 84 |
| 5983. | TTTTCAATCCTTTAAAATTTGTGC[T,C]AGAGAATTAAGAAAATCCGGATCCT | 2,280,097 | 84 |
| 5984. | ATATTTGTCGCTTTTGTTGTCCAT[A,T]ACATTATTGTGGGGTGCAAATCTTT | 2,280,097 | 84 |
| 5985. | TCTTATCTTTGTAGCCCACAGACT[C,T]TAGCTGAAAGCAGAAAGAACTAATG | 2,280,097 | 84 |
| 5986. | TCAAAAGTATTCTATTTATATTTC[T,G]ATAGGTCAAGAATGTTTGGTTTGCT | 2,280,097 | 84 |
| 5987. | TTCTAACACACCTTCGTAGAATAT[A,C]GATCAAAATTAACGCAATTAAATCA | 2,280,097 | 84 |
| 5988. | AATGGTTTGGCGAGGCCCAAAAAa[T,A]ACATTTTAGCCTGATTGGGCCAGA | 2,280,097 | 84 |
| 5989. | TCCCATGTGTTTTTTtGCAAGAAA[A,G]ACCAGAGCGAGCAAAAAGGGTAGCA | 2,280,097 | 84 |
| 5990. | GCAAGAAAAACCAGAGCGAGCAAA[A,C]AGGGTAGCAATGAAGCAGAACATGT | 2,280,097 | 84 |
| 5991. | TTCCTTTTCAATCCTTTAAAATTT[G,A]TGCTAGAGAATTAAGAAAATCCGGA | 2,280,101 | 84 |
| 5992. | AGAATTGGAGTCATTTTAATCCAA[G,A]TTTTAGTGAGATTATTTCTGATTTT | 2,280,239 | 84 |
| 5993. | TCTAACGAGGATAAACAAGAAAAA[C,T]CTAATGATTTCTCCGATGAAAACCC | 2,280,383 | 84 |
| 5994. | AGAATTGGAGTCATTTTAATCCAA[G,A]TTTTAGTGAGATTATTTCTGATTTT | 2,280,383 | 84 |
| 5995. | AAGGCTTAATAACTTACCTAGGTC[T,C]AACGAGGATAAACAAGAAAAACCTA | 2,280,405 | 84 |
| 5996. | GCCATGGCCGTAGAATACTAGCCA[G,A]CAACCAATGTCAGCACTCGGTGCCT | 2,280,607 | 84 |
| 5997. | CTCTCTTCTTTAAACAAAGCACCC[A,G]AATTTTATTCTTTTTCCCTCTTCAT | 2,280,660 | 84 |
| 5998. | AACACTACTAGTCCAGAACCTCTC[T,C]CAGGGTCACCAATTGATCTGGGTTA | 2,280,920 | 84 |
| 5999. | AAAAAAaTAAATATACATAATATT[A,G]TTTGTGTCCAACAATCCTTATCTCT | 2,281,141 | 84 |
| 6000. | TACCTAAACCATCTGAAAACCTTC[C,A]ATATTTGATACGAGCATATGACATA | 2,281,261 | 84 |
| 6001. | CAAGACTATTCGCAATCTAACGTG[C,G]CTAATCCAAATATCCCTTTCTTAAT | 2,281,395 | 84 |
| 6002. | ATGACAAGACTATTCGCAATCTAA[C,T]GTGCCTAATCCAAATATCCCTTTCT | 2,281,399 | 84 |
| 6003. | TTTCTGTCCATGACGAGCTATTCT[T,C]AGTATCACATTTCTATCCATGACAA | 2,281,442 | 84 |
| 6004. | CAAGACTATTCGCAATCTAACGTG[C,G]CTAATCCAAATATCCCTTTCTTAAT | 2,281,442 | 84 |
| 6005. | TACCTAAACCATCTGAAAACCTTC[C,A]ATATTTGATACGAGCATATGACATA | 2,281,442 | 84 |
| 6006. | TGGACCGCTATGGGAGGTCTAATC[A,G]TGGATCTATTTAAGTTGGGCTAGT | 2,281,442 | 84 |
| 6007. | AAAAAAaTAAATATACATAATATT[A,G]TTTGTGTCCAACAATCCTTATCTCT | 2,281,442 | 84 |
| 6008. | CTCTCTTCTTTAAACAAAGCACCC[A,G]AATTTTATTCTTTTTCCCTCTTCAT | 2,281,442 | 84 |
| 6009. | CACATTAACATAATCTGAATCAAT[T,C]AACAGTTATCTTTAGGATTCTGAAC | 2,281,679 | 84 |
| 6010. | ACAAAAATATATATCATATATCAT[C,T]GGATATCCCTCTTCTTCAAACTATT | 2,281,795 | 84 |
| 6011. | CAAAAGAAAATATAAGCTATAAAA[C,T]CTCGTATCATGTATCCAATATAACT | 2,281,859 | 84 |
| 6012. | ATCTGATCAAATTTTTCAATTCGA[G,A]ATCCCAACCTTAGCTAAATATGAAC | 2,282,023 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6013. | ACTGTTATTGATGATGTTCTATCT[G,A]ATCAAATTTTTCAATTCGAGATCCC | 2,282,043 | 84 |
| 6014. | TCAAATTTTATATAATTTATAAAA[C,A]TCAATTATTCAACTGTTATTGATGA | 2,282,079 | 84 |
| 6015. | ACAAAAATATATATCATATATCAT[C,T]GGATATCCCTCTTCTTCAAACTATT | 2,282,079 | 84 |
| 6016. | TATTAACAAATATCAAATTTTATA[T,C]AATTTATAAAACTCAATTATTCAAC | 2,282,091 | 84 |
| 6017. | TTCATAATAAATATTTTATATTAA[C,T]AAATATCAAATTTTATATAATTTAT | 2,282,109 | 84 |
| 6018. | GTCGGCTACATGATGTGGGCCCAT[A,G]AACCTTAGAGTAACATCCTAGAGAT | 2,282,218 | 84 |
| 6019. | CAAACCCAGCACCCAGGTCGGCTA[C,T]ATGATGTGGGCCCATAAACCTTAGA | 2,282,234 | 84 |
| 6020. | TGTATTAGAAGAGCCAAACTAATT[A,G]AAGTGCTGAACAAACTATGCTGGCA | 2,282,309 | 84 |
| 6021. | TCACAAGAGCTGATAAATGTTAGC[A,G]TCCGCCACCGACTCCATTTTTGTCT | 2,282,889 | 84 |
| 6022. | TGTATTAGAAGAGCCAAACTAATT[A,G]AAGTGCTGAACAAACTATGCTGGCA | 2,282,889 | 84 |
| 6023. | CAAACCCAGCACCCAGGTCGGCTA[C,T]ATGATGTGGGCCCATAAACCTTAGA | 2,282,889 | 84 |
| 6024. | GTCGGCTACATGTGGGCCCAT[A,G]AACCTTAGAGTAACATCCTAGAGAT | 2,282,889 | 84 |
| 6025. | CCAACAGCCCCACTGAACTGGCAG[T,G]GCAATTCATGAAAGTTATTTAT | 2,282,889 | 84 |
| 6026. | TTCATAATAAATATTTTATATTAA[C,T]AAATATCAAATTTTATATAATTTAT | 2,282,889 | 84 |
| 6027. | TATTAACAAATATCAAATTTTATA[T,C]AATTTATAAAACTCAATTATTCAAC | 2,282,889 | 84 |
| 6028. | GATACAAGAACCAAATTATCTCAT[T,C]GATGATCTCCTGCTCCATCATTTGC | 2,283,818 | 84 |
| 6029. | AATTAATCAGAAATGGAATCATGT[A,T]CTTCTCTATGTATATATCCATGTTT | 2,283,897 | 84 |
| 6030. | GGGACAATTGTGGAGAGGGCCAAG[T,A]CTTCTCTATGTATATATCCATGTTT | 2,284,596 | 84 |
| 6031. | AGCCATACATCTCCTAGATAACAG[C,T]ATGAGATATGGTTGTAAACTTTGCA | 2,284,596 | 84 |
| 6032. | TGATAGAATATATAAAGTTGGGGA[C,A]AATTGTGGAGAGGGCCAAGTCCAAC | 2,284,616 | 84 |
| 6033. | TTACTTTTCCTACCACTGTCTTGT[G,A]TGACAATCTTGTTTGATTGTTGGGT | 2,285,645 | 84 |
| 6034. | GTATGATGATTTTTCTTAACAAGA[T,C]GGGATTTATGATTTGACCTTTTCTT | 2,285,645 | 84 |
| 6035. | AACAGCTTCTTCCTTAAGCCTTTT[T,C]CTTGCCCCTCCCCTCCTACCATTAC | 2,286,266 | 84 |
| 6036. | TGCCTCGTTGTTTCTAAAGTTCAC[T,A]GTCTCCATAAAGAATGCACCTTTGT | 2,286,321 | 84 |
| 6037. | TGGGGAACTCCGATCCAATCCTTT[A,G]GTCTCGACTGGTGAAATCAAAGCTT | 2,287,839 | 84 |
| 6038. | TCTTGCGTGTGAGGATGGAACTCG[T,C]AGCAGAACCACACCTCCATTGTCAT | 2,288,047 | 84 |
| 6039. | CACATTGGTATCACCAAGTGGGTG[G,A]GAGGTCTTGCGTGTGAGGATGGAAC | 2,288,076 | 84 |
| 6040. | ACGAAATCCAAACATTTGTTATCA[T,C]GACACTAAATTAATTTTGGACTTCC | 2,288,400 | 84 |
| 6041. | TTTATTAAAGTACGAAATCCAAAC[A,T]TTTGTTATCATGACACTAAATTAAT | 2,288,411 | 84 |
| 6042. | ATTGTGGAGTGAAAGAAAATCATC[G,A]GAGTACCATTGACTAGGATGGCAAG | 2,288,656 | 84 |
| 6043. | TATAAGGAGAAAGAGGATAATCTT[G,A]GGGAAATCCGATTGTGGAGTGAAAG | 2,288,691 | 84 |
| 6044. | ACCATCGCCCAACCTAGCAAGAAA[T,C]AGTCATTTGTCAAGAGTAAGTGAGG | 2,288,843 | 84 |
| 6045. | ATACCATCGCCCAACCTAGCAAGA[A,G]ATAGTCATTTGTCAAGAGTAAGTGA | 2,288,845 | 84 |
| 6046. | GCCTTCGATGAGGTTTAATCTTTA[G,A]GCTAAAGTAGATAACCAACTTTAGT | 2,288,962 | 84 |
| 6047. | CTGCCTTCGATGAGGTTTAATCTT[T,C]AGGCTAAAGTAGATAACCAACTTTA | 2,288,964 | 84 |
| 6048. | TACTCCCATGCCCAAATACTCCCT[G,A]ATCGTCTGCCTTCGATGAGGTTTAA | 2,288,994 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6049. | TCTGACCCATGATCGGGACCCCTA[C,A]GTAGTGCCACACTTTGACCTACTCC | 2,289,038 | 84 |
| 6050. | CATCCTCTCCCTAATGCTTTACTT[C,T]ATCTTAATATACTTTGATCTCCACA | 2,289,091 | 84 |
| 6051. | TGATTGGACCAACATCACTTGACC[C,T]ATCATAGATAGCGACTTGACTTGCC | 2,289,148 | 84 |
| 6052. | CATCCTCTCCCTAATGCTTTACTT[C,T]ATCTTAATATACTTTGATCTCCACA | 2,289,148 | 84 |
| 6053. | TACTCCCATGCCCAAATACTCCCT[G,A]ATCGTCTGCCTTCGATGAGGTTTAA | 2,289,148 | 84 |
| 6054. | CTGCCTTCGATGAGGTTTAATCTT[T,C]AGGCTAAAGTAGATAACCAACTTTA | 2,289,148 | 84 |
| 6055. | GCCTTCGATGAGGTTTAATCTTTA[G,A]GCTAAAGTAGATAACCAACTTTAGT | 2,289,148 | 84 |
| 6056. | ATACCATCGCCCAACCTAGCAAGA[A,G]ATAGTCATTTGTCAAGAGTAAGTGA | 2,289,148 | 84 |
| 6057. | ACCATCGCCCAACCTAGCAAGAAA[T,C]AGTCATTTGTCAAGAGTAAGTGAGG | 2,289,148 | 84 |
| 6058. | TATAAGGAGAAAGAGGATAATCTT[G,A]GGGAAATCCGATTGTGGAGTGAAAG | 2,289,148 | 84 |
| 6059. | TTTATTAAAGTACGAAATCCAAAC[A,T]TTTGTTATCATGACACTAAATTAAT | 2,289,148 | 84 |
| 6060. | ACGAAATCCAAACATTTGTTATCA[T,C]GACACTAAATTAATTTTGGACTTCC | 2,289,148 | 84 |
| 6061. | CACATTGGTATCACCAAGTGGGTC[G,A]GAGGTCTTGCGTGTGAGGATGGAAC | 2,289,148 | 84 |
| 6062. | TCTTGCGTGTGAGGATGGAACTCG[T,C]AGCAGAACCACACCTCCATTGTCAT | 2,289,148 | 84 |
| 6063. | TGGGGAACTCCGATCCAATCCTTT[A,G]GTCTCGACTGGTGAAATCAAAGCTT | 2,289,148 | 84 |
| 6064. | GCTGATTGGACCAACATCACTTGA[C,T]CCATCATAGATAGCGACTTGACTTG | 2,289,150 | 84 |
| 6065. | TAGTTCAGGCTGAAGAGAGAGAGG[A,G]AAGAGAGAGAAACTCTCTTTCTCAT | 2,289,286 | 84 |
| 6066. | AGAGAGAAAATAGAGAGAGAAAGT[T,C]CAATTTTAGAGAGAGAAAATACTAG | 2,289,333 | 84 |
| 6067. | GAGAGAGAATTTTAGAGAGAGAAA[A,G]TAGAGAGAGAAAGTTCAATTTTAGA | 2,289,348 | 84 |
| 6068. | CACAGATCAAAAATTCATCATGAG[A,G]ATCATTTAAATTCATCATCATTCTT | 2,289,437 | 84 |
| 6069. | GTCGGTGTACCGTCCGACGATCAG[A,G]GATCAAAAATTCATCATGAGAATCA | 2,289,458 | 84 |
| 6070. | CATGATAAATAAAATCTAAAAATA[T,C]CTGATCTGATCAAAGTGGATGTCGG | 2,289,503 | 84 |
| 6071. | GTCGGTGTACCGTCCGACGATCAC[A,G]GATCAAAAATTCATCATGAGAATCA | 2,289,503 | 84 |
| 6072. | CACAGATCAAAAATTCATCATGAG[A,G]ATCATTTAAATTCATCATCATTCTT | 2,289,503 | 84 |
| 6073. | AGAGAGAAAATAGAGAGAGAAAGT[T,C]CAATTTTAGAGAGAGAAAATACTAG | 2,289,503 | 84 |
| 6074. | GTGAACAATTCAATAAAATCATGA[T,G]AAATAAAATCTAAAAATATCTGATC | 2,289,522 | 84 |
| 6075. | ATTAGATTAAAGAAAGAGATTGAC[T,C]TGCATTAATATAATCATATAGTTCA | 2,321,352 | 84 |
| 6076. | TTTGCAAACCATGGTCATATGGCC[G,A]CCATTAAATCAAAACTCAATAATTT | 2,321,352 | 84 |
| 6077. | AAGCGGCTATATGGCTTAGAAGAC[T,C]ATCAACTATGCCTAAGACATGCTGC | 2,321,650 | 84 |
| 6078. | AGCAGTTATATGGCCTTTTTTTTG[G,C]CGATAAAGCGGCTATATGGCTTAGA | 2,321,680 | 84 |
| 6079. | AATCTCCTAGCTAAGATTAAGAAA[C,T]GAAATCAAAACCAGTCGGAACCAAA | 2,322,179 | 84 |
| 6080. | TTGCGGAAGTCTGAGTGAAACCAT[G,A]GCTTCTATCCGCGAGCACGGTTTCG | 2,323,099 | 84 |
| 6081. | GCTATTATTGTTATGCACATTGCC[G,A]TCATGATCGGCATCTGGCTTCTCGA | 2,323,632 | 84 |
| 6082. | TGTTTTCTACATTCATGCCATTCT[C,G]ATGTGCATCATGTGGATATATACAT | 2,323,632 | 84 |
| 6083. | TTGCGGAAGTCTGAGTGAAACCAT[G,A]GCTTCTATCCGCGAGCACGGTTTCG | 2,323,632 | 84 |
| 6084. | TTTAAAAGAAAAGAAAATAGGAGC[G,A]TGATTTGACATTCAAATCATGATG | 2,323,632 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6085. | TTTCGGTCTCATTCCTTCCTGAGA[G,T]CTGACGCTTAACGCAGTCGGGCACT | 2,323,684 | 84 |
| 6086. | TTTTCGGTCTCATTCCTTCCTGAG[A,C]GCTGACGCTTAACGCAGTCGGGCAC | 2,323,685 | 84 |
| 6087. | ATTCTTTTGACTTACTTCGCTCTG[A,G]TTACCGGATTCTTCTCCTTCATAAT | 2,323,830 | 84 |
| 6088. | AAGTAGAAGAATTCAGTACGCATC[C,T]ATGATTCTTTTGACTTACTTCGCTC | 2,323,858 | 84 |
| 6089. | GCACAACAATCCAAGTAGAAGAAT[T,G]CAGTACGCATCCATGATTCTTTTGA | 2,323,870 | 84 |
| 6090. | AGTTGCATCCAAACTCACTCTTTC[T,A]GACAAATTATGCACTTCTGCAGCAC | 2,324,017 | 84 |
| 6091. | AACTAAGAAGGATTATTCGAGTCA[A,G]GCAGGTTAGTTGCATCCAAACTCAC | 2,324,049 | 84 |
| 6092. | GTTCAGATATCAGGCATTCTTCAT[T,C]TAAGTTATGAATCCAAACTAAGAAG | 2,324,089 | 84 |
| 6093. | GCATTAAAAAACATGAACACTAAA[T,C]TTAGATGGACAAAAATTGTACCTTA | 2,324,211 | 84 |
| 6094. | TAAAAGTGTTATTCGAAATCAATC[A,G]GGCAACCTCTTTCAAAATTCACCAC | 2,324,262 | 84 |
| 6095. | GTCGTCGGTTCTTGTTTTCTGTAT[T,C]TTTTtCAAGTCTAGGCTTCGGTGAT | 2,324,941 | 84 |
| 6096. | CTTCTGCCAAATTATGCAAGGCCT[T,A]TCTCAATCAGCCAGTGCCTGAAATG | 2,325,385 | 84 |
| 6097. | CTCTCGATATACAAAGGGCAGACC[A,G]TGAATGCTGCCCGGAAAGCTCTGGG | 2,325,487 | 84 |
| 6098. | TCCGAACGAGAATTAGCGTGTTAA[C,G]TTGCTGATTTGCAATAGGATAAGCT | 2,325,890 | 84 |
| 6099. | AGAAGGGGATGAATCTTGTTGTGG[C,T]CCAACGTACCAGTCACCGGTTACAA | 2,325,945 | 84 |
| 6100. | TCCGAACGAGAATTAGCGTGTTAA[C,G]TTGCTGATTTGCAATAGGATAAGCT | 2,325,945 | 84 |
| 6101. | CCAATTCAGTGAGAAACATGATTG[G,A]AGAAAGTTAAATGTGAAACAGTTTG | 2,326,544 | 84 |
| 6102. | GTGAGTGAGAATACACCAATTCAG[T,C]GAGAAACATGATTGGAGAAAGTTAA | 2,326,559 | 84 |
| 6103. | CAAAGCTCTTGGCTCTGTTTTTAA[G,T]GGTCAATTACTTGTGTTTTGAAAAG | 2,326,695 | 84 |
| 6104. | CTAGTATGTTTAAAAAAATGTGGA[T,G]GAGATATTCTTTTCCATATGCCAAT | 2,326,775 | 84 |
| 6105. | CTCAAAATAGATTTTATTTATGCA[C,T]TCGACCAATCTCCTAGTATGTTTAA | 2,326,812 | 84 |
| 6106. | ATACAATGCTCCATCCAACTGCAA[A,C]AGTGGTTTGCCCCCAAATTCAACCC | 2,327,434 | 84 |
| 6107. | CAAAGCTCTTGGCTCTGTTTTTAA[G,T]GGTCAATTACTTGTGTTTTGAAAAG | 2,327,434 | 84 |
| 6108. | GAAACAATAACAAGACTTCTCTTA[A,G]GTGCCAAATTTCATTGCTATCCTGG | 2,327,697 | 84 |
| 6109. | AAGCTAAAGACATGAGAGTGAAGA[T,C]TGAAACAATAACAAGACTTCTCTTA | 2,327,723 | 84 |
| 6110. | TCCAAACCTTTCTGGAGAATTGAA[A,G]AACATATGAAACCAAGAAACATCTA | 2,327,819 | 84 |
| 6111. | AGAAATTATTAGCACTGTGCAGGG[T,A]AATGCATGCATGATTTTAAGCAGCC | 2,327,880 | 84 |
| 6112. | TGAAGCTGCTTTAGAGTAATATGC[G,A]GTATGATGATCAATTTGTTGCCTCA | 2,327,949 | 84 |
| 6113. | TGTGTGTGTGTGTGTGTGTGTGTG[A,T]GAGAGAGAGAGAGAGAGAGATTGGA | 2,328,145 | 84 |
| 6114. | TTCTCTTCTTACAGCTCCGGTTCT[G,A]TTTAGTGCCTACTAGATTTTGTTCA | 2,328,378 | 84 |
| 6115. | CACGATGCTTAACATGTGCAGCGG[C,T]AAACTGTTTTGGTCTTATCAAGAAA | 2,328,852 | 84 |
| 6116. | GTTTGATCTGCGGTGCTTCAACCA[C,T]GATGCTTAACATGTGCAGCGGCAAA | 2,328,874 | 84 |
| 6117. | TCAGATACAGGATACAAGCTTCAT[A,T]TTGCTTGTTCATTCTTGGTTTGATC | 2,328,916 | 84 |
| 6118. | GATCGGTCACTTGCAGAATTTGAT[C,A]AGATTTATGACATTATTGGCATCCT | 2,329,102 | 84 |
| 6119. | ATTCAGATTGGATCTTCTATTCAT[C,T]CATTTCTTGCTAGAGATCGGTCACT | 2,329,141 | 84 |
| 6120. | ATTTTTGAAAGGAAGCCTGAAGAT[C,T]CAGGGTACTATATTCTGCTGTCTAA | 2,329,285 | 84 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6121. | GGCATGGGAGTTTATCAGAAAGAT[G,T]CCAGTGAAACCAGATATTGATGTAT | 2,329,403 | 84 |
| 6122. | CAGAAGAGGCTTGCACTACTACAA[T,C]TCCATGATAGAAGACTATGGTATTC | 2,329,517 | 84 |
| 6123. | CAAGTGTGGGTGTCTAGACCTTGG[G,A]AAGAAGGTTTTTGAGCAGATGACAA | 2,329,730 | 84 |
| 6124. | TTGCATGATTTCTGTGAATAATTC[G,A]CTGATAGATATGTACTGCAAGTGTG | 2,329,772 | 84 |
| 6125. | GATGATCTGTGGAACTATGCATCA[T,C]GGAGATTGGTTGGAGGCCTTGAATC | 2,330,564 | 84 |
| 6126. | TGTTCAGAATTATCGGCTCTCGAT[C,A]AGGGCAGACAGGTCCAGGAATCGAT | 2,330,761 | 84 |
| 6127. | ACCCAGCCTCGTGTTAGGCTCGCA[A,G]CTTGTCAACATCTATGTCAGCCTTG | 2,330,996 | 84 |
| 6128. | CCTCTTCCTTCACCTGAGATCAAC[G,T]ACCAGTCCCCATGAAGCTAGAAAGC | 2,331,086 | 84 |
| 6129. | AAATTCGCCTCCAAGTCCATCTCC[C,G]ACGAGCCAGTACCAGGAATCTCATC | 2,331,167 | 84 |
| 6130. | CCTCTTCCTTCACCTGAGATCAAC[G,T]ACCAGTCCCCATGAAGCTAGAAAGC | 2,331,167 | 84 |
| 6131. | ACCCAGCCTCGTGTTAGGCTCGCA[A,G]CTTGTCAACATCTATGTCAGCCTTG | 2,331,167 | 84 |
| 6132. | TGTTCAGAATTATCGGCTCTCGAG[C,A]AGGGCAGACAGGTCCAGGAATCGAT | 2,331,167 | 84 |
| 6133. | GATGATCTGTGGAACTATGCATCA[T,C]GGAGATTGGTTGGAGGCCTTGAATC | 2,331,167 | 84 |
| 6134. | TTGCATGATTTCTGTGAATAATTC[G,A]CTGATAGATATGTACTGCAAGTGTG | 2,331,167 | 84 |
| 6135. | CAAGTGTGGGTGTCTAGACCTTGG[G,A]AAGAAGGTTTTTGAGCAGATGACAA | 2,331,167 | 84 |
| 6136. | CAGAAGAGGCTTGCACTACTACAA[T,C]TCCATGATAGAAGACTATGGTATTC | 2,331,167 | 84 |
| 6137. | GGCATGGGAGTTTATCAGAAAGAT[G,T]CCAGTGAAACCAGATATTGATGTAT | 2,331,167 | 84 |
| 6138. | ATTTTTGAAAGGAAGCCTGAAGAT[C,T]CAGGGTACTATATTCTGCTGTCTAA | 2,331,167 | 84 |
| 6139. | ATTCAGATTGGATCTTCTATTCAT[C,T]CATTTCTTGCTAGAGATCGGTCACT | 2,331,167 | 84 |
| 6140. | TCAGATACAGGATACAAGCTTCAT[A,T]TTGCTTGTTCATTCTTGGTTTGATC | 2,331,167 | 84 |
| 6141. | GTTTGATCTGCGGTGCTTACCAAC[C,T]GATGCTTAACATGTGCAGCGGCAAA | 2,331,167 | 84 |
| 6142. | CACGATGCTTAACATGTGCAGCGG[C,T]AAACTGTTTTGGTCTTATCAAGAAA | 2,331,167 | 84 |
| 6143. | TGAAGCTGCTTTAGAGTAATATGC[G,A]TGATGATGATCAATTTGTTGCCTCA | 2,331,167 | 84 |
| 6144. | AGAAATTATTAGCACTGTGCAGGG[T,A]AATGCATGCATGATTTTAAGCAGCC | 2,331,167 | 84 |
| 6145. | TTCCGCCTTCGCCACATTCGAATT[C,T]CATCGCAAATTCGCCTCCAAGTCCA | 2,331,198 | 84 |
| 6146. | tGGGGgCAAGCGACACTCTGACAA[A,T]TTGGAAGTCAATAGCCATGCCCAAC | 2,331,344 | 83 |
| 6147. | GAGGTACAGAGCCACCATTTGTTC[C,T]GGAAGCTCTCTACCATTGCAGTGCA | 2,331,417 | 83 |
| 6148. | AAGGCGCAAATGCGAGAGTAATTA[G,T]AATCTACTGGGGCTATTTATATATA | 2,331,922 | 83 |
| 6149. | ATCATTTTGTCTGCAATATGTTTG[A,G]CAGAAGAACAAATCATTTGCAGGCC | 2,332,543 | 83 |
| 6150. | ATATGATTGTTACAGTGTCAGGCT[T,G]GCCAGCCCTGGCTTTGGATTGGGCC | 2,332,885 | 83 |
| 6151. | TGGGTAACGTGCTTACTCTCTGCT[T,C]GAGCCACTTGTATAAAAATCATATA | 2,333,000 | 83 |
| 6152. | AGTTGAGGAAGCCTTGGGTAACGT[G,A]CTTCATCTCTGCTTGAGCCACTTGT | 2,333,014 | 83 |
| 6153. | CTTGGATTCATAAATTCAATTTCT[T,G]TCATCATTGTACATCAGGTTTCTGA | 2,333,169 | 83 |
| 6154. | GATGCTGAATCGACGAAGAAGGTA[G,A]TGTGGGAGAAGTTTCTGTCATGACT | 2,333,237 | 83 |
| 6155. | GAAGACTTGGGTCTCCATGATTTC[A,G]GTATTTGTGCTTAACATCCTTTGGA | 2,333,488 | 83 |
| 6156. | TGAAGACTTGGGTCTCCATGATTT[C,T]AGTATTTGTGCTTAACATCCTTTGG | 2,333,489 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6157. | CTTATTCAGTTGTATTAAATACAA[T,C]TTATTCATGCTGTATAATTTAACTT | 2,333,630 | 83 |
| 6158. | CAAATTTCATATCCTTTTTCTCTA[A,T]GAGGTCCATTTTATGCCATGGTTGT | 2,333,861 | 83 |
| 6159. | TTGGGAAACCAACAGGCCTGACAT[A,G]TACTGTATGTCTACTGCTTTATAAG | 2,333,973 | 83 |
| 6160. | ATTTTAGACAGGAACTGGTACAAT[G,T]CTAAAGTTACAATTCTAAGTTTCAC | 2,334,069 | 83 |
| 6161. | TGATCTTTGTCTGTTATTTTGATG[G,A]CAATGCATTTGTTTTGTGGTCTGTT | 2,334,366 | 83 |
| 6162. | GAAGATCTTCTCATCTTAAGGCCA[T,A]TGCTTCAGGTGCATACCAAATCTTA | 2,334,680 | 83 |
| 6163. | ATGCAATTTGTGATCTATATATGC[G,A]TATAAAGTATCATCAGTGGTAGTGT | 2,335,003 | 83 |
| 6164. | GGTTAATCCTCAGGTTATTTTTAG[A,T]ATTAAACCAGAAATTCTTCCATGCA | 2,335,048 | 83 |
| 6165. | CAGGCTCTTTTTTCTCTCATTTCT[A,T]TGTTCTTCCCTAGACTTTCTGAAAG | 2,335,317 | 83 |
| 6166. | GTAGAAGCATAATTTCTTTGTGGC[T,C]GACCAAGCCTCAAAAGGAGTAATAG | 2,335,421 | 83 |
| 6167. | CAGCCAAGGGCGCCTCGCTTGAGC[A,G]CCTAGGCGCGCCTAGACGAGCACCT | 2,335,645 | 83 |
| 6168. | AGGAGGCTGAGGTGCTTTCAGCCA[A,T]GGGCGCCTCGCTTGAGCACCTAGGC | 2,335,663 | 83 |
| 6169. | AAGCGAGCGCTTAGGCGGTAGAGG[C,T]GCTTGTCTGGAGGAGGCTGAGGTGC | 2,335,698 | 83 |
| 6170. | AAGGCGAGAGCCTTGCGCCTTGCT[C,T]CAAGCGAGCGCTTAGGCGGTAGAGG | 2,335,724 | 83 |
| 6171. | GCCAAAGGCGAGAGCCTTGCGCCT[T,C]GCTCCAAGCGAGCGCTTAGGCGGTA | 2,335,728 | 83 |
| 6172. | TAAAACCTATTTGTTTCTTAATTT[C,T]TTTTAATAAATTACTTAAGTACCTT | 2,335,898 | 83 |
| 6173. | CTGTCAACTTCAATGGAGGGAAGG[G,A]AACTACTCTAGCCGTCCAAAGTCCA | 2,336,009 | 83 |
| 6174. | GAAGAAGGAGAGGAGATTAAGAGA[G,A]GGAGAGGAGAAATAAATTGTGAAA | 2,336,108 | 83 |
| 6175. | AAGACAGCCTTCTTTTCGTACTAA[C,A]ATGTCCTCTGCCCTTCTGTGTTGTA | 2,336,108 | 83 |
| 6176. | TGCTAGCATTGGTCGTTGTACCCT[T,C]TGCTGCTGCCATTGTAAAACTAGTG | 2,336,424 | 83 |
| 6177. | TGACAAAATCATCAAAGTCTGGCA[C,T]TTTATGATAATTCTCTTTGTGGTTC | 2,336,682 | 83 |
| 6178. | ATGCCATGGCTTCTTGACATTATC[C,T]ATCCCTTTATTCGTGGCTGAACCAG | 2,336,798 | 83 |
| 6179. | GGTAGAACAGACAAGCAATATATT[G,T]ACAAGCTTCTTCTTTTtTTCTTCTT | 2,336,950 | 83 |
| 6180. | GACCAACCTGCATACCTTAATTCC[A,G]TCCAGCTACTTGGATGAGTTTTCTC | 2,336,950 | 83 |
| 6181. | GAACCATCCAAATCTCGATCAAGA[A,T]AGGTATGTGGTGGATAATAGGATGA | 2,336,950 | 83 |
| 6182. | TCACCAGAAAATTCATTAAACTTC[G,A]ATCCCTCTGATTAGTCCATCCATCT | 2,337,202 | 83 |
| 6183. | CATCAATAGATTTTACGAACATTG[A,T]TCCAGCAGGGTAGTTCACCAGAAAA | 2,337,262 | 83 |
| 6184. | CAGTTGTAACATATGATGAAGCAT[C,T]AATAGATTTTACGAACATTGATCCA | 2,337,262 | 83 |
| 6185. | CATTTTCTCTCCAGTTGTAACATA[T,C]GATGAAGCATCAATAGATTTTACGA | 2,337,273 | 83 |
| 6186. | CCATGATGAAATTAGTTGCATTAT[C,T]GGTAATTACTTGGACAACATTTGCC | 2,337,361 | 83 |
| 6187. | AGTCATACCAGCCATGATGAAATT[A,T]GTTGCATTATCGGTAATTACTTGGA | 2,337,372 | 83 |
| 6188. | ATTTTAAACAAATGCAAAAACAAT[T,A]TGCAATGTAGAATTAGAAATTAGAA | 2,337,495 | 83 |
| 6189. | TTCGTTTAACTTGTGGAATCTCCC[C,T]AATATCTTCCAACATTAGATCTATG | 2,337,605 | 83 |
| 6190. | CCTCATAATGTTTAGAGCACCAAC[G,A]TGGTTGTAAAATAAAACCGGTAAG | 2,337,675 | 83 |
| 6191. | GTGAACTCCCTCATAATGTTTAGA[G,A]CACCAACGTGGTTGTAAAAATAAAA | 2,337,683 | 83 |
| 6192. | TAATGTGCAAAATATGATTTTTCC[A,C]GCCCTAACTAAGTCCCTCCTTTTTG | 2,337,732 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6193. | CGGACAATTGATTTGATTATAGTT[G,A]GTAAATAAGATGTTATCGGTGATGA | 2,337,732 | 83 |
| 6194. | GATGACCATGTCCGCACTTGATCT[G,T]AGCCAAAAGGCTGAGAAAGGTATAC | 2,337,732 | 83 |
| 6195. | GTGAACTCCCTCATAATGTTTAGA[G,A]CACCAACGTGGTTGTAAAAATAAAA | 2,337,732 | 83 |
| 6196. | TCTTTGTGTGGCTCTCGTGGACAC[C,A]AAATATTTTTATATATGTTTGCACG | 2,337,732 | 83 |
| 6197. | GCCAAGTGGTGATGTGTTTGGTC[C,T]GCGGTCACCTTGCACGATGTATCAA | 2,337,732 | 83 |
| 6198. | CCTCATAATGTTTAGAGCACCAAC[G,A]TGGTTGTAAAAATAAAACCGGTAAG | 2,337,732 | 83 |
| 6199. | AAAGTAAGATATAATGTGCAAAAT[A,C]TGATTTTTCCAGCCCTAACTAAGTC | 2,337,743 | 83 |
| 6200. | CCTGTTCAAACACACTCCAATTAC[G,A]CTCACAACCAGATGCACACCATTCC | 2,337,921 | 83 |
| 6201. | GTACCAATCAATCATTTATCAAAA[T,C]TTGTTTAAAAATATAATATTACTAT | 2,338,016 | 83 |
| 6202. | CTTTAAGCTTTTGATTGTACTTGA[C,T]GTACACTAAATCACTAAGCTTCTTT | 2,338,104 | 83 |
| 6203. | CCTTAACATCCATAGAATTGACTC[C,T]TTGCATGCCAGACTTTCCAATCAAC | 2,338,221 | 83 |
| 6204. | ATGAAATAATGAGGTAGGCGAAGA[C,T]CGATATAACCGCCATTATACCGTTA | 2,338,221 | 83 |
| 6205. | CATCTTTGGTCTGTGAAAGGCTTC[A,G]CCAATTATGTATGCATACCCTCACG | 2,338,221 | 83 |
| 6206. | TATGTATGCATACCCTCACGTGAA[A,G]CCATCATGTGCCCCTTGTATGTATG | 2,338,221 | 83 |
| 6207. | TATTTTTCCTTCCTTCTCTAACAC[T,C]TGCTGCCCTAGCTACTGCACCCCAT | 2,338,305 | 83 |
| 6208. | TAAGTTTGGTGGCTTTGAATGTGA[A,G]GTTGAAGCTGCTGTTGATCTTGATC | 2,338,370 | 83 |
| 6209. | TCAATCTCTTCTTCTGAACTAGAA[C,T]GAATCTCTTCATGATTTAAGTTTGG | 2,338,411 | 83 |
| 6210. | CATACCCAAAAGACTAAAACTTTT[C,T]TGAGTTTTCCTGTTTTCTCCATTACT | 2,338,587 | 83 |
| 6211. | ATTGTGTGTGTGTGTGACAAAA[A,C]AGATTAGCAATGCAATGTCTAGAAC | 2,338,587 | 83 |
| 6212. | AAAAAGTAAATAATAAGACACAAG[C,T]AAATACAAAAAAATTTATAGTGATT | 2,338,587 | 83 |
| 6213. | AACACCATACCCAAAAGACTAAAA[C,T]TTTTTCTGAGTTTTCTGTTTTCTCCA | 2,338,592 | 83 |
| 6214. | GGAAAATAGAAAATAAATATAGT[C,T]TATTCTAAACTAAGTCTTAATTACA | 2,338,700 | 83 |
| 6215. | GGTACTAGGCGCTGAAAAAGCGAA[A,C]ACCTGATTGAAGTCAGATGCCATGT | 2,338,755 | 83 |
| 6216. | TCAAAAGTATTCTATTTATATTTC[T,G]ATAGGTCAAGAATGTTTGGTTTGCT | 2,339,344 | 83 |
| 6217. | TTTTCATCACCTTGGTGATTGCTT[T,C]TGATCCTATTGATGTTGCAAACATG | 2,339,476 | 83 |
| 6218. | TGGACCGCTATGGGAGGTCTAATC[A,G]TGGATCTATTTAAGTTGGGGCTAGT | 2,339,532 | 83 |
| 6219. | CCAACACGCCCCACTGAACTGGCAG[T,G]GCAATTCATCAAAGTTATCACACTG | 2,339,628 | 83 |
| 6220. | GATATGGTTGTAAACTTTGCAATA[T,A]GACCCCCTAATTTCTGAGGCAGGCC | 2,339,838 | 83 |
| 6221. | AGCCATACATCTCCTAGATAACAG[C,T]ATGAGATATGGTTGTAAACTTTGCA | 2,339,867 | 83 |
| 6222. | GTATGATGATTTTCTTAACAAGA[T,C]GGGATTTATGATTTGACCTTTTCTT | 2,339,929 | 83 |
| 6223. | AGTACTGTGATGGCTTATGTTGGAP[G,A]TATCGGCTACATGCCAACAAAATTA | 2,340,368 | 83 |
| 6224. | CTATCTATCTTCTGGTGATACACT[G,A]GTGGAGAAATATACTGAGTTATTGT | 2,340,456 | 83 |
| 6225. | TGCAAAAATTTTATCCATAATAAT[T,G]TAAATTCAATTTTAACTGGCTAACT | 2,340,506 | 83 |
| 6226. | TGGTGAAGAACTTATTATTGGTTT[T,C]TCAATGTGAGATATGACTCCAGCCA | 2,340,622 | 83 |
| 6227. | ACCCCTTAAAATGGTGAAGAACTTA[T,C]TATTGGTTTTTCAATGTGAGATATG | 2,340,753 | 83 |
| 6228. | GTTTTTTAATATATCGGCTACCAT[T,C]GTAGCAGCTATGTTCTATGTTTTTG | 2,340,753 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6229. | TCTGCGAGAAGATTGATTTCATTA[A,T]CAAGCAATTTGTTTTTAATATATC | 2,340,788 | 83 |
| 6230. | ATAGTTCTTGATGTGTTCTCTTCC[G,A]CAAGTTGTATTTCAGAAGTGCTTGT | 2,340,942 | 83 |
| 6231. | TCTGCGAGAAGATTGATTTCATTA[A,T]CAAGCAATTTGTTTTTtAATATATC | 2,340,942 | 83 |
| 6232. | GTTTTTtAATATATCGGCTACCAT[T,C]GTAGCAGCTATGTTCTATGTTTTTG | 2,340,942 | 83 |
| 6233. | ACCCTTAAAATGGTGAAGAACTTA[T,C]TATTGGTTTTTCAATGTGAGATATG | 2,340,942 | 83 |
| 6234. | TGGTGAAGAACTTATTATTGGTTT[T,C]TCAATGTGAGATATGACTCCAGCCA | 2,340,942 | 83 |
| 6235. | TGCAAAAATTTTATCCATAATAAT[T,G]TAAATTCAATTTTAACTGGCTAACT | 2,340,942 | 83 |
| 6236. | CTATCTATCTTCTGGTGATACACT[G,A]GTGGAGAAATATACTGAGTTATTGT | 2,340,942 | 83 |
| 6237. | AGTACTGTGATGGCTTATGTTGGA[G,A]TATCGGCTACATGCCAACAAAATTA | 2,340,942 | 83 |
| 6238. | GTGAACAATTCAATAAAATCATGA[T,G]AAATAAAATCTAAAAATATCTGATC | 2,340,942 | 83 |
| 6239. | GTCTGGAATTACATAGTTCTTGAT[G,A]TGTTCTCTTCCGCAAGTTGTATTTC | 2,340,954 | 83 |
| 6240. | GTAGCCTCGGCCTCTGCGTCGTCC[G,A]ATCCTCCGAGGCCAGTGCTTTACGA | 2,341,157 | 83 |
| 6241. | GTCTGGAATTACATAGTTCTTGAT[G,A]TGTTCTCTTCCGCAAGTTGTATTTC | 2,341,157 | 83 |
| 6242. | GTAGTTCGTCTCCTCCTCTTCCCT[T,C]TCCTTCGTCGGCGGCGGTGGAGGAA | 2,341,340 | 83 |
| 6243. | GATGTAATAGATCTTATTGCCAAA[C,T]CTCGTCCAAGTGATCCATGAAAGGT | 2,342,321 | 83 |
| 6244. | GGCTTTTGAGTTTCATTTTATAA[T,C]TAAGTTTTGGATGTAATAGATCTTA | 2,342,355 | 83 |
| 6245. | AAATAGATCCCTCTTATAGTTCAG[G,A]CTAAATTTTTAAAAATAGAAGATA | 2,342,488 | 83 |
| 6246. | GAATTTCTTTCAACCATCTTAATA[T,C]AGAGCTCTCAAAATAATAAATAAAT | 2,342,773 | 83 |
| 6247. | AAGTCAGCAAATTTCTAGATATCA[T,C]GGAATGTGAAAAGTCACCAAGGAAA | 2,343,250 | 83 |
| 6248. | TCTTTTGGAGTTGATTATGAAGTC[A,G]GCAAATTCTAGATATCATGGAATG | 2,343,269 | 83 |
| 6249. | TCTCTCATACCTGGTGCCAAGTGA[C,A]ATTTTCATTTAAGCTGTAGAGCTGA | 2,343,350 | 83 |
| 6250. | TAGGCTATATAAAATTATATTAAC[G,A]AGTTGTATTTTAGCATTCTAGGTGA | 2,343,425 | 83 |
| 6251. | AGTTCCTTAGGCTATATAAAATTA[T,G]ATTAACGAGTTGTATTTTAGCATTC | 2,343,432 | 83 |
| 6252. | GCTTGGTCAACTCCAAGTAATGAA[T,C]CTCAGATATATCACCCTGATTTGGA | 2,343,558 | 83 |
| 6253. | AATGGAGGGCCTGCCATAAAACCT[G,A]CAAGGCTATGTGGCAGGAGGGAAGG | 2,343,607 | 83 |
| 6254. | AGTTCCTTAGGCTATATAAAATTA[T,G]ATTAACGAGTTGTATTTTAGCATTC | 2,343,607 | 83 |
| 6255. | TAGGCTATATAAAATTATATTAAC[G,A]AGTTGTATTTTAGCATTCTAGGTGA | 2,343,607 | 83 |
| 6256. | TCTCTCATACCTGGTGCCAAGTGA[C,A]ATTTTCATTTAAGCTGTAGASCTGA | 2,343,607 | 83 |
| 6257. | TCTTTTGGAGTTGATTATGAAGTC[A,G]GCAAATTCTAGATATCATGGAATG | 2,343,607 | 83 |
| 6258. | AAGTCAGCAAATTTCTAGATATCA[T,C]GGAATGTGAAAAGTCACCAAGGAAA | 2,343,607 | 83 |
| 6259. | GAATTTCTTTCAACCATCTTAATA[T,C]AGAGCTCTCAAAATAATAAATAAAT | 2,343,607 | 83 |
| 6260. | AAATAGATCCCTCTTATAGTTCAG[G,A]CTAAATTTTTAAAAATAGAAGATA | 2,343,607 | 83 |
| 6261. | GGCTTTTGAGTTTCATTTATAA[T,C]TAAGTTTTGGATGTAATAGATCTTA | 2,343,607 | 83 |
| 6262. | CAACATCAATCTTCAAAATGTTGC[G,T]GGATTACAGCCAATGCATCGCACTT | 2,343,658 | 83 |
| 6263. | TAGGACAAAAAGTTAATTCAGGGA[C,T]TAGGATTATGCCTGGGAATATGAAA | 2,344,033 | 83 |
| 6264. | CAACATCAATCTTCAAAATGTTGC[G,T]GGATTACAGCCAATGCATGGCACTT | 2,344,073 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6265. | AGGCAATCTTCACCCTCCATTAAT[G,A]CCATATGGATATATTTAGGACAAAA | 2,344,073 | 83 |
| 6266. | GATAACCTTCTGTTAGATTATTGT[A,C]GGTTTCTTTTTCCtttttttttttt | 2,344,132 | 83 |
| 6267. | TTTGCAAACCATGGTCATATGGCC[G,A]CCATTAAATCAAAACTCAATAATTT | 2,344,339 | 83 |
| 6268. | TAATCTATCTCTTTGAATCGGACT[G,T]GCACCAGAAAGACTTCGAAATTTGA | 2,344,466 | 83 |
| 6269. | TTTAAAAGAAAAGAAAATAGGAGC[G,A]TGATTTTGACATTCAAATCATGATG | 2,344,609 | 83 |
| 6270. | TGTTTTCTACACATTCATGCCATTCT[C,G]ATGTGCATCATGTGGATATATACAT | 2,344,754 | 83 |
| 6271. | ATGGATAATGTACTAAATAATTTT[A,C]TTTCTCATAATGTTTAGGTGATGAA | 2,344,938 | 83 |
| 6272. | TCTACTCTACCTTTGAAATAGGGC[T,C]ATATGGATAATGTACTAAATAATTT | 2,344,965 | 83 |
| 6273. | TTCCTTTTCCTTTTCAAGGAAATA[G,T]GATGGGCATAGCCTGCTCGAACTC | 2,351,380 | 83 |
| 6274. | TAGAACTCGTTTTTGTAAAGTTCT[G,A]CCACTCATTÅATAATGATTTATTACC | 2,351,468 | 83 |
| 6275. | TTTATGTGCCTTACCATATTAATGT[C,G]TTAATTTCTTAGTATTTTGTTTTGA | 2,351,533 | 83 |
| 6276. | TTATTAGCATGAAGAGGGATATTG[T,C]GAAAGGCCCTCTTTCCCAAGATTCA | 2,351,626 | 83 |
| 6277. | ATCTTCTTTATGCTTTGACCCTGG[C,T]GACAATATCTGATAAAACTAGTCTC | 2,352,077 | 83 |
| 6278. | TCAGAGTAGCAGCCAGCAGGCTGC[A,T]GTTGTGTCGTATGATGGACTCAAGC | 2,352,182 | 83 |
| 6279. | TTTGAAGCATTACCTACTTCAGAT[G,A]GCCAAAATACTCTTTTATTTTtCTT | 2,352,448 | 83 |
| 6280. | AAAAGGCTAATCAATCACAGACAA[A,T]TGAATTTGCCTGCTGTTCCCTCTTC | 2,352,596 | 83 |
| 6281. | CATGGCCAATCATGTCATGCCACT[A,T]GTGCCCACCACACATGCACAGCAAG | 2,352,699 | 83 |
| 6282. | TATGGTCATCACAAGCAGATTCCA[G,A]CCGACTTGATTTTGTTACTTATCCA | 2,352,919 | 83 |
| 6283. | AAAATCCTGCACTTCCTCTCTAAC[T,C]AGATCTTCCACCATATGGTCATCAC | 2,352,957 | 83 |
| 6284. | CAAATTTTAGTTTGTTCCATTAAA[G,A]CCCTCAGTGTGATGAGAAGTAGTTTC | 2,353,008 | 83 |
| 6285. | CATTTCATTGAGAGATTGAATTAT[T,G]AAAATGAACAAGACTAACGCCAGCC | 2,353,134 | 83 |
| 6286. | CTTCATTTCATTGAGAGATTGAAT[T,C]ATTAAAATGAACAAGACTAACGCCA | 2,353,137 | 83 |
| 6287. | GACTTCTCAAATGCAGTAATGTAG[C,G]CAATTTTTATGGTTTCTGACCATGC | 2,353,316 | 83 |
| 6288. | GAGATCGGAAATGATCGATTACTT[G,T]AGCTATGTTTTTCGAATTGAAATTC | 2,353,405 | 83 |
| 6289. | TTTTTCATTCACCTTCCTCTTCTC[A,C]CTCGTATCTACATTTGCAACCTCAA | 2,353,570 | 83 |
| 6290. | GTATGTCGTAGTTGTGATTATATC[G,T]AAATGGATTTAGATCCTTAGCCTCA | 2,356,870 | 83 |
| 6291. | GAGCAAATCCCCAGATCAAGTGCA[C,C]CATAAGGTTGACACATCCCAGTAGT | 2,357,591 | 83 |
| 6292. | ATGCTAGGAGCAAATCCCCAGATC[A,G]AGTGCAGCATAAGGTTGACACATCC | 2,357,598 | 83 |
| 6293. | AGGGCCCCTGGTTGATCACCAACT[A,T]GGTGCTAGTGCATGAACCCTCATGG | 2,358,285 | 83 |
| 6294. | CAGTCAAACTAATGAAAGCTGGAT[T,A]CACACCAATTGTATCTGGCTATAAT | 2,360,884 | 83 |
| 6295. | GTGGACTTGGGTGCTAGCATGCAG[G,A]AGCAACCACTCAAAACAATCTAGAA | 2,361,302 | 83 |
| 6296. | ATATGCCTATTTGATTAAATATAC[C,T]TTAGATGTCAAAAGGGGAGCAAGT | 2,361,358 | 83 |
| 6297. | GAAAAGAAACAATTCATCTATAT[T,G]GCATATACACATAGTTTTCATTCAG | 2,361,499 | 83 |
| 6298. | TCTTAGACAATTGATAGTCAAAAT[T,C]TTGAAAAAGAAACAATTCATCTATA | 2,361,528 | 83 |
| 6299. | ATTTCACCATTTACCAATTGCATA[C,T]GAAATCTAGGAAAATTAAAATAATG | 2,361,933 | 83 |
| 6300. | ATTTGATCCAAGTTATGGAGTTTT[T,G]GTCACAAAATTAAAGAAATATGCCA | 2,362,076 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6301. | CCCACCATATTTGATCCAAGTTAT[G,A]GAGTTTTTGTCACAAAATTAAAGAA | 2,362,084 | 83 |
| 6302. | AGGTTTAGCCAGTCCTTAGTGGAT[G,C]ACCATGAATGTTTGAAGCTCAGTT | 2,362,149 | 83 |
| 6303. | TGTCTAAAATCTTGAAGGACCTAG[G,A]TTTAGCCAGTCCTTAGTGGATGACC | 2,362,171 | 83 |
| 6304. | AGGGAATGAAAGTAAGAGAGAGAG[G,A]GAGAGAGAGAGATTCAAGCTAGCTG | 2,362,501 | 83 |
| 6305. | AATAGATAATTGGTTCAACTTCTT[A,G]TCAAGAGGATATGTCCTCCATGGGT | 2,362,759 | 83 |
| 6306. | TCTAAAGTCTAAACTTCTCTTACC[A,G]ATAAAGGTGAACCAAAATACCATGT | 2,362,908 | 83 |
| 6307. | ATTGGAATATTCGTAAAGAAAGAA[T,G]GCAACTGGCCAGTAACTGAAGAGAC | 2,362,994 | 83 |
| 6308. | AGTTCTCTCCATACATCTTCTACT[C,T]TTGGCTCCACATAGTATTACTGATA | 2,363,134 | 83 |
| 6309. | AAAATATATCTAGAATCTAGGCAC[C,A]TAAAGTTCTCTCCATACATCTTCTA | 2,363,162 | 83 |
| 6310. | TCTATTTATATATATAGTCTTAGC[A,G]GAAATGAATGATCTCTCAAAATGAA | 2,377,225 | 83 |
| 6311. | ATTTTTAGTGATATATATTATGAC[G,A]AAAAGTGGATCTTTGAGTTAGATGC | 2,377,348 | 83 |
| 6312. | TTTTGATTTCTAGATATTTTTAGT[G,A]ATATATATTATGACGAAAAGTGGAT | 2,377,363 | 83 |
| 6313. | AGATTATTAAAACACTTGATTTTT[G,T]ATTTCTAGATATTTTTAGTGATATA | 2,377,383 | 83 |
| 6314. | ATGATCTCATATTATCTTAACCCT[T,C]CATTTTTGCACTCACTAGATGCATG | 2,377,472 | 83 |
| 6315. | TAACAAAATATGATCTCATATTAT[C,G]TTAACCCTTCATTTTTGCACTCACT | 2,377,481 | 83 |
| 6316. | ATTAATTAGTAACCCATATATACC[G,A]TATCGGCACAAAAAATGAAATAGTT | 2,377,659 | 83 |
| 6317. | ATACTGAAAGGGGCAAAATCCTTC[T,C]TATGTACATGAGATAGCTTTGCTCC | 2,377,836 | 83 |
| 6318. | CACATGTTTCGGAGCCGGGCACC[A,G]AGGTTTTATCCATAACATATGAATC | 2,377,941 | 83 |
| 6319. | GAGAGAGAGCTTTTGTGAAGAAAA[T,A]TTTTTTGTGAGGGAGAGATTGGGTG | 2,378,452 | 83 |
| 6320. | AGCATGCACAGGTACGGCCCATGC[G,A]ACTTTCAATGGCCCATCGATGGTCC | 2,378,901 | 83 |
| 6321. | GGTGTGACAAGTTGGGACATCTAG[C,T]CAGAGATTGCTCTCAACTCAGGGAT | 2,379,978 | 83 |
| 6322. | AGGAGATGGTAGACAGAGCGATAG[G,A]AGATCACGATGGGGGGTTCAGGTCC | 2,380,002 | 83 |
| 6323. | AGTAGGAGATGGTAGACAGAGCGA[T,C]AGGAGATCACGATGGGGGGTTCAGG | 2,380,065 | 83 |
| 6324. | TtTTTTCTTTCTGCTGCGATGCGT[G,T]GTATCAAAAAAGTCTTGTGGAGGTG | 2,380,821 | 83 |
| 6325. | TTTTATTTTtTTTTCTTTCTGCTG[C,T]GATGCGTGGTATCAAAAAAGTCTTG | 2,380,829 | 83 |
| 6326. | ACAGGTATGGTGGTTCTGTAGAGA[C,T]CTGAAATCGTGGAGTAGAGGATAGC | 2,381,129 | 83 |
| 6327. | AACTCATCCTGTGGCAACAGAGAC[A,G]GGTATGGTGGTTCTGTAGAGACCTG | 2,381,151 | 83 |
| 6328. | GGATGTTTTGGGCTGATTTTTCAC[A,G]GTCTACAAAGATTTTCATGGATCGA | 2,381,321 | 83 |
| 6329. | TCCATCATGGATCGAAGGATGTTT[T,C]GGGCTGATTTTTCACAGTCTACAAA | 2,381,337 | 83 |
| 6330. | GGGTGGGCATTTTTTCTTAGTTTC[A,G]CACAGTCCATCATGGATCGAAGGAT | 2,381,367 | 83 |
| 6331. | AATGAGCCCAAGATCAGTCCAAAC[A,G]GAGATCGGATGAAAAAGATATGCTA | 2,381,651 | 83 |
| 6332. | GAATAGGATTGACTACATTTGTAA[T,C]AGATTGGATATGATTAATATCTATG | 2,383,756 | 83 |
| 6333. | ACTAAGGCTCTAAACCGGAATAGG[A,G]TTGACTACATTTGTAATAGATTGGA | 2,383,773 | 83 |
| 6334. | ATTAAAGGATAAAGTATATTGAAG[T,C]TGATTGTCACTTTGTTCGTGAGAAG | 2,383,886 | 83 |
| 6335. | GATGAGCTTGTTTTCAAAAGTACT[C,G]TGCCTATGAGACTGTGATGTGATAA | 2,383,974 | 83 |
| 6336. | TTTATATTTTTTCCTCGAACTACT[C,T]ACTGGGAGGCAGTTCTGTATATATT | 2,384,286 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6337. | CATAAAGATACAGAAAGTTGATCG[G,A]TAAGCTTAATTATCTTACAGTCACT | 2,384,375 | 83 |
| 6338. | ATTGTGCATGTGGATGATATTGTA[A,G]CTAGTCACAGGAAGTGATGATACTG | 2,384,662 | 83 |
| 6339. | CTTATTTAGATGGGTCAATTCCAT[T,C]ATCTACATTGTATTTCAACTTTTTA | 2,385,909 | 83 |
| 6340. | TTTTACTGCCAATCTAAAAAAaT[T,C]ATCTACATTGTATTTCAACTTTTTA | 2,386,027 | 83 |
| 6341. | TTCAATTAAATTTGATCCAAATCT[T,C]AATGCTCAATCAAATTTAATTAATT | 2,386,427 | 83 |
| 6342. | TTTAGAAACTACCTAATTAGGATC[A,G]TATGACATAAATAAATGCAACATCT | 2,387,678 | 83 |
| 6343. | TTATAAATTATCATACAATCAACT[G,A]AAAATTAATTTCAAATCTAACATAC | 2,388,111 | 83 |
| 6344. | TGGACTGATATAGATTGGGATTCG[G,A]AAAATTAATTTCAAATCTAACATAC | 2,388,171 | 83 |
| 6345. | ATCTAACAATCGAATGATCAGGCC[T,C]GAGTGTAGCTTGGCCAACCTAACCA | 2,389,338 | 83 |
| 6346. | CCATCAATTTAACAATATCTAATA[G,A]TGATCGGAGCGATAAAGTGGTGGCC | 2,389,739 | 83 |
| 6347. | TGTAGGCTTTGTCATTCTATAATG[G,A]GTAAGAAATGAGATGTAGGATTTTG | 2,390,225 | 83 |
| 6348. | TTGAAACAGATTTTTCATCTCCAA[T,C]ATTAAGAAATTTTTCGCCTTCTTCA | 2,390,715 | 83 |
| 6349. | CACAATCATTGACTTCGAAGATTT[T,C]CTCTTGAGTCAATCGATTTATTCTG | 2,391,078 | 83 |
| 6350. | GGTATTAGTTTCTTCCTCAAGAAA[C,T]TTCTTTTTCAAAAGACTGTCCTAT | 2,391,861 | 83 |
| 6351. | GATTTGATCTAATCAAATCCGACT[C,T]TATAGATTTACTATATTATGCCGGT | 2,391,949 | 83 |
| 6352. | TCTTCATCCTAAATATGTAGGATG[C,A]TTCTTCTAAATTCTTCATAGAGAAC | 2,392,780 | 83 |
| 6353. | AGTTACCATGATGATCTCAGATCG[A,G]AGAAACACTTATACCCATATCCTTC | 2,394,103 | 83 |
| 6354. | CAATCTAATCACTAATCAATCCTT[C,T]AATAATTCATCAACTATTAGTAAAT | 2,394,708 | 83 |
| 6355. | CTCATTCAAATTCAAAGGGAATCA[G,A]AAAGTGAGTGTCAATCCTCTTCTGG | 2,395,119 | 83 |
| 6356. | TCCCTCTCAGAAATGATTTTCCAC[G,A]ATAAAGACTCTCTTTTTGTCGCACA | 2,395,459 | 83 |
| 6357. | GGGAGTGCTAGCTCGCACGAAAGA[C,T]ACTGGATGGTTGATTTATGCTCTTT | 2,395,726 | 83 |
| 6358. | GAAAGAAAAATCGATGGTTCAAAG[C,T]ATGCATTTTCAAAATTTTTTAGCGA | 2,396,107 | 83 |
| 6359. | TGGGGATCTTGTTCCATCGAGTCT[A,G]AGTCTGATTTTAGATGCTTTATTAC | 2,397,108 | 83 |
| 6360. | TTTTGAAATTATTCATTCTAATGT[C,T]TGGGGATCTTGTTCCATCGAGTCTA | 2,397,133 | 83 |
| 6361. | TAGAGGTCATGAGTCCAAAAGGCT[A,G]TACACTCTTGAGATTATGTCTGATT | 2,397,382 | 83 |
| 6362. | TATGTTAGTAAGATTACTCATGCT[G,C]TCAACTGTAATGTTCACTTCTTTCC | 2,397,477 | 83 |
| 6363. | TACTTGCCCCATGCCTTCTCTTTT[C,T]TTAAGTTCTGTTCTGTACTTATCTC | 2,397,547 | 83 |
| 6364. | CTATTACTTGTCTCACCTCTTCCT[C,T]ATGCAATTGGGTCATTGATTCAGGT | 2,397,713 | 83 |
| 6365. | TCTTTATTCGGTCAGGTAAATCTA[T,C]TACTTGTCTCACCTCTTCCTCATGC | 2,397,734 | 83 |
| 6366. | GATCGACTTTTAAGATCCCTCTTT[T,C]CTCCTTCTGTAGTGCATGACCCTTT | 2,398,118 | 83 |
| 6367. | GAGATCAATTATGGTATACATTAT[G,A]GTGTATATTTCTGTTTAAGAAATAT | 2,398,523 | 83 |
| 6368. | TAATCTTTTCTTCTCAAATCACCC[C,T]ACAACCCACTGATGAGATATCTATC | 2,398,635 | 83 |
| 6369. | ATAGATTTTATAACTTAGATTATT[A,G]AGAAAATAGTCTCACATTATTTTAA | 2,399,082 | 83 |
| 6370. | CTTCGTACATCAAAGCATACAACA[G,T]CATATCTCTCCCTGCCTAATCAATC | 2,399,204 | 83 |
| 6371. | TTAAGAGGATGTATCGAAGCCTTC[G,A]TACATCAAAGCATACAACAGCATAT | 2,399,224 | 83 |
| 6372. | GAATATGTGGAAATGATCTAGACC[A,T]CAGAGTAAGAATGTAAACTAATTTC | 2,399,620 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6373. | CATCCAATTTCAGAATCCAAATTG[T,C]GGAATATGTGGAAATGATCTAGACC | 2,399,646 | 83 |
| 6374. | AGGACCCATGCACACACATATATA[C,T]AGTACAGGCATAAATACATACATAT | 2,399,752 | 83 |
| 6375. | TTATTAAAATAAACTCTGGTCGAT[A,G]ATACCCCCAACCTCTTTAGTTATAT | 2,399,805 | 83 |
| 6376. | GCAAGTGCTAAATCAAAAAAGTGA[T,G]TTTATTTATTAAAATAAACTCTCCT | 2,399,835 | 83 |
| 6377. | TAATCAATCTTGCTAAATATCACT[G,A]GCTCTTGGCATGTACAATGTGGCTA | 2,399,974 | 83 |
| 6378. | GATCTCTTCTTGTAATTTTTTTTt[C,T]ATAGTGAAGCTTGCATGCCCCATAG | 2,400,400 | 83 |
| 6379. | GGCGGCAGAGGGCCAATAGAAATC[G,T]ATGGTGGCACAGCTAGGCCGGGTAG | 2,401,004 | 83 |
| 6380. | TGGCCTGACTTGACTTTCATATTT[G,A]TCCATAATTGATCAATAGGTGATTG | 2,401,288 | 83 |
| 6381. | TTAGGAGCCAGAAGGAGCCCAGAA[C,T]GAGGTGGAGCTCTAGATAGAGGTGG | 2,401,471 | 83 |
| 6382. | AATTTTAGATTCTGCATGCACCTA[G,C]CATGTATGTTATAAAAAAGAGCAGT | 2,401,830 | 83 |
| 6383. | ATAATGAAGCTTGCATGCCCCATA[G,A]AGGCGAGCTTTTTGACTGATCCACG | 2,402,895 | 83 |
| 6384. | GAGTATGAGAAAAACTCGAAAATA[A,G]ATGGCACAGCCCACAGAGTGGAATA | 2,403,948 | 83 |
| 6385. | ATGATAAATGGAGTATGAGAAAAA[C,T]CCAGGATGATAAATGGAGTATGAGA | 2,404,038 | 83 |
| 6386. | GACCCTCAGTGGTGCTGAAATAGG[C,T]CCAGGATGATAAATGGAGTATGAGA | 2,404,068 | 83 |
| 6387. | AAGGAGATACGCAGCCCACAGAAC[G,C]GTGAAGGCCGACAGGGGCATCTGAT | 2,404,123 | 83 |
| 6388. | CCCAGGTTTGAATCACGAAAGCAC[G,A]GATTAAATATCAAGATACGGGGGTT | 2,404,181 | 83 |
| 6389. | TGGGCTATGAACAGGGAAAAAATA[G,T]AACAGTCTCTATTAATTCTGTCATA | 2,404,824 | 83 |
| 6390. | AGATGGCAGGGACAGAGATGGACC[A,G]AGGGGATTTAACTAATCCAGTGTTT | 2,405,388 | 83 |
| 6391. | ACATTGTCAAAGATGGCAGGGACA[G,T]AGATGGACCAAGGGGATTTAACTAA | 2,405,398 | 83 |
| 6392. | CACCTTACATCATTGGCAAGAATT[T,C]GAGGGAGGGGAAGGAGATTAGGCCC | 2,405,727 | 83 |
| 6393. | ATGGTTGTGATAAGCATTTGGTGG[C,T]TTGATTTCAAAGCATTACAAAATTG | 2,406,720 | 83 |
| 6394. | ACCCATCGTATAGAGATAATCATG[C,T]CCAGTGATTCCTAAATCTGAAAATA | 2,407,241 | 83 |
| 6395. | TACATTCTTTCATATTTCACCAAA[C,T]AAATGAATTCCTCATCCATCCTTCC | 2,407,334 | 83 |
| 6396. | TCATACAAATATTGTTTGTCCTTT[C,T]TTTTATTTTTTATATTAAATAGAA | 2,407,400 | 83 |
| 6397. | AATAAATTAATTTATTAAATTTAT[T,A]AAATTATTTATTAAATTAAATTAAA | 2,407,585 | 83 |
| 6398. | AATTGATATATAAATAAATTAATT[T,C]ATTAAATTTATTAAATTATTTATTA | 2,407,597 | 83 |
| 6399. | ATATTTTTATTTATTAAATTTAT[T,A]AAATTATTTATTAAATTAAATTAAA | 2,407,762 | 83 |
| 6400. | TTTTTCATTCATATTATTTATATT[T,C]TTTATTTATCTTTAATTTCTGTATA | 2,407,781 | 83 |
| 6401. | GCATCCATGTCTAGTTAAGGTTAT[A,G]AGAGGGAAGATGAATGGGATTGTAA | 2,408,036 | 83 |
| 6402. | CGGCTTCTATGACTTTTTGCCTCA[C,T]CTTTAATTCTCATAAAAATTCTGAG | 2,408,854 | 83 |
| 6403. | GGAAGGACCTCTCTAATCTTTTAA[C,T]CGGCTTCTATGACTTTTTGCCTCAC | 2,408,879 | 83 |
| 6404. | TTAGCTGAACTAATATATTCATTT[T,C]ATTATTGTTATATATTTTCATACTA | 2,409,048 | 83 |
| 6405. | ACAGAGTGAGTATTCATAAATGTA[A,T]ATTTCTTGATAAGAGAACTCGTGAA | 2,409,151 | 83 |
| 6406. | AATAAAaCCCGTTCCACTGGGAT[G,A]CCACCTTAATGGTAACAGAGTGAGT | 2,409,190 | 83 |
| 6407. | TCATTCGCATCTTGGTATTTAATC[A,G]CAGTCCGATATCCGTCGTGATTCGA | 2,409,260 | 83 |
| 6408. | TGGACCAGATGCTGTTTCCAGACG[C,T]CATGTCCGAGCCGTCAGGATATGCT | 2,409,321 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6409. | TTTGCAAGGCCTATCTTTGAAAGA[C,T]GGATTAGGGTATAAGTTAACAAATC | 2,409,765 | 83 |
| 6410. | AATACGCATTTAATATCTGCAGAT[T,C]GATTTTTTCGTTtAAAAATTTTTGA | 2,410,140 | 83 |
| 6411. | TTTATTCAAATATTTTTCAATACG[C,T]ATTTAATATCTGCAGATTGATTTTT | 2,410,158 | 83 |
| 6412. | TTTTTtAATTATGATATTCTATGA[C,T]ATATTATAATCTAATATGTCATAAT | 2,410,242 | 83 |
| 6413. | TTCGATTGATTTATGTTGTTATTA[T,C]TTTTtAACATATATTTAATATTTTt | 2,410,336 | 83 |
| 6414. | CACGTGTGGAAAAGCGAATCCACT[C,G]CGGGCCCAGGAAATTGACTGTGGGC | 2,410,910 | 83 |
| 6415. | TGATTGACATGATGTATGGTACAT[G,A]TGATATGCGGTACAGGATATCTTCT | 2,411,110 | 83 |
| 6416. | ATGAGTGCATACAGTCATACGATC[A,C]AGATAAAATGATTGACATGATGTAT | 2,411,143 | 83 |
| 6417. | TCTTCTTCACGTGGATCAATTATC[A,G]AGATGAGTGCATACAGTCATACGAT | 2,411,170 | 83 |
| 6418. | TTCATAAAAAAAAaTAGATCAAC[G,A]GTATAGAATAGAGCAAAATAATATC | 2,411,267 | 83 |
| 6419. | CAATTCAATATGTTATATTATACA[T,A]CATCTCCCCTACCAATCCAACCTTC | 2,411,441 | 83 |
| 6420. | TGCCGACAAATCATGCACACCATG[T,C]CCCTTGAGGGTGCTCTCTCCGAAAA | 2,411,580 | 83 |
| 6421. | ATCAGGCTACTCCAATGGCTACCT[C,T]CCTTTTTTTCCACACTAAAATCTGC | 2,411,627 | 83 |
| 6422. | TTCACGATTGCTGCACTCCCGCGT[C,A]GATATCTTGCAGAAGATTCCGATGG | 2,412,131 | 83 |
| 6423. | GACCACTCAAAACTATGAAAACAA[C,T]GTCATTTTCCATCCAAGTGTCTTTG | 2,414,650 | 83 |
| 6424. | TGAATATATCCTTAAAATTTTCAG[C,G]TGATGATGTACAAAAaTAAATAAA | 2,415,782 | 83 |
| 6425. | TATTGAAAACTGCATACCAATATA[A,C]GGAGTGCAGTCCTAAATTTTATAGT | 2,416,162 | 83 |
| 6426. | TGCAATACACAGAAGCTATTCATA[T,A]ATTGGTGATCAGCTTTGTGACTAAG | 2,416,662 | 83 |
| 6427. | CTAACGCAATGTGCTCGAAATAGC[T,C]TATTAATGCATTTGTGATTATTGAG | 2,416,944 | 83 |
| 6428. | CCCCCGTAGAACTACTGCAGTCAA[T,A]AAAAGAATTATAGAACGAACTAACT | 2,417,921 | 83 |
| 6429. | TTTTAAATGCACAAAATTCTCATG[A,G]TGGTGGTGAGAAAGAATAAAATATA | 2,418,347 | 83 |
| 6430. | TACTTTCTTCTTGCCTTTTTTTt[G,T]GGGGCGATAAAATGACGGTAGAGTC | 2,418,861 | 83 |
| 6431. | TTCCAGCAAATGAGATGGGCCCTT[C,T]AGCATTCGACCGACCGTTAACCATG | 2,420,049 | 83 |
| 6432. | TGTTGGCGTTTTAATTTTATTTCC[T,C]CATAAATGATTAGAAGAGTACAGTT | 2,420,252 | 83 |
| 6433. | ATATACCAAATCATCAAGTGTCCA[T,C]GGGAGGTGGAGGACATTAGAATAAA | 2,420,324 | 83 |
| 6434. | AAAATGCTAATTGGTGCTTATACA[G,T]TTCTGCATAGCTGCTTAAATTCTAA | 2,420,643 | 83 |
| 6435. | ATAATCTCAAAATATAAATTTTAT[A,T]CGTCTTATACTAAATCCTTTTTTTT | 2,420,791 | 83 |
| 6436. | GTTCACATCTTTGATACAGCCATT[G,A]AATGCTCTAGCAGCAGTAACCGTTA | 2,420,975 | 83 |
| 6437. | TATACTTTTATGTTGCTTAAGAAA[G,A]CTAGAAAATAAGATACCCATCCGAA | 2,421,287 | 83 |
| 6438. | CCGTTGCTCTCTTTTGTATTGGAC[T,C]CGAAGCAATCCAACCTTACCTTTTC | 2,421,454 | 83 |
| 6439. | GAGAGAGAGGGgAGAGATTCTGGGG[T,C]TGTGTACCTGTTTCCTAGGACGGCA | 2,422,375 | 83 |
| 6440. | CTGCCGAATGCGGAAAGAAAAGAG[G,A]AGAAACAGAAAGAATGTGTTGGGAA | 2,423,025 | 83 |
| 6441. | TCTCTTTCTCCGCTGTACCAATCT[T,G]CGCGTCAATCTAAATCTGTTCAAAAG | 2,424,121 | 83 |
| 6442. | CAGAGAAGAACTGCTGACATGCAC[A,G]AAATGAGGGTATTACCTTCCGATGT | 2,424,558 | 83 |
| 6443. | ATATACAGTATAAGGTAGCCTTCG[T,A]GGAAGTGCATGTTGACTGCTGGAAA | 2,424,629 | 83 |
| 6444. | ATGTGGAATGAGCCTACAGGAGCC[G,A]GATGCTTTTAGGAAGGAATAGACCC | 2,425,412 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6445. | GAACGATCGGCTGTAAATACATAG[A,G]GATCGGTACTTGGAGCATTTAGACT | 2,426,903 | 83 |
| 6446. | AATCGTCATGGTTGTCCGTTGTTG[G,A]TTGATAATAATCGATTGTCGATTGA | 2,427,020 | 83 |
| 6447. | GAGGTCCGAATGAGCATCGGATGG[T,G]GACTCTGATATATCGATGATCTTCA | 2,427,085 | 83 |
| 6448. | TAACCGTTTATAATGGTTAGGTTC[C,T]GCATATTCCGATTTTATGTGATCGT | 2,427,186 | 83 |
| 6449. | TTTTTATTGTACTAAATTATCGGA[C,T]CATAATCGTGGAGTTCATAGGCTGT | 2,427,269 | 83 |
| 6450. | GTATGGGGTGAGAATTTGCCAGTG[C,T]TCATCTGTTATGTAGGTTTGAGCGT | 2,436,866 | 83 |
| 6451. | TTGAGTATGGGGTGAGAATTTGCC[A,G]GTGCTCATCTGTTATGTAGGTTTGA | 2,436,870 | 83 |
| 6452. | CAGTTGTAGTCTAGGCGATTGAGT[A,G]TGGGGTGAGAATTTGCCAGTGCTCA | 2,436,888 | 83 |
| 6453. | GGGGACCAGGTAGGCTTTTGTTGC[A,T]GAAACAAACTGACGATACAATATGA | 2,436,978 | 83 |
| 6454. | TTATACATCATTGATGTTACTAAC[G,A]AGCGATCAAAGAGAAGGATGCAGAC | 2,437,152 | 83 |
| 6455. | TCTTTTTCCAAGTTATACATCATT[G,A]ATGTTACTAACGAGCGATCAAAGAG | 2,437,164 | 83 |
| 6456. | GAGTGGGCTATGGTCTGAATTTAC[G,A]TCTGAAGTTTTTCTCTTGCTTTTT | 2,437,213 | 83 |
| 6457. | ATTGATTCTCTGTTTTGCCTTCCT[A,G]TGAAAACCTTTAACAGTGGCACCTA | 2,437,278 | 83 |
| 6458. | TTTATGATGCATGGAGGCATTAAC[G,A]GTAATTGATTCTCTGTTTTGCCTTC | 2,437,306 | 83 |
| 6459. | AAATATGTACTTGCATAAGACAAT[A,G]GTCTTTGCCATATCCCTTATTGCTT | 2,437,385 | 83 |
| 6460. | TTATGATGTCAAGGAATTTCATTC[C,A]ATGAAAATTGTAAGTAATTTTGGCA | 2,437,820 | 83 |
| 6461. | TCGTTTCTTCTTCTTCTTCTTCTt[T,C]TTTTTGGGTAAAGGGAGCATAATTT | 2,437,957 | 83 |
| 6462. | GAATCCATTTGTTACAAGGTTTAC[C,T]GGACCAAATTTTCAGGAATGTGGTA | 2,438,149 | 83 |
| 6463. | CTGGGTGATTGGAGGGCTTTCCTC[C,T]CTTGGTGATCATCCATTTGTACCCA | 2,438,300 | 83 |
| 6464. | CTFFFTGATTGGAGGGCTTTCCTC[A,G]CACTTGTTTGCAATTATTTATGGAC | 2,438,551 | 83 |
| 6465. | GCATTGCCCGGTATGGTATGCATA[C,T]GGTGGCAAGCTTAGGTTATTTGAAA | 2,438,993 | 83 |
| 6466. | CATATGTTCGGCTAGATAGTGGCC[G,A]ATGGGAAGCAAGGGATCTTTAAAGA | 2,439,296 | 83 |
| 6467. | AACATCTGCAACACGTGAAGATCT[C,T]CTAAAAGAAGCAATTCATGTAATAA | 2,439,553 | 83 |
| 6468. | TTTTGTAATTTGTAATCATAACCT[G,A]TGAAAGTCCTCGTTATTTTTGCAG | 2,439,932 | 83 |
| 6469. | CTTTGTGGCAATTCTCTGGCACTC[G,A]CCTGCGAAAATTGTGTTTAAGTGTC | 2,440,066 | 83 |
| 6470. | ATTTGCTTGCAAATTCCAAATCTG[G,T]GCAATGCAGTCTGTTCCAGATAATA | 2,440,224 | 83 |
| 6471. | TTCTTTGAGTTGCATCTACTCTAT[A,G]GTGTGTCATTTTGCTGTCAAGAACA | 2,440,273 | 83 |
| 6472. | TGCACATATTCAATGATTTTTCAT[G,A]ATCAATATCTATATAGTTTTTCTTT | 2,440,428 | 83 |
| 6473. | TTGTTTGATGCTCATCCTAAATTC[G,C]GTGCATTTAAGAAAGCTTGTATGCT | 2,440,674 | 83 |
| 6474. | AGATGTATGAAGATGTTTTGATTC[T,C]TGATCTGGATGTATATGCTTGCTTG | 2,440,721 | 83 |
| 6475. | TACAAATGGGATGTATATTCTAAA[C,T]CTTAACTGCAATCACTATGTCAACA | 2,441,097 | 83 |
| 6476. | GCAATTTGTGAAGTCTGTGGTATG[G,A]GTTGATTTGATTTTGCATTTTGGT | 2,441,011 | 83 |
| 6477. | TAGTCCCACATCAGTTGTGCGATA[G,A]GGAGATCTTGAATTTTTATATAGGA | 2,444,151 | 83 |
| 6478. | TTTTATATTTTAAATAATAAAAAT[C,T]ATTTTTAAATTTAAAaTTTTAAAA | 2,444,983 | 83 |
| 6479. | TGTTATGTGCTTCAAATAATACTT[C,T]TGAATTATCTAAAATATATTACCAC | 2,445,062 | 83 |
| 6480. | TCATAAAATACTTCTGATTAATAC[G,T]TTTCACAATTCTAATTTCTCATAAT | 2,445,178 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6481. | TTAATCTATGCCTCTTTATCATCT[A,G]GAGTAGAGGCCTGTCTCTCTGAAAT | 2,445,603 | 83 |
| 6482. | TGAACTCAGACTCTCCTCGGTGGT[C,T]GCAGAGTTGGACCTCCAATCTGTAC | 2,445,745 | 83 |
| 6483. | TCTGCCTCTTCTGACTGGCTCCTT[G,A]ATAGAGGTGGTCCTCCTGAACTCAG | 2,445,786 | 83 |
| 6484. | GTTTTGAATCCTTGCTAGAAAAAG[C,T]ATGTGGATTCAAATCATGAATGGTG | 2,445,904 | 83 |
| 6485. | TCTTATAAAAAAAaTTCATCTTT[T,C]TGAATCTTCTTTATTACTGTCAAGA | 2,446,146 | 83 |
| 6486. | CCATTTATTCTTATAAAAAAAAaT[T,C]CATCTTTTTGAATCTTCTTTATTAC | 2,446,154 | 83 |
| 6487. | TCCAACTGAATCAATCATCTCCTT[C,T]ATCAGTCCAAAGATGTAGGTGGCGT | 2,446,336 | 83 |
| 6488. | TGATGTCCAATAAATATGCGATCG[C,T]CGCTCCATCAGCAACTCGTTGACGG | 2,446,435 | 83 |
| 6489. | GTATCCACTGTCTGTTGCACTTTA[C,T]GAAGCTTCTCAATATTCATCAACAC | 2,446,509 | 83 |
| 6490. | GGGCTGTATCCACTGTCTGTTGCA[C,T]TTTACGAAGCTTCTCAATATTCATC | 2,446,514 | 83 |
| 6491. | TCCGGTCTCAAGATCTCTCCCTCA[A,G]TATTTTTTTGCATCAATGATAGTAC | 2,446,599 | 83 |
| 6492. | CACTGACAAACATCTGATGCAAGG[C,T]TGCTTTCTTCTGTAGAAGGTTATCA | 2,446,682 | 83 |
| 6493. | GACTTCCCTCAGTACCGGCCCTCG[C,T]ATATCTGCTCTCTTCTCACTCGGCA | 2,466,730 | 83 |
| 6494. | CGCTGTCTGCGGTGCGAAGCACCT[T,C]ATATAATGGCTTGATAACCTTCACT | 2,446,832 | 83 |
| 6495. | ATTTGAGCTTTATCTTATTAATCT[G,A]TTTCTTTATTCTCTCCATCATATGA | 2,446,910 | 83 |
| 6496. | TAATGTTGATGTATTCCTAGACAT[A,G]TTTGAGCTTTATCTTATTAATCTGT | 2,446,934 | 83 |
| 6497. | TATGCTGTATTGGAACTTCGGATT[C,T]AAATAGTAAGCTGAAAATAAATTTT | 2,447,105 | 83 |
| 6498. | AGAAGCTCATTATCCATATCTATC[C,T]CGAATATGCTGTATTGGAACTTCGG | 2,447,134 | 83 |
| 6499. | TGCAATTTCAGAATCGGACACCAT[T,C]TTATATATCATATTACGGAGAGCAG | 2,447,186 | 83 |
| 6500. | GTTAAATACTCGCATCTTAATTGA[C,T]CTAACATACCTCTTGTAGACACATA | 2,447,238 | 83 |
| 6501. | ACTATCCAAAATGAATCCATCATT[T,C]AGCTACCAGAATATTAAACAAAATT | 2,447,477 | 83 |
| 6502. | ATAAGGACGAAAGTCAATCAATTA[T,C]GCTCACACCCACTAGAGGAGACCGT | 2,447,571 | 83 |
| 6503. | TTGCTGTGGATAAGGACGAAAGTC[A,G]ATCAATTATGCTCACACCCACTAGA | 2,447,580 | 83 |
| 6504. | AGTTCCAACTCCTGCTGCTTGCCT[G,A]CAAGCCATCCAATCATCAGATCCTC | 2,447,772 | 83 |
| 6505. | TGGCTTATCGGCTGGAATCCTATG[G,T]GGAATATTTGTATCTGCCCACTGTC | 2,447,887 | 83 |
| 6506. | CTTCCTGCTTGAGATGACCTACTT[T,C]GTCTCAGTATTTCTTGCTTAAATAT | 2,448,000 | 83 |
| 6507. | TCATTAATTGAGTCAGGTCTATAC[T,C]GATATCTGCCACATTACATGACTAA | 2,449,158 | 83 |
| 6508. | ATAATCAATCGTACCTTGAAATTC[T,C]TAAGCGACATTAATGATCGCTGTA | 2,449,392 | 83 |
| 6509. | GGAATTTATGGAAGAATATTTTCC[C,T]ATGGATCTTATGCAGAAAATTAGAA | 2,449,490 | 83 |
| 6510. | GATACCAATTGTAGGGAATTTATG[G,A]AAGAATATTTTCCCATGGATCTTAT | 2,449,504 | 83 |
| 6511. | CTAAAAAATATATCATTATTTTAAA[C,T]CAAATGTGAGAGTACTAAATTCATA | 2,450,644 | 83 |
| 6512. | AATCCTCTAAATCAGGGATCAACT[A,C]AAAAATATATCATTATTTAAACCAA | 2,450,666 | 83 |
| 6513. | AATGGGTCACTTTGGTGGTCACCA[T,C]CTATGAAATCTACAATCCTCTAAA | 2,450,705 | 83 |
| 6514. | TATTAATCGAAACATAACTTGTCT[A,G]ATCCTCTTAAATACTGACAGAGGA | 2,450,773 | 83 |
| 6515. | ATTAACCAATCATGCTCATGAATG[G,C]ACTCATTTATCTTGATACACCAATA | 2,450,829 | 83 |
| 6516. | ACTGTGCAAATTTTAATAAATGAG[C,T]CACTTCGGTGGTCACCATCTATTGC | 2,450,903 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6517. | TGCACCAATAGTAAGCAATCAATC[C,A]AAGATTAACATATTTGATTCCATGA | 2,450,969 | 83 |
| 6518. | ATCTATTTGTCCAACTTAATGCAC[C,A]AATAGTAAGCAATCAATCCAAGATT | 2,450,988 | 83 |
| 6519. | TGCAATAGTTTTGCAATGCTTCTC[A,C]ATCCTTTTAAAATATCATACAGAAG | 2,451,133 | 83 |
| 6520. | CACAATCACTAGTCATAAAATATT[T,C]CACTTCAAAATTATAACACATAATA | 2,451,208 | 83 |
| 6521. | ACTATCCTAGACTATGCACAATCA[C,G]TAGTCATAAAATATTTCACTTCAAA | 2,451,224 | 83 |
| 6522. | TGCCAGGCACGGCCCATTGGGGTT[G,A]CTTTTTTAGAAAAAaGAAAAAAAa | 2,451,490 | 83 |
| 6523. | ATATTTTTATTTTtCAAATTATC[T,C]CTAAAATTAGCGTTTTATGATTGT | 2,451,725 | 83 |
| 6524. | ACGAGGAGGGTATTTACAGAAATC[C,T]TAATATTTTTATTTTtCAAATTAT | 2,451,752 | 83 |
| 6525. | GAAAATAGACGAGGAGGGTATTTA[C,T]AGAAATCTAATATTTTTATTTTt | 2,451,760 | 83 |
| 6526. | TTGCTAATTGCTAAATATTGAATA[C,T]TTGCTAAATATTGCTGAAGAGTAA | 2,451,846 | 83 |
| 6527. | GAATAGAGGTAGGTGGAGATTTGG[G,A]GCTTCCTCTTGTGCTCCTCAGGACC | 2,451,960 | 83 |
| 6528. | TTGGTTTCAGAGGAAGCAGAAACA[G,A]TAGTTTCTTCTCCATTAGAAATCAG | 2,452,095 | 83 |
| 6529. | TATACTCTTCAAAATTAAAAGACT[T,C]ATATAAGCTAAAAGATAATTCATTC | 2,452,439 | 83 |
| 6530. | TTACTAAAAAATTAGTCATAGCTA[C,T]TCTTCTAAATGTACATTTACTGGTT | 2,452,520 | 83 |
| 6531. | TATCAATATAATGAGCAGTAGCAG[T,C]AATAAAATAATAACTATCAACATAT | 2,452,643 | 83 |
| 6532. | TTTATTATCTAGAATGTGAAAAAT[C,A]AAAAATACGAAAAGCAAGAATACGT | 2,452,712 | 83 |
| 6533. | TAACAGCAGAATTATTATTAGATA[T,C]ATTGTCAAAAGTAATAGACATAATT | 2,452,811 | 83 |
| 6534. | TTGAACAAAGAGATTTAAAATATG[G,A]CATTCACATCTAATATGCAGTAAAT | 2,452,900 | 83 |
| 6535. | AATAACATCTTGAACCATATGTCA[G,A]ATTGAACAAAGAGATTTAAAATATG | 2,452,926 | 83 |
| 6536. | TTTGCTCTTGAAGTATGAATAAAA[G,A]AAACTGCATTTCTAATTTTTATAAT | 2,452,973 | 83 |
| 6537. | CTATACATATTTGCTTAAATTTTt[A,G]AAGTTTTGCTCTTGAAGTATGAATA | 2,453,002 | 83 |
| 6538. | tCAAAATTTTATCTTTGTTCCAAT[C,A]ATTTTCGATCAATGTAAAACTTAAT | 2,453,176 | 83 |
| 6539. | AAACATCATCATATCTATGTTGTA[C,T]AAATTTTTGGCTAATAAGATATGCT | 2,453,308 | 83 |
| 6540. | CATATCCTATCCCAATACTCATTC[T,C]ATTTAGATTCCATTTTATAAATAAT | 2,453,366 | 83 |
| 6541. | AAGAAGCATGTGTATGTCTCCTAT[C,G]TGCAATGAATGAGAAAATAGATGAT | 2,453,641 | 83 |
| 6542. | GTCATTGTCATCGGATGTTGTATC[G,A]TGTCCACCTTTATCTTGAAGTCTCA | 2,453,995 | 83 |
| 6543. | GTCGGCAGTGTTTGTGTCGTCATT[G,A]TCATCGGATGTTGTATCGTGTCCAC | 2,454,013 | 83 |
| 6544. | AGCAAAATTAAATATAGATGTTAG[A,G]TTTTTTTtGTAAAAaTAAAAAaCCA | 2,454,278 | 83 |
| 6545. | TAGACATGGGCAACAGGCCGGGCC[A,G]CCCAATACACAGCCTGGCCTGGCAC | 2,454,557 | 83 |
| 6546. | TTAGCAAAGTATCATCAACTTTTG[A,G]AGGTTCATCTACTTTGGTAGAATGA | 2,454,617 | 83 |
| 6547. | AATATGAGCAATATATGTGCTTAA[A,G]AAATTTTATAAGCATTATTTCAATG | 2,454,938 | 83 |
| 6548. | ATCCAAATTTCATCAAACATAGTG[A,C]TTGCTCCATTTACGTTTCCATATTT | 2,455,086 | 83 |
| 6549. | CTAAAATGATTCACCTTCTATCAT[A,C]TTCGTAGGCAGTTTATATTCTAAA | 2,455,183 | 83 |
| 6550. | ACTAATGAGGTTAAATAATTACTT[G,A]TAGTCATCATTTTTAAGTTTAACAT | 2,455,274 | 83 |
| 6551. | CTAGTTTCACAATGTAAGCCCTAA[C,T]AGCATCATCGGCATCATACCTAAATA | 2,455,383 | 83 |
| 6552. | TAGGTGCAATACTCTCTAGTTTCA[C,T]AATGTAAGCCCTAACAGCATCATGC | 2,455,398 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6553. | GCAAGAAAAATATTAGGGATAGGG[G,A]TCTCAAACTATTAAACTTAGGTGCA | 2,455,440 | 83 |
| 6554. | CAAATTACATAAGGAGAGAGTTAA[G,A]AGCTTAATGAGCAAGAAAAATATTA | 2,455,475 | 83 |
| 6555. | ATTAGTATTGGATTTCCTACTAAC[G,A]GACAACTCAAAAGAATCTTGTAAAC | 2,455,870 | 83 |
| 6556. | TCTGCATAGTCAATTAAATAACAA[C,T]AATTAGTTCTAGTCCAAACTTTCAT | 2,455,971 | 83 |
| 6557. | TATCTTTAGTATTATCTGCATAG[T,C]CAATTAAATAACAACAATTAGTTCT | 2,455,986 | 83 |
| 6558. | ATTCTTATACCTCTTGTCAGGACA[G,A]TAGAATCTATATACTTTAGTATTAT | 2,456,020 | 83 |
| 6559. | CTGGTATTTCATTAACTGGTTATG[A,G]AGGTGCTATAATCGATTTATATATT | 2,456,234 | 83 |
| 6560. | TGGTCATTAAGAATGATGAGTTTT[C,T]CTTTTTTTtAATGATATCTTTACTG | 2,456,281 | 83 |
| 6561. | TACAAGAGACTGAATTATCCATAT[A,G]GTCAATGCCATAGTCATTCTCATCT | 2,456,343 | 83 |
| 6562. | AATTTTTCTAATGAAGCTGTAGGT[C,T]AAAACGGGTTATCAGTGTTATGATT | 2,456,409 | 83 |
| 6563. | TAGATTTACCTTTTAGGTCTGTAT[G,A]CCATATGTTTTTTCCCACTCTCAAT | 2,456,484 | 83 |
| 6564. | TCTCCCTTGACCACATGTACATCT[C,T]TAGGTTTGCAATTAGACATACCAAA | 2,456,857 | 83 |
| 6565. | CTTTTCTACATTATTCTAAGGACA[C,T]TGGTTTCTACTGAATTTGTCTCCCT | 2,456,900 | 83 |
| 6566. | ATCATATATGCTATATCTGATCTG[A,G]CACAAATCTTTGTATATATAAAACT | 2,456,988 | 83 |
| 6567. | AGCTTATTGCCTTAAGATGATCAG[T,A]CTTTCAAaAAAAAAAaGAGTTGAC | 2,457,137 | 83 |
| 6568. | AAATTCAAAATCACGATAGCTTAT[T,C]GCCTTAAGATGATCAGTCTTTCAAA | 2,457,154 | 83 |
| 6569. | GAAAAGAACATAACTGCACCATAA[T,C]CATAGTAAATCTGAAGTGGTTTCGA | 2,457,401 | 83 |
| 6570. | TATGTATTCAATTACAATGAGTCC[G,C]TTTAATCGAATCTCTGACTGTCAA | 2,457,502 | 83 |
| 6571. | ATATGATGTTCAACAAAAAATAAT[G,A]ATCCCACTAACCAAACATATCAAAA | 2,457,644 | 83 |
| 6572. | ATGCTTAAGGCTTTCATTTAAACA[T,G]CATTTACAAACAACCATATGTGCAT | 2,457,757 | 83 |
| 6573. | TAAGTAATATTTTCATGCTTAAAC[A,G]GCACATTTATGCTTAAGACTTCTAT | 2,457,841 | 83 |
| 6574. | TCTCAAGGCGAATCATGATATCAA[C,T]GATATCATTATAACATAAGTAATAT | 2,457,881 | 83 |
| 6575. | TATACAAAGCTCATCATCAGTCCA[C,T]TTTACGATTTCAAATGAAACCCTTT | 2,458,009 | 83 |
| 6576. | TTCTAGTGATGTAGTGCATGTAGT[A,G]TGAACTTTATATCCATGTGATCAAA | 2,458,060 | 83 |
| 6577. | CCACTAACATTGAATCACAGCAAT[C,T]TTCATATCATTTATTGATATTAGAC | 2,458,151 | 83 |
| 6578. | TTCATTTAGATGGCAACTTAGTCC[G,T]TATTTTTTATAACAAATCAGAATAA | 2,458,420 | 83 |
| 6579. | ATGTCAATAATATGCAATTTAATG[C,T]CATTTTGAGGTTGTATTTATCAATT | 2,458,770 | 83 |
| 6580. | CGCTATCTAACTCAAAATTGAACC[A,C]AAATATGTCAATAATATGCAATTTA | 2,458,799 | 83 |
| 6581. | tCTTTAGTTTTAAGATGACATAGT[A,T]GAAATATAATGTAAATAAATATATG | 2,458,879 | 83 |
| 6582. | AAACCGCCTGGTACGGTGCGTACC[A,C]AGCCGGACCGATGCCTTACCGGTCC | 2,460,433 | 83 |
| 6583. | GTTTGGCGAACTAAGATGTGGGGA[T,A]TGTATTGAAGAATATTTTCCCATGA | 2,460,768 | 83 |
| 6584. | AAAAATACGGTGTAGATGCCACCA[T,C]GATGTTCAAAACCCTAGATATCTCG | 2,460,855 | 83 |
| 6585. | GTCACATTTCAATGATGGTCAACC[T,C]CTACTTCATATTGCTCATATCAAGG | 2,460,983 | 83 |
| 6586. | TCATTTACTTCTGTCTTAATAGAT[G,T]ATTAAAGAACCAAAGGAGTACCTAT | 2,461,089 | 83 |
| 6587. | ATAGATACTTGTATTTGTTCATGC[T,C]GCATACATGCATGACTTCCAAATTG | 2,461,193 | 83 |
| 6588. | TTTATATTTGTTTATTTACTAATC[A,G]TTATATCTGAACTACCTTTATGGTA | 2,461,363 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6589. | TTACTTTTTACTGTTTCATTAAT[G,T]GTTTGTACATTTTTTtCCTGCATA | 2,462,215 | 83 |
| 6590. | AATCCTTATCTCTACAAACTTGTC[A,G]TAAGAAAATAACTACTGCCATCCCC | 2,462,591 | 83 |
| 6591. | TATTTCTCCTTGATTTTATGTATA[A,G]ATCCAAATATGTGTTTATGCACCAA | 2,462,903 | 83 |
| 6592. | TTTTGCCTGTCTTTTCAGTTCTTT[G,A]TGACTATAAGAGTTCTGCTTATTTT | 2,463,360 | 83 |
| 6593. | CAGCTATCGAGAAAGAATATCCAC[G,A]GGAATCAGTCCTAATGAGCTTTAAT | 2,463,820 | 83 |
| 6594. | GAGTTTTAAAACTTTCATCTCCTT[C,A]AAATTGCAGGGAATTGTGCATGCAC | 2,463,939 | 83 |
| 6595. | GAGGCACACCGGTTAGCTGACAT[A,C]CTGATGCTTTTTCAGCCATAAGGAG | 2,464,579 | 83 |
| 6596. | TGACGGACCTGCTATGAATTTATG[T,C]GGAAAGTGGGGAATCAATCATGTCC | 2,464,650 | 83 |
| 6597. | GGGTCTCATCAAGATGGGAGGCCA[C,T]CTCTTGCTTGCAACGAGTGTGGATA | 2,464,707 | 83 |
| 6598. | TCCAAGGCCTTAGTATATCGCTAT[A,G]TTTTTCCAGATCAGAAAGAAAATAC | 2,464,792 | 83 |
| 6599. | TTGAATACATTTGGGTGGTGCAAT[A,G]TTTTTCCAGATCAGAAAGAAAATAC | 2,465,143 | 83 |
| 6600. | TGAAAGTAACTTGCCTTTTAAAAT[G,T]GGCTACCTTCTTTCAACTTTATCTA | 2,465,645 | 83 |
| 6601. | ACGGCTGAAAGTAACTTGCCTTTT[A,G]AAATGGGCTACCTTCTTTCAACTTT | 2,465,650 | 83 |
| 6602. | CTCCTTGGTTTTTATCTTTGCAAA[T,G]CTTCCAGCTCGCTAAGTAATAGCC | 2,465,845 | 83 |
| 6603. | CTTTGTATTGCTAGTCCTCCTTGG[T,C]TTTTATCTTTGCAAATGCTTCCAGC | 2,465,861 | 83 |
| 6604. | GGAATTAAGGATCATGGATTCCAT[A,T]TATCTTTGCCATTTGAAAGCAGTTT | 2,465,952 | 83 |
| 6605. | GTCAACTGCCATACTGAAAAGGTT[A,T]GGAAACATTTATATCAGTACTACTC | 2,466,165 | 83 |
| 6606. | TCTGACTTTGTTCATCTGCTGTGG[G,T]GGTAAAGTAGAAATCTGTATCTAAT | 2,466,334 | 83 |
| 6607. | GATTTTACCTTCCCAGGAGCTGGA[A,G]CCTTCCATACATGTTTTTCATCTTT | 2,466,428 | 83 |
| 6608. | TTGTCGTTTTATGTCTACAAGACA[T,A]ATGAAATTCAATATCTGTAGCATCA | 2,466,569 | 83 |
| 6609. | CCAACCTTTAAATTGTAACTTTTC[C,T]GTACAACTCTTCCAAATTCTTCTTG | 2,466,616 | 83 |
| 6610. | ATATATATATTTATATTTTCTTTTT[T,G]TtATTTtATTTTATGTTATTTTTTG | 2,467,149 | 83 |
| 6611. | CACTGATTCTCTTTTGAATTTGGA[T,C]GTTCCGACCTGTCCCAATCATCTGA | 2,467,259 | 83 |
| 6612. | ATTAAAATATATTTCCTGCCAACT[G,A]GTCTTTTGGTTTTGGTCTTCAGACT | 2,467,833 | 83 |
| 6613. | AAGGAGAGCTGTTGTATTAACTGT[T,G]CTTATTCTTGTAGAACAAAGGAGCA | 2,468,091 | 83 |
| 6614. | GTGGAATCTTTTCTTTTCTTTCCC[T,C]TTTtCTTTTGTCTCCACTAAATCTT | 2,468,620 | 83 |
| 6615. | CTTGTTTCTCTTCCCATTCCTCTT[T,C]CCATTCTTCTGCCAGCACCCCCACC | 2,468,979 | 83 |
| 6616. | CAGGACCGGGTCTTGTTTCTCTTC[C,A]CATTCCTCTTTCCATTCTTCTGCCA | 2,468,990 | 83 |
| 6617. | ATTCGGATCGATTTCTGTGATCTT[T,C]CTCGGATCGAAATATTCATGATCTT | 2,474,169 | 83 |
| 6618. | CTTTGGACTACCAGGATCATGCGA[C,T]GATCTTTTATTCGGATCGATTTCTG | 2,474,202 | 83 |
| 6619. | TAAATCCTTTTCTTTTTGGCTTTG[A,G]CTTTGGACTACCAGGATCATGCGAC | 2,474,227 | 83 |
| 6620. | GTTCACTGTCCAGAATACTGCAAA[T,C]ATTTATAGATTATCTGTTTTATCAA | 2,474,373 | 83 |
| 6621. | AAAGATAAGCAATAACACATAAAA[A,G]TCGATGTTCACTGTCCAGAATACTG | 2,474,403 | 83 |
| 6622. | ATCACATGAATATAATAATATAAT[A,C]TGAAAATAAAGATAAGCATAACAC | 2,474,435 | 83 |
| 6623. | ATCCAGGCCACAGCCAATCATAAG[T,C]ATCCTGTAACTCTGAGAAGAAAAGA | 2,474,529 | 83 |
| 6624. | TTCAATTCTCTGATCAGATACTAT[A,G]ACACTCTTATTTATTCTTCTGCTCA | 2,474,586 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6625. | CAACAATAATTCATAAAATCTTGC[G,A]TAATTACATTTTAAATTTCTTCAAT | 2,474,630 | 83 |
| 6626. | TTATTTCAACAATAATTCATAAAAT[T,C]CTTGCGTAATTACAATTTAAATTTC | 2,474,636 | 83 |
| 6627. | TTATTtTAAAATATAATATTTTTT[C,T]TGTCATGCCTCGAACCCAACATCCG | 2,474,781 | 83 |
| 6628. | GTAGTGGAGAAGATATTGATCAGT[T,C]TTACATAGATCTGAATATTATGGAA | 2,475,317 | 83 |
| 6629. | CGGGGATCGGGGAGGGTTCTCGCA[T,C]CGGGAGGAGGAGGGAGAGGTGGGGC | 2,475,797 | 83 |
| 6630. | GGGCGATTCATAGAGTCATCTTAT[C,A]TTAAGATGACTCTATAAGTTTCCTA | 2,475,987 | 83 |
| 6631. | ATTTTAAACCTAAATATATTCTCA[G,A]GTCTAACAAATAATCCAAGCTCATG | 2,476,937 | 83 |
| 6632. | TGGACATCATCTTTGATCCAAATA[C,T]TCCAACAAAAGACAACCTCCTAATC | 2,477,052 | 83 |
| 6633. | AATCTTAGATACTTATGCAGGTTA[A,C]AGAATCCAAATAACATATTTTGGAC | 2,477,097 | 83 |
| 6634. | TTGATTTAAGGTCGCTTGCCTTCG[T,A]TGCATGCATGGTAACTATCAGACCT | 2,478,290 | 83 |
| 6635. | ACGAGGAAGAAGGGCTTGCACCAG[A,C]GGGGACATCTAAAACTCCAAGTTCA | 2,478,393 | 83 |
| 6636. | GTTTATGCTCTACTATAAATATAT[G,A]TGGACCCGCCGTGAGAATGCCCGTC | 2,478,466 | 83 |
| 6637. | CTTCAATCTGATGAGAAAGTATTT[C,A]GAAATTCCCAGCTTAACTACAACAT | 2,478,789 | 83 |
| 6638. | ACAAGAGTTAACTAAAACAGAATC[T,G]TCAATCTGATGAGAAAGTATTTCGA | 2,478,812 | 83 |
| 6639. | AGGACTGCTTATCTAATAGGCCTA[C,T]TGAAAAATAATTTACAAGAGTTAAC | 2,478,850 | 83 |
| 6640. | ATTTAGATTCATCTCCTGCAACAT[G,A]GAGTAGCAGAAAACCTTTGGTGTTC | 2,478,917 | 83 |
| 6641. | TTTTTTTTTtAGAATTAATTTAG[A,G]TTCATCTCCTGCAACATGGAGTAGC | 2,478,935 | 83 |
| 6642. | GTGTATAGATTCTAATTAAAAGTG[T,C]CATCCATTATTTACACATTTAATTA | 2,479,010 | 83 |
| 6643. | GTGGAAATGGGGTGCCGTAAACTT[A,G]CATAATGCTGATGTGTATAGATTCT | 2,479,047 | 83 |
| 6644. | GGGCGGCGTGAAGGGTGGAAATGG[G,A]GTGCCGTAAACTTACATAATGCTGA | 2,479,061 | 83 |
| 6645. | TTAGAAGATCTAGGTGAACCAATT[A,T]GTTCTTTTAGTAGATACAGTGAATG | 2,479,191 | 83 |
| 6646. | CCTACCCTAATTTCTGTGCCCGTA[G,T]GTCTTTATATGTTTAAATTGCCTTG | 2,479,265 | 83 |
| 6647. | ACTAGTTATGGGCTATCTGAATGA[G,C]AGCAAGTTAACCTGTCTGCCCTCCT | 2,479,536 | 83 |
| 6648. | ATGGAACGGCATCAAACCACATAC[G,C]TTGGTATGAGATAGAAGGATTGGGC | 2,479,951 | 83 |
| 6649. | CTGTGGACCACACGGCTAAAAGAAG[A,C]GTAGTCTTCTGCTTCACCCTATGTC | 2,480,026 | 83 |
| 6650. | CCGATACATGCTGGATAGTAATTT[A,G]AAGTGGGTCTGTCAGCCCATCAAAT | 2,480,677 | 83 |
| 6651. | GATTTGAAAGATTGACTCATATGG[T,C]GGCATTTAAATGCTAAGACTAGAGC | 2,480,868 | 83 |
| 6652. | GATTATTGATATGATGAGCTCTTA[C,T]TTGATAGTTAATATGTGGATATATA | 2,483,324 | 83 |
| 6653. | GTCGTTTCTTGTGATTATTGATAT[G,C]ATGAGCTCTTACTTGATAGTTAATA | 2,483,336 | 83 |
| 6654. | TAAGTATACAATTAGCTGCTATTA[A,C]ATGGCACGGGATTGTTTATAAAATT | 2,483,558 | 83 |
| 6655. | GCTTGCCACATCAAGTCATGGGTT[A,G]GATCATCCAAGCAAGAGGAAAAAAC | 2,484,236 | 83 |
| 6656. | ATGTGGCCTTCATCAATCCGTACA[C,T]GTGATTATTTAAGGAACAATGGATA | 2,484,323 | 83 |
| 6657. | ACATGTGGCCTTCATCAATCCGTA[C,A]ACGTGATTATTTAAGGAACAATGGA | 2,484,325 | 83 |
| 6658. | AACCATCCAAATTTTTTAGATTAC[G,A]AGGAGGCCCACCACCTAACATGTGG | 2,484,367 | 83 |
| 6659. | ATATGGAACATTGAAAATCCTTTC[T,C]AACCATCCAAATTTTTTAGATTACG | 2,484,392 | 83 |
| 6660. | ATATATCTTCATATAGTGTCGGTC[T,C]TTATTTTTTCTTTCTTTTCTTATTG | 2,484,685 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6661. | TTtGATAAAAATAGGAAATAAAAG[T,C]TACTGAAAATCCGGAAGCATCTTCA | 2,484,863 | 83 |
| 6662. | TTTtATTTTTTTTtGATAAAAATA[G,A]GAAATAAAAGTTACTGAAAATCCGG | 2,484,874 | 83 |
| 6663. | GATTTTtATTTTTTTtGATAAAAA[A,T]TAGGAAATAAAAGTTACTGAAAATC | 2,484,877 | 83 |
| 6664. | GGTAAAAAGATACCTTAAAAAGGG[C,A]GTGATCCATTAATTTAAAAACCTAG | 2,485,105 | 83 |
| 6665. | TGATCTCCACGCGGTTTGATGATC[A,T]CCAGGCGAGGGCTCGACAAAAGTG | 2,485,407 | 83 |
| 6666. | TTGAACAAGCACGCCCTTTTCCCA[T,G]ATTAAATCCACTCGCCCTGGACTTT | 2,485,813 | 83 |
| 6667. | ATACGGAGGATTACTTTGAAAATT[T,C]TTAAAGGAAAAGGGGTATGTGTGA | 2,485,886 | 83 |
| 6668. | AGACGTTCATGAACTGGTGGCCGT[A,T]GGAAATGTTGTCCAAACAACTGATA | 2,486,037 | 83 |
| 6669. | TTGGTATGCGTCAAATTGAAAGGC[G,A]CTGCTTCTCAAAGATTGAAACAATG | 2,486,212 | 83 |
| 6670. | CGAGCCACAAGAAAACTTTCCATG[A,G]TGGTCTTGCATACAAAATTTTATTT | 2,486,301 | 83 |
| 6671. | ATACAGTTGTCAACCTAACATGCA[T,C]CGGCACTTAAGGAATGATAGCGTGG | 2,486,357 | 83 |
| 6672. | ATTCTTGTGTACTTCACCTCTTTT[G,T]GTATATTTCTTTTCTTTTTtAAAT | 2,486,783 | 83 |
| 6673. | TAATCTTAATAACCATATGTACAA[T,C]TGTACACTATGCTACAATAGTTCCC | 2,488,451 | 83 |
| 6674. | TTAAGTTAGTAGTATCATTTTGT[A,C]AACATTAAAGAAACAAAACTTTTACT | 2,488,512 | 83 |
| 6675. | CGTCGTCGCCGCCGTCCGGCATGA[A,G]ACGAAGGACGCCGCCGTAATCATCA | 2,489,080 | 83 |
| 6676. | CACGACTGGTGGTAATAGTAGCAG[T,A]CCTAGTGGTGGCAAACAGAAAACAA | 2,489,754 | 83 |
| 6677. | AAATCCCGTGTTGCTTGAATGGCC[G,C]AACGTAGCAACTACTTGGGTTGGAG | 2,490,707 | 83 |
| 6678. | ATTGACCAATCAAAAAGTTAAACA[G,A]CCACTGTATCTTTTTCACGAGATTT | 2,491,016 | 83 |
| 6679. | GTTGATTGACCAATCAAAAGGCTA[G,C]ACAAGTACAGAGCAGTGAATTGACC | 2,491,059 | 83 |
| 6680. | GCTGCTTGTTGGTACTCGACAACA[A,T]ACAATACATCAGTTTTCATCAAAaA | 2,491,133, | 83 |
| 6681. | TGGTAAATGTTTCTTGATGCAATT[C,T]GTCAGCTAATTGACCCATCAAAAGG | 2,491,182 | 83 |
| 6682. | AAGTAACAGCTAACAATGGTGTTT[A,G]TTATACATGAAGAACCTTCACAGCT | 2,491,298 | 83 |
| 6683. | CCACATGCTCAAGAAACTTAGAGA[C,A]ACATATAAAGTAACAGCTAACAATG | 2,491,330 | 83 |
| 6684. | CTCGTCTCCGACTCCGATTGGGAG[C,T]CGGCGAGAGGAGGAAGAAGACTCCC | 2,706,922 | 83 |
| 6685. | TTTGAAGCATGATGGCACCTGAAG[T,A]CTAAGTCATTTGCGGCATTTGAAGA | 2,800,319 | 83 |
| 6686. | GAGGGCTATCAAGGCAACATGGTA[A,T]GGTAACATCATGCCAGTAGCTAGTT | 2,800,654 | 83 |
| 6687. | ACCAAAGAGGTAGTTGATGATTCA[T,A]AAGCTTGTATTTATTAATGACAACA | 2,801,242 | 83 |
| 6688. | ATCTGTTGCACTTAAAAACAAATA[A,G]GAGGAAGGTCCAACCAAAGTAACAA | 2,801,363 | 83 |
| 6689. | CGCGCCCTACTATAAAACGGAGAA[A,G]GCAACAGTGCTGGTAAAGGTTCTTT | 2,801,988 | 83 |
| 6690. | CCATGCCGCGCCCTACTATAAAAC[G,A]GAGAAAGCAACAGTGCTGGTAAAGG | 2,801,994 | 83 |
| 6691. | CACCGATAGGACGCATGACACCGA[T,C]GGGACGCCTGACACCGACGGGACGC | 2,802,698 | 83 |
| 6692. | GTTCGGCCCAACGGCCCCCCGCCA[C,T]GTGGCGGAAGAGTCGTGGCGGTTCG | 2,802,802 | 83 |
| 6693. | CGACCAGCGAGGATCTCCCAGATC[G,A]TGACGCGTGGCAATATCTGGGCCTT | 2,802,919 | 83 |
| 6694. | GGTCGAGATGAAGGCACGACCAGC[G,T]AGGATCTCCCAGATCGTGACGCGTG | 2,802,935 | 83 |
| 6695. | GAAAGAGGAGGACTACGAGGAAGC[G,A]AGGAAGAGAACAAAGGACAATGGGG | 2,803,088 | 83 |
| 6696. | AAAGAGGAAGAAAGAGGAGGACTA[C,T]GAGGAAGCGAGGAAGAGAACAAAGG | 2,803,097 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6697. | AGGAGATATTCTAGCCATTACGCC[G,A]GAACAGAGGTCAAAGAATAAAAGAG | 2,803,141 | 83 |
| 6698. | GACCGACTTCCTCGAGGAGATATT[C,T]TAGCCATTACGCCGGAACAGAGGTC | 2,803,155 | 83 |
| 6699. | CGTTCGGCCCCGAAAGTGAAGAGA[T,C]CTCCACCTCCAGGGTCGATCGAGAA | 2,803,223 | 83 |
| 6700. | GGATGCAGTACTGCTCCCGGAGCC[G,A]ATCAACGTTCGGCCCCGAAAGTGAA | 2,803,253 | 83 |
| 6701. | GCTCTGGGATGCAGTACTGCTCCC[G,A]GAGCCGATCAACGTTCGGCCCCGAA | 2,803,259 | 83 |
| 6702. | AGGGGCGAACAGCTGAAATTGCTC[T,C]GGGATGCAGTACTGCTCCCGGAGCC | 2,803,279 | 83 |
| 6703. | CCTCAGACGGGCTGTTAACCCGAC[C,A]ATTGGCTCCAGGGGCGAACAGCTGA | 2,803,313 | 83 |
| 6704. | TAGAGATGTATTAAAAAGTGAGTA[G,T]TACCACATCATCACAAAATAGATCA | 2,812,889 | 83 |
| 6705. | AGGCCTTTGAGAGATTGTGGCTAC[T,G]CATATCAAATCAAAGAGATTTTCTA | 2,813,811 | 83 |
| 6706. | ACAGTCTAAACTGATGGGCCATG[C,T]GCTGATAAGTCAATCTTCTCATTCT | 2,814,800 | 83 |
| 6707. | ATAAATATATATGCTTTTTTTAAG[C,T]TTTATTCCAGTATCTATGTCATATT | 2,816,787 | 83 |
| 6708. | AATAAATATATATGCTTTTTTTAA[A,A]CTTTATTCCAGTATCTATGTCATAT | 2,816,788 | 83 |
| 6709. | GTCTCACTAAGCAATATCATCTGG[G,A]GTTTTAATGTTCAGCTGAAGCTGAT | 2,816,969 | 83 |
| 6710. | ATCCTTCTATTTCTCTTCAAAGCA[G,A]ATCTGATACAGGATAGAAACTGTTT | 2,817,183 | 83 |
| 6711. | ATAGCAAACAGCAAATGGGGATCC[G,A]AGGGCTGTCGAAACATATAACATGG | 2,818,649 | 83 |
| 6712. | CAATCAGAATTGCTTTATTGTTGG[G,A]GAAAAACATATATTGCCAATTGCAA | 2,819,792 | 83 |
| 6713. | CATATAAAAAaCTTACTTTTTAA[T,A]ATGAAAGAAGGGGAAAAAGGTCTGT | 2,820,563 | 83 |
| 6714. | TGAATGGACTATTTTACCTTTTAT[C,A]TTTTTTtATTTGATGGATTTAAAAT | 2,820,764 | 83 |
| 6715. | TAAAAATTCCAGAATATCAATATC[G,A]CACAACTAATAGAAAGATCAAGTGA | 2,820,811 | 83 |
| 6716. | GCGGCATTTAAAAAACAAGAACCA[C,T]AACTGCAAACTGTTTAAAAGCCGCT | 2,822,617 | 83 |
| 6717. | CTGATACCAGTGACTGAATCTGAA[C,T]CGGATTTGATAAGATCAAATTCGAA | 2,829,117 | 83 |
| 6718. | AAGAACTGATACCAGTGACTGAAT[C,T]TGAACCGGATTTGATAAGATCAAAT | 2,829,122 | 83 |
| 6719. | TGGGAGTCTAATTGTTGAAAAAAT[G,A]CATCAGTTTAGTAATATAACCTAGC | 2,842,761 | 83 |
| 6720. | GAACACCGGTGCTATTGTGGCTAC[T,A]TGTCGAACGAAGAGTACAGGCATTA | 2,843,219 | 83 |
| 6721. | TGAAGGAATCTTATCACGAGACCG[C,T]AATTCAATGGATGCAGATATCCAGC | 2,843,441 | 83 |
| 6722. | AAAATGGTTGTGTGTTTTATACCA[G,A]TGTAAATCTCTACACCGTTGTTACT | 2,843,528 | 83 |
| 6723. | CTTCAAACTTTGGATGGCCATCAA[G,C]CCTGAGATTTACTGCTTGTCTGATG | 2,843,580 | 83 |
| 6724. | TATTCAGGAGGAGAGAGGAGGCTC[G,A]GAGGCTGCTCAAGGAATCGCTTCAA | 2,843,624 | 83 |
| 6725. | TAAAATCTCCTTAATGCAAGTAAT[C,T]GGAGAACAACCAAACAAAGGCGAAC | 2,845,049 | 83 |
| 6726. | ATTTGATCTTTGAGACCGCTGTAC[A,G]TATCCCCTGATTCTTCTGATTTCTA | 2,845,702 | 83 |
| 6727. | TTCCCTCTGCTGTCTGTAATTATT[T,C]GATCTTTGAGACCGCTGTACATATC | 2,845,723 | 83 |
| 6728. | TATTTTTACCCAATTTTTCCCTCT[G,A]CTGTCTGTAATTATTTGATCTTTGA | 2,845,739 | 83 |
| 6729. | TCTTCCTTTGTTAGTAAATTGGGC[C,G]TCAAAAAATCCAATTTTAGTTCACT | 2,847,419 | 83 |
| 6730. | TGAGAGAATAAAATAAGATCAATA[C,T]AAGAGGAACTTACCACTCAATCGTT | 2,847,419 | 83 |
| 6731. | GGAACTTACCACTCAATCGTTGTA[C,T]AAGAGTCTCTCAAGAAAAAATCCCA | 2,847,419 | 83 |
| 6732. | GGCTCAATGTGGACCAAATTTTAA[A,G]GTGTATTTCCTAACAAGCATGCATA | 2,847,419 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6733. | ATTCCTCTTCCTTTGTTAGTAAAT[T,A]GGGCCTCAAAAAATCCAATTTTAGT | 2,847,424 | 83 |
| 6734. | ATATTTGTTGGCTACATTATAGTA[T,G]TGTGATGTGTTTTGGCGGAAATGGG | 2,847,504 | 83 |
| 6735. | ATACAGAAATCAAGGCAGAACCCT[C,A]TTTTTATTTTCTGTTCTTTGAAACT | 2,848,281 | 83 |
| 6736. | AAATTTCTTCAGTCTTTGAGACTT[A,G]TATCTCTATGTTCTTACAATTTTCA | 2,849,480 | 83 |
| 6737. | AGACGGTGCAATCACGGCTTGTGG[C,T]GCTACGGACGTGAAACAGGGGCGAT | 2,850,223 | 83 |
| 6738. | CTCCACCTTTTGCTTTTTTTCCCG[G,A]AGACCCCTTTTTCTCTCTCCTTTTA | 2,854,559 | 83 |
| 6739. | GGTAAGTTTTTAGTTTCATATTTC[C,T]TTGTTTTATCTCTCAAAATCTATAC | 2,855,805 | 83 |
| 6740. | AGATCAGAACACAATTATAATTAT[G,A]TATTGGTAAGTTTTTAGTTTCATAT | 2,855,834 | 83 |
| 6741. | CACTCCAAGGTAAATGTTGGGCAT[C,T]TAGGAGATGTTGTAGGTAAGTTTGG | 2,856,782 | 83 |
| 6742. | CTAGATGGATATTAAGTTCTATGA[A,G]ACATCAGATGACTAGCTTTACTATA | 2,856,918 | 83 |
| 6743. | GCTCTTGGCCAATTAGAGAGTGCT[C,T]CATTTCTCATGCATGGAGTAAGTAG | 2,857,691 | 83 |
| 6744. | CGTGGCCCACTATTTCGACTCATC[T,C]CTTCCGACTCCCAAGACTTCATCA | 2,857,782 | 83 |
| 6745. | ATGAAAACTCTTAAATCTCTACTA[C,T]GTGGCCCACTATTTCGACTCATCTC | 2,857,806 | 83 |
| 6746. | CGATGACCCCTCTTTCTCCCTCCT[C,T]TTCCTCCTCACCCCTTCTCCTCGT | 2,858,318 | 83 |
| 6747. | TCCAAGCCCATCCATCAGCCTTTT[C,G]TCTTCACAGTGACTCCTTTTATGTC | 2,858,506 | 83 |
| 6748. | AACATCCCTCCTTCATCCTCCTCT[C,T]CTTCCTCATTATCCCCTTCTCCTCT | 2,858,704 | 83 |
| 6749. | GATTTGAACTCTAAATCTTTGGAG[G,A]CCTAACCAAAATCTTAATCAATAAG | 2,859,030 | 83 |
| 6750. | TATTAGGTTCAAGTCGGATCATTG[G,A]AATTCAGTAAATCTAGACCATACCT | 2,859,248 | 83 |
| 6751. | GACTTTGTGTCAAGAGCTAAAACA[G,A]ACATTACCTAATTATGTATTTTTA | 2,859,529 | 83 |
| 6752. | ATTAGATTGGATTGTCACGAGTGA[C,T]TTTGGCTCGATCTGGTTCATTGATT | 2,859,877 | 83 |
| 6753. | TTCTCTAAGATAGGGTCGACAGTG[A,G]TAAATGCCGAAGATTTGACCAGGGC | 2,860,349 | 83 |
| 6754. | CAGCCCTATCATTGTCATCTTCTC[C,T]TTGAGCAGCATCGGCAGCAACATCA | 2,860,494 | 83 |
| 6755. | ATGACGTCCGTAGATGTAATAGGT[G,A]TATACTTGCATCAGCATCACGAACT | 2,862,935 | 83 |
| 6756. | ACTGTGATATAAAAATATTGCTAT[C,T]GACAATGGATCGATCGTACCGTACC | 2,863,295 | 83 |
| 6757. | CATCCAAACCCGTTACTTCCAAAA[T,C]TTGACCTTCAATTTAGTATCCCATG | 2,863,493 | 83 |
| 6758. | TCAACTTCAGGACTGCTCTAGCTT[C,A]TATTGAAGGTATACAAGTAGCTTGC | 2,865,195 | 83 |
| 6759. | TGGTGGCTCCACTGGCTCTTGTAT[T,G]TTTCCCCCCTCAATTTAACGAAAA | 2,865,263 | 83 |
| 6760. | CTGCGTCATTTATTTTGATCTTCA[C,A]TTTTTGCCCCAGAAATTCACGAGCA | 2,865,673 | 83 |
| 6761. | GCATGAGCCAAATCAGCACAGACC[A,G]ATATACCGGACCAATAAACGTCATT | 2,866,109 | 83 |
| 6762. | TATGAGCACTTCCAATGGATCTAA[C,A]TTGTAGTGCCCTAAGTAATTATGAC | 2,867,753 | 83 |
| 6763. | TCCACATGGTTCCTGGAGAGTTCT[T,C]GGGCTTCCATATGAGCACTTCCAAT | 2,867,787 | 83 |
| 6764. | CGTCAATTGCCTTTTGACTGCAGT[T,C]GGCTTGGCATCGGAATGTTTGTGCA | 2,867,867 | 83 |
| 6765. | CCGCCAGATGCAGGCTGGGCCTTT[T,C]CACTTAGCTTTAACAAATTGGACTT | 2,869,059 | 83 |
| 6766. | GTGGGACCAAGGAGGAGTGGATGG[T,G]GGTGTGCAGTGAATGGACGAGGGGG | 2,870,470 | 83 |
| 6767. | CATAAGATCAGATTATTGACAAAA[G,A]TTAGCCATATAAGAGATGGATTATT | 2,871,201 | 83 |
| 6768. | TCCAGAATTGTACAAAGACCGAGG[A,T]ATTGTGTTTTACTCATGCCTGATAC | 2,871,834 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6769. | AATTATCAGCCTTTTTTGAATTGT[A,T]ATTGTGTTTTACTCATGCCTGATAC | 2,871,941 | 83 |
| 6770. | GACAATCCATGAAGTTAATTAAAA[A,G]AAaTATGCTTTTGCTATTTATAGAA | 2,872,443 | 83 |
| 6771. | AAGTGGTTATTTAGTCAAATCCAT[T,G]CAATTATAGAATTTTATATTTATTT | 2,873,238 | 83 |
| 6772. | TACTCATAGTTAAAATCATTAAGC[G,T]ATCTCTTGTTACAAGATCCAACAAA | 2,874,531 | 83 |
| 6773. | ATCTGTTGGTTTCCTCAACTTGCA[C,T]ATTCAGGGGAGATGACTGGAAGAAC | 2,875,226 | 83 |
| 6774. | CTTTATCTCTCCCTCTCTTTTTGC[T,G]GGCGCGCGCCTGAAATTAGTATCCT | 2,876,078 | 83 |
| 6775. | ACTCGTTGGATTGAAAATTCTAAT[C,A]ATGGACTTGATCTAACCTAATCCGA | 2,876,988 | 83 |
| 6776. | GACTCAATCCAATCCAAATGACTC[G,A]TTGGATTGAAAATTCTAACCATGGA | 2,877,008 | 83 |
| 6777. | CTGGATTCAAATCTTTTGGATTGA[C,A]GCTGGATTATATTTGGACTCAATCC | 2,877,048 | 83 |
| 6778. | ATATATTTAATATAAAAATATATT[C,T]AGAATTATTTTTGTATCCTAATTTA | 2,877,205 | 83 |
| 6779. | TAAAAAATCCATGGGACTGGATTA[A,G]GTTCTAAAATTGAGTATGTTCTATT | 2,877,424 | 83 |
| 6780. | GCCATATAGAGTCTAGACATAAGA[G,A]CTTCAAATTTAGAGTTATTTTAGAA | 2,878,050 | 83 |
| 6781. | ATTTTTTAAAAATACAAAAGTTAT[T,C]TAAATAATTTACAGATATCTAAATA | 2,878,317 | 83 |
| 6782. | TTTAAATTTAAACTCAAATGGATA[A,G]TTTTTCCTTATTTATCCTACATATT | 2,878,456 | 83 |
| 6783. | TAGCAATTCGAGGTAAATTCCCAT[C,G]GCGGCGCCAATATGAAGCATAAGAA | 2,880,961 | 83 |
| 6784. | TTTCCGTCTTATCCTGCAGCTAGT[A,C]CAGGAAATTTATGCCAAAATGGTGT | 2,881,058 | 83 |
| 6785. | TGCATGGTAAGTATGTATTTCCGT[C,T]TTATCCTGCAGCTAGTACAGGAAAT | 2,881,075 | 83 |
| 6786. | TGGAAACCATGCATGGTAAGTATG[T,A]ATTTCCGTCTTATCCTGCAGCTAGT | 2,881,084 | 83 |
| 6787. | CTATCAGTAAGAAGATATAGAAGC[A,C]GAAGAAATCTCTCGCATATCAAATA | 2,881,283 | 83 |
| 6788. | TACGGATTCTGTTATATAAATGAA[C,T]AGGTATTGCAGTTTTATGCCTCTTC | 2,881,343 | 83 |
| 6789. | GATACGGATTCTGTTATATAAATG[A,T]ACAGGTATTGCAGTTTTATGCCTCT | 2,881,345 | 83 |
| 6790. | AAGCAAAACAACCTTAGATTTCAG[C,T]TCTGCAGATATTCCAAGAGCCTCAG | 2,881,561 | 83 |
| 6791. | TTATCTATCTTTCTTGATATTAAG[T,C]ATGGATGAAAGTCCAACTCCGTCAA | 2,881,962 | 83 |
| 6792. | TGAACCCATAAATGTTGATTACCA[T,A]CTAATAAGAGGGGAAACAAAAGAAA | 2,882,414 | 83 |
| 6793. | ATCTGAACTGCAACAAGTTACTAT[A,G]TTATACATTAAAGAAAGAATGAAAT | 2,882,945 | 83 |
| 6794. | CACCATATTTTGCCAGTAACCCCT[A,G]TTCAGAACTGCAAATTAACATAAAG | 2,883,161 | 83 |
| 6795. | TTATTTTGATAGTTTTAACGGCTG[T,G]TTCTTTGGATTTTCATACCTCATCC | 2,883,410 | 83 |
| 6796. | AATTATGTGCAAGTAAACAGAATT[T,C]ATACCATGTGTTGCAAAAAACACAT | 2,883,716 | 83 |
| 6797. | ATTGGAAGCAATTACGAATACATA[T,A]AATGTGCAACTAAACAAAGTTCATA | 2,883,774 | 83 |
| 6798. | AAATGAAATCAGTGTAACTCCTCA[A,C]AAAATTCTGCAGAACACAGAGATTT | 2,883,825 | 83 |
| 6799. | AGAACAGAGCCTTTTTACTAACAA[G,C]TCACAAAGATGAGAAAAGTCCCAAG | 2,884,081 | 83 |
| 6800. | GAATGATGGGACCTACAGAACAGA[G,T]TCCTTTTTACTAACAAGTCACAAAGA | 2,884,097 | 83 |
| 6801. | AGTAGCAATTGGTTGGATGTGGAT[C,T]GGGTTTGATTTTATCCACACTAGAA | 2,887,764 | 83 |
| 6802. | TTtCGTCTTTCTCTTTTCGTGGTG[C,T]GCAGGGAAACTGAGCTGGTGGGCTA | 2,887,828 | 83 |
| 6803. | CGAGTGAAGCCATATGGACCCCGC[T,G]AACGCCATCCACCTCGCCAGCGAAT | 2,887,908 | 83 |
| 6804. | AGGAAAAATACCATGAAAGTAGTT[T,G]GCAAGCTAACTAATACTATGAAAAT | 2,888,437 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6805. | CAATATTTCTCTCACAATCCCAAC[C,T]AAATACAAAGAATTTGAACTAAAGA | 2,888,488 | 83 |
| 6806. | TTCCCAACTCTATTCAATATTTCT[C,T]TCACAATCCCAACCAAATACAAAGA | 2,888,502 | 83 |
| 6807. | AAATTTTTTGAACCAAATGATAGA[T,C]GGAGATTATCTATTTTCCCAACTCT | 2,888,541 | 83 |
| 6808. | ACTTTCTTTGTATTCCCATAATTT[G,A]TCAGGATTTTACAAAAGGTTAATAA | 2,888,629 | 83 |
| 6809. | CCATCCCTCTATGTTCTATCCAAC[T,C]TTCTTTGTATTCCCATAATTTGGAA | 2,888,651 | 83 |
| 6810. | AAATAAATAAAaaGGTAAAAAaGT[G,A]TCAGGATTTTACAAAAGGTTAATAA | 2,888,724 | 83 |
| 6811. | TATAAATAAAATAAATAAAaGGT[A,C]AAAAaGTGTCAGGATTTTACAAAAG | 2,888,732 | 83 |
| 6812. | TGAAATTTAAAAATATAAGATAAG[C,T]AATATAGATAAAATAAATATATATA | 2,889,853 | 83 |
| 6813. | ATAATTAATTTATAATTTGATTTA[G,A]GTAGTTAACTAATTTTATATAAATA | 2,889,001 | 83 |
| 6814. | TATAAATAATTAATTAAAAATAAT[G,A]AATATTAATAAAAATAGAGTATAAT | 2,889,201 | 83 |
| 6815. | TATAAATACTAAAGAAGTAGAGCA[A,C]TATATAAGGTACAAATTTAAAATTT | 2,889,372 | 83 |
| 6816. | TTTCTCCTCTATTTAATACAAGAG[A,G]AATGAAAGAAAGAATGAATGATATT | 2,889,488 | 83 |
| 6817. | TCCATTCATCCTCTCATATATTTG[G,A]TAAAAtaTAAAAAAaTAGATGAAAA | 2,889,542 | 83 |
| 6818. | ATTTATTTATACTAAAGAAGTAAA[T,C]AATATAGATACTTATAATCTTTGTA | 2,890,200 | 83 |
| 6819. | AAATAAAAAaTGGATGATATTTA[G,C]ATAATATTTTTACTAAAATATCTTT | 2,890,288 | 83 |
| 6820. | AAAATAAATAAAAAAaTGGATGAT[A,A]TTTAGATAATATTTTTACTAAAATA | 2,890,293 | 83 |
| 6821. | TAAAATATGAAAAATGGATAAAA[A,G]TTATTTCTTCTTCTATTTGATATAA | 2,890,341 | 83 |
| 6822. | TCAACTAACATGCACCACTATTAG[C,T]AGGTAAATATCGTGCACATGAATCC | 2,890,495 | 83 |
| 6823. | GAAGCCTAAGCAACCTCATACCTT[A,G]GCTCAACTAACATGCACCACTATTA | 2,890,522 | 83 |
| 6824. | CAATTGTTGCTCCTTTAATCATAT[T,A]TATTGAGGGAAGCCTAAGCAACCTC | 2,890,555 | 83 |
| 6825. | ATCACCATCTCTATGATGATCCTA[C,T]GATTGAGAGCAATTTATGAGTTAAC | 2,890,870 | 83 |
| 6826. | ATCTTTTGGATCGATCACCATCTC[T,C]ATGATGATCCTACGATTGAGAGCAA | 2,890,883 | 83 |
| 6827. | CGAAGAGAGTGATCGTACATCAAT[C,A]TTTTGGATCGATCACCATCTCTATG | 2,890,905 | 83 |
| 6828. | TGTCTGCACACCATAAAATCAAGA[C,T]TCATCTATCCGAAGAGAGTGATCCT | 2,890,939 | 83 |
| 6829. | TCGCTTCGGTGTCTGCACACCATA[A,G]AATCAAGACTCATCTATCCGAAGAG | 2,890,948 | 83 |
| 6830. | TAAACACACAACCGCAGCTATGAA[T,C]ATGCCACTAATGAAAAGTAGATAT | 2,891,060 | 83 |
| 6831. | TCGAATTATGGTGTAGTCAAACTA[T,C]AGCACCCTCAAGATGAATTGTCGAT | 2,891,129 | 83 |
| 6832. | ACTACAGCCAACATACACCTTAAG[A,G]CTCCGTATGGCTAGAAAATCGAATT | 2,891,172 | 83 |
| 6833. | TTAATTTCTGCAATGAATATACTA[C,T]AGCCAACATACACCTTAAGACTCCG | 2,891,192 | 83 |
| 6834. | TCGAGATCTAGAGATTTCATCTTT[A,G]TGCAATTTAATTTCTGCAATGAATA | 2,891,223 | 83 |
| 6835. | CTTTTCTATCTTTCACACTGTCAT[G,A]GCTATAGATTTGTGGACTCAATTTC | 2,891,302 | 83 |
| 6836. | CCAGTAGAACTGAAAGATGAATCT[T,C]ATGTGCTAGCATAACTCCCTTAAAC | 2,891,466 | 83 |
| 6837. | AGTAACATCTAGCAGTATATAGTG[G,A]CAATCCAGTAGAACTGAAAGATGAA | 2,891,495 | 83 |
| 6838. | CATGTAGGAGAAAATGGGTTTAAC[T,C]ATGTGCTAGCATAACTCCCTTAAAC | 2,891,787 | 83 |
| 6839. | CTATCTAATAGGAAACCCAAATCA[T,A]GTAGGAGAAAATGGGTTTAACTATG | 2,891,809 | 83 |
| 6840. | CATGGCCGAACAACATTGGGTGGC[G,A]CCAACATTTGACGCCCCATAAAGCC | 2,891,937 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6841. | AAATCCATATGGGTGTGAGCCCTC[G,A]TCATGGCCGAACAACATTGGGTGGC | 2,891,963 | 83 |
| 6842. | TAGTAGATAAGGCTTATCCCTCTC[C,T]CTCTCTCTTATCTGAATTTGGATGA | 2,892,025 | 83 |
| 6843. | AATCTCTTATCCTCATCCACTAGT[A,G]GATAAGGCTTATCCCTCTCCCTCTC | 2,892,045 | 83 |
| 6844. | TTCAAATCTAAATTTAAATTCAAA[G,A]GAGATCAAATCTCTTATCCTCATCC | 2,892,077 | 83 |
| 6845. | ATCAATGAAAAATTTAGATTGGCA[C,T]GGAGATAGGATAAGGTTGTTGTCGC | 2,892,181 | 83 |
| 6846. | TGTTTTGTCACATAAAATCAATGA[A,G]AAATTTAGATTGGCACGGAGATAGG | 2,892,197 | 83 |
| 6847. | TTTTATACGAATCTGATCAAATCA[T,G]ATGTCTTAAAATAGGACTCTTCTAG | 2,892,272 | 83 |
| 6848. | GACGTCCAAGTGCTTCATATATCA[G,A]AGATAGAAGAGGGAGGAGGCATGGA | 2,892,391 | 83 |
| 6849. | CGAACCCACTAAATAGCGTGTCCA[A,G]CACCCTTGGACGTGGAAGTGCTTCA | 2,892,424 | 83 |
| 6850. | ATGCAAATTTGACAGCCTTCGACA[T,C]TTCGAACCCACTAAATAGCGTGTCC | 2,892,451 | 83 |
| 6851. | TCGAAGCTAGATCACAGCCTTCTC[G,A]TTCTTGATGCAAATTTGACAGCCTT | 2,892,482 | 83 |
| 6852. | CAGGACTCCGATCGAAGCTAGATC[A,G]CAGCCTTCTCGTTCTTGATGCAAAT | 2,892,493 | 83 |
| 6853. | TACTCGAGATTCGCTGTTGAGCTA[C,T]GCACGTGACTGACCTCTATAGGCAT | 2,892,640 | 83 |
| 6854. | CCAAATATAGATCTAAATCAGATC[C,A]ATGAACTATTTATATCAGCATATAA | 2,892,769 | 83 |
| 6855. | TGACCAGACGATCTGATGATAAAC[T,C]TTTCCGAATACTTGGCTACTCAGAT | 2,893,112 | 83 |
| 6856. | TCCTTGCTTCTTCTTATGACCAGA[C,T]GAGCTGATCATAAACTTTTCCGAAT | 2,893,128 | 83 |
| 6857. | CCTACACTTCATAAGAGAATCCAT[C,T]GATTGGACAAGAGAGGGATTATTCC | 2,893,175 | 83 |
| 6858. | TTTCACTGTTCTTCTTTATGGGAT[A,G]TAACCATATGGTGTCCCTACACTTC | 2,893,215 | 83 |
| 6859. | ATCAAATACAAATTTCTTTTCACT[G,A]TTCTTCTTTATGGGATATAACCATA | 2,893,232 | 83 |
| 6860. | GATAGACGTGCCAGCAGCAGGTTT[C,T]AAGATTTTATAAAATTTTAGATTTT | 2,893,433 | 83 |
| 6861. | TCAAAAGGACTAAGTTGCCTCGA[T,C]AGACGTGCCAGCAGCAGGTTTCAAG | 2,893,455 | 83 |
| 6862. | ATCACAGGACTGAGCCGACTAACT[G,A]GTGACAAACAGTAACTCGCTAACCG | 2,893,568 | 83 |
| 6863. | ATGATTTATGAAATTATGTCAGAT[C,T]ATGGACTAGCACAAGTTCAACAAGT | 2,893,766 | 83 |
| 6864. | TAGACTTAATTGAGCTACCCACAC[C,T]CTGAACTCATGATTTATGAAATTAT | 2,893,799 | 83 |
| 6865. | ACAACGGAATTAATTAAAAAACTA[C,T]CATCTATGTACTTACCTTAGACATC | 2,894,043 | 83 |
| 6866. | TAATGGTTATAACTAATCTAGTGG[C,T]ATGGACTAGCACAAGTTCAACAAGT | 2,894,193 | 93 |
| 6867. | CGAGAACAATCAACCCTGTAAAGG[A,G]CCCACACAACTACAATGATAGAAAA | 2,894,302 | 83 |
| 6868. | TCTAATAGTTATAGTTGCATCTTT[T,C]CGATGCAACTGAATCACTGTATCCA | 2,894,354 | 83 |
| 6869. | TCTTGTCCAATGTTTCTCTAAACA[C,T]ATTGCAGCCACCTTCGATCTCTAAT | 2,894,546 | 83 |
| 6870. | TTAAGAGTCTTAAGTGAGTACTAC[G,A]GTCTCACCAATTGACTCACCATCTC | 2,894,639 | 83 |
| 6871. | TTAGGGCTCCTATTTTTTTGATTC[T,C]CCACACTCCTTTAGAAGAGAAGCGA | 2,894,701 | 83 |
| 6872. | TTGGAAGCAGACATTGTTCCTGCA[G,A]AGAGTCAAAGTTTCTAATTAAATTT | 2,894,800 | 83 |
| 6873. | GATGCTTTCTGATCAACGATTGGA[T,C]GGATTGGGAGAGGAGAAAGGTCCTG | 2,894,962 | 83 |
| 6874. | ATAAGATGCTTTCTGATCAACGAT[T,C]GGATGGATTGGGAGAGGAGAAAGGT | 2,894,966 | 83 |
| 6875. | CTCATGTTAGTATTGTAATTCTGG[G,A]GACATTGACGTCAATACATAGCACC | 2,895,047 | 83 |
| 6876. | GCAATAGTCATATCCTCATGTTAT[T,C]ATTGTAATTCGTTGGACATTGACGT | 2,895,061 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6877. | GTTCATATGAATCAGTCAAAGACT[G,A]CAGGATCAGATCAACCTACAAGTCC | 2,895,291 | 83 |
| 6878. | TCAGTAGACTTTCTCTTGAAAAAA[A,G]TCTACTCCATAGCAAGTACAGAGCC | 2,895,438 | 83 |
| 6879. | GTTGTCTTTGTCACAGTAAAAATA[C,T]TTTCTCTTTTCGACGACCTTCTTCT | 2,895,550 | 83 |
| 6880. | CAGGTAAGTAGGGCAGTTCCATTT[T,C]CAATGGTTGTCTTTGTCACAGTAAA | 2,895,580 | 83 |
| 6881. | AGTGTTGTCAGGTAAGTAGGGCAG[T,C]TCCATTTCCAATGGTTGTCTTTGTC | 2,895,588 | 83 |
| 6882. | ACATCCAACTGGATGTAGAAAAAA[C,T]TGTCAGATTTATTTCTATGACGAGC | 2,895,671 | 83 |
| 6883. | CCTCCTACTATCCTCAAGATCCTG[T,G]AAAGAAATGCACAAATGAGCACTAG | 2,895,733 | 83 |
| 6884. | TAGAATCATTTCACTATCCCTTAA[C,T]CTCCTACTATCCTCAAGATCCTGTA | 2,895,757 | 83 |
| 6885. | ATATTTTTCATTAGTAATCGTAGA[G,T]GATAGGTTTTCACGACCATAGTAGC | 2,895,831 | 83 |
| 6886. | GCGTTAAACAAGATACAAAAATCA[G,A]ATTTCTGCTCGCAGTAGATATAAAG | 2,895,902 | 83 |
| 6887. | ATTTCTTAAATAAATAGCACAATG[A,G]TCCTTAAAGAAATTAATTATATAGT | 2,895,958 | 83 |
| 6888. | ATCATTTCTAACTTTATTATTTCT[T,C]AAATAAATAGCACAATGATCCTTAA | 2,895,976 | 83 |
| 6889. | ATAACTAAAAAAGATCATTAATAA[G,A]AAAATCATTTCTAACTTTATTATTT | 2,895,004 | 83 |
| 6890. | TTTTCGTTCACATTATCTCTAAGA[T,C]GTTTAGAACCTATAGCATTCACATT | 2,896,086 | 83 |
| 6891. | TTAATCTTATCTTCGGCAACATGA[C,T]CTAGCCTTAGGTGCCACAAGTACTT | 2,896,134 | 83 |
| 6892. | TGTCTTGAAGGTATGATTCACAGA[C,T]CGAATATGACTCAGAAGTCAATAGA | 2,896,211 | 83 |
| 6893. | CACCAGAGCAAGTCACTCTATGAT[C,T]CTTTCCCCAAGTCTCACAAAAGACA | 2,896,273 | 83 |
| 6894. | CCACTATGAGATAATTCTATTTTT[T,C]TTGAGATAATTCAAAAATTTTTCAC | 2,896,540 | 83 |
| 6895. | ATGTCGACTCACAATCACATTATG[A,G]TCTTTCGAAAGATAGAAATAATATC | 2,896,864 | 83 |
| 6896. | TTCTAAGGCTCATTGCTCTTTGAA[G,A]ACTTTCTCTTCAAGTCTAATTTGTG | 2,896,960 | 83 |
| 6897. | TTGGTTCCTCAAGTTCTAAGGCTC[A,G]TTGCTCTTTGAAGACTTTCTCTTCA | 2,896,973 | 83 |
| 6898. | ATACACTGCAACAGCAAGCAATGT[A,G]CAGATGGACTTAAGCATAGGTATAA | 2,896,424 | 83 |
| 6899. | TCCTCATTATTGATGAAACCAAAG[G,A]ATTTAATTACATCACTGAACTAAGC | 2,897,648 | 83 |
| 6900. | GGAGAATATCATCTATGTACAATA[C,T]AAAGAAAGTGATAGCACTTCATTTG | 2,897,719 | 83 |
| 6901. | TGTTGGGACACATCATTTTGGAGA[A,G]ATGAATGCCATATCTGAAGGGTACT | 2,897,974 | 83 |
| 6902. | ATAAAGAATCTTGCTTATGCATTC[A,G]ATCTCTTTCGATGTGTTGGGACACA | 2,897,012 | 83 |
| 6903. | GCTCCCTATAACGGAAGCATAAAG[A,G]ATCTTGCTTATGCATTCAATCTCTT | 2,898,030 | 83 |
| 6904. | ACAGTATGAGCGATATTAGGTCGT[G,A]TACAAAGTATGACGTACATGAGGCT | 2,898,077 | 83 |
| 6905. | TTTTGAACCAGAACATCTCCTTCA[C,T]AGCCTCTAATGCGGCGATGTATTCT | 2,898,394 | 83 |
| 6906. | GCATCACTCCAAGTTCTGCAATAA[A,T]TTTTTTGAACCAGAACATCTCCTTC | 2,898,421 | 83 |
| 6907. | CTTTCTCAAGGTAATCGCGGATGA[G,A]GTGAAACCATCGCTTGATGTACTTG | 2,898,550 | 83 |
| 6908. | TCTCACTTGACCTAAAGCTAATTG[G,A]CTACAAATCTAAGTTCCATCTTCTC | 2,898,692 | 83 |
| 6909. | TTTACAGACACTATTAAACATAAT[A,G]TAAATAAAAATAACCCAATTTTATT | 2,898,828 | 83 |
| 6910. | CTTATGATTGAGAGTAATTTATGA[A,G]TTAACTAAGATTAGTATATGTTTCA | 2,898,931 | 83 |
| 6911. | TCTTTTGGATCGATCACCATCTCC[A,G]TGATGATCTTATGATTGAGAGTAAT | 2,898,963 | 83 |
| 6912. | TCAAGACTCATCTATCCGAAGAGA[G,A]TGATCATACATCAATCTTTTGGATC | 2,899,002 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6913. | ACTCAGTACTCTTGCTCTTAACAA[A,G]CACCTATACTTTCACTCCGATGTCT | 2,899,065 | 83 |
| 6914. | TTCAATTCTTACAATGAACATACT[G,A]GAGCCAACATACATCTCAAGACTCC | 2,899,274 | 83 |
| 6915. | TTGAAAGATAAACTTCTAGATACA[A,G]TTATCGTGTGATTCGATTCTTCTAT | 2,899,538 | 83 |
| 6916. | GATCCCACAATCCATCAGTGACAC[C,T]CAGCAATATGTAGTGGCAACCTAGC | 2,899,592 | 83 |
| 6917. | AACAACATCATCGAAACTCTTTTC[G,A]ATAGATCAGAACTCTTTTCAATCCAA | 2,899,680 | 83 |
| 6918. | AGCATGATTTTCTTAAATTCAAAA[C,T]TAGGACTCAATTGATCCTAATCCAA | 2,899,836 | 83 |
| 6919. | TTTAACCATGTGCTAGCATGATTT[T,C]CTTAAATTCAAAACTAGGACTCAAT | 2,899,850 | 83 |
| 6920. | CATGGTCGAACAATATTGGGTGGC[A,G]CCAACATTTGACGCCTCGTAAACCC | 2,900,019 | 83 |
| 6921. | CTTTGATTTTCTCTTGTTTTATC[A,G]TACAAAACTAATAAAAAaTTCAGAC | 2,900,294 | 83 |
| 6922. | AACAGAAGGACTCTCTTAGATCCA[C,T]CCTACTTTGATTTTCTCTTGTTTT | 2,900,323 | 83 |
| 6923. | ATGCCTTAAAACAGAAGGACTCTC[T,C]TAGATCCACCCTACTTTGATTTTC | 2,900,332 | 83 |
| 6924. | TATCATAAAGAATCTCTTTTATA[C,T]GAATCTGATCAAATCAGATGCCTTA | 2,900,374 | 83 |
| 6925. | TTCTAGTTTCTTATGCAGTTTTGA[C,T]GGCTTTCGATACTTCGAACCCACCA | 2,900,548 | 83 |
| 6926. | ACCTAGACGGATCCGCAAGCTCCT[C,T]GATCAGATTCAAATCTGATCTCCAA | 2,900,628 | 83 |
| 6927. | CGTCCGACTCACAAGTATCCACTC[G,A]AGCCTGGTCTGAGATGCTCTCTCCT | 2,900,694 | 83 |
| 6928. | ATGCATACGTCCGACTCACAAGTA[T,C]CCACTCGAGCCTGGTCTGAGATGCT | 2,900,701 | 83 |
| 6929. | AGTCCGATAATCAGAGTATCCAAG[G,A]TTCACTGTTCAGCCATGCATACGTC | 2,900,740 | 83 |
| 6930. | AGATCAATAAACTATTTATATCAG[C,T]ATATAAATATAAAACAACATGCAAA | 2,900,835 | 83 |
| 6931. | GAGGCAGTAGAATTCAAAAATTTT[C,T]GATCCGACCCGGTACATCAAACATA | 2,900,895 | 83 |
| 6932. | TAAGAAAGGAGACCGACGGAGACC[G,A]ACGAGAGGTGGCATCAAGCAGAGAA | 2,901,030 | 83 |
| 6933. | AGGTGGCCGTTCGTGAGAGCTCGA[T,C]AAGAAAGGAGACCGACGGAGACCGA | 2,901,054 | 83 |
| 6934. | ACGGACAAAGGGGTGCGGACGGTC[G,A]TCGGTGCTCACACACAACTGCAGGG | 2,901,375 | 83 |
| 6935. | CTTTTAATATCCTGCCAAAGCCAG[G,A]TAAGAAAATAATATTTTAATTAAT | 2,901,854 | 83 |
| 6936. | TTTTATTATCTTATATCAGTGAAT[G,A]ATTAATTTCAACAAAATAATTACAA | 2,902,241 | 83 |
| 6937. | TACACAATATAAAGAATAGAATAC[T,C]AGTTATCATAACAATCATTCAGAAA | 2,902,394 | 83 |
| 6938. | AATGGATTTCTGAAACAACAATTC[A,G]GAGAATATCAACTGCATAGTAATTC | 2,902,564 | 83 |
| 6939. | AACAGTGCAAAAAGAAGCAACAAT[G,A]AATAAGAAAGAACAATTTCACATCT | 2,902,728 | 83 |
| 6940. | ATCCAAAACAAGCTTGTCCAAGC[A,T]CGGTCTATTTAGCAAATTAGTCGAA | 2,902,979 | 83 |
| 6941. | AATTTAAGGGAAAGTAGCTTGTCA[A,G]TAGGGCGAAAGACAAGCAAAGATAT | 2,903,147 | 83 |
| 6942. | ATCAGAGCATAGGTTTCCACAACA[T,G]ACCAACACTATATGCACCAACTTAC | 2,903,240 | 83 |
| 6943. | ACAAAATGCAATGAGCGATCTTCT[G,C]GTTCGTGGCTCTCACAAGGCATGCA | 2,903,299 | 83 |
| 6944. | CTCACTAATTAAATACTTGCAGAG[G,A]CTGGAGACCAGCTCCCACGATGATC | 2,903,369 | 83 |
| 6945. | TAAAAAaTATAAAAATAATAATAT[G,A]AAATATTTTAAATATtTTTTATAAT | 2,903,451 | 83 |
| 6946. | GGAAGAAGAAAAaGATAATAATAA[A,T]AAAaTATTATTTTTTAaAAAaTAAA | 2,903,497 | 83 |
| 6947. | GGTGGCGGGTCCGAAGAAGCAAGG[T,C]CGGGCATAGGAAGGAAGAAGAAAAa | 2,903,534 | 83 |
| 6948. | GGGGACAGAGGAGGCGCAGGTAGC[A,G]CGGACAGGGGGTGGAGGGGGTGGCG | 2,903,577 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6949. | GACGTCGGAGGTGGAGGAACCGCA[G,A]GTGTGCAGGGCTAGGGGAGTATTGC | 2,903,986 | 83 |
| 6950. | AAGATTACGATTAATTCATGTCAC[G,A]ATTAAATTAATTTTTTTtCTAAAAA | 2,904,153 | 83 |
| 6951. | ATTTTTTATCATTAAATTAAACAT[G,A]AATTATTTAGATTTCAACTAATTAA | 2,904,240 | 83 |
| 6952. | AGTACTCCGGAAGATATTTTAGTT[C,T]CTTTATTGTTTATCTATTTTTATC | 2,904,280 | 83 |
| 6953. | ATGTGTAATACATGTCCTAATTAA[G,A]AATTTTACTATAGTACTCCGGAAGA | 2,904,316 | 83 |
| 6954. | ACAACATCATTCCTCTTTTCTTTT[C,T]TTTTTTTTAACTATTTTACTTCATT | 2,904,372 | 83 |
| 6955. | CCTTACCCTTACCAGAGCAAGTTC[G,A]TTCCTTTATTTTCTCTTTAGTTATT | 2,904,424 | 83 |
| 6956. | TGCTTTTTCACTTTCTAACCGACA[A,G]CACTTTCATCCTTACCCTTACCAGA | 2,904,458 | 83 |
| 6957. | AAAACAAAATATCTAATTAATATA[G,A]AAAGTTACTCAACAGAATGGAATTC | 2,904,642 | 83 |
| 6958. | AATTATTATAATTTAATCAAAAAT[C,T]AGAAATTGATGGTGAATATGGAATA | 2,905,296 | 83 |
| 6959. | CTCGAACATTTCCTCGTTGTAAGA[A,T]CCAGGTGAGTACTGCAGAGCGCCGT | 2,905,896 | 83 |
| 6960. | AAGCTGATGAGAAGAAGTTGCCAT[A,G]TGATATATGGGCATTATATATATGT | 2,905,948 | 83 |
| 6961. | ATATATATATATATATGAATCAAT[C,A]CATATCTACCCATACCATATGCGTG | 2,906,203 | 83 |
| 6962. | CTAACAAAGGTTAGGGCTTTATTA[A,C]TTGTCAGTGCAAATATCTTGTCATG | 2,915,782 | 83 |
| 6963. | TTGGGAGTGTACCTAACAAAGGTT[A,T]GGGCTTTATTAATTGTCAGTGCAAA | 2,915,794 | 83 |
| 6964. | CCTTCACTCTTACCAACATGATGA[G,C]TGAACCTGACTCTTCTTTTGTTGAG | 2,915,942 | 83 |
| 6965. | CTGATTAATGAATTCCTTCACTCT[T,C]ACCAACATGATGAGTGAACCTGACT | 2,915,956 | 83 |
| 6966. | ATACCATAATATCTTCCATAGTTA[G,A]AAGCACATCAGCTCTCTCAAGATGC | 2,916,057 | 83 |
| 6967. | TAACCAATGTAGAACCAGTGATCT[T,C]CTTTCTTCTATACCATAATATCTTC | 2,916,091 | 83 |
| 6968. | CTTTCTATATAAGCTAAATTTTtC[C,T]TTAACTCTAACCAATGTAGAACCAG | 2,916,123 | 83 |
| 6969. | AAGCCTTGATCATTGAGAGCCTCA[T,C]GATTTTATTCTTTAAAAAGCATCTC | 2,916,191 | 83 |
| 6970. | AATGGTGTTTAGGTGAAAGGAGCC[C,T]CCCACATTCTATTAAAGGCATGTTG | 2,916,312 | 83 |
| 6971. | CTTTGGGAACATAACCTCTCTAGT[G,C]AAAGGAGAATCTGTGTACTCTACAG | 2,916,362 | 83 |
| 6972. | GACTCAAGATCAAGTAGCAGACAT[A,C]TTCACCAAGATATTACCCAAAGAGA | 2,918,771 | 83 |
| 6973. | TGGATGAGAAGCAAGAAGAAGCTA[T,C]TATACTACTTTGTGACAATAAGTTT | 2,918,935 | 83 |
| 6974. | TGTGGATGAGAAGCAAGAAGAAGC[T,C]ATTATACTACTTTGTGACAATAAGT | 2,918,937 | 83 |
| 6975. | TGAGAAGAATACTAGAAGATGTGG[A,G]TGAGAAGCAAGAAGAAGCTATTATA | 2,918,956 | 83 |
| 6976. | AACATCAAAGAAGCAAGACATTGT[G,A]GTATTGTCATCCACGAAAGTCGAAT | 2,919,045 | 83 |
| 6977. | ATCTTGAACATCAAAGAAGCAAGA[C,T]ATTGTGGTATTGTCATCCACGAAAG | 2,919,051 | 83 |
| 6978. | AGTCAAGTAAGGTTCACTTTGGAG[T,G]GGCACAAAGAGTCTTGAGATACATC | 2,919,250 | 83 |
| 6979. | TTCTAGATTCATGCAAAAGTCAAG[T,C]AAGGTTCACTTTGGAGTGGCACAAA | 2,919,267 | 83 |
| 6980. | GAAGTTAATGAAAAAGATGAAAG[T,C]GATGAAGCCAATGCACCACTATATA | 2,919,388 | 83 |
| 6981. | CAAAACGGAGAATTACAATATTGT[A,G]GTAACACCTTTGATGGTAAATGAGA | 2,919,436 | 83 |
| 6982. | AGATAGTATTGTTATTTATCAAAA[A,G]AAGTATGTAGAAAGCATTCTCAAGA | 2,919,490 | 83 |
| 6983. | ACTTTTTAGAAATTGAAATCATGC[T,C]GAGAGAAGATAGTATTGTTATTTAT | 2,919,521 | 83 |
| 6984. | AAAAGTTTTTAAAGAAGTTCAAGT[G,A]AACCAACACTTTATATGAAGAAGTA | 2,919,704 | 83 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 6985. | AATGAGAAAAGTTTTTAAAGAAGT[T,C]CAAGTGAACCAACACTTTATATGAA | 2,919,710 | 83 |
| 6986. | ATTGAAGCCAACTTCAATGAGAAA[A,G]GTTTTTAAAGAAGTTCAAGTGAACC | 2,919,725 | 83 |
| 6987. | GAGGAAAAATTTATATAGAACAA[C,T]CTCAAGGCTTCATCATCAAAGGTCA | 2,919,848 | 83 |
| 6988. | TTCTTGAATGGGATATTGGAGGAA[A,G]AAATTTATATAGAACAACCTCAAGG | 2,919,866 | 83 |
| 6989. | ACAACTAGACCTCTCATTTCTATG[A,G]TGGCATACAAAGATTGGAAACTACA | 2,919,938 | 83 |
| 6990. | TATCCAGAATTAATTATCAAAAAA[A,T]TTTTGCACCGATTGCTCAACATGAC | 2,919,988 | 83 |
| 6991. | AGCAAAATTAGTAGAAAAGGATA[C,A]TCTCAACTATCCAGAATTAATTATC | 2,920,020 | 83 |
| 6992. | GACAAAATACAATCCGGATGGATC[C,T]ATTCAAAGATACAAAGCAAAATTAG | 2,920,059 | 83 |
| 6993. | AGAATAAGACAATGCAAGAAGAAA[T,A]TGATGTGATTGAGAAGAACAAAACT | 2,920,168 | 83 |
| 6994. | ATACATGAAGTAGTATAGAATAAG[A,G]CAATGCAAGAAGAAATTGATGTGAT | 2,920,184 | 83 |
| 6995. | TAAGTGACATTTATGTCACTTGTA[G,A]CTTTTGCATGATTGAGCCCAAAACT | 2,920,246 | 83 |
| 6996. | TATAAGAATAAGAAGCCTAAGTGA[C,T]ATTTATGTCACTTGTAGCTTTTGCA | 2,920,263 | 83 |
| 6997. | ACTCAAGCTTATCTCCAAATTCCA[C,T]TCCTATAAGAATAAGAAGCCTAAGT | 2,920,291 | 83 |
| 6998. | GAAAATGAAGATGAAGGTTCACCA[C,T]AAACTTCTCAAAGTGTAAGTCCATC | 2,920,352 | 83 |
| 6999. | CTATAGACTTTTTAGTTCGAAGCA[C,T]AACAAGATGATCATAAAAAGAGATA | 2,920,498 | 83 |
| 7000. | ATAGTTCTAAATCAAAGGCTATA[G,A]ACTTTTTAGTTCGAAGCACAACAAG | 2,920,517 | 83 |
| 7001. | AGGCACAAACTTGATGAAGTAAGT[G,A]AAAAATATATTTTTGTTGGCTATAG | 2,920,563 | 83 |
| 7002. | AAGCATTTCAAAGTTTTTGGATGT[A,G]TATACTATACTCGTGTTCCAAAAGA | 2,920,617 | 83 |
| 7003. | TCAAATAAATTTGAAAAATTTTAT[A,G]AAAATATTGGTTTGCAAAGATAATT | 2,920,884 | 83 |
| 7004. | AGAGGTGGTGAATATAACTCAAAT[A,G]AATTTGAAAAATTTTATAAAAATAT | 2,920,902 | 83 |
| 7005. | ATGATATGGGCATACTTTATGAGA[T,C]ATAAGTTTGAGACATTCATCATCTT | 2,921,016 | 83 |
| 7006. | TAACTACTTAAAAATGATATGGGC[A,G]TACTTTATGAGATATAAGTTTGAGA | 2,921,029 | 83 |
| 7007. | ACAAGCTTTTCTCTTTTCTTCAAC[C,A]CCCCCAAGAGAACCTAAGCCTCTAG | 2,930,376 | 83 |
| 7008. | TAGCTGCCTGGATGGGTCGGTGGG[T,C]AGCAGTACTTGAACTAAAAGCTGCC | 2,931,419 | 83 |
| 7009. | TTGACTCCCAAGTATCAGACATCA[A,G]AAGTGTGTGATCTTCTCTCTTCTAA | 2,932,446 | 83 |
| 7010. | ATCAGCATCTCTCAGTATACGATA[A,G]AAATCATCACTGCCAGCTTCTAGAT | 3,090,050 | 51 |
| 7011. | GCACAAATTCACTCCTATATAAAT[G,A]GACAGTCATTGTATCCCTATCAAGT | 3,090,244 | 51 |
| 7012. | ATCTCTTATAAGGGCAATAAGTCC[G,A]TCCTTGATGTAAGAGTGCCGCATTT | 3,090,310 | 51 |
| 7013. | AGAAATCATCTTGTCAATTACTTG[A,G]CGGTCCATGACACACTACCTAAGGA | 3,090,407 | 51 |
| 7014. | ACGGTCCATGACACACTACCTAAG[G,A]ATTTTGCACATACAAATACAAGATA | 3,090,431 | 51 |
| 7015. | GATTTTGCACATACAAATACAAGA[T,C]AATTGCTAAATGATTATTTTATTAT | 3,090,455 | 51 |
| 7016. | TATTATTTCGAATGGCTTATATAG[A,T]AATTACATCTTGCCATCAACTAATA | 3,090,499 | 51 |
| 7017. | TCTTGCCATCAACTAATAGGTATA[G,C]AAGGTCTTATCTCGTTCAAAAATTA | 3,090,531 | 51 |
| 7018. | AATAGGTATAGAAGGTCTTATCTC[G,A]TTCAAAAATTATATTAATTCTATAA | 3,090,545 | 51 |
| 7019. | CCCTATCATTTGATTACTGTAATG[A,G]CCTATAAAATTAATTGTATTTCTCA | 3,090,738 | 51 |
| 7020. | CTGTAATGACCTATAAAATTAATT[G,A]TATTTCTCAAATTATCCATACTGGA | 3,090,754 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7021. | ATTTCTCAAATTATCCATACTGGA[C,A]AATCAATTGATCAATGTATATAATT | 3,090,780 | 51 |
| 7022. | AATTCTTTCATCTGTATAAGAATA[C,T]ATAAATATATAGATACTGTAGAATA | 3,090,826 | 51 |
| 7023. | AGAATACATAAATATATAGATACT[G,A]TAGAATATATATATTAATTAAAAGA | 3,090,844 | 51 |
| 7024. | ACATGTAGACTTGGGTGCACCAGA[T,C]GACTAGACCGTGCTAGCACACCAGC | 3,091,000 | 51 |
| 7025. | GGGTGCACCAGATGACTAGACCGT[G,A]CTAGCACACCAGCATGGCATCTAGG | 3,091,012 | 51 |
| 7026. | TGACTAGACCGTGCTAGCACACCA[G,A]CATGGCATCTAGGCAAATTCCATCC | 3,091,024 | 51 |
| 7027. | ACTTTAGACCAGGCTTAGGCCCTA[A,G]AATCTTTTAAAATATGAGATCCGAG | 3,091,177 | 51 |
| 7028. | ATCTTTTAAAATATGAGATCCGAG[C,T]CCGGCTCAAACCCAATCAGATCGGC | 3,091,203 | 51 |
| 7029. | ATCCCCAAGGGATAGATATTCTCT[A,G]TCGGAAGTACATTGATCATCGAAGA | 3,091,317 | 51 |
| 7030. | CGAAGAACTCACTAGAAGTACATT[T,G]GTCATCGAAGAACTCACTAAGTTGC | 3,091,361 | 51 |
| 7031. | ACTAAGTTGCTTCCACCACCATCG[A,G]AGTAGATGAGCAGGGTAGAGTCGGT | 3,091,401 | 51 |
| 7032. | GACGCCGTCGCTAATACTCACCAA[G,A]TGGCGCAAAGAAGAAGAGGAGACGG | 3,091,722 | 51 |
| 7033. | TGGCGCAAAGAAGAAGAGGAGACG[G,A]CGYAGAGATTGGGGCGTGGGTCTGA | 3,091,747 | 51 |
| 7034. | AGGATGGTCAATTCGGTGCGGGGA[T,C]ATCAGATCCAAGGAGGGGATGACAG | 3,091,988 | 51 |
| 7035. | TTTTTAGGGCATAGTATTAGTGAT[A,G]GCTAATTTGCATCGCTAAAGTCTTC | 3,092,148 | 51 |
| 7036. | TGATAGCTAATTTGCATCGCTAAA[G,A]TCTTCACTAATACTAATTATTTAAA | 3,092,168 | 51 |
| 7037. | TAAAATTAAATTTATAATGATGCA[G,A]AAAAGATCATCGCTAATAAGTCTTC | 3,092,214 | 51 |
| 7038. | CATCGCTAATAAGTCTTCACCCTT[A,G]TAATGATGGATTTAATTTCCATCGT | 3,092,246 | 51 |
| 7039. | ACCCTTATAATGATGGATTTAATT[T,C]CCATCGTAATAAGTAGTTGATAAAT | 3,092,264 | 51 |
| 7040. | ATTACTATTAGCGATGGCTTATTT[A,G]CCGTCGCTATTACACTATTTTCTTA | 3,092,314 | 51 |
| 7041. | CAAGCAACGGAGTAGTCTTTGAAA[A,G]AATAaTACCCTACAAGCCAATCACA | 3,092,492 | 51 |
| 7042. | GCCAATCACATATGAGATATGATG[A,G]AATTTtTTTtAtATTTTATCTTCCA | 3,092,532 | 51 |
| 7043. | GAAATTTtTTTtAtATTTTATCTT[C,T]CAAACTTATGTATTTGACATTGTTA | 3,092,555 | 51 |
| 7044. | TAGGTCTGGACAATGATTTTAGGA[T,C]CACAATGAGATCACGTCAATGAGAT | 3,092,677 | 51 |
| 7045. | GGATGGTTGATCTTATAACTACTT[G,A]TGTAGTGACACTAATATAAAAATAT | 3,092,835 | 51 |
| 7046. | GAATGAGTTCACTGAATTGACCTA[C,T]GAGAGAATATCTAATGGAGTCTTAT | 3,092,899 | 51 |
| 7047. | GTTCACTTTCTAACTTGATTTTTT[G,A]ATCTTTATGTAGGGTGTTCTGGATG | 3,093,045 | 51 |
| 7048. | TCTGGATGTAGTGAAGTGTGTATG[G,A]AGATTGTGAGTGGTCAATAAGGAAT | 3,093,087 | 51 |
| 7049. | TATGATTTCATGCCTACGGCTCGT[T,C]TGGGATATTGTTTGACTGAAGGATT | 3,093,292 | 51 |
| 7050. | GCTCGTTTGGGATATTGTTTGACT[G,A]AAGGATTGAATTACACAGTAACTTG | 3,093,310 | 51 |
| 7051. | TTTTATCAAATTTTATCTCTTCTG[G,A]ATAGTCATAATATTTTACTAGACGT | 3,093,383 | 51 |
| 7052. | GGATAGTCATAATATTTTACTAGA[C,T]GTTAATATTGATTTATGAACTTATT | 3,093,406 | 51 |
| 7053. | TCAAGAGTTTGTGTCTACTGCTAG[T,C]TAGATTTGAAATCTAATAGATCACA | 3,093,550 | 51 |
| 7054. | GAAATCTAATAGATCACACACTTT[G,A]AAATTTGATCTTGATCTAATTTAAT | 3,093,582 | 51 |
| 7055. | AAAGGTTAATTTGATATGCTAGCA[T,C]ATTGTGTTAACCTAAGTTTCCAATT | 3,093,652 | 51 |
| 7056. | GCTTAGGTCTATTTTTATTGAACT[C,A]CTACCTAACTTGGAAGAGTTTTAAG | 3,093,757 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7057. | TAAGAAGAGGAAGAGTCCTTCTTC[T,C]TTAAAGACTCTTATCTATCGCTTTA | 3,093,877 | 51 |
| 7058. | GTGCTACTTAATTCATCAGAGAAA[C,T]AATTTTTCTATGTGAGGGAAGTGGA | 3,094,022 | 51 |
| 7059. | TTTTTCTATGTGAGGGAAGTGGAG[T,C]GTCAAGAGTTGGCACCCCTTGGGTC | 3,094,049 | 51 |
| 7060. | TAAATGGGGTGCCTCTTATGGGAT[A,G]AGGGTTGAGAATTGATAAAAATTCA | 3,094,125 | 51 |
| 7061. | ATGGGATAAGGGTTGAGAATTGAT[A,G]AAAATTCAAAGATCTTGGCATGTGA | 3,094,142 | 51 |
| 7062. | TGTCCTAAGATTTGATTTTTCAT[A,G]TGTTGGAGTACAAAATCAAATCTTA | 3,094,297 | 51 |
| 7063. | TAAGATTTGATTTTTTCATATGTT[G,A]GAGTACAAAATCAAATCTTAGATTA | 3,094,302 | 51 |
| 7064. | AGACAATAGTGCGTTGGTGTGATC[A,G]TTCTTTAAGAAAGAAGCTGGCAGTG | 3,094,402 | 51 |
| 7065. | AGTGCGTTGGTGTGATCATTCTTT[A,G]AGAAAGAAGCTGGCAGTGTTCTTAT | 3,094,409 | 51 |
| 7066. | TTGACAGTTTTAATTGTTAAAATT[T,C]TTTATTTATATATTAAAATTTTTAA | 3,094,671 | 51 |
| 7067. | TTAATTGTTAAAATTTTTTATTTA[T,C]ATATTAAAATTTTTAAAATTCTTAT | 3,094,680 | 51 |
| 7068. | AATTTTTAAAATTCTTATTCTACT[A,G]CATGACCGAAATCTAATAGTCTTGA | 3,094,712 | 51 |
| 7069. | CTGTCCTCACCTTTGGTCCCTACT[T,A]GTCACCTTCCCATCATAGCCTAAGG | 3,094,855 | 51 |
| 7070. | CCTACTTGTCACCTTCCCATCATA[G,C]CCTAAGGGAGGAAGACTGATGGCGA | 3,094,873 | 51 |
| 7071. | TAGCCTAAGGGAGGAAGACTGATG[G,A]CGATAATCCTAATCCTTCTCCTCCA | 3,094,895 | 51 |
| 7072. | CGATGGTCTTAGCTTCATCTCTCG[G,A]TCCCCATTCTCTCACAATATCCTGA | 3,095,074 | 51 |
| 7073. | CTTCACGGTATTTTAGACACTCTC[T,C]TTTGCTTTGGCTTCCTAGCTACCCT | 3,095,225 | 51 |
| 7074. | CACACTTAAATTGTGCAACCTCGA[T,C]GAGTCGGTGGTTATGTCAGCACTCA | 3,095,467 | 51 |
| 7075. | AAGAAGTGAGGCCAAGAAGAGCCT[C,T]ATGTGGGCTTGATGGGAGAAGGGCT | 3,095,669 | 51 |
| 7076. | GGCTTGATGGGAGAAGGGCTCTCT[C,T]GACCATCGAAGAGCCTCAGGTCGAG | 3,095,699 | 51 |
| 7077. | CGGAGATATCTTTACTGACCCTAA[T,C]CGATAAAAACCCCATCGATCAGGAG | 3,095,812 | 51 |
| 7078. | ATACTATTGCTTCTACTATAACCA[T,C]GGTCATAACTCTGAAGAATGTCTCT | 3,095,874 | 51 |
| 7079. | TCCTAATCCATAGAGACTATCTTG[G,A]AAAGTATGTCCGACCGTGTCAGGCC | 3,095,945 | 51 |
| 7080. | CCGTGTCAGGCCCGACCGTCTGAG[G,A]AGCTATCTCAACATCAGTTCGATGA | 3,095,983 | 51 |
| 7081. | ACAGAAGATTTGCTAGGGGGTAGA[C,G]AGATAGTGTGCAGGAAACTTTGCTT | 3,096,074 | 51 |
| 7082. | CAATGAAAACATCCTCTACTGAGT[C,T]TGGCACCTTTTGATTATATCAATAA | 3,096,130 | 51 |
| 7083. | ATATCGCGACTGCAGCTAAGACTT[T,C]CATAATTCTAACCAACGAGGCTCTG | 3,096,397 | 51 |
| 7084. | TGGTCATGAGAAGAAATCCTGACT[C,T]AAGTTAGAACCTCAACAGCAAGACC | 3,096,445 | 51 |
| 7085. | TTCGAACATCCCTATAGGGATCAG[G,A]GTAAGATGATGATGGTAATTTGGCA | 3,096,612 | 51 |
| 7086. | GATCGATTGGATATCGACTTCAAA[T,A]AAGACCTCATCAAGATCTTCTCGGA | 3,096,673 | 51 |
| 7087. | GATCTTCTCGGACATCTCCATAGG[G,A]ATTGGGTTAAGACAATGATGGTGAC | 3,096,711 | 51 |
| 7088. | TATGAACCGATTGGATATTGACTT[C,T]GGATGAGATTTCATCAGGATCTTCC | 3,096,774 | 51 |
| 7089. | AGGATCTTCCCAAACATTCCCATA[G,A]GAACTGGGTTGAGATGACAATGGTG | 3,096,814 | 51 |
| 7090. | TTCCCAAACATTCCCATAGGAACT[G,C]GGTTGAGATGACAATGGTGACTTTG | 3,096,820 | 51 |
| 7091. | ATTGCATCGGATCAATTAGATATC[G,A]ACTTCAGACAAGACCTCATCAGGAT | 3,096,874 | 51 |
| 7092. | TCGGATCAATTAGATATCGACTTC[A,G]GACAAGACCTCATCAGGATCTTTTC | 3,096,880 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7093. | TGTAGGGATCGATTAAGACGATGA[C,T]GGTGACTTGGCAAAATTGTCATGGA | 3,097,044 | 51 |
| 7094. | CTTGGCCTCATCGAATGAGTCCAG[G,A]TTCACTATCGACGGTGTTACTCCTA | 3,097,284 | 51 |
| 7095. | CCGGTGTGGGAAATAGGAGTCATT[T,C]AACACAAGCATCAAAAAGGTAACAA | 3,097,436 | 51 |
| 7096. | TTACAAATAAGGCTAGTCGAGGTC[A,C]TTGTACGTGGGTTCGGCAGAATGTT | 3,097,558 | 51 |
| 7097. | GCCTCCCGGGCAGGGCCCCTCACA[A,G]TGTTCTTGGCAGCAAGGCCAGGAGC | 3,097,613 | 51 |
| 7098. | TCCTCGCTAGGACAGACTGGTCCT[T,C]GAGCGAGGCAGGCTCATCTTCGTCT | 3,097,667 | 51 |
| 7099. | GCTAGGACAGACTGGTCCTTGAGC[G,A]AGGCAGGCTCATCTTCGTCTGATGA | 3,097,672 | 51 |
| 7100. | AGCGCCTCTTACAGGCTTCAAAGC[C,T]GTATATGTAGGCCATTGAGAATCAT | 3,097,796 | 51 |
| 7101. | GCAACCTCATCCTTGAACTCTGTC[A,G]AAGCCTTGAATTTCTCAAAGCCCTT | 3,097,849 | 51 |
| 7102. | TCAAAGCCCTTGAGTTTGGCCTCG[G,A]TAGCAACCTTCATTGTCTCCTCTTA | 3,097,888 | 51 |
| 7103. | TTGTCTCCTCTTAGCCTTGGACTT[G,T]ATGAGCTCCACACTATCTTCGGTAG | 3,097,925 | 51 |
| 7104. | GCTCTAGGACCTCCTCAAGCTCAG[C,T]CGCCTTCTGACGAAGTACCCCGATG | 3,097,996 | 51 |
| 7105. | GATGAAGACAATTATGAACAACAA[A,T]GGACTTATGCCGAGTAGACCAGTGT | 3,098,347 | 51 |
| 7106. | ATCCAAGGGATGAGCCTTTCTCTC[C,T]GACTAATCAGTCGGCAGCAAAATCA | 3,098,416 | 51 |
| 7107. | TAATCAGTCGGCAGCAAAATCATC[T,G]TCACCAACTGTCAAGCGAGCTGGTG | 3,098,444 | 51 |
| 7108. | TCATACCTTGTTTGCCTCCTCAAA[G,A]CTAGGAAAGATGGTGGCTATAGGGT | 3,098,579 | 51 |
| 7109. | TGGCCAGTTGATGGGAATGGTGAC[T,C]GAGCTAACTCTAAAATCATCGGTGC | 3,098,681 | 51 |
| 7110. | GGGCTGATCTAAACACATGCAAAA[A,G]AAATGGTTCTTCCATTCATGAACTG | 3,099,205 | 51 |
| 7111. | CAATAATGTTACATCCTAATCAAG[G,A]AAAAAAGTACCACCATCCTCTCTTA | 3,099,627 | 51 |
| 7112. | CTTTGAAGGGAGAACACCTTAGGA[C,T]AATACTGAGCCAGTTATAAAGAATG | 3,099,345 | 51 |
| 7113. | GGAAAGGTGAAGACCAATCCGAAG[G,A]GATTCCTCTTACAATGCGACTCTAC | 3,099,512 | 51 |
| 7114. | AAGCCTGGCTCGAGGAGGCGGTGA[C,T]TGAGAATTCTGACTGCCATGAAGAT | 3,099,797 | 51 |
| 7115. | GAGGAGGVGGTGACTGAGAATTCT[G,A]ACTGCCATGAAGATTTTCACCCTTG | 3,099,808 | 51 |
| 7116. | AAGGAGGAGGATCGATTGGAGACT[A,G]CAATTGGAGATCACCAGCATCAAGG | 3,100,007 | 51 |
| 7117. | ACTAACAGTCAAGATTCAAGCCCC[G,A]TGCCATTAGATTTTGACACCTGACA | 3,100,183 | 51 |
| 7118. | AGATTTTGACACCTGACATGCATT[G,A]AAAATACCAAATCACATGATTCTTC | 3,100,215 | 51 |
| 7119. | TAAAATCACTTCGGACTTGAGAGT[G,A]GGGAATAAGTATTGTAGAGGTTATC | 3,100,577 | 51 |
| 7120. | TAGAGGTTATCCACCATCCGACTC[A,G]ACATCTCCTTCTTAGATTATGATCA | 3,100,616 | 51 |
| 7121. | CGACCTCCTAACCTAGTATCCACT[G,T]ACCTCGAGGGTAGGATCCTCCTAAT | 3,100,757 | 51 |
| 7122. | CTGACCTCGAGGGTAGGATCCTCC[T,C]AATGACGAAGAGCATAGTCTGACAG | 3,100,779 | 51 |
| 7123. | GAGCATAGTCTGACAGACCTATGC[A,G]AGTGTCGATCCGAGGCAGGACCTTG | 3,100,813 | 51 |
| 7124. | ATCCGAGGCAGGACCTTGGCTCAA[C,T]ATGAACTCAGAACATCAGACCATTC | 3,100,845 | 51 |
| 7125. | TCTGTGCTCTTATTCTCCTATTCT[T,C]TTTTCTCCATTATTCTCAGGCTCCA | 3,101,151 | 51 |
| 7126. | CCATTATTCTCAGGCTCCAACTGA[C,T]TTAATGTTGGGATTTGGTGCCTCGA | 3,101,182 | 51 |
| 7127. | GGATGCATGGCCCAGGCATGGGGG[C,T]GGCCCAGCACGAGTGCGCAGGCGCA | 3,101,344 | 51 |
| 7128. | GCCCAGCACGAGTGCGCAGGCGCA[C,T]GACCCAGCACAGGGAATAGGTGCGC | 3,101,370 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7129. | AGTGCGCAGGCGCACGACCCAGCA[C,T]AGGGAATAGGTGCGCGCGCGTGGCC | 3,101,380 | 51 |
| 7130. | TCCATGGTGGACCGTGGGAGTTGT[C,T]GTGGTCCATGCGACTGTCATGGACT | 3,101,449 | 51 |
| 7131. | CTTCACGGTCGAATGGCTAAGGAG[T,C]GATTCGGGTGATGTTTTGCATGATC | 3,101,541 | 51 |
| 7132. | CGGTCATGATCAAATGGACAAGAA[T,C]ATTTTTAAGTCCTAATAGAGGTTGT | 3,101,610 | 51 |
| 7133. | TTTCTATCTGCAATGGGTTTTGGA[C,T]GCTTGAGGGGCAGACGGGCCGAAGG | 3,101,661 | 51 |
| 7134. | AGCAGCGACCAGAGCCTCAGGTGG[G,A]GTCGAAAGAGGGTCTTCTTGGTTTT | 3,101,799 | 51 |
| 7135. | TGGGGTCGAAAGAGGGTCTTCTTG[G,A]TTTTTTtATGAGAGCTTTTATAAGA | 3,101,820 | 51 |
| 7136. | ATAAGAGATGAGAGGTGAGAGCTT[C,T]TTATTGAAAGAAAGAGGTTTGAGAG | 3,101,864 | 51 |
| 7137. | GTCAGGCTCAATCAAAGTAGAGAT[C,T]AATTAGTATGATGAAAAAAGTAATT | 3,102,172 | 51 |
| 7138. | CTATAGCAAGCGAGGGTGAAGGAT[G,A]CGCTCATCCAACAGGGATTAATCGA | 3,102,227 | 51 |
| 7139. | ATGAGCGAGGGATAGAGCGTGCAG[G,A]AGCATCTCAGCAACTTTTAAAAGAT | 3,102,492 | 51 |
| 7140. | GCATCTCAGCAACTTTTAAAAGAT[T,C]TTCACTGATCTCCTTAGCATTGGTG | 3,102,518 | 51 |
| 7141. | ACTGCTCTTCTTGTGAAAAAGAGC[G,A]CCATTAGGATGGATTACTTCTATAC | 3,102,638 | 51 |
| 7142. | AAGTAGCAATATAGAAGGCAGTGA[C,T]GATGTTCTTCTAGTGTCAGATGAGG | 3,102,932 | 51 |
| 7143. | ACTGTTCACTTATCGGATAAATTG[A,G]GTTGTGAGATCAAGGACAGTGGGAC | 3,103,080 | 51 |
| 7144. | TAAATTGAGTTGTGAGATCAAGGA[C,G]AGTGGGACGGTTAGCTTACAAGCAC | 3,103,097 | 51 |
| 7145. | TTGTGAGATCAAGGACAGTGGGAC[G,A]GTTAGCTTACAAGCACATGATGGAA | 3,103,106 | 51 |
| 7146. | AAGATCCAATACGTACCCAGCTTC[A,T]GGAATAATCTAATTTCATCGAGCAG | 3,103,173 | 51 |
| 7147. | ATGATGGAATCCTGAAGGTCATGT[A,G]TGGCAGTAGGATTGTGATGAAAGAA | 3,103,254 | 51 |
| 7148. | GAAATTATGGAGGATACTACCTCT[T,A]GGTAAAAAGCTTAGCATGAGATAGA | 3,103,305 | 51 |
| 7149. | TTGGCATCTCGAATTCGATCCATA[G,A]GAGAAAAATCAAAGACAGAGGAGTT | 3,103,676 | 51 |
| 7150. | TGCGCACAGGCCCGCAGCAGGGCA[C,T]GGCTCGCAAGCTTGTGCAGGCCCGC | 3,103,767 | 51 |
| 7151. | CAAGGGTGCGCGCGCATGGCCCAG[C,T]AGGATTTTGGCACGGTTGGACCATG | 3,103,890 | 51 |
| 7152. | AAGGGTGCGCGCGCATGGCCCAGC[A,G]GGATTTTGGCACGGTTGGACCATGG | 3,103,891 | 51 |
| 7153. | TCCATGCGATCGCTGTGGATCGAC[A,G]TGGTGCAGGGAGAAAATATAAAGGC | 3,103,953 | 51 |
| 7154. | TCAGGTGGCTTGCGGTCATGATCA[A,G]ATGGCCAAGAATGTTTGTAAGTCCT | 3,104,073 | 51 |
| 7155. | TAGAGAGTAGTCATCGATAGTGAG[T,C]ACTTGAGAGGCAGAGGAGCTATAAA | 3,104,208 | 51 |
| 7156. | GGAGTTGGTAGAGGATTTTTTtGG[A,G]TTTTTTATGAACGCTTTTGTAAGGG | 3,104,288 | 51 |
| 7157. | AGGATTTTTTtGGATTTTTTATGT[A,G]CGCTTTTGTAAGGGATGAGAGGTGA | 3,104,299 | 51 |
| 7158. | GAACGCTTTTGTAAGGGATGAGAG[G,A]TGAGAGTTTCTTGTTGAAAGAGATA | 3,104,321 | 51 |
| 7159. | TTCATAGTAAAATTTTGCATGTTC[T,C]GTGGAGATAAATCTTGGTATAATCC | 3,104,419 | 51 |
| 7160. | GAGTGCGGACTACTATAGTAGGTT[C,T]CTCTTTTACACTTCGAGCTTCAGAC | 3,104,544 | 51 |
| 7161. | TTATGATGACTTTGATGAAGTAAT[T,C]GAGTGATCGTGGTTTTTtCTTTGGT | 3,104,651 | 51 |
| 7162. | TGGCCCCTAAAGTTGCTCAAATAA[A,G]GATGATAATGGATCAGATATGAATC | 3,105,481 | 51 |
| 7163. | TCAAGATATATAAACCATCCGGTC[C,T]CTTTCAGCCTTTTTGAGCATGGCCA | 3,106,104 | 51 |
| 7164. | AATTTTTGAATATAAAATATATGC[T,C]GGTGATCATCCTGATTGGTTAGATT | 3,106,186 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7165. | ACTCTTCTGGTTAGATACGAAAAA[C,T]TAGATCCTAAATTGGCATGATCATA | 3,106,294 | 51 |
| 7166. | GATCCTAAATTGGCATGATCATAA[G,T]CCGATTAGAGAACAAACATCACAAT | 3,106,321 | 51 |
| 7167. | AAGTAATATAACATTTTAAATCAG[C,A]TTATATGGCATACATGATAAAAATC | 3,106,556 | 51 |
| 7168. | TATATATTGATTGGGTCTTAGATA[C,T]ATATACCAGACTAAGTAACTCAAAT | 3,106,669 | 51 |
| 7169. | TTGGTTGGTTGTGCTTTCTACTAA[G,A]ATTTTACATTGTTATAAATGGTATT | 3,106,727 | 51 |
| 7170. | TATCTTTTGGTTGGGATCCTGATC[G,A]TTACAGTGAGCCATCATAAAATCTA | 3,107,010 | 51 |
| 7171. | GTTACAGTGAGCCATCATAAAATC[T,C]AAAAAGGTCTATTACCAATTTGCCT | 3,107,034 | 51 |
| 7172. | AAAACTGTTTCTCTTTGGAAAGCT[C,T]AGGTTGCATCTAAAAATTTTTCTAT | 3,107,367 | 51 |
| 7173. | AATCTACATGAATAAGGATCAAAT[A,C]CTTACTTAATTAGCAGTGGAACCAG | 3,107,418 | 51 |
| 7174. | CAAGGGAGAAGGGGCGGCACCAAA[G,A]GGGAGAGGCTAAGGAGAAGAAGAAG | 3,107,663 | 51 |
| 7175. | ATCAGTCCAATACTCATGAAAGAA[G,A]GATTTCTATATGAGATAAAATTGCT | 3,107,868 | 51 |
| 7176. | ATACTCATGAAAGAAGGATTTCTA[T,C]ATGAGATAAAATTGCTATCACTTAT | 3,107,877 | 51 |
| 7177. | CTATCACTTATGACAACCACTTTG[C,T]ACCCACTCCCTCACCCACATGGGAT | 3,107,916 | 51 |
| 7178. | TTTCAGATGTTGGTCAGCCCATAT[A,G]AGAGAAAAATCTCAGTGCAAATAGG | 3,107,983 | 51 |
| 7179. | TTGAATTTTtGAACTCAATTAAGC[T,C]TAATTAATTTAGATCTAATCTGAAA | 3,108,149 | 51 |
| 7180. | TAGATCTAATCTGAAATTAATCAA[C,T]ACTTAAATTCAATCTTTCATATGCT | 3,108,183 | 51 |
| 7181. | TCCATGGATCATAGATCAGAAACT[G,A]TTCATCCCCAAGATCGAATCTGAAC | 3,108,232 | 51 |
| 7182. | CAGAAACTGTTCATCCCCAAGATC[G,A]AATCTGAACCTCATGTATAGTGCTA | 3,108,248 | 51 |
| 7183. | AAATCCTATCTAGCAATGATTTTC[A,G]ATGTTTAGATAGATCGAATTATCGT | 3,108,504 | 51 |
| 7184. | TTACTGCATAATTCGTCCTTTTGA[T,C]CCTGAATGCTTTAGGATGGTCTCAA | 3,108,584 | 51 |
| 7185. | GGATGGTCTCAAGTTAACTGTCAA[T,C]CAAGATTGTTTCATCCATATTGTAT | 3,108,622 | 51 |
| 7186. | ATGGTCTCAAGTTAACTGTCAATC[A,G]AGATTGTTTCATCCATATTGTATTT | 3,108,624 | 51 |
| 7187. | TTTCAAATCTATCTCATAGATTGT[C,T]CTGATCAAGACTTTGCTAAATTAAA | 3,108,679 | 51 |
| 7188. | TGTTCCCAATAGCCTTCCATCACT[G,A]TATTTAAAATTCAGATAGTCCGACA | 3,108,809 | 51 |
| 7189. | ACTCTTGACAGCAGAATGCTCAGC[A,G]GGTGAGTCATTAGTTCAGTGACAAT | 3,109,455 | 51 |
| 7190. | CATCATCATCCTGTAATGATGTAT[C,T]ATTTGATCACAAATATGTTTAAGAA | 3,109,606 | 51 |
| 7191. | AATGATGTATCATTTGATCACAAA[T,C]ATGTTTAAGAACTATACGATAAATC | 3,109,620 | 51 |
| 7192. | AATTTTATTCAATAATTAATATT[C,T]ATATACAAAAAAATTTAATCGTCA | 3,109,763 | 51 |
| 7193. | TATTCAATAATTAATATTCATATA[C,T]AAAAAAATTTAATCGTCATCCGAT | 3,109,769 | 51 |
| 7194. | TTTAGGATATAATTTTCAACAACT[C,T]CCATTTTGACTAAAGCTAATCAGGA | 3,109,823 | 51 |
| 7195. | TGAAGTCATCGAACTCTTTGATCT[T,C]GAGAGCTTTAGTGAAGGGATCGGCT | 3,109,898 | 51 |
| 7196. | AGTGAAGGGATCGGCTAAGTTCTC[T,C]TTTCCATCGATCTTCTGAAGTTTGA | 3,109,932 | 51 |
| 7197. | TGTGATGGTGTGACTTTGATTCTT[C,T]TGTCTAAGCTATGGCACTGAAGCTG | 3,110,039 | 51 |
| 7198. | TCTGTCTAAGCTATGGCACTGAAG[C,T]TGTCACAGTATAGCAGAATAGAGCC | 3,110,062 | 51 |
| 7199. | GCCATCAATAGAAGATGTAACTCC[T,C]AGCTCGTGATCAATTTTTGCAACCA | 3,110,109 | 51 |
| 7200. | TTTGCAACCATACCATCTTCTTTG[C,T]AGCATCCAATGTAGCAATGTATTCT | 3,110,149 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7201. | TCCATTCATGATAAATACATAATC[C,T]GATACGCTTCTACTGTCATCACAAT | 3,110,258 | 51 |
| 7202. | TCATGATAAATACATAATCCGATA[C,T]GCTTCTACTGTCATCACAATCTGAC | 3,110,263 | 51 |
| 7203. | AGTGTCTCCATAGATAAGCCATTG[G,A]TCTTTAGTATTTCTCAAATACTTAA | 3,110,351 | 51 |
| 7204. | GAATTGCTTTCACAATCTTTCAAT[G,A]CTTCTCATCCAGATCAGAATGGTAC | 3,110,401 | 51 |
| 7205. | ACAATCTTTCAATGCTTCTCATCC[A,G]GATCAGAATGGTACCTACTCACTAT | 3,110,412 | 51 |
| 7206. | AGCATATGGTATTCTACTCATGCG[C,A]TCTCTCTCCTTAGGAGTTGTCGGAT | 3,110,528 | 51 |
| 7207. | TCTCTCTCCTTAGGAGTTGTCGGA[T,C]ATTCTTTTTGGAAAGAGTAATTTT | 3,110,553 | 51 |
| 7208. | GTCGGATATTCTTTTTGGAAAGA[G,A]TAATTTTATGGTCTATTAAAAAATA | 3,110,571 | 51 |
| 7209. | GAAAGAGTAATTTTATGGTCTATT[A,G]AAAAATAGTCTTTTTtAAAATTATC | 3,110,589 | 51 |
| 7210. | CACAGCTTCATACTCTGCAAAGTC[G,A]GGATGTCATTTTCTAGTAATAGTAC | 3,110,781 | 51 |
| 7211. | TCTCCGTTCCTAACGAAGTCATAC[A,G]TTTTGGTCACCTTATCAAAATGCAT | 3,110,898 | 51 |
| 7212. | AGCTTGCTTAAGTCCATAAATAGA[T,C]ATTTTTAGCTTGTACACTTTTGACT | 3,110,963 | 51 |
| 7213. | GCTTGCTTAAGTCCATAAATAGAT[A,C]TTTTTAGCTTGTACACTTTTGACTC | 3,110,964 | 51 |
| 7214. | CCTCTTCTTTCAGCTTTTCATTAA[G,A]GAAAGCGATTTTGACATCCATCTGC | 3,111,052 | 51 |
| 7215. | TTGAGTATTGCCACAGGAGAGAAC[A,G]TCTTGTTATAGTCAATACTATAATG | 3,111,153 | 51 |
| 7216. | TGACGGTATCCTTTGATAATTAGA[C,T]GAGCTTTATAGGTCTCTACCTTTCT | 3,111,204 | 51 |
| 7217. | TTATTTACATCCTATGAATTTTAT[C,T]TCTTCAGATGGATTAACTAGTGTCC | 3,111,281 | 51 |
| 7218. | CTAGTGTAACTACACCATTGATCT[C,T]TATGGACTCCATCTTAGATTTTATA | 3,111,322 | 51 |
| 7219. | ACTCCATCTTAGATTTTATAGTCT[C,T]AAGCTATTTCTGAGAGTCGGGCCTT | 3,111,352 | 51 |
| 7220. | ATCTTAGATTTTATAGTCTCAAGC[T,C]ATTTCTGAGAGTCGGGCCTTTACAT | 3,111,357 | 51 |
| 7221. | TACTCTATCGGATCTTCTTAATGG[T,C]ACTTCTACTGGCTCCAAATTTGATT | 3,111,506 | 51 |
| 7222. | AATCAAATTCAATTCTATATGTGT[T,C]GGTCCTTCCACCTTATAAACTTCAT | 3,111,560 | 51 |
| 7223. | CCACCTTATAAACTTCATCAAGTT[T,C]AATTTTACAGGCATTAGCTCCATCA | 3,111,592 | 51 |
| 7224. | ATAGTATCCTTTAATTTTCTTTGG[G,A]TACCCTACGAACAAACATCTATCGG | 3,111,710 | 51 |
| 7225. | GTATCCTTTAATTTTCTTTGGGTA[C,T]CCTACGAACAAACATCTATCGGATT | 3,111,713 | 51 |
| 7226. | TGACATAAGCTAGATACCCCCAGA[T,C]CCTAAGGTGTGAGAGCACCAGCTTA | 3,111,793 | 51 |
| 7227. | TTGCTGGGCACCTTATTAAAAATG[A,G]AGCAAGCAGTTTTTAGAGCATATCT | 3,111,882 | 51 |
| 7228. | GAGCATATCTCCAAAAGGTGATTG[G,A]CAGACTCATAAAGCCCATCATAGAT | 3,111,922 | 51 |
| 7229. | ATAGATTAAACTATGTCTAAAAAG[A,G]TTCAATTTTCTTCTCCAATCAGCC | 3,111,966 | 51 |
| 7230. | AATACGCCATTATATTGTGGTGTT[T,C]CAGGAGGGGTCCACTGTAAGAGAAT | 3,112,008 | 51 |
| 7231. | CTTAATACTCTTTCTAGTTTGTTT[C,T]TCTACTTCAGCATGGAATCGTTTAA | 3,112,127 | 51 |
| 7232. | GTTTCTCTACTTCAGCATGGAATC[G,T]TTTAAACATTTCAAATAATTTTGAC | 3,112,147 | 51 |
| 7233. | TTATACTTCATAAGACAGACAAAT[T,C]CATACCTCGATAGGTCATCTGTAAA | 3,112,197 | 51 |
| 7234. | TTATGTATATATTATATTTTAATT[A,G]TCCACGTATAATGACAGTATTATTC | 3,112,564 | 51 |
| 7235. | ATTATAAACTTGTAATTAAGTTTG[A,G]CCAAAAGGCCTACAGAGATGACATT | 3,112,641 | 51 |
| 7236. | ACATGATACTACTAGACTCGAAGA[T,C]AAGCTGCAAGGTTTCCAAGGTCAAA | 3,112,726 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7237. | GCTGCAAGGTTTCCAAGGTCAAAA[T,C]TGGAACAAGACTTTCATCTCCAACG | 3,112,753 | 51 |
| 7238. | TCCAACGTTAAGGAACCGCTCGTC[C,A]TCTCAAAACTATCTACTTACCTGTA | 3,112,796 | 51 |
| 7239. | GAGAAATTACAAGAAGTTATCATA[T,C]AAGTATCTTGTGAAGCAATCGATTG | 3,112,917 | 51 |
| 7240. | AAGATGATTCTTTTTtAATGACC[T,C]AGCTTCTTACAGAAGAAGTACTCTA | 3,113,018 | 51 |
| 7241. | AGCTTCTTACAGAAGAAGTACTCT[A,G]CTTGGCTCTTGTCAACTTTTGATAA | 3,113,043 | 51 |
| 7242. | TCCTTCTCAAAAGTCTGCAGTAAC[T,C]CTAGCAAATTATGGTAGTTCACTGC | 3,113,217 | 51 |
| 7243. | AAGTCTGCAGTAACTCTAGCAAAT[T,C]ATDDTAGTTCACTGCAGGCTTCGTC | 3,113,227 | 51 |
| 7244. | GGTAGGATTTTGATAGCGAATTGA[A,G]GAGATCATCCTTGCCTAACTGTTCA | 3,113,302 | 51 |
| 7245. | TCCTTGCCTAACTGTTCATGTAAC[G,A]GAAAGCCAAATTTACTAAGGCATTC | 3,113,334 | 51 |
| 7246. | CGCACACGGGCATTGAATACTGCG[T,C]AGGAGGTTTTATATCTCTCTGCATC | 3,113,433 | 51 |
| 7247. | AATGAGCTCTTCTGGCTTTACATC[C,T]TCGAACTTACGATTAAGTTCGTCGT | 3,113,516 | 51 |
| 7248. | GCTACCTTCATCACACAATGCATA[A,G]TCATGCGGTTATTAAGCCACTTCAT | 3,113,571 | 51 |
| 7249. | TTCATCACACAATGCATAATCATG[C,T]GGTTATTAAGCCACTTCATATAAGT | 3,113,577 | 51 |
| 7250. | ACTTCATATAAGTATCTCTCACGG[T,C]ACGAGGAGCATTGGCTGCAAGTTTT | 3,113,614 | 51 |
| 7251. | TGCAAGTTTTTTGGATGCCTCATC[C,T]GTAAGGACATATACAATCCTCTTGT | 3,113,654 | 51 |
| 7252. | TACCAGCTGTCGAAGTTGGGTCCA[A,G]TAAGCTTGTCGCTGTCCAACAGCGT | 3,113,730 | 51 |
| 7253. | CAAAGATATGGACTTTAGTCTAAA[G,A]ATTTTTTtACTATTTTTACGAATTG | 3,113,851 | 51 |
| 7254. | TAGGTTCATAATCAATTATTTTTt[C,T]AAATAATTTTTAGTAATTGGATTTT | 3,114,014 | 51 |
| 7255. | ATTTTACCCCAAGCATCCCTTCAG[T,C]AGGCGTGTGGCGCCTTCACTGAAAA | 3,114,059 | 51 |
| 7256. | GAAGGTACATCATGATGGTCATAT[G,A]ATGAATGATAATTCCAATACGTAAT | 3,114,205 | 51 |
| 7257. | CTCCAATGCCTATTTAAAATATTG[G,A]ACTCATTATCATACATCTTAATAGG | 3,114,275 | 51 |
| 7258. | TCATGACTTTATCACTTTATGGAC[C,A]TAATAATTTAGAAGATTTGATTTCA | 3,114,344 | 51 |
| 7259. | GATAACCTGCAAACTGCAAATTCT[C,T]CCACTGACTTCATTAAGTCATGCAA | 3,114,417 | 51 |
| 7260. | TTCTCCCACTGACTTCATTAAGTC[A,G]TGCAAAGGATTAGACACAAGTTGGT | 3,114,437 | 51 |
| 7261. | CAAAATATAATCTACTATGTTGGT[C,A]AGATAAATGAGATCAGTGGGAGGGA | 3,114,561 | 51 |
| 7262. | TTAACTCACCGTAGATGCATCTAG[A,G]TGAATAGCTCCCAATTAAAAATCAC | 3,114,618 | 51 |
| 7263. | ATTCAAAGCTTAATTCATAATTAA[T,G]TGTATGAAATATGTGTTTCAGTCTG | 3,115,004 | 51 |
| 7264. | AATAAATTTTATAATATGTTTAA[C,T]AATTAAACATACATAGGTATGATCT | 3,115,110 | 51 |
| 7265. | GGTATGATCTAAACTTCATACATA[C,T]ATCTCATGCATCATGATAACTTTTA | 3,115,150 | 51 |
| 7266. | CTAAACTTCATACATACATCTCAT[G,A]CATCATGATAACTTTTCGATTAATA | 3,115,158 | 51 |
| 7267. | ATCATGATAACTTTTCGATTAATA[C,T]CGATTACATCTTATGTAATATGCAA | 3,115,184 | 51 |
| 7268. | GAATTTTATCCTATTATAATAAAT[T,C]ATAAATTATTTTAGATCTAATCTAA | 3,115,260 | 51 |
| 7269. | ATCCTATTCTAATAAATTATAAAT[T,C]ATTTTAGATCTAATCTAAATATATT | 3,115,267 | 51 |
| 7270. | TAATTTTATATATAATTACATCAA[T,C]ATATAATTATTGATAAAATAATTTT | 3,115,507 | 51 |
| 7271. | ATTTTAATAAAATCTATTTTCGT[A,G]CAGTGCTGAATTTCAATAGAATTTA | 3,115,739 | 51 |
| 7272. | TCTATTTTCGTACAGTGCTGAATT[T,C]CAATAGAATTTAGATCTAAATATCT | 3,115,752 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7273. | CATCTAATCCAATCAAAGTTAGAT[C,A]AAAAAAAAaTTTATACAAATAGATTC | 3,115,989 | 51 |
| 7274. | GATTTAATATCTCATAAAAAATCT[C,T]AGTTACATCTTATGTAATTAATCTC | 3,116,045 | 51 |
| 7275. | GACCTGCTCTGATACCAATTAAAG[G,A]GAAGGAAAACTATTTCTCTTCAGAA | 3,116,126 | 51 |
| 7276. | CTCTGATACCAATTAAAGGGAAGG[A,G]AAACTATTTCTCTTCAGAAGGCCCA | 3,116,132 | 51 |
| 7277. | TtATTAATCTATATAAATAAAGAT[C,T]AAATTTTTACCTAATTAGTAATAAA | 3,116,200 | 51 |
| 7278. | TAATCAAATGAAGGAGGAGATATA[T,C]TGGTGTGACACCTCACACTAGCAGG | 3,116,374 | 51 |
| 7279. | GTGGAATGCCCAAGGAGGGCCCAC[G,A]CCCAAGGAAGAAGGGGCGGCACCAA | 3,116,423 | 51 |
| 7280. | TATTTATAAATAAATTTTATGACC[C,T]AATAAGTATAGGCATTCTAACTTAA | 3,116,595 | 51 |
| 7281. | GAATCAGTCCATGAAATAAGAATT[G,C]CTACATGAGATAGAATTGTCATCAC | 3,116,654 | 51 |
| 7282. | ACCAGCACCATTTTAGGTGTTGGT[T,C]GGTCCATATGAGAGGAGAATCTCAA | 3,116,754 | 51 |
| 7283. | GAGAGGAGAATCTCAATGCAAATA[A,G]AATTTTTCATATCTCATCCCAAATG | 3,116,788 | 51 |
| 7284. | ATCCCAAATGGATCCGATTTGAAT[C,T]CAATTCGAAGCAGGTTCGAAATAAT | 3,116,828 | 51 |
| 7285. | TCCGATTTGAATCCAATTCGAAGC[A,G]GGTTCGAAATAATTTTGAAAGGCTA | 3,116,840 | 51 |
| 7286. | GCAGGTTCGAAATAATTTTGAAAG[G,A]CTATTAATCACAAACTCTTTAGAAC | 3,116,862 | 51 |
| 7287. | AAGTCTAACTTAAATTTTTAGATT[C,T]AATTAAATATAATTAATTTAGATCT | 3,116,921 | 51 |
| 7288. | CAACTCTTCAATTCTATTTGACCC[A,C]TAATTTAATTTTTCAATCAAGTTAG | 3,117,091 | 51 |
| 7289. | TATTTGACCCATAATTTAATTTTT[C,T]AATCAAGTTAGCTTATATGCTTAAT | 3,117,105 | 51 |
| 7290. | TTTCTATTTTGTCTGACTTATGTG[C,T]GTGACTCCATAGGTTCCAACACTAA | 3,117,201 | 51 |
| 7291. | AGTCGGTAACATAAGAATCAATTT[T,C]TGTACTAATCGAGATACCATCTAGC | 3,117,250 | 51 |
| 7292. | CTAATCGAGATACCATCTAGCAAT[A,G]ATTTTTGATATCCAGATAGATCAAA | 3,117,279 | 51 |
| 7293. | TGCTTCACGAGCAGCTCTTGACAG[C,T]AAAATACTCAGTAGATGAGTCACAT | 3,117,581 | 51 |
| 7294. | ATCTCATCTGTATGCCATATCAGT[A,G]TCACCACACTCTTTGGTTAAGAAGA | 3,117,654 | 51 |
| 7295. | CTCTTTGGTTAAGAAGACAACCAA[T,C]CTATATGGCACACAACGACCTCTAC | 3,117,687 | 51 |
| 7296. | TACGATAAATCTTTTTTTtATCAT[G,A]CACTAACATAGTTTTAAGGACTTTA | 3,117,798 | 51 |
| 7297. | TTTTtATCATGCACTAACATAGTT[T,C]TAAGGACTTTATTATAGCACAAGAG | 3,117,812 | 51 |
| 7298. | TTTGTAATGAAAAATATCAGAATA[A,T]TTTTTATTCAATAATCAATAATTTA | 3,117,879 | 51 |
| 7299. | TAATCAATAATTTATATACAAAGA[G,A]AAATTCAATCATCACACGATTAATT | 3,117,915 | 51 |
| 7300. | AACATAATTTCCAACAGACTCTTC[G,A]ATGCTTAAATCAATTAGAGTTTTAG | 3,117,969 | 51 |
| 7301. | GACTGTAATCTGACAAGGGGATGT[C,T]GGATCGGATGGATAACCCCTATAAC | 3,118,506 | 51 |
| 7302. | ATCACTATACTAGACTTCAATCAA[T,C]GACCCAACCTTCTCTCTAGAAGTTT | 3,118,616 | 51 |
| 7303. | ATACTAGACTTCAATCAATGACCC[A,G]ACCTTCTCTCTAGAAGTTTAATTGC | 3,118,622 | 51 |
| 7304. | CTCTTGGGGCATCATTAATATGCT[G,T]CTTCATAAATCTTGTCACATTTATG | 3,118,690 | 51 |
| 7305. | ATCTTGTCACATTTATGAGGGCTG[A,G]ATGGCTTGAAGTATGGTGCCACAAT | 3,118,723 | 51 |
| 7306. | CTTTTAGATCCCATGTCGCACCCC[G,A]TCGATTACCCTATGTGGCTTAATTT | 3,118,838 | 51 |
| 7307. | CATCACAGTTGATCGAAGGAGGGC[T,C]TTTTGTCATTACCATCTTCCTCAGC | 3,119,077 | 51 |
| 7308. | CTCTTTCTCTTTCTCGTCTCTTCA[A,G]TTTTTTTTtGCGTCCAGTAGCTTCT | 3,119,239 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7309. | TtGCGTCCAGTAGCTTCTTCCTCT[A,G]TATGTCTTCTGATAGTAGTGAGGCT | 3,119,271 | 51 |
| 7310. | TCGATCCCTTAGACCATGATGTAC[A,G]AGTAGCCCCATATGCAGGTTTAGAG | 3,119,426 | 51 |
| 7311. | TCATCTTCTCGATGAAGGAAAAAT[T,C]GCCTTTTTCCTGTGTAGGATCTTTC | 3,119,549 | 51 |
| 7312. | TAAATTTTAAATTTTtATCCTATG[C,T]TATTTTAGATCTAATGTCTATTAGA | 3,119,624 | 51 |
| 7313. | TTAAATTTTtATCCTATGCTATTT[T,C]AGATCTAATGTCTATTAGATCTAAT | 3,119,630 | 51 |
| 7314. | AAATTTTtATCCTATGCTATTTTA[G,A]ATCTAATGTCTATTAGATCTAATTT | 3,119,632 | 51 |
| 7315. | ATCCTATGCTATTTTAGATCTAAT[G,A]TCTATTAGATCTAATTTTATTATCT | 3,119,640 | 51 |
| 7316. | CATACCTCAAGGGTAATCTAATTA[T,C]CCTGTAGATGATCGCAGTACTGCTT | 3,119,736 | 51 |
| 7317. | CTGCTTGAGGTTCTGATGTAGCCA[C,T]GCAAGCACCTGGCCTCTACCAGTAT | 3,119,780 | 51 |
| 7318. | TGCTTGAGGTTCTGATGTAGCCAC[G,A]CAAGCACCTGGCCTCTACCAGTATC | 3,119,781 | 51 |
| 7319. | AGGTTCTGATGTAGCCACGCAAGC[A,G]CCTGGCCTCTACCAGTATCCACTCA | 3,119,787 | 51 |
| 7320. | TATCCACTCAGGTAGGATCTGGAA[C,T]ATCTTCTTCTCATGATTCTATGCTC | 3,119,827 | 51 |
| 7321. | TGATAGAAGAATAACCCTTTTATT[T,C]ATTTATAGTCAAAATTATAATTTTG | 3,129,037 | 51 |
| 7322. | TTATAGTCAAAATTATAATTTTGT[T,C]CTTAGATTTGTACAGAAATGTGTCA | 3,129,064 | 51 |
| 7323. | CTTTGATTTCTACTCTATCCCTTC[A,T]TCTATAATATTTTTGACTTCTATAA | 3,129,248 | 51 |
| 7324. | GTTTAGCTTGGTCTAGGGCAATCC[T,C]CACTTGTCTCCTAATAAAGATAAAT | 3,129,550 | 51 |
| 7325. | TCCTCACTTGTCTCCTAATAAAGA[T,C]AAATTTTTATCCTTCTTGAGGATGA | 3,129,571 | 51 |
| 7326. | GAGCCACTGGTGGTTGAGCCATTG[A,C]GGTCCGTTGTGCCGATGACTTCAGA | 3,129,977 | 51 |
| 7327. | GGAGTTGGTGAAGATGACTTTGCT[G,A]TTGGTTGATTGATCAGAGAGGAGGG | 3,130,262 | 51 |
| 7328. | AGATTATTGGTGCTTCTTGTGCCA[A,T]CCTCCTCAGGGTGAGTATTTCATCT | 3,130,327 | 51 |
| 7329. | TGAGGGTTTGGTTGGTTTCAACTG[A,G]GCAAAACTTTTGCTAGAGATAAAAT | 3,130,459 | 51 |
| 7330. | AGAGGAGAAGGTGAAGGTCATCAC[C,T]GAGGCCAAATTCAAGGGCATCGAAA | 3,130,806 | 51 |
| 7331. | TGAGGGCTTCATGGTGGCCTATCT[G,A]TACGATTTCAAAGCCTATAAGTTGC | 3,130,892 | 51 |
| 7332. | ATTGAGAATGCCATGGGGGCACT[T,C]CAAAGGAGACCGTCAATCATACTAT | 3,131,071 | 51 |
| 7333. | TTCTAATGAAATGAATTTCCTCTT[G,A]TTATCTTTTGATGCTTGTATTGAGT | 3,131,207 | 51 |
| 7334. | AAGTCGATGAGAAGTTGATCCATG[A,G]TAATTTTTGCCAAATCTCCATCATC | 3,131,503 | 51 |
| 7335. | TAATGTTTGCCAAATTGCCATCAT[C,T]ATCTTAACCCGATCCTTAGAGGGAT | 3,131,740 | 51 |
| 7336. | AAAAGATCCTAATGAAGTCGCAG[T,C]CGAAACTGATGCCAAGTCGATCTGT | 3,131,794 | 51 |
| 7337. | CATTATTGTCTTAACCCAATCCCA[G,A]GAGAGACTTTTGGGAAGATCCTAAC | 3,131,864 | 51 |
| 7338. | CTATCATCGTCTTAATCTAATTCT[T,A]TGAGGGATGTTCAAAAAGATCCCAA | 3,131,969 | 51 |
| 7339. | AGTCAATTCAAAGTCAATCAGTGG[C,T]AATTTTTGTCAGTCGTCATTGTCGT | 3,132,256 | 51 |
| 7340. | GGTAATTTTTATCAAATCACCATC[C,A]TCATCTTAATCCGATCTCTAGAGAG | 3,132,489 | 51 |
| 7341. | GATCACCATTATAAAGGTCTTAGT[T,C]GTAGCCAAAATATCTTCATGAGGTC | 3,132,621 | 51 |
| 7342. | ACATGAGGAGCCCGAAAATACAGT[C,T]TGAAGGCCTAGGCATGCAGCCTGCA | 3,132,837 | 51 |
| 7343. | CCGAAAATACAGTCTGAAGGCCTA[G,A]GCATGCAGCCTGCAGCATGCACGGC | 3,132,848 | 51 |
| 7344. | AAAATCATAGTGCATAGGAGGATT[T,G]GTGCGATCCAGCGGTCAGGAAGGCA | 3,133,086 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7345. | GCATAGGAGGATTTGTGCGATCCA[G,A]CGGTCAGGAAGGCATGCGATCGTGA | 3,133,097 | 51 |
| 7346. | GCATGATCGAAAGTTGTATTATGT[A,G]ATCGGATGGCCAAAAGCGCTTGTGG | 3,133,162 | 51 |
| 7347. | ATTATGTAATCGGATGGCCAAAAG[C,T]GCTTGTGGCAAAGATCGAATGGTCA | 3,133,179 | 51 |
| 7348. | AAAGAGTTTGGAGAGGCTGTGGAG[C,T]AGAGGTGAAGCAGCTTGATGTCAGT | 3,133,290 | 51 |
| 7349. | GCATTAGGAGCAGCTTGTGTGTAG[T,C]TGCAAAAGTAGTCGAGAGTGTCCTA | 3,133,355 | 51 |
| 7350. | AGTAGTCGAGAGTGTCCTAGAACG[A,G]TCATGGGAGTGACCGTCAGTATAGG | 3,133,386 | 51 |
| 7351. | AGGGTCTCCTTGTGGGATTTTATA[T,C]GAGCTTTTATGAGTGTTGTGCATGT | 3,133,524 | 51 |
| 7352. | TCTTTCTACTGCAACAAGTGGTAC[C,T]AGATCTCCAATAATTGGTATCAGAG | 3,133,726 | 51 |
| 7353. | AGCGTCAGCTTGTTCGAACTGTGG[T,G]GGTATTGATCAAGATTGAAGAAGAT | 3,133,808 | 51 |
| 7354. | GTATTGATCAAGATTGAAGAAGAT[G,A]GAGAAGTCAGGTATAATCATGGTGG | 3,133,834 | 51 |
| 7355. | TACTCTCTTGTGTAAAGAGAAGCC[G,A]TCTACCAAAGAAGATGTCAGTGGGA | 3,133,909 | 51 |
| 7356. | GTGTAAAGAGAAGCCGTCTACCAA[A,G]GAAGATGTCAGTGGGAGCCCAGTAT | 3,133,918 | 51 |
| 7357. | AGAAGCCGTCTACCAAAGAAGATG[T,C]GAGTGGGAGCCCAGTATGAGGTGGA | 3,133,926 | 51 |
| 7358. | TCGACCCCATGTTTGTCCATCTAT[G,A]AATAGCTGGCGTATGACTCAGGATG | 3,134,105 | 51 |
| 7359. | CATGTTTGTCCATCTATGAATAGC[T,A]GGCGTATGACTCAGGATGTGGGGC | 3,134,112 | 51 |
| 7360. | TATGAATAGCTGGCGTATGACTCA[G,A]GATGTGGGGCAAGAAGATCCAAAA | 3,134,126 | 51 |
| 7361. | AGATAGAGATAGTTGAGATTTGGT[A,G]CCTTGAATTCGATCTACAACAGAAG | 3,134,212 | 51 |
| 7362. | CTACAACAGAAGAGAAGCCCAGAT[T,G]TGGAGAAATTCATATGCGAGGAGCC | 3,134,250 | 51 |
| 7363. | GAAGCCCAGATTTGGAGAAATTCA[T,G]ATGCGAGGAGCCTAAAAATGCAGTT | 3,134,263 | 51 |
| 7364. | CCTAGGTGCGTAGTGTGTGACGTG[A,C]GTGGCCCAGCGGGGCCTGCTGCACT | 3,134,343 | 51 |
| 7365. | GGTGGACCGTTGGAGGAAGTCACG[A,G]TCCACACATGTTCTATGGACCATCA | 3,134,489 | 51 |
| 7366. | ACCAAGAAGGCATGCGGTCATAAT[C,T]GAATGGCGATCGAGTGTGATCGGGG | 3,134,591 | 51 |
| 7367. | GCATGCGGTCATAATCGAATGGCG[A,G]TCGAGTGTGATCGGGGCTGTATTG | 3,134,600 | 51 |
| 7368. | AGTGTGATCGGGGCTGTATTGCA[T,C]GATCGATGGCCAGAAGCGCTTGCGG | 3,134,628 | 51 |
| 7369. | TGATCGGGGCTGTATTGCATGAT[C,T]GATGGCCAGAAGCGCTTGCGGAAAA | 3,134,632 | 51 |
| 7370. | TCTAGATTGGTTTGGACCCTATAA[A,C]AGAGTTCAAAGAGGTTGTGGAGCAG | 3,134,732 | 51 |
| 7371. | GCAGCCGAGAGTATCCTGGAATAG[C,T]CGTGGGAGTGATCATGAGTGTAAGG | 3,134,855 | 51 |
| 7372. | GCCGAGAGTATCCTGGAATAGCCG[T,C]GGGAGTGATCATGAGTGTAAGGACG | 3,134,858 | 51 |
| 7373. | TGGGAGTGATCATGAGTGTAAGGA[C,T]GAGGCTGAGACATGATGTAGTGGCT | 3,134,882 | 51 |
| 7374. | GTGAGTGCTCTCCTTTTGTACTTG[T,C]TATTTTCTCTCATAGTAAAGCTTAG | 3,135,073 | 51 |
| 7375. | TATTTCATCTCTTCTTTTTTCTG[T,C]TGCAACAAATGGTACCAGATCTCCA | 3,135,253 | 51 |
| 7376. | TCGATCTCATCCTTGAGCTAGAGG[C,T]ATTTCTCGATGTCGTAATTAGGCTC | 3,135,698 | 51 |
| 7377. | TATTCAGCCTACTTCCCTGTGGCC[C,T]GAGCCTCTTTTGTCTATGCATATTT | 3,135,997 | 51 |
| 7378. | GAGAGGATCATCGACAAAAGGCAT[T,C]GGAGTTATATGCTCTTATTCTAGCC | 3,136,428 | 51 |
| 7379. | GCCATTCTCTTCTTCCTCATTAAT[T,C]GAGTTAATCACCCTTCCTCTGGTAT | 3,136,475 | 51 |
| 7380. | AATTGAGTTAATCACCCTTCCTCT[G,A]GTATCCATCTATTGCTGCAAGATTC | 3,136,496 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7381. | ATTGATGTGGCTGAGGATGGATAT[C,G]ATTTGGGGACCGAGATGCCAAAGAA | 3,136,555 | 51 |
| 7382. | TTTATTACCTCTTTATATAAAGGT[G,A]AAAATTTATGTTGTCATGCTGGAAC | 3,136,769 | 51 |
| 7383. | TGCTGGAACTTAGTAGGCTATTTG[A,G]TCCTAATTTTCTAGGCTGCTAGGTC | 3,136,810 | 51 |
| 7384. | AGGCTATTTGATCCTAATTTTCTA[G,A]GCTGCTAGGTCTCAATCTGATATAC | 3,136,824 | 51 |
| 7385. | GGAGGTTGGATAGAAACCGATGAC[G,A]TAAAGCTGCTTTGCCTTGGTTTCTC | 3,137,118 | 51 |
| 7386. | CAATTGAAAGTTTAGTGAAATAGG[A,G]CTTGGACAATAAAGGCCTTTACGGT | 3,137,423 | 51 |
| 7387. | GGGGGGAGTTGGGGTCTGAAATGG[A,G]AATGACAATGGATAACTCTCATTCT | 3,137,537 | 51 |
| 7388. | ATTCTGAAGTGGAATGAAAATGAT[C,T]GAATCCCCCTAAAACCCAATCCTCA | 3,137,623 | 51 |
| 7389. | TATTTCAATTTCGATTCTAGTTTC[A,G]ATTTCGATTGTAAATTAAACACCCT | 3,137,779 | 51 |
| 7390. | ACTGCTTTTGTCACTAAAGTCTTA[G,T]gTTAGCATATGTTAACTTGTTTTGG | 3,138,088 | 51 |
| 7391. | ACTGGGCAACATGGATGGCCAAGC[G,A]TTTACATGCCTATAAACAAATCAAG | 3,138,286 | 51 |
| 7392. | TGGGCAACATGGATGGCCAAGCGT[T,C]TACATGCCTATAAACAAATCAAGAT | 3,138,288 | 51 |
| 7393. | TTAGAACTACTTTGATCGATAAAG[A,G]AAGATTTATCGTGTAGTCCTTAAAT | 3,138,868 | 51 |
| 7394. | TGATCGATAAAGAAAGATTTATCG[T,C]GTAGTCCTTAAATTGGTTTATGACC | 3,138,880 | 51 |
| 7395. | TATAGGTCGTTGTGTGCCATATAC[G,A]TTGGTTGTCCTCGTAACCAAATGGT | 3,138,968 | 51 |
| 7396. | AAATGGTGTGGAGATACTGGTATG[G,A]CATGCGGGTGAGATATAGAAGTACA | 3,139,011 | 51 |
| 7397. | CTAACTGAGTTTCTAATTCAGTGA[C,T]GAAAGATTTTTAGTTACAATCAAGT | 3,139,195 | 51 |
| 7398. | CGAAAGATTTTTAGTTACAATCAA[G,A]TACTTATGAAGTTGGTGTATAAGTC | 3,139,219 | 51 |
| 7399. | CAAGTACTTATGAAGTTGGTGTAT[A,G]AGTCAAGATGGGATTGATCCCTTCG | 3,139,240 | 51 |
| 7400. | CATGTGATGGATTTAAAAAAAaTT[G,A]AAATACAATGTGGATGACTTATCTA | 3,139,351 | 51 |
| 7401. | TCGATCTATCCGGATGTTGGGTCA[C,T]CATTGCTAGATGATTACATCGATTG | 3,139,506 | 51 |
| 7402. | ATCATGCGGCTGATCAACGATTGA[G,A]AATCGTTCAAGGGCTTAATCATCAA | 3,139,630 | 51 |
| 7403. | AAGGGCTTAATCATCAATTCGATT[A,G]ATGGTTAACCTTATGCAAAAATTAT | 3,139,663 | 51 |
| 7404. | ATTAAATTATTGATTAGCTTAGTT[T,C]GATTGAGCAAAGAGGATCAAATAAA | 3,139,763 | 51 |
| 7405. | ATTATTGATTAGCTTAGTTTGATT[G,A]AGCAAAGAGGATCAAATAAAATCTA | 3,139,768 | 51 |
| 7406. | TTAGTTTGATTGAGCAAAGAGGAT[C,T]AAATAAAATCTAATTGAGTTGGATT | 3,139,781 | 51 |
| 7407. | AAAGGAGAATTATCCCTGATTTAT[C,T]AGGATTTTGATTCAATCAATTTCTA | 3,139,875 | 51 |
| 7408. | TCATATATTTTATTTGGGCTAAAA[C,T]AGACATGATTTGGTTTGGATTCAAA | 3,139,963 | 51 |
| 7409. | ATATTTTATTTGGGCTAAAACAGA[C,T]ATGATTTGGTTTGGATTCAAATAAG | 3,139,967 | 51 |
| 7410. | TGGATTCAAATAAGGAAATTAAGA[G,A]TCCTTATTGGAATAGAACTCTTCTT | 3,140,003 | 51 |
| 7411. | GTTTTGTATAAAATTTTTTATG[T,C]CAAAGAGTGCTTTCCCTTCTCTATC | 3,140,098 | 51 |
| 7412. | CTCACATCTAAATTTGAATAGGAT[T,C]AGATTTTAAATGGTGTGTTCAAATC | 3,140,147 | 51 |
| 7413. | GTGCTACATTTTAAGGATATTTTT[T,C]ATGAAAAATTATTTGGAGAACTATT | 3,140,280 | 51 |
| 7414. | GTGCATAAAAAATTAGGTTTCTAGG[A,G]TTTTGGTCCTTAGGGTTTGAGAAGA | 3,140,591 | 51 |
| 7415. | GCTAGCACTTTCGAGAAGATCGAT[T,C]AGATCGAGGCTTCAAGTAGATTTTT | 3,140,783 | 51 |
| 7416. | CCTACCTATCAGCAAAACTTGGGA[A,G]TGTGGCGGAGGCTCGGCCGCCCGGG | 3,152,554 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7417. | ACTTGGGAATGTGGCGGAGGCTCG[G,A]CCGCCCGGGAGGTTTGAAGAGATGT | 3,152,570 | 51 |
| 7418. | CCCGGGAGGTTTGAAGAGATGTTG[T,C]CGGAGGTCGAAAGTCAGTTGGATCC | 3,152,570 | 51 |
| 7419. | CCCGGGAGGTTTGAAGAGATGTTG[T,C]CGGAGGTCGAAAGTCAGTTGGATCC | 3,152,598 | 51 |
| 7420. | CTATAGCTAAAACTATCAACGAAA[C,A]GATATAATTTTGTAACTTTCTTTAC | 3,152,857 | 51 |
| 7421. | GCTTCGGTTGTAAACAAAGCAACT[T,A]TATCTTGAAGTGTAGTTTTCTAACT | 3,152,932 | 51 |
| 7422. | ATATATTAAGCTACCAACTATACC[G,A]GTATGTAGAACACATGATATGTGCT | 3,153,229 | 51 |
| 7423. | TATGTAGAACACATGATATGTGCT[G,T]TACCTCCTCCATCATTTGCAATGAT | 3,153,255 | 51 |
| 7424. | TTTGAGATAAATACAATCGACCTG[T,G]GCTTATCTCTATAAATTTATGTCTC | 3,153,398 | 51 |
| 7425. | TCCAAATTTTTCATTTTAAATTCA[T,C]CATTCAATATAATTAAAGTTTCAAC | 3,153,467 | 51 |
| 7426. | TCTGCATGCTTCGAGATCTCCACT[A,T]TATAAAATGGTCCAATTTTGGCTCT | 3,153,571 | 51 |
| 7427. | TGGATGTGTGAAAAATGTAGTAGT[A,C]TCACACTATATATTGTTTAACAGAA | 3,153,689 | 51 |
| 7428. | AAGTGGTATAAGGTGAAGCCAGAT[G,A]TGGAGGAGTCTAGTTGGCTATTGCC | 3,154,528 | 51 |
| 7429. | ATCTATGCGGATGTATATTTAATC[T,C]CACATTAATTATTCACCGAAAGATC | 3,154,947 | 51 |
| 7430. | TTTAATCTCACATTAATTATTCAC[C,T]GAAAGATCTTGAATACTTATATAGG | 3,154,964 | 51 |
| 7431. | GGATGAGGTCCTAAATTATTATAC[T,C]TAGCTAATTAGGTATGCAACTCCAT | 3,155,053 | 51 |
| 7432. | TATGCAACTCCATCCAATCTTTGT[A,G]GCATATGCAGGGTGGATGTCTGGCC | 3,155,090 | 51 |
| 7433. | TCCATCCAATCTTTGTAGCATATG[C,T]AGGGTGGATGTCTGGCCAGAACACC | 3,155,098 | 51 |
| 7434. | AAGAAAGAAGAAATAAACAGAAAA[C,T]AATCAAATACGTGGATCAGCCAAAA | 3,155,187 | 51 |
| 7435. | TGGGGCATGCAAACTTCACTATGA[A,G]AAAATAAATATTACAAGAGGAGATC | 3,155,525 | 51 |
| 7436. | GTTCACTATTTCCTGGTTTCCATG[C,T]GAAGACGTCCACGCCCATGAAACCA | 3,155,469 | 51 |
| 7437. | CTCCTAATCAACCTCAAATCAAGT[T,C]CCAAACCGTTGGATCAAGATCAGGA | 3,155,549 | 51 |
| 7438. | TCGCACTCCGATCTATGAAATAGT[G,A]CCGTGGACCGTAAGAAATAGATGAG | 3,155,662 | 51 |
| 7439. | GGACCGTAAGAAATAGATGAGAAA[C,T]GGCTCTGCGGTCCACGTGCTCCTCT | 3,155,691 | 51 |
| 7440. | CTGCCGTTGCTCCACCGGCCCGCC[A,G]CCGGCCGCCGATGGTCCTCCACCAC | 3,155,947 | 51 |
| 7441. | TTCAAACGTATGTATCTCCTCCGT[C,T]CGAGCTCTGTTTGAGATGATCTTGG | 3,156,015 | 51 |
| 7442. | TTCACTGTGAGCTCAATGTGGATT[G,A]AATTTTGAGGCATCAAATCCTAACA | 3,156,095 | 51 |
| 7443. | AATCAACTGCTGATCATAGATTGA[T,C]AAATATAGGAGTCGAGCCAGGCCAC | 3,156,223 | 51 |
| 7444. | GCTGTGCTTCTCCTAACTTAAGAC[A,C]TGCTCGGGGTATCATCCTACAGCAA | 3,156,294 | 51 |
| 7445. | ATAGCCTCTTGAATTCAGTCTGCT[T,C]AATGAGATAAGATTTCATCTAAAAT | 3,156,575 | 51 |
| 7446. | GCTTAATGAGATAAGATTTCATCT[A,G]AAATCAGATATGTATCGAACCTCCC | 3,156,596 | 51 |
| 7447. | AATCAGATATGTATCGAACCTCCC[C,T]CAATCTTCTTACTGCACCATCATGT | 3,156,622 | 51 |
| 7448. | GTCCTCTAGCTGACCATCCCGATG[T,G]CTCTGATAGCGCAGCTCGATCTATC | 3,156,672 | 51 |
| 7449. | CGATCTATCCGACAGATAAATAGT[A,G]TCTTCACTGTTCTCTAAGGAGTCAA | 3,156,713 | 51 |
| 7450. | GCAGAATCTAATATCCACTGTTGG[G,A]AAGAAGTAGATACCTCGTCAGATGG | 3,156,798 | 51 |
| 7451. | CAGATGGCTCCAAGATATCTCCCT[C,T]TGAATTGTTACTGGCCGTCGCCACA | 3,156,841 | 51 |
| 7452. | TCCAAGATATCTCCCTcTGAATTG[T,C]TACTGGCCGTCGCCACAGCAGTCAT | 3,156,849 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7453. | AATTGTTACTGGCCGTCGCCACAG[C,T]AGTCATCGTCTGATTTTTGAATTGA | 3,156,868 | 51 |
| 7454. | TGTTACTGGCCGTCGCCACAGCAG[T,C]CATCGTCTGATTTTTGAATTGAGAG | 3,156,871 | 51 |
| 7455. | AACTCGTCACACTGGTAACACCTG[A,G]TCTTGCTCAAGTCTCTCATGGACTT | 3,156,942 | 51 |
| 7456. | AAGTCTCTCATGGACTTGGACCGC[T,C]CTCGTCGCGATCTCCTATCACACCA | 3,156,975 | 51 |
| 7457. | GGACCGCTCTCGTCGCGATCTCCT[A,G]TCACACCATCTACTGCCTCCTGCTC | 3,156,992 | 51 |
| 7458. | TCTTGATGGTGCTCTTCTCCACTA[G,A]AAGAGCAGTCACCAAGGACTCGTAC | 3,157,144 | 51 |
| 7459. | GAGAGACTTCGCTATATACAACTC[C,T]TCGAGCTTCAACCACAGCACCATTG | 3,157,367 | 51 |
| 7460. | GATCACCACCTCATCCGTCAGGAA[C,T]ATGTGGATGGTACTCACTGCCTGCA | 3,157,439 | 51 |
| 7461. | TCTCATTAGACTCTGTTTTTAATC[A,G]CGGACCTCGCTGTAGAATTAATATA | 3,159,053 | 51 |
| 7462. | ATTAATATAGATCAAATCTCAAGA[C,T]GTCAAATcTTAACGACATATGCTTT | 3,159,094 | 51 |
| 7463. | AGATCAAATCTCAAGACGTCAAAT[C,T]TTAACGACATATGCTTTTATACCCA | 3,159,102 | 51 |
| 7464. | TTTATACCCATCCAATCTTTGTGG[C,T]AAGCTCCAACCTACGTGTTTTCATC | 3,159,142 | 51 |
| 7465. | TCTTTGTGGCAAGCTCCAACCTAC[G,A]TGTTTTCATCGAGAACTTGCACTAC | 3,159,157 | 51 |
| 7466. | GGCTCTTAAACCCCTGGACTGGCT[G,C]AAAATGGTTGGCCCTACTTTAATCT | 3,159,221 | 51 |
| 7467. | AGAAGAAGAGACGGAGAACGTTGT[T,G]CTCTTCTCTCTCTTCCTTTTATTTA | 3,159,820 | 51 |
| 7468. | TTTAAAATTTTTTTtCACTAGATT[A,G]TTTTCTCTAGGAGTCTCGTAGACTA | 3,159,985 | 51 |
| 7469. | TAGATTATTTTCTCTAGGAGTCTC[G,A]TAGACTAGTGGAGGGTCCAAGTACT | 3,160,003 | 51 |
| 7470. | TTAAATTTTAGTTGACCGTAGGAA[G,A]AGTCCTGGATTTATAATATTAGGAT | 3,160,062 | 51 |
| 7471. | AAATTTTAGTTGACCGTAGGAAGA[G,A]TCCTGGATTTATAATATTAGGATCA | 3,160,064 | 51 |
| 7472. | TTTTATTTCGAGTTCATAGATCGA[G,A]GAGTTCATCGATTTCTGTATATGGG | 3,160,214 | 51 |
| 7473. | GTATCATATGTTTATATCAAACAA[C,T]AATTATTTTTCGGATGGTTTGGGAT | 3,160,477 | 51 |
| 7474. | GACATAAATTAAGACTTAATAAAT[G,T]GATGATCAAGAGAGGATATTTGAAC | 3,160,571 | 51 |
| 7475. | ACAGATGCGTGGTATTTGAATTTT[T,C]CACTTTAAGCTGAAGCACAGTTATT | 3,160,757 | 51 |
| 7476. | CATGATCGTGATTAGTCCAAAATT[C,T]TAAAGATAATTATAGATTAATCCAG | 3,160,920 | 51 |
| 7477. | CCAGATTAAGTTAATGAGATATGG[G,A]TGATAAGATATAAACCATGATTAAG | 3,160,966 | 51 |
| 7478. | TGAATTGAGGTCGATAATGATTAT[A,G]TTATATTGAGATTGTAAGAAATTTT | 3,161,406 | 51 |
| 7479. | TTACTCTACCACGTGTGTTGAAGA[C,T]AAAGCCAATGAAAAACATAACATCG | 3,161,826 | 51 |
| 7480. | ATAAGAGAAATTGTTAGTTAGAAT[T,C]GTTCTACCATGTATATCTTAGACTA | 3,161,911 | 51 |
| 7481. | GATGTGTTGATTTTTtATTGAATA[A,G]TCTAAGGTACACATGACAGAGAACA | 3,162,120 | 51 |
| 7482. | TTTTTtATTGAATAATCTAAGGTA[C,G]ACATGACAGAGAACAATACTAACCA | 3,162,130 | 51 |
| 7483. | GCACATTGTTTATATGATTGGTC[T,A]ACATAGCCACCACTTCTCAATGCAT | 3,162,464 | 51 |
| 7484. | AATATCCTATGGCATATTATGACT[G,T]CTTATACGCCGGATGTCATAATATG | 3,162,520 | 51 |
| 7485. | TGCATGCAAGATGTCATAATATAG[A,G]CCAAGATGTTATAATATAGAAGAGG | 3,162,631 | 51 |
| 7486. | ACGACAAAAATACCCTTGCTCTTT[G,A]AAAAAAATTATGATATCCTGCGTCA | 3,162,752 | 51 |
| 7487. | TTGTTTCTCTACAGACCATTGAAG[C,T]ACCAAAAAGGGGTTGATGTTGAAGA | 3,163,550 | 51 |
| 7488. | CTGGGAGATAAAGCCACCTCAGGT[T,A]ATCCGAAATACAAATCAAAAGTTG | 3,165,060 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7489. | AGGATTTAAAAAGATATATCCACC[G,A]GAGACAAAAGGATGCTCACCGCGCT | 3,165,708 | 51 |
| 7490. | CGCTCTTCGTATGTTTCTGATCTT[T,A]GTATGTAAGTAGAGGCAAACAAGGA | 3,165,754 | 51 |
| 7491. | CCTCAAAGGTATGAATAACTCTAA[A,G]TGCTCACTCTCTCCCATTTGTTCTC | 3,165,805 | 51 |
| 7492. | TTTTAACTTGAGCATTGGAGAGTC[T,C]CCACTGGAGTCATCTCCAGCTAGGG | 3,165,858 | 51 |
| 7493. | ACTTTATTTGCAGATCCTACTATC[A,G]TCGTTCTCGCCGAACCTCGATCTAC | 3,165,908 | 51 |
| 7494. | TCCAGAGCGGACAATATCTCACAG[T,C]AGAAGCTGAGGGGGATGGGGGTAGG | 3,166,195 | 51 |
| 7495. | GAGCGGACAATATCTCACAGTAGA[A,G]GCTGAGGGGATGGGGGTAGGAATT | 3,166,199 | 51 |
| 7496. | GAGTCATGTTAGAGTGGAGGGTGA[C,A]TCCCTTACTGTCATCCGTTGGATCG | 3,166,935 | 51 |
| 7497. | ATTGCATATAAAATCTGAAAAaAA[T,C]TAAATATAAAATCAGCATGCATGCA | 3,167,965 | 51 |
| 7498. | CTTTTTTCACACCATGAAACCATA[C,A]CCAAGACTCCTCTCAATGTGAAGAC | 3,168,418 | 51 |
| 7499. | GTTGGCGACAAGGTGTTAGAGATA[A,T]TGTCAAACATTATCTATATGATATC | 3,168,725 | 51 |
| 7500. | TAAAACCTGCTCGTATCTAAATTT[G,A]GATGTGAGATAGAGAAGGAAAAGGA | 3,168,805 | 51 |
| 7501. | AAGAACCTATTGGCGTATGGTTCC[A,G]TATAATTCATTTCTTTGATCCTAAT | 3,169,554 | 51 |
| 7502. | GTTCCATATAATTCATTTCTTTGA[T,C]CCTAATACTTGAGGACAATCAAAAA | 3,169,573 | 51 |
| 7503. | TTTAGAGGAGTCAATCCCATCTTG[G,A]CTCATGTACTGACTTGACAAGTACT | 3,169,747 | 51 |
| 7504. | GAGTCAATCCCATCTTGGCTCATG[T,C]ACTGACTTGACAAGTACTTGACTGC | 3,169,754 | 51 |
| 7505. | TCTTAGATTCTTTGGAATATCCTA[T,C]AAAATAATACATATAGAATTGAGAT | 3,171,596 | 51 |
| 7506. | TATCAAACTATATCTAACAAAGTT[G,A]ATTTCAATAAGAGAGAATCTTATTT | 3,171,846 | 51 |
| 7507. | CATCGGAAGGACATTCTCCTCTTT[G,A]TTCTGATCGAAGAGTTTCAATGCTC | 3,171,918 | 51 |
| 7508. | AATTTATTTTCTATCTTATTATG[G,A]AATTATTTGAATATTTTAAATAATC | 3,171,973 | 51 |
| 7509. | TATGTTCGTATATCCAATACATCA[A,G]TATGTATCAGACTCAGAACACTATT | 3,172,038 | 51 |
| 7510. | CATGATCGAGCCTAAATTGCCAAA[A,G]ATAGGCTTCTAAGATATAATCTACT | 3,172,212 | 51 |
| 7511. | TCTTAGTTGTCCACATGATTTTGA[T,C]ATCATTCATAATGATATCACAAAAA | 3,172,322 | 51 |
| 7512. | AGACAATAGTGACAATCACCAAAA[T,C]GATATTGATAGAATTGAAAATAAGC | 3,172,377 | 51 |
| 7513. | TGATAGAATTGAAAATAAGCTCAA[C,T]GATTCTTAAAATCAGGATTAAAACA | 3,172,407 | 51 |
| 7514. | ACCGAGACAGTAGTGTTATAGATA[G,T]AGAAATCACAAGGTGTTATTATATA | 3,172,556 | 51 |
| 7515. | TGATTTTCTTCCTTAGCCTGTTC[G,A]TATCAAGGAACTCTATCAGACTAGA | 3,172,631 | 51 |
| 7516. | CTCCTTCAACATTTGAAGGATTTC[C,G]TCCTACTGAATATTAACAAATTTAC | 3,172,809 | 51 |
| 7517. | CAACATTTGAAGGATTTCCTCCTA[C,T]TGAATATTAACAAATTTACAACTAA | 3,172,815 | 51 |
| 7518. | TTCTTTGCTGCTCTCAAAATACAA[C,T]ACATAGTGATACGATCATTTGGCCA | 3,172,872 | 51 |
| 7519. | AGAACTATTTGCAACTTCTGATAC[C,T]ATATATCAAAGTTGGGTCCTATAAA | 3,173,016 | 51 |
| 7520. | ACTATTTGCAACTTCTGATACCAT[A,C]TATCAAAGTTGGGTCCTATAAATAA | 3,173,019 | 51 |
| 7521. | AAAaAACTCAAGACCTCTATGTTT[A,G]TGAATTGATTAAGCCTAAAGACTTG | 3,173,121 | 51 |
| 7522. | ATCCACACAAACTGCATACAAGTC[T,C]GAGGATAGTTCTGTCAACTCATATG | 3,173,266 | 51 |
| 7523. | CTATGGGTAGATTCTCAACTAATT[A,G]TTTCTTCAAACAATTTCTAGTAATT | 3,173,319 | 51 |
| 7524. | TTCTCAACTAATTATTTCTTCAAA[C,T]AATTTCTAGTAATTAATTTTATCCC | 3,173,330 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7525. | GCGATAGATCTCCACTAAAAGTTT[C,T]AGTTAGATCAAACCATTAACATGTA | 3,173,397 | 51 |
| 7526. | CATAAATTATGATATTATTTACTA[G,A]CGTATTAGTTAAATACCATGATAGT | 3,173,790 | 51 |
| 7527. | ACTCCATCAGGTCGGATTTTGGAT[G,T]GTTGCAGATCGACACTAAAAAGGG | 3,174,898 | 51 |
| 7528. | CTAAGATCATAAAGTTCAAGAGGA[A,C]CAGCCACTAATCCACATTCAACCAA | 3,174,966 | 51 |
| 7529. | ATTCCTTGAGAGTCCAATCCTACA[T,A]GCTATGCTAATTTCCATGGTTTTG | 3,175,479 | 51 |
| 7530. | CAATCCTAAATGGTTACAACACAA[C,A]TCCAAGCTATTAAGATACGATTCAC | 3,176,060 | 51 |
| 7531. | ATCCCCTCGTCGCCTGGTCACCGG[G,A]AACAAGTGCCTGCAAAAGAAGTCCG | 3,176,852 | 51 |
| 7532. | TCGCCTGGTCACCGGGAACAAGTG[C,T]CTGCAAAAGAAGTCCGCACTGACCG | 3,176,861 | 51 |
| 7533. | CCCTCCGACGGTCAAGTCAGAGAG[G,A]AGACTAGGCAACAGTAGAAAAGAAT | 3,176,930 | 51 |
| 7534. | GGGGGAGAGAGAGGGTAAGCCCAA[A,G]GGTTTCAAAAGAACCTCCTCCAGCA | 3,176,997 | 51 |
| 7535. | TTTTATAGTAGAGCGTGGTATGGC[T,G]CCGTCATTAATGGCACAGACAATGA | 3,177,061 | 51 |
| 7536. | GAGTCGCCGTGGGGCTGTCAAATC[A,G]TCGTGGGGCTGTCAAATCACTAGGG | 3,177,140 | 51 |
| 7537. | TTTGGGTGGAACGATGTCCCAGGG[T,C]GGCTACGCCGCATGACTTTGTCAGG | 3,177,201 | 51 |
| 7538. | GTTTGGGAGAGCTGGCCGACCATA[C,T]GTCGGTATTCGCTGTCGGGACGTCG | 3,177,277 | 51 |
| 7539. | GGTGCCTTGCTTAAGTCGGACGTC[G,A]GCTGCCACCTCCGACGGTGAGTCGG | 3,177,359 | 51 |
| 7540. | CAGTTGCCCCCCcACTCCTGAGTC[T,C]GATGTCATGTTGGCTCGCGTGAATA | 3,177,618 | 51 |
| 7541. | CCCCCcACTCCTGAGTCTGATGTC[A,G]TGTTGGCTCGCGTGAATACGTGGGC | 3,177,625 | 51 |
| 7542. | TCAACGAACGATCCGATGTCGGTC[A,G]TCTCGACTGTAGGTCGAGTGAGCAC | 3,177,736 | 51 |
| 7543. | CATTCCGCAAAGTCGAGTAGCGTC[T,C]GACATATTCAGATAGGATAACGATG | 3,177,834 | 51 |
| 7544. | GTGGTAAGCCGAATATCCTTCGAC[C,T]GATCGTGACCAAGTCGGTATGTCGC | 3,177,947 | 51 |
| 7545. | TAGCATGTCGAGTCGTATGATAGA[T,C]GGTGGCAAGCCGAATATCCTTCGAC | 3,178,017 | 51 |
| 7546. | AAGCCGAATATCCTTCGACCGGTC[A,G]TGACCGGGTCGGTATGTCGCAAGTC | 3,178,048 | 51 |
| 7547. | CGGGTATGTCGCGGTTGTCTTGGC[G,A]TTTTGCCCTTTCTTAGTCGAAGCTA | 3,178,127 | 51 |
| 7548. | TAAGTTGGCAAGTTAGCCAGCCGC[G,A]TTGGTCGAAGCTTTTTGCCCTCAGA | 3,178,175 | 51 |
| 7549. | CATAGGCCGTCGGTTCGGTGATCG[A,G]TGATCGAGCTGTTGATTCGACGATC | 3,178,227 | 51 |
| 7550. | CGGTTCGGTGATCGATGATCGAGC[T,C]GTTGATTCGACGATCGACGATCGAG | 3,178,237 | 51 |
| 7551. | GATTCGACGATCGACGATCGAGCC[A,G]TATTGGTCGAGGCCCTTTTGCTTTC | 3,178,265 | 51 |
| 7552. | CCATATTGGTCGAGGCCCTTTTGC[T,C]TTCAGAGGTCGAGGCCGTCTGTTCG | 3,178,287 | 51 |
| 7553. | TTGCTTTCAGAGGTCGAGGCCGTC[T,A]GTTCGGCGATCGGTGATCGAATCGT | 3,178,307 | 51 |
| 7554. | GCGATCGACGATCGAGCCATATTG[G,A]TCAATGCCCTTTTGCCTTCAAAGGT | 3,178,364 | 51 |
| 7555. | TCAATGCCCTTTTGCCTTCAAAGG[T,C]CGAGGCCGTCGGTTCGGCGATCAGT | 3,178,389 | 51 |
| 7556. | GTCGAGGCCGTCGGTTCGGCGATC[A,G]GTGATCGAGCCGTTGATTCGGTGAT | 3,178,412 | 51 |
| 7557. | TCAGTGATCGAGCCGTTGATTCGG[T,C]GATCGACGATCGAGCCGTATTGGTC | 3,178,434 | 51 |
| 7558. | CCTTTTGCCTTCAGAGGCCGAGGC[A,C]GTCGGTTCGACGATCGATGATCGAG | 3,178,570 | 51 |
| 7559. | TCAGAGGCCGAGGCAGTCGGTTCG[A,C]CGATCGATGATCGAGCCATTGATTC | 3,178,580 | 51 |
| 7560. | CCGAGGCAGTCGGTTCGACGATCG[A,G]TGATCGAGCCATTGATTCGGCGATC | 3,178,587 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7561. | GGTTCGACGATCGATGATCGAGCC[A,G]TTGATTCGGCGATCGACGATCGAGC | 3,178,598 | 51 |
| 7562. | ATCGATGATCGAGCCATTGATTCG[G,A]CGATCGACGATCGAGCCGTATTGGT | 3,178,607 | 51 |
| 7563. | CGAGGCCCTTTTGCCTTCAGAGGC[T,C]GAGGCCGTCGGTTCGGCAATCGGTG | 3,178,738 | 51 |
| 7564. | AGAGGCTGAGGCCGTCGGTTCGGC[A,G]ATCGGTGATCGAGCCATTGATTCGG | 3,178,756 | 51 |
| 7565. | GGTTCGGCAATCGGTGATCGAGCC[A,G]TTGATTCGGCGATCGACGATTTAGC | 3,178,772 | 51 |
| 7566. | CCGAGGCCGTCGGTTCGGCGATCG[A,G]TGATCAAGCCATTGATTCGACGATC | 3,178,854 | 51 |
| 7567. | CCGTCGGTTCGGCGATCGATGATC[A,G]AGCCATTGATTCGACGATCGACGAT | 3,178,860 | 51 |
| 7568. | GATTCGACGATCGACGATCGAGCC[A,G]TATTGGTCGAGGCCCTTTTGCCTTC | 3,178,892 | 51 |
| 7569. | TTCGACGATCGACGATCGAGCCAT[A,G]TTGGTCGAGGCCCTTTTGCCTTCAG | 3,178,894 | 51 |
| 7570. | CAGAGGCCGAGgCCGTCGGTTCGA[C,T]GATCGATGATCGAGCTGTTGATTCG | 3,178,941 | 51 |
| 7571. | ATCGATGATCGAGCTGTTGATTCG[G,A]CGATCGACGATTGAGCCATATTGGT | 3,178,967 | 51 |
| 7572. | CGAGCTGTTGATTCGGCGATCGAC[G,A]ATTGAGCCATATTGGTCGAGGCCCT | 3,178,976 | 51 |
| 7573. | TCGAGGCCCTTTTGCCTTCAGAGG[C,T]CGAGGCCGTCAGTTCGACGATCGGT | 3,179,016 | 51 |
| 7574. | TTGCCTTCAGAGGCCGAGGCCGTC[A,G]GTTCGACGATCGGTGATCGAGTCGT | 3,179,027 | 51 |
| 7575. | TCAGTTCGACGATCGGTGATCGAG[T,C]CGTTGATTCGGCGATCGACGATCGA | 3,179,049 | 51 |
| 7576. | ATCGGTGATCGAGTCGTTGATTCG[G,A]CGATCGACGATCGAGCCGTATTGGT | 3,179,060 | 51 |
| 7577. | TTCGGCGATCGACGATCGAGCCGT[A,G]TTGGTCGAGGCCCTTTTGCCTTCAG | 3,179,060 | 51 |
| 7578. | GATTCGGCGATCGACGATCGAGCC[G,A]TATTGGTCGAGGCCCTTTTGCCTTC | 3,179,078 | 51 |
| 7579. | TTCGGCGATCGACGATCGAGCCGT[A,G]TTGGTCGAGGCCCTTTTGCCTTCAG | 3,179,080 | 51 |
| 7580. | GCGATCGACGATCGAGCCGTATTG[G,A]TCGAGGCCCTTTTGCCTTACGAGGC | 3,179,084 | 51 |
| 7581. | GAGGCCGAGGCCGTTGGTGATTGA[G,A]CCATTGATTCGACGATCGACGATCG | 3,179,129 | 51 |
| 7582. | AGCCATATTGGTCGAGGCCCTTTT[A,G]CCTTCAGAGGCCGAGGCCGTCGGTT | 3,179,179 | 51 |
| 7583. | CAGAGGCCGAGGCCGTCGGTTCGA[T,C]GATCTGTGATCGAGCTGTTGATTCG | 3,179,208 | 51 |
| 7584. | GGCCAAGGCTGTCGTAGATACTCC[G,A]CTCCTTCGATCTCTATCAGGATCTG | 3,179,305 | 51 |
| 7585. | AGGAGTCATACCTGCGATGCATCG[G,A]TCTCGGACTCCGTCGTCGGGGCAAG | 3,179,381 | 51 |
| 7586. | CAGACGTCGGTTGGAAGCTCCTTC[G,A]TCTGCGCGCATGTATTTGTACGCGC | 3,179,516 | 51 |
| 7587. | GTCGGAGGTTCATGGAGGCTTCCG[A,G]CTGGTGCTGAAATGGGCCACGAAAG | 3,179,761 | 51 |
| 7588. | TAAACCGACTAGGGATCGGCTCAT[C,T]GAGGATGAGTCGGGAGAGAGGTTGG | 3,180,012 | 51 |
| 7589. | TTCTGTCCGRCCACCTGCAGCTGG[G,A]CAAGCTGATGGTTGATTTCTTCGAA | 3,180,092 | 51 |
| 7590. | GACCCCGGGGTGGAGRCTCCCGA[T,C]GAATCTGAGAGGGAGGCGGACGGTG | 3,180,178 | 51 |
| 7591. | GTTCCAGCTGGGAAGGAGATGGTC[G,A]TCGGGATCGGTGGGCATCATGTTGT | 3,180,255 | 51 |
| 7592. | TCGGGTGTGCCGTCGGTTGCTCCG[C,T]CGGTGAGTGTGGCAACTGGGTTGGT | 3,180,401 | 51 |
| 7593. | TTGCTCCGCCGGTGAGTGTGGCAA[C,T]TGGGTTGGTTGCTGTTGAAGGcTCT | 3,180,417 | 51 |
| 7594. | AGCACGGTCATCTGCCGCACGATC[G,A]TCGCGAACTGCACCTCCGTGGTCAC | 3,180,481 | 51 |
| 7595. | TGTGGCCAATCTCCTCGTCGCCTG[A,G]TCATCGGAAACGAGTGCCTGCAAAA | 3,180,717 | 51 |
| 7596. | AATCTCCTCGTCGCCTGATCATCG[G,A]AAACGAGTGCCTGCAAAAGAAGTCC | 3,180,724 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7597. | TCCTCGTCGCCTGATCATCGGAAA[C,T]GAGTGCCTGCAAAAGAAGTCCGCAC | 3,180,728 | 51 |
| 7598. | GGAGAGAGAGAGGGTAAGCCCAAG[G,A]GTTTCGAAAGAACCTCTTCCAGCAC | 3,180,871 | 51 |
| 7599. | TCATCGGAGGCTGTCAGAGTCACC[A,G]TGGGGTTGTCAAATCACTGTGGGGC | 3,180,998 | 51 |
| 7600. | GACTGTCAAATCACTAGGGTTGAC[T,C]CATGTCTTGGGTGGGACGATGTCCC | 3,181,065 | 51 |
| 7601. | CATGTCTTGGGTGGGACGATGTCC[C,T]AGGGCTACGCCGCATGCCTTTGGGC | 3,181,090 | 51 |
| 7602. | TAATATGGGTTCGACCGCTCAGTC[A,G]GTCGGAAACAACATGGGTCGGTTCG | 3,181,304 | 51 |
| 7603. | AGTTGGACGTCCGTCGGAGTCGTC[C,T]GTCGGTCGTCGATCAGATCGGTCCG | 3,181,423 | 51 |
| 7604. | GTCGTCCGTCGGTCGTCGATCAGA[T,C]CGGTCCGAGAGTAAGTCGGCGTATG | 3,181,441 | 51 |
| 7605. | CGTCGGTCGTCGATCAGATCGGTC[C,T]GAGAGTAAGTCGGCGTATGGGGTC | 3,181,447 | 51 |
| 7606. | TCAGTCGGTATATCCCAATAACCT[C,T]TAAGATAATAGAAAAAGGTCTCGGC | 3,181,495 | 51 |
| 7607. | CGAAAAAGCCTCAGCTTGACTGAT[C,T]AGAGGAGTCATCCTAGGATTGACTG | 3,181,587 | 51 |
| 7608. | GAAAAAGCCTCAGCTTGACTGATC[A,G]GAGGAGTCATCCTAGGATTGACTGA | 3,181,588 | 51 |
| 7609. | ATTAGCGATGACAATTTTATCATC[G,A]ATAAAAAGAAGTCTTCGTATGACCA | 3,181,623 | 51 |
| 7610. | ATTAGCGATGACAATTTTATCATC[C,A]TAATAATATTTTTTATTGATAATAA | 3,181,715 | 51 |
| 7611. | AGTGATGGTATTTTTGATTTTTAA[T,C]GACAGCTAATTACGTCACTAATAAA | 3,181,801 | 51 |
| 7612. | GATGGTATTTTTGATTTTTAATGA[C,T]AGCTAATTACGTCACTAATAAAAAA | 3,181,804 | 51 |
| 7613. | TTTGATTCAAGAATTATTAGTGAC[G,A]GAGTTATCTTATTAGCAAtGGTATT | 3,181,871 | 51 |
| 7614. | GTGACAGAGTTATCTTATTAGCAA[T,C]GGTATTTTACCGTCACTAATAACCT | 3,181,890 | 51 |
| 7615. | ACGATTTTTATCTAATTGTGTGCC[C,T]CAATTTTCCCCACCCCCcTCTCATT | 3,181,983 | 51 |
| 7616. | CCGAGCATCCAAATCCTATTTTTC[T,C]CCATCGACGGCCGACTGACTGCTGG | 3,182,077 | 51 |
| 7617. | AAGCCCCGACTGCCTCCTCGAGCC[C,T]CCGTCCACCGAATCCAAGCCCCTCG | 3,182,140 | 51 |
| 7618. | CGTCGTCAGATCCGGCTTTCCCAA[G,A]CTGTCGGCCGCCTCCTCGAGCCCCG | 3,182,360 | 51 |
| 7619. | ATTTCCATCAACCTCATCGGTCGT[T,C]GCCTCACCACGCCACCTCACCACAC | 3,182,498 | 51 |
| 7620. | CAACATATATATCCCTGTATTGGT[G,A]TTTGCTTTCATGCCTATCTAATAAA | 3,183,117 | 51 |
| 7621. | AATTATCTTTATTTTTAAAATTG[G,A]TCGAACTGAGAGAAGAAACCAGGTT | 3,183,262 | 51 |
| 7622. | TTATCTTTATTTTTAAAATTGGT[C,T]GAACTGAGAGAAGAAACCAGGTTAA | 3,183,264 | 51 |
| 7623. | CTCTGTTCTTTTATGCAATTTGTC[G,A]GACACCTTAGATTCTATCTATTTAT | 3,184,744 | 51 |
| 7624. | CTAGCCATCGGAGCACTACGTTGT[C,T]AGACCCGCAATGTCAGACCCGCACC | 3,184,903 | 51 |
| 7625. | TGTCAGACCCGCAATGTCAGACCC[G,A]CACCACCTTGCACCGTGAGTATTAA | 3,184,924 | 51 |
| 7626. | TCACCATCGTCACACCCCATTTTC[A,T]TCTTTTTAAATTTTAAATATTTAAA | 3,185,009 | 51 |
| 7627. | CATCTTTTTAAATTTTAAATATTT[A,T]AAATTAGATTTATTTGATTATTTTA | 3,185,032 | 51 |
| 7628. | TTAAATTTTAAATATTTAAAATTA[G,A]ATTTATTTGATTATTTTAAATTAAT | 3,185,039 | 51 |
| 7629. | GGCTCTGACCCACTCATCTACTCT[G,A]ACGGCGATCGGAGTAACTCGGCAAT | 3,185,236 | 51 |
| 7630. | TGACCCACTCATCTACTCTGACGG[C,T]GATCGGAGTAACTCGGCAATTGAAT | 3,185,241 | 51 |
| 7631. | CACTCATCTACTCTGACGGCGATC[G,A]GAGTAACTCGGCAATTGAATTCTAG | 3,185,246 | 51 |
| 7632. | CACTCATCTACTCTGACGGCGATC[G,A]GACTCAAGGAGGCCAACATGATACC | 3,185,313 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7633. | GTATCCCTACGCCACTTCTCCATT[G,A]TCGTCATCCACTTATCGGATTTCCT | 3,185,474 | 51 |
| 7634. | TCCTCCTCTATCGATAAGGTGAGG[C,T]AGCTTTGGAAGGTATGTTATTCCGT | 3,185,595 | 51 |
| 7635. | TTGATACTCTCAGATTCGAACAAT[A,G]TGGAGTCACCAGTAGCTCCACATTT | 3,185,992 | 51 |
| 7636. | AGCTCCACATTTACATGGAGCAGT[G,T]TCCAACTCTCAGAGCAGGTAAGTTT | 3,186,030 | 51 |
| 7637. | AGTAAAGGTTCAAGGTCAGACCAC[C,A]ATCGAACTGACTCTATCCCGATGGT | 3,186,422 | 51 |
| 7638. | TCATCGTGATGGGGACAGATCATT[G,A]CAATAATTGATCTTCAACGTGATAA | 3,186,568 | 51 |
| 7639. | TGGGGACAGATCATTGCAATAATT[G,A]ATCTTCAACGTGATAAACTCTAATA | 3,186,577 | 51 |
| 7640. | ATTTAATATAATATTCTTTATGAT[G,A]TCTTGATACTCTCAGGTTCAGACGA | 3,186,665 | 51 |
| 7641. | GTAAGTCTATTAATAATTTTTTtA[C,T]TTATTTTAAATATCTATATTTAGAA | 3,186,779 | 51 |
| 7642. | GCTTCACATATCTAGGCTTGAGTC[C,T]GAAAAAAGAATCTAGGGATAAAAAT | 3,186,829 | 51 |
| 7643. | GAAAAAAGAATCTAGGGATAAAAA[T,A]TTAATCTAACCATTCAATCGATGGG | 3,186,854 | 51 |
| 7644. | AATCTAACCATTCAATCGATGGGC[C,T]GGGAGTGTTTATATCTTCGTATCAT | 3,186,881 | 51 |
| 7645. | ATTCGAAAATTAGAGTAGTATATC[G,A]AAATATATACCTCTGTATCGATATA | 3,186,956 | 51 |
| 7646. | AAATTAGAGTAGTATATCGAAATA[T,C]ATACCTCTGTATCGATATATACACT | 3,186,962 | 51 |
| 7647. | TCATCCTTCAGCTACTAGAGAGGA[C,T]GTATAGAGGTAGGAGGAGGATGAGA | 3,187,055 | 51 |
| 7648. | CAGCTACTAGAGAGGACGTATAGA[G,A]GTAGGAGGAGGATGAGAAGGATGAT | 3,187,063 | 51 |
| 7649. | TTAATTTTATATTTATGATTATGT[T,C]AAATAATTATTATTTTATTTATAAA | 3,187,217 | 51 |
| 7650. | ACGGTAGTAGTAACGATAAAGGCC[G,A]TTGCTAATAATTTTTTGATATTTTA | 3,187,428 | 51 |
| 7651. | TAGCAGCGGCATTCCATCGCTAAT[G,A]CTATTAGTGACGATAAACTGACAAT | 3,187,608 | 51 |
| 7652. | ACGATAAACTGACAATTAGTGACG[A,G]CAATTAGCCGTCGCTAATTGTCAAT | 3,187,642 | 51 |
| 7653. | GAGGACTAAAGTTTGCCATATCAA[T,C]CCCCTTTCTCTATGAAATTTTGGCT | 3,187,981 | 51 |
| 7654. | TTTATCGCATTCTGATCATATAAC[G,A]GTCTACCTTTAAATGTCGTTATACC | 3,188,143 | 51 |
| 7655. | TATTATGGCATTATGGGCTTATAT[C,T]GACATGTCTCCAAGGGCATTATGAT | 3,188,275 | 51 |
| 7656. | CTCCCCAACACCATTCCTGGAAGG[G,C]CTGAAGCTACTGAGATTCTATAAAT | 3,188,799 | 51 |
| 7657. | ATATCTGCTTTCACTATTCTAACC[G,A]CATTCTTTGTTAGTCTATGCATTAT | 3,189,057 | 51 |
| 7658. | AGCGAAGTCCACAACAGCAAAACA[T,C]AGATGGAAAAGCCCATAGGTGTGCA | 3,189,580 | 51 |
| 7659. | AAAAGCCCATAGGTGTGCAAGCCT[G,A]CAAGCGTGGCTCATGGGCGCGCAAG | 3,189,611 | 51 |
| 7660. | GCCTGCAAGCGTGGCTCATGGGCG[C,T]GCAAGGCCCGCAAGCATGTGGCCCA | 3,189,631 | 51 |
| 7661. | AGCATGTGGCCCACAAGTGCACAG[G,A]CCCGCAGGCGTGCATGGCCAGTGCG | 3,189,668 | 51 |
| 7662. | CCACAAGTGCACAGGCCCGCAGGC[G,A]TGCATGGCCAGTGCGTGTGGCCCAA | 3,189,678 | 51 |
| 7663. | CCGTGGTTCACTGCACGGTTCATG[C,T]GCGGTCTATGGCACCATGCAGGAGG | 3,189,770 | 51 |
| 7664. | CGCGGTTCATGGAATGGATGTGCG[C,T]GATCCAAAGGTCGAGATGGTGTGCA | 3,189,905 | 51 |
| 7665. | CAGGGGTGATCCAATTGTGGCTGG[T,G]GTCTTGGACTCCCATTAGGACTTTG | 3,189,953 | 51 |
| 7666. | CGCTCGAAAAGAGAGGATTCATGG[C,T]CGAGAGCATCATAGGAAGCATCCAG | 3,190,110 | 51 |
| 7667. | ACTTCTCTAACAGCGATGAAAGTT[C,T]AAGGAGATGTACATGGTGAAGTCAC | 3,190,781 | 51 |
| 7668. | GTTCAAGGAGATGTACATGGTGAA[G,C]TCACTTACCAAAACTCTTTTTCTTT | 3,190,802 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7669. | AGAGAAGAGCACCATCAGATGGAT[G,T]AAGTTACTTCTATATTTCTTCAGAA | 3,191,035 | 51 |
| 7670. | AGGTAGTGGCAGAGGATAAAGGGG[T,G]AAAAGATCGTAAGATGGATGGTCCA | 3,191,154 | 51 |
| 7671. | CAGAGGATAAAGGGGTAAAAGATC[G,A]TAAGATGGATGGTCCAGATCCAAAT | 3,191,163 | 51 |
| 7672. | GGATGGATCGAGCTGTGTGATCAA[G,A]gATATTAGAACTGTCAGCTTATAGA | 3,191,484 | 51 |
| 7673. | AGCTCGAATTTCATATTTGTCCAT[T,C]AATAAGTAGTCAGATATTTATCCTA | 3,191,938 | 51 |
| 7674. | ATTTCATATTTGTCCATTAATAAG[T,C]AGTCAGATATTTATCCTAGGGCATG | 3,191,945 | 51 |
| 7675. | AAGCTCTTAGAGTTAGATAGAGAC[C,T]GAATGTCGAATCGAGATGGAGATTG | 3,192,013 | 51 |
| 7676. | GATGGAGATTGTTAGATTTTGGCA[C,T]CTAAAATTTGACCCACAGTACCAAA | 3,192,052 | 51 |
| 7677. | CCCAGATGGAGGAGCTTGCAGGGG[C,T]GCAGGGTGCAGGCGCGGCCCATAGG | 3,192,103 | 51 |
| 7678. | TGCAGGCGCGGCCCATAGGCGTGC[A,G]AGGACCACAGACGCGTAGGCCCACA | 3,192,134 | 51 |
| 7679. | CGTAGGCCCACAAGCATCCAAGGC[T,C]AGCATGCATGGCCCGTAGTAGGCGG | 3,192,172 | 51 |
| 7680. | AGCACGCACGCATGGCCCAAAGGC[G,A]CGGGATGCATGGCCCAGACCACATT | 3,192,226 | 51 |
| 7681. | AACAAAAAAaTAACTCAACTCAAT[G,A]CTAAAGTTATGAATGTTTTATATTG | 3,194,626 | 51 |
| 7682. | CACTAATCAAGTTAAGAAACTGTC[C,T]TTTATTTGTTATGAATGTAAGAAGT | 3,194,763 | 51 |
| 7683. | CAAGAAGTACAAGAAAAAGACTAT[G,A]ATGGCTACATGAAGTGATAGTGATG | 3,194,856 | 51 |
| 7684. | AATGACTTTATTTTTGAAGAACTT[T,C]AAGAAGCATTTTATGATCTAGTTGA | 3,194,995 | 51 |
| 7685. | TTATTTTTGAAGAACTTTAAGAAG[C,T]ATTTTATGATCTAGTTGATGATTTA | 3,195,002 | 51 |
| 7686. | CTTTGTGAACTCATCAAGCAACAA[G,A]TTTTTAAATATTACTTACTTTAAAT | 3,195,318 | 51 |
| 7687. | TTTTAAATATTACTTACTTTAAAT[G,A]TAGTAAAGTAGGACACAAATCATAT | 3,195,344 | 51 |
| 7688. | AAATTCTAATGTGAAGAAAATATG[G,A]GTTCCAAAAGAAACTATTGTGACTA | 3,195,417 | 51 |
| 7689. | AGGCACATGACCGATGATGAATCT[T,C]AATTCATCACACATGATGCAAAAGA | 3,195,584 | 51 |
| 7690. | AGAAAAGATCATCGGTATAAGTAA[C,T]ATTGGTATGACTCCCTCTAAGTATA | 3,195,667 | 51 |
| 7691. | CATCGGTATAAGTAACATTGGTAT[G,C]ACTCCCTCTAAGTATATTAAAAATA | 3,195,676 | 51 |
| 7692. | TGAATGCCAAAATTAATGAGACTA[G,A]TTGGTTTTGGCACCGTAGGCTTGCA | 3,195,933 | 51 |
| 7693. | GTTGGTTTTGGCACCGTAGGCTTG[C,A]ACATATTAGTATGCATTCACTTTTA | 3,195,957 | 51 |
| 7694. | AGGCCATTAGAATTATTGTACATG[G,A]ATTTATTTGGACCCACTAGAACTAC | 3,196,139 | 51 |
| 7695. | TTGTCATTATTGATGATTTCTCTC[A,G]TTTTATATAAAGCTTTTTTGGCAT | 3,196,215 | 51 |
| 7696. | ATGATTTCTCTCATTTTATATAAG[C,T]TTTTTTTGGCATATAAGGATGAAA | 3,196,227 | 51 |
| 7697. | TTTATGTGTTCTCAAATTTTATC[G,A]AAAAGTTACTAATGAAAAAATTTT | 3,196,280 | 51 |
| 7698. | TCGAAAAGTTACTAATGAAAAAAA[T,A]TTTTAATTCAAAATATTCAAAGTG | 3,196,302 | 51 |
| 7699. | AAAGTGATCATGGAACCAAATTTA[A,C]AAATCAAGAATTTAAAAAATTTTGT | 3,196,346 | 51 |
| 7700. | TAAAAATTTATTGAACCAAATTTT[G,A]AACTCAATTCTCATCTCTTCTTTCT | 3,203,563 | 51 |
| 7701. | TTCTAGCCATGAATCGATCCTAAG[A,G]TAAACTTGTAATTTTCATTAAAATC | 3,203,715 | 51 |
| 7702. | ACACTCTTTTTTTtGAAAAATCTC[C,T]GTTAGTTAAGCAGGCTGACCCTTTG | 3,203,771 | 51 |
| 7703. | AAGTCTCTCTTCCCATCGGGTTTT[C,T]CCCTTCAATCGTCCTTTTAGAAACT | 3,203,897 | 51 |
| 7704. | GATCAAGCTTACCCTAGCTTCAAA[C,T]CCTCTTCTCCAAACCGATGGTCTAT | 3,203,980 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7705. | AGCTTCAAACCCTCTTCTCCAAAC[C,T]GATGGTCTATCTCTCCAAAATCTTT | 3,203,995 | 51 |
| 7706. | TCTACCTCTCATTAGGTCTTCTAA[G,A]CTGTTTGCAAGTCTCTCTTGTCTGA | 3,204,070 | 51 |
| 7707. | TTGATCCATTACTTTTGGGATAAA[T,A]CTTGCACTTGCCTTGTGAATGTTAT | 3,204,885 | 51 |
| 7708. | ATATTATTTTAGGAAGAGCATTTA[C,T]TAAAAATTTAAATAAATTAgAAGCA | 3,204,972 | 51 |
| 7709. | TTTACTAAAAATTTAAATAAATTA[G,A]AAGCAAGGATACTTTCAGTAAAGAT | 3,204,992 | 51 |
| 7710. | TTAgAAGCAAGGATACTTTCAGTA[A,G]AGATGAGACTTTTGCATCACATGAT | 3,205,013 | 51 |
| 7711. | CCTTCCTACTCTGATGTTTGAGGC[T,C]ATGAGGGAGATCCTAAATAGGTCTA | 3,205,159 | 51 |
| 7712. | CAAAGACTGATGGCGGTTGGTCGA[A,C]GGGTGTTGAGGAGAGAGCAGAGGAG | 3,205,344 | 51 |
| 7713. | AGAGCATCTGCTGATATTCAGTTC[G,A]TGTTTGATCACGAGACTGGTCCCTC | 3,205,424 | 51 |
| 7714. | AGCATCTGCTGATATTCAGTTCGT[G,A]TTTGATCACGAGACTGGTCCCTCAG | 3,205,426 | 51 |
| 7715. | ATTAGCCTTAGCCCATCTCCAACC[G,A]TAAGAGAACATCATGGAGGTCTCCA | 3,205,777 | 51 |
| 7716. | GAACATCATGGAGGTCTCCAACCT[G,A]TCTACAGAGGCGGCTAGGCTTCGTG | 3,205,807 | 51 |
| 7717. | AGGTCTCCAACCTGTCTACAGAGG[C,T]GGCTAGGCTTCGTGGCATTTTGGAG | 3,205,818 | 51 |
| 7718. | TCTTCCCAGGCTCCAAGACCTTCT[T,C]GTCCTTCTGCTCGTGCCGGTACTTC | 3,206,009 | 51 |
| 7719. | GTGCCGGTACTTCTACCTGTGGCC[A,G]AGGCAGATGTGGTCGAGGATGTGCC | 3,206,046 | 51 |
| 7720. | CATGATATTTATTAGATCTAGCAT[T,A]GTTAATCTTTTATGTCTAGGATCTA | 3,206,159 | 51 |
| 7721. | TATTTATTAGATCTAGCATTGTTA[A,G]TCTTTTATGTCTAGGATCTAACTTA | 3,206,164 | 51 |
| 7722. | ATCCAATTCACCCCCTCTCCTCTT[A,G]GGTTGCATAGCTGGGTAACAGAGGT | 3,208,757 | 51 |
| 7723. | CTCCTCTTAGGTTGCATAGCTGGG[T,C]AACAGAGGTGGATGTGCGGTCCATG | 3,208,773 | 51 |
| 7724. | CGGGGGTGATCCAACAGTGGCTGG[T,G]GTCTTGGACTCCTATCAGGATAATG | 3,208,929 | 51 |
| 7725. | GTGTGGAAGAGAGGCATAGATAAC[A,G]GCTAAGAGTATCTGAGAGAAGAGGA | 3,209,041 | 51 |
| 7726. | GCTAAGAGTATCTGAGAGAAGAGG[A,T]TTCATCGTTGAGAGCATCATAGAAA | 3,209,066 | 51 |
| 7727. | AGAGGATTCATCGTTGAGAGCATC[A,C]TAGAAAGCATCCAGGGGCATCAGAG | 3,209,085 | 51 |
| 7728. | AAAGTTTTGTAAGAGCTTTTGTAA[A,G]GAGTTATGCTTTTATTGAGAGAAA | 3,209,173 | 51 |
| 7729. | ATGCCCCATGGAGATAAGCCTTGG[A,G]CTAATCCACGTATTTGATCATGTTC | 3209290 | 51 |
| 7730. | TTATCACATAATCTGTCGGTTGCT[C,T]TATATAGACCTCCTCATCAATATAG | 3,210,661 | 51 |
| 7731. | ATCTCTTCATCTATGGCATACTTC[T,C]ATATTTTACTTTTTATAGCATCTTC | 3,211,001 | 51 |
| 7732. | AAAGATGAGCTTTGAGCTTTTATC[C,A]TCTAGCTTGACTCTCCTCTGCTTCA | 3,211,408 | 51 |
| 7733. | CAAAATATGTGCAAAGCTATACAT[C,T]TGAAGATCTTCATGTGTGAGATATT | 3,211,456 | 51 |
| 7734. | CCCACAAAATACTTCAAATGAATT[G,A]AAGGTGAACTCGCCGCCTCGATCTA | 3,211,740 | 51 |
| 7735. | TTCAAATGAATTGAAGGTGAACTC[G,A]CCGCCTCGATCTAAGCGAATGACTT | 3,211,752 | 51 |
| 7736. | GCCTCAAGTGCCACAATCATGAGG[C,T]ATCTTTTACATAGAGTTTCAAGCAC | 3,212,156 | 51 |
| 7737. | GATACAGCAGGAAGAAAGAAGAAA[C,T]AAAATAGAAAATAATCAAAATACGT | 3,212,422 | 51 |
| 7738. | AAAGGACTCGCCTCCACGGGGCAT[G,A]CAAACTTTACTACGaAAAAAAATT | 3,212,484 | 51 |
| 7739. | ATAAAGTTTTTTCTCACAAAAGCT[C,T]TCTCTCTTAAAAGACCCCCTGAATC | 3,212,584 | 51 |
| 7740. | CTCTCTTAAAAGACCCCCTGAATC[C,T]CTAAAGCGACCATTGTTCGCTGTCC | 3,212,610 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7741. | AAAAGACCCCCTGAATCCCTAAAG[C,T]GACCATTGTTCGCTGTCCAGAAGCC | 3,212,617 | 51 |
| 7742. | CGTCATACAGAAAACTCAAGTCAC[G,A]GATTCTGTTTTCATGAGAAACCAAG | 3,212,729 | 51 |
| 7743. | TCATGATCGATCCACAAAATAGTA[T,C]CGTGGACCGCACAAAATGCATGGGA | 3,212,927 | 51 |
| 7744. | TAGTATCGTGGACCGCACAAAATG[C,T]ATGGGAAATGCCCATGCAGTCCACA | 3,212,946 | 51 |
| 7745. | AAATGCCCATGCAGTCCACAGACC[C,T]GACCGTGGACTGTCCAGTCCACTGT | 3,212,976 | 51 |
| 7746. | CATGCAGTCCACAGACCCGACCGT[G,A]GACTGTCCAGTCCACTGTGGATCGG | 3,212,983 | 51 |
| 7747. | GTGCGCCTGGCCCATGTGCTGCCA[C,T]GCACTGGGCGGCATCCCACCGCCTA | 3,213,133 | 51 |
| 7748. | CACTGGGCGGCATCCCACCGCCTA[T,C]GGTCGCACCGCTATCACTCCGTCGG | 3,213,159 | 51 |
| 7749. | TGGACTCAATATGGATCAAATCTC[G,A]AGATATCAAATTCTAACAATCTCTA | 3,213,346 | 51 |
| 7750. | TGACCTGAGACCTACTCAAGGTAT[C,T]GTCCTACGGTAATAGGAATCCCACC | 3,213,551 | 51 |
| 7751. | ATTCTCCCGAGTCTCCTGTCTCGT[A,G]TCCGATCCAGCTCCACTTACAGCTC | 3,213,618 | 51 |
| 7752. | CTCCTTCTTCCCCTCCAGCATAAT[C,T]CTATCACCACGTAGCACCTTCAGAA | 3,213,749 | 51 |
| 7753. | GTAGCACCTTCAGAATTTCTCCAT[C,T]AGCTACTGTCCTGTAGCCTCTCGAA | 3,213,784 | 51 |
| 7754. | GAAATTGGATATGTATCGGATCTC[T,C]CCTAATCTTCTCACTATACCATCAT | 3,213,866 | 51 |
| 7755. | CTGAATCGCTACCGGCCGTCGCTA[C,T]AGCAGCCACCATCCAATTTTTGAGT | 3,214,087 | 51 |
| 7756. | CCGGCCGTCGCTACAGCAGCCACC[A,G]TCCAATTTTTGAGTTGAGAGCAATC | 3,214,098 | 51 |
| 7757. | GGCCGTCGCTACAGCAGCCACCAT[C,T]CAATTTTTGAGTTGAGAGCAATCTT | 3,214,100 | 51 |
| 7758. | CCGTCCTCATCGCGATCTCCTGTC[G,A]CTCCGTCTACCACCTTCTGCTCCTC | 3,214,217 | 51 |
| 7759. | CCTCATCGCGATCTCCTGTCGCTC[C,T]GTCTACCACCTTCTGCTCCTCCAAA | 3,214,221 | 51 |
| 7760. | TCTTCTCTACTAGAAGAGCAGTCA[T,C]CAAGGACTCGTATGAAGATGGAAGT | 3,214,378 | 51 |
| 7761. | TACTCCTGCATGCTCTGTCCCTCG[A,G]CCATCCGTAGCTGATAAAACTGCCT | 3,214,518 | 51 |
| 7762. | TAGCTGATAAAACTGCCTCCAGAG[G,A]AAAAGAGTGCTGGTGAGAGACTTCA | 3,214,550 | 51 |
| 7763. | AGTGCTGGTGAGAGACTTCACCAT[G,A]TACAACTCCTCGAGCTTTGATCAAG | 3,214,580 | 51 |
| 7764. | GAGCTTTGATCAAGCACCATCGGG[G,A]AAGTCTCGCTCAGCACATGAATCAC | 3,214,616 | 51 |
| 7765. | AATCACCACCTCATCCGTTAGGTA[T,C]ATGCGGATGGTACTCACCGCCTGCA | 3,214,660 | 51 |
| 7766. | GTATATGCGGATGGTACTCACCGC[C,T]TGCATCTGTAGCCATTTCCAATCCC | 3,214,681 | 51 |
| 7767. | TCTATCTTCAGTCTTGCTCACCAC[C,T]GCTGCAATCTGCATCCTTGTACCAC | 3,214,880 | 51 |
| 7768. | CCGCACGCCCCACGCCAGGCTGTG[A,C]CCTGCGTGCTTGGCCCGTGCACTGC | 3,215,734 | 51 |
| 7769. | TTTAAAAGTACGTATCTTCTCTTT[T,C]CGAGCTCCGTTTGGGGTGTTCTTGA | 3,215,837 | 51 |
| 7770. | ACGTATCTTCTCTTTTCGAGCTCC[G,A]TTTGGGGTGTTCTTGATCTTGTTGG | 3,215,846 | 51 |
| 7771. | AAGATGCTCTCAGATTCCTTCATC[C,T]GTAAGGCTTCAAATTCTCCTTGTAG | 3,216,776 | 51 |
| 7772. | AGATGCTCTCAGATTCCTTCATCC[G,A]TAAGGCTTCAAATTCTCCTTGTAGC | 3,216,777 | 51 |
| 7773. | ATTAACGCTTTTGTAGGCCAGAAT[C,T]TCCCACACTTTCTTGGAAGTTGTTG | 3,216,853 | 51 |
| 7774. | TCCAGAACTATCCAACTAAAATTT[C,T]TAATTCAAAATTAAGTTTATCTTTT | 3,217,241 | 51 |
| 7775. | GTCTGAAACTTATTTTGTTTGGGT[T,A]TTTTTtAGATCAGCTTGGATATACC | 3,217,630 | 51 |
| 7776. | AACTTATTTTGTTTTTTTTTTTTT[T,A]AGATCAGCTTGGATATACCTAATAT | 3,217,636 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7777. | GAAATAGTTAAAAAAATGAATGCA[G,A]TAAGTCGGATGGATTTGGCAAGGTC | 3,217,995 | 51 |
| 7778. | CACGTTGGTATCCGACGCGTTCCC[A,G]TCCAAATCCAACACGAAGACGTAGT | 3,219,200 | 51 |
| 7779. | GGCCGCCGTGATCGCCGGCGTCGG[C,A]GGCAGGTGGAGGCGGGTGGCCTCCT | 3,220,018 | 51 |
| 7780. | TTCTCTTTTGGAATTTACGGCTGG[T,G]GAAATCAGATCAGCTAGTTTATAGG | 3,220,881 | 51 |
| 7781. | ATGAGATAATCTGGATTGCTAAGG[G,A]AAGGGATGGCTATCCAGATTACCAC | 3,221,482 | 51 |
| 7782. | AGATAATCTGGATTGCTAAGGGAA[G,A]GGATGGCTATCCAGATTACCACCAC | 3,221,485 | 51 |
| 7783. | TGTGTTCGCGCATGGCCCCCGACC[G,A]CCACCACAGGTGGAGGAACTCCCGA | 3,221,793 | 51 |
| 7784. | AATAAGTATTATAAAATAGTATAA[A,T]TTTTTTtCATATAATAATTTTTATC | 3,222,309 | 51 |
| 7785. | ATATTACCAATAATCTGATTGTCA[T,G]ACCAAATATGTCAATCAAGATTCTC | 3,222,434 | 51 |
| 7786. | TAGATTATTGGGATAGAAAATTTT[T,C]CTACTAACCTACAAATCAAAATTGT | 3,222,644 | 51 |
| 7787. | TCGACATAGAGCTGAGGCTCCATA[C,T]TGATGGCTATATTTGATGTCATCTC | 3,222,745 | 51 |
| 7788. | CATTTTCTATCTTCGGTGAGATCT[A,G]ACCATAGGATTGGTAATGTTCCGAC | 3,222,818 | 51 |
| 7789. | CAAAGAGTCGGTCCGTCTTGTTTT[C,T]TTGACTCTCTCCGATGTTCGAGGTA | 3,222,915 | 51 |
| 7790. | CCGACAGGCCAAGTGGAGAGATCC[A,G]ACAATTTGGTAGTTGAATTTATACT | 3,223,439 | 51 |
| 7791. | GCAATGAGTTTTGGAGTGAAAATC[C,T]CTATGGCAACCACAATCGTAGGCCA | 3,223,788 | 51 |
| 7792. | GGCTGGCTCCTCATCCAGGGACTA[G,A]ATCTCCACATCCCATAGTGCAGGTA | 3,223,885 | 51 |
| 7793. | TCCTGTGTGCGAGTTCAAAGATTT[C,T]TGCGATTCAGGTAACGAGGAGTCAA | 3,223,936 | 51 |
| 7794. | TGACGTTCTCCTTTATTTAAGAAA[A,T]TTTTTTTGATTACTACTAAACTAAC | 3,224,603 | 51 |
| 7795. | AGGATAGAAATGGCAGTCAAACGG[A,G]TTTTTCCGAGTATCTAACCCATTCC | 3,224,762 | 51 |
| 7796. | TCCATTTGGGTTTGGAATGGGTTT[A,G]GGATTTAACCCTTGGGTACCCACCA | 3,224,881 | 51 |
| 7797. | TTAGGATTTAACCCTTGGGTACCC[A,G]CCATCCAAACTCGTTTATATATAAA | 3,224,903 | 51 |
| 7798. | TGGGGGGAAGGAGAGATCCAAAGG[A,G]AGGTTGGAGGGGTTTTTAGATTCCA | 3,225,995 | 51 |
| 7799. | GGATTTTTATTTAATTTTGTAATC[G,A]GGTTTGAGATGGATTCAGGTAGAAA | 3,226,272 | 51 |
| 7800. | TAAACAGCTTCGAAAATGGGTAGG[G,A]CAAATTTTGTAGGTATCCTATCCAT | 3,226,327 | 51 |
| 7801. | CTCCAGCCTCAGCACCATCTTCAA[G,T]GATGTCAAGTACTGACCCAATGGAA | 3,226,417 | 51 |
| 7802. | AATAGAGTGCAGAGAGATTATTCT[G,A]CTCTTTAAAATCATCAGCTTGCTTG | 3,226,677 | 51 |
| 7803. | AGAGATTATTCTACTCTTTAAAAT[C,T]ATCAGCTTGCTTGGGAGTAGATGAG | 6,226,689 | 51 |
| 7804. | GCCAAGTCCAAGCTGTTGGTTGCC[T,C]AGGAGAAATTTGAAGCTTTAGAGGA | 3,227,042 | 51 |
| 7805. | CCTAGTGAGGCACTACAGCAAAAG[G,A]TGGCCGAGCTTGAAGGAGCATTGGA | 3,227,092 | 51 |
| 7806. | CGAGCCGACCATTGAAGGCATCGC[T,C]ATCGGTCCTGCTACCGAGCCCATTC | 3,227,467 | 51 |
| 7807. | GCAAGATTGTTACTTCGATCAAC[C,G]TCTTGAGTTGGTTAGAGTATAGAAA | 3,227,655 | 51 |
| 7808. | TGATTTGAAATCAAAATTTTCATT[G,A]TCAATTTGTGACGATCTTGCCAAGT | 3,227,753 | 51 |
| 7809. | AGCCTTTGCTCGATTCATTCATGG[A,C]TAAGGAGCACCAGATGCCATATGGG | 3,227,905 | 51 |
| 7810. | ATATGGGATCTCTAGAGGATTAGT[C,T]CCTTTATAATCATCATCGACCTTCG | 3,227,948 | 51 |
| 7811. | CCTTCATAGTTGTCATCAGCCTCC[A,G]CTCAACTCATCCATAGACAAAGAGT | 3,228,058 | 51 |
| 7812. | ATCTGTGGATAAGGAGTGCTAAAT[G,A]GCCATACGAGGTCTCTGGAGGATTA | 3,228,262 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7813. | TGACCCATCTATGAACAAAGAGCG[C,T]CAGATAGCTATATGGGTCCCTAGA | 3,228,342 | 51 |
| 7814. | CCAAGCATTATAATAGTGGTCTAC[T,C]CATTATTGATATGATGCCATTTTGA | 3,228,769 | 51 |
| 7815. | TGATATGATGCCATTTTGATCTGA[G,T]CTTGCTTCCTAGTTTTTTCGAACAA | 3,228,800 | 51 |
| 7816. | ACAAGTTCAAGTTCATTTGAAGTC[A,G]GCCCGAATTCTCTTACTCATCATAG | 3,228,846 | 51 |
| 7817. | GATAAGCCCATAATACCTTATAAA[A,G]TTTTTCGATCTAGAGCCCTTTGGCT | 3,228,992 | 51 |
| 7818. | AATGGATTCTAAATAAAATCCTAG[A,G]CCTTCTTCTTGATAATTTAAGCCAA | 3,229,223 | 51 |
| 7819. | TATTTATTTGGTGAAATAGTCGAC[T,A]GCAATGATCAAAAACTTTCTCTAAC | 3,229,285 | 51 |
| 7820. | CTCTAACCAGTGGTCATCAGGAAC[G,A]GCCTGAGGATGTCAATTTCTCACAT | 3,229,328 | 51 |
| 7821. | GACAATAATTAGTGCAAGCTCCAT[A,T]GCTGGCCTCTGCTAGCTATTGGCAT | 3,229,393 | 51 |
| 7822. | GCTATTGGCATAATTCTGGCACTG[C,T]CGTCGGTTGTATCCTATTGTAGAGT | 3,229,432 | 51 |
| 7823. | TAGAGGTAGTGAATATGATTTTTT[A,G]TAAAGTCTCTCTTCTAAGTAAACAC | 3,229,608 | 51 |
| 7824. | GGTGCTTGATCCTCTGAGTTTCAA[C,T]AGGACTGGTTAGTAAGGCACCGTTA | 3,229,670 | 51 |
| 7825. | AACAGGACTGGTTAGTAAGGCACC[G,A]TTAAGAAGGTAGTTGATTAGAGGGT | 3,229,692 | 51 |
| 7826. | TTCTCTGACCTTGGTATATGTTGT[A,T]CCTTCTAATTTTAGAAGGCCTCTAA | 3,229,885 | 51 |
| 7827. | TCCTCGAGCCTCATATTCTTCTCA[A,G]ATTTATTCGATGATGAGTTGCAAGT | 3,229,974 | 51 |
| 7828. | GGCAGTAAAGTCGAATCAAAGTGT[C,A]TATTCCATCACGTCCCCTATCGGGC | 3,230,110 | 51 |
| 7829. | GAATCAAAGTGTCTATTCCATCAC[G,A]TCCCCTATCGGGCTTGCAAGGATGA | 3,230,122 | 51 |
| 7830. | GCTTGGAGAGCAATGAGGATGATC[T,A]GAGATATCGTTTGAGCTCTTCAAAT | 3,230,658 | 51 |
| 7831. | GAAACTCTTCATTTGCCTGAGGAT[A,G]TTGAAGAATGGAAGGTACTTTTTTC | 3,230,734 | 51 |
| 7832. | CTGAGGATATTGAAGAATGGAAGG[T,C]ACTTTTTTCGACCGACCTCAAAATG | 3,230,750 | 51 |
| 7833. | ATCCCCATCAGATTACCATAAATC[C,T]TAAAAATTTtTTTGATGTCACACCA | 3,230,906 | 51 |
| 7834. | CATTTAGTTTCACCTCAACCCAAC[C,A]AATGCTTCCTCCAAATCGATGATAT | 3,230,982 | 51 |
| 7835. | GCATCATTTGTTAGCAATACAAAA[T,C]TTAATCGGTTATGAATGCCATCTTC | 3,231,161 | 51 |
| 7836. | TTTGGAGGCCATTTGAATCTGATT[G,A]TAGTCGGAGAAAGCATTCATGAAGC | 3,231,219 | 51 |
| 7837. | AGAGGAAGAAAAAAGAGAGACAAT[C,T]AAATAACGTGGATTGACTCAAGACT | 3,231,360 | 51 |
| 7838. | TTGACTCAAGACTTATCTCCATGG[G,T]GTATACAAACTTCACTATAAAAAAA | 3,231,397 | 51 |
| 7839. | CTCTCATAAAACTCTCAACTCTCA[C,T]AGGAAGATCCTCTCAGCTACTATCT | 3,231,522 | 51 |
| 7840. | AAGATCCTCTCAGCTACTATCTCT[A,T]AGACTCTCTGCCGCCACACATGATA | 3,231,550 | 51 |
| 7841. | TAGGATTCTAAGTCTAAACCGTGT[C,T]TAGAACCACCTATAGACCGCAGTAG | 3,231,665 | 51 |
| 7842. | CAGTAGACCACCATAGACCCCTCC[A,T]CATGAATCGAAGCCATGGACCAGCT | 3,231,709 | 51 |
| 7843. | GCCACATGTGCCACGCTCACCCTC[G,A]CTCGTGTGCATCGTGACAAAGACCA | 3,231,770 | 51 |
| 7844. | CGCTCACCCTCGCTCGTGTGCATC[G,A]TGACAAAGACCATGCATCGTGCGGT | 3,231,783 | 51 |
| 7845. | GCAACTCCCGCACTCTTGGACAGC[A,G]TGGTGGTCCGTGCATCTCGTGCAGC | 3,231,869 | 51 |
| 7846. | CCGTGCATCTCGTGCAGCCTGGGC[T,C]GTGCCTGTGGGCCTGCGTACCTAGT | 3,231,901 | 51 |
| 7847. | GAGGCATCAAAATCTAATAATCTC[C,T]ATCTTGACTCGACATTCGGCCTCCA | 3,232,050 | 51 |
| 7848. | TTCATATACTATGACCTGCTTGAC[C,T]TGAGATCTGCTCGAGGTAGCATCCT | 3,232,212 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7849. | TCTCCATCTCTAGCTGCTTGAATC[T,C]AGTCTGCTTAGTGAAATCAGATTAC | 3,232,488 | 51 |
| 7850. | AACTTGCTCACTGCTCCATCATAT[A,G]TCTACAAGCTAACTGTTCCAATATC | 3,232,570 | 51 |
| 7851. | AAACATGCTGAATCTAAAATCTAC[T,A]AAGAAAAAGAAGTAGATATCTTATC | 3,232,713 | 51 |
| 7852. | CTGCCACCACCACCTTTAGTCACT[T,G]CCAAAGTCGAGTTGCTATCTGAATT | 3,232,962 | 51 |
| 7853. | GTCGAGTTGCTATCTGAATTTGAA[G,A]CTCGATTCTCTCATTTGAAGATCTT | 3,232,992 | 51 |
| 7854. | AAGTCTCAATAAGCACATGGATCA[T,C]CATATTATTTATCAAGAATAAGTAG | 3,233,350 | 51 |
| 7855. | ACCACCTGCATCTAGAGCTGCTTC[A,G]AACTTTTATCCTCCATGATAGTCGA | 3,233,409 | 51 |
| 7856. | AAACTTTTATCCTCCATGATAGTC[G,A]ATTTTCTTCGCACAAGAGAGTATC | 3,233,433 | 51 |
| 7857. | CTCTCGCTTGCTATAGGAAGAAAT[G,A]ACTCTTCCCATCATACCGATTGATC | 3,233,515 | 51 |
| 7858. | TCCTATCAGGATTCTAAGTCCAAA[C,T]TGTGTCCAGAGCCGCCTATAGACCA | 3,234,035 | 51 |
| 7859. | CAAGCCCCCACTCACGTGCCCTGC[G,A]ACAAAGACCATGCATCACCCGATGG | 3,234,149 | 51 |
| 7860. | TGCGACAAAGACCATGCATCACCC[G,A]ATGGACCGCATGAAGACCGCACGTG | 3,234,170 | 51 |
| 7861. | CATGCGGCGGTCCATGCATCTCGT[A,G]CATCTTAGGCCATGCCTATGGGCCG | 3,234,264 | 51 |
| 7862. | CTATGGGCCGCGCTTGCAGGCCTA[C,A]GTGCCTGCGGGTCATGCTCCTGTGG | 3,234,321 | 51 |
| 7863. | AGTTTTACTGCTGTAGATCGAATT[T,C]GAGATACCAAAACCCAATATTGATA | 3,234,413 | 51 |
| 7864. | TAAATCCCATTGTCAGGAGTTTGT[T,C]AACTTTCTCCTCAATTACTTATTGT | 3,234,618 | 51 |
| 7865. | TCCTCAATTACTTATTGTCATTCT[G,A]GGGTGAAGCTTCTTTTCTTTATCA | 3,234,650 | 51 |
| 7866. | TTCAACTTATGAACAATGATATCG[A,G]AAGGTACATCTGGCATGTCTGATGC | 3,234,725 | 51 |
| 7867. | TAAGGTTCGGTGTCAATTATGCTC[C,T]AAGCTAAATGGTTCTGCTCGAATCA | 3,234,828 | 51 |
| 7868. | TTTATTATCACCAAAAAGGATTGA[C,A]AAGCCAGTATTTGATCTTCTCATAC | 3,234,980 | 51 |
| 7869. | TTATTATCACCAAAAAGGATTGAC[A,G]AGCCAGTATTTGATCTTCTCATACT | 3,234,981 | 51 |
| 7870. | TCGATCAATAGACAGTTTCATTCT[T,A]TGAAAACTATTGTAAAACAACACAT | 3,235,278 | 51 |
| 7871. | GAGGATTTCTTTTCTGCTCAAGTC[G,A]TTCAAGGATCCTCCTAACCTCACTT | 3,235,895 | 51 |
| 7872. | GGTCAGCATAATTTTTTGAAAAAA[A,T]TTTATCGAGGGAGAAGATGTGGTAC | 3,236,031 | 51 |
| 7873. | CTCAAGCTTCGACGTGAGGATAAT[C,T]GAGGTGTAAAAGTGGGAGCAGAGTA | 3,236,698 | 51 |
| 7874. | TTATTGCTCTGCCACCTATTGAGG[C,T]CATTGTACGGCATAGTTAGAGTTTG | 3,236,841 | 51 |
| 7875. | GAACCAGGGCATCCAATGGTAGTG[T,G]ATTCTGTTGGGAATAGTGTTTCAAA | 3,236,899 | 51 |
| 7876. | CATCCAATGGTAGTGTATTCTGTT[G,A]GGAATAGTGTTTCAAAGCCAATCGT | 3,236,908 | 51 |
| 7877. | TTATAAATTAATAAAAATTATTTT[A,G]GTATTTTTCATCATAAAATATTTCA | 3,237,002 | 51 |
| 7878. | GATGACAATATTTATCAAGCATAG[G,A]TCATTGTGTACCATATAGGTTGGTT | 3,237,170 | 51 |
| 7879. | TTTATCAAGCATAGGTCATTGTGT[A,G]CCATATAGGTTGGTTGTCCTCTTAA | 3,237,180 | 51 |
| 7880. | TAACCAATGAGTGTGGAGACACTG[A,G]TATGGCATACAGGTGAGATGTAAGG | 3,237,227 | 51 |
| 7881. | GAGATGTAAGGGTACATCTGCACT[A,G]AACGTGACCGACTCCAGAGCTATTT | 3,237,266 | 51 |
| 7882. | GGGTACATCTGCACTAAACGTGAC[C,T]GACTCCAGAGCTATTTCTGCTGTCA | 3,237,275 | 51 |
| 7883. | CTCCAGAGCTATTTCTGCTGTCAA[A,G]ATTTGCTCTGATGGAATATGGGTAT | 3,237,302 | 51 |
| 7884. | GTGTCAAGATGGGATTGACCACTC[T,C]AGTTTAAGAGCTGTGTACAGTCATA | 3,237,487 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7885. | GATGGGATTGACCACTCTAGTTTA[A,G]GAGCTGTGTACAGTCATATTTTAAT | 3,237,494 | 51 |
| 7886. | TGTGTACAGTCATATTTTAATTTA[G,T]CAAAACCTTGGTCAGGATAGTCTTT | 3,237,523 | 51 |
| 7887. | AGTCATATTTTAATTTAGCAAAAC[C,T]TTGGTCAGGATAGTCTTTGCGAGGA | 3,237,530 | 51 |
| 7888. | AAACCTTGGTCAGGATAGTCTTTG[C,T]GAGGAGTCACAGGACTGTTTGAGTT | 3,237,550 | 51 |
| 7889. | TCACAGGACTGTTTGAGTTGATCA[T,C]GATTCGGATGATCTAATCAGGGTTG | 3,237,581 | 51 |
| 7890. | GGACGATCAGCAGAGGTCAGACAT[G,A]CTGTGTAGCTATATTATGATGATCA | 3,269,074 | 51 |
| 7891. | TATATTATGATGATCAGACTCTCC[T,C]GACGGTGATCAGATTGCGGCGATCT | 3,269,108 | 51 |
| 7892. | CTCCTGACGGTGATCAGATTGCGG[C,T]GATCTACTACCCGCACAAAGGTATT | 3,269,128 | 51 |
| 7893. | GTATTGTGTTCTGAACACATTACA[A,G]TAAAGTGTTTACTGTTCAAATTCGA | 3,269,173 | 51 |
| 7894. | GCATGCTATATATCATATTTAGAT[T,C]CTAATGTAGGATAAATTTTTATTAA | 3,269,242 | 51 |
| 7895. | TTAGATTCTAATGTAGGATAAATT[T,C]TTATTAATTAATTAGATTAATTAAT | 3,269,260 | 51 |
| 7896. | TTAATTAGATTAATTAATAATTTT[C,T]ACTGTAAAATAGTGATTTTGAAAAA | 3,269,292 | 51 |
| 7897. | ATTACCATTTTACCCCTGCACTGA[T,A]TTTCCCCACAAATTCATCGTAATAG | 3,269,350 | 51 |
| 7898. | TGAGAGATGGTGGAATTATGTACT[C,A]TCGTCTGTACCATGCTCTCTTTCCT | 3,269,461 | 51 |
| 7899. | TGCGGTTGAGGTTGGTGCCAATTT[G,T]AGGCCGACACATCCAAAGAGAACCT | 3,269,581 | 51 |
| 7900. | GATTGTTAAGGTAGAAAATCTTTC[T,A]ACTAATCTGCAAATCAAAATTGTTA | 3,269,866 | 51 |
| 7901. | ATCTTGATTTTTCAGCTCTCTTCA[G,A]GGTTCGAGATAGTCCTGCTGAGCCA | 3,270,146 | 51 |
| 7902. | AGAAAAGAAAGGTTGCTTCATACG[G,A]TAGATTGCCTCCGTAACAAGTAGGC | 3,270,224 | 51 |
| 7903. | ATTTATTTTTATTTTtATTTTtTT[G,A]TGCGTTAGAAATCATTGCATTAGTG | 3,270,373 | 51 |
| 7904. | GATCCTAGATCCAAACAGAATCCC[G,A]AATAGCTTCTATCCAAAAACTGAGT | 3,270,950 | 51 |
| 7905. | GAGTCGGCTCATCTGAAACTGAGT[G,T]AGTTCAAACTAAAACTGAGTCGACT | 3,271,017 | 51 |
| 7906. | ACCTTGATGCTCCTAAGCCCTTGT[G,A]AACTCAACTTTATTCTTCAGACCTA | 3,271,319 | 51 |
| 7907. | AAGCCTCTTCAACCACAATGCTTC[T,C]TTAGAAGCATCTGTGATACCTATGT | 3,271,616 | 51 |
| 7908. | AGGTCCATCTTGCTATCCAAAAAT[T,C]AGACCAAACCTTCGAGTTTCCTGAA | 3,271,853 | 51 |
| 7909. | AACCTTCGAGTTTCCTGAAGATAC[C,A]GCAAAATTCACTTCAATGCCTGCCG | 3,271,884 | 51 |
| 7910. | CTGCTGCTTTGAAAGAGACATATA[G,A]CTTGTCAATGGTGTTCCAACCAGTT | 3,272,901 | 51 |
| 7911. | TAGCTTGTCAATGGTGTTCCAACC[A,G]GTTTGGCCTTCTTCATCCCAAACCT | 3,272,113 | 51 |
| 7912. | ACTGCATCTGCACTTCTTTTGGCA[T,A]TGAGCATATCGTCCACATGCAGAAG | 3,272,311 | 51 |
| 7913. | GGCATTGAGCATATCGTCCACATG[C,T]AGAAGCAAGTATAATGCATCATCTT | 3,272,331 | 51 |
| 7914. | GCTCCAACTCCATATCATGCTAAG[C,A]TACAAGCGACAGCAACATCCGGATT | 3,272,618 | 51 |
| 7915. | ATCTAACTCCATCTTACTCTGAAG[G,A]TGCCTCCTTCCATGTGAACACCCAC | 3,272,756 | 51 |
| 7916. | TCCAGTGACTCCATCTCTTCTCTC[A,G]TGGCCTGTATCCATGACTCCCGATC | 3,272,866 | 51 |
| 7917. | CCATACCTAAGCGATCTGTAAATT[A,G]TACGTTGGAGCTTGTGCAATGCCAC | 3,272,995 | 51 |
| 7918. | AATCCTACAATAGATACCCTTTGA[A,C]TCTCTATGGATACCTGATGAATGTC | 3,273,332 | 51 |
| 7919. | GAATGTCATCTTCTGAGACTTTGG[G,A]TCCAACTTGCTTCTTTTCAGTTGCC | 3,273,375 | 51 |
| 7920. | TCACTGTGTAATGATGTTTGATAC[T,C]ATTCTCCTCACAGTACCTTTTGAAC | 3,273,678 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7921. | TTTTGAACTCTAGACTTGTGTATT[C,T]TCCTCCATTATCAGACCTCAAGCAT | 3,273,720 | 51 |
| 7922. | ATACATCAGCTGCTCCTCCTGTAC[C,T]GCTACAAGCACTTCCCTACTATCAT | 3,274,138 | 51 |
| 7923. | GCTCCTCCTGTACCGCTACAAGCA[C,T]TTCCCTACTATCATTCACCACTGAG | 3,274,149 | 51 |
| 7924. | ACATAATATCACACTCTGTGGATC[C,T]ATCTGATACAACCAGCAGATCTTCC | 3,274,545 | 51 |
| 7925. | CTACTCCCAGATGCCGTATCATCA[T,C]TTTTGCTGGCCTTTCCCTTCTTTGA | 3,274,598 | 51 |
| 7926. | AGAATTTTCTTTGCAAATCTTTTT[C,T]CGTTGCTTATTAGACTTGAGCACTC | 3,274,809 | 51 |
| 7927. | GATCTTTTGCTGAACCACCAAATT[C,T]TTTACCCTTTGCTGTCATAGGATAA | 3,275,282 | 51 |
| 7928. | CCTATGTCTTGCCATGCATTCATC[C,T]CTTGAACTTAATTCTAGCCCAAACA | 3,275,928 | 51 |
| 7929. | ATGCTAAGACTGAGTTGACTCACC[T,C]GAGATTGAGTTGACTCACCTACATG | 3,276,066 | 51 |
| 7930. | GATTAAGCAGAAACATTCTATCCT[G,T]ACTGATTCTTCTGTTGGTTTTCTCC | 3,276,237 | 51 |
| 7931. | TTGGTTTTCTCCTTTGACCTCTTG[A,G]TTTCTTCTCATGTGTTTTCAAGGCT | 3,276,275 | 51 |
| 7932. | CCAGACTCAATCTTATAGAAAAGT[A,G]GATCGGATCTACGGCCAAGACTTTC | 3,277,030 | 51 |
| 7933. | TGCTCATACTAGTCTTAAATCACA[G,A]TTTAAAGGTTTAAATAGGTTTGAAT | 3,277,296 | 51 |
| 7934. | GTTTGAATCCTAATGGCATACCTG[G,A]TTTGGGTCGTGTTGGATCCAAATTC | 3,277,338 | 51 |
| 7935. | GAATTGGATGGATTGGATCAGCTA[G,A]TTTGGGTCGTGTTGGATCCAAATTC | 3,277,460 | 51 |
| 7936. | CTATGCCTTCCCGATTAGCGCCCT[C,A]TGTTCGCTGCCTGCAATCTATGAAT | 3,277,532 | 51 |
| 7937. | CCGCTCCTGGTGCACAAAAATTTC[G,A]CTTGGAGGAGAACTAGAGTTGGTGT | 3,278,435 | 51 |
| 7938. | TAACTCCCACGCCCTTGATGCCTT[T,C]CATGCCATCACCCACATTAAGGGCT | 3,278,660 | 51 |
| 7939. | GCTAGTCCGAGACCGTTCAAGGGG[G,T]CAAACCCCTGCACCAACAACCACAA | 3,279,158 | 51 |
| 7940. | CCACAACAGTGAGCATCGCGGTTC[C,G]GACCTCCATCCAACCAAGAATTTGA | 3,279,202 | 51 |
| 7941. | TCACTGCAAGATCCTCAATGTCTT[C,T]CTTCTCGTCGCCACCATTGATGCCC | 3,279,277 | 51 |
| 7942. | GGTAGCCCAACCGTTTCCTAGGCA[A,T]TAAGATGCAACCCCCTTCTATCCGA | 3,281,021 | 51 |
| 7943. | ATCAACATATCAAATAAAAaAaTA[A,G]AAAGGTAACGAAAATTTTTGACGAG | 3,281,602 | 51 |
| 7944. | AAAaAaTAAAAAGGTAACGAAAAT[T,C]TTTGACGAGACCTTCTGATCGGAGT | 3,281,618 | 51 |
| 7945. | TTGACATTATGTAATCATGGAATG[A,G]ACGGTTATACCCATTATTGATCATG | 3,281,941 | 51 |
| 7946. | TCTGCACTGACAGTTTTTGATATA[C,A]TGACTCTACGTTGGTAGTCTGAGTG | 3,282,012 | 51 |
| 7947. | GGATGGAGTTGTCACGTGCTATCT[T,C]GAGCTCTGATTTAACTGTAAACATT | 3,282,455 | 51 |
| 7948. | ATCTTGAGCTCTGATTTAACTGTA[A,G]ACATTAATGATTTCTTCGAAAAATG | 3,282,475 | 51 |
| 7949. | CTGGCGGTAGGTGCGTCAAACCAT[C,T]CGATCGATGGTTGATTTTGATGCAG | 3,282,708 | 51 |
| 7950. | ATATATATAATATCACTTTCATTT[G,A]AATTTTTtATTTTTGTATTTGTCAT | 3,282,824 | 51 |
| 7951. | TGAAGTCCTCTTTGTATTTCCACG[G,A]TCTTCCAAATCATCCCCTAGTTCCG | 3,282,926 | 51 |
| 7952. | GTATTTCCACGGTCTTCCAAATCA[T,C]CCCCTAGTTCCGGGGCATGTTTtTT | 3,282,939 | 51 |
| 7953. | GTCTTCCAAATCATCCCCTAGTTC[C,T]GGGGCATGTTTtTTTtCTTTCTTTT | 3,282,950 | 51 |
| 7954. | TCCTCGAGATAGTCAATCGAAAAA[C,T]CCGATTGACGATTCTCTTTCGGATC | 3,283,085 | 51 |
| 7955. | AAACCCGATTGACGATTCTCTTTC[G,A]GATCGGATATGAAAGTTTCTTCCT | 3,283,106 | 51 |
| 7956. | CCTCTGAGTCAAATAGCAATTTAT[G,A]TAGAGGACCTTCAGGCTGGTCTTCA | 3,283,258 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7957. | ACCTTCAGGCTGGTCTTCATTTTT[T,C]GATTCCGAAGTTTATCCAAAATCTC | 3,283,289 | 51 |
| 7958. | TTCGTCTCCATCCAAAAACCAAGG[G,A]TTGGTGGTTCTTCAACTTAAGAAAG | 3,283,467 | 51 |
| 7959. | GAATAAATCCCAACGAACATAGTC[G,A]GATCGATGTTATCAATCGAGAGAAC | 3,283,628 | 51 |
| 7960. | ACTGATGGAGCAATCTCTCTATAA[C,T]GCTGGACTTAGTCTGATGACTTCTC | 3,283,722 | 51 |
| 7961. | TCGATGTTTGCCAACATGTTGCTA[A,C]GAAGAAAGCAGTGATCGATGCTGGA | 3,284,885 | 51 |
| 7962. | TATCACACTGTCAGCTCCAACAGT[G,A]CTTCCTCCAATCGATGTACCATCGA | 3,284,032 | 51 |
| 7963. | AGTGCTTCCTCCAATCGATGTACC[A,G]TCGATCAAAGTGAAATTAACCAGAG | 3,284,053 | 51 |
| 7964. | TTCAACTGGGCCGATGCTGTTTCA[A,G]GTGCCATTAACTTCTGACTTCATGA | 3,284,242 | 51 |
| 7965. | AGCTGTTTCTGTCGATGATGGATC[A,G]TCAACAAGCTTCACCGTGCTTTTTG | 3,284,338 | 51 |
| 7966. | GACGTAAGTTGATGATACTTTTCT[G,A]ATACTCTTCTATTTTTTGTTTTtGT | 3,284,537 | 51 |
| 7967. | CATCGAAAAATTATCGAGTTTCAT[T,C]GAGCATGGATGGATAAAACTACAGC | 3,284,652 | 51 |
| 7968. | AAGAACAAAAAGCACTCAATCAAA[C,T]GGCTTCGAAGGGAGTGTGATGGCTG | 3,284,886 | 51 |
| 7969. | AGCAGCATCGTTGCCCTTGGTTCG[G,A]GGAAGAGATTGCCGAGGAGATTGCA | 3,285,186 | 51 |
| 7970. | TGCCCTTGGTTCGGGGAAGAGATT[G,A]CCGAGGAGATTGCACCAACTGAAGA | 3,285,197 | 51 |
| 7971. | AGATTGCTAATTATCAATCGGTGT[G,A]TTGAATGTCGATCAGTAGTCATAGT | 3,285,562 | 51 |
| 7972. | CTAGTCGGATATCACCTGACTTAG[A,C]TTTTAAATAATTTTTTtAAAATAT | 3,285,627 | 51 |
| 7973. | TTTGATCTAAAGATTTTGAAACTT[C,T]TGTCTTTCTTAAGACTAGGTCTCTT | 3,286,125 | 51 |
| 7974. | TGGCTCATTATATTGGTCGACTCT[C,T]ACTGACAGCAATCCAATCTCGAGCA | 3,286,312 | 51 |
| 7975. | AATTAAATGGCAATTCTCCTATTG[G,C]TATATGTAGAGTTGTCCGATATACT | 3,286,389 | 51 |
| 7976. | GCCTTAAGACCATGTAGAATTATT[C,T]GATTTGTCACTTTCACTTCATCGTT | 3,286,493 | 51 |
| 7977. | TCGTTAGATTATGGATGACCGACA[T,G]AAGTGAGTTTGTACGTAATGTGAAG | 3,286,538 | 51 |
| 7978. | CATTATCGGTGATGATGGTGTGTG[G,A]TAAATCGAATCTACATATGATTGAT | 3,286,632 | 51 |
| 7979. | CTTTCATCTTATTTTCAGTGATTT[G,A]TGTCAAAGGTTGCGGCTTCCATCCAT | 3,286,695 | 51 |
| 7980. | CTGACTGGTCGGTTGATGTTGTAT[G,A]TTGGCATACTTCTGACATGATTTAT | 3,286,864 | 51 |
| 7981. | TTGATGTTGTATGTTGGCATACTT[C,T]TGACATGATTTATATTTTCCAAAAA | 3,286,876 | 51 |
| 7982. | ACTTCTGACATGATTTATATTTTC[C,A]AAAAATTTAGCTGCATCTTTCTTT | 3,286,896 | 51 |
| 7983. | GGTGGGCCAATAATATCCTTATCG[C,T]AAAACTTTATAAGCCAATGATTTAT | 3,286,948 | 51 |
| 7984. | ATGATTTATCCTCCTAAGTAATTT[C,T]CACAAATTCCTTCGTAAACTTTTCG | 3,286,989 | 51 |
| 7985. | ATTTATCCTCCTAAGTAATTTCCA[C,T]AAATTCCTTCGTAAACTTTTCGGAG | 3,286,992 | 51 |
| 7986. | CTTTAGTAAGGGAAGAGAGAATGA[C,T]CTTTTATAAAGTTATTCATTCATCA | 3,287,072 | 51 |
| 7987. | ATTATGAGGCCGTCCACCTTAGTC[G,A]TTTGATCTCTGAAAGATCTGTAGGT | 3,287,128 | 51 |
| 7988. | TTGGTTCATCATTAATTTGTAGCA[T,C]TTTATCAATTTTATCAATACTCGAT | 3,287,221 | 51 |
| 7989. | GATATTTAATGAAAACGTACGGTCGA[A,G]CGAGCTGAATGAGGAAGTTGCGAGT | 3,287,278 | 51 |
| 7990. | AGCTGAATGAGGAAGTTGCGAGTC[G,A]AAAAAATGCATTAGCTTGAGCATTC | 3,287,305 | 51 |
| 7991. | ATTAGCTTGAGCATTCTCTATTTT[C,T]GAGATGTGAGAGATCTCGAAAGTATT | 3,287,339 | 51 |
| 7992. | CTTTTACTTTCTGAAGATACATCA[T,C]AATAGAATTTCGGGCTCCAAATTCA | 3,287,407 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 7993. | TACTTTCTGAAGATACATCATAAT[A,G]GAATTTCGGGCTCCAAATTCATTCT | 3,287,411 | 51 |
| 7994. | TAATATAAAATTGCTCTCAATGGT[C,T]GATCTGTTAAGACAACTATTGGATG | 3,287,892 | 51 |
| 7995. | AGCCTTTATGTTACATTTGATTT[G,A]TGTCTTGAACAGTCTGTTGACTAGC | 3,288,568 | 51 |
| 7996. | TAAAGGCAGTATGCTTCTCATCTT[C,T]AGGTGTCATTCGAATTTAGTTGTAG | 3,288,675 | 51 |
| 7997. | ATCGATTTTTGATAAAGAAAAGAT[G,A]TTTTTCAGACAAACTTCATTTAAAT | 3,288,784 | 51 |
| 7998. | AAGAAAAGATGTTTTTCAGACAAA[C,T]TTCATTTAAATTGGTATAGTTGATG | 3,288,798 | 51 |
| 7999. | TTACTATATTATGAAGCTAATCTG[G,A]ATAGTTAGCTTCTCTTATGAAGTCA | 3,288,882 | 51 |
| 8000. | TCAAGTAAAAATGTTGGCATTTGC[T,C]CTTAGTAGGTTCACTAGTTATTTTC | 3,289,084 | 51 |
| 8001. | ATGGTATGTTGATACTATTGCTCT[C,T]AAGACATTAAGTCCTGATCATCCAA | 3,289,381 | 51 |
| 8002. | TGTGGTTGAGGTTGTCGGTCAGTG[G,A]GAAGTTGAATCAGGCAGTCTTGTTA | 3,289,891 | 51 |
| 8003. | ATCGTGACCGTGATCATGATAAAA[C,T]CGACAATACTtTTTTTTGTCGCAGC | 3,290,010 | 51 |
| 8004. | TACTtTTTTTTGTCGCAGCTCCTC[G,A]GTGGTGCTTTCATCGATGGGGATG | 3,290,041 | 51 |
| 8005. | ACTtTTTTTTGTCGCAGCTCCTCG[G,A]TGGTGCTTTCATCGATGGGGATGA | 3,290,042 | 51 |
| 8006. | TCCCTCAATCTCTATTAGGATCTA[C,T]ACATGAAGAGCAAAAAGAAAAATAT | 3,290,106 | 51 |
| 8007. | GGAGTCATACCTGCTATCATAATT[G,A]TTCGATCTTGGACTCCATCGATGGA | 3,290,157 | 51 |
| 8008. | GTCATACCTGCTATCATAATTGTT[C,T]GATCTTGGACTCCATCGATGGAGTG | 3,290,160 | 51 |
| 8009. | TTGTTGATCGATTTGGTTCGATCG[G,A]AGCTTCATCTTTTtTTTGCTTCTTT | 3,290,225 | 51 |
| 8010. | TTTTGATATTTTTTTTtGCTTGAC[G,A]TTGGTCAGAAGTATCCTCATTCATG | 3,290,275 | 51 |
| 8011. | GGACCACGAACAAATGTTTGAGCT[G,A]CTCAAAAAAATTTATGCTCCCCGGT | 3,290,578 | 51 |
| 8012. | GCTCAAAAAAATTTATGCTCCCCG[G,A]TTGGAGCCCAGAATACCAGACTCGA | 3,290,602 | 51 |
| 8013. | AGGACTTCCAGCCTTCCACTTGGA[G,A]TCGGAGGAGTTGACAATCGATCTTT | 3,290,865 | 51 |
| 8014. | CCACTTGGAGTCGGAGGAGTTGAG[A,G]ATCGATCTTTTTAAATTTGTGCTCG | 3,290,880 | 51 |
| 8015. | GTTGTTGCTGGAAAAATTCAGGGG[C,T]AGTCACCTGAAGAACTTAAGGATTG | 3,290,943 | 51 |
| 8016. | CTGTATTAAAGTAGTAATTTGAAC[G,A]TCTGCAGTGACTACAGGATGTGAAG | 3,291,293 | 51 |
| 8017. | CCTATGGAGTTATTTTGAGCTCTA[G,A]TTTTTACCATAATTTTTTGTAAGCC | 3,291,408 | 51 |
| 8018. | AAATTATGTCCGACAAAGATCTTT[C,T]GATGCTTAAGTTAGTGAAGAGTAGT | 3,291,549 | 51 |
| 8019. | TTAGCCTAGAAGTATCTTACCAAT[A,G]CTGTTCATTTACCTCCTTTTTATAG | 3,291,631 | 51 |
| 8020. | GAAGTCGGTTAAGTCACCATGGTT[T,G]AATTGTATTTGCCAGCAAAGTTGAG | 3,291,933 | 51 |
| 8021. | TGCCAGGAAAGTTGAGAATAGCTG[A,G]CTGTTGATCGGCTTACTGATTGATA | 3,291,967 | 51 |
| 8022. | ATGTAGCTTTGATGGTTTATCATC[A,C]ATAATCGATAGATATCCGATCGACC | 3,292,091 | 51 |
| 8023. | GTCATAACAATAAATAAAAAAaGC[C,T]AGTGAATCTTGTCATAGGCCTCCTC | 3,292,263 | 51 |
| 8024. | AGAAAGAGGTACTTTGTGCAGTGA[A,C]TGCAATATTTCATAGGCAAAAAAGG | 3,292,347 | 51 |
| 8025. | GACAATCTTATAAGGAGAATTGCA[C,A]AAGCCAATTGGTCTATAATCTGTAG | 3,292,497 | 51 |
| 8026. | TTTGAAAATGTCGCATAAGGACTT[G,A]CTGGATTAGGTGTTGATCTTCCACC | 3,292,859 | 51 |
| 8027. | GATCTTCCACCTTTTCTCCATCCT[C,T]ATTTTTTATAGAATGAATTTTATTA | 3,292,898 | 51 |
| 8028. | CCTATTGTTCCACCAAGTATAATT[A,G]GGCCCTCAATAGCCTACATTAATCA | 3,293,511 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 8029. | TCTGTTGGGAATAGTGTCCCAAAG[C,T]CAATTGTTAGCCTGTTGACAGTTGT | 3,293,579 | 51 |
| 8030. | TGGGAATAGTGTCCCAAAGCCAAT[T,C]GTTAGCCTGTTGACAGTTGTGCTCC | 3,293,584 | 51 |
| 8031. | GAATAGTGTCCCAAAGCCAATTGT[T,C]AGCCTGTTGACAGTTGTGCTCCTTT | 3,293,587 | 51 |
| 8032. | TATGTACAGTCGTGTTTCAATTTA[T,G]CAAAATCTTGGCCAGGGTAGTCCTA | 3,299,964 | 51 |
| 8033. | CAGTCGTGTTTCAATTTATCAAAA[T,C]CTTGGCCAGGGTAGTCCTAGTGAAG | 3,299,970 | 51 |
| 8034. | CAGGGTAGTCCTAGTGAAGAGTCA[T,C]AGGACTAATTGAGTTGAGCACGATT | 3,300,001 | 51 |
| 8035. | TGAGTTGAGCACGATTCGGATGAT[C,A]TCATCAGGGTTGACAGTTTAACCCT | 3,300,035 | 51 |
| 8036. | TTCCTAAACACAGGGGTCAAAAGG[A,G]ATGAATTATACGGTAACCATATTCA | 3,300,090 | 51 |
| 8037. | TATACGGTAACCATATTCACGTAG[A,G]TTCTGAATGTTGCGATTGCGACTAT | 3,300,121 | 51 |
| 8038. | CGTAGATTCTGAATGTTGCGATTG[C,T]GACTATTCGATCTATCCGATCGTCG | 3,300,140 | 51 |
| 8039. | TCCTTTCTGATCTGATGGCTGATT[T,A]TGAGTCTTATGTATCTGGGACTCTA | 3,300,286 | 51 |
| 8040. | CTGGGACTCTATGATTGAGAATTA[A,G]GATTCTTTGATCATGAGTTCCACAC | 3,300,325 | 51 |
| 8041. | TCTATGATTGAGAATTAAGATTCT[T,C]TGATCATGAGTTCCACACATTTTGG | 3,300,332 | 51 |
| 8042. | ATGAGTTCCACACATTTTGGATAC[T,C]GGGGTCAAAATTTTGAATTTCAAAT | 3,300,362 | 51 |
| 8043. | AATTTGATTGAGTAATTATTTTTA[A,G]ATGAAGTCCAATTGAATTGGATTCA | 3,300,540 | 51 |
| 8044. | TTGATTGAGTAATTATTTTTAAAT[G,C]AAGTCCAATTGAATTGGATTCAGTT | 3,300,543 | 51 |
| 8045. | GAGTAATTATTTTTAAATGAAGTC[C,T]AATTGAATTGGATTCAGTTTGGATT | 3,300,549 | 51 |
| 8046. | AATTGGATTCAGTTTGGATTGACC[T,C]GATTAGGTTAAGTGTTGATCTAATC | 3,300,579 | 51 |
| 8047. | AGGGGGCGTGGGCAATGAAAGAAA[T,G]AAGAAATAAGGGGCGTGGGGAGGTT | 3,300,755 | 51 |
| 8048. | GCGTGGGCAATGAAAGAAATAAGA[A,G]ATAAGGGGCGTGGGGGGGTTCTAGA | 3,300,760 | 51 |
| 8049. | AAATAAGGGGCGTGGGGAGGTTCT[A,G]GAAAAATTTTGAAGTGTTCAAAATT | 3,300,783 | 51 |
| 8050. | GAGAGAAAAGGAGAGAGAAGTGGG[C,T]GCAGGGTTTTTGGTGTGTACCCTAG | 3,300,842 | 51 |
| 8051. | TTTTGGTGTGTACCCTAGGGTTTC[T,A]ACTTAGGGTTCAGGAAGTGAGATTG | 3,300,874 | 51 |
| 8052. | TGGTGTGTACCCTAGGGTTTCTAC[T,C]TAGGGTTCAGGAAGTGAGATTGGTA | 3,300,877 | 51 |
| 8053. | CCCTAGGGTTTCTACTTAGGGTTC[A,G]GGAAGTGAGATTGGTATGCCACGAG | 3,300,886 | 51 |
| 8054. | TCCATCAGCCTCTCAACCAACCAT[G,A]CAGATGATCCAAAGCATCCGAGGAG | 3,300,967 | 51 |
| 8055. | GATCCAAAGCATCCGAGGAGTCAG[G,C]ACATATCGATCGAAGGAGTTCGATC | 3,300,997 | 51 |
| 8056. | CAAAGCATCCGAGGAGTCAGGACA[T,C]ATCGATCGAAGGAGTTCGATCAACA | 3,301,001 | 51 |
| 8057. | CGATCAACATCAGCCATCAAAAGG[A,G]TGAAATCACGAACTAGCATTCGTGA | 3,301,042 | 51 |
| 8058. | GCATTCGTGAGGAGCCGATCAGAC[A,G]GGAGCTTTGTGTGGATGATCCGCAG | 3,301,082 | 51 |
| 8059. | GAGGAGCCGATCAGACAGGAGCTT[T,C]GTGTGGATGATCCGCAGAGGCCAGA | 3,301,090 | 51 |
| 8060. | GATCAGACAGGAGCTTTGTGTGGA[T,C]GATCCGCAGAGGCCAGACACTAGTG | 3,301,098 | 51 |
| 8061. | ACAGGAGCTTTGTGTGGATGATCC[G,A]CAGAGGCCAGACACTAGTGTGGCTG | 3,301,104 | 51 |
| 8062. | TCGACTACCCGCAAAAGGTGATGT[G,A]TTCTGAACACAGTACAGTAAAAAGT | 3,301,199 | 51 |
| 8063. | TTTGAATTTCAAATTTAAATGCAT[G,A]CTGTTGTATCATATTTAGATCCTAG | 3,301,262 | 51 |
| 8064. | ATGAGATTAATTAATAATTTTACT[A,G]TAAAATAATAATTATGAAAAaGTTT | 3,301,335 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 8065. | AATTAATAATTTTACTATAAAATA[A,G]TAATTATGAAAAaGTTTTAAAAaTT | 3,301,343 | 51 |
| 8066. | TAATTTTACTATAAAATAATAATT[A,T]TGAAAAaGTTTTAAAAaTTATCATT | 3,301,349 | 51 |
| 8067. | CCTATTAGGAAATGTTAAGATGCA[C,T]AGCAGAAAAATAATAATAACTTTTC | 3,301,929 | 51 |
| 8068. | AATTTTTTATTTATGTATATAGCA[G,A]AAAATAATTTTAGATTTAAATAATT | 3,303,152 | 51 |
| 8069. | TCCATCATAAATATCATTGAAATC[C,T]ATTTCAATAGATTGAAACACTTCCA | 3,304,375 | 51 |
| 8070. | CTTGGTGTGTTAACGTGTGATTCA[G,A]TTCTTTTATCATGAGTTCTGATAAG | 3,304,538 | 51 |
| 8071. | TAAGATGGAGATCATGAAAAACTC[G,A]TCAAACCTCATCATATATCATATAT | 3,304,584 | 51 |
| 8072. | CAGCTCAAGTTCAACTCGTGATTT[T,C]TCATAAAAATTTCTTTCCATCAATC | 3,304,644 | 51 |
| 8073. | CTCAAGATGTTGAGAATTTGAGAC[G,A]TACATCATTAGTAGTTAATTTTTAA | 3,304,959 | 51 |
| 8074. | TGCTTTCGATTGAAGGATCGTCAC[G,A]AAGGATGGTGATCAATCCATTCAAA | 3,305,010 | 51 |
| 8075. | CGATTGAAGGATCGTCACGAAGGA[T,C]GGTGATCAATCCATTCAAAATTGGT | 3,305,016 | 51 |
| 8076. | CCTCTCTTTGGGGCAGATAAGTCT[C,T]GAGTCTATGGTGTAGAGATACTAAG | 3,305,076 | 51 |
| 8077. | CTGAGCGTGATCAATACAAAAAAT[T,C]ACTTGGATGTCTACTCACTCATCAG | 3,305,162 | 51 |
| 8078. | GTTTGACTGCACATTCTCTTAGTC[T,C]CTAGCCATTCAGGTTCTTATTATAT | 3,305,289 | 51 |
| 8079. | TTCAGGTTCTTATTATATATGTTG[G,A]CTATTGTAGGTTCAGATTCGTTATT | 3,305,321 | 51 |
| 8080. | TTCTTATTATATATGTTGGCTATT[G,A]TAGGTTCAGATTCGTTATTTGAAGT | 3,305,327 | 51 |
| 8081. | AGAAAATCTCTGGCCAGACTAAGT[G,A]TGAATACTGAAAAAGAGTTTTCATA | 3,305,451 | 51 |
| 8082. | TGAATACTGAAAAAGAGTTTTCAT[A,G]GATTTACAAATGAACTCAAGTCAA | 3,305,476 | 51 |
| 8083. | TTTGACGAGTTCTCCATGACCTCC[G,A]TCAAGTCGAAACTCATAATAGAGAA | 3,305,555 | 51 |
| 8084. | ATATGATAACTACACCTAAGGGTT[C,T]ATTTtTTTATTCTACTAGATTATCA | 3,305,613 | 51 |
| 8085. | TTAAATTTTAAAAATTGCTAATTT[G,A]TAATTGTTATAATTTTGGTAGCTGC | 3,305,908 | 51 |
| 8086. | AGCTTTTTGAATTCGACTTGATTC[G,A]GACTCAATTTGAATCCGATTAAGAC | 3,306,148 | 51 |
| 8087. | AGGTCTTGCGTGAACAAGAAGTGC[G,A]ACTTTTTTAGGACATCACAATCCTT | 3,306,659 | 51 |
| 8088. | CAGAGAGAAAAAGAGAAGAATAAG[A,G]AATTTTCTTCTCTTCATGGTGATCT | 3,306,785 | 51 |
| 8089. | AGATCTAGATCCAAAGTTGAGGAG[C,T]GAGATCTATAAAGTGCTAGCACATC | 3,306,905 | 51 |
| 8090. | GTGTGCAGCTACGATTAGAATTCG[G,A]ATATCCGCATATCCAAGGTATAGAG | 3,307,013 | 51 |
| 8091. | CCATTCGATGGGTTCTCTCTTATG[A,G]CGTGTAGGGGTATCGACTGTGATAT | 3,307,808 | 51 |
| 8092. | TTCTCTCTTATGACGTGTAGGGGT[A,G]TCGACTGTGATATTTTTCATGAAGA | 3,307,820 | 51 |
| 8093. | GACATACGATCTAAAACTTAATTT[C,T]TGTAAAATTTTAGATCCAAAATCCT | 3,307,982 | 51 |
| 8094. | AGGTCAGCTCACTTACTGATGAGC[C,G]AACTCAATTGTGCAGGTTAGGTCAC | 3,308,162 | 51 |
| 8095. | GGTCAGCTCACTTACTGATGAGCC[A,G]ACTCAATTGTGCAGGTTAGGTCACA | 3,308,163 | 51 |
| 8096. | CTTAAACCCATGTACATAATGCAG[T,C]TAATTGAGAATTAATATTTGAAATT | 3,308,358 | 51 |
| 8097. | CATGTACATAATGCAGTTAATTGA[G,A]AATTAATATTTGAAATTATAAAATC | 3,308,366 | 51 |
| 8098. | ATTAATATTTGAAATTATAAAATC[T,A]AAAATTATGAATTTAAGATCTAAAT | 3,308,392 | 51 |
| 8099. | ATTATGAATTTAAGATCTAAATTT[T,C]AATACATAAAATATGAGTTTCAGGT | 3,308,420 | 51 |
| 8100. | CCAATTTGGTATCTAAGACAAGTA[C,T]TAGATAGTGATTATTTAATTGATTC | 3,308,730 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 8101. | CATTGGTGTTTAAGAAAAGCAACG[G,A]AGAAACCTTACTCATCTTTATTTGT | 3,308,801 | 51 |
| 8102. | GAGAAACCTTACTCATCTTTATTT[G,A]TCTGATCATTTTGAAAGATTATATT | 3,308,825 | 51 |
| 8103. | TATATTTTGTATTAGGTTACTTGT[A,G]GATCCGAGTTCACCCATGCCAACTA | 3,308,869 | 51 |
| 8104. | TGTAGAGATGTGGGTGTCTTTTTC[G,A]ACGTTGATCGTTCTCGACTAGTTAC | 3,309,046 | 51 |
| 8105. | TAGAGATGTGGGTGTCTTTTTCGA[C,T]GTTGATCGTTCTCGACTAGTTACAG | 3,309,048 | 51 |
| 8106. | AAGAAATATGCCAATAACTGTTAG[G,A]TGAGACCACAGGACTTAGAGATCCA | 3,309,242 | 51 |
| 8107. | AATAACTGTTAGGTGAGACCACAG[G,A]ACTTAGAGATCCAGTCGCTGCAACA | 3,309,254 | 51 |
| 8108. | ACAGGACTTAGAGATCCAGTCGCT[G,T]CAACATGCTTGGAGAAGCATCTGGA | 3,309,274 | 51 |
| 8109. | GAAGCATCTGGATAAAGAGTTGTC[C,T]ACATATTGATATACGTGTTATCAAT | 3,309,312 | 51 |
| 8110. | TTATCAATAACTGTTAGGTGAGGT[G,A]CCGTATATCGATAGGACCACAACAT | 3,309,354 | 51 |
| 8111. | CGTGTTAGGATTTTCTTCTCCATC[C,T]GAGTGTGAGAGACTCGAAAAATTAG | 3,309,421 | 51 |
| 8112. | AAAATTAGTGAGAGCCTTTGTTTG[T,C]TTTTAAAGTCCTTAGATCAAATTAT | 3,309,463 | 51 |
| 8113. | AGAGCCTTTGTTTGTTTTTAAAGT[C,T]CTTAGATCAAATTATTACAAGTACA | 3,309,473 | 51 |
| 8114. | CTTTACTCTCTATGATCAATTTTT[T,C]AGCTTCCAACACTCAAGCTCGAATC | 3,309,538 | 51 |
| 8115. | CAATAGTTGTAAGATGATCAGAGT[C,T]GCACAGTGCATGAGATGCATGATCG | 3,309,857 | 51 |
| 8116. | AATAAATATTATAACATCTTAATT[G,A]AATTGGTCGATATGCTGGTAACTAA | 3,310,042 | 51 |
| 8117. | TCAAATTACTCAAAATTGATATTA[C,T]AATTTTTTtCTTTTTCATTAGACTC | 3,310,164 | 51 |
| 8118. | AATGATGCAAATATTGCACTGAGA[C,T]CGTGAGTACCTAATCTCAGTGATTA | 3,310,295 | 51 |
| 8119. | ACCTAATCTCAGTGATTATCATTT[G,A]GATTTAATTCTTTATCATTTGCATG | 3,310,327 | 51 |
| 8120. | GCTAAGTCATGTATGAGAAGAAAT[G,A]ATTTGCCGACCGAAGAAAATGGGCT | 3,310,475 | 51 |
| 8121. | GTATGAGAAGAAATGATTTGCCGA[C,T]CGAAGAAAATGGGCTTTTTGGGCTC | 3,310,485 | 51 |
| 8122. | TCATATCTAGTCTACAAATCATCT[C,A]TTTGAGGATTAATGACTAAACTGTC | 3,310,548 | 51 |
| 8123. | GAGATACTTATCTTAGTACACATA[C,T]AATATGCATGGCCTATTTGATGAAC | 3,310,626 | 51 |
| 8124. | AGATTTTGAAAGGTTCAAAGAATT[T,C]AGGTGTAAAGTAAAAAGATAAATG | 3,310,759 | 51 |
| 8125. | AAGATACTTTGATCAGATCGAGGA[T,C]GCAATACCAAATGGAGAATTTATCG | 3,310,821 | 51 |
| 8126. | ATTTAATTTTTGAAATTTAAATTA[T,G]ATTTCCTCTGAAGTTGGTTTCACCA | 3,311,023 | 51 |
| 8127. | ATATGATATGGTGGACAGGTTAGA[A,G]AATAGGTCTGTGAGAACTCATTTAT | 3,311,084 | 51 |
| 8128. | GGAATGATCCCAAAAGTCCTACAA[C,T]GATGTGATATGAAGAATCATGTAGT | 3,311,421 | 51 |
| 8129. | TAGGAGAGTCCCATACTGACATCG[G,A]TTAAGATATGGTTATATATAGAATT | 3,311,485 | 51 |
| 8130. | AGAGGGATCCATTATCCTCTTAGG[C,T]ATGGGTGTATACAATGCTATGTACT | 3,311,667 | 51 |
| 8131. | ATTATTCCTCATCTTTGAAGAAGG[G,A]TTAGAGTTAAGAGTGGGAGGATACA | 3,311,828 | 51 |
| 8132. | TTGGAAGGGTTTTAGGCAATCAAC[T,C]AATGAAAGCTGAATATGCTATAGAT | 3,311,940 | 51 |
| 8133. | AGATGTGTAGAATGCATTCTGGTT[C,T]TTATGATAGTTACAGAACTGGATGT | 3,311,986 | 51 |
| 8134. | GGATGTCATACCATTGGATGCTTT[G,A]ACATTATACTACAAAGATAATGATC | 3,312,030 | 51 |
| 8135. | GACAGATTGGCTTTAGTGCAAGTG[G,A]AACCTTTTTAGATGTGTGTTCTAGA | 3,312,268 | 51 |
| 8136. | TGCAAGTCCAACCTTTTTAGATGT[G,A]TGTTCTAGAAGCCAATCTTGGCTAA | 3,312,284 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 8137. | AAGCCAATCTTGGCTAACACATAC[C,T]TTTCTCTAAGGCATGTTTTGTACTT | 3,312,317 | 51 |
| 8138. | ATCTTGGCTAACACATACCTTTCT[C,T]TAAGGCATGTTTTGTACTTGATGGG | 3,312,323 | 51 |
| 8139. | GGCTAACACATACCTTTCTCTAAG[G,A]CATGTTTTGTACTTGATGGGTAGTC | 3,312,328 | 51 |
| 8140. | ATACTTTCAATCGAAGGATCATCA[C,T]GAAAGATAATGATCAATCCATTTAA | 3,312,497 | 51 |
| 8141. | CACTGAGCATAACCAACATGAAAA[T,A]CCATTTGGATGTCTACTCACTCATC | 3,312,648 | 51 |
| 8142. | TCGTAGTGAGGCTACTTAGTTTGA[C,T]TGCACATTCTCTTGATCCCTAACCA | 3,312,759 | 51 |
| 8143. | ATCATGGTGTGTCTCACTACCAGA[C,T]AGAATAGAATTTGAGAGATCATGCA | 3,313,863 | 51 |
| 8144. | ACAGAATAGAATTTGAGAGATCAT[G,A]CATAAAAGGAGCATGATCTGATCAA | 3,313,886 | 51 |
| 8145. | TGGATCATATTCAAATTATTAATC[G,A]GATTGATAGTTTGAATTTTAGAAAC | 3,313,941 | 51 |
| 8146. | CTCGATTTGAATCCGATTAAGATC[C,T]AACTTGAACTAGAAGAATCATGACT | 3,314,225 | 51 |
| 8147. | GGATAAGGAGGGCGTGCGTTAATT[G,A]TGAGTGGAGGTTTCTTTCTTACATC | 3,314,505 | 51 |
| 8148. | GTGTGACAAAAATAAAAaGGAAGG[T,C]GTGAGGTCTTGTGTGAATAAGAAGT | 3,314,669 | 51 |
| 8149. | AAGAGAGAGAAGAAGAGAAGAAAA[A,T]TTTTTTtCTTTTCTTCATGGTGAT | 3,314,821 | 51 |
| 8150. | CGAATCTACACAAAATAGTTCACG[T,C]GGTGATCTCCTTCTTCAAGATCTAG | 3,314,887 | 51 |
| 8151. | TTCAAGATCTAGAAGAAGAGATCT[A,C]GATCCAAAATTGAGGAGTGAGATCT | 3,314,925 | 51 |
| 8152. | TAGCACACCGATGATCTCAGCACT[C,T]TGATCAGATATTTTGTGTGGATAC | 3,314,984 | 51 |
| 8153. | TTTTTAAACTACACGTATGAAATC[G,A]TTGCAATTTTTTAACAGAACCTACT | 3,315,272 | 51 |
| 8154. | GAACCTACTGTAGCCAACATACAC[C,A]GCAAAAATCTATATAACTAGGAGAT | 3,315,313 | 51 |
| 8155. | TTTAGAAATTAACCATCAATGACA[C,T]ATGTCTCAAATTTTTAATTCTTGAG | 3,315,661 | 51 |
| 8156. | TTATTCGACTCAAATTTTTGATAT[G,A]AAAATGGTGAAAATTTTTTTCACTA | 3,316,071 | 51 |
| 8157. | AGAGATCATGTATGTATAATCAAA[C,T]TATAGTAACTTTATTGTAAATAGCC | 3,316,266 | 51 |
| 8158. | ATAGCCGGGGCACGATGGGTCAAA[G,A]GACTAGTCACCCTATTGCAACATCG | 3,316,310 | 51 |
| 8159. | CCTCCTGAGAAATGGAAGTAGTCT[C,T]CTTCGGATCTTTAGTCAATTCTTCT | 3,316,872 | 51 |
| 8160. | TTTTTtGCTTTTGATGAAGTACCA[G,A]TAACCTCAACTTGTAAATAACTAGC | 3,317,174 | 51 |
| 8161. | TTCGAATTTACTTTTTGGACAAAT[T,G]TTCTTGGTAATATCGATCTTCACAC | 3,317,623 | 51 |
| 8162. | AGTCAATATAAAGTATATGAATT[G,A]GTAAATTAATAAAATTATTATTTAA | 3,318,323 | 51 |
| 8163. | CTTAGGACTATTCTAATCGATATA[A,G]GAGGATATATCATTAAGTCCTTAAA | 3,318,433 | 51 |
| 8164. | GATACGCTGTTACTAGGATGATAG[T,C]GTTTATCGAGTGTAGGTCATTGTGT | 3,318,501 | 51 |
| 8165. | TGAAGACACTGGTATGGCATACAA[G,A]TGAGATGTAGGAGTACATTTCATTG | 3,318,585 | 51 |
| 8166. | GCATACAATGAGATGTAGGAGTA[C,T]ATTTCATTGAATGTGACCAACTACT | 3,318,601 | 51 |
| 8167. | CAAGTGAGATGTAGGAGTACATTT[C,T]ATTGAATGTGACCAACTACTGAGTA | 3,318,606 | 51 |
| 8168. | AGGATATGGGTATAAGTATCCCTC[T,C]GATCTAAGATCATCATGGTGACTTA | 3,318,681 | 51 |
| 8169. | CAAGCAACTCATTATACTTTGGTG[T,C]CAGACTATCTGAATTTTTAATTCAG | 3,318,731 | 51 |
| 8170. | TGACCCCTCCGAATAAGAAGAAGT[A,T]AGTGCATCAGTATATTTTAATTCAA | 3,318,844 | 51 |
| 8171. | CTTGAGCATTAGGATCAAAGGGAT[A,G]AATTATATGGTAACCATATGTCAAT | 3,318,990 | 51 |
| 8172. | CCATATGTCAATAGGTTCATGAAT[A,G]ATGCTTTGCAATCTTTCGATCTATC | 3,319,028 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 8173. | TAAGGTACACTTAAAAGAAATTTT[C,T]AACTAATCATGTAGCTGATCAATGA | 3,319,162 | 51 |
| 8174. | TAATCATTAATTCGATTAACCTTG[T,C]ACAAAAGTAATAATAAATTAATTTG | 3,319,232 | 51 |
| 8175. | TAATTAGATCAGATAATCTAATTA[G,T]ATCTAACATAATTTGGTTGCGTTAA | 3,319,505 | 51 |
| 8176. | TGGGCATCCATGCATGAGAAAAAG[G,A]GGAAGAAGATCCTCTTTGGGGCGTA | 3,320,108 | 51 |
| 8177. | TTCTAATCTGGAGATATCCATTG[A,G]TCTAAAGAAAGGAGTCTCTATCAGC | 3,320,270 | 51 |
| 8178. | CAATGGTGATCGTCGACCCATGAT[C,T]AGGTAATGGGTTCTGAACTCATCGG | 3,320,456 | 51 |
| 8179. | GATGCAGTCTTTTCTTTCTGATCA[A,G]ATTTTTTtTATATATTATTTTCATG | 3,320,550 | 51 |
| 8180. | CAAATTTTTtTATATATTATTTT[C,T]ATGTCATAAATTTTTAGATAGGTAG | 3,320,572 | 51 |
| 8181. | TAAATAGTTTAATCTACTACTTTC[G,T]CTATAAAAaTTTTAAAaAATACATA | 3,320,654 | 51 |
| 8182. | ATTTCTTATGACATGAATTTTTTA[C,T]ATATAATCTGATATTAATCTAATTT | 3,320,745 | 51 |
| 8183. | GTTTTACGATCCTTTCTTTTCATT[C,T]GATGAGATTCTCATATGGCTTGTAG | 3,320,889 | 51 |
| 8184. | ATGAGATTCTCATATGGCTTGTAG[G,A]GATGCTGCGTAGTCTTTTTCATGAA | 3,320,915 | 51 |
| 8185. | CTCGATTCAAATCTATTTAACTGG[A,G]TTAGACCTAGGATTAGAAATCATTG | 3,322,754 | 51 |
| 8186. | TTTTTTGATTAATTCTCAATAGTT[G,A]TAGTTGGTCAAGTCTATGTCTTTGA | 3,322,868 | 51 |
| 8187. | TCATAGCTCTGTAGTCAAACCCAA[G,A]TCTATAAGTTGATCAAGTTGAAACA | 3,322,939 | 51 |
| 8188. | TGAGTTAACGGCATATCCCTCCCA[C,T]CGATCTCACTTATCTGACCAACATG | 3,323,076 | 51 |
| 8189. | TAATTGATTTAGGTGCCCCTAATT[C,T]AACTTGTCTTGAGTCCTCTTCATAA | 3,323,192 | 51 |
| 8190. | TCTGACTTAGTGAAGTCAGTAGGA[G,C]GATTAAAAATAACTGATTGAGTCTT | 3,323,309 | 51 |
| 8191. | CATCTATCAATTCAATTAATTAAA[A,T]TTTTTAAAATTATTAGGTCTCTAAA | 3,323,363 | 51 |
| 8192. | GTCTCTAAATATAAAATAGTTATG[G,A]AGATAACTAGATCATAACCTCCTAT | 3,323,404 | 51 |
| 8193. | GTGATCAGGATGACCGACCAAAGC[T,C]GGATCAAATCACTTATGGTTAGATT | 3,323,575 | 51 |
| 8194. | AGCCGACCAAAGTCGAGCTCATGT[G,A]CAACTATGTGGATTCTAGTATCTGC | 3,323,770 | 51 |
| 8195. | TCAATGCCAGGATGAGGGAGGGGG[C,T]GTCAGTGATCGATCATATATTGTAC | 3,324,316 | 51 |
| 8196. | AAGATCACCAGCTCCACAAAGAGA[C,T]GGTGAATGTAATGGGAGCATCTTCT | 3,324,544 | 51 |
| 8197. | AGTCTGATCAAAGTCAGGCAGAGT[G,A]CTTCTACTATAAGAAGCAAGGTTAT | 3,324,681 | 51 |
| 8198. | TTTTAATTTATGATACAATGATCT[G,A]AGTATTAGATATTGATAGTCCTATT | 3,324,840 | 51 |
| 8199. | AATTCTCATATCATTATTCTTAGT[A,G]ATTATCATTATTGTCCTAGTTTCTT | 3,325,018 | 51 |
| 8200. | TAATTATCATTATTGTCCTAGTTT[C,T]TTATTGAATGTAATTTTTGTAGGCC | 3,325,041 | 51 |
| 8201. | ATAATGTCTTGAAGAGCTATCTTT[G,A]GCATTGTAAGCTAAGTCATATCAAC | 3,325,245 | 51 |
| 8202. | GGTCTTGTATATACTGATGTATAT[G,A]GACCGATGAGCACAAGTATGAGAGG | 3,325,439 | 51 |
| 8203. | ATGGACTCCTCCTAGAATGCCACA[A,G]TATAATGGTATCTCAGAAAGGAGAA | 3,325,711 | 51 |
| 8204. | GGATGTCCGACTTATATCAGATAT[T,C]TAAAAACAGACAAATTAGGATCTAA | 3,325,946 | 51 |
| 8205. | CGACTTATATCAGATATTTAAAAA[C,T]AGACAAATTAGGATCTAAGTCTGAC | 3,325,953 | 51 |
| 8206. | TCTTCATAGGGTATCCTAAAAAAa[C,T]TAAGGGATATTACTTCTACCTTATT | 3,326,010 | 51 |
| 8207. | CTAAGGGATATTACTTCTACCTTA[T,C]TGATAAATAAAATATATTCGTGACT | 3,326,034 | 51 |
| 8208. | GTTCGATGGATAGAAGAACCGACA[C,T]AATCTAGTGAACCCACAGAATCCAA | 3,326,157 | 51 |

TABLE A-continued

Table of SNPs identified in the genomic region (SEQ ID NO: 8218) containing SHP1

| SEQ ID NO: | SNP | position in Genomic region SEQ ID NO: 8218 | Estimated prediction success |
|---|---|---|---|
| 8209. | ACAATCTAGTGAACCCACAGAATC[C,T]AATTTGATTGAATCAAATCTAGAAC | 3,326,180 | 51 |
| 8210. | TAAGTGGCTAGAAGTCATGAAATC[C,T]GAAATAGAGTCCATAAAGGCCAATA | 3,326,384 | 51 |
| 8211. | GAAAGTGGATCTTTAAGAGGAAGA[A,G]GGGCACAGACGGCAAGGTAGAGACC | 3,326,482 | 51 |
| 8212. | AATGAGTCTAAGGTATGCAAGCTT[T,C]AGAGATCCATTTATGGATTGAAGCA | 3,326,754 | 51 |
| 8213. | TGTGTTTTGATAAAGTGATCAGAA[C,T]GTATAACTTTGTTAAGAATGAAAAA | 3,326,824 | 51 |
| 8214. | GAACGTATAACTTTGTTAAGAATG[A,G]AAAAGAATCCTAAATGGGTTAACAA | 3,326,845 | 51 |
| 8215. | ATCCACATACTTCGACATCATGCT[G,A]AAATGGTTTAGTATAAAAAATTTCA | 3,327,084 | 51 |
| 8216. | TGTAGAGTTTATAGACTTCAATTT[T,C]CAATCGAAGCATGATGACATAAGA | 3,327,419 | 51 |
| 8217. | GTGAAACAATCTACTAAAAAAATT[A,C,T]TAAGCAGCACACAGTAGCCGACTCT | 3,327,499 | 51 |

REFERENCES

Beirnaert, A. and Vanderweyen, R. 1941. Contribution a l'etude genetique et biometrique des varieties *d'Elaeis guineensis* Jacq. Pubis. INEAC, Series Ser. Sci. (27):101.

Bhasker, S. & Mohankumar, C. Association of lignifying enzymes in shell synthesis of oil palm fruit (*Elaeis guineensis—dura* variety). 2001. *Indian J Exp Biol* 39: 160-4.

Billotte, N., Marseillac, N., Risterucci, A. M., Adon. B., Brotteir. P., Baurens, F. C., Singh, R., Herran, A., Asmady, H., Billot, C., Amblard, P Durrand-Gasselin, T., Courtois, B., Asmono, D., Cheah, S. C., Rohde, W and Charrier, A. 2005. Microsatellite-based high density linkage map in oil palm (*Elaeis guineensis* Jacq.). Theoretical and Applied Genetics 110; 754-765.

Birchler, J. A., Auger, D. L. & Riddle, N. C. 2003. In search of the molecular basis of heterosis. *Plant Cell* 15: 2236-9.

Cheah, S. C. 1996. Restriction Frarent Length Polymorphism (RFLP) in Oil Palm. Project Completion Report No. 0011/95, 4 Jul. 1996, Malaysian Palm Oil Board (MPOB), Bangi, Malaysia.

Cheah, S. C. and Rajinder, S. 1998. Gene expression during flower development in the oil palm. Project Completion Report No. 0057/98, 16 Jul. 1999. Palm Oil Research Institute of Malaysia (PORIM), Bangi, Malaysia.

Corley, R. H. V. and Tinker, P. B. 2003. Care and maintenance of oil palms. In *The Oil Palm* (4th edition), pp: 287-326. Oxford: Blackwell Science.

Danielsen, F. et al. 2009. Biofuel plantations on forested lands: double jeopardy for biodiversity and climate. *Conserv Biol* 23: 348-58.

Devuyst, A. 1953. Selection of the oil palm (*Elaeis guineensis*) in Africa. *Nature* 172: 685-686.

Dinneny, J. R. and Yanofsky, M. F. 2005. Drawing lines and borders: how the dehiscent fruit of *Arabidopsis* is patterned. *Bioessays* 27: 42-9.

Donough, C. R. and Law, T. H. 1995. Breeding and selection for seed production at Pamol Plantations Sdn Bhd and early performance of Pamol DxP. *Planter* 71:513-530.

Doyle, J. J. and Doyle, J. L. 1990. Isolation of plant DNA from fresh tissue. *FOCUS* 12:13-15.

Ferrandiz, C., Liljegren, S. J. & Yanofsky, M. F. 2000. Negative regulation of the SHATTERPROOF genes by FRUITFULL during *Arabidopsis* fruit development. *Science* 289: 436-8.

Godding, R. 1930. Observation de la production de palmiers selectionnes a Mongana (Equateur). *Bull Arig. Congo belge* 21: 1263.

Gschwend, M. et al. 1996. A locus for Fanconi anemia on 16q determined by homozygosity mapping. *Am J Hum Genet* 59: 377-84.

Gu, Q., Ferrandiz, C., Yanofsky, M. F. & Martienssen, R. 1998. The FRUITFULL MADS-box gene mediates cell differentiation during *Arabidopsis* fruit development. *Development* 125: 1509-17.

Hardon, J. J., Rao, V., and Rajanaidu, N. 1985. A review of oil palm breeding. In Progress in Plant Breeding, ed G. E. Rusell, pp 139-163, Butterworths, UK.

Hartley, C. W. S. 1988. The botany of oil palm. In *The oil palm* (3rd edition), pp: 47-94, Longman, London.

Huang, H., Tudor, M., Su, T., Zhang, Y., Hu, Y., and Ma, H. 1996. DNA binding properties of two *Arabidopsis* MADS domain proteins: Binding Consensus and Dimer Formation. *The Plant Cell* 8: 81-94.

Immink, R. G., Kaufmann, K. & Angenent, G. C. 2010. The 'ABC' of MADS domain protein behaviour and interactions. *Semin Cell Dev Biol* 21: 87-93.

Jack, P. L., James, C., Price, Z., Rance, K., Groves, L., Corley, R. H. V., Nelson, S and Rao, V. 1998. Application of DNA markers in oil palm breeding. In: 1998 International Oil Palm Congress—Commodity of the past, today and future, Sep. 23-25, 1998, Bali, Indonesia.

Krieger, U., Lippman, Z. B. & Zamir, D. 2010. The flowering gene SINGLE FLOWER TRUSS drives heterosis for yield in tomato. *Nat Genet* 42: 459-63.

Lander, E. S. and Botstein, D. 1987. Homozygosity mapping: a way to map human recessive traits with the DNA of inbred children. *Science* 236: 1567-70.

Latiff, A. 2000. The Biology of the Genus *Elaeis*. In: *Advances in Oil Palm Research*, Volume 1, ed. Y. Basiron, B. S. Jalani, and K. W. Chan, pp: 19-38, Malaysian Palm Oil Board (MPOB).

Liljegren, S. J., Ditta, G. S., Eshed, Y., Savidge, B., Bowman, J. L., Yanofsky, M. F. 2000. SHATTERPROOF MADS-box genes control seed dispersal in *Arabidopsis*. *Nature* 404: 766-770.

Maria, M., Clyde, M. M. and Cheah, S. C. 1995. Cytological analysis of *Elaeis guineensis* (*tenera*) chromosomes. *Elaeis* 7:122-134.

Mayes, S., Jack, P. L., Marshall, D. F. and Corley, R. H. V. 1997. Construction of a RFLP genetic linkage map for oil palm (*Elaeis guineensis* Jacq.). *Genome* 40:116-122.

Moretzsohn, M. C., Nunes, C. D. M., Ferreira, M. E. and Grattapaglia, D. 2000. RAPD linkage mapping of the shell thickness locus in oil palm (*Elaeis guineensis* Jacq.). *Theoretical and Applied Genetics* 100:63-70.

Ooijen, J. W. V. 2006. JoinMap 4.0: Software for calculation of genetic linkage maps. In experimental populations. Kyazma B. V., Wageningen, Netherlands Pinyopich, A. et al. 2003. Assessing the redundancy of MADS-box genes during carpel and ovule development. *Nature* 424: 85-8.

Purseglove, J. W. 1972. Tropical Crops. Monocotyledons. Longman, London. pp: 607.

Rajanaidu, N., Rao, V., Abdul Halim, H. & A. S. H., O. 1989. Genetic resources: New developments in Oil Palm breeding. *Elaeis* 1: 1-10.

Rajanaidu, N. 1990. Major developments in oil palm (*Elaeis guineensis*) breeding. In Proceedings of the 12th Plenary Meeting of AETFAT, pp: 39-52. Hamburg, Germany.

Rajanaidu, N. et al. 2000. in *Advances in Oil Palm Research* (eds. Basiron, Y., Jalani, B. S. & Chan, K. W.) 171-237 (Malaysian Palm Oil Board (MPOB), Bangi, Selangor).

Sambrook, J., Fritsch, E. F. and Maniatis, T. 1989. Molecular cloning: A Laboratory manual, (2nd edition). Cold Spring Harbor Laboratory Press, Cold Spring Harbor, N.Y.

Singh R, Tan S G, Panandam J M, Rahman R A, Ooi L C L, Low E T L, Sharma M, Jansen J and Cheah S C. 2009. Mapping quantitative trait loci (QTLs) for fatty acid composition in an interspecific cross of oil palm. *BMC Plant Biology* 9: 114.

Sousa, J., Barata, A. V., Sousa, C., Casanova, C. C. and Vicente, L. 2011. Chimpanzee oil-palm use in southern Cantanhez National Park, Guinea-Bissau. *Am J Primatol* 73: 485-97.

Tani, E., Polidoros, A. N. & Tsaftaris, A. S. Characterization and expression analysis of FRUITFULL- and SHATTERPROOF-like genes from peach (*Prunus persica*) and their role in split-pit formation. 2007. *Tree Physiol* 27: 649-59.

Vrebalov, J., Pan, I. L., Arroyo, A. J. M., McQuinn, R., Chung, M., Poole, M., Rose, J., Seymour, G., Grandillo, S., Giovannoni, J., and Irish, V. F. 2009. Fleshy fruit expansion and ripening are regulated by the tomato SHATTERPROOF gene TAGL1. *The Plant Cell* 21: 3041-3062.

Whitmore, T. C. 1973. The Palms of Malaya. Longmans, Malaysia, pp: 56-58.

The term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

EXEMPLARY SEQUENCES

```
SEQ ID NO: 1-8217

SNPs in Table A

SEQ ID NO: 8218

~3.4 MB sequence of genetic region comprising the SHELL gene

SEQ ID NO: 8219 - SHELL locus

GTGAAGTTTAGATACTACCTGGGTAGCACTATCATCAAGCTGCCATGCATTGCACTCATT

TTAAATTGAGATGACTCAAATGAGTGCTATGTGTCTCCAAAATTATAGATTTACAACTAT

TAATTAATGTTTTTAAATTTTAACAAATACGTGCCAACAATCAAAGTAACACATGTCCAA

TGGGAGTATTTGGACAGGGGTTAGCATCATCTGGCTGCCTGCATGTAAGTCAATATGTAT

TTAATTTCTAACTATGAACAACTTAATAGACTCAATTGTTATGGTTTTCGTGGCAAAGCT

GCAGACGACATGGGCAGACATTATTTTTGCTAGACTAAAGAGCAGAGAGACGATTGACGG

GGATTCCATCATGGTGGTAGCCTGATTACATAAACAATTATCATCAGCAGCAGCGCATCT

TCTCATTCATGATAGTCAGTGTCAGGGAGCTGCTTTTCTATTGAGATTCGTTATATTTAT

CGAGAGGTCAATAGCTCTACTGACTGGATGATCTTTTATGTGACTGAGCATATCGGAGAG

ACGGTGTGGACTAAGATCAAAGATCTTCCTTCGACCTTCAAGAATATTTATTTTTTAATT

TTTTTtGGATGTATTCGTATGAATAATCTAGCCTATCAAAAAAaTAAAGTGACATGTGG

CCTGGCACAAAGTCACGTGACCTTGAATTCCAACAAGCATTTTAGATTATAAGCTTACAC

CATGGGCGAGGGAAGTTTTCCACATTTTCTTGCTACTTCTAGACGCTTGGCATACACTTA

CATGTCTAACCAAATCTCATAGTAACAGCAAATTGCTTGAAATACAGATTGCTCTATGTC

AAATTCTTTAGGCTGCAGTGAGAAAGGAGATAGGCGAAACTGAAGAAGGGTGGAAAATC
```

-continued

```
TAAAGTTCCATACCACCAGTTCATGCAAACATCACTGGTTGGTCAGCTGACCTCTAACAA
GAAAGACTATTCACATGGAGGGATGACCCACTGATGCCCCAAAACAATAATGCAAACAAA
GAGAGGGTCGCTCTCTCACTTGAGCAGCGTAGGGATGCCAGTGAGTGCAATAAAGAAGTG
GGGACGAGGTATTAGAATTTCGATACATGTGTGCGTGTGTGAGTATCACAGAGAGAGAGA
GAGAGAGAGAGAGAGAGAGAGAGATTGCATGAAAGTCCTCAGAGTATGGGACATCTCCAAAA
CCAAGTCCAATATCTAGTGATGGGCTCTTTTATACAAAGAGTGATGCGCAAGAAATAGAA
GACATGGAGGTGAGAAGCTTGATCCATGCATGCATGAACATGATGTGAGAGAGACCATGA
AGCTGAAGAAAGGTCCATAGCCACAGAGGCAATAAAAGAACATGGTTGGGATGTTAAATC
ACAGTAAATGGTGAAAAGAACATGGTGCAACTATAAGGGGAACTAGTTTTAGTAGTTCAT
CTTTTTAGGACCACACCGCAAGGTGGACAGTTGGTGTTACATTTAGTCTCTCTTCATTCT
CTTTTAAGGGAAAATGTCATCTAGAGTTTGCAGAAGTTTTGAAGTTTTACAATATCGCTT
AATTTAATTCAATTGATGAACAATAATATTTAGTGATTGAAGGTGTGAACTGTAAGGTCA
CTTGAAATTTAGAGTCTATACACATTGGGAGTTCAAAATATCTGGTCAATTTTATTAAAA
TGTATTGTTCCAATATTAAAATTTTCTCGAGTTTTCTTTAAAGGACTCTAGTGTTCCTTT
GATCTAAAAACAGTCTAATTTTTTGCTACCACAAATATACTACAGTAGAGGCAAAAAAAT
CTAGATAACACAAAGGAACAAACAACTTTATGTTTTTAAGCAAGCAAATAAGTACATATT
CTTCCAACGTTTTCTCCAAGAACATGATCAATAGTTCAAAATGTTTGTCCCTTGATATTC
TTTACAGAAAAAACTCACGGACAATAAGCTTAAATCTTCATGGCCAGTATATTTTGTAAT
ATATGGTGAAACTGGAGTTCAGTTGTTCTACAATCCTAATAAGATCATAGGGGTGCAATT
CTTGTGTCCTTACACTTAGGGAAAAAGCTTTATGCCCCAGCTAGAAAGATTATATCGATG
GTCCCGGAGGAGTCTTGATTTAGTACATAACTTCTAAATGTGGAGCATCGCCCAGGAAGG
AAATATATCCATATTAACAAAGTTTGCAACATTTGGATTGGATGATAGTCCAATGAAGAA
AAATTGACCTACTCAACCATGACAATGGAGCTGTCCTCCTAACATGATAAGGACATAGCA
ACCATACTTTGGTGACATTTTAAAATCATGCAATTACTTCATCATGTTTACCATGGAAAA
TTACACAAGAAGATGGAAAACATAGCATAGCATTTACCATAAAGAACCATGCATCGTTAC
GTCATCCAAGCGATTCAGGTGCATGCATGTAGATTTTCCTCTCTTTGATCTATATATATA
TATATATATATATATATATATATaTATAtATaNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNATATATATATATATATATATATATAT
ATATATATATCTAACTTAATAACGAAGTCTTATGTATGCTAaGTTTTCCCTTTAGAATAC
TTGGAAGGCTTGACAGCATGCAATCATTCAATCAAAACAAGAGAGATAATAGATTGTTTC
AGAGCTAGGCTTTTGGAACAAGTAAATATAGTAATACAAATAGACAATACAAAAGACAAC
ATTTTTGTTTCCAGAAAACCATTATAGAATTTTCTAAGCCTTTCCCTTCTAATGAGGAAC
ATGTTCATTGCAATGTTAGAGCTATATGACTAACTTGTATAACGGACATGCCACGTTAGC
CTTGAGTGATCTTGAAATTGTTGAATTAGTCCAACAAATACGACTATTTGCTGACGCCTA
GCCCAAATAAAACAGAATTAACATGCAGTCTAGTCTGAATTAGTGGCTTCCACTAAGGAT
TAGAATGTTTCTCCTAACTATAGAGCAAGAAGACCTCTTGTATTTAGCAATGTTATCCAA
GCTGGTCGTTATTATTCCTCTAGAATTGGCTCCCACTGATCAGCTACCAAAGTTAGTCCA
CAGCACATAGTCCCAAACATGTCATTAGGTTTACCATAAATTTAGTATTTCTTGGTAAAT
```

```
AGAGGCAAACTTGCTGACTGTTCATGCAATTAAGTTACCTTGACATATGTGATGCATTAA

TTACATGCAAAGAAACCATCTATCATTTGGAGCTTATACTGGAAATTGAATTTCCCGAGA

GAATCTATATATTCATATTCGTTCATCCCTCGATTGTATTTTCAAGAAAAGATTTGAATT

TTAGGCAACATACCTTTTTCTCTATTGGTCTTAATTTTTTACATTTCCAACTACTTAATG

ATATGATTCAGATACATAGGGTTTCTACCCATTTTTCTTGAAAAGAAAaGAAGGAAAGGA

AAATCCAATAGAATTTACAGTGCATTGTTGAATCTGCCTAATCTGAACCATGACTTTAAA

AaAAAaAaaAaaGAAGAAGAAGAAGTTTCTGGCTACATTTTTATATCAGCTTATAATTAGT

TTTTATTAATAGTACTCACCAGGAAAAGTGTAAATATTAATTGTTCTTATGTATTATTGC

TTTTCTTAGTGTTTTTCTGTTAGGAAAACAAAAGAAACTTGAAATTGCACTAACTACAAG

TATAAAAATGAAAAAAGGTAAGGCCAATGTTAGAGAGCACTAAGGCTTCATGGTATAACC

TTCAAAAGTTGTGATGGATACAATACCATAGGTATTTGTTCTTGCTAGCCATAAAAATAT

ACAAGCATATGAGGGTAGCACATGGTAAGTAGACACAAGGTATATTTATCTTCATGATAT

CACTACAATAACCTGATGATATGGTGATGATGTTATCCATAACCTTATCAATAATTTGGT

TTTGATTTTCTACAAACAGGGATGTGTTTTtATTCTTTTtGAaTAtATATATATATATAT

ATATATATATATATATAAaGAAAAAAaaCCTTGGCACCGGTAGGGCATCATGTTAATTAA

CAGACATGATAATGTAGTACTAAAAGCTACATCTAATATAATTGTACTTTTACTAACTTG

ATGTGAAACTTAAAATTGTATTGCTTGGGATCACCACTTTATGTTGCACCACTTTTGTGT

GTTCTTGAGCATATCTGCGCATATCCTCTTTCACTCGCATTATTTAGATATTAAGTGCAA

ACATTTAAGAACCAGTTATCCTTGAAAGACATTTGAGACTGCATGAATGCCATCAGATTT

CTTGGCCAATGGAATGAAGCAGGAATGGATGTAATGTGATGTACGTGGGTAGAAGGGACA

GCGTTAACATGAAACATGTGGAAGTTTTAATATTTTGAGAAGAGATACATGCAAGTTACA

AAAAAaTTAAAAAaGAACATACAAAAAAAAaCTATTTATAGATGAAAGAAATGAAAAGA

AAGAAAAaCTTTAAAAGAAaGAAAAAAAaCTTTAAAATACACCGCAACGATTAATTTCTT

ATTCACCATGTCACCTCTTCTATGAATAACGAATCAAGAAAAGATCTGTGGCAGGTATTG

CCAAGCCAAGCTTCAATAAGGTTTTGTTACTTCTAGAATCCAAACTCCCTTGACCTCATA

GTTATGCGAGAGTCTAGTCTATTCATTACTTAATTCCCCCACCTAACCCTAATCTGAGAA

GGAATTATTATGGCTTGGGGAGATCACGTGCGGAGGAGGCGCCACCGATCGTTTTCACTT

TACCGCGCGCTTTTCAGTCCTAGCAGTGCCCCCCCAGTCCCCACCACTTCCCTGTCAACT

GCTCCACCGCAACCTCTCAATCTCCTAACAATCACTCCAATAACGACAAAATGATGGAGC

TAACCCATGACATTTTATATCGAAGATATAGTAGCACAAACTCCATCCGGCGGTACAGCT

TACCCAGCCAACCCACCCTCCACTCTTTAAGAGGAAACCCACATATCCGATGCCAATTGC

ATGCAGTGGAAAGAGAGAGAGAGAGAGCGCTGAGCTCCCTTCTTTTCCCTCGGAATTT

GCGGTGTTGGACTTCACCTTCTCTTCCGGCGTGGAAGCTGAGTTCCCGGAGTGGTAGTTT

TTTCCTTTTtTTTTTTTttGAGAACAATTTCTGTCTTTCTTTCTTTGTTGTTTCGG

CTtTTTtGATATTTGTTTCCTTTCTTGAGGAATAGTTTTTATGATAATACCGGAATTGGG

GGTTGCTAGAAATCGTGAGGTGTCATTGTTATAGGTTTTTTTTTTtGCTGGATCTTCGG

CGATCTTTTGCTGATATTATCCGTTTTTAACGATCGGAACGTTGGTTGCGTCACCAACA

AAATGCGACTTTGTTCTCGCTTCTCGCTAGATTTGCTCCACGAAAACAGTAGCTTTGTCG

GATCGGATCGTTTGCTCCATGTCTAGTTTTTAGGGTTATCTTTTCACATGTTCTTGAATA

TATCTTTGTCAAGaaaAAaaAAAAAAaCTTTaCCTTTTGTTCTATAACAAAAATCTTTTC

TTCCACGTATTTTGGTTGCCCTAGTTtTTtCTTTTTTTtGTTTGTTTGTATTTGTTAGAG
```

-continued

```
AATCGAGATTTGAGCCGTACATCTCGTTCATAAACTGTTTCATTTGTCAGAATTTAAAGA

AACTAAACTTCACGTATGCATCGTTATCCATTTGTCATGATCTTGTCTCATGAATATATG

TATTCTGTTCTTGTCTTCGCCTTAATTtTTTTCTCACTTTCTTTTCCGAACCCTAACCCA

TTCAAAGTTCCCACCTTTTCTCTCTTACTTGCTTTCATGTTTTTTtCCTTTTttTTTTtG

TTGCTTTTAATTTTGCTTGAATACCTTTTGATCTATGGAAATTAATAAGTCAATATGTCA

GTATGTGAAGGTCTAGGCCATGTTAGTCCCATCATTTCATTTATAGTTTAGATGATGATT

TtTTCTTTGTTCTTGGCAATATTCTAGACCAACTTCAGCAGACAGAGGTGAAAGAGAGAT

CATGGGTAGAGGAAAGATTGAGATCAAGAGGATCGAGAACACCACAAGCCGGCAGGTCAC

TTTCTGCAAACGCCGAAATGGACTGCTGAAGAATGCTTATGAGTTGTCTGTCCTTTGTGA

TGCTGAGGTTGCCCTTATTGTCTTCTCCAGCCGGGGCCGCCTCTATGAGTACGCCAATAA

CAGGTATGCTTTGATGACGCCTTCTCTTCCTTCGCTCATATCAAGTTAATTTTATGGCTT

CATTTGTTCTATGGCCAAGCCAAATTCTTTTTAAAGTTCTAGAATGTTAATGATGGTAGT

TTTGCTCCTCTTCAATTTATTTGCTTCCCTTTTATCCCTGATCCAAATGGTTTtTTTCTT

ATTTAAAATTACCCTTTCAAATTATCACATTTAATTCAGCTTTTATTATTATTATTATTG

CTATGAGATTAGTTTGTTGTTAAGATTCTATATAGGAAGGAATGATCAAGTGATCATTAC

TTTATGTAGTAAGAAATTAACAAGCAAAAGCAGCGTGCTTGGTCTTACCATGAGGATAGA

GGAAGAGTTTTACCTTGACTAGGGCAACTAAAAAGGGTTTGAGTTTTGCCTAACATTCTT

GTTATATGAATTCGATCTGTACACGACTTACTACTCTGGTATTAGAACGTATGTACTAAG

AAGTTTTCTTGGGATGGAAAGAAAGAAATAGTGAAGTAAATCTTATTAATTTGTCTTTAC

ATGTTCTTCTCATATTTTCTCATACTCTTTTCTTATGTTCAGACTTACACCGAAAAATTA

AGATGGATGATATTATGTTCTTGGTATAGGATTTCTTTTCCGACGTACCAATGTTTTGTT

AAGGAAACTTTGTAGTTGACTTTTCGATTATAATATTTTCCAAAGGACTCCACGAAATGG

TAACATCTCCAGTCGTTTCAATAAACTTCCGATCATATTATGGGTTTGCATTTAAGGTTT

TCTTCTTCCCTTCGCTTCCTCTTTGCCTTTGCCTTTCTCGTGTTACACTTCTGGCTCGTC

AATCTGCAGTACTCTCTAGCCATCTCTCTCTCTCTCCATCCACccaccCCCCCCCcCCCc

AAaCAACACACACACCCTCCCACCCTGTGCAACTAATTCCGACAAAATAAGGGTCTCCCA

TTGTTAGAGCACCTCCTGTATGGACTGCATTCTAAAGATACGGGAAAATGAGCCAGATAT

CTATTCATCAATCATTTAGTAGAGTCTCTAAGGTTCCTTTTTAAAACTGTCTTGAACCGG

CTTTTGCACAAAGAGCACCACTCCCTTTATTTATAAGTTGAACCTTCCTGAAAGCTAACT

TGGGTTTCAGCTTTCACTGTTCAAGTAAGTCATAAAGTTTTTCTGGTCATTAAACCTTGT

GATATGGAGATGGAAACTGCTTTTCTCCCTGCCGGATTTCTCTTCTGGTGCTAAGCGGCT

AAAACCCATCATCCATGTCTGCCTTCCTCTTTTATGGGTAGTTGCTGGACTTCGGACACC

GGTGAAGGATGAAGGCTCTTTGTGATTGGTTATGAGATATTTCTTGGGCCCCGTGCCTTT

GCTGTCATTCCCCACAACTCGGTGGCCATCATAGCTTTTTTGTTAGCTTTCGTCCTTACA

AATTCCTCTCTGGTTCTTTCTTTCACCTTTTCATGCATTTAGCTTCATTGTCAACATCAA

GGGAACACAGACCGGAAGAAGAGCAAGAAGAACCCAATCAAGACTGGATTTTACAAATCA

CCAAaAAAAAAAAaGACTGGATTTTACTCGACGACGCTGCAGTCTTCTCTGCTCTCACT

CAATTAAAATAGGAACAAGGAAAATGTAGATATTTTTtCCCTtTTCGTTATGATAATTAT

AATCTAAGAAAGATTTTAAAAGCTTACTGTAATCATCTCATGTTCAACTATTGTGTTGCA

CCCAACGAAATTTCTGTGTGCCTCATGACGAGCATTACCTTTCCATGGTTCTGACACGAC
```

-continued
ATTGCATACTAGATTTTACTGTGTACGTAAAAAAGCACTGCATGACATCATCTCTATTCT

TCTTCTTCATtCCCttTtTTTtTTTTTTtGGTAATATCTATTCTTCTTTAATGTCCTCTC

TGATAACTGGTCTTATGTACAGGTACATCTTTACAAGCCTTCCGAGAGAATATGAATGCG

TATTTTCTGCAACCGAGTATATTCTACAAATAAAATGTTAGAGATTGTCTCGAACTGGTA

TACAAGCACATTCCTGTACGTGTTGACATGAAAGAAGCATAGATCAGACAAAATAATAG

TACGTGACAAAGATCATAAAGGGACTACAACATTAGGAGGGCTACAATTAATAATAACAA

CGGGAGCAACTAGCAGTGTATACGGTTCAGACCAGATCAGTTTAGAGTTATTTTGGAAC

CGAGCTGACTTAGTTGTTTTTCTAAAGCCTAAATTGAAAGAGAAACCGATTCAACCTGAT

CCGAAATACTCGATTTGGTTTCATTCAGTTTATTTGGGTTGATGTTCCATAGTTTGGGCT

ACATTGATTGCACTAAGTCTAAATATAAAAATTTCATTTTATATAGAATTGATGTTCAAT

GGACCGGACTAAGTTTAAACATATAAAAATATTTAAATTTTGAAATATATATGTACATAT

ACACATGTAGGTCGGGTAGGTTTAAATATAGATACTTACATATAAATGGATTGGGTCTGG

TTGGGTCAATGCGAGTCTGCTTAAATATATATATACATATGGGCTAGGTCAAATCAGGTT

AGTTTATATATATATATATATGTGTATGTGTGTATCGGATTTGTTGGTTTGCACTG

ATTTTCTAAAAAaTAAAATCGAAATCGAATCAAATTTTTTCTGTTCAAGAGTATCTCAAA

CTAATTTTTAaAAAAAAAAaTGATATAACTAGATCAAAAAAGACCGATTTGAATAGGCAC

TTTATGATTTTGTCACTTTTTTGTATACCTCTACGAGCAACAATAATAGAAACAATAATA

ACAATTGTAATAATCAATATAAAAATTATTAATAGTAATTAaAAAATATATACAAAATTT

TTGCAAGCATTCAAGTGGACACAAATCAAAGGGCACTAATGCATTCATAAAAGGTTGCTA

GCTTTGATCCATGGTAGCATCGTGTATCCTGAATCATTTGTAGGTTAATTGAAACCTCCT

AAATTGCATTTTAAATAAAAATAGCATGCATTTTATGAAGATAACCTTACTATTATTAGG

TAATAAGGTTGTTAAATTCTAACCTAATTAATATCTCCTAATTAAGAGATAATAGTTGTG

GTGGAAACGAGATGGAGAGAAAGCACTTCATCTCTCATCTTTCCTCTCTAAATAACATTT

CACTAAGAGATTTAATTATTGGATCAAGGCTAGCCAGTTTGTTATCTtTTTTTGTTCTAG

AAGTGTTGACCTTTTACCATTTCTCATATGAAAAAAAaCATTATCTAAGAAGAATAAATT

ATTATGATCATGAGGAGAGAGAAGGGGTGTTAAGGTTATTGGATTAAAATCAAACTGATT

AGAGGACCTTGTTTGCTATTATAAACCCATGACAACAATCAATATGCACTAAAGTTTTGG

TATAATAAGTTATCATCAAGGGCCAAAAAGGATTAACTCGAGAACACAAGCATACAATTT

AACATCGTACATAGATAAATTCAATTTAGGAGGTAATTATTGATGTATATGCTTAGACAA

GAAGAAAGTATAGAAAGTAAGGAAAATTGCTTGAATGATTTAGAAGTGCATAAATATAAT

CTAAATTTGAGGAGTCTTATTTATATTTTGAGAATTAGAAAGGGGAGAAAATTGAACAA

AACTTTGATAAATTGATTGTAAGAATTTTCAAACCTTAAAGCGAAAGTGATAGTGAAGTG

GAACCATTAACCATAATTTGATATTAAAAGGTTATCTATATTCATTAATATCATtTTTTT

AAATTATTGTATATATTTTTTGGGAGGAAAATTATGTTCTTTAAAAGTTAGATTGGTTTC

GTACTTATCATAAATGATAAATGATCTGAATTTAGTTTGAAAATTATTTGACATATAACC

TTTGATAAGAAATTACATATTAGGATTTTATGGTTTACTGTCATATAGTTCTTTGTTTTG

TATTTATTTAACTTTGACCATAAATGATTTGAAGTCAAGATACTTTAATTCTAGCCTCCC

CATCAACATGTTGATGGCTTATGATTTTtATTTTTtATAACATTTATTTTTATCTATAAT

ATTTTTCATTATTAATTTAATGAAAGTGGATTACACGACATCTAACTTATATTTTTGAAA

ATAGAGAATGATATGGTATACTATTTTGAACATGTTCAGAAATTAGAATCTTATTATTGT

TTTCATAAATTTAAAATATTATACTTGTCAATATGAAACATATTAAAAATGATCTAAAAT

-continued

ATtTTTTAAAATTTAAATGTCATAGGTTTGAAAAATTCTTACTTGTAAATATATGATTTG

TAACTAAATATTTTTAATGGCATGATATTATTTTCTAATTCCATCAAAGATCTAGAACCT

TTCAAATTAGTTGAACTTAGATACGTGTTTTAATATGTCTTAATCAAGATCAACAATTTG

ACTTCTTATTTTATATGATATATGGTATATTCTCACTTGATGCATCTGTAAGAAAATTTA

AAATTCTTTTATTTTATTTTATATATGTGTCAATACTATAATTCTTGATTATATGGATTT

CTAGTACACTTAGATTGTGATTGTTGTTTGGCATTGGAAGATCGAGACAATTAATACCAT

AAGTGGGATATATACTTGCTTAACCCAACATTAAACCAAAATCACCTCTCGACAATCACA

CAAGGACAAGTGTACTCAAGATAAACATGGATTGTCAAGATATATATAAGAATAATAAAT

CATGTATATAATTTtTTTTCATCTACAAACTTCTCTTCTTTCTCTTAATTTAGTATATAA

CTTCCATACCAATAGATTACtTTTTATTTGACCCAAAAATCAATTTAACCTTTTGTTTTt

AATTTAATCCTTTGTCTTCTTAAATGACTCAGCTTGTAATTTAAATATATCATTACTTAT

GCAGTAATGTCCATTTGTTGTAAATAAATATTTGGCAATAGAAGAAATACTATAAGGTCA

AAAAATATAAACAGGACAATGAAGCATTTCGTATAGTCTATTATAAATGTAGAATGAAAC

ATAATAGGCTTTTCATTTGATCTATAATTAAATATAATTATCAAATATCAAAATTAATGT

ACCAATTTATGAGACATCAATATTATAAAGGGATACTAAGAAACTAACGAGAGTACACTG

ATCAAGAAATGTGATCGACCAGTGAGGCATGTTGTTTATAAATTAATTAGACACGTTTTC

AATTTATGAGAATTTGTATTCAAATATTTATAATTGATAAATGGATCACTTTTTATTTGC

TCTTTATATTTAGACTCCAAATAGTGCTGTAAGAGAaAAAAATTTGAAAAAaTAATTTAT

ATTTTCAaAAAAAATATTTTTATCAATTTTCATTACCATAAAaAAAGATCGAAAATAAAA

TTAAGAAAGAATGAGATAAGTTTGATAATTTTAGACATCCGCTTGCATAATAGTTCATGT

TTAATATTAATTTATCACTGAGAATGCAAAAATATATAAAATTTTTAATTAAGCTTTGCT

ACATATAATTATTATATATCACTTACATAAATGATTTGATTAAATATTTTTAAAATTTTA

ATCTAATTTTTAATTGCATAGATATCTATTGCAGTAATTTTCCTCTAAATAATAAATTAA

ACTAAGAAAATAAAAAATATTTAATAACAATTGGAATATACTTATCAATCCTATAAGAAT

AATTCCTGTAAAACTCCATCCATTTAACTTGCATCATGCATCATTTATTTTTTTATTTTt

AATCATTTAGAAATTTAAAATCAAAATTCAACTTTTATAGATTTATTAGAATGCATGGAA

TGATTTCATAAATGTTGCATTGTACTAAAAGAATTTATGATAATCTATACAAGTCAAGCA

TTTAAATTACTTATTATACTTTACAATAGTAAACTACCTTTTGAGCAAAATGGTGGTAAC

CCATCATAATATGTCATATGATAAATAAAATGAAGTACAAGGCTAGATAAAGAAGGGGGA

CAGAAAGAGAGATATAGGGCTCCCGAGCTTAAGCAACCAAGCAATTCAATATAGTTGCAA

CCAATAAAATCCGATATGAGCAAATATAAATATAACTCACTAAAAGCCCAAAATACACCC

AATAAGCCCAGGTAACCACTAGCCCAAACATAATGGCCTACTAAGTTTGAATTTTAAAGT

TTAAGTCTTTGCCCATTCACCACCTCTACCTTCCAAGCTCTAATTATTTTAATGCCATTG

CAAATCATCATGTCTTCTCTTCTTCTAATTTGGTGTACTATCATTTTCAATGTATTGCAA

CTCTATTGCCAATCGATGCTCCTCCAAGGCATCTCTCAAGATCTCATTTGGCTCTATTGC

GCTACCACTACCATCCATCCTATTACTCTCTAGATCAATATCAAAATTAATGCAGCTCTT

TTCTCGATACTTTTTGCATCATCATCTCACTCCATCATCACAGTCTATACTTGTTATTTG

GAGCCTATGCTTGCTACTATATTGTGACCTCAATATTACAATCTCTACTTGTTACCACTC

AATGTCCATGCCCATCTTCCATGAAAGCTACTTGGCAAACAATCCTAATAGGTTCCAAAA

AACCCCACAGCTAAGGACTAAACACACAACCACACAGGTTCTCTTATACTCTCTTTATTT

-continued

```
AGATTCAAATCTACATACTAGGCTAAGAGTCCAATTCTAGTCAAACTGAATCATAAACAT

CATAATCAATCCATGGTCAACTCCAACCATTTATGAAGCATAAGATCTTATCTAAAAAAA aTCAACCAAAAGTTATTATTTGGCTTCCTTATCCCTATATAAGTATCTAAATATCCTTTG

TGTACAACCAATATCAAATAAAATACATGCTTGTGCGGAGATCCTCACAAAAATATTTAG

CAAAATAATCCTATCAATGTTGTTAGGATTGATGTTGAGTCATAAATCATATATATAGTG

GATTGGATTAGATTCATCATCGATCGAATTATAGATCATTAGATCTTTTTGAATTATTTA

AGATTTTTAAAATATACAAGAAATGCAAAAATTAAAAGTATAAGATGAATATAGAATTGA

TGAATAAAGAACCAAAAAATATACTGAACTAAAAGAGAGAGTATGTTGGCTTAACCAATT

GTAGCAAGGTAGAAACCCCACTATGGTATGTATAACATAAGAAAGACCGTTATTAAAGA

GAAACAGATGCAAATCACTTTATTCTAAGATTAAAAATACTATCTTAGCTAGCTACTTTA

AGGATACAACTTTTACACATTCACTCACAAATCCTAGAGATTTAGCAAAAGAGAAAAGAG

AGAAAAAAGAGGAAAGGCAAGGGAAGAATAGTTCCTATAATAGAATTTTCACTAGTTAAT

AACTCAAGTATCTCTAGGATGACTACAAGAGTAGCTCCAATAGGATATTTGTAGGTAATA

TATAGGAACTCAATTCTTAAACTTTTCAATGTGGGATTCCAAATTTCATTCTAACTCCAA

TAATTGTAATGCAAATTTTTCTAACAACATCAAAAGTTATTAACAATAAACTCATAACAA

TTAAAACTTTTCAAAATTTATTAATATCAAACTCTCCTAACTTAGACAAAAAATGGATAG

AAAAATAAGTAATCATAAAAAAaCTAGTTGACCCAAGTTTATAGGATTTGAGACCTATGT

AGCCTAAACCTATAACCCATGTGGTTAGAACCCACGATCTATGTTGTTAGGACTTGCAAC

CCGCTCTAGCATCACATACATTTAAGAAATCTAATTTGCTTCCTTATAAGTTCATATATA

TGGAATGTCTAATAAACAAATATTGTGCCTGATTATTCAAGATCTATATTTGTACCATCT

GCCAATTAATTATCATTTTATTTAGAATGTGGTTAAAAAATATAAAAATTTCTCTTTTAA

GTCCATAAACTCCAATACTATATTAGTTACCTTACTAACCAAGATCTAGAAATAATTTAA

AATCTATAAAATTTAATGAATTATAGAAATTGGACTACATAATCCATAATATGACATTAA

ATTCTAATTTCTTAATAGATAATGATTCAAAGATAAGGTCCGGATTGTTTATGGCCATTT

TATCTAGATTGTAAGATGCATAACTTGAATGATAAGATTTTAACAACAATAGCTCCTATT

AAAAaTTAAAAAAaTATTTCTTATATAGTTATCATAAAAGGTGGTAATCAAGTCATATTA

TATTTATCAAAGCACTGTCTAAGCAATAGCTACATGATACTCTATAGTATCTAAGCACTA

TTCTCATTATCTTTATTTCTCTTTTTAAAATTTAGTGAGATGGTTGCATTGCCTCCATCT

ATGACTTAAATTTTTGGATAACAAAGCCATATCTATTAAGTTTCTTTAATGAACATATTT

TGGCTCAAGTCCATTAGGATAAAAATCTTTTAGAGAGCATGAAAATTATATGGTTAGAAA

ATGTTACTAAAGGTGATTTCATATGATTCTTAATGTCTAAAATAGTGTTTAACTTTCTTT

TCTCTATTTTTAGTAACCAATGTCAACAACCTTAATGAAGCACTTGAAAAGATCGTCTCC

TTAATAATTTATATTGTAAGTTTAAATTTTAGTTCCTTGAACTATTGATAACTAATTGTT

ACTTCAGTAACTCATCAAACTATTTTTAATAATTCTCTCCATGATTCTCTTACATGTCCT

TTTAAAATGCAACATGATATATCAATATGCTTTTCTATTAGACAATTCAACTTCTAATTA

TGAGTAATTAAATATATAATTTTTATTAAAATGGATCTAATTTTTTTGGTTTGGCAACT

CTTTTGTTCAGCATAAGATCAACAATTGATAGGTACAAGAAGGCATGTGCCAACAGTTCA

AACTCAGGTGCCACCATAGAGATTAATTCTCAAGTAAGAAAGACATGGCAATTTAATCTA

AAATAGATTTCTCTGAAGTCCATATATTTTTGCCTCATATGCTTATCAGTTAAAATTCTT

CATGCTCATAAAGGCATAAAAGCAAGTCAGTAAATTATTTGTACAGTTGATCTTTTTGTT

GTTTGTTCATAGCCTTACATGTATCTTTGAATATTTTGTTGATATATTGATTGCACAGAT
```

-continued

```
TTTTTTtCTTATTTCCATTGATTGTTGCTTTTCTTGGATATATTTGATAGGTTTGATTGA

GAATAGTGGATTAAGGTGGTTTACAACCTTTCTTTGAGAGTTGTAAGGGTGTAAAGGGCT

AGATCTACTAAGAGATGAGGGTGATGATACTACTAACTATTAAGACTATGTCGGAGTCCT

TTTTCTTATGGATAACATATATTTGAAGTTGTCATTCCTATAATGTAAGAGGTAATGAA

AAGATTTTTCTTGCAAATTAGAATCACTTTGCATCAACTCCAATACTTTTCTTTATGCTA

ATAAGGTAGTGAATTTTAGTGATATCGTCTAGGAATGATTCAACTAATACCTCATTGCTT

TTGAACCATAATTGCTTTTCCTCTATTTTCTTTTTTTtCATTTCAATCATATTTGTTATG

GTGTAGGAGGGAAGGTATCATTAATCCCATATTAGTTGTGAGTCAAGGAGGACTCTGAAG

GAACTACCCATCCTACATGAGGTGCTTTTTGGATTGAAATCCAAAGGGATAAAATTTTGA

GACCTATGAGCCAAAACGGACAATACGTAATAGCCGAGCCATGAGCTCTTGGTTGCAACA

GTGGCACACTAGGAAAGGAATCACCCTTATGACTGTGGGATCCCTCTCATCCGTACACAA

ACTCCTTGACTGGAGGGCGGTAATAAAATAAAGATGATGGTACCTTCCGTCTATCCATAG

ACTTCTTCTTGACTGGGGGCTATATTGTGGCGTAGGAAGGAGGGCATCATTAGTCCCACA

TTAATTATGAATTAAAAGGCTGGGACTCTAACTTATATAGGAAGGAAACACTCATCCTAC

ATAAGGTGTCTTTTGGATTGAAATTCAAAGAGACAATCATGAGGCCCATGGGCAAAAACG

GACAATACTTCACATGCCAAGCCATGAGCTCTTAATCATAATAGTGGAGGGAGGGCATCA

TTAGTCTCATATTGGTTGTAAATCAAAGAAGATCCTAGCTTATATGGGATGGGACCTTTT

CTTCTCTGTGACGCCCCATGCCATGTCAATCAAAGATCGAAGTGGATAATACCTCACATA

TACAAGAACGGAGATCAATCTACCCGAGCCATGAGCCCTTGACTGCAATATTGATGTGCC

AGATAAGGGACCTCCCCTACGACTGTGGGGCCTATCCCTCTGTACATAGACTCTTCCTTG

ATTATAGAGCTATATTATGGTGTAAGAGGGAGGACATCATTAATCTTACATAGGTTGTGA

GTTAAGAGAGACTCTGATTTATATGAAATGGAATCTTCTCTCCTCTGTGAGGTCCCATAT

CATAGTGGCTAAAGATCGAAACGAATAATACATCACATATGCGGGAGTGCAGACTGACCC

ATCTGAGCCATAGGCTAACAATATTATCATAGAATCATGATTTGTAGTGAGCATTCATCT

ACTATTTTTTTtCCAGAACTCATTTCAATTTATCTCAATTTTCATGTTTTAAAAGAAGGA

TAGATCTTGCCCAATAATACATATAATATTTATGAAAGTCCTATGAAAGCCTTATTGTAG

TCAGAAAACAAGGTCAAAAATACATTCTAGTCTATGGTTGAGAACTTCAACCAATTGACT

ACGTTGCCTGAATGTTCAAAAGAATTCAATAGTTCAATCAACAAATAGAGATGGGATCAT

ATCATCTTTTtATTTCATCAATTTTGCTGAATGATATCTATAATATATATGTGCCTTCGC

TCTAAAAATCTTTGGCCTAAGTTCAGATTTATGATAGCAACTCTTCAAAAAaCCAAAAaT

TGTGATGACAACTGTTGCCTAGGCGACATGTAAGTGGTTAAGATTGAAAACTCTAAAATA

GAGTGCAGCTACTCTAGGTAAAAGATCACTGACATAGACATACATCAAAGTTCGTCTGCT

CCTTAATTATTTCTTTTACTAAAGTAGATGTTGAATCATAGGCGAACAATACTACTGAAC

AATACATATTTCTTGCATACATTGGCTTGACTATTAGTGCTATGCACTCTAGGTTCATTT

ATACTTCACAAGAGTTTTTATTTGTTTGCCAACATCAAATTTCATGCAATCAAAAACACA

ACTTGCAGAAAAAATGAATAAGAGTTAAGTAAAAGGACCTAATTATCATAAGCTATGGAA

GACAAGACAAGGGATACTGCCATTGATACTCTTAGTAAAATAGTGTTATAAGTGATAGTA

ATAGCAATATGAAGAAAGTATGAAAGAACTAGTTTTTTCTTAAAAGAGTATGAAATGCA

TACAAGTTGCGGTATCATTTGTGAAAGAGAAAGTATTTTCTTTTATTTACGTTTAGTCAA

AACCATATTTATTTGTTATAGCTGATCCCTGAAATTTCATAACTCACACCAATTGGCATG
```

```
ATGTTATTAGCTTAGATTTGCCATTATACCGCCATTGGTAAGAACAAAATGCCCTCAATA

CCAAAATAAACTGCATTTGCAAGTTATTTGAAAGAAGTGCAACTCTATTATTGTGGCATG

TTAACGAGCTTTTCTATAATTTGAATTTTTTGTACCGTCTATGATGGTTATCAAATTGTA

TAACGAAGGCAAAAAACTATGGCTAAATGATTCGTTTTTATGAATTATTGTATGCTACTC

ATGCTATACTTTGTTTGTTTCATCATGATCATTACCTGCAAATCATCTACTCGCATGATA

CAGCTACGCATTTGTCACATTCCGAACCTAGCATCTGGGTCAGCCATGCGATGGCCTCAT

ATTCCCTAAGGCAAGGCTCTAAAGAATATACAAAGTCTTAACTTCTTTACATCCTCAAAA

TCACATGAGCACTATTGATATCAATTTAAAATAAATATTTTTAATTAATAAATACCAAAC

TTTATACAATTTATAGAACTCAAGTATCTGATTGGTGTTGATAATGCTCCATCTAATTAA

TTCCTTCAATCTTGATCTCAACTATAACCAAAATACATATATCCTATGACTCTTAAAAA

GAAAaGGAAAAGAGGAGATGTAAGCTTTACAATCCAATAAGAATTTTCACACACCAACAC

TAATATAATAATAATAAATAAaAAATAAGTAATAGTTGTTACTCTTATAAGTCTTCTGTC

ACAAGATACCATAATAATAAAACATGCAAAGAAAGTACATCTTTTTATATAATAAATCAT

ATTAAATACTTTTCTCAATTTATAGTTACTGGATTCGATAATATTTAGGTACTCGACACT

GAACTATCACAATCATGTTTCTGGCTCATGGCAAGATATCGACATAGTGGCTAGTCTCCT

AAACTATCACAATCATATTTTTGATCAGTGGTAGGATATCAACATGATGGCTAATCTAGA

GGGCCATATGTGCTTAACTCTGACTACTACAGCTAGATTTTCAATCTATGATCAGACACT

AATAAAGTAGCTTATCTAAAGGATTATAAGTGCTCAATTCTAAACTATCATAATCACATT

TTCAGATTACGGTAAGGATCAATATAGTGGCTTATCACACGACTACCACAACTATATTT

CCAGCTTGTGGTGGGGCATCAACAATATTAATAGCCTAAAGCACCACAACCCACTATTCA

GTTACACAATTCAATTAACAATTCAAGATCATACTCTTTTGTAAAATTCAATACACAAGA

TTATCGAAACTACTCAAGTTAGGATTAGTGATATATGATACATAACTTCATACAGATCTC

TCTCTATATATATGTATGTATATGTATGTGTTTGTATACATACAATTAACAAATAA

GCACATAGCATGCAACTATCAAAAATCATATAAATCAAAATCACTATGCACAAAATAATT

GTTATATAAATAGATGATCAATGTCTAGAAATTTTTCGCTCTACGTACTGATGACAAACT

TGGTTATAACTATTTATTAGTCCATGCCTAGCATGTCCAATCAATCAATATAATTTCAGT

TCATCCTGAATCAACCATTAGCATAAAAATTAAATAACTTATTGCCAGTGTTTTAATTTC

AAAGCTCTAATATTCGAATTAATCTTACTTTTAATTTCTCTATACTTTCTAATTAAAAAT

TACATAATTAAATAAAAAATTTGGATTTTATCTTGACTATAAACTAGAGCATAAAATCCC

TTGCTCAGTATTTCTTAATTGGATGATTGGTCCCATCCAAAATCAAAATCAATAATTAGA

AAGAGCCATAAAATGGTTATCATCGATGGTAGAAAATTTAGAAGAAGAATATAGCTAGTC

GAATAATAGCATCTGGCAACCTAAGTGGGTCAGGTCTGGCTGATTTAGCTGGTTATTCAT

GAATACAACAAAGATCATCTATGATAGATTTTGAGGTTGCTTGATCAAGACCAAGGTGGA

GAAAGGCAATGCTAGTAGCATCCAGTGACTAGTGTTAGCCCAATATACATAATCCAAATG

ATTAGTCTACAAATCAAAAGCCAAATTATAGCTCAATAGGAATTTGGTGATGATAAAATC

AAACAATGCTTAGCAGGGTCGGGTTTGGAGTTAACTATTATACAGAACAAGTCCAAAACC

TTCTTCTAGGATCAACATAGGGTCTACTATCAAGTCTTCAAAATCCATCTTTTTTtCTtC

TTTTTtATCCCTAAATATAAGAAGAGAGAGAAAAAGATAGAGGAAGAAAGCTGGTAGAAA

GAGATGTGAGAGAGAAGGGAGAAAAAaaGAACAAACCAAATCTCTCTCTTTCTCTCTTCA

TTATCTTCTTTCTTCAAAAAGGGGATTTTCCCCTTTCTCCCTCTCTTTCTCCTAGCGGAT

GGCTAAGGCCAGCAGTCTATGGTGGTGTCTAGTGGTGAAGATGCGATGGCCGCAGTGCTA
```

-continued

```
CAGCGATGGCAGTTGTCGGTTGGTAGTGGTAGTGGGCGATCCAATAGAAAGAAAAGGAAA

TCAAAACAAAATAGAAAAAGAAGCCTTGCTTTGATATGATAAGAAGACTACAAGGTGGTC

AGCGGTAATGACAAGCATCCGCATTAGCTTAACCTCTTATGATAGTTGCAAAGGCAATAA

TAGCCACAGTGGCTGACGGTGGATAAACTAAAGAAAACAGAAGGTCCTTAGTGCGGCAAC

ATCCGACGGTCTTCCAAGAAGATTTCAGCCAATGATGGCTGTATGAAAATAaAAAaGAAa

AAAaGGTACCAATAAGATGGGAGGCCACGATGCCTCGATCATCTCTAATGATGGCGTGAC

CATGGTTGTGCCAAAACTTtTTTTTCCTATCTTTCCAGTGATATGATCAATTGATCACTG

ATCAATACAGTGGAAGCTTGGCTTTATAAATGATGGAGGCTAGGGTTTTCTAGCCTCCGA

TGAGTTGGAGAAGGAGCCAGAGTCAAACTCTTTCTTCGACTCAAATAGGGGAAGGGAAGG

TCTTTCCTTCCTTCCCATTGTTTCTTGGGCTTGATGAGATTTTTATTTTAGAAAAATTTC

AAGCCTCTACAACCATATGAAATCATAATGTCAAAGCTAGAAAAGGAGATCTATGCCATA

ATATTCCAATTCCAAGCCTAATCAAAGAACCATCAATCCATTAACACTAACTTTAAGATA

CCTAAGTTCTCCCTAGCATTATCTATGGTAAGAAAATCTATTAATTAAAATTGCATAATT

ATATCTAAATCAGTCAAAGAACAAATAATATTCTCTCTTTCTTTATCAAAATTATACTCC

TTTACCAGGAAACTAATTCGAATCTTCCATAATATCTTTTGGATCAAAGAATTAATGTAT

TTAATTAGTTTCAAAATAACTCAAACCATCACACTTCTGCTATACACTCTAATCTAAATC

CATCGATTCCTCTGGGTTGACTAGGTGAATTCTAACAAAATACCGCTTAATATCGGAACC

AAGAAGATCCAAAATTTTAACTTAAGGCAAACTAGAACAAAACTTTTGCATCTTTTTATC

CTTACAAAATCTTGAGCATACCACATCAAAAGTAAACCTTGAGCCACTATCCATGTTTGA

AGCATGACATAAGCTTCGCCATCCTCTCAAAACTTAATAACTCTAGATAAATTTAAATTA

ATCCTGACTTCTCTAACAGTTCAATTAGACTATCAAGATCACCTTTTCTCTTGGAAAGTT

AACTCAAAATTCTAACAAGTTAGAAAACTCTAAATCAACATTCTTATTAACTTGTTTATT

TTTtATAGAGCTTCGTTCACTACAATTCTTAGTATCAATCGACAAACCACATGAACGCCC

CTTATATGTTAGACATATACAAGTCCACCAGAATCAATTTCTCTACTCAATTAAATATCG

ATAGCAAGATACTATAGACCTGCTCATAAGCCTAACTCTGATTAGAATTTAACACATCCA

ACTATCTCCAACAAATATAAGAAAGACCAAGTAAGCTGATCTAAAGATGATAATTTAAAT

TATCAAAGATTCTACCAAGATGCATATCTCATATCCAATTGATAAAATCTAATCCATTAA

TAGAATCAAACATACTTTTCTTTTACATGCCAGTTTCATATATGATCTTCTTATAGGTTT

GATTCTCGAAGAATGTTTATTTTTAACACTATGTAATTCTTTCTTAGGCCATATCCTAAA

CAACTTGCTAGTAAAGTCTAAAATTTTAATGATCAAACAATTAATAATAAAaTTAAAAAa

GTTATTATGATCTCCCCCTATATTAAGTTTAGAATTTCAAAAATATCTAAGTGACAATTG

AGCAAGTACACACAGCATAACACAATCTACCAATATATCATACTTTATTCTAGGGTCTAC

AGCTCCTATACTTAGGTCAAATCTTACTTATTGAAATTAGAGACATAACTTATCCATTCC

TTTTGTACTCATAATATGCCAAGTCTTATGCATAAATTTTTATCATAATGCTTAGTGAGC

TTAAACCTGAGCTTTGAATCTATTTCTACTATGTACATTACATCCCTAGTGATCACAACT

TTAAGTTCAAATATCAATTAAGTTATAATCCCTAATAATCATAACCTAGCTCTGACACTA

CTTTGTCATATCTCGATCCCAGCATCTGGATTGGCCACATGATGGCCGTATACTTTCTAG

GACAAGATCCTAAAGAATATGCAAGATTTTAAATTCATTACAATCTTAAAATCCCATGAG

TACTATTGATCTGAATTCAAAATGAATATTACACATTAACAAATACCAAACCTTGTATAA

TTTATAAAATTTGATCATCTGATTGGTATTGATGATATTCCATCTAATCAATTCTTTCAA
```

-continued

CCTTGATCCCACCTATAGTAAAATACATATATCCTATTACTCTGAAAATGAAAAGAAAGA

TGTGAGCTTCATAGATCAGTAAGAATTTTCACACATCAATATTAATATAATAATAAATAA

AAAaTTATCAATAGTTATTACTCATATAAATCTCATACAATAGGATATCACGATCATAAA

ATATATATAAAAAAaTATATTTTTTtGTATAATAAATCACATCAAATACTTTTCTCAATT

TATAGTGTATCAGATCCTATAATATTTAGGTGCTAGGCTCTAAATTATTACAACTATATT

TTCCACTCATGGCATGACATCGACATAGTGGCTAATCTCGTGGACTATCACAATCACATT

TTTAGCATGAGGTTGGACATAAGCATAGTGGCTAATCTAGAGGGTCATAAGTGCTCAACT

CTGACTACCACAATCATATTTATAGTCCATATTGGGATATCAATAAAATGGCTAGTTCAG

AAAACTACAAGTACTCAACTCTAAACTATCATAACCATTTTCTAGCCCATAATGATGCAT

CAACAAAATAGCAAGCCTAGAGCACCACAATCCACCATTCAAGGACACAATTCAATTAAT

AATTTAAGATCATATTTCTTTGTAAAATTTAATACATAAAATTACCAAAACCACTCAAGT

TGGGATAAGTGACATGTGATATATAACTTTATACAGAATCATATATATACTTAAGAAATA

AATGTATAGCATATAACTATCAAAAACTATATAGATCAAAATCATTAATTCACAAAAATA

ATTTTTATATAAATAGATGATTATTATCCAGAAATTCTTATCTCTACTAATGACAAACTC

GGTTACAACTATTTTCTTGTCCATGCCTAATATATCCAACCAATCAACATAATTCCAACT

CATCCTTAATCAACCATTAGCATAaAAAATAAATAAATTACTCATAGTGTTTTAATTTCA

AAGCTTTAATATCCAAATTAATCTTAAATCTAATTTTTTtGTACTTTCTAATTTAAAATT

ATATAATTAAATAAGAAATTAAGATTTTATCTTGACTTGTAAACTAAAGCATAACATTTC

TTGCTTTGCATTTTCTTATTGGGATGATTGCTCTCATCCAAAATCAAAACCAACAATCAA

AAAAaGCTATAAAATAGTTATTGTCGATGGTGGAAAACTTAGAAGAAGAACAGTTGGTCG

AATAATAACATCCGATGGCCCAAGTGGGTTTGATCTAGATGCCTTAGCTAGTGATTCAAG

AATATGACAAAGATCGTCTATGATGGGTTTCGTGGTTACTTGATCAAGATCAAGGTGAAG

AAGGGCAAGATTAGTAGGATCCAATGACCAGTGTCAGCCCATCTAGGTGATCCAAATGAT

TAATCTATAATTAAGAGCCAAATTATAGCTCAATAGAAATTTGGCGATGATAAAATCCAA

CAATGCCCGGCAAGAGTCGGGTTAGGAGTGAACAATTATAGAGCAAACCTAGAATCTTCT

TTTGGGATCAACCTAGGGTCTACCATCAAGTCTTCTAAATCTATCTTTCTTtCTTTTTTT

TTtATGCCTAAATCCAAGAAGAGAGATAACAATAAAGGGAGAATGTAGAGAGAGATGTGA

GAGAGGGAAGAACAAATCGAATCTCTCTCTCTCTTCCTTGTCTTCTTTCTTCAAATAGAA

GATTTTCCTTTCTCCCTCTCGTCCTCCAAACATGGCAGTGGATGGCTGAGGCCAATAGCC

TGCGATGGCATCCAACAGTGAAGAGGCGACAACCCCAGTAGCAACAATGATGGCAGCTGG

TGGCAGCAGTGGGCAATCGGATATAAAGAAGAAGAAAATCAAAGCAAAATAAGGCAAGAG

GCCTTGCTTTGATCCAATGAAGAGGACTTCAAGGTAATCGGTAGCAATGGTAAGCATCTG

CACCAGCTCAACCTTTGGTAATGGTCGCAATGGCAATAATGGCCATGGTGGCCAATGGTG

GATGAATCAAAGAAAATAGGGGATCCTTGGTGCGGCAAGATCTAATGGTCTTTCAAGAAG

ATCTTAGCCAACAATGGCTACACGAGGATAGGAAGGAAGGAGAGAAAGTGCCCATGAGAT

GGGAGGCGATGCCTCATCTCCTATGATGGTTCAACCACGATTGGGCTAAAACTTTTtTCT

CCTCCTTTTTtGACAATGCAATCAATTGATTTCTCAATAGAATGGAAGCTCAGCTTTATA

GACAATGGAGGCTAAGGTTTCCTAGCATCCAATGAGTTTGAGAAGAAGCAGGAGTCGGAC

TCCTTCGACTCAAACAAAGGAAAGGAAGGTCTTTCCTTCCTTCCTATTGTTTCTTGGGCT

TGATTTTGGGCCTATTTCGATGATGGGCTGGGTAGGGTATCACAACAGTTTTGTTTCTAA

ATTGTCATTATCAGGAAGAGTAATTCTTTGTACACCACATTCGATGTAGAAAAACTGCAC

-continued

```
CACTCCGCCTAATTGAGCCACATATAACCACCACTTTTCAATGTAATTTAGTATTCGCAA

TTCTGCTTTtTTTTTTGAAATTTTGAATGGCAAAAATGTCCATCCTCTTTTAAAAAAATA

TGATATCTTATGGCCATATTATAATATCCTGCAATCAAATTATGATTTCTTATATACAGA

AAGTTATAATTTGACCACAGGATGTCATAAGAAAGGGGTGGACATTTTCATCATTTAAAA aTTTTtAAATTTTtAATAATGAAAATGTCCTTtCCTTTTtATGACTTTTGGAAGAAAAaT

TATGACATCCTATGTGTATTAAGACATAATTTGACCGCAAAATGTCATAATTTTTTtAAA

AAaGGATAAGCATTTTCATCATGCAAAATTTCAAAAGAAAAAGCAGAAATGCGGATATTA

AATACACATTGGAAAACGGTGCATTACATGACTCAATCAGATGGCGCGGTGCATTTTTC

TACACCAAGTGCGGTGTACAAAGAATTTCTCTTACTAGGAAATATCTTGAGTCTAGACCG

GCCCATTTGTCATTTAGACCAATCAAGGACTATGAATTTTGGTCCATAATAAGTATGAGA

TCGTCATGGGATTGAAAAGATGGGAAATAACTCCTCAGTTTGCCCCTTGACAGCTCACA

ATTCTTCAAATAATAGCATAAATCATTTTTTGAATCATCAAATTTATTACATTTTAGCCT

TTTAGAAGAAACCAATGCTATCCATATAAAAGGTATTTGTTTTCTATTAATGTCATTGCA

CTAATGAAGACAGCTTCAGCAAAGATAGAGCAGAAATCCTTTAAATTTTGTAAGATTCAT

TTGATCATCTTGAATTTTCTTTGATGATGTGGTTGCAGCAATACTATCAGCAGGAATCAG

CAAAGTTGCGCCACCAGATACAGATTTTACAAAATGCAAACAGGTGAACCTCAAACTTAG

ATCAGAACTGATTGGTCTCAAATACAATGTATATGCATTTTCAAAGCTTAAGATTATGTC

TTACCATGATTCCTAATCTACCACCTCTACCTTTCAGGCACTTAATGGGTGAAGCTTTGA

GCACTCTGACTGTAAAGGAGCTCAAGCAACTCGAAAACAGACTTGAAAGAGGTATCACAC

GGATCAGATCGAAGAAGGTAATCTGCATCTATATTTTCTTCAAACTGAGATCTTCATATT

GCCACCAGCACATGGCTTATCTGAAGTACATGATTATTAATCATGAAACATCATGCTATG

CAGCATTGAAAAGGGAAATCATTGTGGTTCACAGGTGGGGGTAGAGCATGTAAGATACGA

TGGGATCTAAAAATCGAGTCAATATAAATAAGTGTAATTTGTATTCTGTTCTGCCCCCAG

AAATCAGCATAGGCACCATGATGCATGTACCATCACCTAATAATATGCAACTTCAGAATT

TTTTGGCCCATCCAGCTCTTTAATTTGATTTTTGATGCATCTCATTGTTTTTTtCGCATC

AGCATGAGCTGTTGTTTGCAGAGATCGAGTATATGCAGAAAAGGGTAATATTCTAAACTT

ATTCCCTGCAACTTAATTCAAAGTATTGATTTCTTTCATTCATGTCTCCCTCTGAGTGGT

TCTTTGTTGTTGAACTGTAGGAAGTAGAACTCCAAAATGACAATATGTACCTCAGAGCTA

AGGTATCAATGAGAACAAAACTCTCTTCCTTGTCCTTGTCTGCTATTTCTTTCTGATATA

AACAAAAGAAATGGATATCATATTCGTAAAATATTTGATATCATCTATCATGCTTTTAGA

CTTATATGTGGTACTAGCATGGAGCCAAATTATATGCATTTTCATATGTTTAGAATGCAT

GACTAACGAAACAGTGACTTATGTTTAAAATGCATTTTCTCATTGATCAAATTTTTTTTt

ACATACTGTTGAATTTAACAGAGGAGAATAGTTTCCAAGAGATATTACAAAACAAGAGTT

TATTTGTATTTGCTTGTCTTCAAGAAATGAATTCAGCTCCACTAGTGGTAATCATGTGGT

CATCATCCATAGTGGCCTGTATGGCATGGCATAAAAACTAGGTGAGATTGTAAACAATCT

TCATGATGATAGTATATATATCATAGAACATTGAGCCTTTGTGTGGAGGCTCATCTGAAA

ATTAGTCATATCTGAATGAGAACCAGATTGATGGACCGTTTGAATCAAGAGATAGGACAA

GCAATACTCGAAAAAGTGCCTTAGTTACAGCCCAAATTCTGGATTGCTGATTTCTCTATT

TATCGATGCACCAACACCCTTCATGGGCAAGAATATTGTTTAAATCAGTGTTGCATTTGA

CTTCAAACCTCTAACATCTCAACAACCATAACTGAAGCCCCTTCAAAGCTAAATGCCTG
```

-continued

```
TTAATTTGTTCTTCACAAAGAAAATGGCATTTTTTCCTAGATGTCCATACCGATACTAAC

GGTATTTTGGAGGCTTGATGATGTGCTAATGACACTTTGGATTCCTCAAAGAAATGGCTC

CTCTGCTCCATCTCGGTCACAAGTCTCTAAAATTTTCACTTGTTGTTTCCATTGATTCTA

TTTCTTTATATTTTATTTAGATCTTCACAGACACAGTCTCAAAGTAGCAAGGTGGCATCT

ACATTCTTATTTCTCACTTCAAAATTTTTGGTGTTCTCAGATAGCAGAGAATGAGCGAGC

ACAGCAAGCAGGTATTGTGCCGGCAGGGCCTGATTTTGATGCTCTTCCAACGTTTGATAC

CAGAAACTATTACCATGTCAATATGCTGGAGGCAGCACAACACTATTCACACCATCAAGA

CCAGACAACCCTTCATCTTGGATATGAAATGAAAGCTGATCCAGCTGCAAAAAATTTACT

TTAAGTATGTCGCTGCTTGTTAATGACATGTTCTAATAACATAGGCTACAAGACCTGTAC

TCTTACTGATAAAGGTGTGTTAGAAGACTTGTCTGATTTCTATATTCCTAATATCAATAG

ACATGTTAGTGTGCCTTAATTTGTCTTGATTTCAGTAATATTTTGCAGATTGGAAGAAAA

AGCACTTTTTTATTCATAGAAGTTCTCTCCACCAACCATCATCTATTGAGTAGATCAGAG

TAGCATAAATGACATGTGTATGCATATCCTAGAGCTATAATTGACATGCCAAATGAAAAA

CCTAAAATGCTGAAAGGAATCTCCACAATTATGGAGGAATTAGTACTTCTTAGACCACGA

AGCTAAAACTAGATCTGCAATCCTCATAAAGAATGGCTACCCCCTACTGCCGAGTGTCAC

CAAAACATTATTGAAGTTGCTAAGCCAAGCCCTCAAAGTTCTCTTTTGCTATGTTTCTCC

CCAGCTGCGAGCTTTTGATTTTGTTGCTTCTTCAAAGATCATGTACATGTAAGTGGTTTC

TTTTGCTGCTGTCTCTCGGATCTTTTTGCGTGATGCATATAGGCCTGGTAGATCACCAAA

ACCAGACTCGCCATTTGTGTAAGTCCAGGTTTTCCAGTAGTCCTGTGATTCTTGCCTCCA

GCTAATGCTTTAGCAGACCATTGCAAGCAAATCTCTGTCAGCAACTATATGGTCACTTGG

AGTAGATGGATATTAAACATGCTTGTCTTTTTGCTTATAGCCTTCAATTTATTTGATATT

ATAGTATTAACCCAAGCTCAAGCTCGACTCGATGAAAAATAGACAAAACTCGAGTTGAGC

TTGAATATCAATGGAGTTATACTCGAGTTCGAGATCAAGTCTTAGCTTACTAATAAGATA

TATATATATATATATATATATATATATATACAAACTCAAATAGGCTCATAAGTTTTTt

AAACTGAGTATCCTGTTATTCAAGGTTGATAATAATCGAGTTGAGTCAAGCTTGAATAGT

TTATAAGCAACTTTGACTCATTTGTATACATCGTAAGCTTCTAAAGATAGCCATAAGAGA

TCAGAGATGTCCATGCCTGTGGTACCAACCTATGGTAAGCATTAAGGAGGGTGGTACCAA

CCTATCGGCTGAAGTTTCGTTGGTGAATGTTAATTTTTGCAAATCTCTAACACTATAATA

TAAAAATCTCTAGGATCTTACATGGTCAAAAATGGTTGTAGACGTTATATGCTAAATAAT

GTGTTGTTGTCCATGTCAGGATCTAATGAAGAATAACCACTTGTTTTGTTGTGAGAATCT

AATCAGTGTAGTGCTATACAAGCCAATGATCTGTATTTAATTAGCTCCCAGTTGCTAGAT

GGAATCGTACTAAAGTTTTTTTTTttGGATTGAAGGTACTAAAGCATTTAAAAaTAAAA

AaTTTCTCACAATCCGGCATTAGCTTAGTTGGTAGAGCAGAGGACTTTAGTTGGTATTAA

TCAGCAATCACTAGGTCGCAGGTTTGAATTCGGCAAGTTAGATTTTTTAAATTAAATGCC

AATTATTTGTAGTTTTTtCTAAACAATTTGACACTATTTTTCAAAATTATGCAAGACAAA

AATTGAAAAATTCCAAGGTGTCATGTTATCCTTTAAAATTTTTACATCATAAACTTTAAA

TTATAATTTACAAATATTTATTTCATTTACAACAACAGAACATATAGCATGAGAAGAATT

ATGCAAAAGAATAACTAAGAATTTCTGATAAAATATACACCTTTTTCTGACCCCAATTTA

TATCACTAAATTCAAAGATGAGGATTATGCAATGTTGGAGCTAGTATGGCTGAAAATCTA

ACATCCTTGCTAAGCATTTCTGCTTTAGGAAGGCTAATATTCTTGAAAAAaCAAAaTAAT

TGGCTTGGGGTTTAAGACAGCTTCAAACTGGGAGTGGCTTACATGTATACAATCAGAACT
```

-continued

```
ACTATAAAAGCCATGGAAGCAGGATGGGAAAAAaGAAAATGATTTAGTAATTTTTTATTT
ATATTTAATTTTTTTtttATTAAGCTATCAACTATTTCCCTAAATATCATAAGACCCACAT
CAAAGCTATTAAAAACAAATAAAGGTTTTGCATCAATGTATTGGGTACATCCCAATCTTA
TTTCTCAAAAATGTTTTTGTGTCAACACATCTAACAATATCATTGTCAAACTTTTATATA
AAGCACCTACTACACAAGCTATACTACACTCTGCAAGTTAAACCCATTTATTTATCAATT
TTCTGCCAAATTATTTATTAATTATTTAAACAAAAAaTTTAAATTACTATAATGCTAAAC
AATTTTATAGCTACTTAAAAGAAGCATGTTCGGTTGCTAAACTATCTCACTTGCACATAT
CTTCCGTATACTTTATATCATTCCAAATTTTTTTCATAGGACTTATTTGGACAATCGGGA
AACATGTTTTCTTTACTATGAAATTGCATTCAAGAGTATTGACAAATCCCATTGTCTTTT
TtATTACTAAATATGCATTTTGTATGCTCATATACTAGTACATAAATCTATTGGTTTTTt
ATTCTCTTGGTTAGTATAAATTGACTATCTCAAGATAGCAATTAATATGTATTATATTAT
TCAATACTTTTAATCTTGCCTTTGCTATGCCGCTTTTAGTTTCTTTAATATTAAATATCA
AATGAAATGATAACTAATCTCATTTTAGTGATATTGCCTGACATTTTGATATCCTATTCT
TCAATATCACTTGAGATATCAAGATATCTTGACTATTTAAGATCTATTTTCTATTGAAAT
GAAGGTAAATTGGTATGTTGGTTTGTCTTGGTTAGAAATGAATTTGAGACTTAAAATTTC
AATAGAATTTGATGAATGATTTAACCTGAATATATAAAAACAGCACGCAAGTTAGCTGAT
ATTCATCCTTTTGATCTTGTTTCAAATTATTTATCGGGATAATTGATATTTATGTATTTA
TAAAACAATATTACAGGTAAGAGAAATCAAAATACAATGATTCACTCCACATTCCTATCC
TCCACATCCAAAACTCCTCAAAATTAAAACCAAACTCTAAAATGCTCTCTATATATTAAA
ATTTCAATGTAGCTTTTGATAATGTTATAAAAATAGTTGTTTTGATATAAATGGTTGTTG
AAGCTCATATGGATGATCCCTTAGAAACTGGAGTGTATTATAAATGATCGTTGAAGCTCG
TATGGATGATCCCTTAGAAACTGGAGTGTATTATAAATGATCGTTGAAGCTCGTATGGAT
GAGTCCTTAGAAATTGATATAAGAAATATTATTTCCTTCAAATGAAAAATATTATTCCCT
TGGTAAATAAATAAGAAATATTATTTCTTTTGTAAATAAATGAAAAATATTATTTTtCTT
TATAATTTAGATTAAAAATCTATAAAAGAGCTTGGAATGAAATGAGAATTGTTGCGGCCA
ACTCTCCGTCGCCTGTCGCCGGTAACGAGCACCCGCAAGACAGCATCCACATAGACCGAA
TTGATGTCCGACGAAGACCCTCCGATGCTTAAGTCAGATAAGGAAGTTGATGAACAATAA
TTTTTGAATGTAGAAAGTAGCAGAGTTCTGGCCCTGAGATGGCTTACCAGTACTGCTCAC
TTAACCCCTTTTTATAGATGCTTTTGATGTAACCGTCGAGCACATAGTCCCACTTTTTAT
GACGCTAAATTATCGGGCCATAAATATAAAATTAATGAGGCGTTAATTCTCCTTAATAGC
CGTGACACACAGTTGATAACCGTTTGTGACGGTTATGATATGTTGAGCAGATTAGCCGAT
CATATATCGGTAGAACCGACTATATGTCGGTAGAATCTATGAGCGACCATCGGCTAGTAG
TTCTGTTATGCCGACGGTCTAAGTCATTCACTGTCGATCGGTAGTAGTCGAATCATTAGT
CGGTCAGCCGATAGTAAGTCGGCGCGGTTCGCTCAGTCGGTCGATGAAGAGTCAGAACTG
CATGTTCAACCGATATGCAGTTGGAGTCGTGGTGACCAAAGTCTGAGGTCGGTCAGTTTA
CCCCAACAGTTACCCCCACTCTCAAAGTCCAAGGTGAACCGACGTGTATATTGTCACGTA
GTTCGTCATATTAGATGAAGGGAGTTATTTCTATCATATCGAACCTCGATTTTGATGTCG
CTTTCTTCGAGATATGGGCGATCGACTGCTTTGTCGTTGTGGCGGATACGGTCATCTTTA
AACTGTCACACTAATCAGACGATTCGGTATCAGTTGTCAGTGTCAGACATCATTTTGGAA
AATCAATTCGACGTCGGATGATATGATTCTGACAAATAGATTTGTGCCATATGTCTGAAT
```

```
GTTATTGGGTCGGATCTGTTTACGCGGATTAGGATGACGTGGCTCGATCTGGGGCAAATA
CGTCGAACCATCTGATTAATGGTCGGTCTAGATGTTGCCACATGTCACATCTGATAAATT
TTCGATTCAATCACCTTCATCTCCACTGTTGAGGGATCCTATATATATAGGATCGCTCTC
AACCAAACTTCTACTTTTCATTTTATCTTTCTTGGTGCCGAAACTCTGTCGGACAGTCGT
CCCAACGTCTGAGGTTGTTATTTTCGTCTTTTTCAGATCAAGTTTCTGTCTTTTCTTGAG
TCCTTTTTCTTTCAGAATCTCCGTCTTCTTTAGAATCTTGTCTCTTATGGCTAGGACTTC
TTCTTGGGACGGTCGGTTGGAGAATCCGACTGACGAATCTCAATCAGATCCAGAGGTTGA
GGTTTCTTCACTTTTGGAGTCAAATATCGAGCAGCTTCAGGAACAGTATTGTATCCCGGA
GCAGTTTCAGCTTTTTGCCCCTAGGGCTGATGGTCGGATGAATATCCCTTTTTTGGGCCA
GGTGGCCTTCTATGTCGAAGATTTTCGAGTGGATCTTCGATTTTTGATTTTAAAATTTAT
CCGAAATATTTTGGATTACTACGGACTTTGTCTGGCTCAGCTGGCACCGAACTTGATCTG
GCTGGTAATTAGTTTTGCCTTGTTGTGTCAGTTGCTACCGACTAAACCTCGTCCTTCTCT
TTTTCGAGTTTTCTTCATCCTCCGACCTCATCCGAAGATCCGAGGGTGGTGGTTCTTCAA
CCCTCGAAAAGATTTTTCTtTTATTACTGATCTTCTATCATCCATTCATAGATGGAAGAA
TCAATTCTTCTTCGCTTCCTCTACCCTTCCTTGGGGTTTTCCTTCTCGTTGGAGCGATCT
ACGAACTGATTGCACGACAACAGCCGAGTAGAGATTGACGATCGGGAGGACTTCCATTGA
CTGAAAGACATGACGGTCCTGGCACAGAAGGAGCTTGTGAACGAACAGACCCTTTATGAT
GCCGACCTTAGTTCGATTGCCCGATTAGATATAGTACAGTCGGTCGGTTATTTCGGACTT
TACTTTTCTTTTACTTGTTTAGTTGTACTGACTTCTATTGTAATTGCAGCCATGTAGCCG
AGGGTGCGAGTGTCGAGCATCGATATTTGTCAGCACGCTGCCAGGAAGAGGGCAGCGTCC
GAGGTTGGACCTTCTCGACCATCGATGAGGCATCATACTTTGGTGCAAGTTCGAGCGGCA
CTAGCTTCAGTCGTCGCTTCAATGCCGACTGAGGAACCCGATGCTCCATCTGCATCGGTT
CCTGAGCCGATCCCGATACTATCAGCCCCGACAGTGCTCCCTGCTGCATCATCCGAAGAA
AGGGTGGCAAGGAGAACTGCCGAAGCACCATCGGTAGTTCCATCAATTGAGGAGGTTTGG
GTCAGGGCTGGAGAATCTGAACAATCTGTGGCTGCGCCAGTTGCTCCTTCAGCTGGGGCG
CAGTCGAGTTCAAGTTTTCCCTCGCTTTCGAACATGGGACTGCCGGCAAGGGATCGGGGG
AAAGCTCTGGTGACTTCGACGGAAGATGCAGCATCGGAGGGCTACACGGTTCACTTCGAC
CTTCAAGTACCTGATGATAAATTGACCCTGGCCAATCCGACATTGGCCAAGCGACTGTGC
CAAGCCGCTCTTCCTTCGCTTTATCAGGAGCATCGAAAGAAACGGACAGTGGCCGAGATG
TTTTCATCCTTTTACTTGATGATAATTAGGGTAAGTTTCTTTTCTTCTTTTTTtCTTTTT
TTtAACCTAA
```

SEQ ID NO: 8220 SHELL predicted protein sequence

[dura]

MGRGKIEIKRIENTTSRQVTFCKRRNGL*L*KKAYELSVLCDAEVALIVFSS
RGRLYEYANNSIRSTIDRYKKACANSSNSGATIEINSQYYQQESAKLRHQ
IQILQNANRHLMGEALSTLTVKELKQLENRLERGITRIRSKKHELLFAEI
EYMQKREVELQNDNMYLRAKIAENERAQQAA

SEQ ID NO: 8221 SHELL predicted protein sequence

[pisifera, Zaire allele; sh$^{AVROS}$]

MGRGKIEIKRIENTTSRQVTFCKRRNGLLK

-continued

IQILQNANRHLMGEALSTLTVKELKQLENRLERGITRIRSKKHELLFAEI

EYMQKREVELQNDNMYLRAKIAENERAQQAA

SEQ ID NO: 8222 SHELL predicted protein sequence

[pisifera, Nigerian allele; sh$^{MPOB}$]

MGRGKIEIKRIENTTSRQVTFCKRRNGL*P*KKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09481889B2). An electronic copy of the "Sequence Listing" will also be available from the USPTO upon request and payment of the fee set forth in 37 CFR 1.19(b)(3).

What is claimed is:

1. A method for determining the shell phenotype of an *E. oleifera* or *E. guineensis* palm plant or seed, the method comprising,
   providing a sample from the plant or seed;
   amplifying nucleic acids from a genomic region corresponding to SEP ID NO:8218 from the sample to generate amplified nucleic acids and assaying or sequencing the amplified nucleic acids to determine the genotype of at least one polymorphic marker in the genomic region corresponding to SEQ ID NO: 8218, wherein heterozygosity within the region indicates the presence of the *tenera* shell phenotype.

2. The method of claim 1, wherein the plant or seed is generated from (i) a cross between a plant having the *dura* shell phenotype and a plant having the *pisifera* shell phenotype, (ii) selfing of a *tenera* palm, (iii) a cross between two plants having the *tenera* shell phenotype, (iv) a cross between *dura* and *tenera* palms or (v) a cross between *tenera* and *pisifera* palms.

3. The method of claim 1, wherein the plant is less than 5 years old.

4. The method of claim 1, wherein the plant is less than one year old.

5. The method of claim 1, wherein the polymorphic marker is within a position in the genomic region corresponding to SEQ ID NO: 8219.

6. The method of claim 1, wherein the polymorphic marker is within 1000 kb from a position in the genomic region corresponding to SEQ ID NO: 8219.

7. The method of claim 1, wherein the polymorphic marker is at least 86% predictive of the *tenera* phenotype.

8. The method of claim 1, further comprising selecting the plant for cultivation if the plant is heterozygous for the polymorphic marker.

9. The method of claim 1, further comprising selecting the plant for cultivation if the plant has a *dura* genotype.

10. The method of claim 1, further comprising selecting the plant for cultivation if the plant has a *pisifera* genotype.

11. The method of claim 1, wherein the plants or seeds are discarded if the plants or seeds do not have a genotype predictive of the *tenera* shell phenotype.

12. A method for segregating a plurality of *E. oleifera* or *E. guineensis* palm plants into different categories based on predicted shell phenotype, the method comprising,
    providing a sample from each plant in the plurality of plants;
    amplifying nucleic acids from a genomic region corresponding to SEQ ID NO:8218 from the sample to generate amplified nucleic acids and assaying or sequencing the amplified nucleic acids to determine the genotype of at least one polymorphic marker in the genetic region corresponding to SEQ ID NO: 8218; and
    segregating the plants into groups based on the genotype of the polymorphic marker, wherein at least one group only contains one of (i) plants predicted to have the *tenera* shell phenotype, (i) plants predicted to have the *dura* shell phenotype, or (iii) plants predicted to have the *pisifera* shell phenotype.

13. The method of claim 12, wherein the palm plant or seed is an *E. oleifera* palm plant or seed.

14. The method of claim 12, wherein the palm plant or seed is an *E. guineensis* palm plant or seed.

15. The method of claim 12, wherein the plant is less than 5 years old.

16. The method of claim 12, wherein the plant is less than one year old.

17. The method of claim 12, wherein the polymorphic marker is within a position in the genomic region corresponding to SEQ ID NO: 8219.

18. The method of claim 1, wherein the palm plant or seed is an *E. oleifera* palm plant or seed.

19. The method of claim 1, wherein the palm plant or seed is an *E. guineensis* palm plant or seed.

20. The method of claim 1, wherein the polymorphic marker is within 20 kb from a position in the genomic region corresponding to SEQ ID NO: 8219.

* * * * *